United States Patent
Liotta et al.

(10) Patent No.: US 11,497,744 B2
(45) Date of Patent: Nov. 15, 2022

(54) CHEMOKINE CXCR4 RECEPTOR MODULATORS AND USES RELATED THERETO

(71) Applicant: Emory University, Atlanta, GA (US)

(72) Inventors: Dennis Liotta, Atlanta, GA (US); Edgars Jecs, Decatur, GA (US); Robert James Wilson, Gansevoort, NY (US); Huy Hoang Nguyen, Norcross, GA (US); Michelle Bora Kim, Chamblee, GA (US); Lawrence Wilson, Atlanta, GA (US); Eric James Miller, Atlanta, GA (US); Yesim Altas Tahirovic, Atlanta, GA (US); Valarie Truax, North Haven, CT (US)

(73) Assignee: Emory University, Atlanta, GA (US)

( * ) Notice: Subject to any disclaimer, the term of this patent is extended or adjusted under 35 U.S.C. 154(b) by 0 days.

(21) Appl. No.: 16/487,825

(22) PCT Filed: Feb. 21, 2018

(86) PCT No.: PCT/US2018/018973
§ 371 (c)(1),
(2) Date: Aug. 21, 2019

(87) PCT Pub. No.: WO2018/156595
PCT Pub. Date: Aug. 30, 2018

(65) Prior Publication Data
US 2020/0054623 A1 Feb. 20, 2020

Related U.S. Application Data

(60) Provisional application No. 62/461,682, filed on Feb. 21, 2017, provisional application No. 62/461,690, filed on Feb. 21, 2017, provisional application No. 62/461,695, filed on Feb. 21, 2017, provisional application No. 62/461,698, filed on Feb. 21, 2017.

(51) Int. Cl.
| | |
|---|---|
| *C07D 401/12* | (2006.01) |
| *C07D 401/14* | (2006.01) |
| *C07D 405/14* | (2006.01) |
| *C07D 413/14* | (2006.01) |
| *C07D 417/12* | (2006.01) |
| *C07D 417/14* | (2006.01) |
| *C07D 471/04* | (2006.01) |
| *C07D 487/04* | (2006.01) |
| *C07D 487/08* | (2006.01) |
| *A61K 31/4725* | (2006.01) |
| *A61P 35/00* | (2006.01) |
| *A61K 31/496* | (2006.01) |
| *A61K 31/4985* | (2006.01) |
| *A61K 31/4995* | (2006.01) |
| *A61K 31/5377* | (2006.01) |
| *A61K 31/541* | (2006.01) |

(52) U.S. Cl.
CPC ........ *A61K 31/4725* (2013.01); *A61K 31/496* (2013.01); *A61K 31/4985* (2013.01); *A61K 31/4995* (2013.01); *A61K 31/5377* (2013.01); *A61K 31/541* (2013.01); *A61P 35/00* (2018.01); *C07D 401/12* (2013.01); *C07D 401/14* (2013.01); *C07D 405/14* (2013.01); *C07D 413/14* (2013.01); *C07D 417/12* (2013.01); *C07D 417/14* (2013.01); *C07D 471/04* (2013.01); *C07D 487/04* (2013.01); *C07D 487/08* (2013.01)

(58) Field of Classification Search
CPC .. C07D 401/12; C07D 401/14; C07D 405/14; C07D 413/14; C07D 417/12; C07D 417/14; C07D 171/04; C07D 487/04; C07D 487/08; C07D 471/04
See application file for complete search history.

(56) References Cited

U.S. PATENT DOCUMENTS

| | | | |
|---|---|---|---|
| 7,354,934 B2 * | 4/2008 | Bridger | ................ A61P 11/06 514/314 |
| 7,863,293 B2 | 1/2011 | Bridger et al. | |
| 3,008,312 A1 | 8/2011 | Shim | |
| 8,969,381 B2 | 3/2015 | Wilson | |
| 9,545,403 B2 | 1/2017 | Wilson | |

(Continued)

FOREIGN PATENT DOCUMENTS

| | | |
|---|---|---|
| CN | 102675305 | 11/2014 |
| CN | 103570683 | 4/2018 |

(Continued)

OTHER PUBLICATIONS

Cancer and Metastasis Reviews (1998), 17(1), 91-106.*
Science (1999), vol. 286, 531-537.*
Huff, Joel R., "HIV Protease: A Novel Chemotherapeutic Target for AIDS," Journal of Medicinal Chemistry, vol. 34, No. 8, Aug. 1991, pp. 2305-2314.*
Catalano, et al., Synthesis of a Novel Tricyclic 1,2,3,4,4a,5,6,10b-Octahydro-1,10-Phenanthroline Ring System and CXCR4 Antagonists with Potent Activity Against HIV-1, Bioorg. Med. Chem. Lett., 2010, 20, 2186-2190.

(Continued)

*Primary Examiner* — Rebecca L Anderson
(74) *Attorney, Agent, or Firm* — Emory Patent Group

(57) ABSTRACT

The disclosure relates to chemokine CXCR4 receptor modulators and uses related thereto. The receptor modulators can be formulated to form pharmaceutical compositions comprising the disclosed compounds or pharmaceutically acceptable salts or prodrugs thereof. The compositions may be used for managing CXCR4 related conditions, typically prevention or treatment of viral infections abnormal cellular proliferation, retinal degeneration, inflammatory diseases, or as an immunostimulant or immunosuppressant or for managing cancer and may be administered with another active ingredient such as an antiviral agent or chemotherapeutic agent.

21 Claims, No Drawings

(56) References Cited

U.S. PATENT DOCUMENTS

| | | |
|---|---|---|
| 10,016,408 B2 | 2/2018 | Wilson |
| 2010/0280010 A1 | 11/2010 | Gudmundsson et al. |

FOREIGN PATENT DOCUMENTS

| | | | |
|---|---|---|---|
| WO | WO 03/055876 | * | 7/2003 |
| WO | 20060020415 | | 2/2006 |
| WO | 2006023400 | | 3/2006 |
| WO | 2006026703 | | 3/2006 |
| WO | 2007027999 | | 3/2007 |
| WO | 2007087548 | | 8/2007 |
| WO | 2007087549 | | 8/2007 |
| WO | 2009121063 | | 10/2009 |
| WO | 2012075362 | | 6/2012 |
| WO | 2017011517 | | 1/2017 |
| WO | 2017106291 | | 6/2017 |
| WO | 2017223239 | | 12/2017 |
| WO | 2017223243 | | 12/2017 |
| WO | 2019060860 | | 3/2019 |

OTHER PUBLICATIONS

Debnath, et al., Small Molecule Inhibitors of CXCR4, Theranostics, 2013, 3(1), 47-75.

Gudmundsson, et al., Amine Substituted N-(1H-Benzimidazol-2ylmethyl)-5,6,7,8-Tetrahydro-8-Quinolinamines as CXCR4 Antagonists with Potent Activity against HIV-1, Bioorg. Med. Chem. Lett., 2009, 19, 5048-5052.

Gudmundsson, et al., 1midazopyridine-5,6,7,8-tetrahydro-8-quinolinamine derivatives with potent activity against HIV-1, Bioorg. Med. Chern. Lett., 2009, 19, 6399-6403.

Jecs, et al., Synthesis of Novel Tetrahydroisoquinoline CXCR4 Antagonists with Rigidified Side-Chains, ACS Med. Chem. Lett., 2018, 9(2), 89-93.

Jenkinson, et al., Blockade of X4-Tropic HIV-1 Cellular Entry by GSK812397, a Potent Noncompetitive CXCR4 Receptor Antagonist, Antimicrob. Agents Chemother, 2010, 54(2), 817-824.

Li, et al., Design, Synthesis, and Structure-Activity-Relationship of a Novel Series of CXCR4 Antagonists, Eur. J. Med. Chem., 2018, 149, 30-44.

Li, et al., Design, Synthesis, and Evaluation of Pyrrolidine Based CXCR4 Antagonists with in Vivo Anti-Tumor Metastatic Activity, Eur. J. Med. Chem., 2020, 205, 112537.

Lin, et al., Design, Synthesis, and Evaluation of Novel CXCR4 Antagonists Based on an Aminoquinoline Template, Bioorg. Chem., 2020, 99, 103824.

Miller, et al., Novel N-Substituted Benzimidazole CXCR4 Antagonists as Potential Anti-HIV Agents, Bioorg. Med. Chem. Lett, 2010, 20, 2125-2128.

Miller, et al., Synthesis and SAR of Novel Isoquinoline CXCR4 Antagonists with Potent Anti-HIV Activity, Bioorg. Med. Chem. Lett., 2010, 20, 3026-3030.

Miller, et al., Discovery of Tetrahydroisoquinoline-Containing CXCR4 Antagonists with Improved in Vitro ADMET Properties, J. Med Chem., 2018, 61, 946-979.

Nguyen, et al., Design, Synthesis, and Pharmacological Evaluation of Second-Generation Tetrahydroisoquinoline-Based CXCR4 Antagonists with Favorable ADME Properties, J. Med Chem 2018, 61, 7168-7188.

Peng, et al., The Chemical Diversity and Structure-Based Evolution of Non-Peptide CXCR4 Antagonists with Diverse Therapeutic Potential, Eur. J. Med. Chem., 2018, 149, 148-169.

Skerlj, et al., Synthesis and SAR of Novel CXCR4 Antagonists That Are Potent Inhibitors of T-Tropic (X4) HIV-1 Replication, Bioorg. Med. Chem. Lett., 2011, 21, 1414-1418.

Skerlj, et al., Discovery of Novel Small Molecule Orally Bioavailable C-X-C Chemokine Receptor 4 Antagonists That Are Potent Inhibitors of T-Tropic (X4) HIV-1 Replication, J Med. Chem., 2010, 53(8), 3376-3388.

Tahirovic, et al., Discovery of N-Alkyl Piperazine Side Chain Based CXCR4 Antagonists with Improved Drug-like Properties, ACS Med. Chem. Lett., 2018, 9, 446-451.

Tahirovic, et al., Small Molecule and Peptide-Based CXCR4 Modulators as Therapeutic Agents. A Patent Review for the Period from 2010 to 2018, Expert Opin. Ther. Pat., 2020, 30(2), 87-101.

Truax, et al., Discovery of Tetrahydroisoquinoline-Based CXCR4 Antagonists, ACS Med. Chem. Lett., 2013, 4, 1025-1030.

Wilson, et al., Synthesis and SAR of 1,2,3,4-Tetrahydroisoquinoline-Based CXCR4 Antagonists, ACS Med. Chem. Lett., 2018, 9, 17-22.

Zhang, et al., Discovery of non-peptide small molecular CXCR4 antagonists as anti-HIV agents: Recent advances and future opportunities, European Journal of Medicinal Chemistry, 114, 2016, 65-78.

Zhao, et al., Discovery of Novel N-Aryl Piperazine CXCR4 Antagonists, Bioorg. Med. Chem. Lett., 2015, 25, 4950-1955.

Zhu, et al., Structural Optimization of Aminopyrimidine-Based CXCR4 Antagonists, Eur. J. Med. Chem., 2020, 187, 111914.

Balabanian, et al., CXCR4-tropic HIV-1 envelope glycoprotein functions as a viral chemokine in unstimulated primary CD4+ T lymphocytes, J Immun, 2004,173(12), 7150-7160.

Briz, et al., HIV entry inhibitors: mechanisms of action and resistance pathways, J Antimicrob Chemother, 2006, 57(4), 619-627.

Cameron, et al., Establishment of HIV-1 latency in resting CD4+ T cells depends on chemokine-induced changes in the actin cytoskeleton, PNAS USA, 2010, 107(39), 16934-16939.

Challita-Eid, et al., Inhibition of HIV Type 1 Infection with a RANTES-IgG3 Fusion Protein, AIDS Research and Human Retroviruses, 1998, 14, 1617-1624.

Crane, et al., CXCR4 Receptor Expression on Human Retinal Pigment Epithelial Cells from the Blood-Retina Barrier Leads to Chemokine Secretion and Migration in Response to Stromal Cell-Derived Factor 1α, J. Immunol., 2000, 165, 4372-4278.

Dwinell, et al., Chemokine receptor expression by human intestinal epithelial cells, Gastroenterology, 1999, 117, 359-367.

Gupta, et al., Chemokine receptors in human endothelial cells. Functional expression of CXCR4 and its transcriptional regulation by inflammatory cytokines, J Biol Chem , 1998, 273, 4282-4287.

Kang, et al., A multigenic program mediating breast cancer metastasis to bone, Cancer Cell, 2003, 3, 537-549.

Lin, et al., Design, Synthesis, and Characterization of Novel CXCR4 Antagonists Featuring Cyclic Amines, ChemMedChem, 2020, 15, 1150-1162.

Mitra, et al., CXCR4 mRNA expression in colon, esophageal and gastric cancers and hepatitis C infected liver, Int J Oncol, 1999, 14, 917-925.

Moyle, et al., Proof of activity with AMD11070, an orally bioavailable inhibitor of CXCR4-tropic HIV type 1, Clin Inf Diseases, 2009,48(6), 798-805.

Muller, et al., Involvement of chemokine receptors in breast cancer metastasis, Nature, 2001, 410, 50-56.

Murdoch, et al., Functional expression of chemokine receptor CXCR4 on human epithelial cells, Immunology, 1998, 98 (1), 36-41.

Staller, et al., Chemokine receptor CXCR4 downregulated by von Hippel-Lindau tumour suppressor pVHL, Nature, 2003, 425, 307-311.

Volin, et al., Chemokine Receptor CXCR4 Expression in Endothelium, Biochem Biophys Res Commnun, 1998, 242, 46-53.

Wald, et al., Involvement of the CXCL12/CXCR4 pathway in the advanced liver disease that is associated with hepatitis C virus or hepatitis B virus, Eur J Immun, 2004, 34(4), 1164-1174.

Westby, et al., Emergence of CXCR4-Using Human Immunodeficiency Virus Type 1 (HIV-1) Variants in a Minority of HIV-1-Infected Patients following Treatment with the CCR5 Antagonist Maraviroc Is from a Pretreatment CXCR4-Using Virus Reservoir, Journal of Virology, 2006, 80,4909-4920.

Wu, et al., Chemokine Coreceptor Signaling in HIV-1 Infection and Pathogenesis, PLoS Pathogens, 2009, 5(12).

* cited by examiner

CHEMOKINE CXCR4 RECEPTOR MODULATORS AND USES RELATED THERETO

CROSS-REFERENCE TO RELATED APPLICATIONS

This application is the National Stage of International Application No. PCT/US2018/018973 filed Feb. 21, 2018, which claims the benefit of U.S. Provisional Application No. 62/461,682 filed Feb. 21, 2017, U.S. Provisional Application No. 62/461,690 filed Feb. 21, 2017, U.S. Provisional Application No. 62/461,695 filed Feb. 21, 2017, and U.S. Provisional Application No. 62/461,698 filed Feb. 21, 2017. The entirety of each of these applications is hereby incorporated by reference for all purposes.

FIELD

The disclosure relates to chemokine CXCR4 receptor modulators and uses related thereto. In certain embodiments, the disclosure relates to pharmaceutical compositions comprising compounds disclosed herein or pharmaceutically acceptable salts or prodrugs thereof. In certain embodiments, the compositions disclosed herein are used for managing CXCR4 related conditions, typically prevention or treatment of viral infections such as HIV or for managing cancer.

BACKGROUND

As of the end of 2007, an estimated 33 million people worldwide were living with HIV/AIDS, and the Centers for Disease Control and Prevention (CDC) estimates that 1,200,000 U.S. residents are living with HIV infection (*UNAIDS/WHO AIDS epidemic update, December* 2008; *The Henry J Kaiser Family Foundation HIV/AIDS Policy Fact Sheet, July* 2007). Although new infections have decreased in recent years, an estimated 2.6 million new HIV infections occurred worldwide during 2007 and approximately 40,000 new HIV infections occur each year in the United States.

HIV entry within the target cells involves a series of molecular events. The three main steps of virus entry within the cell are: (i) attachment of the virus to the subject cells; (ii) interaction of the virus with the co-receptors; and (iii) fusion of the virus and subject cell membranes. Considering the complexity of the molecular events involved in viral infection, all three of these steps have been considered for drug design. The T-lymphocyte cell surface protein CD4 is the primary receptor involved in the interaction with the viral glycoprotein gp120, but a cellular co-receptor is also needed for the successful entry of the virus within the cell. At least two types of such co-receptors have been identified so far, both of which are chemokine receptors, CCR5 and CXCR4. These chemokine receptors are therefore gateways for HIV entry, determinants of viral tropism and sensitivity.

Compounds targeting viral entry have two advantages over those that target the HIV-1 reverse transcriptase or protease enzymes: entry inhibitors do not depend on efficient cellular uptake or intracellular activation processes to exert their biological effects, and they are highly unlikely to show any cross-resistance with protease inhibitors or reverse transcriptase inhibitors. Viral entry has been validated as a clinically effective pathway for targeted intervention by the first fusion inhibitor, enfuvirtide. Other classes of entry inhibitors under development target the initial binding of viral gp120 to CD4 and the interaction of gp120 with cell surface chemokine receptors that serve as co-receptors for HIV entry (CCR5 or CXCR4). (Westby et al., *Journal of Virology*, 2006, 80(10), 4909-4920).

Compounds targeting CXCR4 have been developed primarily for treatment of HIV because CXCR4 is a major co-receptor for T-tropic HIV infection. For example, U.S. Pat. No. 6,429,308 discloses an antisense oligonucleotide to CXCR4 to inhibit the expression of the CXCR4 protein for use as an anti-HIV agent. PCT application publication number WO 2001/56591 describes peptide fragments of viral macrophage inflammatory protein II, which are described as selectively preventing CXCR4 signal transduction and co-receptor function in mediating entry of HIV-I. Additional molecular antagonists of the chemokine CXCR4 receptor are disclosed in PCT application publication numbers WO 2009/121063 and WO 2006/020415 and U.S. Pat. No. 8,969,381.

Studies have shown that CXCR4 interactions also regulate the migration of metastatic cells. Hypoxia, a reduction in partial oxygen pressure, is a micro-environmental change that occurs in most solid tumors and is a major inducer of tumor angiogenesis and therapeutic resistance. Hypoxia increases CXCR4 levels (Staller et al., 2003, *Nature* 425: 307-311). Microarray analysis on a sub-population of cells from a bone metastatic model with elevated metastatic activity showed that one of the genes increased in the metastatic phenotype was CXCR4. Furthermore, over-expression of CXCR4 in isolated cells significantly increased the metastatic activity (Kang et al., 2003, *Cancer Cell* 3: 537-549). In samples collected from various breast cancer patients, Muller et al. (2001, *Nature* 410: 50-56) found that CXCR4 expression levels are higher in primary tumors relative to normal mammary gland or epithelial cells. These results suggest that the expression of CXCR4 on cancer cell surfaces may direct the cancer cells to sites that express high levels of SDF-I. Consistent with this hypothesis, SDF-I is highly expressed in the most common destinations of breast cancer metastasis including lymph nodes, lung, liver, and bone marrow. Moreover, CXCR4 antibody treatment has been shown to inhibit metastasis to regional lymph nodes when compared to control isotypes that all metastasized to lymph nodes and lungs (Muller et al., 2001, *Nature* 410: 50-56).

In addition to regulating migration of cancer cells, CXCR4-SDF-1 interactions may regulate vascularization necessary for metastasis. Blocking either CXCR4/SDF-1 interaction or the major G-protein of CXCR4/SDF-1 signaling pathway ($G\alpha_i$) inhibits VEGF-dependent neovascularization. These results indicate that SDF-1/CXCR4 controls VEGF signaling systems that are regulators of endothelial cell morphogenesis and angiogenesis. Numerous studies have shown that VEGF and MMPs actively contribute to cancer progression and metastasis.

Thus, there is a need to identify CXCR4 antagonists for therapeutic applications in treating or preventing viral infections such as HIV and for treating or preventing cancer.

SUMMARY

The disclosure relates to chemokine CXCR4 receptor modulators and their uses in therapeutic and diagnostic applications.

In accordance with a first embodiment of the invention there is provided a compound of Formula (I)

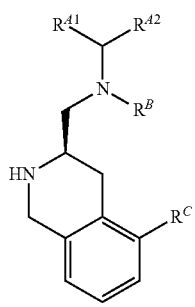

Formula (I)

or salts thereof wherein $R^{A1}$ is an optionally substituted heterocyclyl, wherein the substituents are selected from one or more, and the same or different $R^{X1}$; $R^{A2}$ is a hydrogen or an alkyl; $R^B$ is selected from the group comprising alkyl, an optionally substituted aminoalkyl and an optionally substituted heterocyclyl; wherein the substituents are selected from one or more, and the same or different $R^{X1}$; $R^C$ is a hydrogen, optionally substituted alkyl or an optionally substituted heterocyclyl; and $R^{X1}$ is selected from the group comprising alkyl, cyloalkyl, halogen, methoxy and triflouromethyl.

Further features of this embodiment provide for $R_{A1}$ to be selected from:

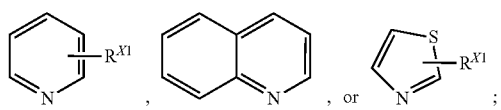

for $R^B$ to be selected from the group comprising: methyl,

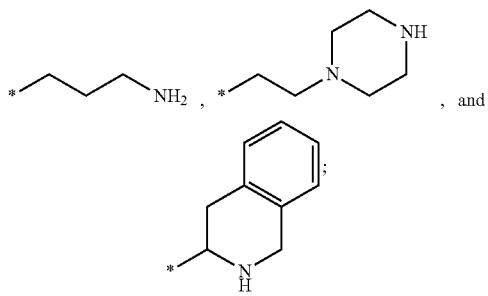

for $R^C$ to be H,

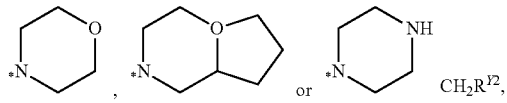

$CH=CHCH_2R^{Y2}$, $OCH_2CH_2R^{Y2}$, $NHR^{Y2}$, $N(R^{Y2})_2$,

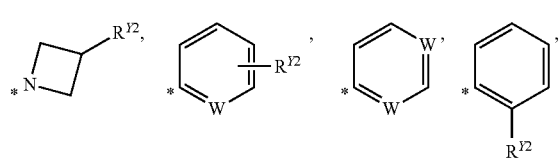

-continued

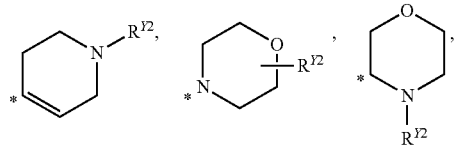

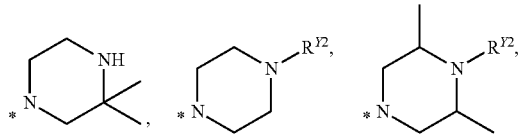

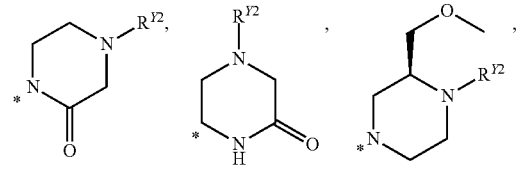

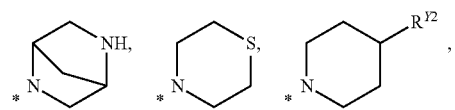

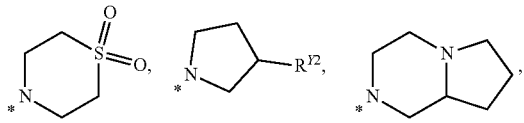

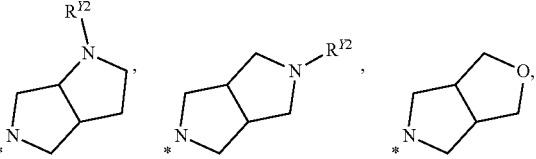

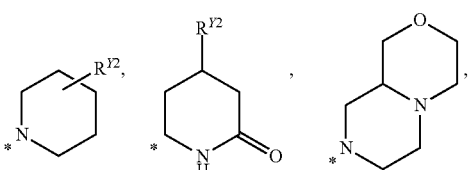

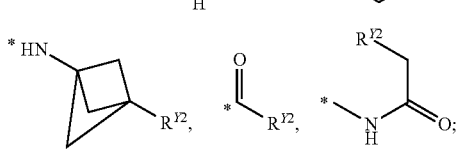

for $R^{Y2}$ to be selected from the group comprising H, OH, F, $CH_3$, $CH_2CH_3$, $CH_2OCH_3$, $CH_2F$, $CF^3$, $NH_2$,

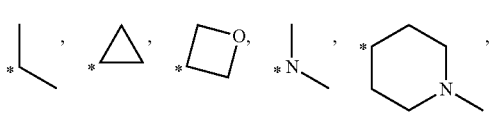

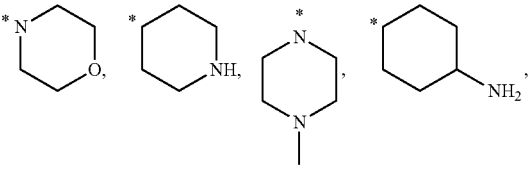

wherein the substituent $R^{Y2}$ may be individually and independently mono- or di-substituted onto $R^{X2}$ where appropriate; and for $R^{X1}$ to be selected from the group comprising methyl, ethyl, ethene, propyl, cyclopropyl, fluorine, chlorine, methoxy and trifluoromethyl.

In yet further features of this embodiment $R^{41}$ is selected from the group comprising:

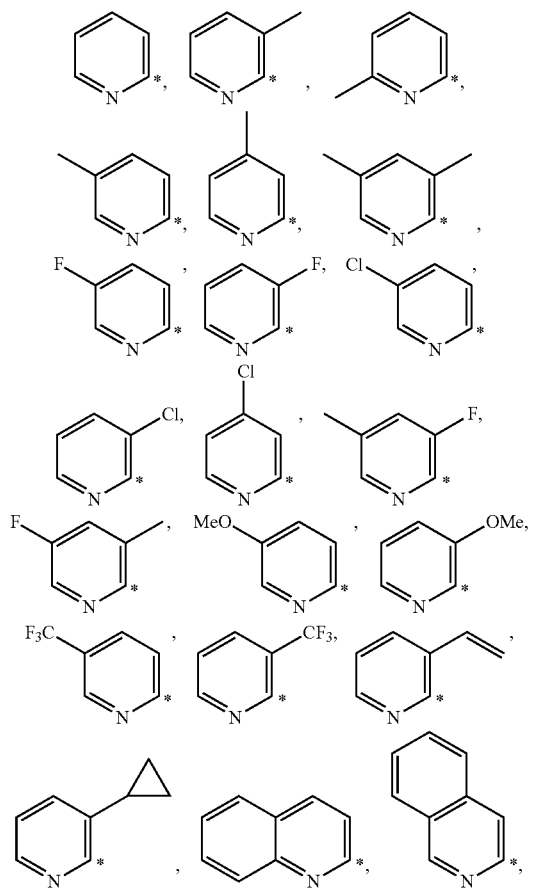

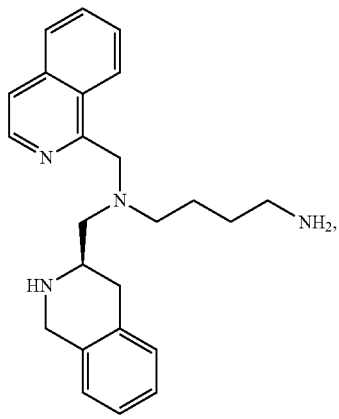

In an exemplary embodiment, the compound of Formula (I) is selected from the group comprising:

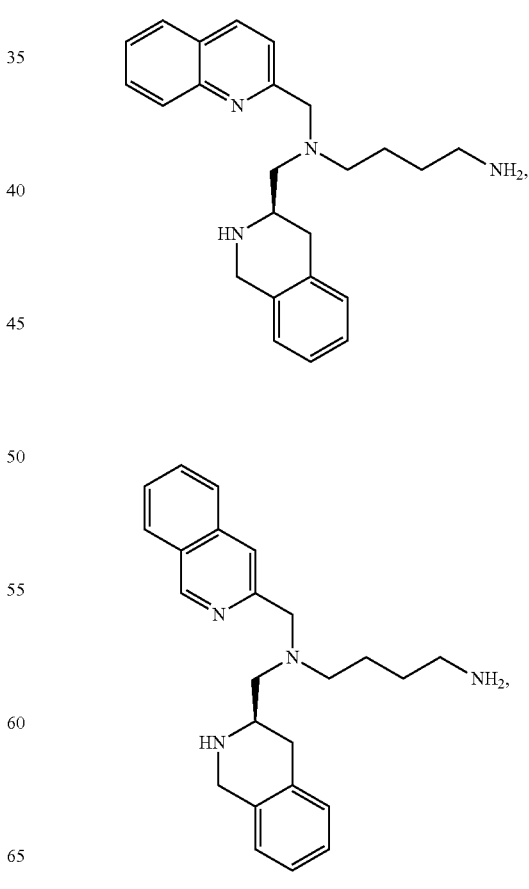

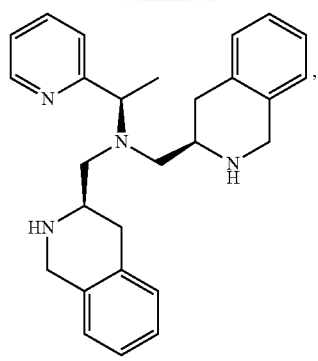
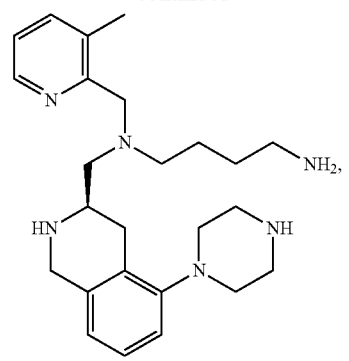
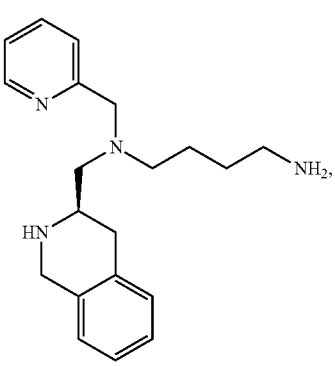
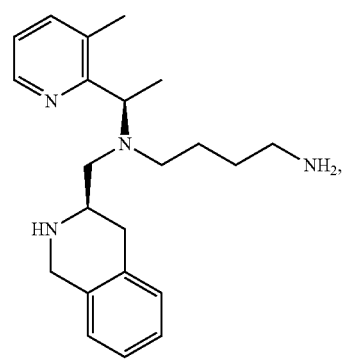
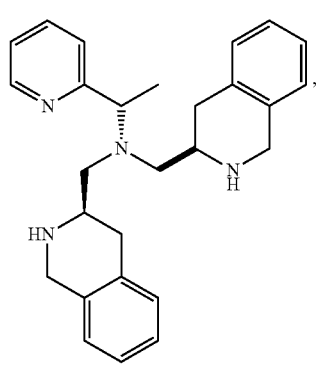
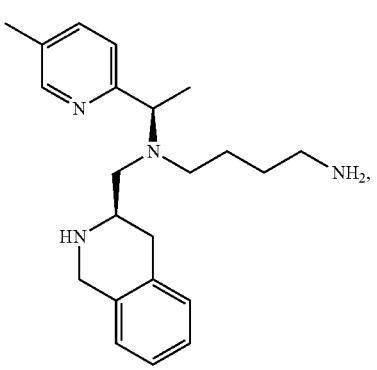
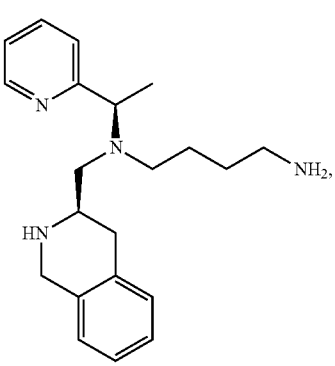
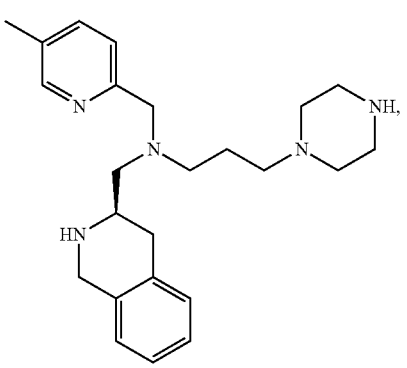

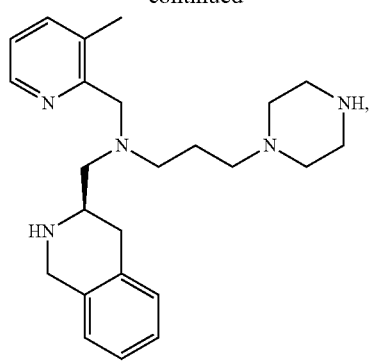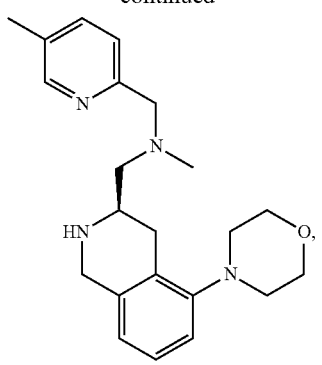

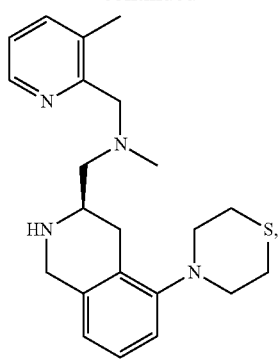
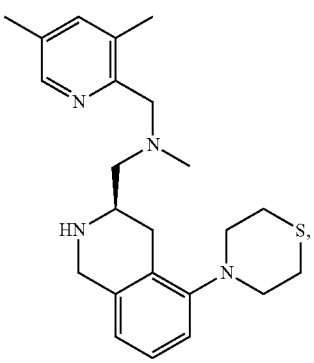
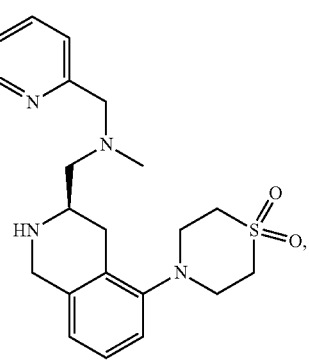
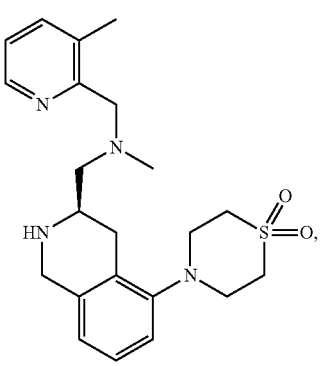
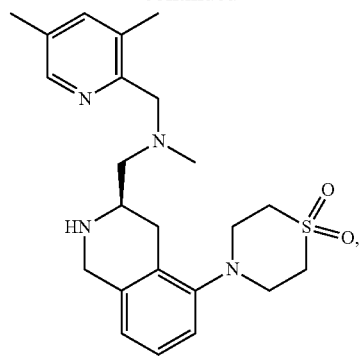
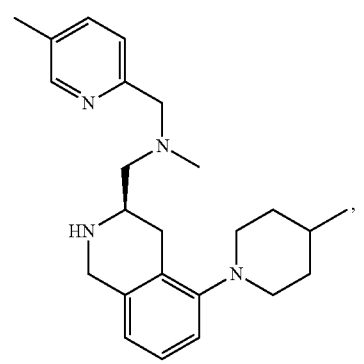
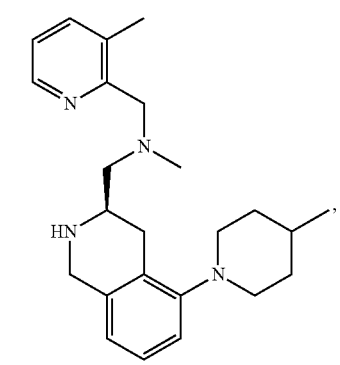
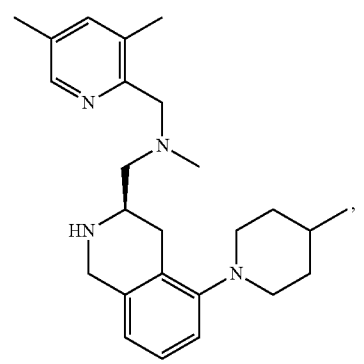

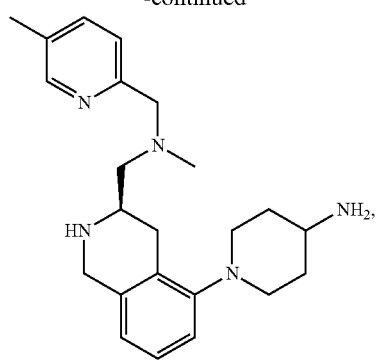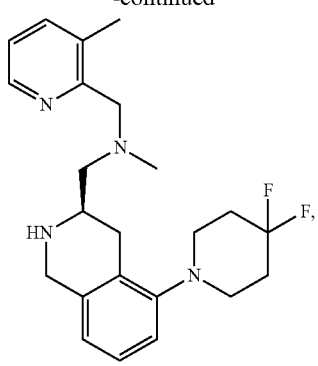

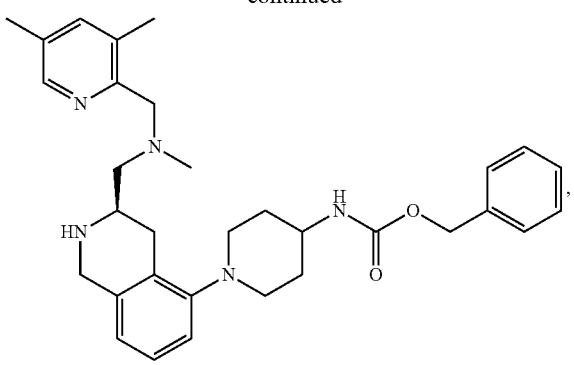
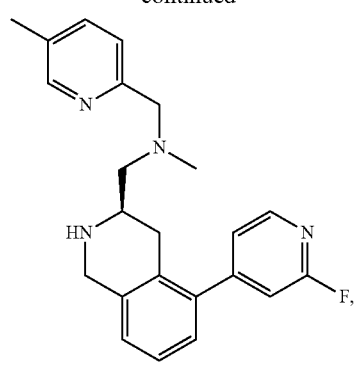
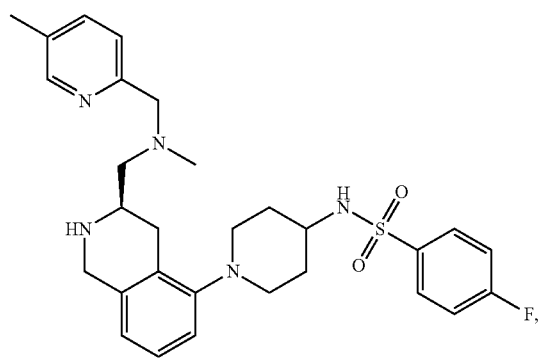
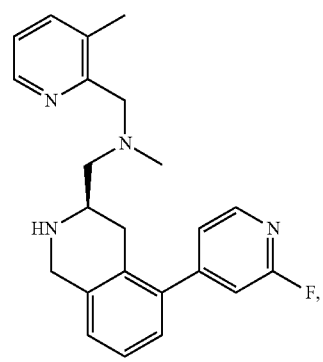
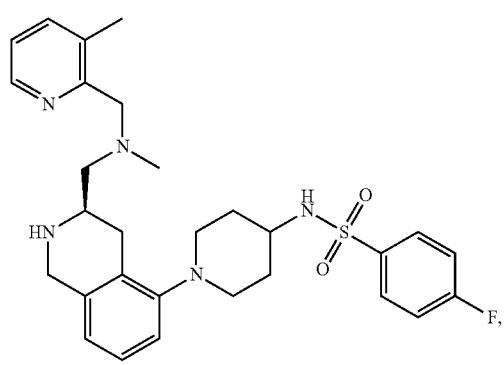
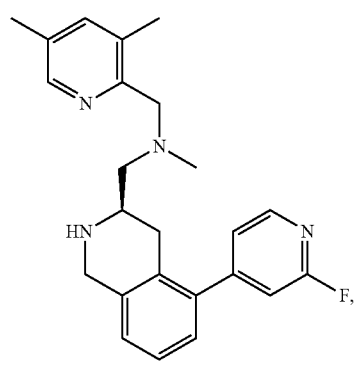
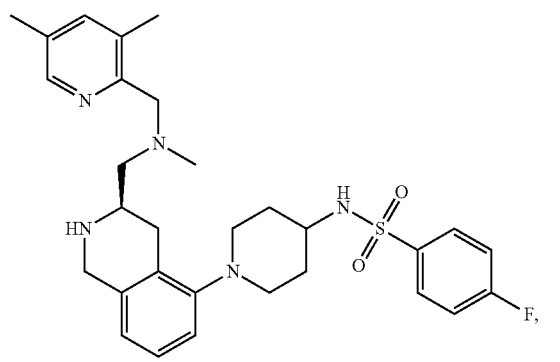
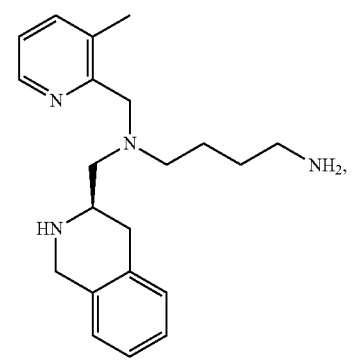

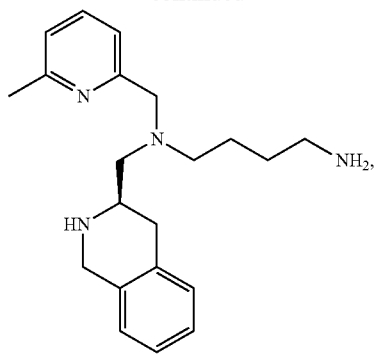
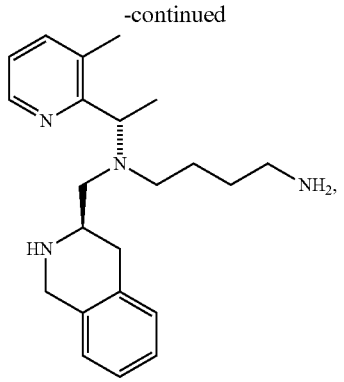

-continued
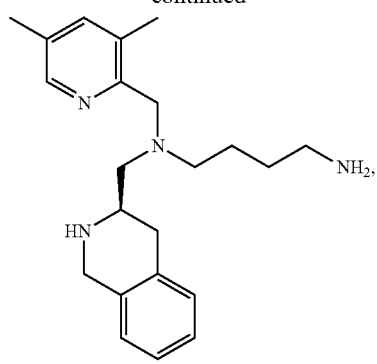
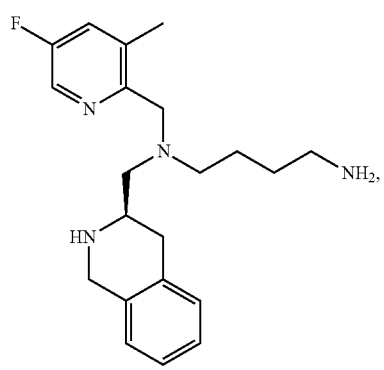
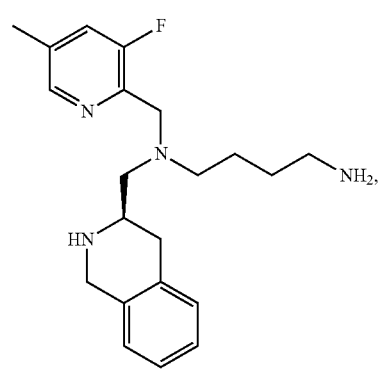
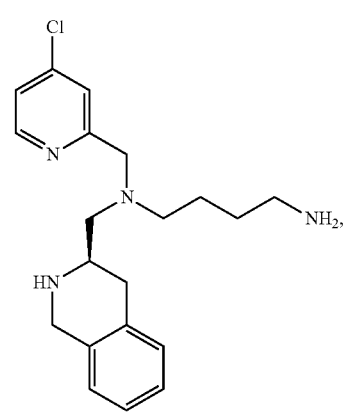
-continued
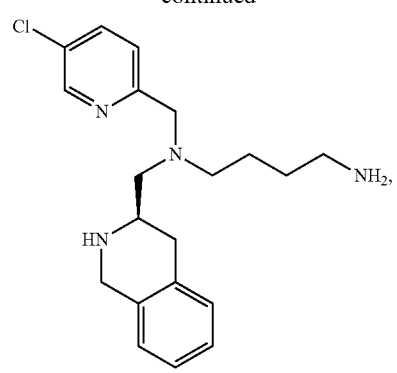
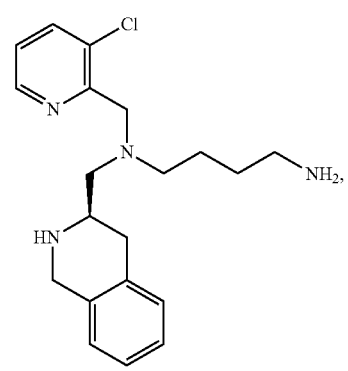
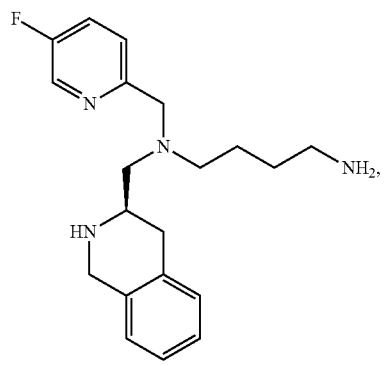
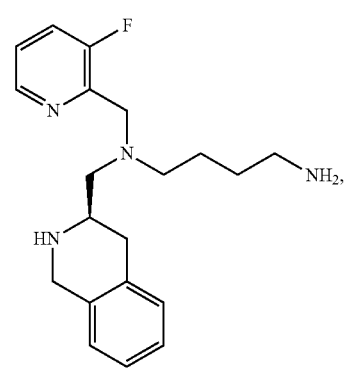

-continued
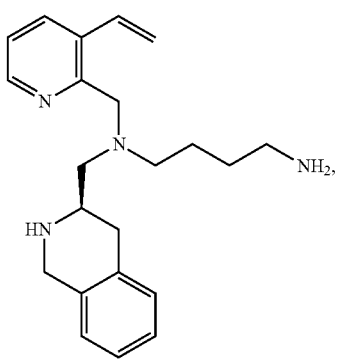
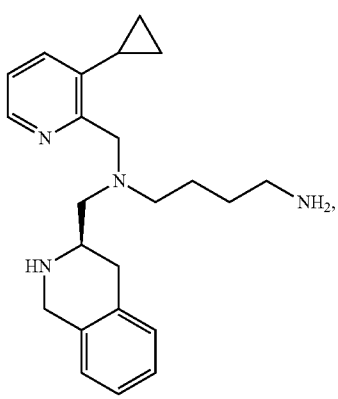
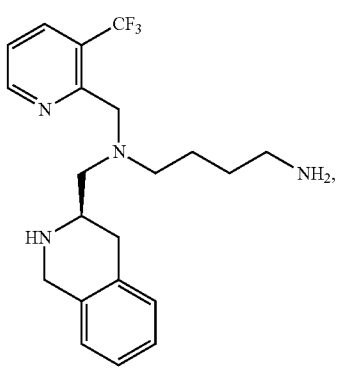
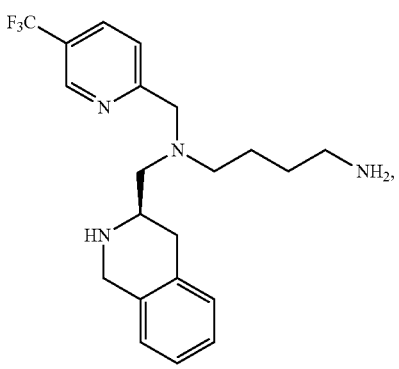
-continued
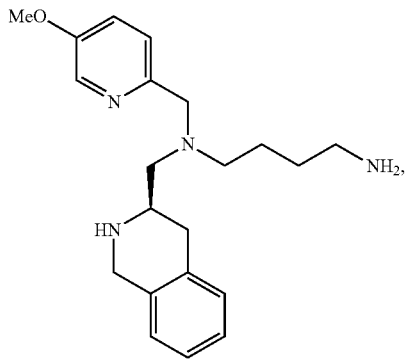
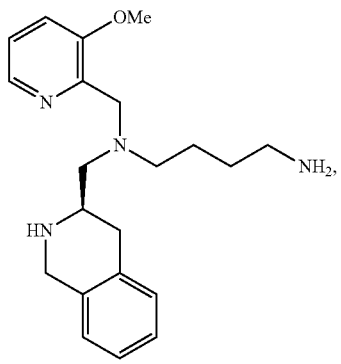
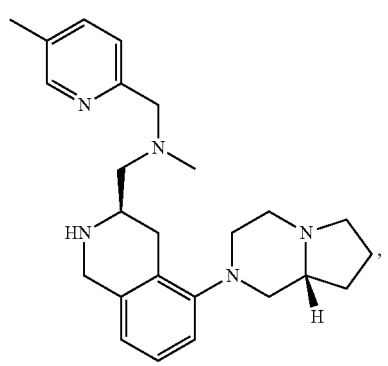
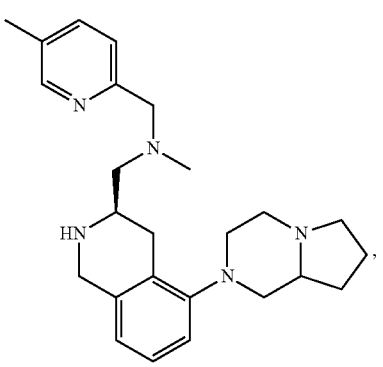

-continued

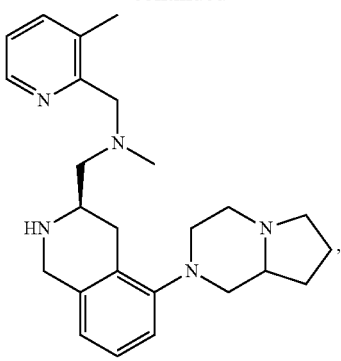

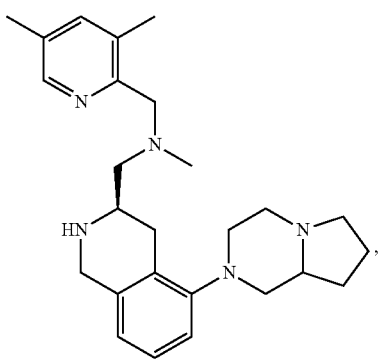

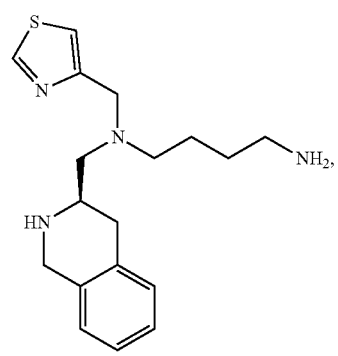

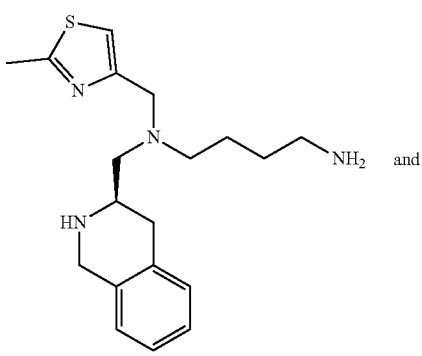 and

-continued

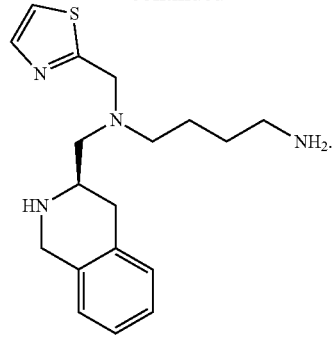

In accordance with a second embodiment of the invention there is provided a compound of Formula (II)

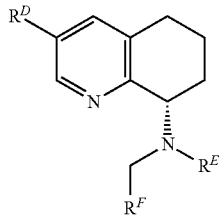

Formula (II)

or salts thereof wherein $R^D$ is H or alkyl, $R^E$ is methyl, isopropyl or an amino substituted carbocyclyl; $R^F$ is an optionally substituted heterocyclyl; wherein the substituents of $R^F$ are selected from one or more and the same or different $R^{X2}$; and $R^{X2}$ is optionally substituted aryl, optionally substituted heterocyclyl or optionally substituted amino, and wherein the substituents of $R^{X2}$ are selected from one or more and the same or different $R^{Y2}$; and $R^{Y2}$ is selected from the group comprising methyl, ethyl, isopropyl, cyclopropyl, oxetane, amino, dimethylamino, methylpiperazine, pyridine, pyridinylmethyl, pyrimidine and trifluoromethylbenzene; with the proviso that when $R^D$ is H and $R^E$ is $CH_3$, then $R^F$ is not:

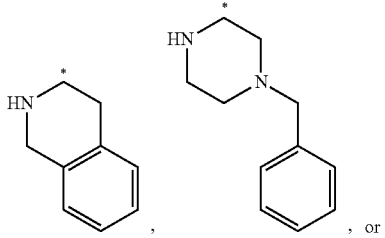

, or

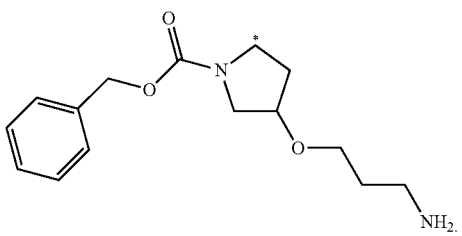

Further features of this embodiment provide for $R^E$ to be selected from the group comprising:

*$CH_3$,

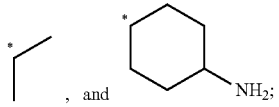

, and ;

for $R^F$ to be selected from the group comprising:

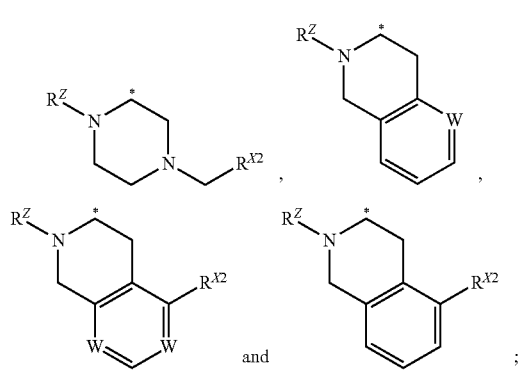

and ;

for $R^2$ to be selected from the group comprising:
$CH_2R^{Y2}$, $CH=CHCH_2R^2$, $OCH_2CH_2R^{Y2}$, $NHR^{Y2}$, $N(R^{Y2})_2$,

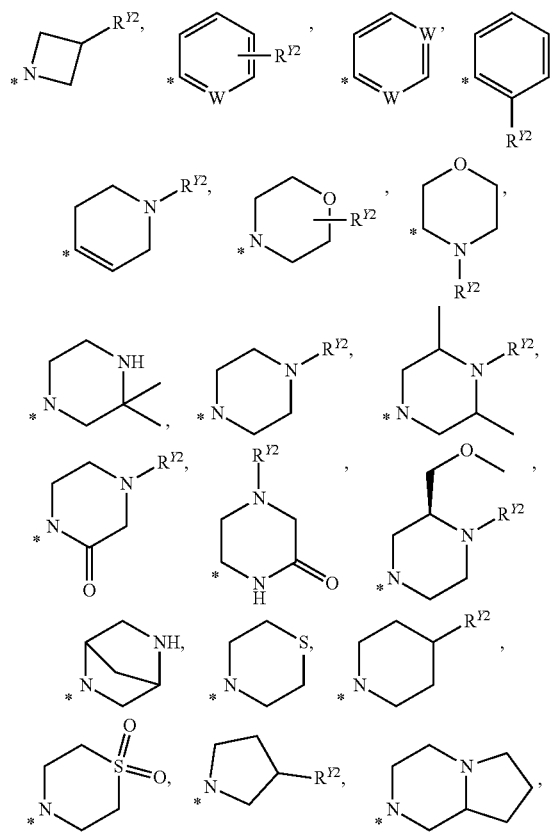

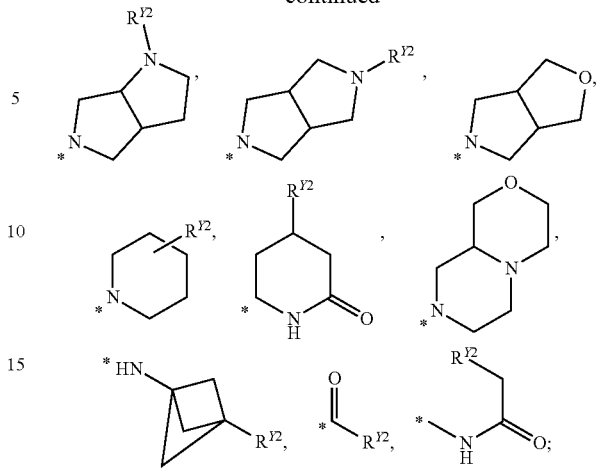

for $R^{Y2}$ to be selected from the group comprising H, OH, F, $CH_3$, $CH_2CH_3$, $CH_2OCH_3$, $CH_2F$, $CF^3$, $NH_2$,

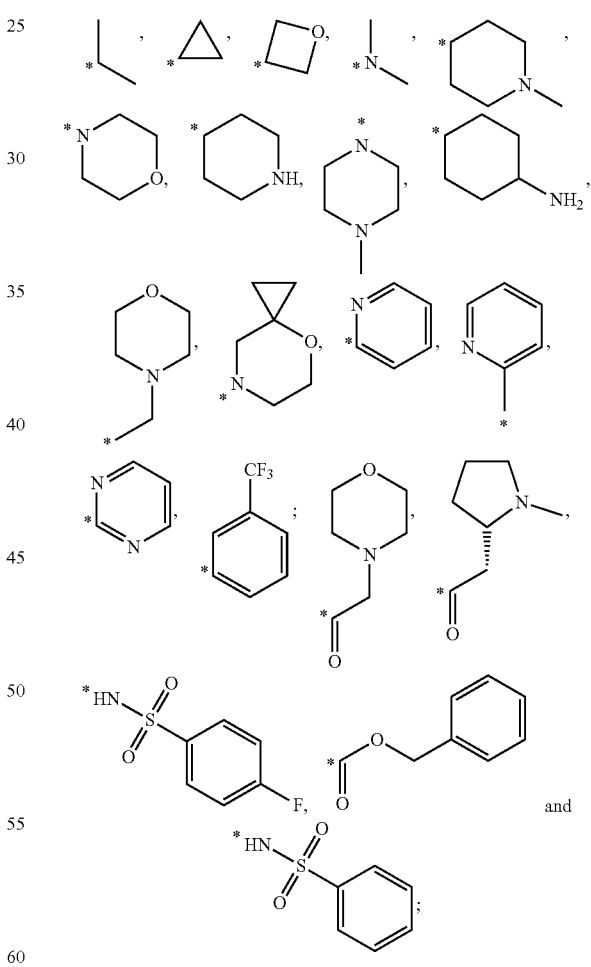

wherein the substituent $R^{Y2}$ may be individually and independently mono- or di-substituted onto $R^{X2}$ where appropriate; and
wherein $R^Z$ is H or $CH_3$ and W is CH or N.

Yet further features of this embodiment provide for $R^F$ to be selected from the group comprising:

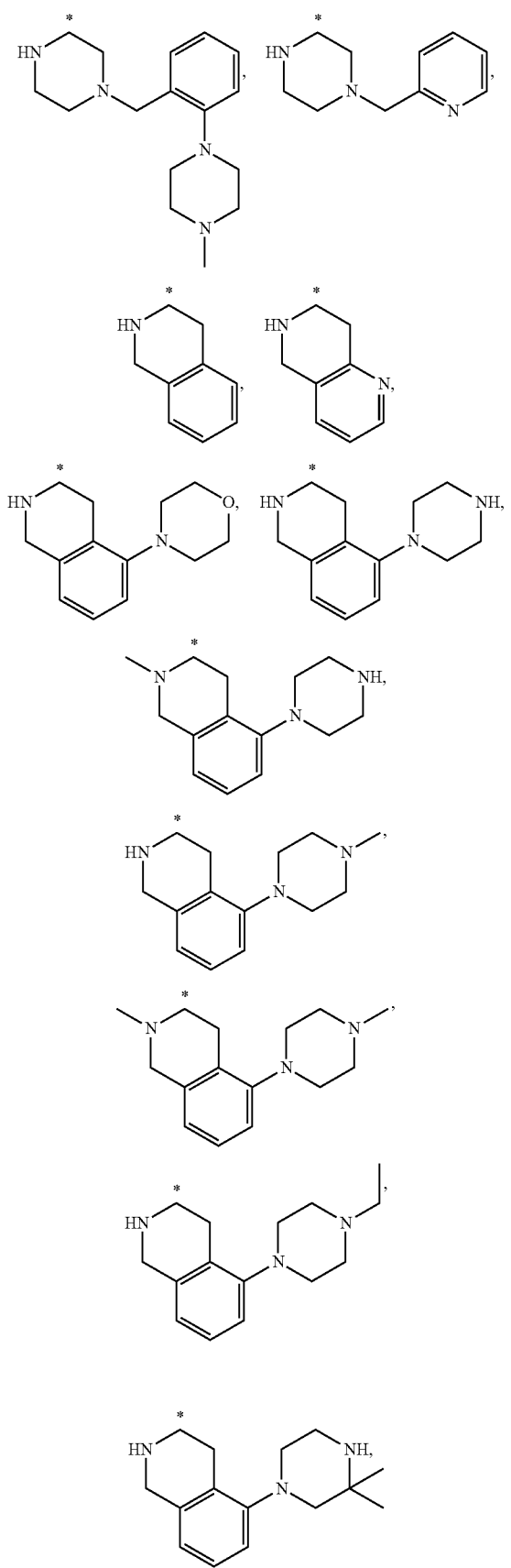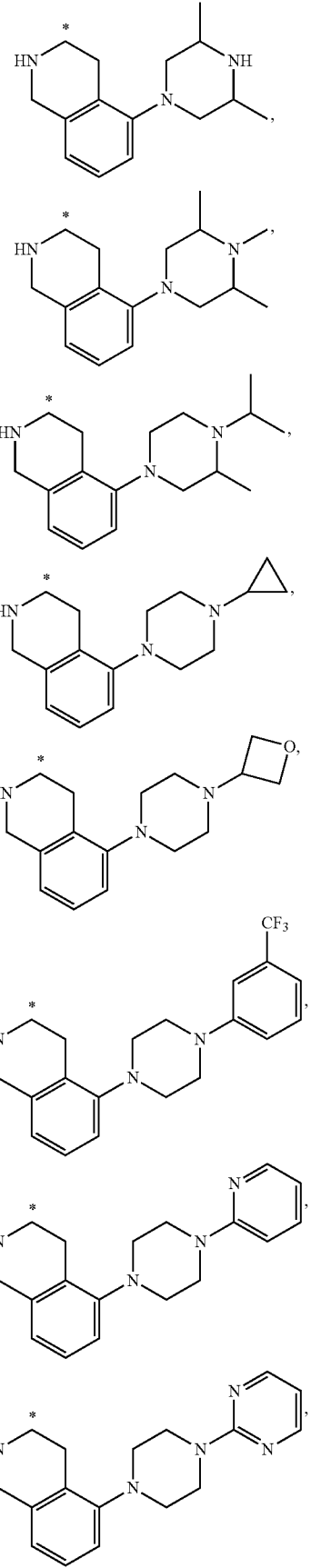

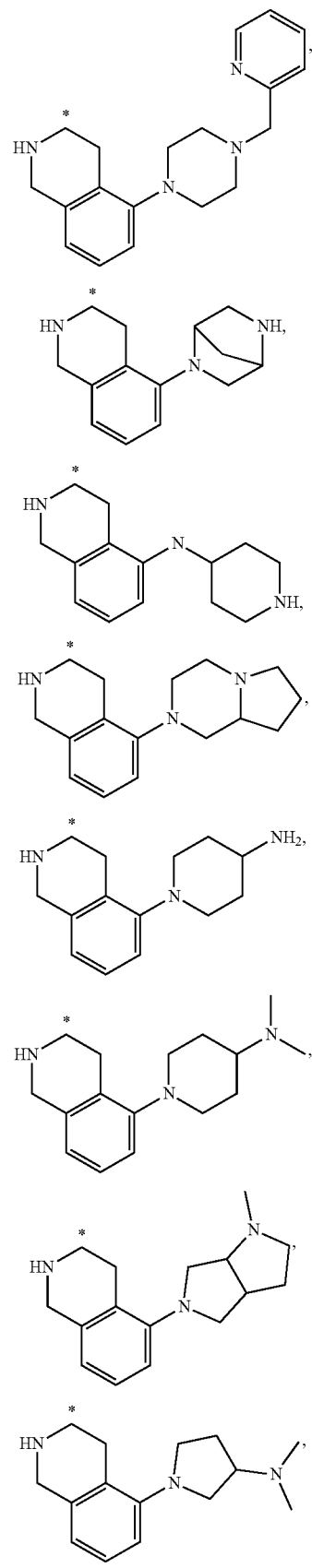
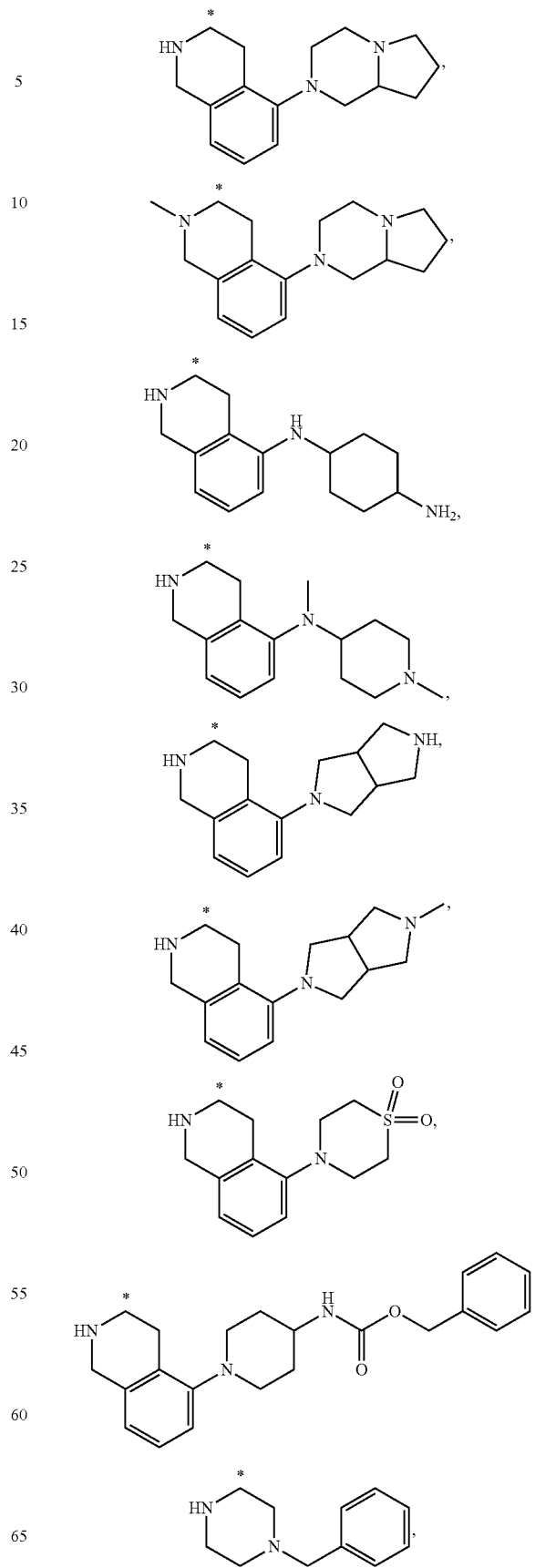

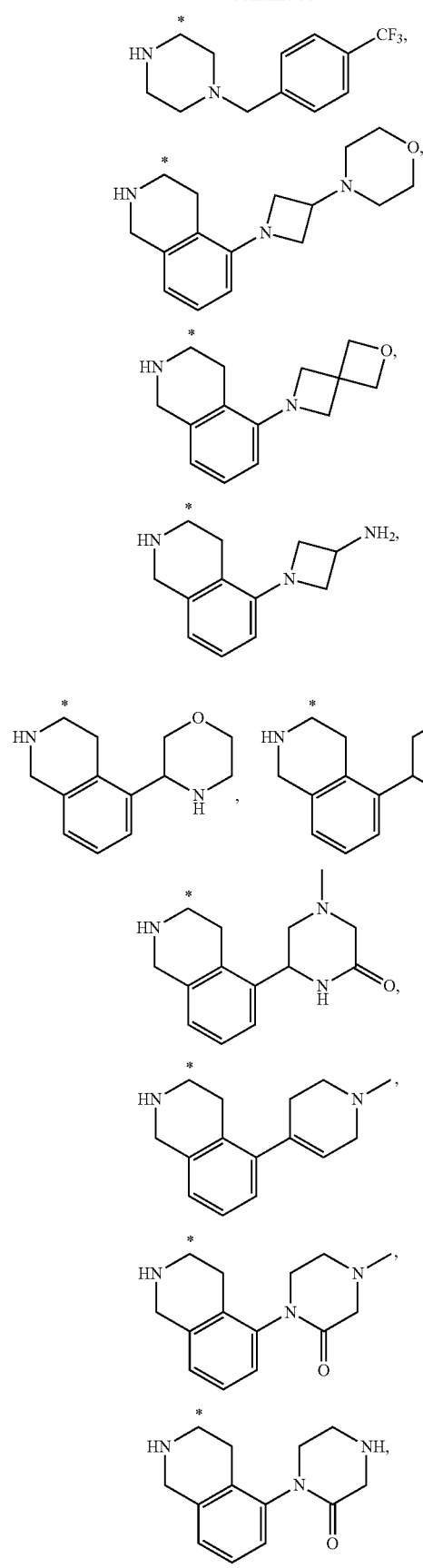
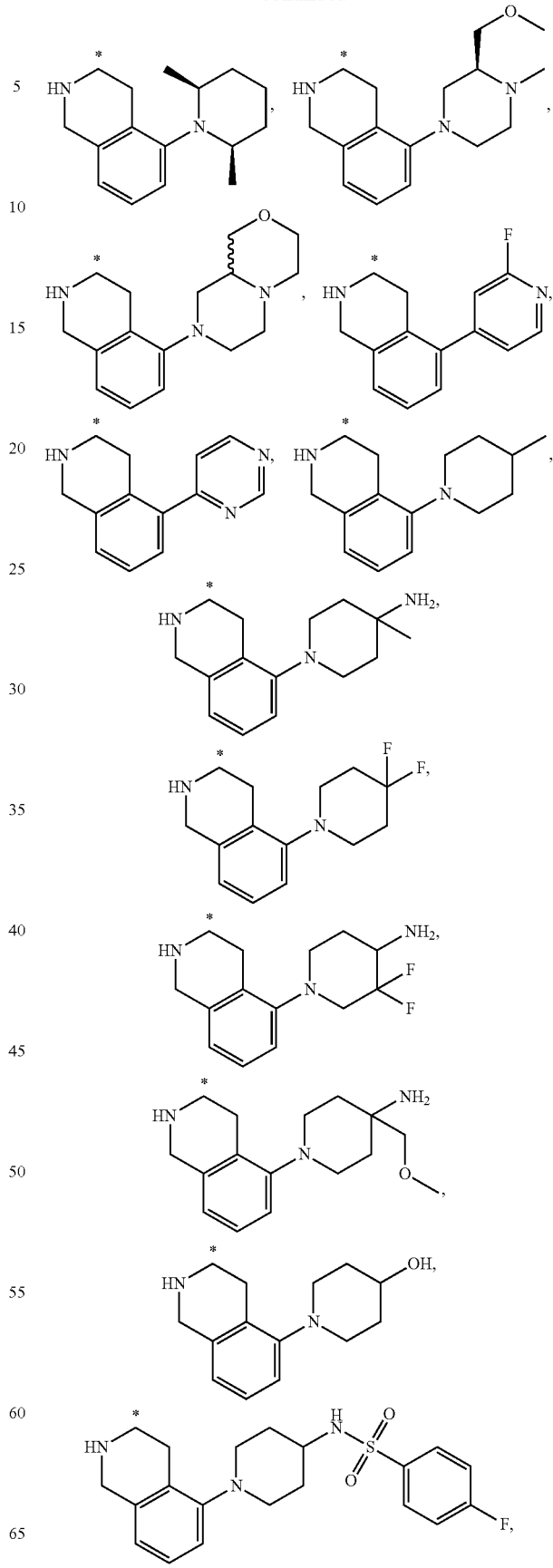

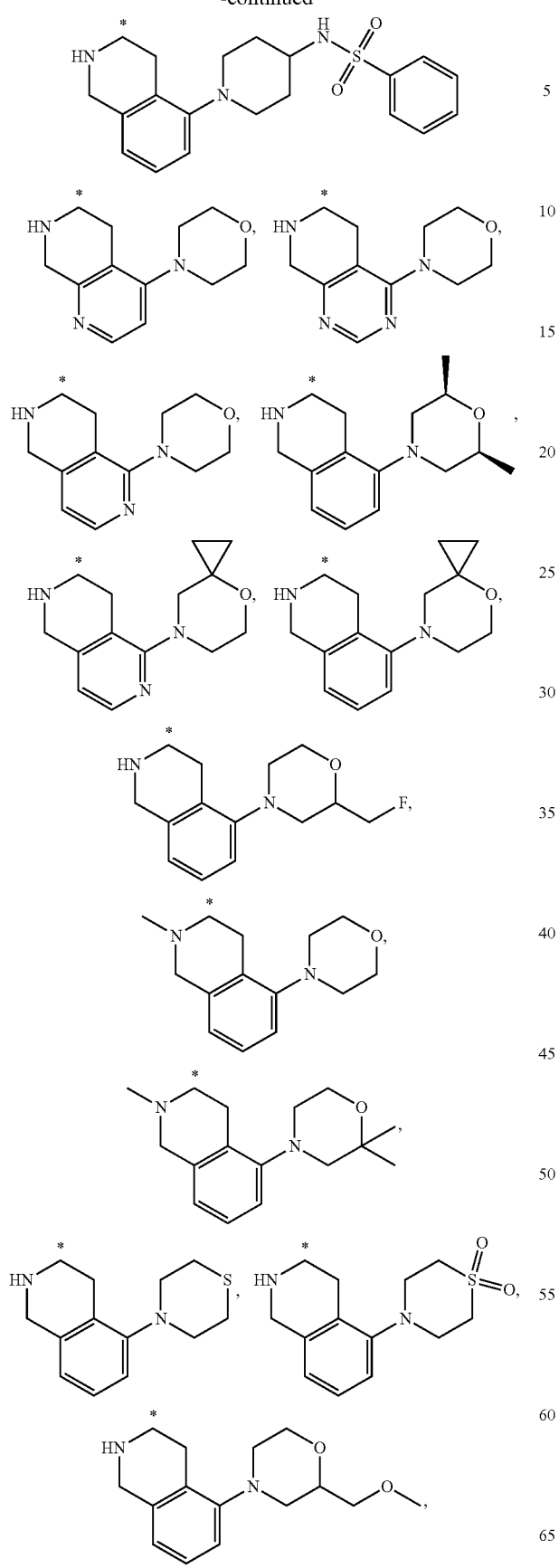
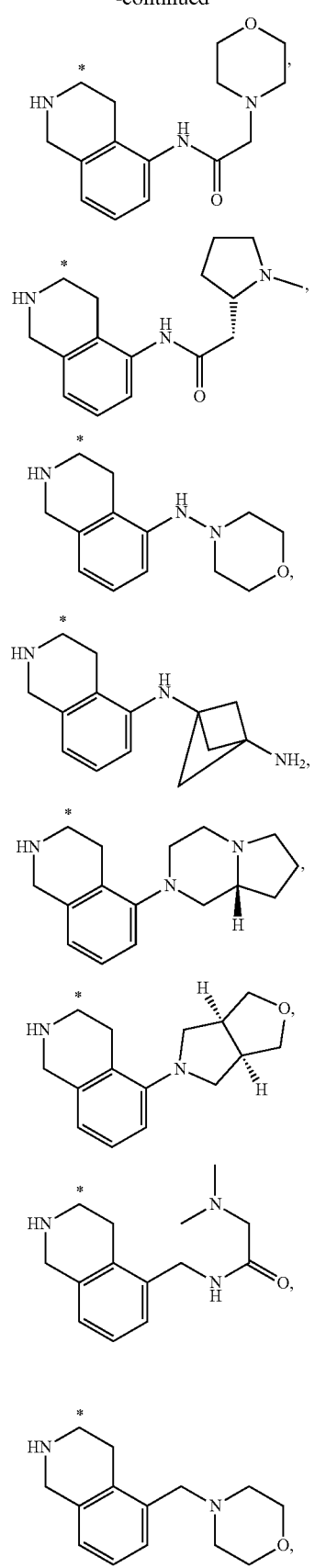

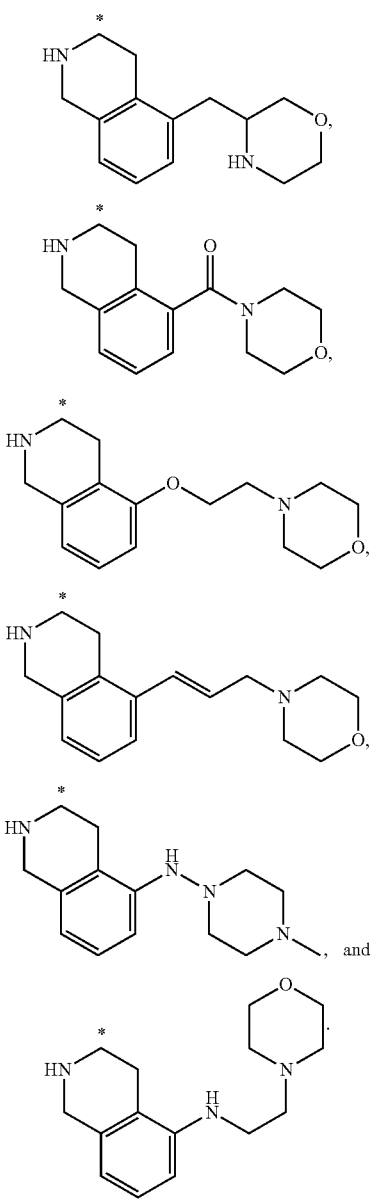
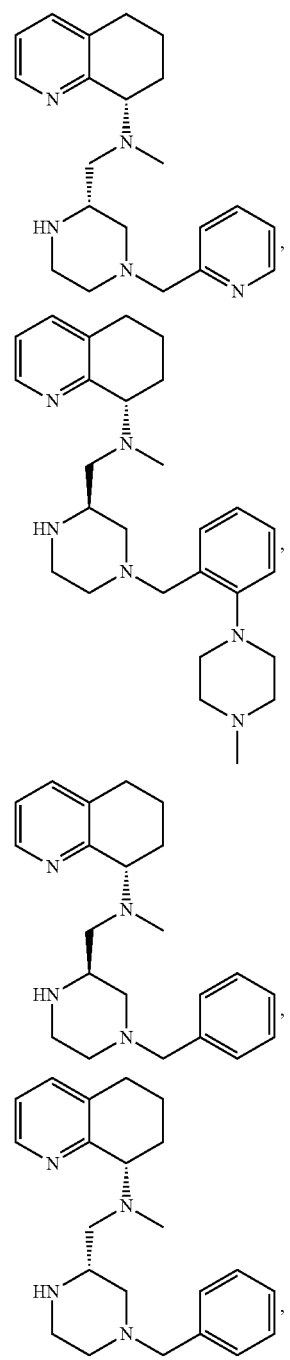
In an exemplary embodiment of this invention, the compounds of Formula (II) may be selected from the group comprising:
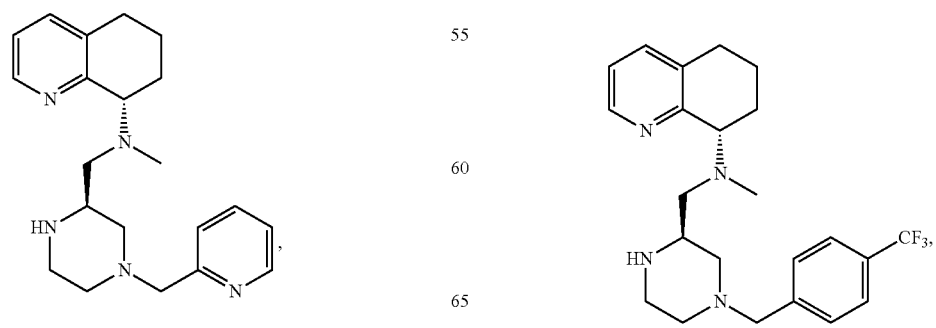

37
-continued
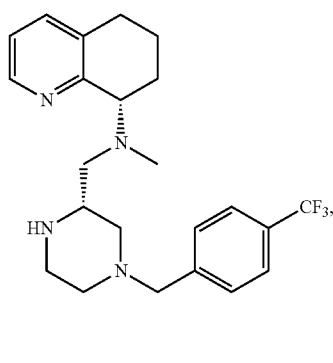
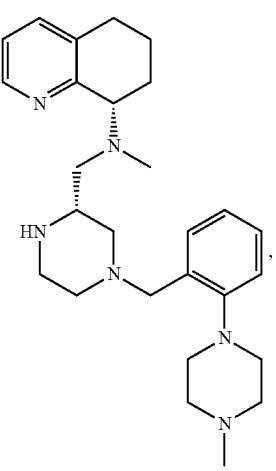
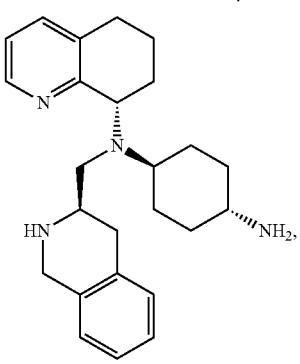
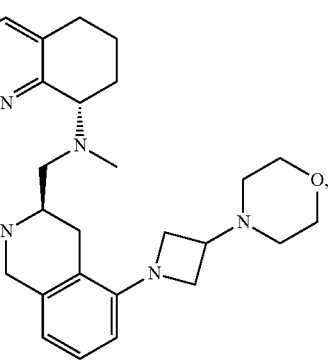
38
-continued
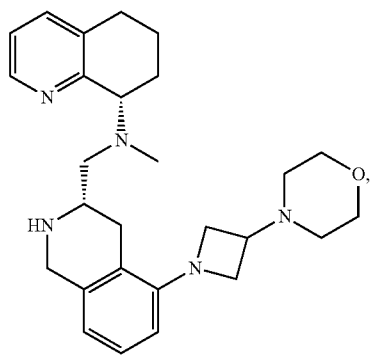
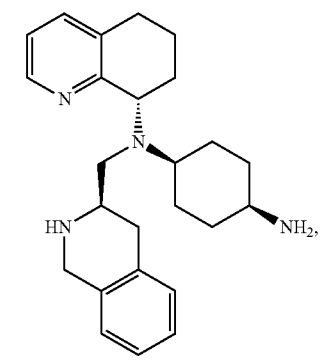
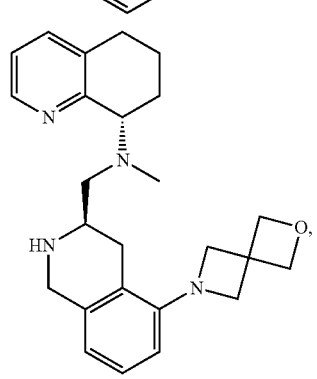
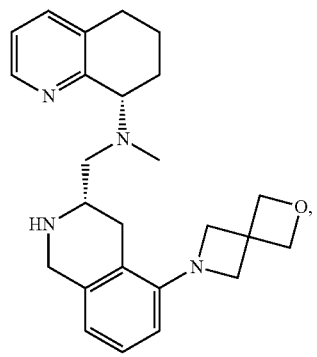

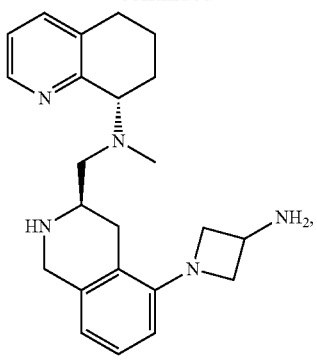
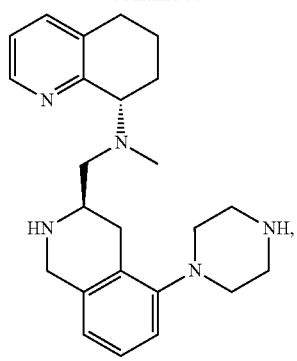
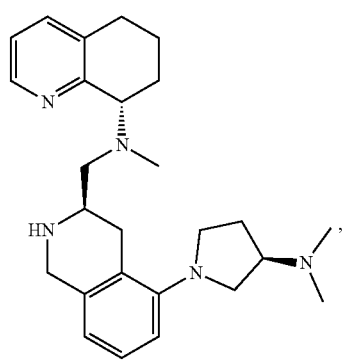
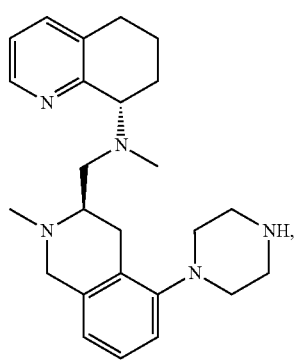
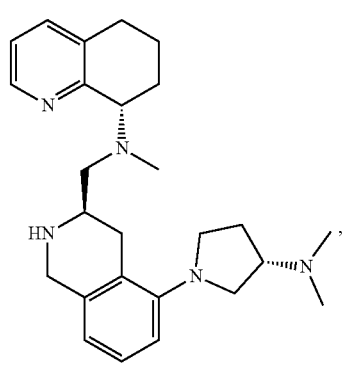
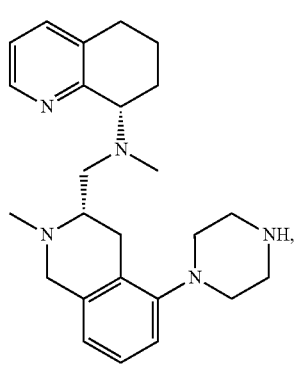

41
-continued
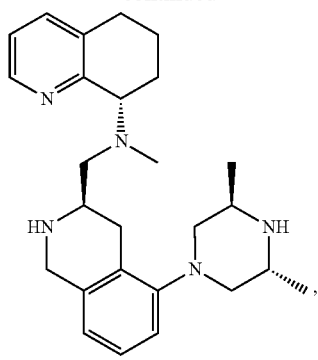
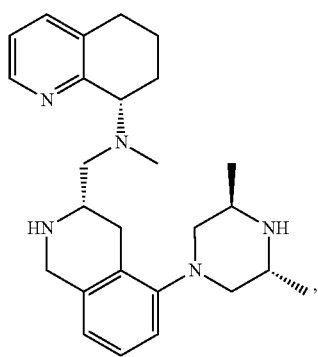
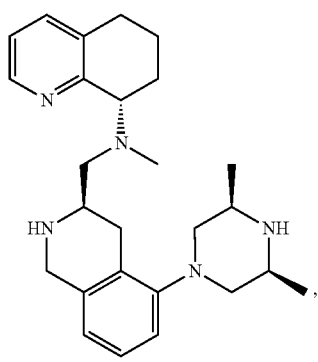
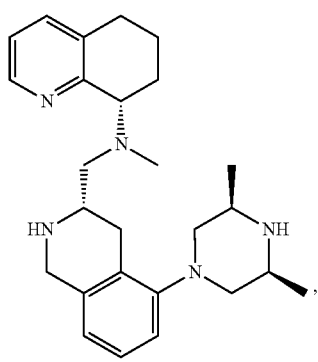
42
-continued
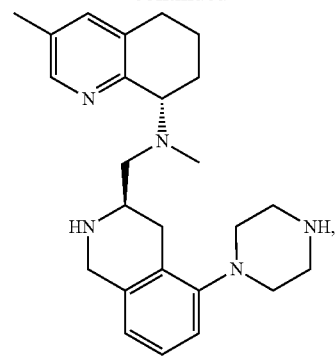
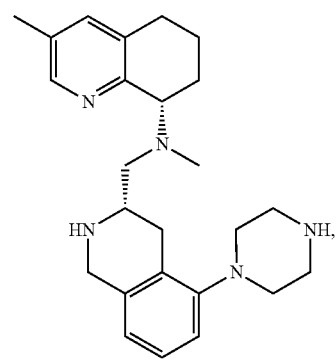
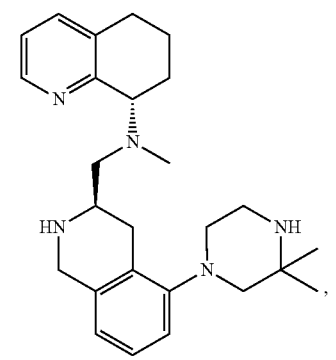
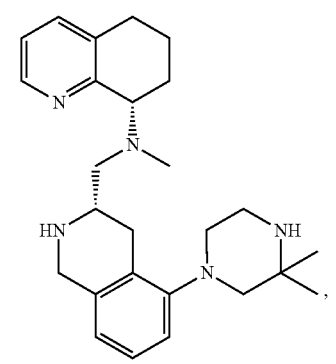

43
-continued
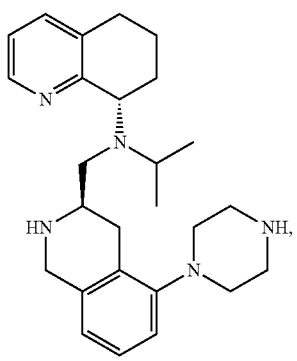
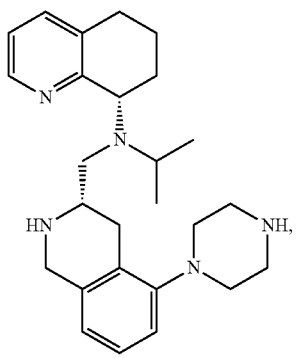
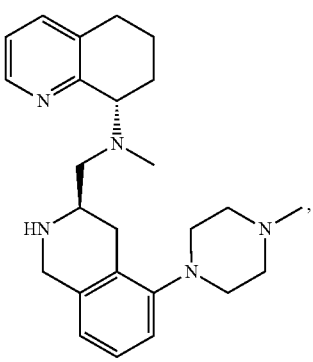
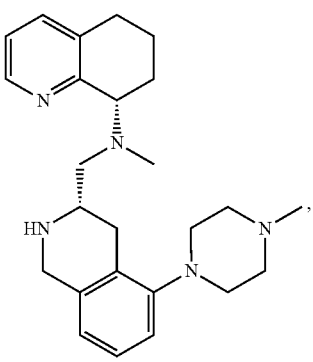
44
-continued
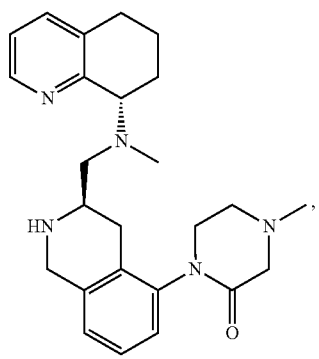
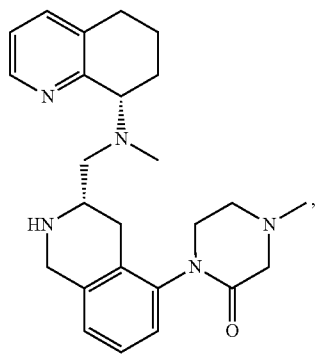
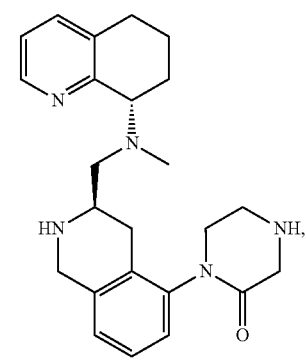
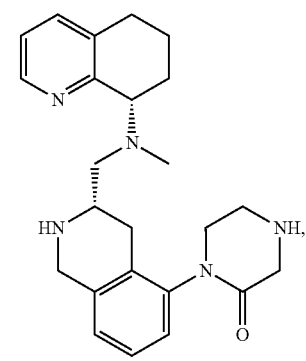

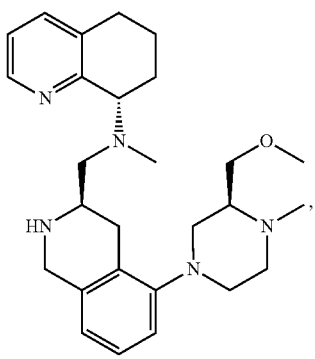
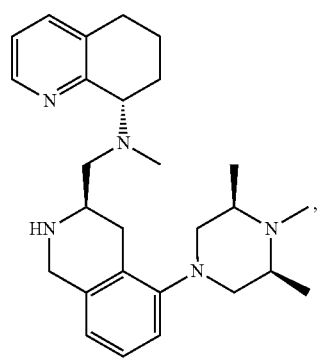
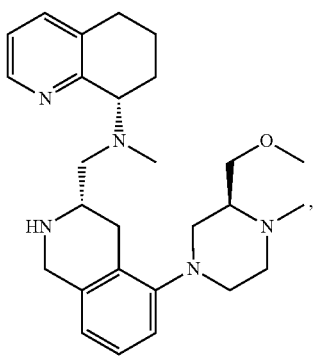
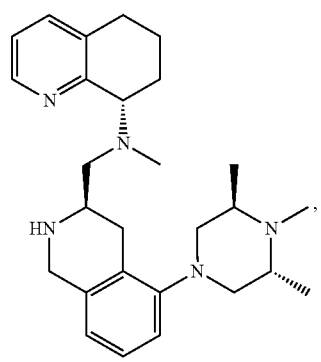
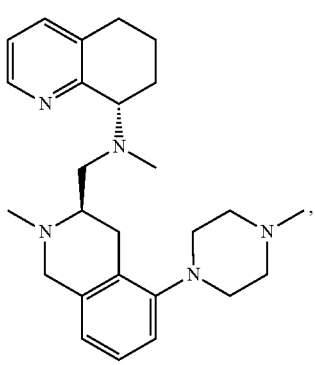
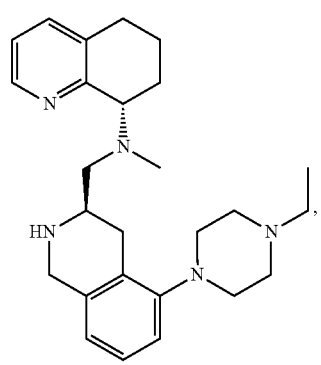
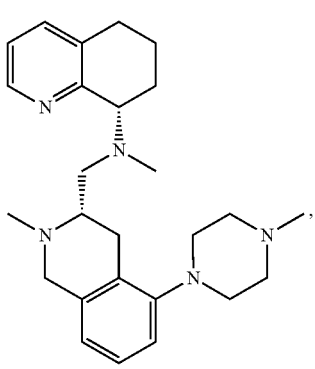
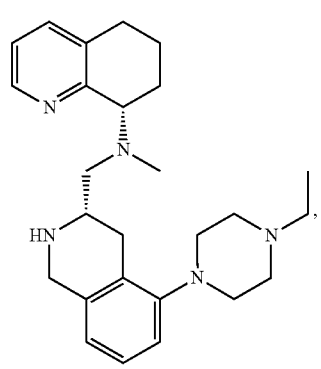

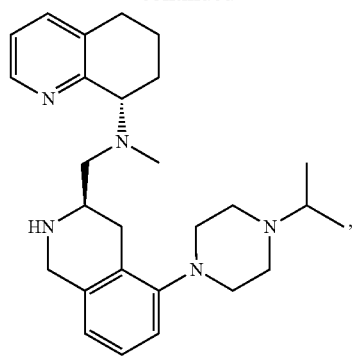
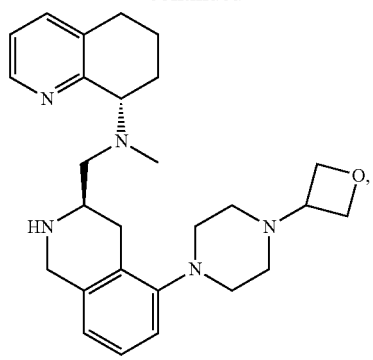
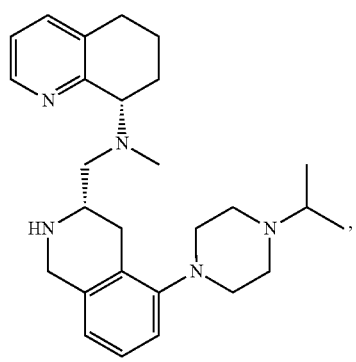
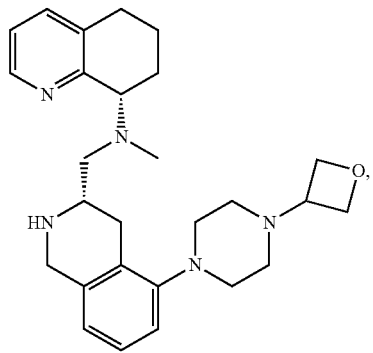
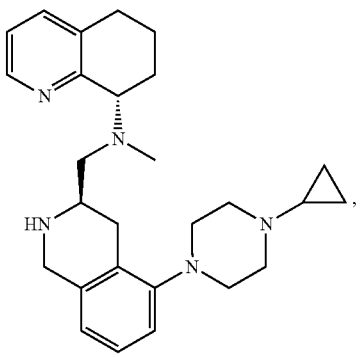
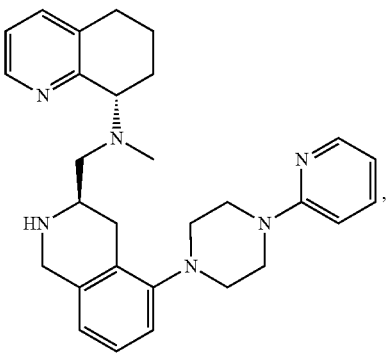
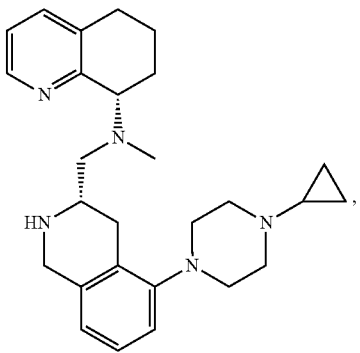
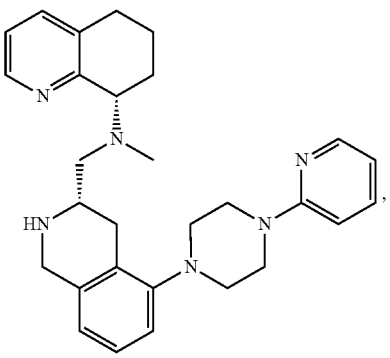

49
-continued
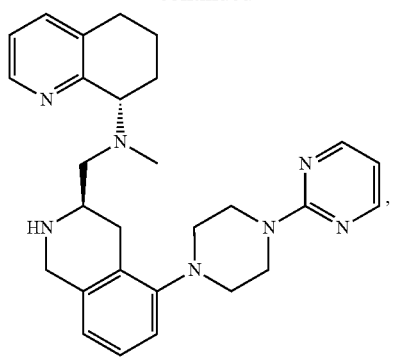
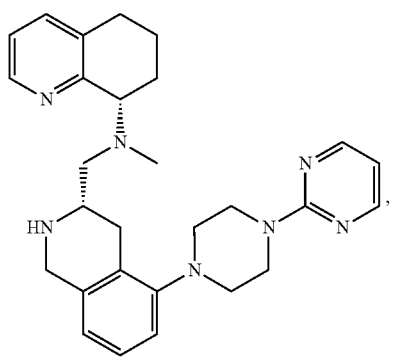
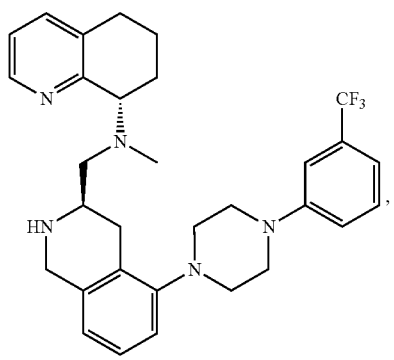
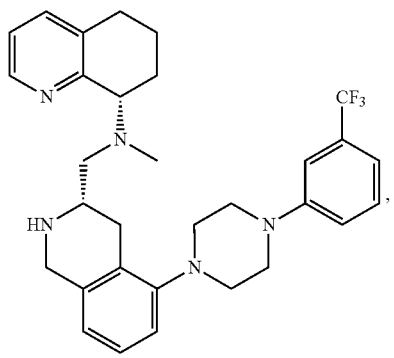
50
-continued
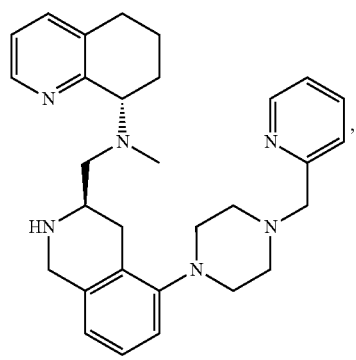
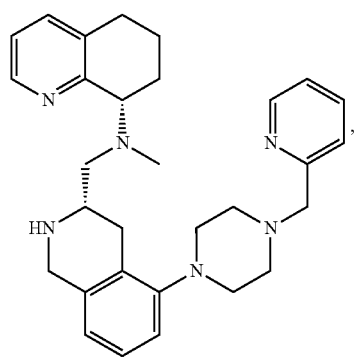
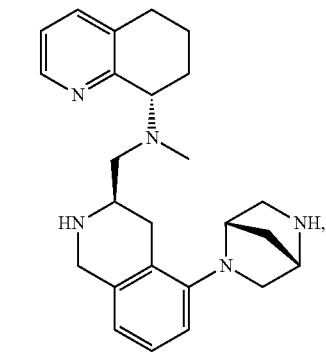
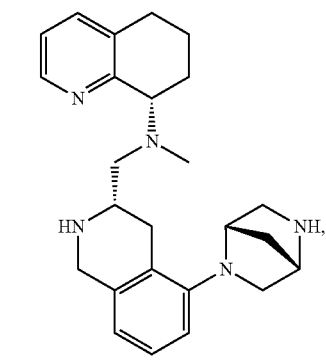

51
-continued
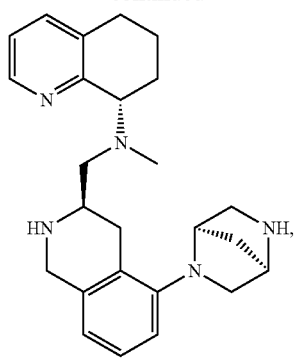
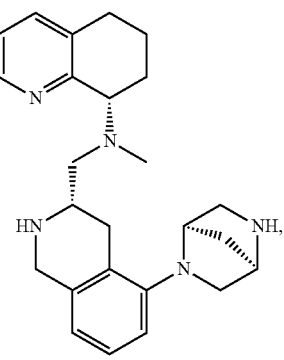
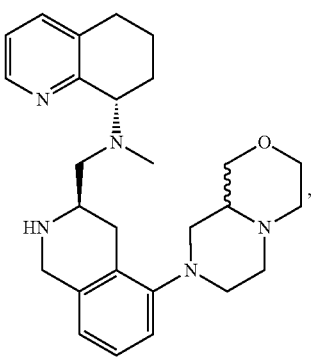
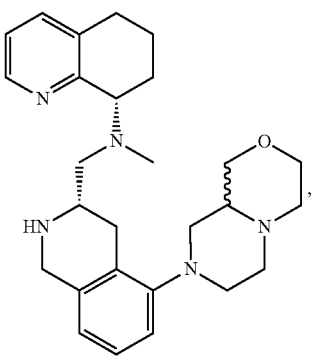
52
-continued
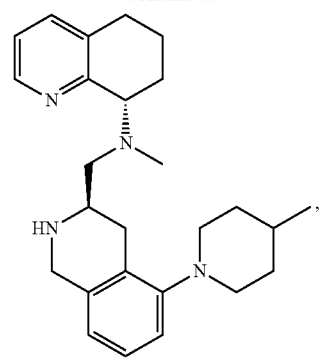
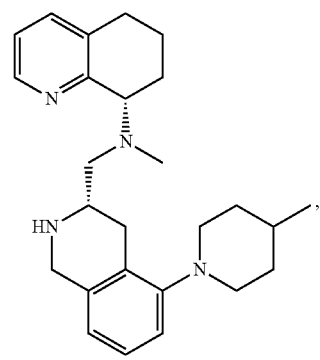
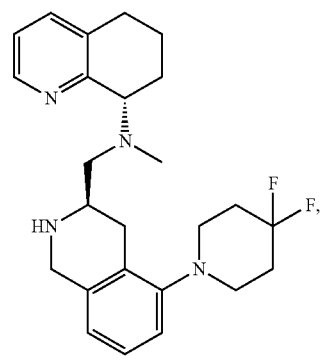
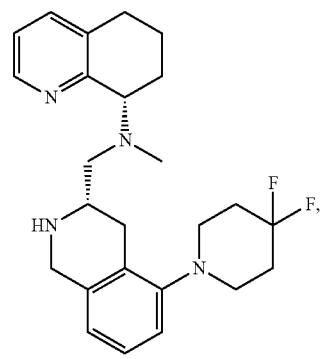

53
-continued
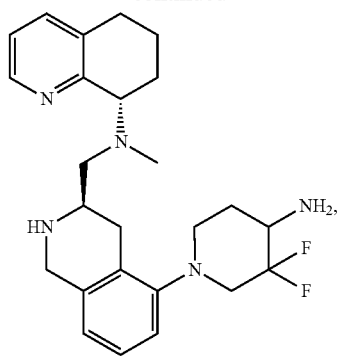
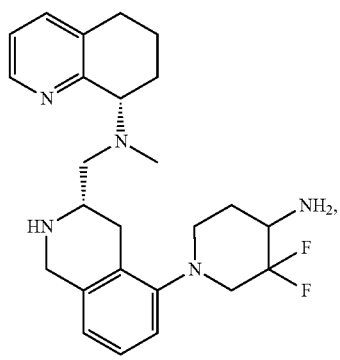
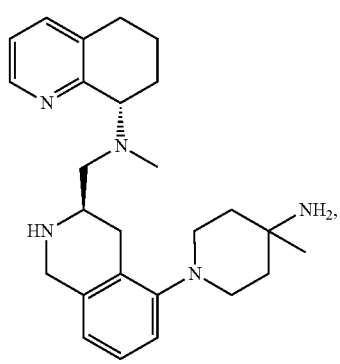
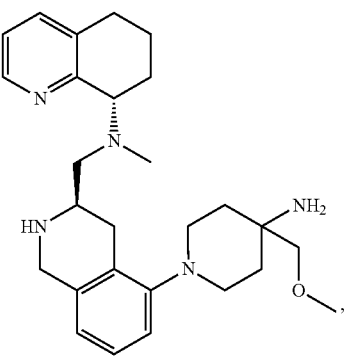
54
-continued
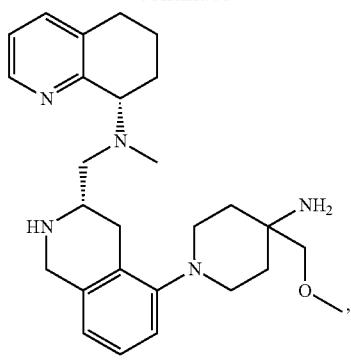
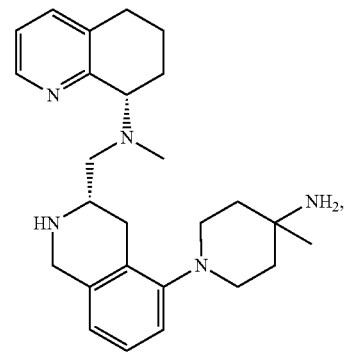
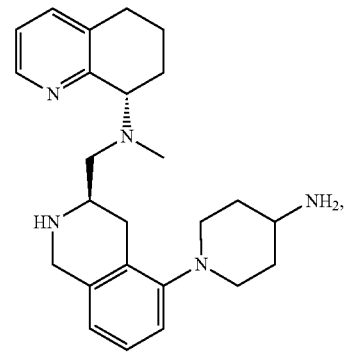
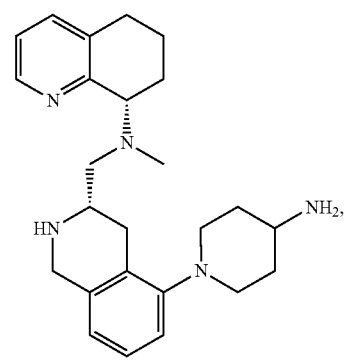

55
-continued
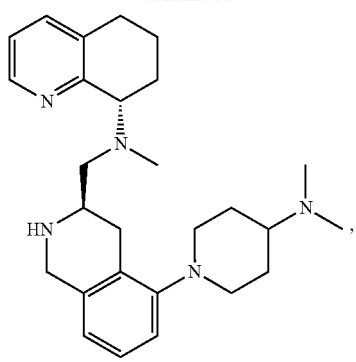
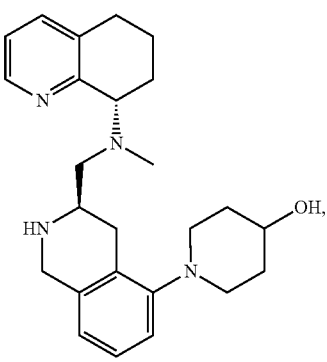
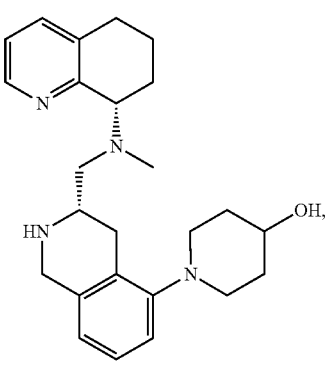
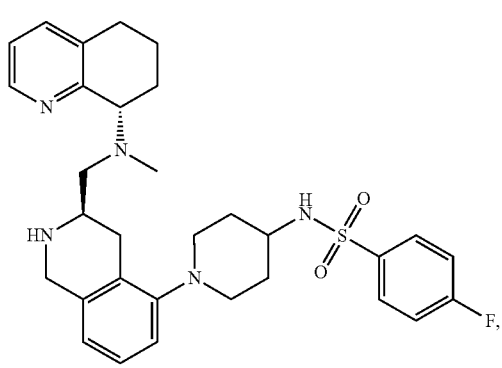
56
-continued
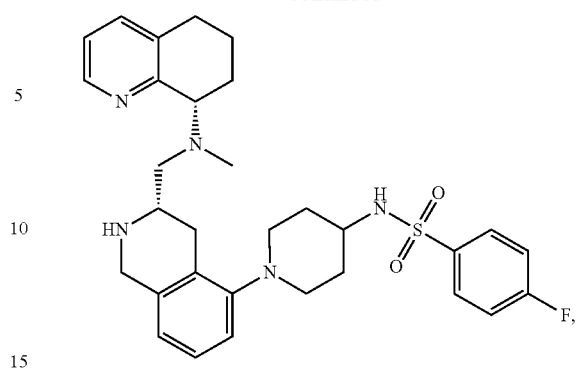
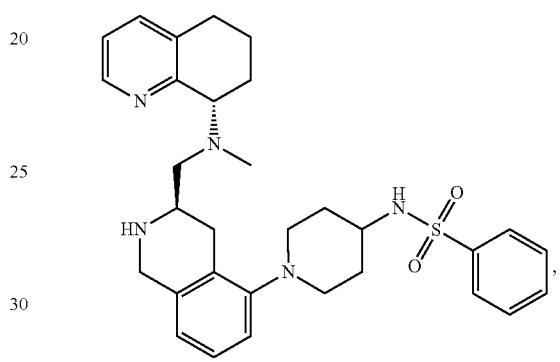
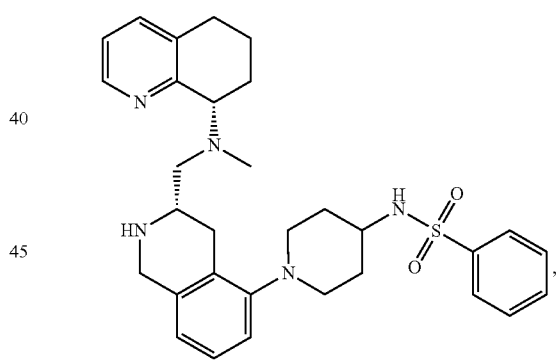
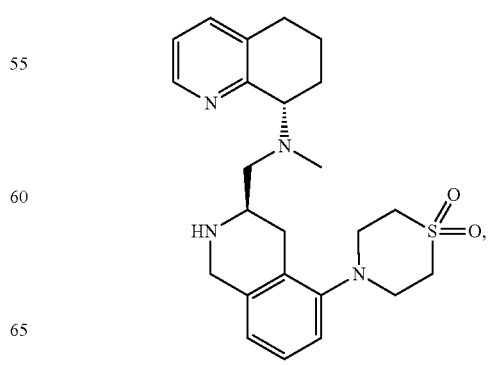

57
-continued

58
-continued

59
-continued
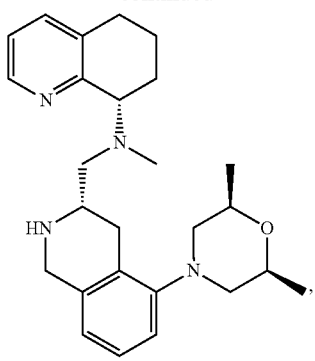
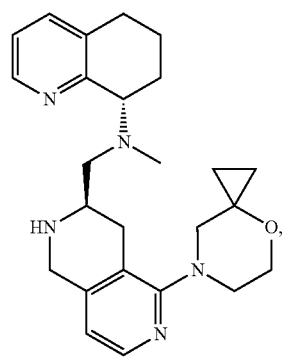
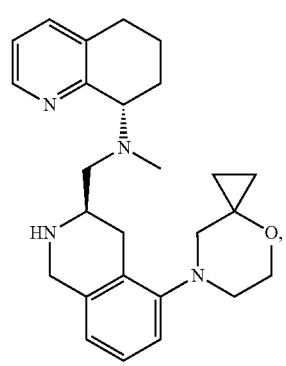
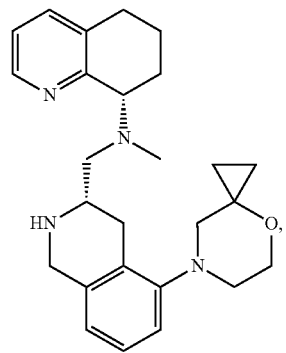
60
-continued
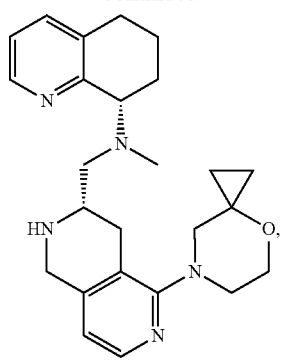
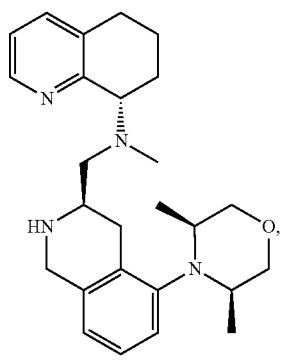
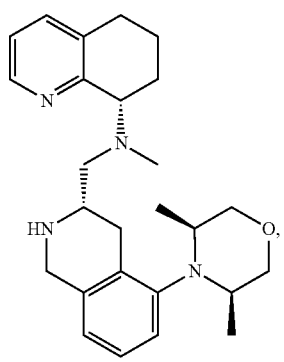
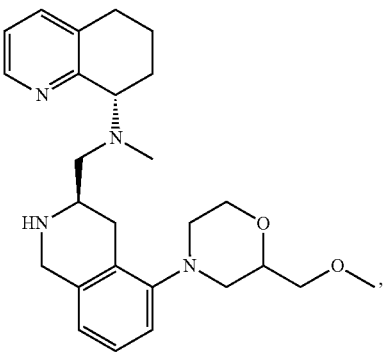

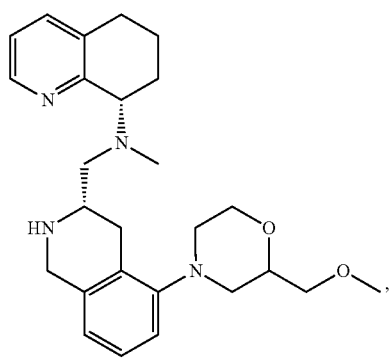
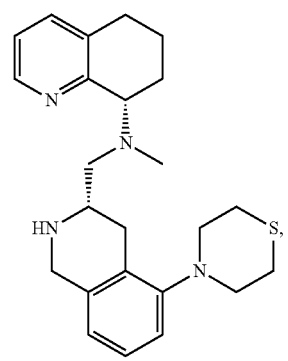
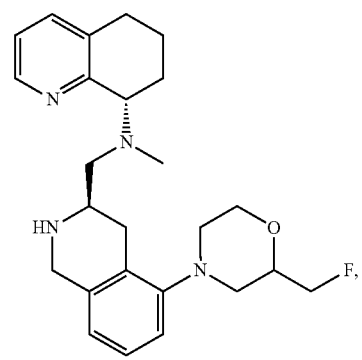
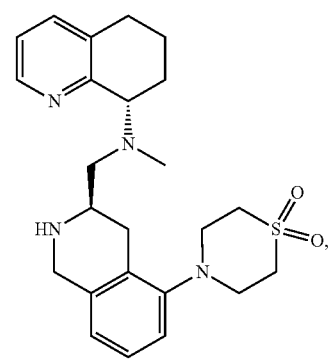
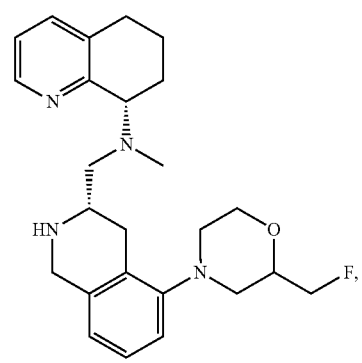
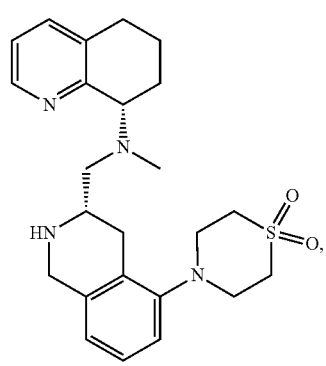
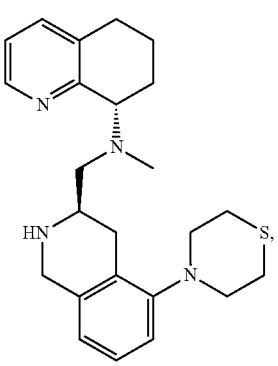
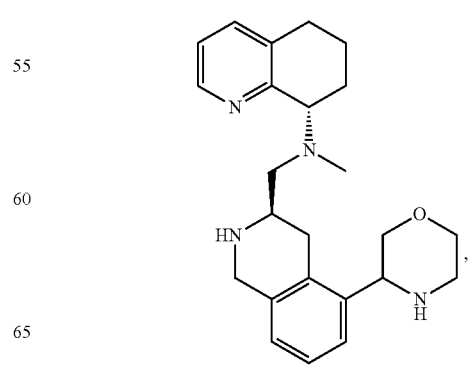

63
-continued
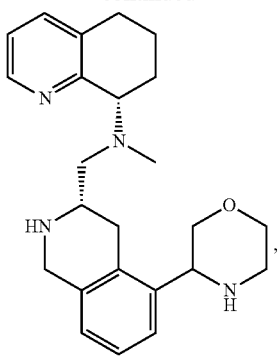
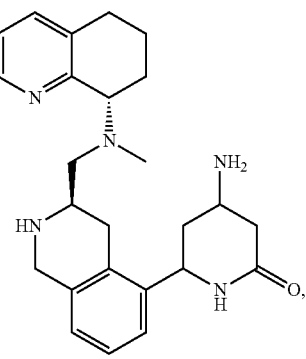
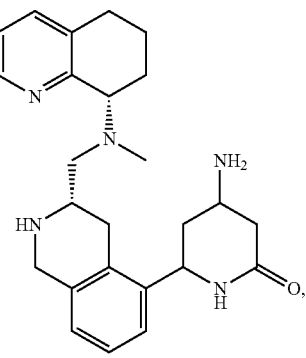
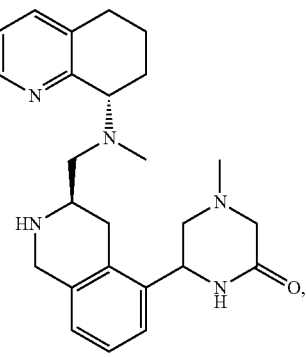
64
-continued
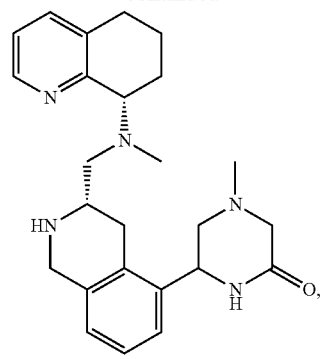
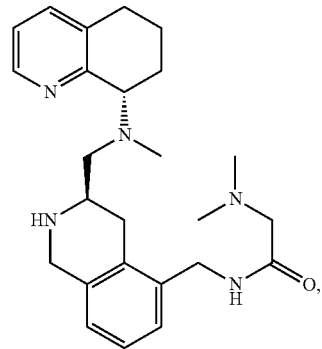
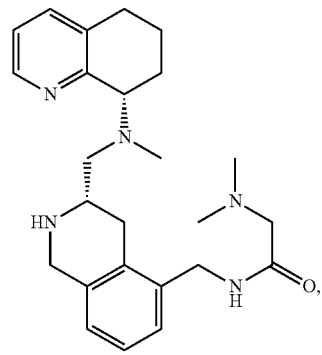
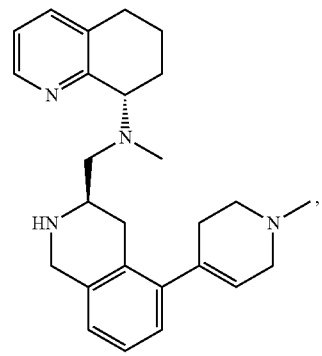

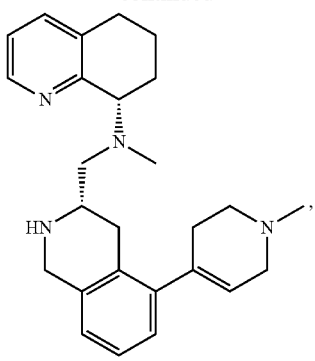
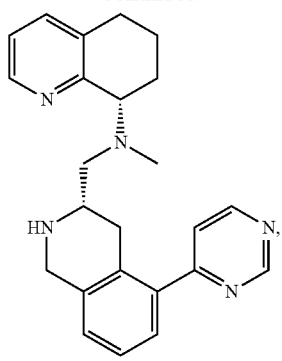
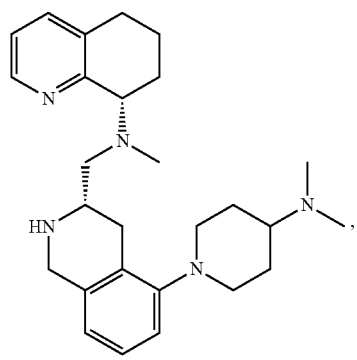
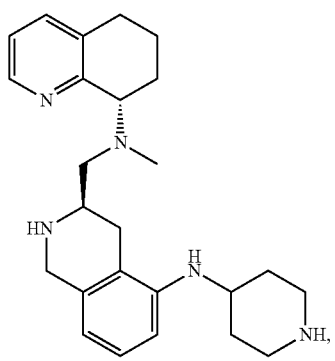
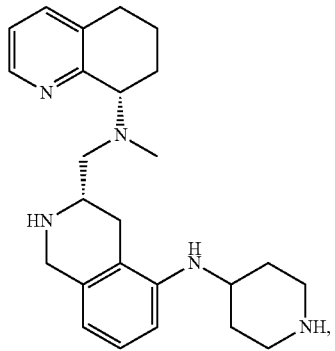

67
-continued
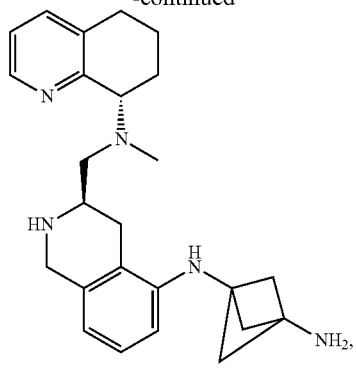
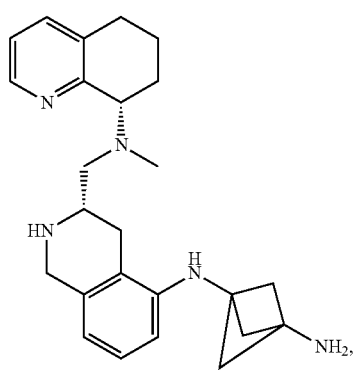
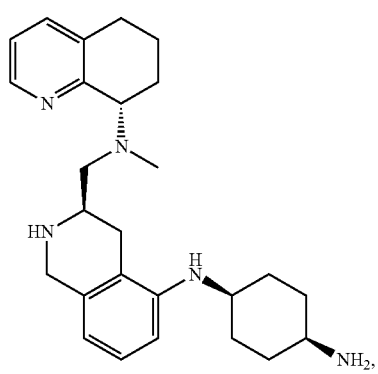
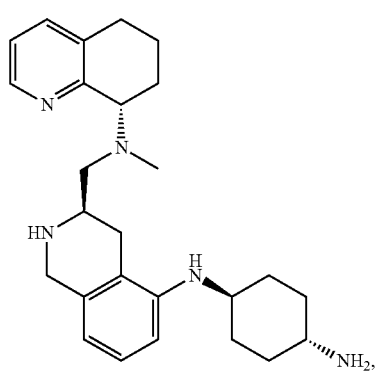
68
-continued
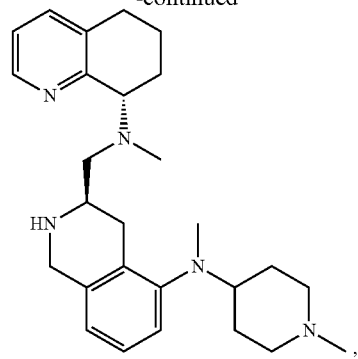
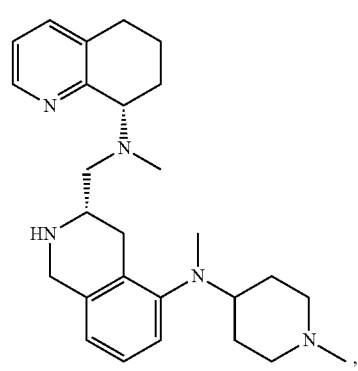
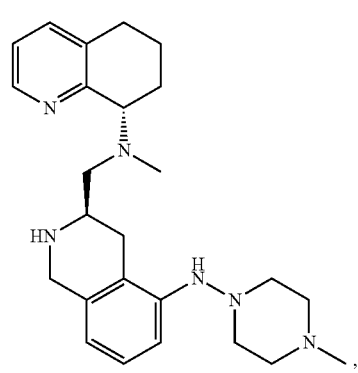
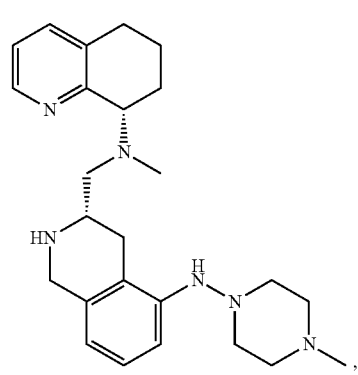

69
-continued
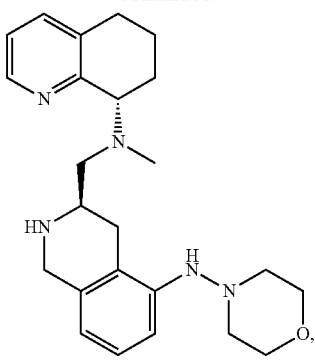
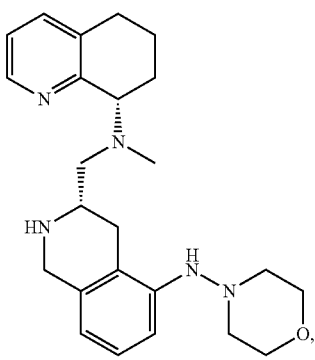
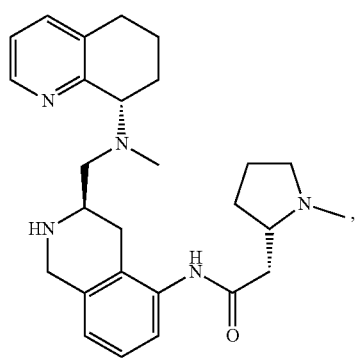
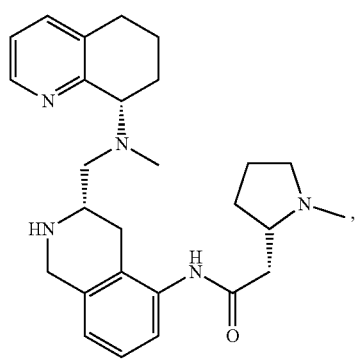
70
-continued
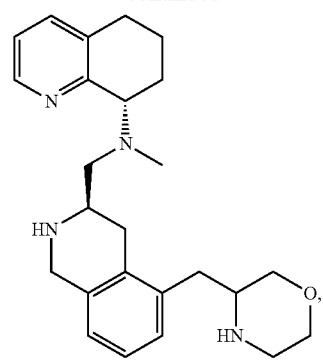
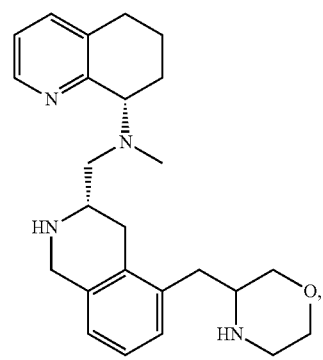
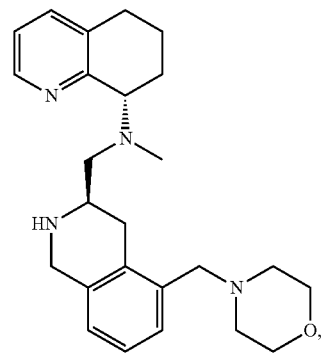
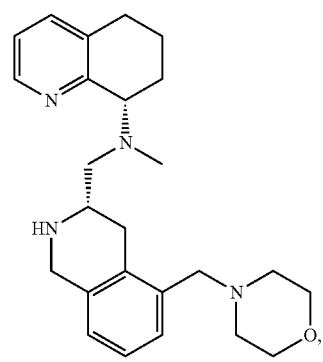

71
-continued
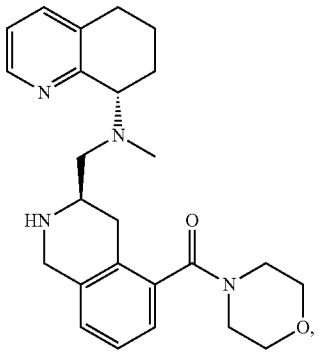
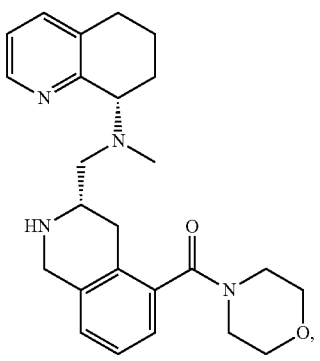
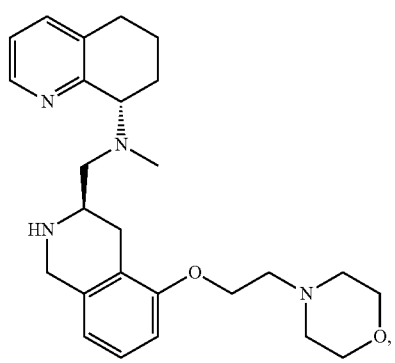
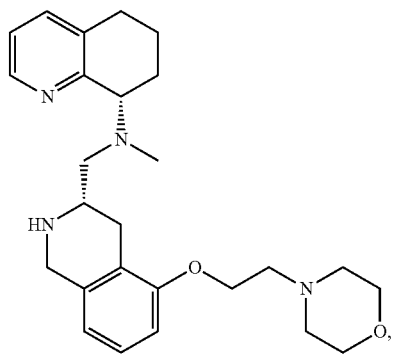
72
-continued
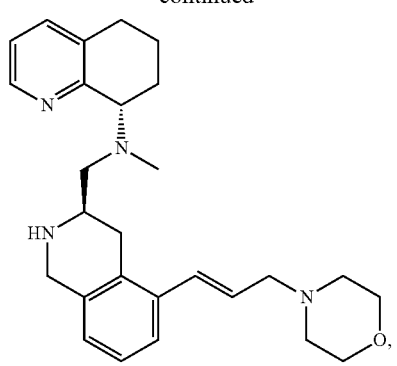
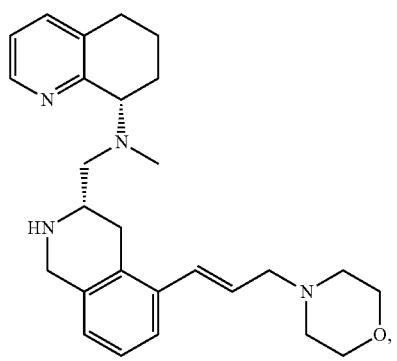
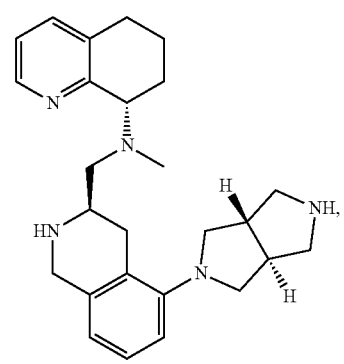
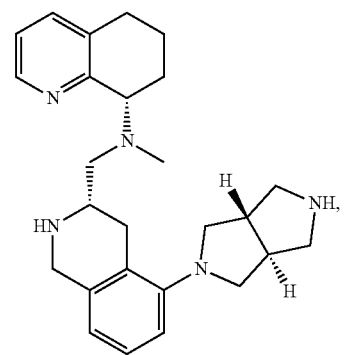

| 73 -continued | 74 -continued |
|---|---|
| 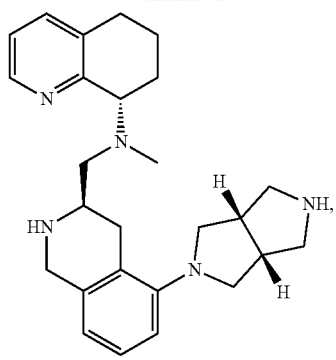 | 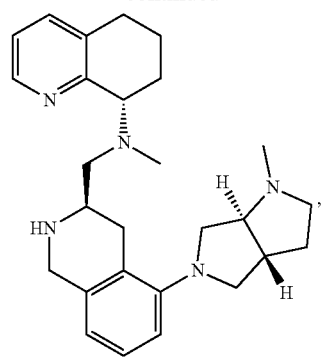 |
| 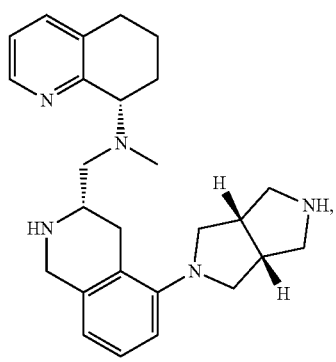 | 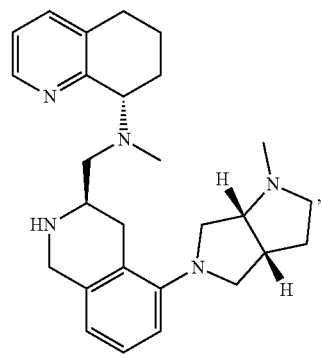 |
| 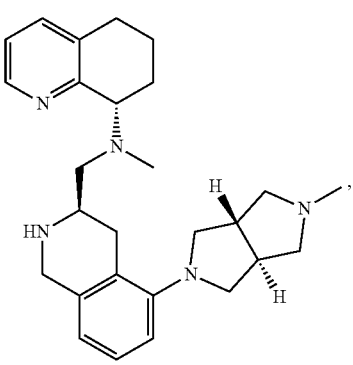 | 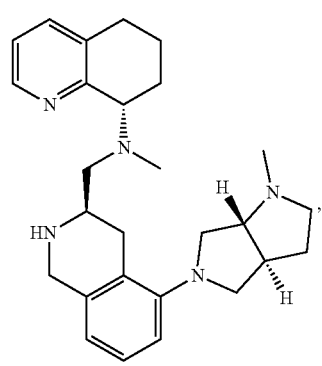 |
| 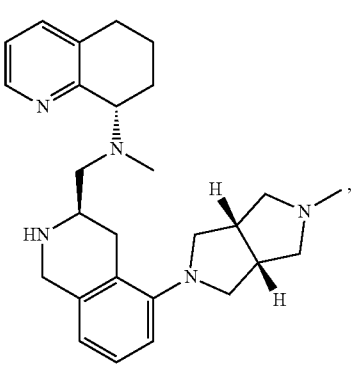 | 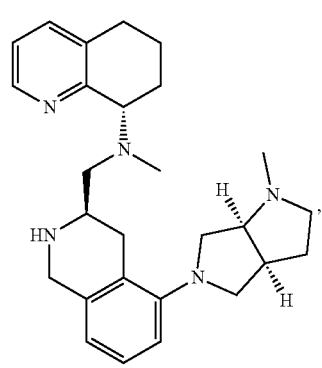 |

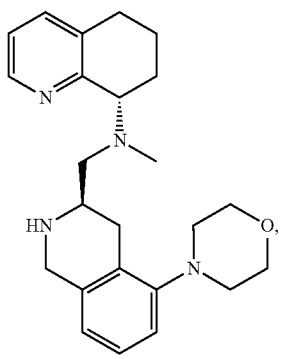
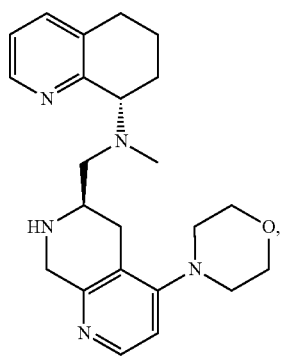
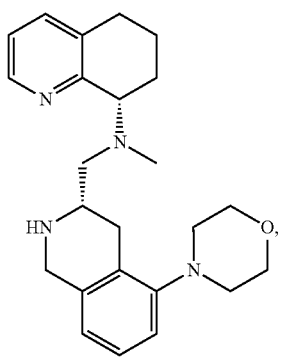
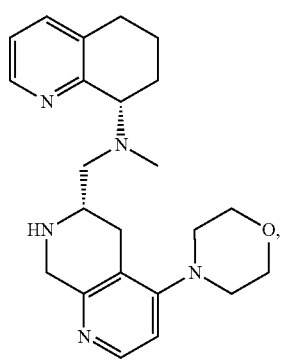
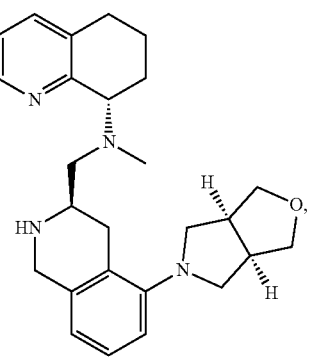
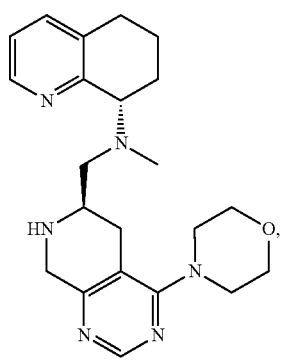
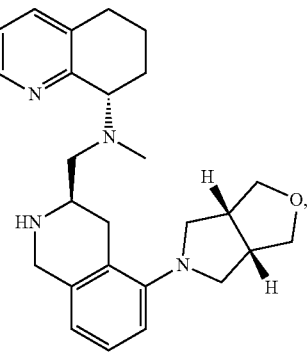
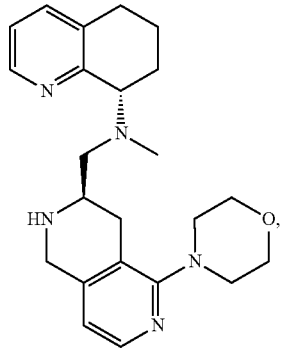

77
-continued
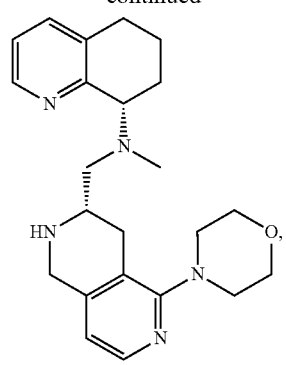
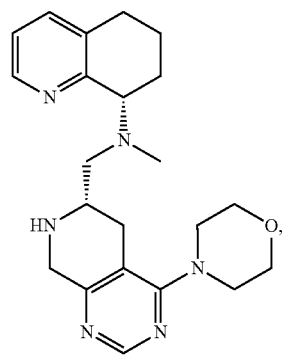
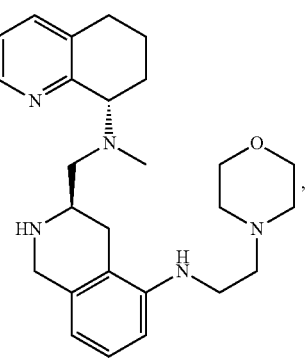
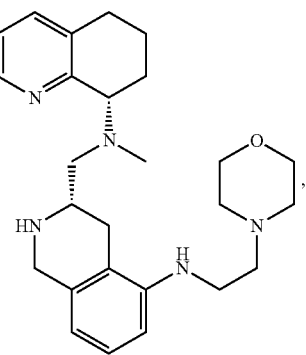
78
-continued
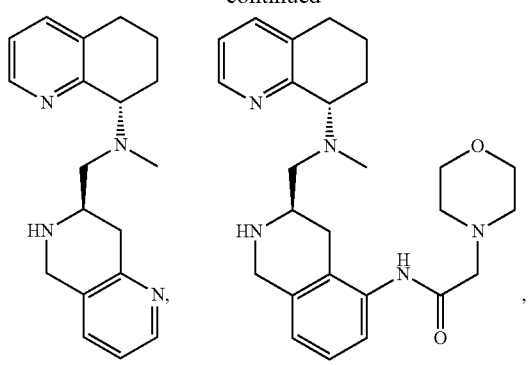
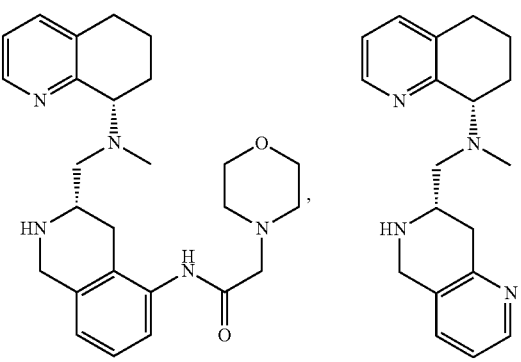
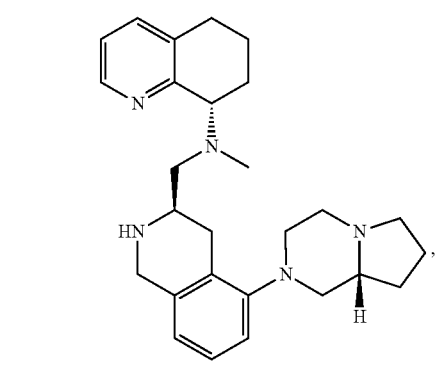

-continued

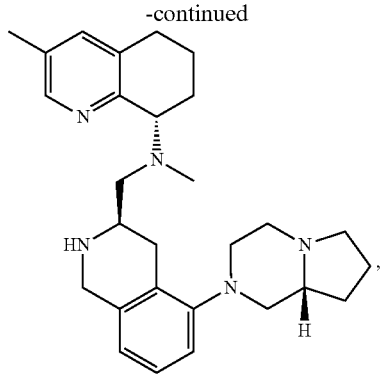

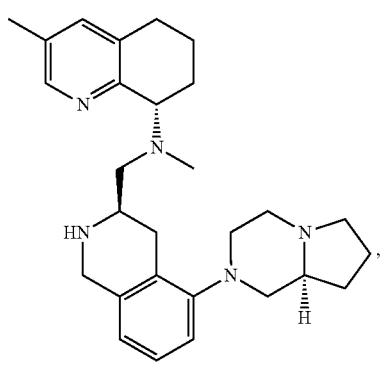

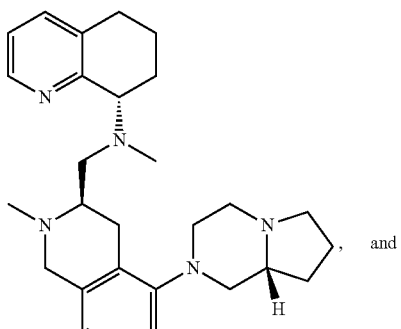

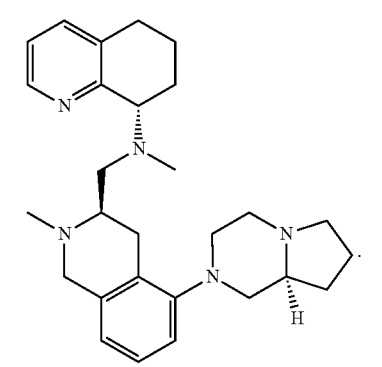

In accordance with a third embodiment of this invention there is provided a compound of Formula (III)

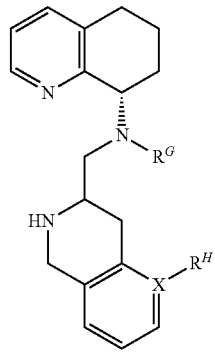

Formula (III)

or salts thereof wherein $R^G$ is an optionally substituted alkene, which may be E or Z, an optionally substituted carbocyclyl, optionally substituted aryl, optionally substituted heterocyclyl or an optionally substituted quaternary carbon; X is C or N, and $R^H$ is a hydrogen or a heterocyclyl when X is C or absent when X is N.

Further features provide for $R^G$ to be selected from the group comprising:

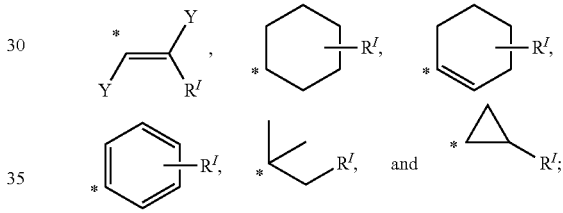

wherein Y is H, alkyl or halogen; $R^I$ is selected from the group comprising H, $NH_2$, halogen, $CH_2NHR^J$, and in the case of the carbocycles, aryls and heterocycles $R^I$ may include one or more and the same or different substituent for each cycle; and $R^J$ is selected from the group comprising:

H

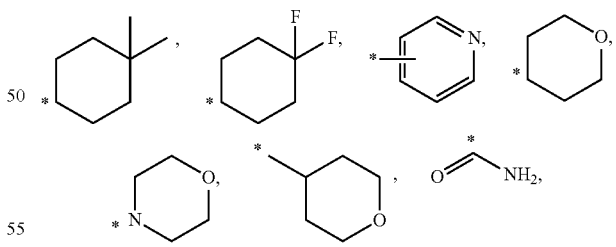

or for $R^G$ to be an alkyl linking the attached NMe to the tetrahydroquinoline;

and for $R^H$ to be H,

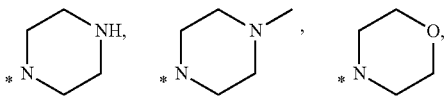

-continued

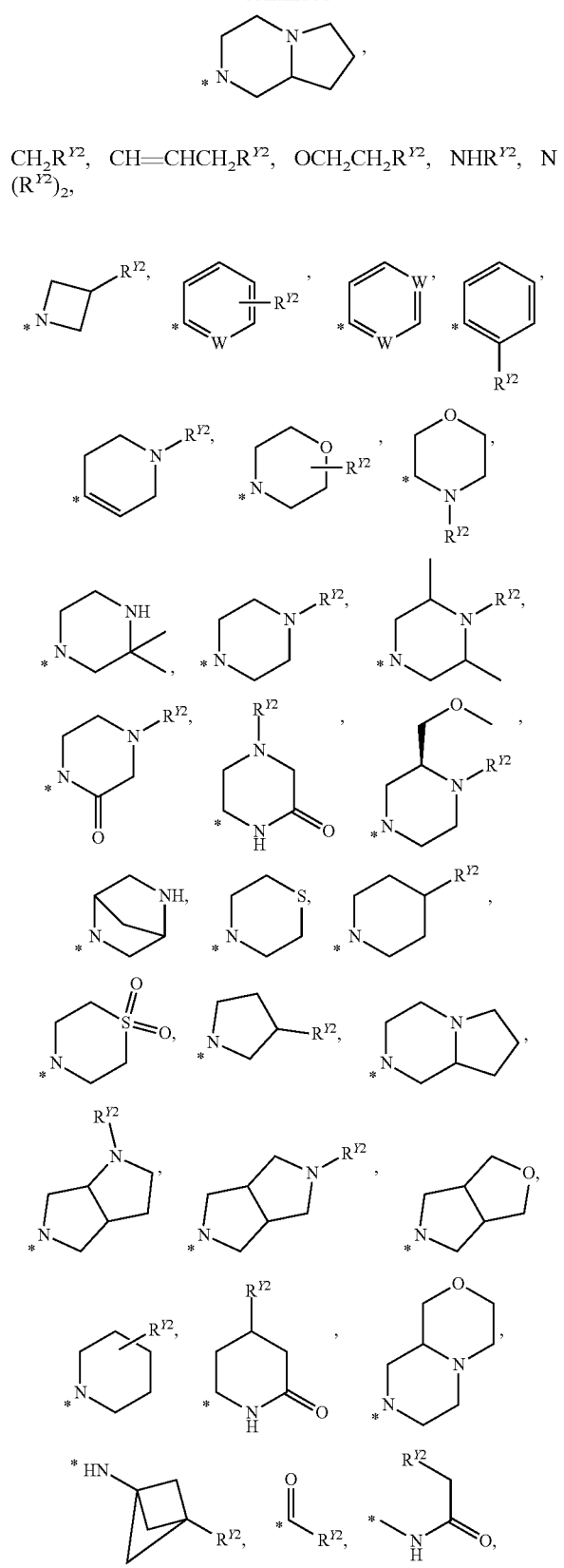

$CH_2R^{Y2}$, $CH=CHCH_2R^{Y2}$, $OCH_2CH_2R^{Y2}$, $NHR^{Y2}$, $N(R^{Y2})_2$, for $R^{Y2}$ to be selected from the group comprising H, OH, F, $CH_3$, $CH_2CH_3$, $CH_2OCH_3$, $CH_2F$, $CF^3$, $NH_2$, wherein the substituent $R^{Y2}$ may be individually and independently mono- or di-substituted onto $R^{X2}$ where appropriate when X is C or absent when X is N.

Yet further features of this embodiment provide for $R^G$ to be selected from the group comprising:

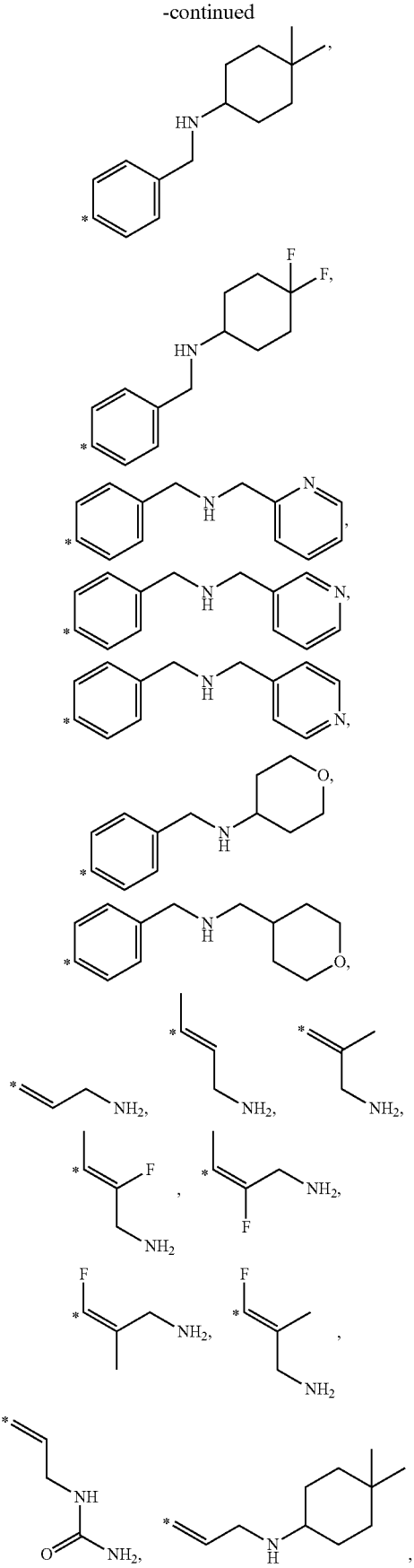
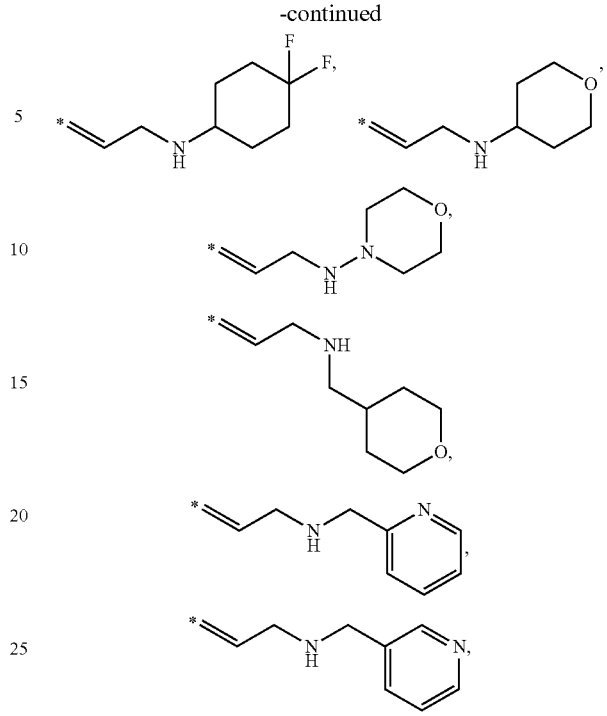
and a $CH_2CH_2$ group linking the $NCH_3$ to the tetrahydroquinoline.
In an exemplary embodiment, the compound of Formula (III) is selected from the group comprising:
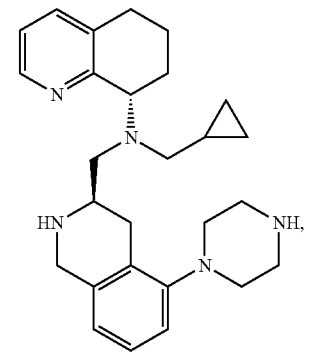
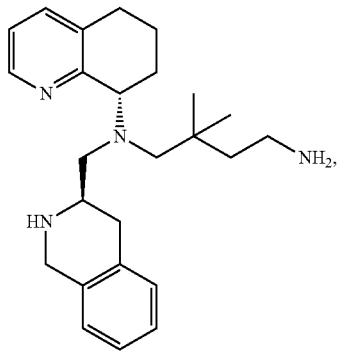

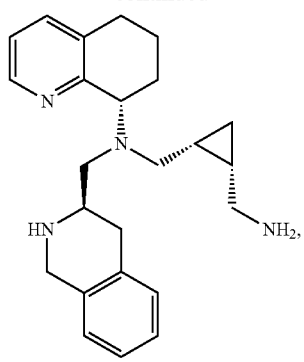
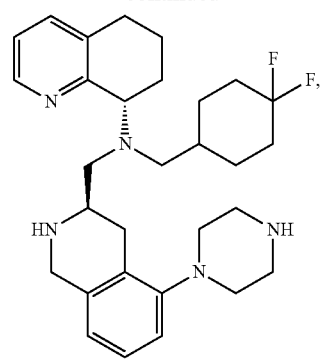
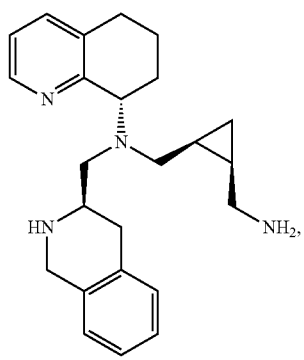
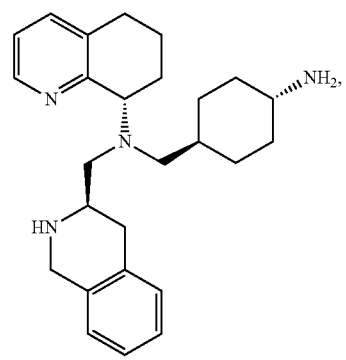
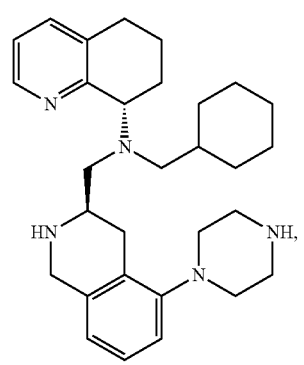
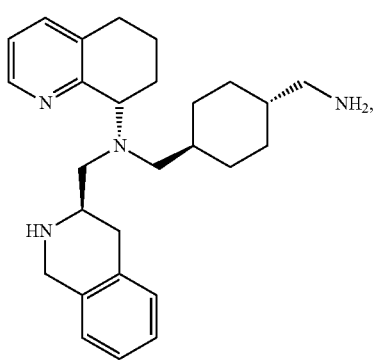
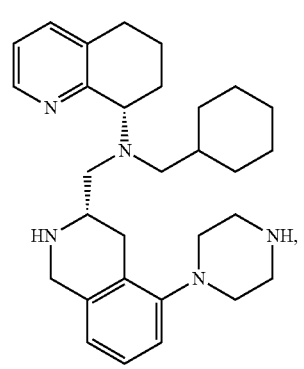
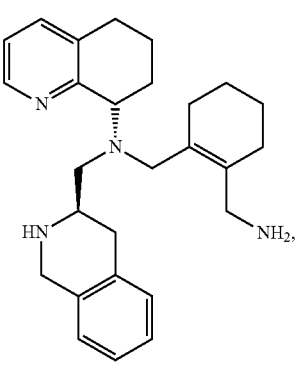

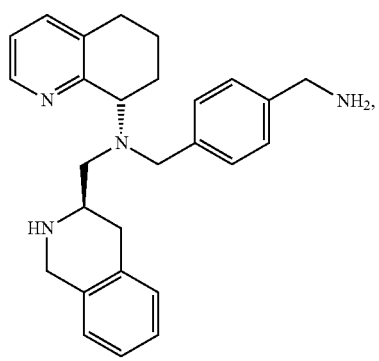
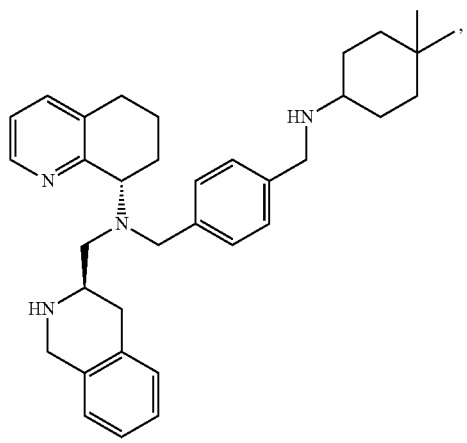
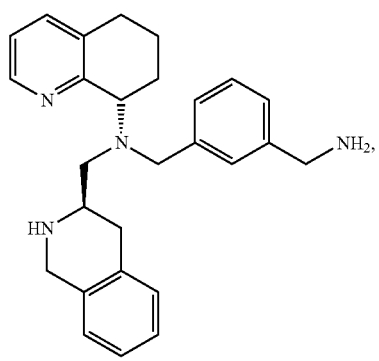
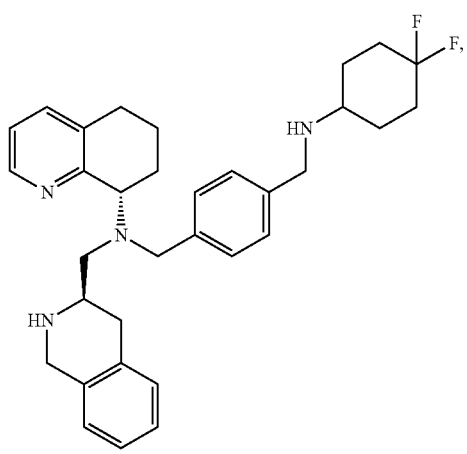
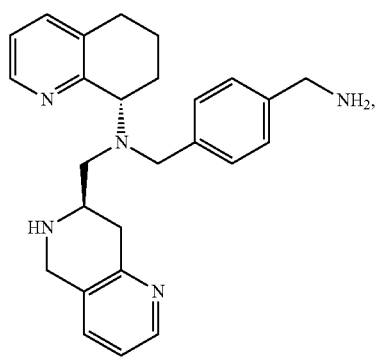
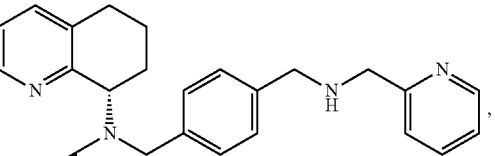
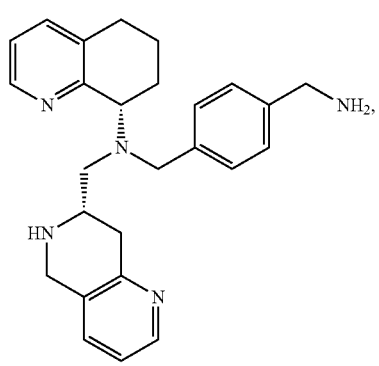
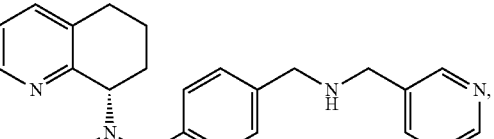
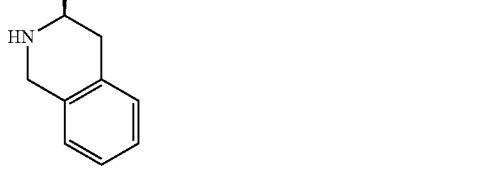

89
-continued
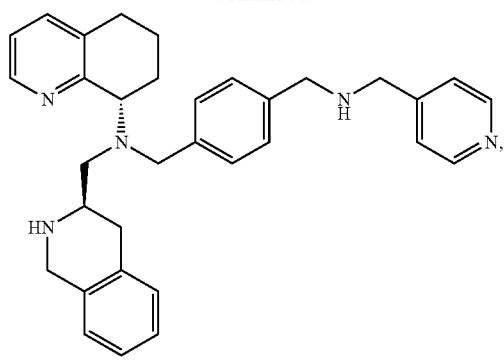
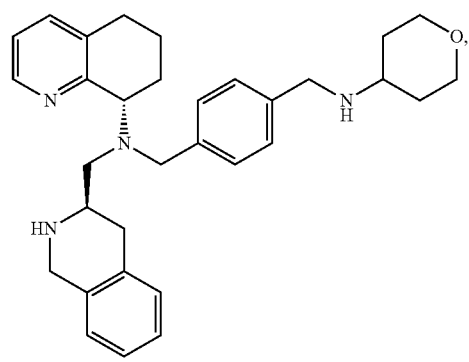
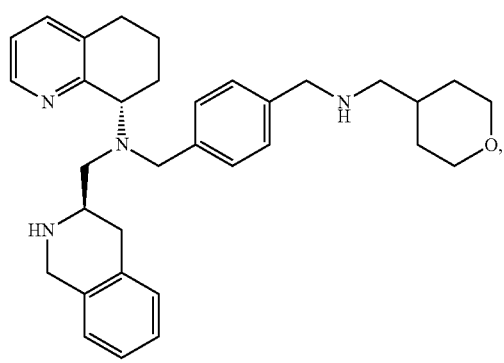
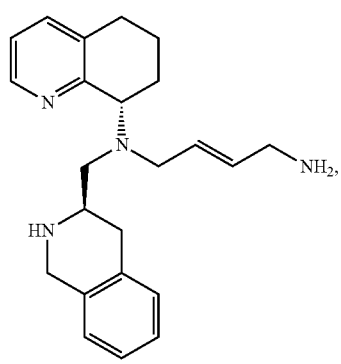
90
-continued
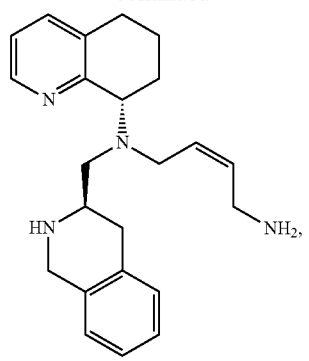
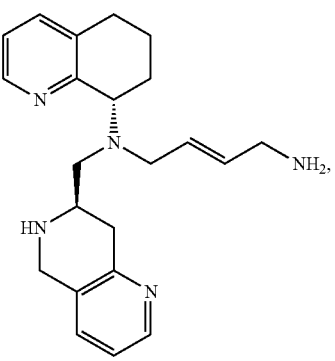
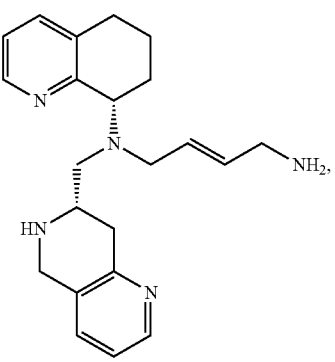
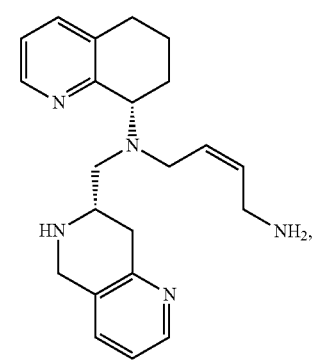

91
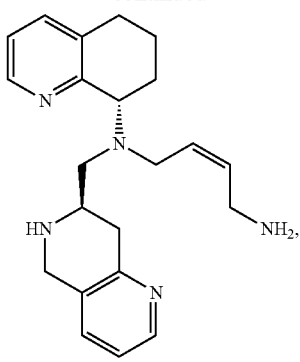
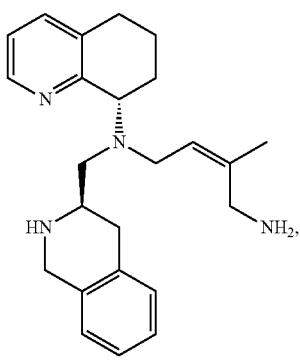
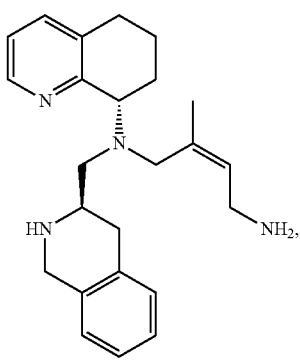
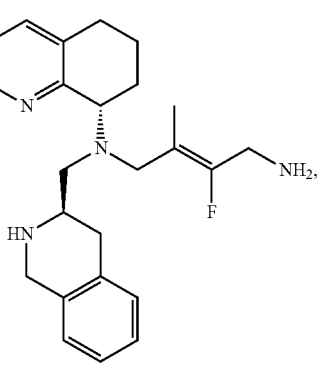
92
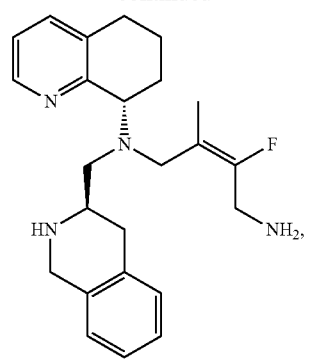
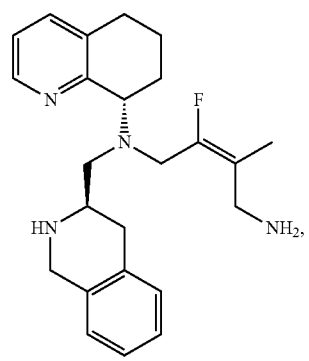
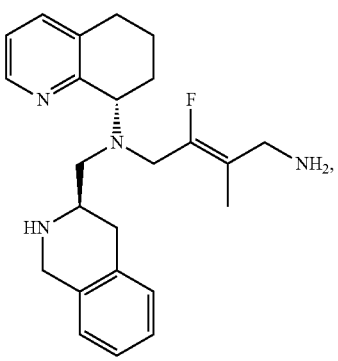
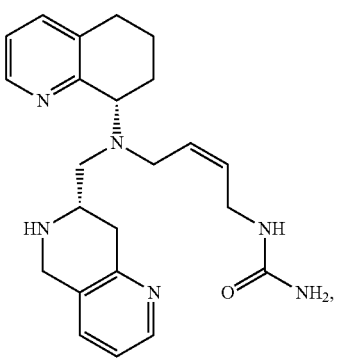

93
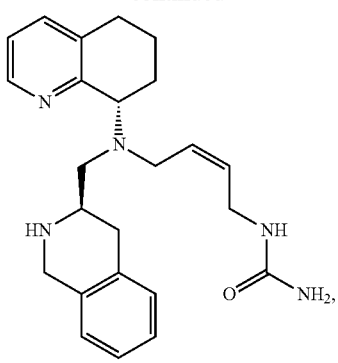
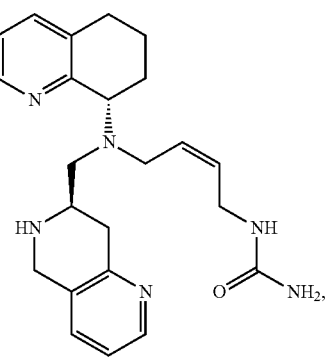
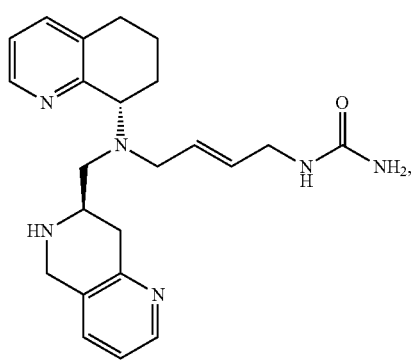
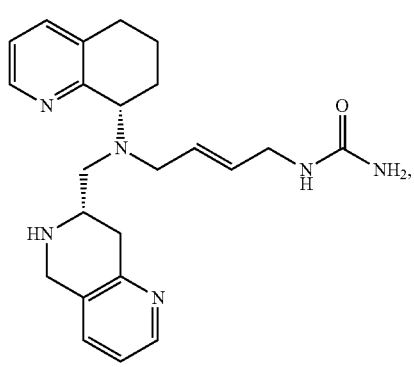
94
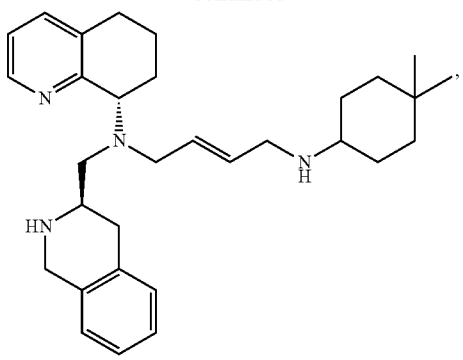
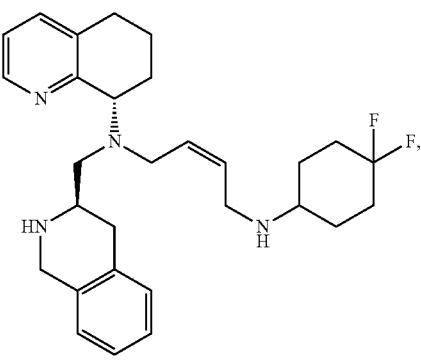
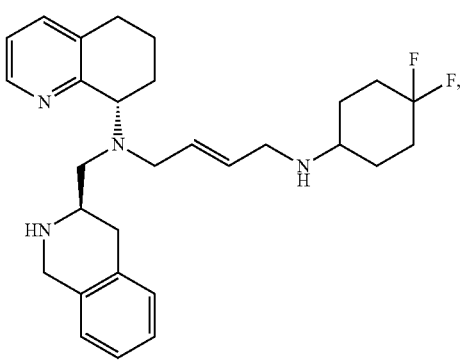
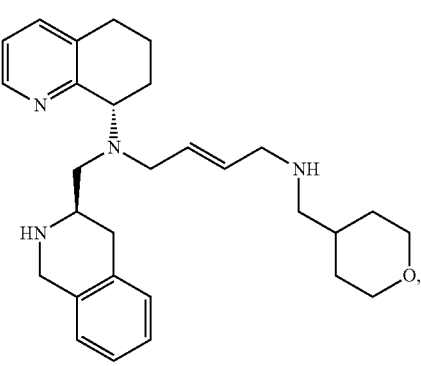

95
-continued
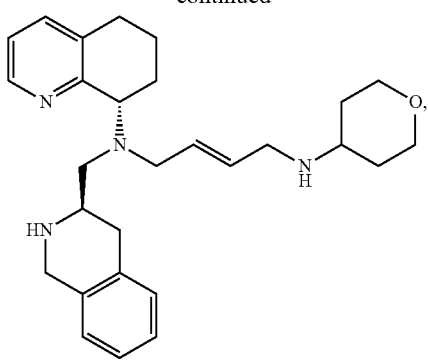
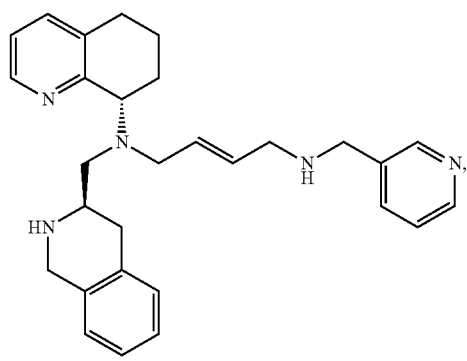
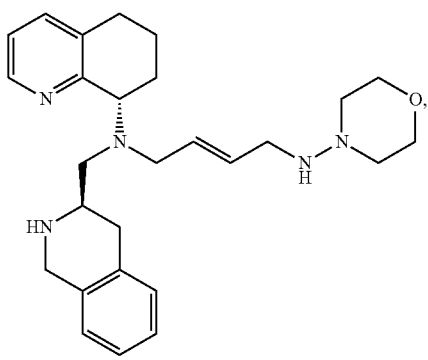
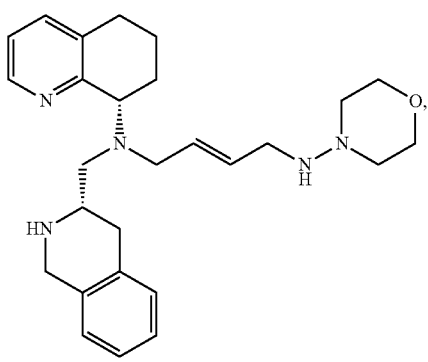
96
-continued
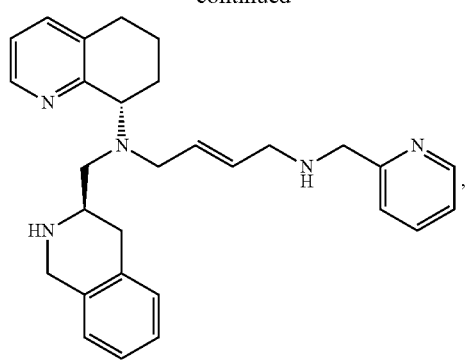
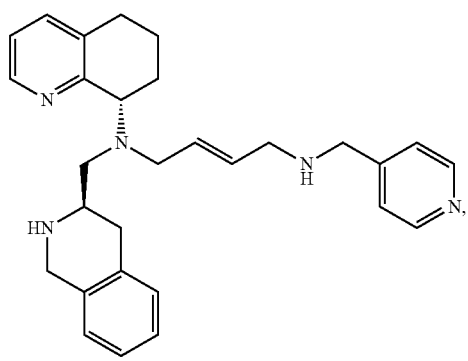
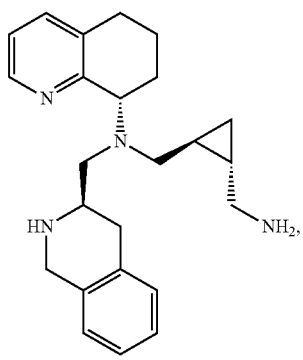
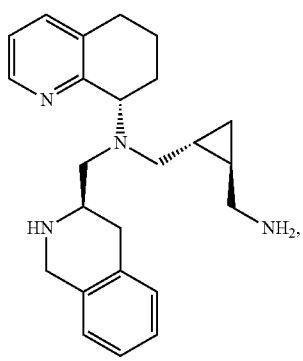

97
-continued
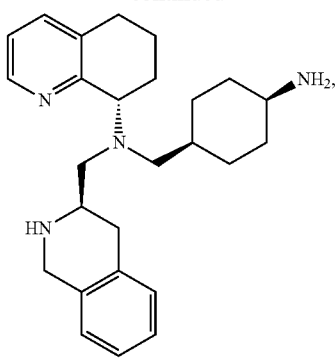
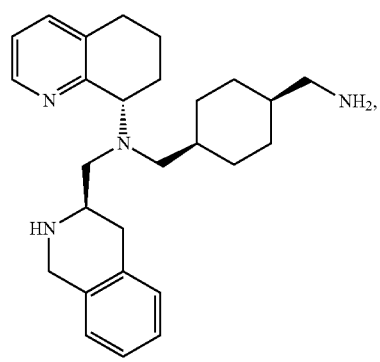
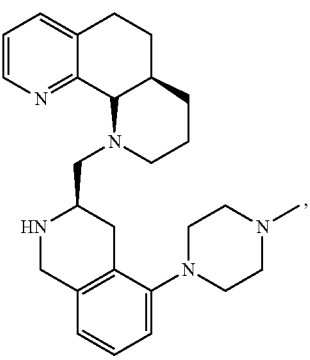
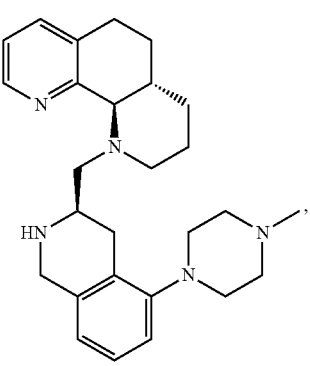
98
-continued
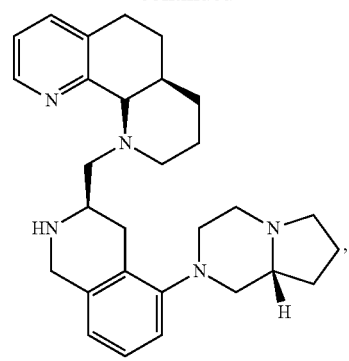
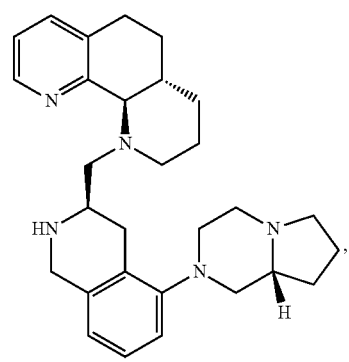
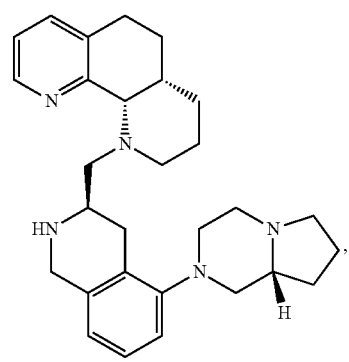
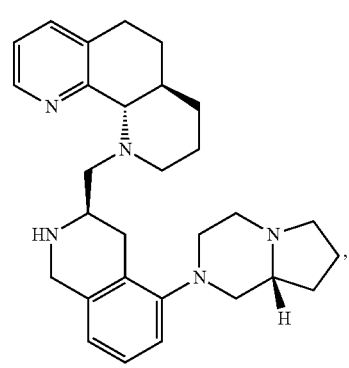

-continued

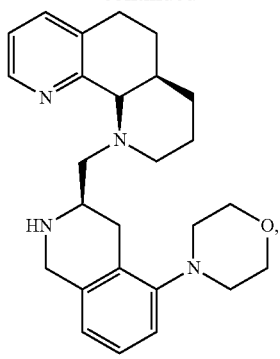

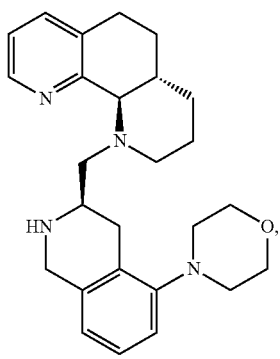

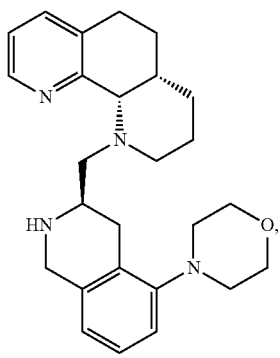

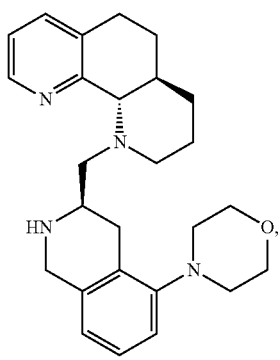

-continued

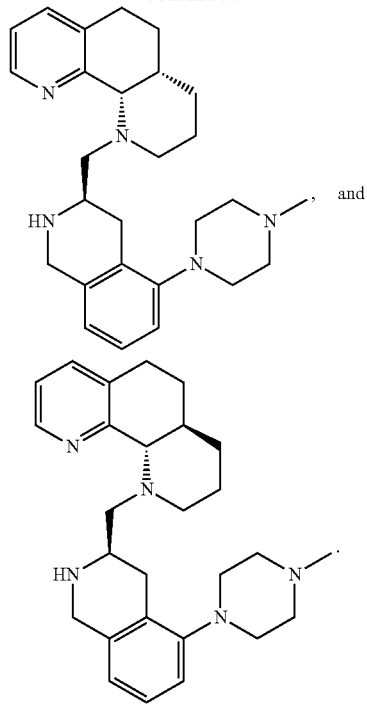

In accordance with a fourth embodiment of the invention there is provided a compound of Formula (IV)

Formula (IV)

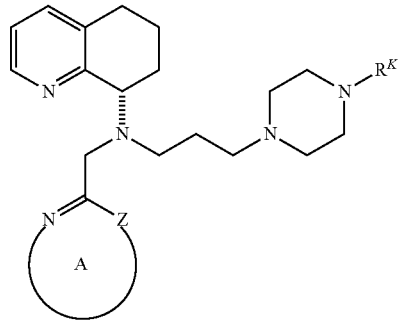

or salts thereof wherein ring A is an heteroaromatic ring system, with or without a fused benzene ring system, $R^K$ is a C1 to C6 alkyl and Z is CH, NH, N or S.

Further features of this embodiment provide for A to be selected from the group comprising:

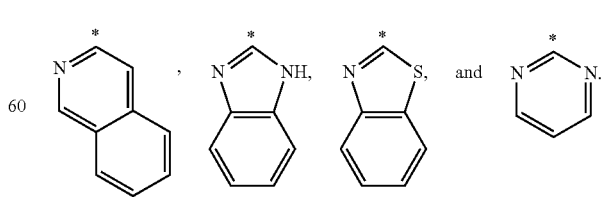

In an exemplary embodiment, the compound of Formula (IV) is selected from the group comprising:

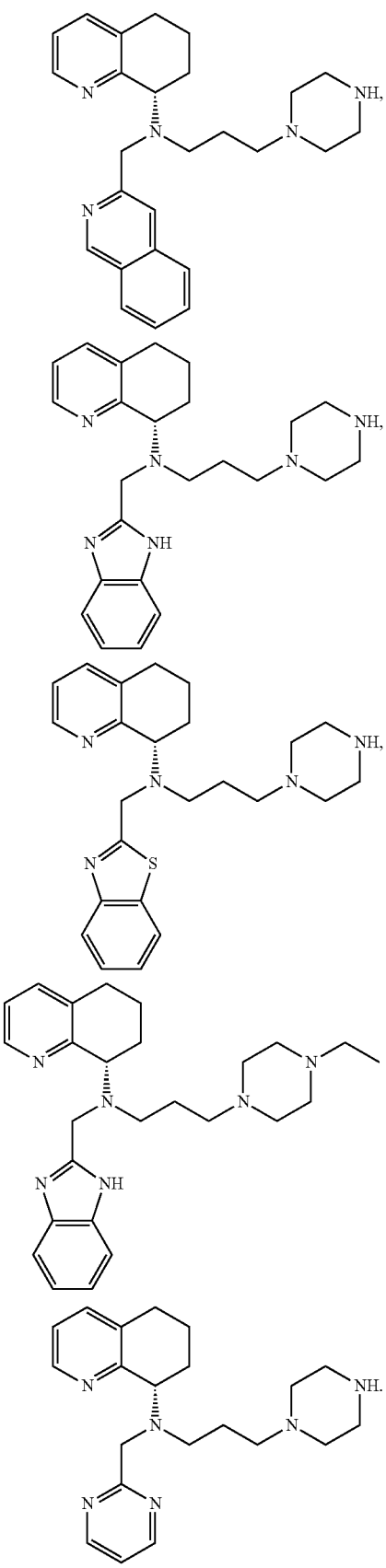

and

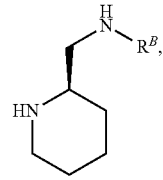

In certain embodiments, the disclosure relates to isolated compositions comprising compounds disclosed herein in substantially pure form.

In certain embodiments, the disclosure relates to a pharmaceutical composition comprising a compound as described herein including salts and prodrugs thereof and a pharmaceutically acceptable excipient, diluent, or carrier.

In certain embodiments, the pharmaceutical composition comprises compounds in greater than 60%, 70%, 80%, 90%, 95%, 98% diastereomeric or enantiomeric excess.

In certain embodiments, the disclosure relates to uses of compounds disclosed herein in the production of a medicament for the treatment of CXCR4 related conditions, such as viral infections, abnormal cellular proliferation, retinal degeneration, inflammatory diseases, or as an immunostimulant or immunosuppressant.

In certain embodiments, the disclosure relates to pharmaceutical compositions comprising a compound as described herein and another active ingredient such as an antiviral agent or chemotherapeutic agent.

In certain embodiments, the disclosure relates to administering a CXCR4 antagonist disclosed herein in combination with a CCR5 antagonist such as maraviroc (selzentry) or vicriviroc.

In certain embodiments, the disclosure relates to methods of treating or preventing a viral infection comprising administering a pharmaceutical composition comprising a compound as described herein optionally in combination with another active ingredient to a subject in need thereof. In further embodiments, the subject is at risk of, exhibiting symptoms of, or diagnosed with a viral infection.

In certain embodiments, the disclosure relates to uses of a compound as described herein in the production of a medicament for the treatment of a viral infection. In typical embodiments, the viral infection is an HIV infection.

In certain embodiments, the disclosure relates to methods of treating or preventing cancer comprising administering a pharmaceutical composition comprising a compound as described herein optionally in combination with another active ingredient to a subject in need thereof. In further embodiments, the subject is at risk of, exhibiting symptoms of, or diagnosed with cancer.

DETAILED DESCRIPTION

Terms

When describing the compounds for use in the disclosure, the terms used are to be construed in accordance with the following definitions, unless a context dictates otherwise.

For R substituents, the symbol * indicates the carbon which forms the point of attachment to the Markush structure. For example, in the Formula:

wherein $R^B$ is

the proposed species is

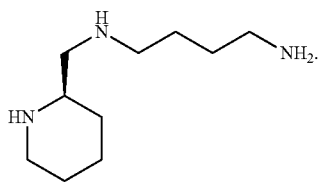

As used herein, "alkyl" means a noncyclic straight chain or branched, unsaturated or saturated hydrocarbon such as those containing from 1 to 10 carbon atoms, typically 1 to 4 otherwise designated $C_{1-4}$alkyl. Representative saturated straight chain alkyls include methyl, ethyl, n-propyl, n-butyl, n-pentyl, n-hexyl, n-septyl, n-octyl, n-nonyl, and the like; while saturated branched alkyls include isopropyl, sec-butyl, isobutyl, tert-butyl, isopentyl, and the like. Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1-butynyl, and the like.

Non-aromatic mono or polycyclic alkyls are referred to herein as "carbocycles" or "carbocyclyl" groups. Representative saturated carbocycles include cyclopropyl, cyclobutyl, cyclopentyl, cyclohexyl, and the like; while unsaturated carbocycles include cyclopentenyl and cyclohexenyl, and the like.

"Heterocarbocycles" or heterocarbocyclyl" groups are carbocycles which contain from 1 to 4 heteroatoms independently selected from nitrogen, oxygen and sulfur which may be saturated or unsaturated (but not aromatic), monocyclic or polycyclic, and wherein the nitrogen and sulfur heteroatoms may be optionally oxidized, and the nitrogen heteroatom may be optionally quaternized. Heterocarbocycles include morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, and the like.

The term "aryl" refers to aromatic homocyclic (i.e., hydrocarbon) mono-, bi- or tricyclic ring-containing groups preferably having 6 to 12 members such as phenyl, naphthyl and biphenyl. Phenyl is a preferred aryl group. The term "substituted aryl" refers to aryl groups substituted with one or more groups, preferably selected from alkyl, substituted alkyl, alkenyl (optionally substituted), aryl (optionally substituted), heterocyclo (optionally substituted), halo, hydroxy, alkoxy (optionally substituted), aryloxy (optionally substituted), alkanoyl (optionally substituted), aroyl, (optionally substituted), alkylester (optionally substituted), arylester (optionally substituted), cyano, nitro, amino, substituted amino, amido, lactam, urea, urethane, sulfonyl, and, the like, where optionally one or more pair of substituents together with the atoms to which they are bonded form a 3 to 7 member ring.

As used herein, "heteroaryl" or "heteroaromatic" refers an aromatic heterocarbocycle having 1 to 4 heteroatoms selected from nitrogen, oxygen and sulfur, and containing at least 1 carbon atom, including both mono- and polycyclic ring systems. Polycyclic ring systems may, but are not required to, contain one or more non-aromatic rings, as long as one of the rings is aromatic. Representative heteroaryls are furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, and quinazolinyl. It is contemplated that the use of the term "heteroaryl" includes N-alkylated derivatives such as a 1-methylimidazol-5-yl substituent.

As used herein, "heterocycle" or "heterocyclyl" refers to mono- and polycyclic ring systems having 1 to 4 heteroatoms selected from nitrogen, oxygen and sulfur, and containing at least 1 carbon atom. The mono- and polycyclic ring systems may be aromatic, non-aromatic or mixtures of aromatic and non-aromatic rings. Heterocycle includes heterocarbocycles, heteroaryls, and the like.

"Alkylthio" refers to an alkyl group as defined above attached through a sulfur bridge. An example of an alkylthio is methylthio, (i.e., —S—CH$_3$).

"Alkoxy" refers to an alkyl group as defined above attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. Preferred alkoxy groups are methoxy, ethoxy, n-propoxy, i-propoxy, n-butoxy, s-butoxy, t-butoxy. "Alkylamino" refers an alkyl group as defined above attached through an amino bridge. An example of an alkylamino is methylamino, (i.e., —NH—CH$_3$).

"Aminoalkyl" refers to an amino group attached through an alkyl bridge as defined above (i.e., NH$_2$-alkyl-).

"Alkanoyl" refers to an alkyl as defined above attached through a carbonyl bridge (i.e., —(C=O)alkyl).

"Alkylsulfonyl" refers to an alkyl as defined above attached through a sulfonyl bridge (i.e., —S(=O)$_2$alkyl) such as mesyl and the like, and "arylsulfonyl" refers to an aryl attached through a sulfonyl bridge (i.e., —S(=O)$_2$aryl).

"Alkylsulfamoyl" refers to an alkyl as defined above attached through a sulfamoyl bridge (i.e., —NHS(=O)$_2$alkyl), and an "arylsulfamoyl" refers to an alkyl attached through a sulfamoyl bridge (i.e., —NHS(=O)$_2$aryl).

"Alkylsulfinyl" refers to an alkyl as defined above attached through a sulfinyl bridge (i.e. —S(=O)alkyl).

The terms "halogen" and "halo" refer to fluorine, chlorine, bromine, and iodine.

The term "substituted" refers to a molecule wherein at least one hydrogen atom is replaced with a substituent. When substituted, one or more of the groups are "substituents". The molecule may be multiply substituted. In the case of an oxo substituent ("=O"), two hydrogen atoms are replaced. Example substituents within this context may include halogen, hydroxy, alkyl, alkoxy, nitro, cyano, oxo, carbocyclyl, carbocycloalkyl, heterocarbocyclyl, heterocarbocycloalkyl, aryl, arylalkyl, heteroaryl, heteroarylalkyl, —NR$_a$R$_b$, —NR$_a$C(=O)R$_b$, —NR$_a$C(=O)NR$_a$NR$_b$, —NR$_a$C(=O)OR$_b$, —NR$_a$SO$_2$R$_b$, —C(=O)R$_a$, —C(=O) OR$_a$, —C(=O)NR$_a$R$_b$, —OC(=O)NR$_a$R$_b$, —OR$_a$, —SR$_a$, —SOR$_a$, —S(=O)$_2$R$_a$, —OS(=O)$_2$R$_a$ and —S(=O)$_2$OR$_a$. R$_a$ and R$_b$ in this context may be the same or different and independently hydrogen, halogen hydroxyl, alkyl, alkoxy, alkyl, amino, alkylamino, dialkylamino, carbocyclyl, carbocycloalkyl, heterocarbocyclyl, heterocarbocycloalkyl, aryl, arylalkyl, heteroaryl, heteroarylalkyl.

The term "optionally substituted", as used herein, means that substitution is optional and therefore it is possible for the designated atom to be unsubstituted.

As used herein, "salts" refer to derivatives of the disclosed compounds where the parent compound is modified making acid or base salts thereof. Examples of salts include, but are not limited to, mineral or organic acid salts of basic residues such as amines, alkylamines, or dialkylamines; alkali or organic salts of acidic residues such as carboxylic acids; and the like. In preferred embodiment the salts are conventional nontoxic pharmaceutically acceptable salts including the quaternary ammonium salts of the parent compound formed, and non-toxic inorganic or organic acids. Preferred salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

"Subject" refers any animal, preferably a human patient, livestock, or domestic pet.

The term "prodrug" refers to an agent that is converted into a biologically active form in vivo. Prodrugs are often useful because, in some situations, they may be easier to administer than the parent compound. They may, for instance, be bioavailable by oral administration whereas the parent compound is not. The prodrug may also have improved solubility in pharmaceutical compositions over the parent drug. A prodrug may be converted into the parent drug by various mechanisms, including enzymatic processes and metabolic hydrolysis.

As used herein, the terms "prevent" and "preventing" include the prevention of the recurrence, spread or onset. It is not intended that the present disclosure be limited to complete prevention. In some embodiments, the onset is delayed, or the severity of the disease is reduced.

As used herein, the terms "treat" and "treating" are not limited to the case where the subject (e.g. patient) is cured and the disease is eradicated. Rather, embodiments, of the present disclosure also contemplate treatment that merely reduces symptoms, and/or delays disease progression.

"Cancer" refers any of various cellular diseases with malignant neoplasms characterized by the proliferation of cells. It is not intended that the diseased cells must actually invade surrounding tissue and metastasize to new body sites. Cancer can involve any tissue of the body and have many different forms in each body area. Within the context of certain embodiments, whether "cancer is reduced" may be identified by a variety of diagnostic manners known to one skilled in the art including, but not limited to, observation in the reduction in size or number of tumor masses or if an increase of apoptosis of cancer cells observed, e.g., if more than a 5% increase in apoptosis of cancer cells is observed for a sample compound compared to a control without the compound. It may also be identified by a change in relevant biomarker or gene expression profile, such as PSA for prostate cancer, HER2 for breast cancer, or others.

METHODS OF USE

In certain embodiments, the compounds described herein are useful for the treatment of viral infections where the virus utilized CXCR4 to infect cells.

In one embodiment, the disclosure relates to a method of treating or preventing HIV infection or reduction of symptoms associated with AIDS is provided, including administering a compound disclosed herein to a subject. In certain embodiments, the compound can be provided to a subject before treatment of infection with another compound. In a separate embodiment, the compound is provided to a patient that has been treated for HIV infection to reduce the likelihood of recurrence, or reduce mortality associated with AIDS related symptoms. In another embodiment, the compound is administered to a subject at high risk of suffering from HIV infections.

Subjects, including humans suffering from, or at risk for, HIV infection can be treated by administering an effective amount of the active compound or a pharmaceutically acceptable prodrug or salt thereof in the presence of a pharmaceutically acceptable carrier or diluent.

The administration can be prophylactically for the prevention of HIV infection or reduction of symptoms associated with AIDS. The active materials can be administered by any appropriate route, for example, orally, parenterally, intravenously, intradermally, subcutaneously, or topically, in liquid or solid form. However, the compounds are particularly suited to oral delivery.

In a separate embodiment, a method for the treatment or prevention of HIV infection or reduction of symptoms associated with AIDS by administering a compound of the present disclosure, or a pharmaceutically acceptable salt, solvate, prodrug, or ester thereof to a subject in need of treatment is provided. The compounds of the disclosure, or a pharmaceutically acceptable salt, solvate, prodrug, or ester thereof can be administered to a subject in need thereof to reduce the severity of AIDS related disorders. In one embodiment of the disclosure, the subject is a human.

In a separate embodiment, a method for the treatment of, prevention of, or reduced severity of liver disease associated with viral infections including administering at least one compound described herein is provided.

Chronic hepatitis C virus (HCV) and hepatitis B virus (HBC) infection is accompanied by inflammation and fibrosis eventually leading to cirrhosis. A study testing the expression and function of CXCR4 on liver-infiltrating lymphocytes (LIL) revealed an important role for the CXCL12/CXCR4 pathway in recruitment and retention of immune cells in the liver during chronic HCV and HBV infection (Wald et al., (2004) *European Journal of Immunology*. 34(4): 1164-1174). High levels of CXCR4 and TGFβ have been detected in liver samples obtained from patients infected with HCV. (Mitra et al., (1999) *Int. J. Oncol.* 14: 917-925). In vitro, TGFβ has been shown to up-regulate the expression of CXCR4 on T cells and to increase their migration. The CD69/TGFβ/CXCR4 pathway may be involved in the retention of recently activated lymphocytes in the liver (Wald et al., *European Journal of Immunology*, 2004; 34(4): 1164-1174).

In another embodiment, the disclosure relates to a method of treating symptoms associated with other infections associated with chemokine receptor activation, for example, liver diseases associated with flavivirus or pestivirus infection, and in particular, HCV or HBV, by contacting a cell with a compound of the present disclosure, or a pharmaceutically acceptable salt, solvate, prodrug, or ester thereof. The cell can be in a subject animal, in particular in a human.

The compounds can be used to treat disorders of abnormal cell proliferation generally, examples of which include, but are not limited to, types of cancers and proliferative disorders listed below. Abnormal cellular proliferation, notably hyperproliferation, can occur as a result of a wide variety of factors, including genetic mutation, infection, exposure to toxins, autoimmune disorders, and benign or malignant tumor induction.

There are a number of skin disorders associated with cellular hyperproliferation. Psoriasis, for example, is a benign disease of human skin generally characterized by plaques covered by thickened scales. The disease is caused by increased proliferation of epidermal cells of unknown cause. In normal skin the time required for a cell to move from the basal layer to the upper granular layer is about five weeks. In psoriasis, this time is only 6 to 9 days, partially due to an increase in the number of proliferating cells and an increase in the proportion of cells which are dividing (G. Grove, *Int. J Dermatol.* 18:111, 1979). Chronic eczema is also associated with significant hyperproliferation of the epidermis. Other diseases caused by hyperproliferation of skin cells include atopic dermatitis, lichen planus, warts, pemphigus vulgaris, actinic keratosis, basal cell carcinoma and squamous cell carcinoma.

Other hyperproliferative cell disorders include blood vessel proliferation disorders, fibrotic disorders, autoimmune disorders, graft-versus-host rejection, tumors and cancers.

Blood vessel proliferative disorders include angiogenic and vasculogenic disorders. Proliferation of smooth muscle cells in the course of development of plaques in vascular tissue cause, for example, restenosis, retinopathies and atherosclerosis. The advanced lesions of atherosclerosis result from an excessive inflammatory-proliferative response to an insult to the endothelium and smooth muscle of the artery wall (Ross, R. *Nature,* 1993, 362:801-809). Both cell migration and cell proliferation play a role in the formation of atherosclerotic lesions.

Fibrotic disorders are often due to the abnormal formation of an extracellular matrix. Examples of fibrotic disorders include hepatic cirrhosis and mesangial proliferative cell disorders. Hepatic cirrhosis is characterized by the increase in extracellular matrix constituents resulting in the formation of a hepatic scar. Hepatic cirrhosis can cause diseases such as cirrhosis of the liver. An increased extracellular matrix resulting in a hepatic scar can also be caused by viral infection such as hepatitis. Lipocytes appear to play a major role in hepatic cirrhosis.

Mesangial disorders are brought about by abnormal proliferation of mesangial cells. Mesangial hyperproliferative cell disorders include various human renal diseases, such as glomerulonephritis, diabetic nephropathy, malignant nephrosclerosis, thrombotic microangiopathy syndromes, transplant rejection, and glomerulopathies.

Another disease with a proliferative component is rheumatoid arthritis. Rheumatoid arthritis is generally considered an autoimmune disease that is thought to be associated with activity of autoreactive T cells (See, e.g., Harris, E. D., Jr. (1990) *The New England Journal of Medicine,* 322:1277-1289), and to be caused by auto-antibodies produced against collagen and IgE.

Other disorders that can include an abnormal cellular proliferative component include Behcet's syndrome, acute respiratory distress syndrome (ARDS), ischemic heart disease, post-dialysis syndrome, leukemia, acquired immune deficiency syndrome, vasculitis, lipid histiocytosis, septic shock and inflammation in general.

Examples of cancers or proliferative disorders which can be the primary tumor that is treated include but are not limited to neoplasms located in the: colon, abdomen, bone, breast, digestive system, liver, pancreas, peritoneum, endocrine glands (adrenal, parathyroid, pituitary, testicles, ovary, thymus, thyroid), eye, head and neck, nervous (central and peripheral), lymphatic system, pelvis, skin, soft tissue, spleen, thorax, and urogenital tract.

In certain embodiments, the subject is diagnosed with acute childhood lymphoblastic leukemia; acute lymphoblastic leukemia, acute lymphocytic leukemia, acute myeloid leukemia, adrenocortical carcinoma, adult (primary) hepatocellular cancer, adult (primary) liver cancer, adult acute lymphocytic leukemia, adult acute myeloid leukemia, adult Hodgkin's disease, adult Hodgkin's lymphoma, adult lymphocytic leukemia, adult non-Hodgkin's lymphoma, adult primary liver cancer, adult soft tissue sarcoma, AIDS-related lymphoma, AIDS-related malignancies, anal cancer, astrocytoma, bile duct cancer, bladder cancer, bone cancer, brain stem glioma, brain tumors, breast cancer, cancer of the renal pelvis and ureter, central nervous system (primary) lymphoma, central nervous system lymphoma, cerebellar astrocytoma, cerebral astrocytoma, cervical cancer, childhood (primary) hepatocellular cancer, childhood (primary) liver cancer, childhood acute lymphoblastic leukemia, childhood acute myeloid leukemia, childhood brain stem glioma, childhood cerebellar astrocytoma, childhood cerebral astrocytoma, childhood extracranial germ cell tumors, childhood Hodgkin's disease, childhood Hodgkin's lymphoma, childhood hypothalanic and visual pathway glioma, childhood lymphoblastic leukemia, childhood medulloblastoma, childhood non-Hodgkin's lymphoma, childhood pineal and supratentorial primitive neuroectodermal tumors, childhood primary liver cancer, childhood rhabdomyosarcoma, childhood soft tissue sarcoma, childhood visual pathway and hypothalamic glioma, chronic lymphocytic leukemia, chronic myelogenous leukemia, colon cancer, cutaneous T-cell lymphoma, endocrine pancreas islet cell carcinoma, endometrial cancer, ependymoma, epithelial cancer, esophageal cancer, Ewing's sarcoma and related tumors, exocrine pancreatic cancer, extracranial germ cell tumor, extragonadal germ cell tumor, extrahepatie bile duct cancer, eye cancer, female Breast cancer, Gaucher's disease, gallbladder cancer, gastric cancer, gastrointestinal carcinoid tumor, gastrointestinal tumors, germ cell tumors, gestational trophoblastic tumor, hairy cell leukemia, head and neck cancer, hepatocellular cancer, Hodgkin's disease, Hodgkin's lymphoma, hypergammaglobulinemia, hypopharyngeal cancer, intestinal cancers, intraocular melanoma, islet cell carcinoma, islet cell pancreatic cancer, Kaposi's sarcoma, kidney cancer, laryngeal cancer, lip and oral cavity cancer, liver cancer, lung cancer, lympho proliferative disorders, macroglobulinemia, male breast cancer, malignant mesothelioma, malignant thymoma, medulloblastomia, melanoma, mesothelioma, metastatie occult primary squamous neck cancer, metastatie primary squamous neck cancer, metastatie squamous neck cancer, multiple myeloma, multiple myeloma/plasma cell neoplasm, myelodysplasia syndrome, myelogenous leukemia, myeloid leukemia, myeloproliferative disorders, nasal cavity and paranasal sinus cancer, nasopharyngeal cancer, neuroblastoma, non-Hodgkin's lymphoma during pregnancy, nonmelanoma skin cancer, non-small cell lung cancer, occult primary metastatie squamous neck cancer, oropharyngeal cancer, osteo/malignant fibrous sarcoma, osteosarcoma/malignant fibrous histiocytoma, osteosarcoma/malignant fibrous histiocytoma of bone, ovarian epithelial cancer, ovarian germ cell tumor, ovarian low malignant potential tumor, pancreatic cancer, paraproteinemias, purpura, parathyroid, cancer, penile cancer, pheochromocytoma, pituitary tumor, plasma cell neoplasm/multiple myeloma, primary central nervous system lymphoma, primary liver cancer, prostate cancer, rectal cancer, renal cell cancer, renal pelvis and ureter cancer, retinoblastoma, rhabdomyosarcoma, salivary gland cancer, sarcoidosis sarcomas, sezary syndrome, skin cancer, small cell lung cancer, small Intestine cancer, soft tissue sarcoma, squamous neck cancer, stomach cancer, supratentorial primitive neuroectodermal and pineal tumors, T-cell lymphoma, testicular cancer, thymoma, thyroid cancer, transitional cell cancer of the renal pelvis and ureter, transitional renal pelvis and ureter cancer, trophoblastic tumors, ureter and renal pelvis cell cancer, urethial cancer, uterine cancer, uterine sarcoma, vaginal cancer, visual pathway and hypothalamic glioma, vulvar cancer, Waldenstrom's macroglobulinemia, Wilm's tumor, and any other hyperproliferative disease located in an organ system listed above.

In certain embodiments, the compound disclosed herein can be used to treat or prevent hyperplastic disorders including, but are not limited to, angiofollicular mediastinal lymph node hyperplasia, angiolymphoid hyperplasia with eosinophilia, atypical melanocytic hyperplasia, basal cell hyperplasia, benign giant lymph node hyperplasia, cementum hyperplasia, congenital adrenal hyperplasia, congenital sebaceous hyperplasia, cystic hyperplasia, cystic hyperplasia of the breast, denture hyperplasia, ductal hyperplasia, endometrial hyperplasia, fibromuscular hyperplasia, foca epithelial hyperplasia, gingival hyperplasia, inflammatory fibrous hyperplasia, inflammatory papillary hyperplasia, intravascular papillary endothelial hyperplasia, nodular hyperplasia of prostate, nodular regenerative hyperplasia, pseudoepitheliomatous hyperplasia, senile sebaceous hyperplasia, and verrucous hyperplasia; leukemia (including acute leukemia (e.g., acute lymphocytic leukemia, acute myelocytic leukemia (including myeloblasts, promyelocyte, mylomonocytic, monocytic, and erythroleukemia)) and chronic leukemia (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and, carcinomas such as fibrosarcoma, myxosarcoma, fiposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, emangioblastoma, acoustic neuroma, oligodendrogliomia, menangioma, melanoma, neuroblastoma, and retinoblastoma.

In a separate embodiment, the disclosure relates to a method for the treatment of, prevention of, or reduced severity of, age-related macular degeneration (ARMD) and other pathogenic states involving macular retinal pigment epithelial (RPE) cells by administering at least one compound described herein to a subject in need thereof.

CXCR4 plays a role in ocular diseases involving the retina such as age-related macular degeneration (ARMD). The retinal pigment epithelium has a major role in the physiological renewal of photoreceptor outer segments in the provision of a transport and storage system for nutrients essential to the photoreceptor layer. The retinal pigment epithelial (RPE) cells predominantly express CXCR4 receptors. (Crane, et al. (2000) *J. Immunol.* 165: 43 72-4278). CXCR4 receptor expression on human retinal pigment epithelial cells from the blood-retina barrier leads to chemokine secretion and migration in response to stromal cell-derived factor Ia. (*J. Immunol.* 200; 165: 4372-4278). The level of CXCR4 mRNA expression increases upon stimulation with IL-1β or TNFα (Dwinell, et al. (1999) *Gastroenterology.* 117: 359-367). RPE cells also migrated in response to SDF-1α indicating that SDF-1α/CXCR4 interactions may modulate the effects of chronic inflammation and subretinal neovascularization at the RPE site of the blood-retina barrier. (Crane U, Wallace C A, McKillop-Smith S, Forrester J V. *CXCR4 receptor expression on human retinal pigment epithelial cells from the blood-retina barrier leads to chemokine secretion and migration in response to stromal cell-derived factor Ia. J Immunol.* 200; 165: 4372-4278).

Age-related macular degeneration is characterized by both primary and secondary damage of macular RPE cells. Early stages of ARMD are characterized by macular drusen, and irregular proliferation and atrophy of the RPE. The late stages of ARMD present with geographic RPE atrophy, RPE detachment and rupture, choroidal neovascularaization and fibrovascular disciform scarring. Common first symptoms include metamorphopisia and/or general central vision loss resulting in reading disability and difficulties in detecting faces. Late stages of ARMD cause central scomota, which is extremely disabling if occurrence is bilateral (Bressler and Bressler (1995) *Ophthalmology.* 1995; 102: 1206-1211).

In a separate embodiment, a method for the treatment of, prevention of, or reduced severity of inflammatory disease states, neovascularization, and wound healing including administering at least one compound described herein to a subject in need thereof. Vascular endothelial cells express a multitude of chemokine receptors, with CXCR4 being particularly prominent (Gupta, et al. (1998) *J Biol Chem.* 273: 4282; Volin, et al. (1998) *Biochem Biophys Res Commnun.* 242: 46).

A RT-PCR based strategy which utilized CXCR4 specific primers demonstrated that mRNA for the chemokine receptor CXCR4 is expressed not only in primary cultures and transformed type II alveolar epithelial cells (pneumocytes) but also in a number of epithelial cell lines derived from various other tissues. (Murdoch, et al. (1998) *Immunology.* 98(1): 36-41). Unlike with endothelial cells, CXCR4 is the only chemokine receptor expressed on epithelial cells. The receptor may have a functional role in epithelial pathology. CXCR4 expressed on the epithelium may facilitate the recruitment of phagocytic cells to sites of inflammation by direct effects on epithelial cells. CXCR4 may also have other functional roles within the immune response or participate in wound healing or neovascularization. CXCR4 may also be involved in the pathophysiology of several acute or chronic inflammatory disease states associated with the epithelium.

Certain inflammatory chemokines can be induced during an immune response to promote cells of the immune system to a site of infection. Inflammatory chemokines function mainly as chemoattractants for leukocytes, recruiting monocytes, neutrophils and other effector cells from the blood to sites of infection or tissue damage. Certain inflammatory chemokines activate cells to initiate an immune response or promote wound healing. Responses to chemokines include increasing or decreasing expression of membrane proteins, proliferation, and secretion of effector molecules.

In a particular embodiment, the compounds of the disclosure can be administered to a host at risk of, or suffering from, an inflammatory condition. In one embodiment, the compounds are administered for the treatment or prophylaxis of an inflammatory disorder. In certain embodiments, the inflammatory disorder or condition is mediated by chemokines.

Generally, inflammatory disorders include, but are not limited to, respiratory disorders (including asthma, COPD, chronic bronchitis and cystic fibrosis); cardiovascular related disorders (including atherosclerosis, post-angioplasty, restenosis, coronary artery diseases and angina); inflammatory diseases of the joints (including rheumatoid and osteoarthritis); skin disorders (including dermatitis, eczematous dermatitis and psoriasis); post transplantation late and chronic solid organ rejection; multiple sclerosis; autoimmune conditions (including systemic lupus erythematosus, dermatomyositis, polymyositis, Sjogren's syndrome, polymyalgia rheumatica, temporal arteritis, Behcet's disease, Guillain Barre, Wegener's granulomatosus, polyarteritis nodosa); inflammatory neuropathies (including inflammatory polyneuropathies); vasculitis (including Churg-Strauss syndrome, Takayasu's arteritis); inflammatory disorders of adipose tissue; and proliferative disorders (including Kaposi's sarcoma and other proliferative disorders of smooth muscle cells).

In one embodiment, compounds, compositions and methods of treatment of respiratory disorders comprising administering a compound as described herein to a subject in need thereof. Respiratory disorders that may be prevented or treated include a disease or disorder of the respiratory system that can affect any part of the respiratory tract. Respiratory disorders include, but are not limited to, a cold virus, bronchitis, pneumonia, tuberculosis, irritation of the lung tissue, hay fever and other respiratory allergies, asthma, bronchitis, simple and mucopurulent chronic bronchitis, unspecified chronic bronchitis (including chronic bronchitis NOS, chronic tracheitis and chronic tracheobronchitis), emphysema, other chronic obstructive pulmonary disease, asthma, status asthmaticus and bronchiectasis. Other respiratory disorders include allergic and non-allergic rhinitis as well as non-malignant proliferative and/or inflammatory disease of the airway passages and lungs. Non-malignant proliferative and/or inflammatory diseases of the airway passages or lungs means one or more of (1) alveolitis, such as extrinsic allergic alveolitis, and drug toxicity such as caused by, e.g. cytotoxic and/or alkylating agents; (2) vasculitis such as Wegener's granulomatosis, allergic granulomatosis, pulmonary hemangiomatosis and idiopathic pulmonary fibrosis, chronic eosinophilic pneumonia, eosinophilic granuloma and sarcoidoses.

In one embodiment, the compounds of the disclosure are administered to a patient suffering from a cardiovascular disorder related to inflammation. Cardiovascular inflammatory disorders include atherosclerosis, post-angioplasty, restenosis, coronary artery diseases, angina, and other cardiovascular diseases.

In certain embodiments the disorder is a non-cardiovascular inflammatory disorder such as rheumatoid and osteoarthritis, dermatitis, psoriasis, cystic fibrosis, post transplantation late and chronic solid organ rejection, eczematous dermatitis, Kaposi's sarcoma, or multiple sclerosis. In yet another embodiment, the compounds disclosed herein can be selected to treat anti-inflammatory conditions that are mediated by mononuclear leucocytes.

In addition, the disclosure is directed to methods of treating animal subjects, in particular, veterinary and human subjects, to enhance or elevate the number of progenitor cells and/or stem cells. The progenitor and/or stem cells may be harvested and used in cell transplantation. In one embodiment, bone marrow progenitor and/or stem cells are mobilized for myocardial repair. Further, the disclosure is directed to methods of treating animal subjects, in particular, veterinary and human patients, who are defective in white blood cell (WBQ 8 count, or who would benefit from elevation of WBC levels using the compounds disclosed herein. Moreover, the disclosure is directed to methods of effecting regeneration of cardiac tissue in a subject in need of such regeneration using the disclosed compounds.

The compounds of the disclosure may be used for the treatment of diseases that are associated with immunosuppression such as individuals undergoing chemotherapy, radiation therapy, enhanced wound healing and burn treatment, therapy for autoimmune disease or other drug therapy (e.g., corticosteroid therapy) or combination of conventional drugs used in the treatment of autoimmune diseases and graft/transplantation rejection, which causes immunosuppression; immunosuppression due to congenital deficiency in receptor function or other causes; and infectious diseases, such as parasitic diseases, including but not limited to helminth infections, such as nematodes (round disclosure thus targets a broad spectrum of conditions for which elevation of progenitor cells and/or stem cells in a subject would be beneficial or, where harvesting of progenitor cells and/or stem cell for subsequent stem cell transplantation would be beneficial. In addition, the method of the disclosure targets a broad spectrum of conditions characterized by a deficiency in white blood cell count, or which would benefit from elevation of said WBC count.

Combination Therapies

In certain embodiments, the disclosure relates to pharmaceutical compositions comprising CXCR4 modulators disclosed herein with another active ingredient.

In certain embodiments, the disclosure relates to administering chemokine CXCR4 receptor modulators disclosed herein in combination with natural ligands of CCR5 and CXCR4. The natural ligands for the chemokine receptors CCR5 (RANTES, MIP-1α, and MIP-1β) and CXCR4 (SDF-1) can act as potent inhibitors of infection by the human immunodeficiency virus type 1 (HIV-1) at the level of viral entry. Unlike antibody-mediated inhibition, chemokine-mediated inhibition is broadly effective. Different HIV-1 strains can utilize the same co-receptor(s) for viral entry and, therefore, can be blocked by the same chemokine(s). HIV-1 strains that are highly resistant to neutralization by V3-specific antibodies are sensitive to inhibition by chemokines Therefore, the use of chemokine-modulators constitutes a therapeutic approach to prevent infection by HIV-1. (Alkhatib et al., *Science*. 1996, 272: 1955-1988 and Challita-Eid et al., *AIDS Research and Human Retroviruses*, 1998, 14(18): 1617-1624).

In some embodiments, the disclosure relates to treating a viral infection by administering a CXCR4 modulator in combination with another, second antiviral agent. In specific embodiments, the compounds described herein are administered in combination or alternation with at least one compound that inhibits HIV entry into a cell through a mechanism not dependent on CXCR4, and in particular embodiments, are administered in combination or alternation with a compound that inhibits CCR5, gp120, gp41 or CD4 binding or activity. In some embodiments, such a compound is at least one of Maraviroc (Celsentri) or Enfuvirtide (Fuzeon). In yet further embodiments such compound is selected from TNX-355, PRO 250, BMS-488043, a theaflavin, Vicriviroc, Gruffithsin, DCM205, ESN196, TBR220, TMB355, Nifeviroc, BMS663068, CYT107, Sifuvirtide, AMD070, PF232798, SP01A.

In further embodiments, the subject is co-administered with abacavir, acyclovir, acyclovir, adefovir, amantadine, amprenavir, ampligen, arbidol, atazanavir, atripla, boceprevir, cidofovir, combivir, darunavir, delavirdine, didanosine, docosanol, edoxudine, efavirenz, emtricitabine, enfuvirtide, entecavir, famciclovir, fomivirsen, fosamprenavir, foscarnet, fosfonet, ganciclovir, ibacitabine, imunovir, idoxuridine, imiquimod, indinavir, inosine, interferon type III, interferon type II, interferon type I, lamivudine, lopinavir, loviride, maraviroc, moroxydine, methisazone, nelfinavir, nevirapine, nexavir, oseltamivir (Tamiflu), peginterferon alfa-2a, penciclovir, peramivir, pleconaril, podophyllotoxin, raltegravir, ribavirin, rimantadine, ritonavir, pyramidine, saquinavir, stavudine, tenofovir, tenofovir disoproxil, tipranavir, trifluridine, trizivir, tromantadine, truvada, valaciclovir (Valtrex), valganciclovir, vicriviroc, vidarabine, viramidine zalcitabine, zanamivir (Relenza), and/or zidovudine.

HIV is typically treated with a combination of antiviral agent, e.g., two nucleoside-analogue reverse transcription inhibitors and one non-nucleoside-analogue reverse transcription inhibitor or protease inhibitor. The three drug combination is commonly known as a triple cocktail. In certain embodiments, the disclosure relates to treating a subject diagnosed with HIV by administering a chemokine CXCR4 receptor modulator disclosed herein in combination with two nucleoside-analogue reverse transcription inhibitors and/or one non-nucleoside-analogue reverse transcription inhibitor or protease inhibitor.

In certain embodiments, the disclosure relates to treating a subject by administering a chemokine CXCR4 receptor modulator disclosed herein, emtricitabine, tenofovir, and efavirenz. In certain embodiments, the disclosure relates to treating a subject by administering a chemokine CXCR4 receptor modulator disclosed herein, emtricitabine, tenofovir and raltegravir. In certain embodiments, the disclosure relates to treating a subject by administering a chemokine CXCR4 receptor modulator disclosed herein, emtricitabine, tenofovir, ritonavir and darunavir. In certain embodiments, the disclosure relates to treating a subject by administering a chemokine CXCR4 receptor modulator disclosed herein, emtricitabine, tenofovir, ritonavir and atazanavir.

In certain embodiments, the disclosure relates to administering a CXCR4 antagonist disclosed herein in combination with a CCR5 antagonist such as maraviroc (selzentry) or vicriviroc.

Banana lectin (BanLec or BanLec-1) is one of the predominant proteins in the pulp of ripe bananas and has binding specificity for mannose and mannose-containing oligosaccharides. BanLec binds to the HIV-1 envelope protein gp120. In certain embodiments, the disclosure relates to treating viral infections, such as HIV, by administering a chemokine CXCR4 receptor modulator disclosed herein in combination with a banana lectin.

The cancer treatment may be applied as a sole therapy or may involve, conventional surgery or radiotherapy or chemotherapy. Such chemotherapy may include one or more of the following categories of anti-tumour agents:

(i) antiproliferative/antineoplastic drugs and combinations thereof, as used in medical oncology, such as alkylating agents (for example cis-platin, carboplatin, cyclophosphamide, nitrogen mustard, melphalan, chlorambucil, busulfan and nitrosoureas); antimetabolites (for example antifolates such as fluoropyrimidines like 5-fluorouracil and gemcitabine, tegafur, raltitrexed, methotrexate, cytosine arabinoside and hydroxyurea); antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere); and topoisomerase inhibitors (for example epipodophyllotoxins like etoposide and teniposide, amsacrine, topotecan and camptothecin); and proteosome inhibitors (for example bortezomib [Velcade®]); and the agent anegrilide [Agrylin®]; and the agent alpha-interferon (ii) cytostatic agents such as antioestrogens (for example tamoxifen, toremifene, raloxifene, droloxifene and iodoxyfene), oestrogen receptor down regulators (for example fulvestrant), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) agents which inhibit cancer cell invasion (for example metalloproteinase inhibitors like marimastat and inhibitors of urokinase plasminogen activator receptor function);

(iv) inhibitors of growth factor function, for example such inhibitors include growth factor antibodies, growth factor receptor antibodies (for example the anti-Her2 antibody trastuzumab and the anti-epidermal growth factor receptor (EGFR) antibody, cetuximab), farnesyl transferase inhibitors, tyrosine kinase inhibitors and serine/threonine kinase inhibitors, for example inhibitors of the epidermal growth factor family (for example EGFR family tyrosine kinase inhibitors such as: N-(3-chloro-4-fluorophenyl)-7-methoxy-6-(3-morpholinopropoxy)quinazolin-4-amine (gefitinib), N-(3-ethynylphenyl)-6,7-bis(2-methoxyethoxy)quinazolin-4-amine (erlotinib), and 6-acrylamido-N-(3-chloro-4-fluorophenyl)-7-(3-morpholinopropoxy)quinazoli-n-4-amine (CI 1033), for example inhibitors of the platelet-derived growth factor family and for example inhibitors of the hepatocyte growth factor family, for example inhibitors or phosphotidylinositol 3-kinase (PI3K) and for example inhibitors of mitogen activated protein kinase kinase (MEK1/2) and for example inhibitors of protein kinase B (PKB/Akt), for example inhibitors of Src tyrosine kinase family and/or Abelson (AbI) tyrosine kinase family such as dasatinib (BMS-354825) and imatinib mesylate (Gleevec™); and any agents that modify STAT signalling;

(v) antiangiogenic agents such as those which inhibit the effects of vascular endothelial growth factor, (for example the anti-vascular endothelial cell growth factor antibody bevacizumab [Avastin™]) and compounds that work by other mechanisms (for example linomide, inhibitors of integrin ocvβ3 function and angiostatin);

(vi) vascular damaging agents such as Combretastatin A4;

(vii) antisense therapies, for example those which are directed to the targets listed above, such as an anti-ras antisense; and (viii) immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies, and approaches using the immunomodulatory drugs thalidomide and lenalidomide [Revlimid®].

Formulations

Pharmaceutical compositions disclosed herein may be in the form of pharmaceutically acceptable salts, as generally described below. Some preferred, but non-limiting examples of suitable pharmaceutically acceptable organic and/or inorganic acids are hydrochloric acid, hydrobromic acid, sulfuric acid, nitric acid, acetic acid and citric acid, as well as other pharmaceutically acceptable acids known per se (for which reference is made to the references referred to below).

When the compounds of the disclosure contain an acidic group as well as a basic group, the compounds of the disclosure may also form internal salts, and such compounds are within the scope of the disclosure. When a compound contains a hydrogen-donating heteroatom (e.g. NH), salts are contemplated to covers isomers formed by transfer of said hydrogen atom to a basic group or atom within the molecule.

Pharmaceutically acceptable salts of the compounds include the acid addition and base salts thereof. Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts. Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts. Hemisalts of acids and bases may also be formed, for example, hemisulphate and hemicalcium salts. For a review on suitable salts, see Handbook of Pharmaceutical Salts: Properties, Selection, and Use by Stahl and Wermuth (Wiley-VCH, 2002), incorporated herein by reference.

The compounds described herein may be administered in the form of prodrugs. A prodrug can include a covalently bonded carrier which releases the active parent drug when administered to a mammalian subject. Prodrugs can be prepared by modifying functional groups present in the compounds in such a way that the modifications are cleaved, either in routine manipulation or in vivo, to the parent compounds. Prodrugs include, for example, compounds wherein a hydroxyl group is bonded to any group that, when administered to a mammalian subject, cleaves to form a free hydroxyl group. Examples of prodrugs include, but are not limited to, acetate, formate and benzoate derivatives of alcohol functional groups in the compounds. Methods of structuring a compound as prodrugs can be found in the book of Testa and Mayer, Hydrolysis in Drug and Prodrug Metabolism, Wiley (2006). Typical prodrugs form the active metabolite by transformation of the prodrug by hydrolytic enzymes, the hydrolysis of amide, lactams, peptides, carboxylic acid esters, epoxides or the cleavage of esters of inorganic acids. Pharmaceutical compositions for use in the present disclosure typically comprise an effective amount of a compound and a suitable pharmaceutical acceptable carrier. The preparations may be prepared in a manner known per se, which usually involves mixing the at least one compound according to the disclosure with the one or more pharmaceutically acceptable carriers, and, if desired, in combination with other pharmaceutical active compounds, when necessary under aseptic conditions. Reference is again made to U.S. Pat. Nos. 6,372,778, 6,369,086, 6,369,087 and 6,372,733 and the further references mentioned above, as well as to the standard handbooks, such as the latest edition of Remington's Pharmaceutical Sciences.

Generally, for pharmaceutical use, the compounds may be formulated as a pharmaceutical preparation comprising at least one compound and at least one pharmaceutically acceptable carrier, diluent or excipient and/or adjuvant, and optionally one or more further pharmaceutically active compounds.

The pharmaceutical preparations of the disclosure are preferably in a unit dosage form, and may be suitably packaged, for example in a box, blister, vial, bottle, sachet, ampoule or in any other suitable single-dose or multi-dose holder or container (which may be properly labeled); optionally with one or more leaflets containing product information and/or instructions for use. Generally, such unit dosages will contain between 1 and 1000 mg, and usually between 5 and 500 mg, of the at least one compound of the disclosure, e.g. about 10, 25, 50, 100, 200, 300 or 400 mg per unit dosage.

The compounds can be administered by a variety of routes including the oral, ocular, rectal, transdermal, subcutaneous, intravenous, intramuscular or intranasal routes, depending mainly on the specific preparation used. The compound will generally be administered in an "effective amount", by which is meant any amount of a compound that, upon suitable administration, is sufficient to achieve the desired therapeutic or prophylactic effect in the subject to which it is administered. Usually, depending on the condition to be prevented or treated and the route of administration, such an effective amount will usually be between 0.01 to 1000 mg per kilogram body weight of the patient per day, more often between 0.1 and 500 mg, such as between 1 and 250 mg, for example about 5, 10, 20, 50, 100, 150, 200 or 250 mg, per kilogram body weight of the patient per day, which may be administered as a single daily dose, divided over one or more daily doses. The amount(s) to be administered, the route of administration and the further treatment regimen may be determined by the treating clinician, depending on factors such as the age, gender and general condition of the patient and the nature and severity of the disease/symptoms to be treated. Reference is again made to U.S. Pat. Nos. 6,372,778; 6,369,086; 6,369,087; and 6,372,733 and the further references mentioned above, as well as to the standard handbooks, such as the latest edition of Remington's Pharmaceutical Sciences.

Depending upon the manner of introduction, the compounds described herein may be formulated in a variety of ways. Formulations containing one or more compounds can be prepared in various pharmaceutical forms, such as granules, tablets, capsules, suppositories, powders, controlled release formulations, suspensions, emulsions, creams, gels, ointments, salves, lotions, or aerosols and the like. Preferably, these formulations are employed in solid dosage forms suitable for simple, and preferably oral, administration of precise dosages. Solid dosage forms for oral administration include, but are not limited to, tablets, soft or hard gelatin or non-gelatin capsules, and caplets. However, liquid dosage forms, such as solutions, syrups, suspension, shakes, etc. can also be utilized. In another embodiment, the formulation is administered topically. Suitable topical formulations include, but are not limited to, lotions, ointments, creams, and gels. In a preferred embodiment, the topical formulation is a gel. In another embodiment, the formulation is administered intranasally.

Formulations containing one or more of the compounds described herein may be prepared using a pharmaceutically acceptable carrier composed of materials that are considered safe and effective and may be administered to an individual without causing undesirable biological side effects or unwanted interactions. The carrier is all components present in the pharmaceutical formulation other than the active ingredient or ingredients. As generally used herein "carrier" includes, but is not limited to, diluents, binders, lubricants, disintegrators, fillers, pH modifying agents, preservatives, antioxidants, solubility enhancers, and coating compositions.

Carrier also includes all components of the coating composition which may include plasticizers, pigments, colorants, stabilizing agents, and glidants. Delayed release, extended release, and/or pulsatile release dosage formulations may be prepared as described in standard references such as "Pharmaceutical dosage form tablets", eds. Liberman et. al. (New York, Marcel Dekker, Inc., 1989), "Remington—The science and practice of pharmacy", 20th ed., Lippincott Williams & Wilkins, Baltimore, Md., 2000, and "Pharmaceutical dosage forms and drug delivery systems", 6th Edition, Ansel et al., (Media, Pa.: Williams and Wilkins, 1995). These references provide information on carriers, materials, equipment and process for preparing tablets and capsules and delayed release dosage forms of tablets, capsules, and granules.

Examples of suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides.

Additionally, the coating material may contain conventional carriers such as plasticizers, pigments, colorants, glidants, stabilization agents, pore formers and surfactants.

Optional pharmaceutically acceptable excipients present in the drug-containing tablets, beads, granules or particles include, but are not limited to, diluents, binders, lubricants, disintegrants, colorants, stabilizers, and surfactants. Diluents, also referred to as "fillers," are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powdered sugar.

Binders are used to impart cohesive qualities to a solid dosage formulation, and thus ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone.

Lubricants are used to facilitate tablet manufacture. Examples of suitable lubricants include, but are not limited to, magnesium stearate, calcium stearate, stearic acid, glycerol behenate, polyethylene glycol, talc, and mineral oil.

Disintegrants are used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross linked polymers, such as cross-linked PVP (Polyplasdone XL from GAF Chemical Corp).

Stabilizers are used to inhibit or retard drug decomposition reactions which include, by way of example, oxidative reactions.

Surfactants may be anionic, cationic, amphoteric or nonionic surface active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-3-alanine, sodium N-lauryl-3-iminodipropionate, myristoamphoacetate, lauryl betaine and lauryl sulfobetaine.

If desired, the tablets, beads, granules, or particles may also contain minor amounts of nontoxic auxiliary substances such as wetting or emulsifying agents, dyes, pH buffering agents, or preservatives.

The concentration of the compound(s) to carrier and/or other substances may vary from about 0.5 to about 100 wt. % (weight percent). For oral use, the pharmaceutical formulation will generally contain from about 5 to about 100% by weight of the active material. For other uses, the pharmaceutical formulation will generally have from about 0.5 to about 50 wt. % of the active material.

The compositions described herein can be formulated for modified or controlled release. Examples of controlled release dosage forms include extended release dosage forms, delayed release dosage forms, pulsatile release dosage forms, and combinations thereof.

The extended release formulations are generally prepared as diffusion or osmotic systems, for example, as described in "Remington—The science and practice of pharmacy" (20th ed., Lippincott Williams & Wilkins, Baltimore, Md., 2000). A diffusion system typically consists of two types of devices, a reservoir and a matrix, and is well known and described in the art. The matrix devices are generally prepared by compressing the drug with a slowly dissolving polymer carrier into a tablet form. The three major types of materials used in the preparation of matrix devices are insoluble plastics, hydrophilic polymers, and fatty compounds. Plastic matrices include, but are not limited to, methyl acrylate-methyl methacrylate, polyvinyl chloride, and polyethylene. Hydrophilic polymers include, but are not limited to, cellulosic polymers such as methyl and ethyl cellulose, hydroxyalkylcelluloses such as hydroxypropylcellulose, hydroxypropylmethylcellulose, sodium carboxymethylcellulose, and Carbopol® 934, polyethylene oxides and mixtures thereof. Fatty compounds include, but are not limited to, various waxes such as carnauba wax and glyceryl tristearate and wax-type substances including hydrogenated castor oil or hydrogenated vegetable oil, or mixtures thereof.

In certain preferred embodiments, the plastic material is a pharmaceutically acceptable acrylic polymer, including but not limited to, acrylic acid and methacrylic acid copolymers, methyl methacrylate, methyl methacrylate copolymers, ethoxyethyl methacrylates, cyanoethyl methacrylate, aminoalkyl methacrylate copolymer, poly(acrylic acid), poly(methacrylic acid), methacrylic acid alkylamine copolymer poly(methyl methacrylate), poly(methacrylic acid)(anhydride), polymethacrylate, polyacrylamide, poly(methacrylic acid anhydride), and glycidyl methacrylate copolymers.

In certain preferred embodiments, the acrylic polymer is comprised of one or more ammonio methacrylate copolymers. Ammonio methacrylate copolymers are well known in the art, and are described in NF XVII as fully polymerized copolymers of acrylic and methacrylic acid esters with a low content of quaternary ammonium groups.

In one preferred embodiment, the acrylic polymer is an acrylic resin lacquer such as that which is commercially available from Rohm Pharma under the tradename Eudragit®. In further preferred embodiments, the acrylic polymer comprises a mixture of two acrylic resin lacquers commercially available from Rohm Pharma under the tradenames Eudragit® RL30D and Eudragit® RS30D, respectively. Eudragit® RL30D and Eudragit® RS30D are copolymers of acrylic and methacrylic esters with a low content of quaternary ammonium groups, the molar ratio of ammonium groups to the remaining neutral (meth)acrylic esters being 1:20 in Eudragit® RL30D and 1:40 in Eudragit® RS30D. The mean molecular weight is about 150,000. Edragit® S-100 and Eudragit® L-100 are also preferred. The code designations RL (high permeability) and RS (low permeability) refer to the permeability properties of these agents. Eudragit® RL/RS mixtures are insoluble in water and in digestive fluids. However, multiparticulate systems formed to include the same are swellable and permeable in aqueous solutions and digestive fluids.

The polymers described above such as Eudragit® RL/RS may be mixed together in any desired ratio in order to ultimately obtain a sustained-release formulation having a desirable dissolution profile. Desirable sustained-release multiparticulate systems may be obtained, for instance, from 100% Eudragit® RL, 50% Eudragit® RL and 50% Eudragit® RS, and 10% Eudragit® RL and 90% Eudragit® RS. One skilled in the art will recognize that other acrylic polymers may also be used, such as, for example, Eudragit® L.

Alternatively, extended release formulations can be prepared using osmotic systems or by applying a semi-permeable coating to the dosage form. In the latter case, the desired drug release profile can be achieved by combining low permeable and high permeable coating materials in suitable proportion.

The devices with different drug release mechanisms described above can be combined in a final dosage form comprising single or multiple units. Examples of multiple units include, but are not limited to, multilayer tablets and capsules containing tablets, beads, or granules. An immediate release portion can be added to the extended release system by means of either applying an immediate release layer on top of the extended release core using a coating or compression process or in a multiple unit system such as a capsule containing extended and immediate release beads.

Extended release tablets containing hydrophilic polymers are prepared by techniques commonly known in the art such as direct compression, wet granulation, or dry granulation. Their formulations usually incorporate polymers, diluents, binders, and lubricants as well as the active pharmaceutical ingredient. The usual diluents include inert powdered substances such as starches, powdered cellulose, especially crystalline and microcrystalline cellulose, sugars such as fructose, mannitol and sucrose, grain flours and similar edible powders. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders include substances such as starch, gelatin and sugars such as lactose, fructose, and glucose. Natural and synthetic gums, including acacia, alginates, methylcellulose, and polyvinylpyrrolidone can also be used. Polyethylene glycol, hydrophilic polymers, ethylcellulose and waxes can also serve as binders. A lubricant is necessary in a tablet formulation to prevent the tablet and punches from sticking in the die. The lubricant is chosen from such slippery solids as talc, magnesium and calcium stearate, stearic acid and hydrogenated vegetable oils.

Extended release tablets containing wax materials are generally prepared using methods known in the art such as a direct blend method, a congealing method, and an aqueous dispersion method. In the congealing method, the drug is mixed with a wax material and either spray-congealed or congealed and screened and processed.

Delayed release formulations are created by coating a solid dosage form with a polymer film, which is insoluble in the acidic environment of the stomach, and soluble in the neutral environment of the small intestine.

The delayed release dosage units can be prepared, for example, by coating a drug or a drug-containing composition with a selected coating material. The drug-containing composition may be, e.g., a tablet for incorporation into a capsule, a tablet for use as an inner core in a "coated core" dosage form, or a plurality of drug-containing beads, particles or granules, for incorporation into either a tablet or capsule. Preferred coating materials include bioerodible, gradually hydrolyzable, gradually water-soluble, and/or enzymatically degradable polymers, and may be conventional "enteric" polymers. Enteric polymers, as will be appreciated by those skilled in the art, become soluble in the higher pH environment of the lower gastrointestinal tract or slowly erode as the dosage form passes through the gastrointestinal tract, while enzymatically degradable polymers are degraded by bacterial enzymes present in the lower gastrointestinal tract, particularly in the colon. Suitable coating materials for effecting delayed release include, but are not limited to, cellulosic polymers such as hydroxypropyl cellulose, hydroxyethyl cellulose, hydroxymethyl cellulose, hydroxypropyl methyl cellulose, hydroxypropyl methyl cellulose acetate succinate, hydroxypropylmethyl cellulose phthalate, methylcellulose, ethyl cellulose, cellulose acetate, cellulose acetate phthalate, cellulose acetate trimellitate and carboxymethylcellulose sodium; acrylic acid polymers and copolymers, preferably formed from acrylic acid, methacrylic acid, methyl acrylate, ethyl acrylate, methyl methacrylate and/or ethyl methacrylate, and other methacrylic resins that are commercially available under the tradename Eudragit® (Rohm Pharma; Westerstadt, Germany), including Eudragit® L30D-55 and L100-55 (soluble at pH 5.5 and above), Eudragit® L-100 (soluble at pH 6.0 and above), Eudragit® S (soluble at pH 7.0 and above, as a result of a higher degree of esterification), and Eudragits® NE, RL and RS (water-insoluble polymers having different degrees of permeability and expandability); vinyl polymers and copolymers such as polyvinyl pyrrolidone, vinyl acetate, vinylacetate phthalate, vinylacetate crotonic acid copolymer, and ethylene-vinyl acetate copolymer; enzymatically degradable polymers such as azo polymers, pectin, chitosan, amylose and guar gum; zein and shellac. Combinations of different coating materials may also be used. Multi-layer coatings using different polymers may also be applied.

The preferred coating weights for particular coating materials may be readily determined by those skilled in the art by evaluating individual release profiles for tablets, beads and granules prepared with different quantities of various coating materials. It is the combination of materials, method and form of application that produce the desired release characteristics, which one can determine only from the clinical studies.

The coating composition may include conventional additives, such as plasticizers, pigments, colorants, stabilizing agents, glidants, etc. A plasticizer is normally present to reduce the fragility of the coating, and will generally represent about 10 wt. % to 50 wt. % relative to the dry weight of the polymer. Examples of typical plasticizers include polyethylene glycol, propylene glycol, triacetin, dimethyl phthalate, diethyl phthalate, dibutyl phthalate, dibutyl sebacate, triethyl citrate, tributyl citrate, triethyl acetyl citrate, castor oil and acetylated monoglycerides. A stabilizing agent is preferably used to stabilize particles in the dispersion. Typical stabilizing agents are nonionic emulsifiers such as sorbitan esters, polysorbates and polyvinylpyrrolidone. Glidants are recommended to reduce sticking effects during film formation and drying, and will generally represent approximately 25 wt. % to 100 wt. % of the polymer weight in the coating solution. One effective glidant is talc. Other glidants such as magnesium stearate and glycerol monostearates may also be used. Pigments such as titanium dioxide may also be used. Small quantities of an anti-foaming agent, such as a silicone (e.g., simethicone), may also be added to the coating composition.

The formulation can provide pulsatile delivery of the one or more compounds. By "pulsatile" is meant that a plurality of drug doses is released at spaced apart intervals of time. Generally, upon ingestion of the dosage form, release of the initial dose is substantially immediate, i.e., the first drug release "pulse" occurs within about one hour of ingestion. This initial pulse is followed by a first time interval (lag time) during which very little or no drug is released from the dosage form, after which a second dose is then released. Similarly, a second nearly drug release-free interval between the second and third drug release pulses may be designed. The duration of the nearly drug release-free time interval will vary depending upon the dosage form design e.g., a twice daily dosing profile, a three times daily dosing profile, etc. For dosage forms providing a twice daily dosage profile, the nearly drug release-free interval has a duration of approximately 3 hours to 14 hours between the first and second dose. For dosage forms providing a three times daily profile, the nearly drug release-free interval has a duration of approximately 2 hours to 8 hours between each of the three doses.

In one embodiment, the pulsatile release profile is achieved with dosage forms that are closed and preferably sealed capsules housing at least two drug-containing "dosage units" wherein each dosage unit within the capsule provides a different drug release profile. Control of the delayed release dosage unit(s) is accomplished by a controlled release polymer coating on the dosage unit, or by incorporation of the active agent in a controlled release polymer matrix. Each dosage unit may comprise a compressed or molded tablet, wherein each tablet within the capsule provides a different drug release profile. For dosage forms mimicking a twice a day dosing profile, a first tablet releases drug substantially immediately following ingestion of the dosage form, while a second tablet releases drug approximately 3 hours to less than 14 hours following ingestion of the dosage form. For dosage forms mimicking a three times daily dosing profile, a first tablet releases drug substantially immediately following ingestion of the dosage form, a second tablet releases drug approximately 3 hours to less than 10 hours following ingestion of the dosage form, and the third tablet releases drug at least 5 hours to approximately 18 hours following ingestion of the dosage form. It is possible that the dosage form includes more than three tablets. While the dosage form will not generally include more than a third tablet, dosage forms housing more than three tablets can be utilized.

Alternatively, each dosage unit in the capsule may comprise a plurality of drug-containing beads, granules or particles. As is known in the art, drug-containing "beads" refer to beads made with drug and one or more excipients or polymers. Drug-containing beads can be produced by applying drug to an inert support, e.g., inert sugar beads coated with drug or by creating a "core" comprising both drug and one or more excipients. As is also known, drug-containing "granules" and "particles" comprise drug particles that may or may not include one or more additional excipients or polymers. In contrast to drug-containing beads, granules and particles do not contain an inert support. Granules generally comprise drug particles and require further processing. Generally, particles are smaller than granules, and are not further processed. Although beads, granules and particles may be formulated to provide immediate release, beads and granules are generally employed to provide delayed release.

In one embodiment, the compound is formulated for topical administration. Suitable topical dosage forms include lotions, creams, ointments, and gels. A "gel" is a semisolid system containing a dispersion of the active agent, i.e., Nox inhibitor, in a liquid vehicle that is rendered semisolid by the action of a thickening agent or polymeric material dissolved or suspended in the liquid vehicle. The liquid may include a lipophilic component, an aqueous component or both. Some emulsions may be gels or otherwise include a gel component. Some gels, however, are not emulsions because they do not contain a homogenized blend of immiscible components. Methods for preparing lotions, creams, ointments, and gels are well known in the art.

The compounds described herein can be administered adjunctively with other active compounds. These compounds include but are not limited to analgesics, anti-inflammatory drugs, antipyretics, antidepressants, antiepileptics, antihistamines, antimigraine drugs, antimuscarinics, anxioltyics, sedatives, hypnotics, antipsychotics, bronchodilators, anti-asthma drugs, cardiovascular drugs, corticosteroids, dopaminergics, electrolytes, gastro-intestinal drugs, muscle relaxants, nutritional agents, vitamins, parasympathomimetics, stimulants, anorectics and anti-narcoleptics. "Adjunctive administration", as used herein, means the compounds can be administered in the same dosage form or in separate dosage forms with one or more other active agents.

The additional active agent(s) can be formulated for immediate release, controlled release, or combinations thereof.

The present disclosure will now be described in more detail with reference to the following non-limiting examples. It should be noted that the particular assays used in the examples section are designed to provide an indication of activity. There are many other assays available to determine the activity of given compounds and a result in any one particular assay is therefore not determinative.

EXPERIMENTAL

General Procedures:

Unless otherwise indicated, all reactions were conducted in oven (150° C.) or flame-dried glassware using distilled and degassed solvents under positive pressure of dry argon with standard Schlenk techniques. Stainless steel syringes or cannulae that had been oven-dried (150° C.) and cooled under an argon atmosphere or in a desiccator were used to transfer air- and moisture-sensitive liquids. Yields refer to chromatographically (LC-MS (ESI-API, 254 nm) MeOH in $H_2O$ (0.1% $HCO_2H$), C18 (Agilent Zorbax XDB-18, 50 mm×4.6 mm, 3.5 µm), m/z and spectroscopically ($^1$H NMR) homogeneous materials, unless otherwise stated. Reactions were monitored by thin-layer chromatography (TLC) carried out on pre-coated glass plates of silica gel (0.25 mm) 60 $F_{254}$ using the indicated solvent system. Visualization was accomplished with ultraviolet light (UV 254 nm), or by shaking the plate in a sealed jar containing silica gel and Iodine. Alternatively, plates were treated with one of the following solutions (this was accomplished by holding the edge of the TLC plate with forceps or tweezers and immersing the plate into a wide-mouth jar containing the desired staining solution) and carefully heating with a hot-air gun (450° C.) for approximately 1-2 min (NOTE: excess stain was removed by resting the TLC on a paper towel prior to heating): 10% phosphomolybdic acid in ethanol, 1% potassium permanganate/7% potassium carbonate/0.5% sodium hydroxide aqueous solution, and/or anisaldehyde in ethanol with 10% sulfuric acid. Flash column chromatography was performed using Silica Flash® P60 silica gel (40-63 µm) from Silicycle, or Teledyne Isco Combiflash. All work-up and purification procedures were carried out with reagent grade solvents in air.

General Procedure A:

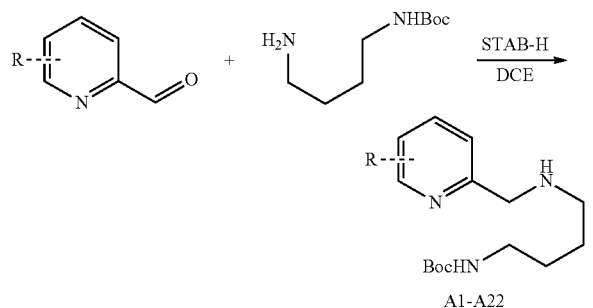

Tert-butyl (4-aminobutyl)carbamate (1.05-1.1 equiv.), DCE (0.5M) and substituted aldehyde (1.0 equiv.) were stirred at room temperature followed by the addition of STAB-H (1.5-1.8 equiv.) in three portions. The reaction was stirred at RT over-night (12-18 h) then diluted with DCM and washed with 1.0M NaOH. The organics were separated, dried with $Na_2SO_4$, filtered and concentrated then purified via silica gel chromatography (combiflash, DCM:Mixture B{80:20:3, DCM:MeOH:$NH_4OH$}, 0% B for 5 minutes, 10% B for 8 minutes, 50% B for 8 minutes). All purifications were conducted using this standard mixture unless otherwise noted. To afford A1-A22

Following general procedure A, tert-butyl (4-aminobutyl) carbamate (1.933 g, 10.27 mmol), DCE (Volume: 20 ml) and picolinaldehyde (0.888 ml, 9.34 mmol) followed by STAB-H (2.97 g, 14.00 mmol) were combined and stirred overnight. Purification via combiflash yielded tert-butyl (4-((pyridin-2-ylmethyl)amino)butyl)carbamate A1 (1.8 g, 6.44 mmol, 69% yield) as a yellow oil. $^1$H NMR (400 MHz, $CDCl_3$): δ=8.55 (dd, J=5.0, 1.2 Hz, 1H), 7.63 (dt, J=7.6, 1.8 Hz, 1H), 7.29 (d, J=7.8 Hz, 1H), 7.15 (dd, J=7.5, 5.0 Hz, 1H), 4.76 (s, 1H), 3.90 (s, 2H), 3.12 (q, J 4.1 Hz, 2H), 2.67 (t, J=6.6 Hz, 2H), 1.60-1.50 (m, 4H), 1.43 (s, 9H); LC/MS 75-95% MeOH in $H_2O$ over 3 minutes, $r_t$=0.527 at 254 nM, MS (+) 280.2.

Following general procedure A, tert-butyl (4-aminobutyl) carbamate (2.1 g, 11.15 mmol), DCE (Volume: 40 mL) and 3-methylpicolinaldehyde (0.98 g, 8.1 mmol) followed by STAB-H (3.25 g, 15.3 mmol) were combined and stirred overnight. Purification via combiflash yielded tert-butyl (4-((3-methylpyridin-2-ylmethyl)amino)butyl)carbamate A2 (1.98 g, 6.72 mmol, 83% yield) as a yellow oil. $^1$H NMR (400 MHz, $CDCl_3$): δ=8.38 (d, J=4.7 Hz, 1H), 7.42 (dq, J=7.6, 0.8 Hz, 1H), 7.07 (dd, J=7.6, 4.8 Hz, 1H), 4.76 (s, 1H), 3.87 (s, 2H), 3.13 (q, J=7.2 Hz, 2H), 2.72 (t, J=6.4 Hz, 2H), 1.61-1.56 (m, 4H), 1.43 (s, 9H); LC/MS 75-95% MeOH in $H_2O$ over 3 minutes, $r_t$=0.488 at 254 nM, MS (+) 292.2.

Following general procedure A, tert-butyl (4-aminobutyl) carbamate (1.318 g, 7.00 mmol), DCE (Volume: 15.91 ml), quinoline-2-carbaldehyde (1.0 g, 6.36 mmol) and STAB-H (2.023 g, 9.54 mmol) were stirred overnight. Purification via combiflash yielded tert-butyl (4-((quinolin-2-ylmethyl) amino)butyl)carbamate A3 (1.1 g, 3.34 mmol, 53% yield). $^1$H NMR (400 MHz, $CDCl_3$): δ=8.12 (d, J=8.5 Hz, 1H), 8.05

(d, J=8.5 Hz, 1H), 7.80 (d, J=8.4 Hz, 1H), 7.70 (dt, J=8.4, 1.2 Hz, 1H), 7.52 (dt, J=8.4, 1.2 Hz, 1H), 7.45 (d, J=8.5 Hz, 1H), 4.76 (s, 1H), 4.12 (s, 2H), 3.14 (q, J=6.6 Hz, 2H), 2.77 (t, J=6.4 Hz, 2H), 1.63-1.57 (m, 4H), 1.42 (s, 9H); LC/MS 75-95% MeOH in H$_2$O over 3 minutes, r$_f$=0.509 at 254 nM, MS (+) 330.2.

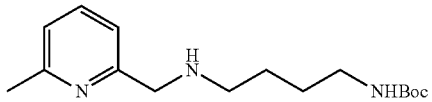 [SMILES: Cc1cccc(CNCCCCNC(=O)OC(C)(C)C)n1]

Following general procedure A, tert-butyl (4-aminobutyl) carbamate (1.658 ml, 8.67 mmol), DCE (Volume: 16.51 ml), 6-methylpicolinaldehyde (1 g, 8.26 mmol) and STAB-H (2.62 g, 12.38 mmol) were stirred overnight. Purification via combiflash yielded tert-butyl (4-(((6-methylpyridin-2-yl)methyl)amino)butyl)carbamate A4 (0.7 g, 2.386 mmol, 29% yield). $^1$H NMR (400 MHz, CDCl$_3$): δ=7.51 (t, J=7.6 Hz, 1H), 7.09 (d, J=7.6 Hz, 1H), 7.00 (d, J=7.6 Hz, 1H), 4.77 (s, 1H), 3.84 (s, 2H), 3.12 (q, J=6.4 Hz, 2H), 2.66 (t, J=6.3 Hz, 2H), 1.59-1.47 (m, 4H), 1.43 (s, 9H); LC/MS 75-95% MeOH in H$_2$O over 3 minutes, r$_f$=0.503 at 254 nM, MS (+) 294.2.

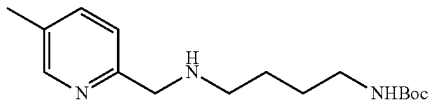 [SMILES: Cc1ccc(CNCCCCNC(=O)OC(C)(C)C)nc1]

Following general procedure A, tert-butyl (4-aminobutyl) carbamate (1.658 ml, 8.67 mmol), DCE (Volume: 16.51 ml), 5-methylpicolinaldehyde (1 g, 8.26 mmol) and STAB-H (2.62 g, 12.38 mmol) were stirred overnight. Purification via combiflash yielded tert-butyl (4-(((5-methylpyridin-2-yl)methyl)amino)butyl)carbamate A5 (0.82 g, 2.79 mmol, 34% yield). $^1$H NMR (400 MHz, CDCl$_3$): δ=8.37 (dd, J=2.4, 1.0 Hz 1H), 7.44 (dd, J=7.9, 2.3 Hz, 1H), 7.18 (d, J=7.8 Hz, 1H), 4.77 (s, 1H), 3.84 (s, 2H), 3.12 (q, J=6.0 Hz, 2H), 2.64 (t, J=6.0 Hz, 2H), 1.58-1.53 (m, 4H), 1.43 (s, 9H); LC/MS 75-95% MeOH in H$_2$O over 3 minutes, r$_f$=0.501 at 254 nM, MS (+) 294.2.

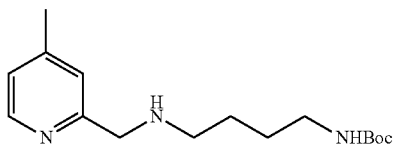 [SMILES: Cc1ccnc(CNCCCCNC(=O)OC(C)(C)C)c1]

Following general procedure A, tert-butyl (4-aminobutyl) carbamate (1.597 ml, 8.35 mmol), DCE (Volume: 15.90 ml), 4-methylpicolinaldehyde (0.963 g, 7.95 mmol) and STAB-H (2.53 g, 11.92 mmol) were stirred overnight. Purification via combiflash yielded tert-butyl (4-(((4-methylpyridin-2-yl)methyl)amino)butyl)carbamate A6 (1.87 g, 6.37 mmol, 80% yield). $^1$H NMR (400 MHz, CDCl$_3$): δ=8.36 (d, J=4.8 Hz, 1H), 7.09 (d, J=4.1 Hz, 1H), 6.96 (d, J=6.0 Hz, 1H), 4.73 (s, 1H), 3.82 (s, 2H), 3.09 (br s, 2H), 2.63 (t, J 5.6 Hz, 2H), 2.32 (s, 3H), 1.53-1.50 (m, 4H), 1.43 (s, 9H); LC/MS 75-95% MeOH in H$_2$O over 3 minutes, r$_f$=0.505 at 254 nM, MS (+) 294.2.

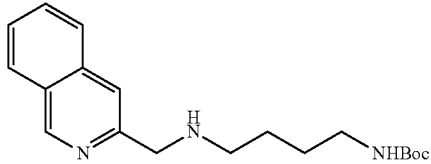 [SMILES: CC(C)(C)OC(=O)NCCCCNCc1cc2ccccc2cn1]

Following general procedure A, tert-butyl (4-aminobutyl) carbamate (0.320 ml, 1.670 mmol), DCE (Volume: 3.18 ml), isoquinoline-3-carbaldehyde (0.25 g, 1.591 mmol) and STAB-H (0.506 g, 2.386 mmol) were stirred overnight. Purification via combiflash yielded tert-butyl (4-((isoquinolin-3-ylmethyl)amino)butyl)carbamate A7 (0.41 g, 1.245 mmol, 78% yield). $^1$H NMR (400 MHz, CDCl$_3$): δ=9.22 (s, 1H), 7.95 (d, J=8.2 Hz, 1H), 7.79 (d, J=8.2 Hz, 1H), 7.68 (dt, J=6.8, 1.3 Hz, 1H), 7.63 (s, 1H), 7.57 (dt, J=8.2, 1.2 Hz, 1H), 4.75 (s, 1H), 4.04 (s, 2H), 3.13 (q, J 6.0 Hz, 2H), 2.70 (t, J 6.0 Hz, 2H), 1.60-1.51 (m, 4H), 1.43 (s, 9H); LC/MS 75-95% MeOH in H$_2$O over 3 minutes, r$_f$=0.508 at 254 nM, MS (+) 330.2.

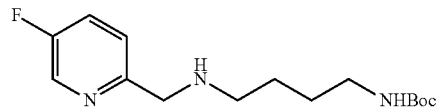 [SMILES: CC(C)(C)OC(=O)NCCCCNCc1ccc(F)cn1]

Following general procedure A, tert-butyl (4-aminobutyl) carbamate (1.655 g, 8.79 mmol), DCE (Volume: 15.99 ml), 5-fluoropicolinaldehyde (1 g, 7.99 mmol) and STAB-H (2.54 g, 11.99 mmol) were stirred overnight. Purification via combiflash yielded tert-butyl (4-(((5-fluoropyridin-2-yl)methyl)amino)butyl)carbamate A8 (1.64 g, 5.52 mmol, 69% yield). $^1$H NMR (400 MHz, CDCl$_3$): δ=8.40 (d, J=2.7 Hz, 1H), 7.35 (dd, J=8.5, 2.8 Hz, 1H), 7.32 (dd, J=8.6, 4.7 Hz, 1H), 4.73 (s, 1H), 3.89 (s, 2H), 3.12 (q, J 6.0 Hz, 2H), 2.67 (t, J 6.6 Hz, 2H), 1.58-1.54 (m, 4H), 1.43 (s, 9H); LC/MS 75-95% MeOH in H$_2$O over 3 minutes, r$_f$=0.498 at 254 nM, MS (+) 298.2.

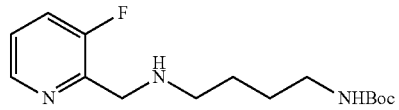 [SMILES: CC(C)(C)OC(=O)NCCCCNCc1ncccc1F]

Following general procedure A, tert-butyl (4-aminobutyl) carbamate (1.655 g, 8.79 mmol), DCE (Volume: 15.99 ml), 3-fluoropicolinaldehyde (1 g, 7.99 mmol) and STAB-H (2.54 g, 11.99 mmol) were stirred overnight. Purification via combiflash yielded tert-butyl (4-(((3-fluoropyridin-2-yl)methyl)amino)butyl)carbamate A9 (1.44 g, 4.84 mmol, 61% yield). $^1$H NMR (400 MHz, CDCl$_3$): δ=8.38 (dt, J=4.7, 1.5 Hz, 1H), 7.35 (ddd, J=9.6, 8.3, 1.4 Hz, 1H), 7.20 (ddd, J=8.3, 4.7, 4.2 Hz, 1H), 4.72 (s, 1H), 3.98 (s, 2H), 3.12 (q, J 4.4 Hz, 2H), 2.68 (t, J 6.8 Hz, 2H), 1.61-1.54 (m, 4H), 1.43 (s, 9H); LC/MS 75-95% MeOH in H$_2$O over 3 minutes, r$_f$=0.484 at 254 nM, MS (+) 298.2.

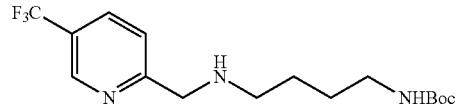 [SMILES: CC(C)(C)OC(=O)NCCCCNCc1ccc(C(F)(F)F)cn1]

Following general procedure A, tert-butyl (4-aminobutyl) carbamate (0.591 g, 3.14 mmol), DCE (Volume: 5.71 ml), 5-(trifluoromethyl)picolinaldehyde (0.5 g, 2.86 mmol) and STAB-H (0.908 g, 4.28 mmol) were stirred overnight. Purification via combiflash yielded tert-butyl (4-(((5-(trifluoromethyl)pyridin-2-yl)methyl)amino)butyl)carbamate A10 (0.716 g, 2.061 mmol, 72% yield). $^1$H NMR (400 MHz, CDCl$_3$): δ=8.81 (s, 1H), 7.88 (dd, J=8.3, 2.4 Hz, 1H), 7.46 (d, J 8.1 Hz, 1H), 4.71 (s, 1H), 3.97 (s, 2H), 3.13 (q, J 6.2 Hz, 2H), 2.66 (t, J 6.5 Hz, 2H), 1.59-1.53 (m, 4H), 1.43 (s, 9H); LC/MS 75-95% MeOH in H$_2$O over 3 minutes, r$_f$=0.497 at 254 nM, MS (+) 348.2.

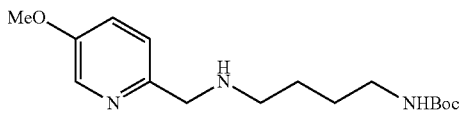 [SMILES: COc1ccc(CNCCCCNC(=O)OC(C)(C)C)nc1]

Following general procedure A, tert-butyl (4-aminobutyl) carbamate (0.755 g, 4.01 mmol), DCE (Volume: 7.29 ml), 5-methoxypicolinaldehyde (0.5 g, 3.65 mmol) and STAB-H (1.159 g, 5.47 mmol) were stirred overnight. Purification via combiflash yielded tert-butyl (4-(((5-methoxypyridin-2-yl)methyl)amino)butyl)carbamate A11 (0.91 g, 2.94 mmol, 81% yield). $^1$H NMR (400 MHz, CDCl$_3$): δ=8.24 (d, J 2.8 Hz, 1H), 7.21 (d, J=8.4 Hz, 1H), 7.15 (dd, J=8.4, 2.8 Hz, 1H), 4.77 (s, 1H), 3.84 (s, 3H), 3.82 (s, 2H), 3.11 (q, J 6.4 Hz, 2H), 2.66 4 (t, J 7.8 Hz, 2H), 1.58-1.47 (m, 4H), 1.43 (s, 9H); LC/MS 75-95% MeOH in H$_2$O over 3 minutes, r$_f$=0.487 at 254 nM, MS (+) 310.2.

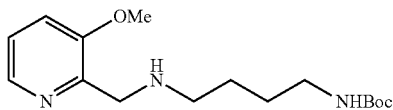 [SMILES: COc1cccnc1CNCCCCNC(=O)OC(C)(C)C]

Following general procedure A, tert-butyl (4-aminobutyl) carbamate (0.755 g, 4.01 mmol), DCE (Volume: 7.29 ml), 3-methoxypicolinaldehyde (0.5 g, 3.65 mmol) and STAB-H (1.159 g, 5.47 mmol) were stirred overnight. Purification via combiflash yielded tert-butyl (4-(((3-methoxypyridin-2-yl)methyl)amino)butyl)carbamate A12 (0.77 g, 2.489 mmol, 68% yield). $^1$H NMR (400 MHz, CDCl$_3$): δ=8.13 (d, J 4.5, 1.6 Hz, 1H), 7.15 (dd, J=8.4, 4.2 Hz, 1H), 7.11 (dd, J=8.4, 1.6 Hz, 1H), 4.76 (s, 1H), 3.93 (s, 2H), 3.84 (s, 3H), 3.12 (q, J 6.8 Hz, 2H), 2.66 (t, J 7.4 Hz, 2H), 1.57-1.51 (m, 4H), 1.43 (s, 9H); LC/MS 75-95% MeOH in H$_2$O over 3 minutes, r$_f$=0.498 at 254 nM, MS (+) 310.2.

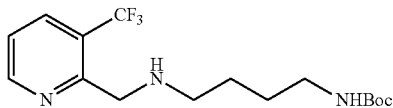 [SMILES: CC(C)(C)OC(=O)NCCCCNCc1ncccc1C(F)(F)F]

Following general procedure A, tert-butyl (4-aminobutyl) carbamate (1.075 g, 5.71 mmol), 3-(trifluoromethyl)picolinaldehyde (0.5 g, 2.86 mmol), DCE (Volume: 5.71 ml) and STAB-H (0.908 g, 4.28 mmol) were stirred overnight. Purification via combiflash yielded tert-butyl (4-(((3-(trifluoromethyl)pyridin-2-yl)methyl)amino)butyl)carbamate A13 (0.660 g, 1.900 mmol, 67% yield). $^1$H NMR (400 MHz, CDCl$_3$): δ=8.73 (d, J 5.0 Hz, 1H), 7.92 (d, J 8.0 Hz, 1H), 7.30 (dd, J 8.5, 5.0 Hz, 1H), 4.73 (s, 1H), 4.05 (s, 2H), 3.12 (q, J 6.1 Hz, 2H), 2.65 (t, J 7.4 Hz, 2H), 1.59-1.51 (m, 4H), 1.43 (s, 9H); LC/MS 75-95% MeOH in H$_2$O over 3 minutes, r$_f$=0.503 at 254 nM, MS (+) 348.2.

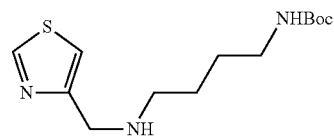 [SMILES: CC(C)(C)OC(=O)NCCCCNCc1cscn1]

Following general procedure A, tert-butyl (4-aminobutyl) carbamate (0.998 g, 5.30 mmol), DCE (Volume: 8.84 ml), thiazole-4-carbaldehyde (0.4 g, 3.54 mmol) and STAB-H (1.349 g, 6.36 mmol) were stirred overnight. Purification via combiflash yielded tert-butyl (4-((thiazol-4-ylmethyl)amino)butyl)carbamate A14 (0.653 g, 2.288 mmol, 65% yield). $^1$H NMR (400 MHz, CDCl$_3$): δ=8.77 (d, J 1.6 Hz, 1H), 7.16 (d, J 1.6 Hz, 1H), 4.75 (s, 1H), 3.95 (s, 2H), 3.12 (q, J 5.0 Hz, 2H), 2.65 (t, J 5.9 Hz, 2H), 1.58-1.50 (m, 4H), 1.43 (s, 9H); LC/MS 75-95% MeOH in H$_2$O over 3 minutes, r$_f$=0.491 at 254 nM, MS (+) 286.0.

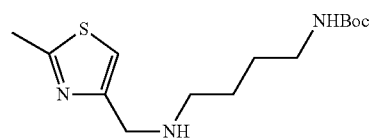 [SMILES: Cc1nc(CNCCCCNC(=O)OC(C)(C)C)cs1]

Following general procedure A, tert-butyl (4-aminobutyl) carbamate (0.666 g, 3.54 mmol), DCE (Volume: 5.90 ml), 2-methylthiazole-4-carbaldehyde (0.3 g, 2.359 mmol) and STAB-H (0.750 g, 3.54 mmol) were stirred overnight. Purification via combiflash yielded tert-butyl (4-(((2-methylthiazol-4-yl)methyl)amino)butyl)carbamate A15 (0.21 g, 0.701 mmol, 30% yield). $^1$H NMR (400 MHz, CDCl$_3$): δ=6.89 (s, 1H), 4.81 (s, 1H), 3.80 (s, 2H), 3.07 (q, J 6.4 Hz, 2H), 2.64 (s, 3H), 2.60 (t, J 7.0 Hz, 2H), 1.50-1.47 (m, 4H), 1.38 (s, 9H).

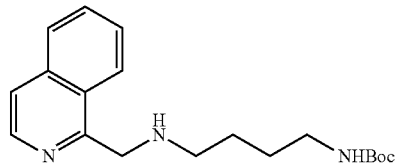 [SMILES: CC(C)(C)OC(=O)NCCCCNCc1nccc2ccccc12]

Following general procedure A, tert-butyl (4-aminobutyl) carbamate (0.659 g, 3.50 mmol), DCE (Volume: 7.95 ml), isoquinoline-1-carbaldehyde (0.5 g, 3.18 mmol) and sodium triacetixyborohydride (1.011 g, 4.77 mmol) were stirred overnight. Purification via combiflash yielded tert-butyl (4-((isoquinolin-1-ylmethyl)amino)butyl)carbamate A16 (0.779 g, 2.365 mmol, 74% yield). $^1$H NMR (400 MHz, CDCl$_3$): δ=8.45 (d, J 5.7 Hz, 1H), 8.17 (dq, J 8.4, 0.9 Hz, 1H), 7.82 (d, J 8.0 Hz, 1H), 7.68 (ddd, J 8.1, 6.8, 1.3 Hz, 1H), 7.60 (ddd, J 8.3, 6.8, 1.4 Hz, 1H), 7.55 (d, J 5.8 Hz, 1H), 4.74 (s, 1H), 4.41 (s, 2H), 3.14 (q, J 6.4 Hz, 2H), 2.80 (t, J 6.8 Hz, 2H), 1.67-1.52 (m, 4H), 1.43 (s, 9H); LC/MS 75-95% MeOH in H$_2$O over 3 minutes, r$_f$=0.518 at 254 nM, MS (+) 330.2.

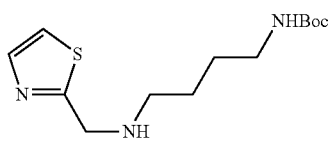 [SMILES: CC(C)(C)OC(=O)NCCCCNCc1nccs1]

Following general procedure A, tert-butyl (4-aminobutyl) carbamate (0.915 g, 4.86 mmol), DCE (Volume: 8.84 ml), thiazole-2-carbaldehyde (0.5 g, 4.42 mmol) and STAB-H (1.405 g, 6.63 mmol) were stirred overnight. Purification via combiflash yielded tert-butyl (4-((thiazol-2-ylmethyl)amino)butyl)carbamate A17 (1.01 g, 3.54 mmol, 80% yield). $^1$H NMR (400 MHz, CDCl$_3$): δ=7.71 (d, J 3.3 Hz, 1H), 7.26 (d, J 4.8 Hz, 1H), 4.64 (s, 1H), 4.12 (s, 2H), 3.12 (q, J 5.1 Hz, 2H), 2.71 (t, J 6.6 Hz, 2H), 1.57-1.53 (m, 4H), 1.43 (s, 9H); LC/MS 75-95% MeOH in H$_2$O over 3 minutes, r$_t$=0.485 at 254 nM, MS (+) 286.2.

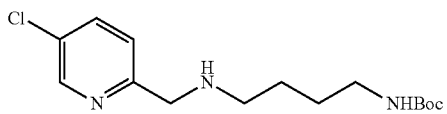 [SMILES: CC(C)(C)OC(=O)NCCCCNCc1ccc(Cl)cn1]

Following general procedure A, tert-butyl (4-aminobutyl) carbamate (1.596 g, 8.48 mmol), DCE (Volume: 17.66 ml), 5-chloropicolinaldehyde (1 g, 7.06 mmol) and STAB-H (2.70 g, 12.72 mmol) were stirred overnight. Purification via combiflash yielded tert-butyl (4-(((5-chloropyridin-2-yl)methyl)amino)butyl)carbamate A18 (1.24 g, 3.95 mmol, 56% yield). $^1$H NMR (400 MHz, CDCl$_3$): δ=8.50 (dd, J=2.5, 0.7 Hz, 1H), 7.61 (dd, J 8.3, 2.5 Hz, 1H), 7.27 (d, J 8.8 Hz, 1H), 4.72 (s, 1H), 3.87 (s, 2H), 3.12 (q, J 6.4 Hz, 2H), 2.65 (t, J 6.7 Hz, 2H), 1.56-1.53 (m, 4H), 1.43 (s, 9H); LC/MS 75-95% MeOH in H$_2$O over 3 minutes, r$_t$=0.483 at 254 nM, MS (+) 314.0.

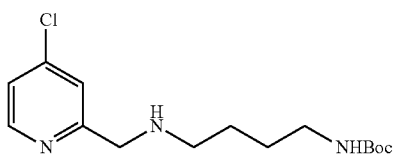 [SMILES: CC(C)(C)OC(=O)NCCCCNCc1cc(Cl)ccn1]

Following general procedure A, tert-butyl (4-aminobutyl) carbamate (1.596 g, 8.48 mmol), DCE (Volume: 14.13 ml), 4-chloropicolinaldehyde (1 g, 7.06 mmol) and STAB-H (2.70 g, 12.72 mmol) were stirred overnight. Purification via combiflash yielded tert-butyl (4-(((4-chloropyridin-2-yl)methyl)amino)butyl)carbamate A19 (1.45 g, 4.62 mmol, 65% yield). $^1$H NMR (400 MHz, CDCl$_3$): δ=8.44 (d, J=5.4 Hz, 1H), 7.35 (d, J 2.0 Hz, 1H), 7.17 (dd, J 5.2, 2.0 Hz, 1H), 4.71 (s, 1H), 3.88 (s, 2H), 3.12 (q, J 5.0 Hz, 2H), 2.65 (t, J 6.8 Hz, 2H), 1.56-1.53 (m, 4H), 1.43 (s, 9H); LC/MS 75-95% MeOH in H$_2$O over 3 minutes, r$_t$=0.480 at 254 nM, MS (+) 314.0.

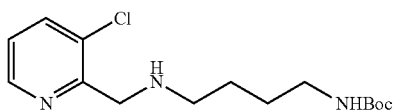

Following general procedure A, tert-butyl (4-aminobutyl) carbamate (0.798 g, 4.24 mmol), DCE (Volume: 8.83 ml), 3-chloropicolinaldehyde (0.5 g, 3.53 mmol) and STAB-H (1.348 g, 6.36 mmol) were stirred overnight. Purification via combiflash yielded tert-butyl (4-(((3-chloropyridin-2-yl)methyl)amino)butyl)carbamate A20 (0.81 g, 2.58 mmol, 73% yield). $^1$H NMR (400 MHz, CDCl$_3$): δ=8.46 (dd, J=4.6, 1.5 Hz, 1H), 7.64 (dd, J 8.0, 1.5 Hz, 1H), 7.14 (dd, J 8.0, 4.6 Hz, 1H), 4.74 (s, 1H), 4.02 (s, 2H), 3.12 (q, J 6.0 Hz, 2H), 2.69 (t, J 6.7 Hz, 2H), 1.60-1.53 (m, 4H), 1.43 (s, 9H); LC/MS 75-95% MeOH in H$_2$O over 3 minutes, r$_t$=0.488 at 254 nM, MS (+) 314.0.

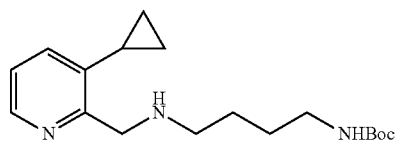 [SMILES: CC(C)(C)OC(=O)NCCCCNCc1ncccc1C1CC1]

Following general procedure A, tert-butyl (4-aminobutyl) carbamate (0.352 g, 1.869 mmol), DCE (Volume: 5.66 ml), 3-cyclopropylpicolinaldehyde (0.25 g, 1.699 mmol) and STAB-H (0.648 g, 3.06 mmol) were stirred overnight. Purification via combiflash yielded tert-butyl (4-(((3-cyclopropylpyridin-2-yl)methyl)amino)butyl)carbamate A21 (0.405 g, 1.268 mmol, 75% yield). $^1$H NMR (400 MHz, CDCl$_3$): δ=8.36 (dd, J=5.5, 0.6 Hz, 1H), 7.33 (d, J 7.6 Hz, 1H), 7.14 (dd, J 7.9, 5.0 Hz, 1H), 4.79 (s, 1H), 4.25 (s, 2H), 3.15 (q, J 6.2 Hz, 2H), 2.90 (t, J 7.2 Hz, 2H), 1.89-1.82 (m, 1H), 1.79-1.53 (m, 4H), 1.43 (s, 9H), 1.03-0.98 (m, 2H), 0.67-0.63 (m, 2H); LC/MS 75-95% MeOH in H$_2$O over 3 minutes, r$_t$=0.498 at 254 nM, MS (+) 320.2.

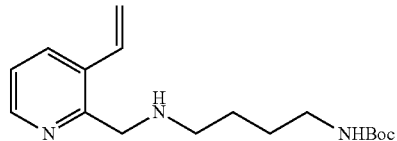 [SMILES: C=Cc1cccnc1CNCCCCNC(=O)OC(C)(C)C]

Following general procedure A, tert-butyl (4-aminobutyl) carbamate (0.296 g, 1.570 mmol), DCE (Volume: 3.57 ml), 3-vinylpicolinaldehyde (0.190 g, 1.427 mmol) and STAB-H (0.544 g, 2.57 mmol) were stirred overnight. Purification via combiflash yielded tert-butyl (4-(((3-vinylpyridin-2-yl)methyl)amino)butyl)carbamate A22 (0.31 g, 1.015 mmol, 71% yield). $^1$H NMR (400 MHz, CDCl$_3$): δ=8.45 (dd, J=4.8, 1.8 Hz, 1H), 7.76 (dd, J 7.8, 1.8 Hz, 1H), 7.19 (dd, J 7.8, 4.8 Hz, 1H), 6.91 (dd, J 17.4, 11.0 Hz, 1H), 5.69 (d, J 17.4 Hz, 1H), 5.44 (d, J 11.0 Hz, 1H), 4.74 (s, 1H), 4.02 (s, 2H), 3.13 (q, J 6.4 Hz, 2H), 2.76 (t, J 6.7 Hz, 2H), 1.67-1.52 (m, 4H), 1.43 (s, 9H); LC/MS 75-95% MeOH in H$_2$O over 3 minutes, r$_t$=0.497 at 254 nM, MS (+) 306.2.

General Procedure B: Scheme 1: Two Step Procedure

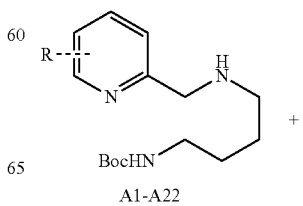

A1-A22

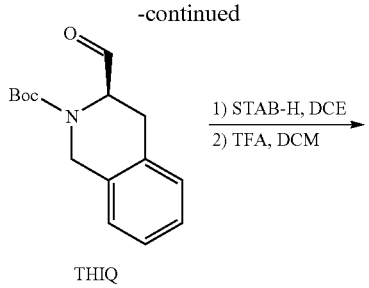

THIQ

1) STAB-H, DCE
2) TFA, DCM

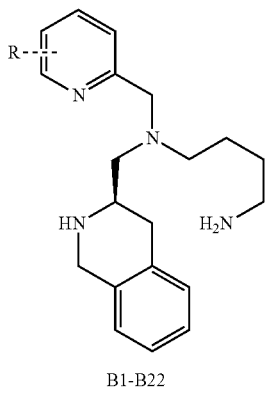

B1-B22

To a 20 mL vial was added aminopyridine (A1-A22, 1.0 equiv.), DCE (0.4M), (R)-tert-butyl 3-formyl-3,4-dihydroisoquinoline-2(1H)-carboxylate (THIQ, 1.1 equiv.) and STAB-H (1.5 equiv.) The reaction was allowed to stir overnight (12-24 h) then diluted with DCM and quenched with 1.0M NaOH. The organic layer was dried with MgSO$_4$, filtered, concentrated and purified via silica gel chromatography (combiflash, DCM:Mixture B{80:20:3, DCM:MeOH:NH$_4$OH}, 0% B for 5 minutes, 10% B for 8 minutes, 50% B for 8 minutes). All purifications were conducted using this standard mixture unless otherwise noted. The purified carbamate protected material was dissolved in DCM (0.1M) and TFA (ratio DCM:TFA, 5:1). The reaction was allowed to stir overnight (12-24 h). The reaction was diluted with DCM and quenched with 1.0M NaOH. The organics were dried with MgSO$_4$, filtered, concentrated and purified via combiflash to afford final compounds EMU013-EMU015, EMU025-EMU028, EMU047-EMU048, EMU079-EMU081, EMU103-EMU104, EMU110-EMU112, EMU128-EMU129, EMU131, and EMU189-EMU190.

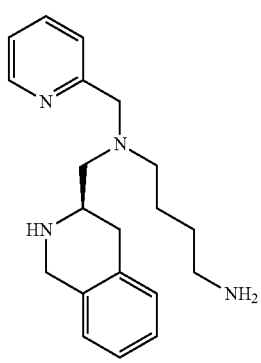 [SMILES: NCCCCN(Cc1ccccn1)C[C@H]1Cc2ccccc2CN1]

EMU015

Following general procedure B, A1 (0.515 g, 1.843 mmol), DCE (Volume: 4.61 ml), THIQ (0.530 g, 2.028 mmol) and STAB-H (0.586 g, 2.77 mmol) were stirred overnight. Purification via combiflash provided (R)-tert-butyl 3-(((4-((tert-butoxycarbonyl)amino)butyl)(pyridin-2-ylmethyl)amino)methyl)-3,4-dihydroisoquinoline-2(1H)-carboxylate (Carbamate 1 0.7 g, 1.334 mmol, 72.4% yield) as a yellow semi solid. Carbamate 1 (0.46 g, 0.877 mmol), DCM (Volume: 8.77 ml) and TFA (1.351 ml, 17.53 mmol) were stirred overnight. Purification via combiflash yielded (R)—N1-(pyridin-2-ylmethyl)-N1-((1,2,3,4-tetrahydroisoquinolin-3-yl)methyl)butane-1,4-diamine (0.241 g, 0.743 mmol, 85% yield) as a yellow-brown oil. (79% over two steps). $^1$H NMR (400 MHz, CDCl$_3$): δ=8.51 (dd, J=4.8, 1.0 Hz, 1H), 7.66 (dt, J=7.7, 1.8 Hz, 1H), 7.45 (d, J=7.8 Hz, 1H), 7.15 (t, J=5.0 Hz, 1H), 7.09-7.05 (m, 3H), 7.00-6.98 (m, 1H), 4.01 (d, J=15.2 Hz, 1H), 3.93 (d, J=15.0 Hz, 1H), 3.47 (d, J=14.6 Hz, 1H), 3.71 (d, J=14.4 Hz, 1H), 2.90-2.86 (m, 1H), 2.68-2.60 (m, 6H), 2.58-2.52 (m, 1H), 2.46 (dd, J=16.5, 11.5 Hz, 1H), 1.59-1.52 (m, 2H), 1.49-1.36 (m, 2H); $^{13}$C NMR (100 MHz, CDCl$_3$): δ=160.2, 149.1, 136.4, 135.6, 134.5, 129.1, 126.4, 126.0, 125.6, 122.8, 122.0, 61.6, 60.7, 55.5, 51.8, 48.6, 42.1, 33.9, 31.6, 24.7; HRMS (ESI) [M+H]$^+$, calcd for C$_{20}$H$_{28}$N$_4$ 325.23867, found 325.23840; LC/MS 75-95% MeOH in H$_2$O over 3 minutes, r$_f$=0.816 at 254 nM, MS (+) 325.2, MS(+)/2 163.2; purity (>95%) 10-95% MeOH in H$_2$O over 10 minutes, r$_f$=6.356 at 254 nM, MS (+) 325.2, MS(+)/2 163.2.

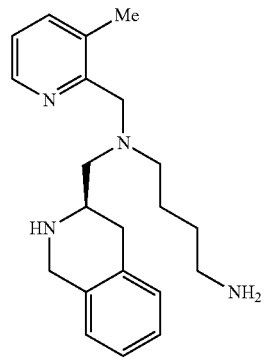 [SMILES: Cc1cccnc1CN(CCCCN)C[C@H]1Cc2ccccc2CN1]

EMU013

Following general procedure B, A2 (0.206 g, 0.702 mmol), DCE (Volume: 10 ml), THIQ (0.202 g, 0.772 mmol) and STAB-H (0.223 g, 1.053 mmol) were stirred overnight. Purification via combiflash provided (R)-tert-butyl 3-(((4-((tert-butoxycarbonyl)amino)butyl)((3-methylpyridin-2-yl)methyl)amino)methyl)-3,4-dihydroisoquinoline-2(1H)-carboxylate (Carbamate 2, 0.289 g, 0.536 mmol, 76% yield). Carbamate 2 (0.16 g, 0.297 mmol), DCM (Volume: 3 ml) and TFA (1.0 ml) were stirred overnight. Purification via combiflash yielded (R)—N1-((3-methylpyridin-2-yl)methyl)-N1-((1,2,3,4-tetrahydroisoquinolin-3-yl)methyl)butane-1,4-diamine (0.042 g, 0.124 mmol, 41.8% yield) 59% over 2 steps. $^1$H NMR (400 MHz, CDCl$_3$): δ=8.34 (dd, J=4.8, 1.2 Hz, 1H), 7.42 (dd, J=7.6, 0.8 Hz, 1H), 7.10-7.06 (m, 3H), 7.03 (dd, J 9.0, 5.4 Hz, 1H), 6.97 (dd, J 5.4, 3.2 Hz, 1H), 3.97 (d, J 15.0 Hz, 1H), 3.89 (d, J 15.0 Hz, 1H), 3.87 (d, J 12.4 Hz, 1H), 3.67 (d, J 12.6 Hz, 1H), 2.89-2.87 (m, 1H), 2.63-2.55 (m, 6H), 2.50 (dd, J 8.4, 5.6 Hz, 1H), 2.43 (s, 3H), 1.55-1.46 (m, 2H), 1.41-1.30 (m, 2H); $^{13}$C NMR (100 MHz, CDCl$_3$): δ=157.2, 146.3, 138.1, 135.5, 134.5, 132.8, 129.2, 126.4, 126.0, 125.6, 122.5, 60.8, 60.7, 55.4, 51.8, 48.6, 42.0, 33.9, 31.6, 24.2, 18.4; LC/MS 50-95% MeOH in H₂O over 3 minutes, r_t=0.797 at 254 nM, MS (+) 339.2, MS(+)/2 170.2

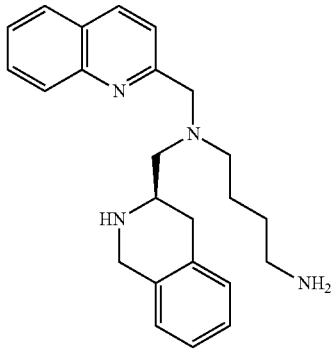 [SMILES: NCCCCN(Cc1ccc2ccccc2n1)C[C@H]1Cc2ccccc2CN1]

EMU014

Following general procedure B, A3 (0.390 g, 1.184 mmol), DCE (Volume: 2.96 ml), THIQ (0.340 g, 1.302 mmol) and STAB-H (0.376 g, 1.776 mmol) were stirred overnight. Purification via combiflash provided (R)-tert-butyl 3-(((4-((tert-butoxycarbonyl)amino)butyl)(quinolin-2-ylmethyl)amino)methyl)-3,4-dihydroisoquinoline-2(1H)-carboxylate (Carbamate 3, 0.59 g, 1.027 mmol, 87% yield). Carbamate 3 (0.34 g, 0.592 mmol), DCM (Volume: 6.0 ml) and TFA (1.0 ml) were stirred overnight. Purification via combiflash yielded (R)—N1-(quinolin-2-ylmethyl)-N1-((1,2,3,4-tetrahydroisoquinolin-3-yl)methyl)butane-1,4-diamine (0.187 g, 0.499 mmol, 84% yield) as a yellow-brown oil. 86% over two steps. ¹H NMR (400 MHz, CDCl₃): δ=8.14 (d, J=8.3 Hz, 1H), 8.03 (d, J=8.6 Hz, 1H), 7.80 (d, J=8.0 Hz, 1H), 7.69 (dt, J=8.3, 1.2 Hz, 1H), 7.63 (d, J=8.5 Hz, 1H), 7.51 (dt, J=7.9, 0.8 Hz, 1H), 7.09-7.03 (m, 3H), 6.99-6.97 (m, 1H), 4.03 (d, J=14.2 Hz, 2H), 3.94 (d, J=15.1 Hz, 1H), 3.88 (d, J=14.6 Hz, 1H), 2.99-2.93 (m, 1H), 2.71-2.63 (m, 6H), 2.61-2.53 (m, 1H), 2.47 (dd, J=15.0, 10.4 Hz, 1H), 1.62-1.54 (m, 2H), 1.51-1.36 (m, 2H); ¹³C NMR (100 MHz, CDCl₃): δ=160.9, 147.6, 136.4, 135.6, 134.5, 129.5, 129.2, 129.0, 127.6, 127.4, 126.4, 125.6, 120.8, 62.5, 60.9, 55.6, 51.8, 48.6, 42.1, 33.9, 31.6, 24.7; HRMS (ESI) [M+H]⁺, calcd for C₂₄H₃₀N₄ 375.25432, found 375.25391; LC/MS 75-95% MeOH in H₂O over 3 minutes, r_t=0.689 at 254 nM, MS (+) 375.2, MS(+)/2 188.2

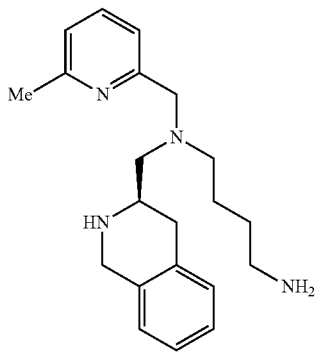 [SMILES: Cc1cccc(CN(CCCCN)C[C@H]2Cc3ccccc3CN2)n1]

EMU025

Following general procedure B, A4 (0.486 g, 1.656 mmol), DCE (Volume: 4 ml), THIQ (0.476 g, 1.822 mmol) and STAB-H (0.527 g, 2.485 mmol) were stirred overnight. Purification via combiflash provided (R)-tert-butyl 3-(((4-((tert-butoxycarbonyl)amino)butyl)((6-methylpyridin-2-yl)methyl)amino)methyl)-3,4-dihydroisoquinoline-2(1H)-carboxylate (Carbamate 4, 0.780 g, 1.448 mmol, 87% yield). Carbamate 4 (0.379 g, 0.704 mmol), DCM (Volume: 6.0 ml) and TFA (1.0 ml) were stirred overnight. Purification via combiflash yielded (R)—N1-((6-methylpyridin-2-yl)methyl)-N1-((1,2,3,4-tetrahydroisoquinolin-3-yl)methyl)butane-1,4-diamine (0.124 g, 0.366 mmol, 52% yield) as a yellow oil. 70% over 2 steps. ¹H NMR (400 MHz, CDCl₃): δ=7.55 (t, J=7.0 Hz, 1H), 7.28 (d, J=8.7 Hz, 1H), 7.10-7.03 (m, 3H), 7.01-6.99 (m, 2H), 4.03 (d, J=15.1 Hz, 1H), 3.94 (d, J=15.3 Hz, 1H), 3.82 (d, J=14.7 Hz, 1H), 3.67 (d, J=14.7 Hz, 1H), 2.93-2.87 (m, 1H), 2.69-2.57 (m, 7H), 2.52 (s, 3H), 2.50-2.48 (m, 1H), 1.59-1.51 (m, 2H), 1.49-1.37 (m, 2H); ¹³C NMR (100 MHz, CDCl₃): δ=159.5, 157.4, 136.5, 135.4, 129.0, 126.2, 125.8, 125.4, 121.2, 119.3, 61.5, 60.5, 55.4, 51.6, 48.4, 41.9, 33.7, 31.3, 24.5, 24.3; HRMS (ESI) [M+H]⁺, calcd for C₂₁H₃₀N₄ 339.25432, found 339.25410; LC/MS 55% MeOH in H₂O over 3 minutes, r_t=0.822 at 254 nM, MS (+) 339.2, MS(+)/2 170.2

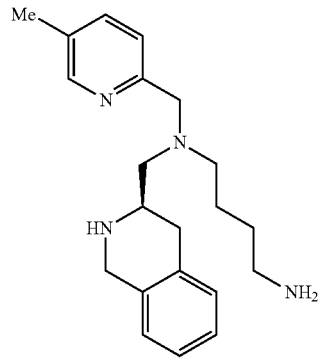 [SMILES: Cc1ccc(CN(CCCCN)C[C@H]2Cc3ccccc3CN2)nc1]

EMU026

Following general procedure B, A5 (0.519 g, 1.767 mmol), DCE (Volume: 4.5 ml), THIQ (0.508 g, 1.944 mmol) and STAB-H (0.562 g, 2.65 mmol) were stirred overnight. Purification via combiflash provided (R)-tert-butyl 3-(((4-((tert-butoxycarbonyl)amino)butyl)((5-methylpyridin-2-yl)methyl)amino)methyl)-3,4-dihydroisoquinoline-2(1H)-carboxylate (Carbamate 5, 0.762 g, 1.414 mmol, 80% yield). Racemic Carbamate 5 was synthesized using racemic THIQ and analyzed by Chiral HPLC, (254 nm) 5% iPrOH in hexanes, isocratic, 30 minutes, 1.0 mL/min, AD-H (Daicel, ChiralPak, 150 mm, 4.6 mm, 5 um), t₁=13.820, t₂=14.888, er=52:48. Carbamate 5 was analyzed by Chiral HPLC, (254 nm) 5% iPrOH in hexanes, isocratic, 30 minutes, 1.0 mL/min, AD-H (Daicel, ChiralPak, 150 mm, 4.6 mm, 5 um), t₁=13.892, t₂=14.977, er=98.5:1.5. Carbamate 5 (0.305 g, 0.566 mmol), DCM (Volume: 5.0 ml) and TFA (1.0 ml) were stirred overnight. Purification via combiflash yielded (R)—N1-((5-methylpyridin-2-yl)methyl)-N1-((1,2,3,4-tetrahydroisoquinolin-3-yl)methyl)butane-1,4-diamine (0.091 g, 0.269 mmol, 48% yield) as a yellow oil 64% over 2 steps. ¹H NMR (400 MHz, CDCl₃): δ=8.30 (s, 1H), 7.43 (d, J=7.8

Hz, 1H), 7.28 (d, J=7.8 Hz, 1H), 7.04-6.99 (m, 3H), 6.95-6.94 (m, 1H), 3.99 (d, J 15.0 Hz, 1H), 3.88 (d, J 15.0 Hz, 1H), 3.78 (d, J 14.3 Hz, 1H), 3.63 (d, J 14.3 Hz, 1H), 2.89-2.82 (m, 1H), 2.63-2.53 (m, 6H), 2.49-2.39 (m, 2H), 2.25 (s, 3H), 1.85 (bs, 3NH), 1.54-1.47 (m, 2H), 1.37-1.32 (m, 2H); $^{13}$C NMR (100 MHz, CDCl$_3$): δ=156.9, 149.3, 137.1, 135.4, 131.3, 129.1, 126.3, 125.9, 125.5, 122.4, 61.1, 60.4, 55.3, 51.6, 48.4, 41.8, 33.7, 31.2, 24.6, 18.1; HRMS (ESI) [M+H]$^+$, calcd for $C_{21}H_{30}N_4$ 339.25432, found 339.25411; LC/MS 55% MeOH in H$_2$O over 3 minutes, $r_t$=0.810 at 254 nM, MS (+) 339.2, MS(+)/2 170.2.

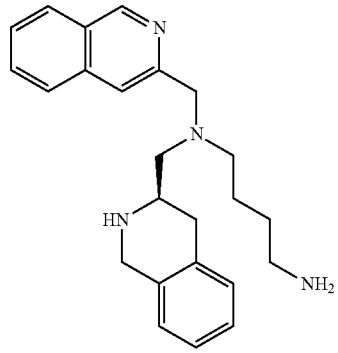 [SMILES: NCCCCN(Cc1cc2ccccc2cn1)C[C@H]1Cc2ccccc2CN1]

EMU027

Following general procedure B, A6 (0.519 g, 1.767 mmol), DCE (Volume: 4.5 ml), THIQ (0.508 g, 1.944 mmol) and STAB-H (0.562 g, 2.65 mmol) were stirred overnight. Purification via combiflash provided (R)-tert-butyl 3-(((4-((tert-butoxycarbonyl)amino)butyl)((4-methylpyridin-2-yl)methyl)amino)methyl)-3,4-dihydroisoquinoline-2(1H)-carboxylate (Carbamate 6, 0.72 g, 1.336 mmol, 76% yield). Carbamate 6 (0.293 g, 0.544 mmol), DCM (Volume: 4.5 ml) and TFA (1.0 ml) were stirred overnight. Purification via combiflash yielded (R)—N1-((4-methylpyridin-2-yl)methyl)-N1-((1,2,3,4-tetrahydroisoquinolin-3-yl)methyl)butane-1,4-diamine (0.064 g, 0.189 mmol, 35% yield) as a yellow oil. 56% over 2 steps. $^1$H NMR (400 MHz, CDCl$_3$): δ=8.33 (d, J=5.2 Hz, 1H), 7.20 (s, 1H), 7.06-7.01 (m, 3H), 6.97-6.92 (m, 2H), 3.98 (d, J=15.1 Hz, 1H), 3.89 (d, J=15.5 Hz, 1H), 3.77 (d, J=14.2 Hz, 1H), 3.65 (d, J=14.2 Hz, 1H), 2.88-2.81 (m, 1H), 2.65-2.61 (m, 3H), 2.57-2.56 (m, 3H), 2.52-2.40 (m, 2H), 2.32 (s, 3H), 1.56-1.49 (m, 2H), 1.47-1.33 (m, 2H); $^{13}$C NMR (100 MHz, CDCl$_3$): δ=159.8, 148.8, 147.5, 135.6, 134.5, 129.1, 126.4, 126.0, 125.6, 123.7, 123.1, 61.5, 60.7, 55.6, 51.8, 48.4, 42.0, 33.8, 31.4, 24.7, 21.2; HRMS (ESI) [M+H]$^+$, calcd for $C_{20}H_{28}N_4$ 339.25432, found 339.25415; LC/MS 65% MeOH in H$_2$O over 3 minutes $r_t$=1.069 at 254 nM, MS (+) 339.2, MS(+)/2 170.2

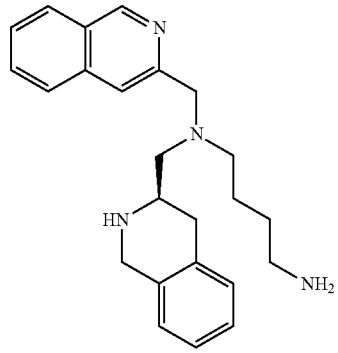 [SMILES: NCCCCN(Cc1cc2ccccc2cn1)C[C@H]1Cc2ccccc2CN1]

EMU028

Following general procedure B, A7 (0.38 g, 1.153 mmol), DCE (Volume: 3 ml), THIQ (0.322 g, 1.269 mmol) and STAB-H (0.367 g, 1.730 mmol) were stirred overnight. Purification via combiflash provided (R)-tert-butyl 3-(((4-((tert-butoxycarbonyl)amino)butyl)(isoquinolin-3-ylmethyl)amino)methyl)-3,4-dihydroisoquinoline-2(1H)-carboxylate (Carbamate 7, 0.429 g, 0.746 mmol, 65% yield). Carbamate 7 (0.2 g, 0.348 mmol), DCM (Volume: 3 ml) and TFA (0.6 ml) were stirred overnight. Purification via combiflash yielded (R)—N1-(isoquinolin-3-ylmethyl)-N1-((1,2,3,4-tetrahydroisoquinolin-3-yl)methyl)butane-1,4-diamine (0.071 g, 0.19 mmol, 55% yield) as a yellow oil. 60% over 2 steps. $^1$H NMR (400 MHz, CDCl$_3$): δ=9.18 (s, 1H), 7.90 (d, J=7.8 Hz, 1H), 7.77 (d, J=7.8 Hz, 1H), 7.69 (s, 1H), 7.63 (ddd, J=8.1, 6.9, 1.2 Hz, 1H), 7.51 (ddd, J=8.0, 6.9, 1.0 Hz, 1H), 7.08-6.93 (m, 4H), 4.03 (d, J=15.4 Hz, 1H), 3.98 (d, J=14.8 Hz, 1H), 3.90 (d, J=15.4 Hz, 1H), 3.84 (d, J=14.7 Hz, 1H), 2.96-2.89 (m, 1H), 2.67-2.62 (m, 6H), 2.59-2.53 (m, 1H), 2.46 (dd, J=16.0, 10.8 Hz, 1H), 1.63-1.55 (m, 2H), 1.48-1.35 (m, 2H); $^{13}$C NMR (100 MHz, CDCl$_3$): δ=153.2, 152.2, 136.4, 135.7, 134.5, 130.4, 129.1, 127.7, 127.6, 126.8, 126.5, 126.4, 125.9, 125.6, 118.7, 61.2, 60.5, 55.6, 51.9, 48.6, 42.1, 33.9, 31.7, 24.7; HRMS (ESI) [M+H]$^+$, calcd for $C_{24}H_{30}N_4$ 375.25432, found 375.25406; LC/MS 75-95% MeOH in H$_2$O over 3 minutes, $r_t$=0.689 at 254 nM, MS (+) 375.2, MS(+)/2 188.2

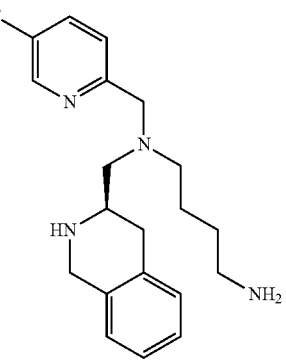

EMU047

Following general procedure B, A8 (0.379 g, 1.276 mmol), DCE (Volume: 3.19 ml), THIQ (0.35 g, 1.339 mmol)

and STAB-H (0.406 g, 1.913 mmol) were stirred overnight. Purification via combiflash provided (R)-tert-butyl 3-(((4-((tert-butoxycarbonyl)amino)butyl)((5-fluoropyridin-2-yl)methyl)amino)methyl)-3,4-dihydroisoquinoline-2(1H)-carboxylate (Carbamate 8, 0.621 g, 1.144 mmol, 90% yield). Carbamate 8 (0.275 g, 0.507 mmol), DCM (Volume: 2.5 ml, Ratio: 3) and TFA (Volume: 0.833 ml, Ratio: 1) were stirred overnight. Purification via combiflash yielded (R)—N1-((5-fluoropyridin-2-yl)methyl)-N1-((1,2,3,4-tetrahydroisoquinolin-3-yl)methyl)butane-1,4-diamine (0.141 g, 0.412 mmol, 81% yield). 86% over 2 steps. $^1$H NMR (400 MHz, CDCl$_3$): δ=8.33 (d, J=2.2 Hz, 1H), 7.42 (dd, J=8.5, 4.5 Hz, 1H), 7.34 (dd, J=8.3, 2.6 Hz, 1H), 7.07-6.96 (m, 4H), 3.99 (d, J=15.1 Hz, 1H), 3.92 (d, J=15.1 Hz, 1H), 3.79 (d, J=14.4 Hz, 1H), 3.66 (d, J=14.4 Hz, 1H), 2.87-2.85 (m, 1H), 2.65-2.41 (m, 10H), 1.55-1.32 (m, 4H); $^{13}$C NMR (100 MHz, CDCl$_3$): δ=158.5 (d, C—F J=252.8 Hz), 156.0 (d, C—F J=4.0 Hz), 137.0 (dd, C—F J=23.2, 2.3 Hz), 135.4, 134.3, 129.1, 126.3, 125.9, 125.6, 123.6 (d, C—F J=3.9 Hz), 123.3 (d, C—F J=18.3 Hz), 60.6, 60.4, 55.2, 51.6, 48.5, 42.0, 33.8, 31.4, 24.5; $^{19}$F NMR (375.8 MHz, CDCl$_3$): δ=−129.7 (dd, J=7.7, 4.6 Hz); LC/MS 50-95% MeOH in H$_2$O over 3 minutes, r$_t$=0.778 at 254 nM, MS (+) 343.2, MS(+)/2 172.2

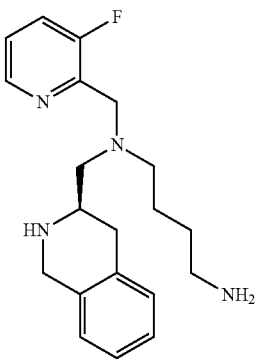 [SMILES: NCCCCN(Cc1ncccc1F)C[C@H]1Cc2ccccc2CN1]

EMU048

Following general procedure B, A9 (0.270 g, 0.908 mmol), DCE (Volume: 2.270 ml), THIQ (0.249 g, 0.953 mmol) and STAB-H (0.289 g, 1.362 mmol) were stirred overnight. Purification via combiflash provided (R)-tert-butyl 3-(((4-((tert-butoxycarbonyl)amino)butyl)((3-fluoropyridin-2-yl)methyl)amino)methyl)-3,4-dihydroisoquinoline-2(1H)-carboxylate (Carbamate 9, 0.621 g, 1.144 mmol, 90% yield). Carbamate 9 (0.210 g, 0.387 mmol), DCM (Volume: 2.5 ml, Ratio: 3) and TFA (Volume: 0.833 ml, Ratio: 1) were stirred overnight. Purification via combiflash yielded (R)—N1-((3-fluoropyridin-2-yl)methyl)-N1-((1,2,3,4-tetrahydroisoquinolin-3-yl)methyl)butane-1,4-diamine (0.121 g, 0.353 mmol, 91% yield). 91% over 2 steps. $^1$H NMR (400 MHz, CDCl$_3$): δ=8.39 (d, J=4.8 Hz, 1H), 7.38 (ddd, J=9.7, 8.3, 1.3 Hz, 1H), 7.23 (dd, J=8.5, 4.3 Hz, 1H), 7.11-7.00 (m, 4H), 4.04 (d, J=15.2 Hz, 1H), 3.99 (d, J=15.2 Hz, 1H), 3.98 (dd, J=13.2, 2.0 Hz, 1H), 3.73 (dd, J=13.4, 1.6 Hz, 1H), 3.03-2.96 (m, 1H), 2.69-2.45 (m, 10H), 1.60-1.34 (m, 4H); $^{13}$C NMR (100 MHz, CDCl$_3$): δ=158.6 (d, C—F J=258.2 Hz), 147.5 (d, C—F J=14.4 Hz), 144.7 (d, C—F J=5.2, 2.0 Hz), 135.6, 134.5, 129.1, 126.4, 125.9, 125.5, 123.7 (d, C—F J=3.9 Hz), 123.0 (d, C—F J 19.5 Hz), 60.1, 54.9, 54.8, 51.6, 48.5, 41.9, 33.7, 31.3, 24.4; $^{19}$F NMR (375.8 MHz, CDCl$_3$): δ=−124.4 (d, J=8.3 Hz); LC/MS 50-95% MeOH in H$_2$O over 3 minutes, r$_t$=0.778 at 254 nM, MS (+) 343.2, MS(+)/2 172.2

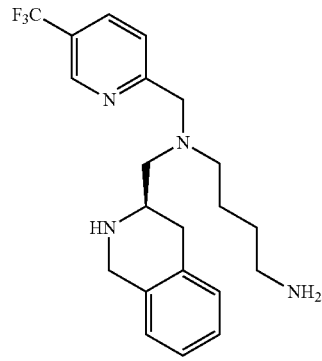

EMU081

Following general procedure B, A10 (0.350 g, 1.008 mmol), DCE (Volume: 2.52 ml), THIQ (0.290 g, 1.108 mmol) and STAB-H (0.320 g, 1.511 mmol) were stirred overnight. Purification via combiflash provided (R)-tert-butyl 3-(((4-((tert-butoxycarbonyl)amino)butyl)((5-(trifluoromethyl)pyridin-2-yl)methyl)amino)methyl)-3,4-dihydroisoquinoline-2(1H)-carboxylate (Carbamate 10, 0.525 g, 0.886 mmol, 88% yield). Carbamate 10 (0.269 g, 0.454 mmol), DCM (Volume: 2.5 ml, Ratio: 3) and TFA (Volume: 0.833 ml, Ratio: 1) were stirred overnight. Purification via combiflash yielded (R)—N1-((1,2,3,4-tetrahydroisoquinolin-3-yl)methyl)-N1-((5-(trifluoromethyl)pyridin-2-yl)methyl)butane-1,4-diamine (0.140 g, 0.357 mmol, 79% yield). 84% over 2 steps. $^1$H NMR (400 MHz, CDCl$_3$): δ=8.77 (d, J=2.0 Hz, 1H), 7.89 (dd, J=8.2, 2.2 Hz, 1H), 7.60 (d, J=8.0 Hz, 1H), 7.09-6.97 (m, 4H), 4.02 (d, J=15.5 Hz, 1H), 3.94 (d, J=15.5 Hz, 1H), 3.91 (d, J=14.9 Hz, 1H), 3.76 (d, J=15.1 Hz, 1H), 2.98-2.91 (m, 1H), 2.69-2.63 (m, 1H) 2.66 (t, J=7.0 Hz, 2H), 2.61-2.56 (m, 3H), 2.53 (dd, J=10.2, 3.1 Hz, 1H), 2.48 (dd, J=16.8, 10.8 Hz, 1H), 2.21 (bs, 3NH), 1.56-1.48 (m, 2H), 1.46-1.35 (m, 2H); $^{13}$C NMR (100 MHz, CDCl$_3$): δ=164.3 (q, C—F, J=1.4 Hz), 145.9 (q, C—F, J=4.1 Hz), 135.2, 134.1, 133.6 (q, C—F, J=3.6 Hz), 129.0, 126.3, 126.0, 125.6, 125.0 (q, C—F, J=33.2 Hz), 123.5 (q, C—F, J=272.2 Hz), 122.3, 61.0, 60.4, 55.2, 51.6, 48.3, 41.8, 33.6, 31.0, 24.5; $^{19}$F NMR (375.8 MHz, CDCl$_3$): δ=−62.25; HRMS (ESI) [M+H]$^+$, calcd for C$_{21}$H$_{27}$N4F$_3$ 393.22606, found 393.22585; LC/MS 85% MeOH in H$_2$O over 3 minutes, r$_t$=0.692 at 254 nM, MS (+) 393.2, MS(+)/2 197.2

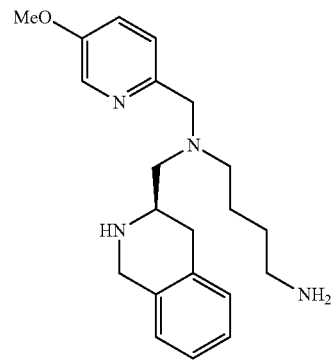 [SMILES: COc1ccc(CN(CCCCN)C[C@H]2Cc3ccccc3CN2)nc1]

EMU080

Following general procedure B, A11 (0.290 g, 0.937 mmol), DCE (Volume: 2.5 ml), THIQ (0.269 g, 1.031 mmol) and STAB-H (0.298 g, 1.406 mmol) were stirred overnight. Purification via combiflash provided (R)-tert-butyl 3-(((4-((tert-butoxycarbonyl)amino)butyl)((5-methoxypyridin-2-yl)methyl)amino)methyl)-3,4-dihydroisoquinoline-2(1H)-carboxylate (Carbamate 11, 0.448 g, 0.808 mmol, 86% yield). Carbamate 11 (0.206 g, 0.371 mmol), DCM (Volume: 3 ml, Ratio: 3) and TFA (Volume: 1 ml, Ratio: 1) were stirred overnight. Purification via combiflash yielded (R)—N1-((5-methoxypyridin-2-yl)methyl)-N1-((1,2,3,4-tetrahydroisoquinolin-3-yl)methyl)butane-1,4-diamine (0.088 g, 0.248 mmol, 67% yield) 77% over 2 steps. $^1$H NMR (400 MHz, CDCl$_3$): δ=8.18 (d, J=2.8 Hz, 1H), 7.30 (d, J=8.7 Hz, 1H), 7.16 (dd, J=8.7, 3.0 Hz, 1H), 7.07-6.96 (m, 4H), 3.99 (d, J=15.4 Hz, 1H), 3.91 (d, J=15.0 Hz, 1H), 3.81 (s, 3H), 3.77 (d, J=14.1 Hz, 1H), 3.60 (d, J=14.1 Hz, 1H), 2.90-2.83 (m, 1H), 2.65-2.59 (m, 1H), 2.64 (t, J=6.9 Hz, 2H), 2.57-2.52 (m, 3H), 2.49-2.41 (m, 2H), 2.31 (bs, 3NH), 1.55-1.47 (m, 2H), 1.45-1.33 (m, 2H); $^{13}$C NMR (100 MHz, CDCl$_3$): δ=154.6, 151.8, 136.1, 135.5, 134.4, 129.1, 126.4, 126.0, 125.6, 123.3, 121.4, 60.7, 60.3, 55.6, 55.2, 51.7, 48.5, 41.9, 33.8, 31.3, 24.6; HRMS (ESI) [M+H]$^+$, calcd for C$_{21}$H$_{30}$ON$_4$ 355.24924, found 355.24899; LC/MS 75% MeOH in H$_2$O over 3 minutes, r$_t$=0.730 at 254 nM, MS (+) 355.2, MS(+)/2 178.2

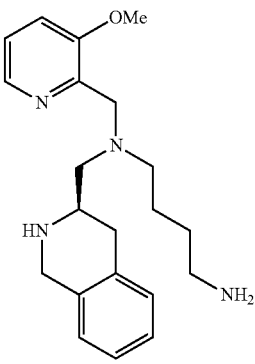 [SMILES: COc1cccnc1CN(CCCCN)C[C@H]1Cc2ccccc2CN1]

EMU079

Following general procedure B, A12 (0.330 g, 1.067 mmol), DCE (Volume: 2.67 ml), THIQ (0.307 g, 1.173 mmol) and STAB-H (0.339 g, 1.600 mmol) were stirred overnight. Purification via combiflash provided (R)-tert-butyl 3-(((4-((tert-butoxycarbonyl)amino)butyl)((3-methoxypyridin-2-yl)methyl)amino)methyl)-3,4-dihydroisoquinoline-2(1H)-carboxylate (Carbamate 12, 0.446 g, 0.804 mmol, 75% yield). Carbamate 12 (0.192 g, 0.346 mmol), DCM (Volume: 3 ml, Ratio: 3) and TFA (Volume: 1.000 ml, Ratio: 1) were stirred overnight. Purification via combiflash yielded (R)—N1-((3-methoxypyridin-2-yl)methyl)-N1-((1,2,3,4-tetrahydroisoquinolin-3-yl)methyl)butane-1,4-diamine (0.061 g, 0.172 mmol, 50%). 63% over 2 steps. $^1$H NMR (400 MHz, CDCl$_3$): δ=8.11 (dd, J 4.1, 1.7 Hz, 1H), 7.25-7.11 (m, 2H), 7.07-7.01 (m, 3H), 6.99-6.97 (m, 1H), 4.01 (d, J 15.0 Hz, 1H), 3.95 (d, J 15.2 Hz, 1H), 3.93 (d, J 13.0 Hz, 1H), 3.82 (s, 3H), 3.61 (d, J 13.0 Hz, 1H), 2.99-2.92 (m, 1H), 2.66-2.56 (m, 6H), 2.50-2.42 (m, 2H), 2.37 (bs, 3NH), 1.50-1.43 (m, 2H), 1.42-1.25 (m, 2H); $^{13}$C NMR (100 MHz, CDCl$_3$): δ=154.4, 148.8, 140.3, 135.6, 134.6, 129.1, 126.4, 125.9, 125.5, 123.0, 117.3, 60.3, 55.4, 55.3, 55.0, 51.7, 48.5, 41.8, 33.7, 31.2, 24.3; LC/MS 75% MeOH in H$_2$O over 3 minutes, r$_t$=0.708 at 254 nM, MS (+) 355.2, MS(+)/2 178.2

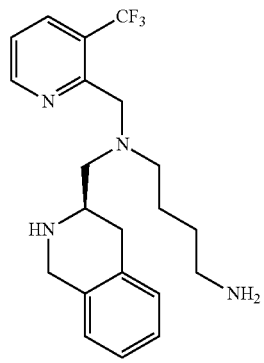 [SMILES: NCCCCN(Cc1ncccc1C(F)(F)F)C[C@H]1Cc2ccccc2CN1]

EMU103

Following general procedure B, A13 (0.318 g, 0.915 mmol), DCE (Volume: 2.266 ml), THIQ (0.237 g, 0.906 mmol) and STAB-H (0.288 g, 1.360 mmol) were stirred overnight. Purification via combiflash provided (R)-tert-butyl 3-(((4-((tert-butoxycarbonyl)amino)butyl)((3-(trifluoromethyl)pyridin-2-yl)methyl)amino)methyl)-3,4-dihydroisoquinoline-2(1H)-carboxylate (Carbamate 13, 0.44 g, 0.742 mmol, 82% yield). Carbamate 13 (0.44 g, 0.742 mmol), DCM (Volume: 4 ml, Ratio: 4) and TFA (Volume: 1.000 ml, Ratio: 1) were stirred overnight. Purification via combiflash yielded ((R)—N1-((1,2,3,4-tetrahydroisoquinolin-3-yl)methyl)-N1-((3-(trifluoromethyl)pyridin-2-yl)methyl)butane-1,4-diamine (0.189 g, 0.482 mmol, 65% yield). 74% over 2 steps. $^1$H NMR (400 MHz, CDCl$_3$): δ=8.73 (d, J=4.3 Hz, 1H), 7.89 (d, J=7.0 Hz, 1H), 7.26 (dd, J=8.0, 4.8 Hz, 1H), 7.07-6.94 (m, 4H), 4.03 (d, J=13.9 Hz, 1H), 3.96 (d, J=15.0 Hz, 1H), 3.86 (d, J=15.0 Hz, 1H), 3.85 (d, J=13.9 Hz, 1H), 2.77-2.71 (m, 1H), 2.68-2.51 (m, 5H), 2.60 (t, J=7.0 Hz, 2H), 2.42 (dd, J=15.6, 10.9 Hz, 1H), 2.06 (bs, 3NH), 1.54-1.45 (m, 2H), 1.4-1.28 (m, 2H); $^{13}$C NMR (100 MHz, CDCl$_3$): δ=158.0, 151.7, 135.6, 134.4, 134.4 (q, C—F, J=5.7 Hz), 129.0, 126.4, 125.8, 125.4, 125.1 (q, C—F, J=32.0 Hz), 123.9 (q, C—F, J=274.4 Hz), 121.7, 60.6, 58.4, 55.7, 51.6, 48.4, 41.9, 33.6, 31.4, 24.1; $^{19}$F NMR (375.8 MHz, CDCl$_3$): δ=−59.86; HRMS (ESI) [M+H]$^+$, calcd for C$_{21}$H$_{28}$N$_4$F$_3$ 393.22606, found 393.22577; LC/MS 55% MeOH in H$_2$O over 3 minutes, r$_t$=0.883 at 254 nM, MS (+) 393.2, MS(+)/2 197.2

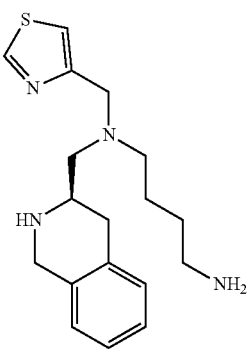 [SMILES: NCCCCN(Cc1cscn1)C[C@H]1Cc2ccccc2CN1]

EMU104

Following general procedure B, A14 (0.4 g, 1.402 mmol), THIQ (0.374 g, 1.430 mmol), DCE (Volume: 3.50 ml) and STAB-H (0.446 g, 2.102 mmol) were stirred overnight. Purification via combiflash provided (R)-tert-butyl 3-(((4-((tert-butoxycarbonyl)amino)butyl)(thiazol-4-ylmethyl)amino)methyl)-3,4-dihydroisoquinoline-2(1H)-carboxylate (Carbamate 14, 0.576 g, 1.085 mmol, 77% yield). Carbamate 14 (0.576 g, 1.085 mmol), DCM (Volume: 4.5 ml, Ratio: 5) and TFA (Volume: 1.000 ml, Ratio: 1) were stirred overnight. Purification via combiflash yielded (R)—N1-((1,2,3,4-tetrahydroisoquinolin-3-yl)methyl)-N1-(thiazol-4-ylmethyl)butane-1,4-diamine (0.211 g, 0.638 mmol, 59% yield). 68% over 2 steps. $^1$H NMR (500 MHz, CDCl$_3$): δ=8.74 (d, J=2.0 Hz, 1H), 7.16 (d, J=1.8 Hz, 1H), 7.07-6.97 (m, 4H), 4.01 (d, J=15.1 Hz, 1H), 3.96 (d, J=15.1 Hz, 1H), 3.89 (d, J=14.9 Hz, 1H), 3.81 (d, J=14.6 Hz, 1H), 2.95-2.89 (m, 1H), 2.65 (t, J=6.9 Hz, 2H), 2.63-2.56 (m, 5H), 2.50-2.44 (m, 2H), 2.02 (bs, 3NH), 1.57-1.53 (m, 2H), 1.49-1.37 (m, 2H); $^{13}$C NMR (125 MHz, CDCl$_3$): δ=155.8, 152.6, 135.6, 134.4, 129.1, 126.4, 125.9, 125.6, 115.3, 60.1, 55.0, 54.5, 51.7, 48.6, 42.0, 33.9, 31.4, 24.8; HRMS (ESI) [M+H]$^+$, calcd for C$_{18}$H$_{27}$N$_4$S 331.19509, found 331.19501; LC/MS 65% MeOH in H$_2$O over 3 minutes, r$_t$=0.747 at 254 nM, MS (+) 331.2, MS(+)/2 166.2

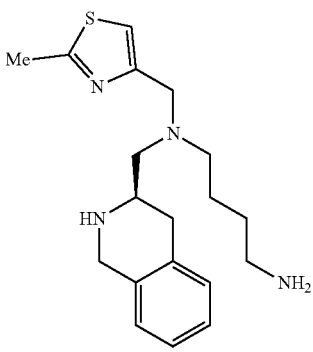 [SMILES: Cc1nc(CN(CCCCN)C[C@H]2Cc3ccccc3CN2)cs1]

EMU110

Following general procedure B, A15 (0.095 g, 0.317 mmol), THIQ (0.087 g, 0.333 mmol), DCE (Volume: 0.8 ml) and STAB-H (0.101 g, 0.476 mmol) were stirred overnight. Purification via combiflash provided a yellow oil which was dissolved in DCM (Volume: 4.5 ml, Ratio: 5) and TFA (Volume: 1.000 ml, Ratio: 1) and stirred overnight. Purification via combiflash yielded (R)—N1-((2-methylthiazol-4-yl)methyl)-N1-((1,2,3,4-tetrahydroisoquinolin-3-yl)methyl)butane-1,4-diamine (0.071 g, 0.206 mmol). 65.0% yield over 2 steps. $^1$H NMR (500 MHz, CDCl$_3$): δ=7.09-6.99 (m, 4H), 6.94 (s, 1H), 4.03 (d, J 15.2 Hz, 1H), 3.98 (d, J 15.2 Hz, 1H), 3.80 (d, J 14.7 Hz, 1H), 3.71 (d, J 14.7 Hz, 1H), 2.95-2.89 (m, 1H), 2.70-2.67 (m, 2H), 2.68 (s, 3H), 2.64-2.60 (m, 2H), 2.58-2.57 (m, 2H), 2.53-2.45 (m, 2H), 2.03 (bs, 3NH), 1.59-1.51 (m, 2H), 1.49-1.41 (m, 2H); $^{13}$C NMR (125 MHz, CDCl$_3$): δ=165.7, 154.6, 135.5, 134.4, 129.1, 126.3, 125.9, 125.6, 114.7, 60.0, 55.2, 54.9, 51.7, 48.5, 42.0, 33.8, 31.4, 24.7, 19.2; HRMS (ESI) [M+H]$^+$, calcd for C$_{19}$H$_{29}$N$_4$S 345.21074, found 345.21076; LC/MS 10-95% MeOH in H$_2$O over 10 minutes, r$_t$=7.781 at 254 nM, MS (+) 345.2, MS(+)/2 173.2

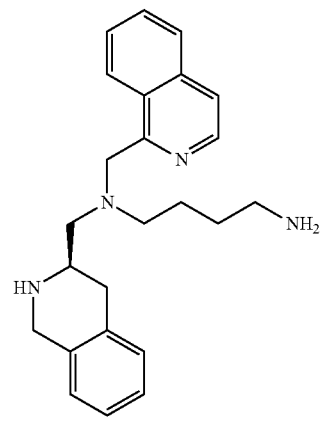 [SMILES: NCCCCN(Cc1nccc2ccccc12)C[C@H]1Cc2ccccc2CN1]

EMU112

Following general procedure B, A16 (0.358 g, 1.087 mmol), THIQ (0.284 g, 1.087 mmol), DCE (Volume: 2.72 ml) and STAB-H (0.345 g, 1.630 mmol) were stirred overnight. Purification via combiflash provided (R)-tert-butyl 3-(((4-((tert-butoxycarbonyl)amino)butyl)(isoquinolin-1-yl-methyl)amino)methyl)-3,4-dihydroisoquinoline-2(1H)-carboxylate (Carbamate 16, 0.494 g, 0.859 mmol, 79% yield). Carbamate 16 (0.264 g, 0.459 mmol), DCM (Volume: 5 ml, Ratio: 5) and TFA (Volume: 1.000 ml, Ratio: 1) were stirred overnight. Purification via combiflash yielded (R)—N1-(isoquinolin-1-ylmethyl)-N1-((1,2,3,4-tetrahydroisoquinolin-3-yl)methyl)butane-1,4-diamine (0.13 g, 0.347 mmol, 76% yield) as a yellow oil. 78% yield over 2 steps. $^1$H NMR (400 MHz, CDCl$_3$): δ=8.43 (d, J=8.4 Hz, 1H), 8.39 (d, J=5.7 Hz, 1H), 7.78 (d, J=8.1 Hz, 1H), 7.67 (dt, J=6.8, 1.0 Hz, 1H), 7.60 (dt, J=6.8, 1.0 Hz, 1H), 7.54 (d, J=5.7 Hz, 1H), 7.04-7.02 (m, 2H), 6.97-6.95 (m, 2H), 6.92-6.90 (m, 1H), 4.30 (d, J=12.5 Hz, 1H), 4.18 (d, J=12.5 Hz, 1H), 3.82 (d, J=15.0 Hz, 1H), 3.61 (d, J=15.0 Hz, 1H), 2.71-2.60 (m, 1H), 2.58 (t, J=6.9 Hz, 3H), 2.34 (dd, J=16.0, 9.3 Hz, 1H), 1.80 (bs, 3NH), 1.59-1.49 (m, 2H), 1.41-1.27 (m, 2H); $^{13}$C NMR (100 MHz, CDCl$_3$): δ=158.8, 141.5, 136.4, 135.4, 134.3, 130.0, 129.1, 127.6, 127.3, 126.8, 126.3, 125.9, 125.5, 120.7, 61.3, 60.8, 55.9, 51.8, 48.3, 41.9, 33.8, 31.5, 24.1; HRMS (ESI) [M+H]$^+$, calcd for C$_{24}$H$_{31}$N$_4$ 375.25432, found 375.25423; LC/MS 10-95% MeOH in H$_2$O over 10 minutes, r$_t$=7.624 at 254 nM, MS (+) 375.2, MS(+)/2 188.2

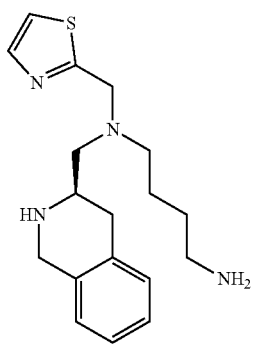 [SMILES: NCCCCN(Cc1nccs1)C[C@H]1Cc2ccccc2CN1]

EMU111

Following general procedure B, A17 (0.176 g, 0.617 mmol), THIQ (0.161 g, 0.617 mmol), DCE (Volume: 3.08 ml) and STAB-H (0.196 g, 0.925 mmol) were stirred overnight. Purification via combiflash provided a yellow oil which was dissolved in DCM (Volume: 5 ml, Ratio: 5) and TFA (Volume: 1.000 ml, Ratio: 1) and stirred overnight. Purification via combiflash yielded (R)—N1-((1,2,3,4-tetrahydroisoquinolin-3-yl)methyl)-N1-(thiazol-2-ylmethyl)butane-1,4-diamine (0.130 g, 0.393 mmol) as a pale yellow oil B17 64% yield over 2 steps. $^1$H NMR (400 MHz, CDCl$_3$): δ=7.65 (d, J=3.3 Hz, 1H), 7.24 (d, J=3.3 Hz, 1H), 7.09-7.02 (m, 3H), 7.00-6.99 (m, 1H), 4.04 (d, J=15.2 Hz, 1H), 3.99 (d, J=15.7 Hz, 1H), 3.98 (d, J=15.2 Hz, 1H), 3.94 (d, J=15.7 Hz, 1H), 2.98-2.90 (m, 1H), 2.69-2.58 (m, 6H), 2.57-2.46 (m, 2H), 1.73 (bs, 3NH), 1.59-1.50 (m, 2H), 1.49-1.35 (m, 2H); $^{13}$C NMR (100 MHz, CDCl$_3$): δ=171.7, 142.4, 135.4, 134.2, 129.1, 126.3, 125.9, 125.6, 119.2, 60.5, 56.7, 55.4, 51.8, 48.5, 42.0, 33.7, 31.4, 24.8; HRMS (ESI) [M+H]$^+$, calcd for C$_{18}$H$_{27}$N$_4$S 331.19509, found 331.19607; LC/MS 75% MeOH in H$_2$O over 3 minutes, r$_t$=0.757 at 254 nM, MS (+) 331.2, MS(+)/2 166.2

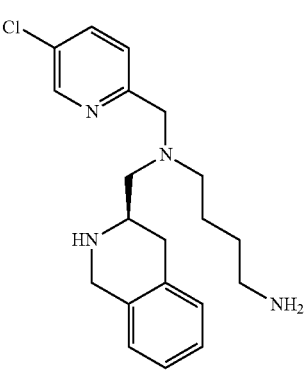 [SMILES: NCCCCN(Cc1ccc(Cl)cn1)C[C@H]1Cc2ccccc2CN1]

EMU129

Following general procedure B, A18 (0.5 g, 1.593 mmol), DCE (Volume: 3.79 ml), THIQ (0.397 g, 1.517 mmol) and STAB-H (0.579 g, 2.73 mmol) were stirred overnight. Purification via combiflash provided (R)-tert-butyl 3-(((4-((tert-butoxycarbonyl)amino)butyl)((5-chloropyridin-2-yl)methyl)amino)methyl)-3,4-dihydroisoquinoline-2(1H)-carboxylate (Carbamate 18, 0.666 g, 1.191 mmol, 78% yield). Carbamate 18 (0.335 g, 0.599 mmol), DCM (Volume: 5 ml, Ratio: 5) and TFA (Volume: 1.000 ml, Ratio: 1) were stirred overnight. Purification via combiflash yielded (R)—N1-((5-chloropyridin-2-yl)methyl)-N1-((1,2,3,4-tetrahydroisoquinolin-3-yl)methyl)butane-1,4-diamine (0.154 g, 0.429 mmol, 72% yield) as a yellow oil. 76% yield over 2 steps. $^1$H NMR (500 MHz, CDCl$_3$): δ=8.42 (d, J=1.8 Hz, 1H), 7.59 (dd, J 8.2, 1.8 Hz, 1H), 7.37 (d, J 8.2 Hz, 1H), 7.05-7.00 (m, 3H), 6.96-6.95 (m, 1H), 3.98 (d, J 15.0 Hz, 1H), 3.92 (d, J 15.0 Hz, 1H), 3.78 (d, J 14.6 Hz, 1H), 3.64 (d, J 14.6 Hz, 1H), 2.91-2.85 (m, 1H), 2.62 (t, J 6.6 Hz, 3H), 2.58-2.51 (m, 3H), 2.49-2.41 (m, 2H), 1.68 (s, 3H), 1.54-1.47 (m, 2H), 1.42-1.33 (m, 2H); $^{13}$C NMR (125 MHz, CDCl$_3$): δ=158.3, 147.8, 136.2, 135.4, 134.3, 130.2, 129.1, 126.3, 125.9, 125.6, 123.5, 60.7, 60.4, 51.6, 48.5, 42.0, 33.8, 31.5, 24.5; HRMS (ESI) [M+H]$^+$, calcd for C$_{20}$H$_{28}$N$_4$Cl 359.19970, found 359.19966; LC/MS 10-95% MeOH in H$_2$O over 10 minutes, r$_t$=7.900 at 254 nM, MS (+) 359.4, MS(+)/2 180.3

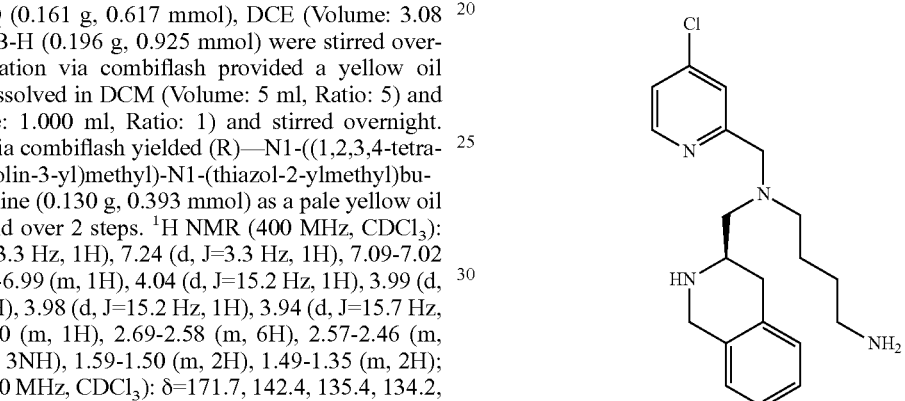

EMU128

Following general procedure B, A19 (0.430 g, 1.370 mmol), DCE (Volume: 3.26 ml), THIQ (0.341 g, 1.305 mmol) and STAB-H (0.498 g, 2.349 mmol) were stirred overnight. Purification via combiflash provided (R)-tert-butyl 3-(((4-((tert-butoxycarbonyl)amino)butyl)((4-chloropyridin-2-yl)methyl)amino)methyl)-3,4-dihydroisoquinoline-2(1H)-carboxylate (Carbamate 19, 0.616 g, 1.102 mmol, 84% yield). Carbamate 19 (0.319 g, 0.571 mmol), DCM (Volume: 5 ml, Ratio: 5) and TFA (Volume: 1.000 ml, Ratio: 1) were stirred overnight. Purification via combiflash yielded (R)—N1-((4-chloropyridin-2-yl)methyl)-N1-((1,2,3,4-tetrahydroisoquinolin-3-yl)methyl)butane-1,4-diamine (0.162 g, 0.451 mmol, 79% yield) as a yellow oil. 83% yield over 2 steps. $^1$H NMR (500 MHz, CDCl$_3$): δ=8.37 (d, J=5.4 Hz, 1H), 7.44 (d, J=1.8 Hz, 1H), 7.13 (dd, J=5.4, 1.8 Hz, 1H), 7.09-7.03 (m, 3H), 6.99-6.97 (m, 1H), 4.02 (d, J=15.3 Hz, 1H), 3.93 (d, J=15.3 Hz, 1H), 3.81 (d, J=15.3 Hz, 1H), 3.70 (d, J=15.3 Hz, 1H), 2.89-2.83 (m, 1H), 2.66-2.65 (m, 3H), 2.64-2.54 (m, 3H), 2.52-2.43 (m, 2H), 1.72 (s, 3H), 1.54-1.50 (m, 2H), 1.45-1.34 (m, 2H); $^{13}$C NMR (125 MHz, CDCl$_3$): δ=162.1, 149.9, 144.5, 135.5, 134.3, 129.1, 126.3, 125.9, 125.6, 122.9, 122.4, 61.1, 60.7, 55.5, 51.7, 48.4, 42.0, 33.8, 31.5, 24.5; HRMS (ESI) [M+H]$^+$, calcd for C$_{20}$H$_{28}$N$_4$Cl 359.19970, found 359.19973; LC/MS 10-95% MeOH in H$_2$O over 10 minutes, r$_t$=7.804 at 254 nM, MS (+) 359.4, MS(+)/2 180.3

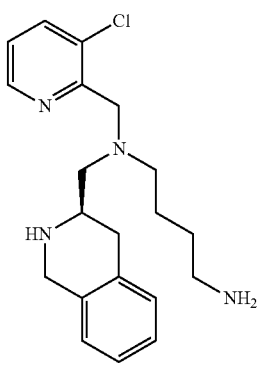 [SMILES: NCCCCN(Cc1ncccc1Cl)C[C@H]1Cc2ccccc2CN1]

EMU131

Following general procedure B, A20 (0.491 g, 1.565 mmol), DCE (Volume: 3.73 ml), THIQ (0.389 g, 1.490 mmol), and STAB-H (0.568 g, 2.68 mmol) were stirred overnight. Purification via combiflash provided (R)-tert-butyl 3-(((4-((tert-butoxycarbonyl)amino)butyl)((3-chloropyridin-2-yl)methyl)amino)methyl)-3,4-dihydroisoquinoline-2(1H)-carboxylate (Carbamate 20, 0.592 g, 1.058 mmol, 71% yield). Carbamate 20 (0.331 g, 0.592 mmol), DCM (Volume: 5 ml, Ratio: 5) and TFA (Volume: 1.000 ml, Ratio: 1) were stirred overnight. Purification via combiflash yielded (R)—N1-((3-chloropyridin-2-yl)methyl)-N1-((1,2,3,4-tetrahydroisoquinolin-3-yl)methyl)butane-1,4-diamine (0.157 g, 0.437 mmol, 74% yield) as a yellow oil. 73% yield over 2 steps. $^1$H NMR (500 MHz, CDCl$_3$): δ=8.46 (dd, J=4.5, 1.4 Hz, 1H), 7.67 (dd, J=8.0, 1.4 Hz, 1H), 7.16 (dd, J=8.0, 4.5 Hz, 1H), 7.09-7.04 (m, 3H), 7.01-6.99 (m, 1H), 4.03 (d, J=13.0 Hz, 1H), 4.00 (d, J=14.9 Hz, 1H), 3.94 (d, J=14.9 Hz, 1H), 3.74 (d, J=13.0 Hz, 1H), 2.95-2.89 (m, 1H), 2.70-2.60 (m, 6H), 2.58-2.50 (m, 1H), 2.46 (dd, J=15.9, 10.9 Hz, 1H), 1.62 (s, 3H), 1.55-1.46 (m, 2H), 1.44-1.30 (m, 2H); $^{13}$C NMR (125 MHz, CDCl$_3$): δ=156.2, 146.9, 137.4, 135.6, 134.4, 132.1, 129.1, 126.4, 125.9, 125.5, 123.4, 60.4, 58.6, 55.1, 51.5, 48.5, 41.9, 33.7, 31.4, 24.7; HRMS (ESI) [M+H]$^+$, calcd for C$_{20}$H$_{28}$N$_4$Cl 359.19970, found 359.19972; LC/MS 75% MeOH in H$_2$O over 3 minutes, r$_t$=0.783 at 254 nM, MS (+) 359.2, MS(+)/2 180.2

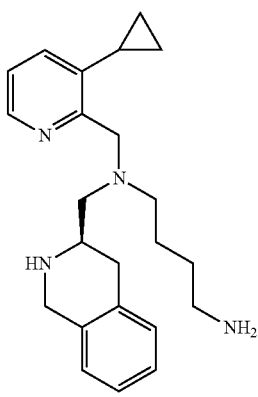 [SMILES: NCCCCN(Cc1ncccc1C1CC1)C[C@H]1Cc2ccccc2CN1]

EMU189

Following general procedure B, A21 (0.2 g, 0.626 mmol), DCE (Volume: 1.491 ml), STAB-H (0.227 g, 1.073 mmol) and THIQ (0.156 g, 0.596 mmol) were stirred overnight. Purification via combiflash provided a yellow oil which was dissolved in DCM (Volume: 5 ml, Ratio: 5) and TFA (Volume: 1.000 ml, Ratio: 1) and stirred overnight. Purification via combiflash yielded (R)—N1-((3-cyclopropylpyridin-2-yl)methyl)-N1-((1,2,3,4-tetrahydroisoquinolin-3-yl)methyl)butane-1,4-diamine. (0.157 g, 0.431 mmol, 72% yield over two steps). $^1$H NMR (500 MHz, CDCl$_3$): δ=8.29 (dd, J=4.6, 1.1 Hz, 1H), 7.14 (d, J 7.2 Hz, 1H), 7.08-7.04 (m, 3H), 7.00-6.98 (m, 1H), 6.94-6.92 (m, 1H), 4.02 (d, J 12.6 Hz, 1H), 3.93 (d, J 15.1 Hz, 1H), 3.82 (d, J 12.3 Hz, 1H), 3.77 (d, J 14.8 Hz, 1H), 2.74-2.69 (m, 1H), 2.63-2.49 (m, 7H), 2.58 (t, J 7.0 Hz, 2H), 2.37 (dd, J 15.9, 10.9 Hz, 1H), 2.30-2.25 (m, 1H) 1.82 (br s, 3NH), 1.51-1.44 (m, 2H), 1.39-1.28 (m, 2H), 0.9 (dd, J 8.6, 1.6 Hz, 1H), 0.69-0.62 (m, 1H); $^{13}$C NMR (125 MHz, CDCl$_3$): δ=157.9, 145.6, 138.2, 135.4, 134.4, 132.1, 129.1, 126.3, 125.9, 125.5, 122.5, 60.6, 60.6, 55.6, 51.8, 48.5, 41.9, 33.8, 31.5, 24.2, 11.4, 8.4, 8.1; HRMS (ESI) [M+H]$^+$, calcd for C$_{23}$H$_{33}$N$_4$ 365.26997, found 365.26970; LC/MS 10-95% MeOH in H$_2$O over 10 minutes, r$_t$=2.723 at 254 nM, MS (+) 365.2, MS(+)/2 183.2

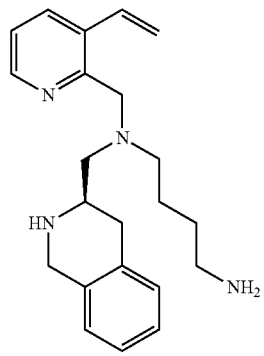 [SMILES: C=Cc1cccnc1CN(CCCCN)C[C@H]1Cc2ccccc2CN1]

EMU190

Following general procedure B, A22 (0.2 g, 0.655 mmol), DCE (Volume: 1.559 ml), STAB-H (0.238 g, 1.123 mmol) and THIQ (0.163 g, 0.624 mmol) were stirred overnight. Purification via combiflash provided a yellow oil which was dissolved in DCM (Volume: 5 ml, Ratio: 5) and TFA (Volume: 1.000 ml, Ratio: 1) and stirred overnight. Purification via combiflash yielded (R)—N1-((1,2,3,4-tetrahydroisoquinolin-3-yl)methyl)-N1-((3-vinylpyridin-2-yl)methyl)butane-1,4-diamine. (0.134 g, 0.382 mmol, 61% yield over two steps). $^1$H NMR (500 MHz, CDCl$_3$): δ=8.40 (dd, J=4.5, 1.0 Hz, 1H), 7.80 (d, J=7.0 Hz, 1H), 7.18 (dd, J=7.6, 5.0 Hz, 1H), 7.15 (dd, J=17.6, 11.1 Hz, 1H), 7.07-7.04 (m, 2H), 7.02-7.00 (m, 1H), 6.97-6.96 (m, 1H), 5.71 (d, J=17.4 Hz, 1H), 5.40 (d, J=10.8 Hz, 1H), 3.96 (d, J=15.2 Hz, 1H), 3.95 (d, J=12.6 Hz, 1H), 3.87 (d, J=15.2 Hz, 1H), 3.74 (d, J=12.6 Hz, 1H), 2.75-2.70 (m, 1H), 2.62-2.47 (m, 6H), 2.39 (dd, J=15.9, 10.7 Hz, 1H), 1.86 (br s, 3NH), 1.53-1.46 (m, 2H), 1.41-1.27 (m, 2H); $^{13}$C NMR (125 MHz, CDCl$_3$): δ=156.1, 147.9, 135.5, 134.5, 133.4, 133.4, 133.1, 129.1, 126.4, 126.0, 125.6, 122.9, 116.4, 60.8, 60.4, 55.4, 51.8, 48.5, 42.0, 33.8, 31.6, 24.1; HRMS (ESI) [M+H]$^+$, calcd for C$_{22}$H$_{31}$N$_4$ 351.25423, found 351.25390; LC/MS 75% MeOH in H$_2$O over 3 minutes, r$_t$=0.450 at 254 nM, MS (+) 351.2, MS(+)/2 176.2

General Procedure C:

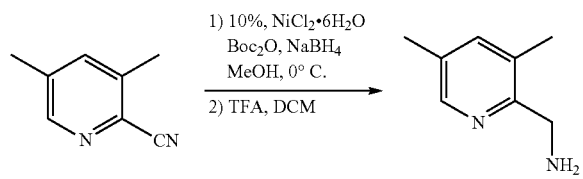

To a stirred solution of 3,5-dimethylpicolinonitrile (1 equiv.) in MeOH (0.1M) at 0° C. was added BOC-Anhydride (2 equiv) and Nickel (II) Chloride hexahydrate (0.1 equiv). To the stirred mixture was added $NaBH_4$ (7-10 equiv) in small portions over 30 minutes to prevent exothermic eruption and the reaction was allowed to stir for 3 h. Additional $NaBH_4$ was added if the reaction was not complete and allowed to stir overnight. N1-(2-aminoethyl)ethane-1,2-diamine (2 equiv.) was added to complete the reaction. The mixture was concentrated to an oil, dissolved in EtOAc, washed with saturated sodium bicarbonate, brine and dried with $MgSO_4$, filtered and concentrated to afford a solid. The solid was dissolved in DCM (0.7M) and TFA (Ratio DCM:TFA, 5:1) was added and the reaction was stirred overnight. The reaction was quenched with 2M NaOH, extracted with DCM, dried with $MgSO_4$, filtered and concentrated to afford the pyridylamine.

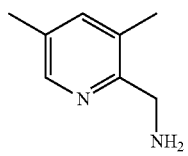

Following the general procedure C, 3,5-dimethylpicolinonitrile (3.67 g, 27.8 mmol), MeOH (Volume: 214 ml) BOC-Anhydride (12.89 ml, 55.5 mmol), Nickel (II) chloride hexahydrate (0.660 g, 2.78 mmol), $NaBH_4$ (7.35 g, 194 mmol) An additional 2 g of $NaBH_4$ was added and the reaction was allowed to stir overnight. N1-(2-aminoethyl)ethane-1,2-diamine (6.00 ml, 55.5 mmol) was added to complete the reaction. Work-up and concentration to afford a white solid (2.05 g). The solid (1 g, 4.23 mmol), DCM (Volume: 5 ml, Ratio: 5) and TFA (Volume: 1 ml, Ratio: 1.000) were stirred overnight then work-up and concentrated to afford (3,5-dimethylpyridin-2-yl)methanamine (0.45 g, 3.30 mmol, 78% yield), 55% over 2 steps. $^1$H NMR (400 MHz, $CDCl_3$): $\delta$=8.33 (s, 1H), 7.44 (s, 1H), 3.89 (s, 2H), 2.49 (s, 3H), 2.36 (s, 3H);

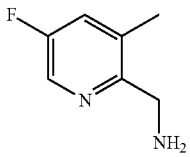

Following the general procedure C, 5-fluoro-3-methylpicolinonitrile (0.672 g, 4.94 mmol), MeOH (Volume: 38.0 ml), di-tert-butyl dicarbonate (2.155 g, 9.87 mmol), Nickel (II) Chloride hexahydrate (0.117 g, 0.494 mmol) then sodium borohydride (1.868 g, 49.4 mmol). N1-(2-aminoethyl)ethane-1,2-diamine (1.067 ml, 9.87 mmol) was added to the light brown reaction and stirred for 30 minutes (brown to pink). The reaction was then concentrated to an oil, diluted with EtOAc, washed with $NaHCO_3$, dried with $MgSO_4$, filtered and concentrated to a yellow oil which solidified on high vac (0.9 g, 3.75 mmol, 76% yield). The solid (0.755 g, 3.14 mmol), DCM (Volume: 5 ml, Ratio: 5) and TFA (Volume: 1 ml, Ratio: 1.000) were allowed to stir overnight. Work-up and concentrated to a yellow oil which was purified via silica gel chromatography (30% EtOAc in hexanes) to afford (5-fluoro-3-methylpyridin-2-yl)methanamine (0.18 g, 1.284 mmol, 41% yield). 59% over 2 steps. $^1$H NMR (400 MHz, $CDCl_3$): $\delta$=8.26 (d, J=2.7 Hz, 1H), 7.18 (dd, J=9.0, 2.7 Hz, 1H), 3.92 (s, 2H), 2.30 (s, 3H).

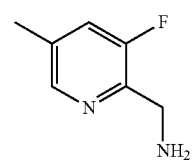

Following general procedure C, 3-fluoro-5-methylpicolinonitrile (2.04 g, 14.99 mmol), MeOH (Volume: 100 mL), di-tert-butyl dicarbonate (6.54 g, 30.0 mmol), NiCl2 6H2O (0.355 g, 1.499 mmol), $NaBH_4$ (5.67 g, 150 mmol). N1-(2-aminoethyl)ethane-1,2-diamine (3.24 mL, 30.0 mmol) was added to the light green reaction and stirred for 30 minutes turned to pink. The reaction was then concentrated to an oil and purified via combiflash (gradient 10-30% EA in hexanes) to afford a solid (1.22 g, 5.08 mmol, 33.9% yield). The solid (0.5 g, 2.081 mmol), DCM (Volume: 8.67 ml, Ratio: 5), TFA (Volume: 1.734 ml, Ratio: 1.000) were stirred overnight work-up and concentrated to afford (3-fluoro-5-methylpyridin-2-yl)methanamine (0.220 g, 1.570 mmol, 75% yield). 55% over 2 steps. $^1$H NMR (500 MHz, $CDCl_3$): $\delta$=8.22 (s, 1H), 7.17 (d, J=8.3 Hz, 1H), 4.01 (s, 2H), 2.36 (s, 3H)

Procedure for EMU078, EMU102, EMU109

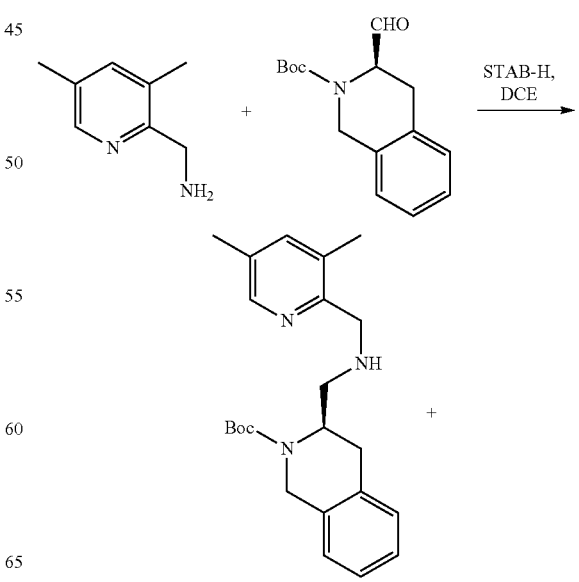

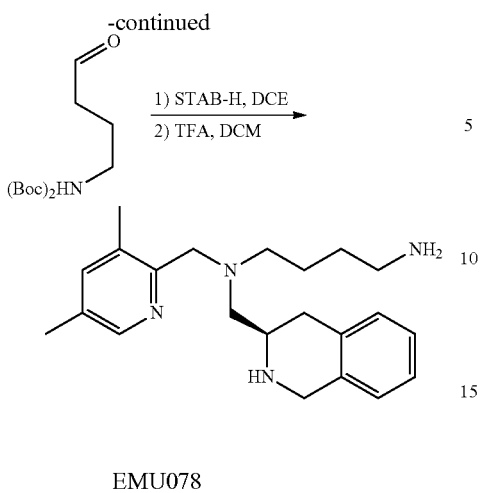

EMU078

To a 20 mL vial was added (3,5-dimethylpyridin-2-yl)methanamine (0.250 g, 1.836 mmol), THIQ (0.504 g, 1.927 mmol), DCE (Volume: 4.59 ml) and Na(OAc)$_3$BH (0.584 g, 2.75 mmol). The mixture was stirred vigorously for 2 h then quenched with 2M NaOH, extracted with DCM, dried with MgSO$_4$, filtered and concentrated to an oil which was purified via combiflash (DCM 5 min, 10% B (80:20:3, DCM:MeOH:NH$_4$OH) 7 min, 50% B 10 min) to afford a yellow semi-solid (0.4 g, 1.048 mmol, 57% yield). To a 20 mL vial was added the yellow semi-solid (0.165 g, 0.432 mmol), DCE (2.0 mL) butyl-aldehyde (0.249 g, 0.865 mmol), and STAB-H (0.137 g, 0.649 mmol). The reaction was allowed to stir overnight then quenched with 2M NaOH, extracted with DCM, dried with MgSO$_4$, filtered and concentrated to a yellow oil. The oil was dissolved in DCM (4 mL) and TFA (0.5 mL) was added dropwise and the mixture was allowed to stir overnight. The reaction was quenched with 2M NaOH, extracted with DCM, dried MgSO$_4$, filtered and concentrated to a yellow oil. The crude material was purified via combiflash (DCM 5 min, 10% B-(80:20:3, DCM:MeOH:NH$_4$OH) 7 min, 50% B 10 min) to afford (R)—N1-((3,5-dimethylpyridin-2-yl)methyl)-N1-((1,2,3,4-tetrahydroisoquinolin-3-yl)methyl)butane-1,4-diamine (64 mg, 0.182 mmol, 41% yield) 46% over 3 steps. $^1$H NMR (400 MHz, CDCl$_3$): δ=8.15 (d, J=1.6 Hz, 1H), 7.24 (d, J=1.6 Hz, 1H), 7.07-6.95 (m, 4H), 3.97 (d, J=14.9 Hz, 1H), 3.89 (d, J=15.1 Hz, 1H), 3.84 (d, J=12.5 Hz, 1H), 3.59 (d, J=12.5 Hz, 1H), 2.86-2.79 (m, 1H), 2.61 (t, J=7.0 Hz, 1H), 2.60-2.53 (m, 3H), 2.45 (dd, J=8.3, 5.3 Hz, 1H), 2.42 (dd, J=11.6, 6.1 Hz, 1H), 2.37 (s, 3H), 2.24 (s, 3H), 2.05 (bs, 3NH), 1.54-1.43 (m, 2H), 1.42-1.28 (m, 2H); $^{13}$C NMR (100 MHz, CDCl$_3$): δ=154.0, 146.4, 138.8, 135.4, 132.0, 131.8, 129.0, 126.3, 125.9, 125.5, 60.3, 60.2, 55.2, 51.7, 48.4, 41.9, 33.7, 31.4, 24.1, 18.2, 17.9; HRMS (ESI) [M+H]$^+$, calcd for C$_{21}$H$_{30}$N$_4$ 353.26997, found 353.26968; LC/MS 75% MeOH in H$_2$O over 3 minutes, r$_t$=0.779 at 254 nM, MS (+) 353.2, MS(+)/2 177.2

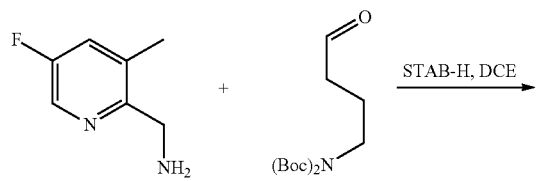

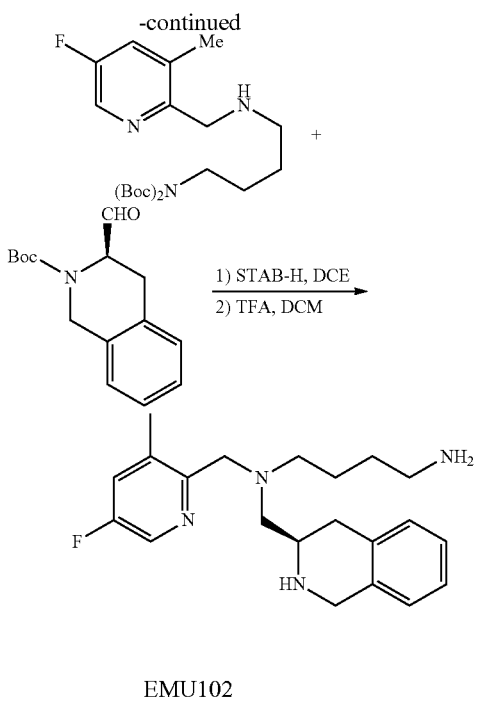

EMU102

To a 20 mL vial was added (5-fluoro-3-methylpyridin-2-yl)methanamine (0.186 g, 1.327 mmol), DCE (Volume: 5 ml, Ratio: 5.00), Methanol (Volume: 1 ml, Ratio: 1.000), butyl-aldehyde (0.400 g, 1.393 mmol) and STAB-H (0.506 g, 2.389 mmol). The reaction was stirred overnight and quenched with 2M NaOH, extracted with DCM, dried with MgSO$_4$, filtered and concentrated to afford secondary amine (0.45 g, 1.094 mmol, 82% yield). To a 20 mL vial was added THIQ (0.254 g, 0.972 mmol), DCE (Volume: 2.4 ml), secondary amine (0.4 g, 0.972 mmol) and STAB-H (0.371 g, 1.750 mmol). The reaction was stirred overnight, diluted with DCM, washed with 1M NaOH, dried with MgSO$_4$, filtered and concentrated to a yellow oil. The residue was purified via combiflash (DCM 2 minutes, 10% B (80:20:3, DCM:MeOH:NH$_4$OH) 5 minutes and 50% B 9 minutes). The fractions were concentrated to afford the boc protected intermediate which was dissolved with 4 mL DCM followed by the addition of 1 mL TFA and then stirred overnight. The mixture was diluted with DCM and washed with 2M NaOH, dried with MgSO$_4$, filtered and concentrated to a yellow oil. Purified via combiflash (DCM 2 minutes, 10% B (80:20:3, DCM:MeOH:NH$_4$OH) 5 minutes and 50% B 9 minutes). The fractions were concentrated to afford (R)—N1-((5-fluoro-3-methylpyridin-2-yl)methyl)-N1-((1,2,3,4-tetrahydroisoquinolin-3-yl)methyl)butane-1,4-diamine (0.201 g, 0.564 mmol, 58% yield). 66% over 3 steps. $^1$H NMR (400 MHz, CDCl$_3$): δ=8.17 (d, J 2.8 Hz, 1H), 7.15 (dd, J 9.0, 2.7 Hz, 1H), 7.07-6.94 (m, 4H), 3.95 (d, J 15.2 Hz, 1H), 3.88 (d, J 15.2 Hz, 1H), 3.82 (d, J 12.7 Hz, 1H), 3.61 (d, J 12.6 Hz, 1H), 2.84-2.77 (m, 1H), 2.59 (t, J 6.8 Hz, 2H), 2.56-2.50 (m, 3H), 2.46 (dd, J 8.3, 5.3 Hz, 1H), 2.41 (s, 3H), 2.38 (dd, J 16.3, 10.9 Hz, 1H) 1.82 (bs, 2NH), 1.52-1.43 (m, 2H), 1.39-1.27 (m, 2H); $^{13}$C NMR (100 MHz, CDCl$_3$): δ=158.6 (d, C—F, J 259.8 Hz), 153.1 (d, C—F, J 3.9 Hz), 135.2, 134.5 (d, C—F, J 3.9 Hz), 134.2, 133.8 (d, C—F, J 22.4 Hz), 129.0, 126.2, 125.8, 125.4, 124.6 (d, C—F, J 17.7 Hz), 60.2, 59.7 (d, C—F, J 0.8 Hz), 55.0, 51.5, 48.3, 41.8, 33.6, 31.4, 23.9, 18.3 (d, C—F, J 0.9 Hz); $^{19}$F NMR (375.8 MHz, CDCl$_3$): δ=−130.19 (d, J 9.1 Hz); HRMS (ESI) [M+H]$^+$, calcd for $C_{21}H_{30}ON_4$ 357.24490, found 357.244769; LC/MS 75% MeOH in $H_2O$ over 3 minutes, $r_t$=0.808 at 254 nM, MS (+) 357.2, MS(+)/2 179.2

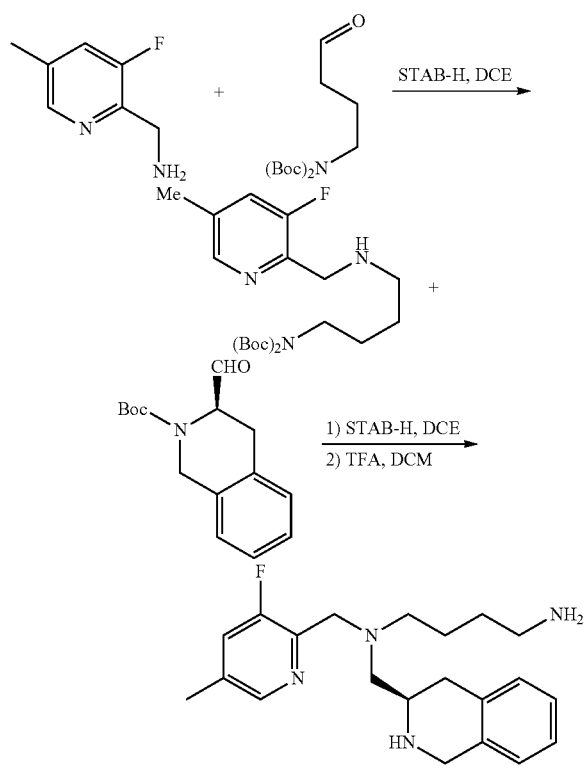

EMU109

To a 20 mL vial was added (3-fluoro-5-methylpyridin-2-yl)methanamine (0.09 g, 0.642 mmol), butyl-aldehyde (0.194 g, 0.674 mmol), DCM (Volume: 2.5 ml) and STAB-H (0.245 g, 1.156 mmol). The reaction was allowed to stir overnight. The reaction was diluted with DCM, washed with 2M NaOH, died with $MgSO_4$, filtered and concentrated to afford secondary amine as a clear oil which was used without purification. To a 20 mL vial was added THIQ (0.088 g, 0.336 mmol), secondary amine (0.145 g, 0.352 mmol), DCE (Volume: 0.8 ml) and STAB-H (0.107 g, 0.503 mmol). The reaction was stirred overnight then diluted with DCM, washed with 2M NaOH, dried with $Na_2SO_4$, filtered and concentrated to a yellow oil. The oil was dissolved in 2 mL DCM and 0.5 mL TFA was added and the mixture was stirred overnight. The reaction was diluted with DCM and quenched by the addition of 1M NaOH. The aqueous layer was extracted with DCM (3×10 mL) and the combined organics were dried with $Na_2SO_4$, filtered and concentrated to a yellow oil. Purified via combiflash (DCM 2 minutes, 10% B (80:20:3, DCM:MeOH:$NH_4OH$) 5 minutes and 50% B 9 minutes) to afford (R)—N1-((3-fluoro-5-methylpyridin-2-yl)methyl)-N1-((1,2,3,4-tetrahydroisoquinolin-3-yl)methyl)butane-1,4-diamine (0.037 g, 0.104 mmol, 31% yield) as a yellow gum. 55% over 3 steps. $^1$H NMR (400 MHz, $CDCl_3$): δ=8.17 (s, 1H), 7.17 (d, J=10.3 Hz, 1H), 7.08-6.98 (m, 4H), 3.99 (overlapping d, J=15.0 Hz, 2H), 3.91 (dd, J=13.3, 2.0 Hz, 1H), 3.64 (dd, J=13.2, 1.8 Hz, 1H), 3.00-2.93 (m, 1H), 2.66-2.54 (m, 3H), 2.61 (t, J=7.0 Hz, 2H), 2.52-2.42 (m, 2H), 2.32 (s, 3H), 2.09 (bs, 3NH), 1.57-1.45 (m, 2H), 1.44-1.31 (m, 2H); $^{13}$C NMR (100 MHz, $CDCl_3$): δ=159.1 (d, C—F, J=323.5 Hz), 145.5 (d, C—F, J=5.0 Hz), 144.6 (d, C—F, J=17.4 Hz), 136.0, 134.8, 134.7 (d, C—F, J=5.0 Hz), 129.4, 126.7, 126.2, 125.8, 123.7 (d, C—F, J=23.8 Hz), 59.9, 54.9, 54.5 (d, C—F J=3.8 Hz), 51.5, 48.4, 41.8, 33.5, 31.1, 24.3, 17.6 (d, C—F J 1.3 Hz); $^{19}$F NMR (375.8 MHz, $CDCl_3$): δ=−126.33 (d, J=9.6 Hz); HRMS (ESI) [M+H]$^+$, calcd for $C_{21}H_{29}FN_4$ 357.24490, found 357.24496; LC/MS 75% MeOH in $H_2O$ over 3 minutes, $r_t$=0.779 at 254 nM, MS (+) 357.2, MS(+)/2 179.2

General Procedure D: (S)-Methylaminopyridines

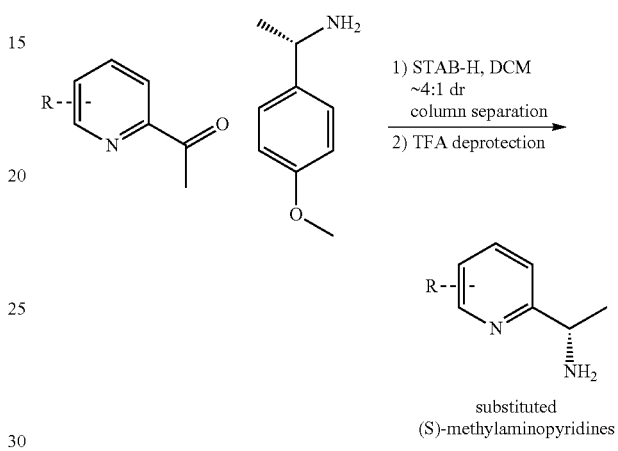

Following the procedure adapted from Boggs, S.; Elitzin, V. I.; Gudmundsson, K.; Martin, M. T.; Sharp, M. J. *Organic Process Research & Development* 2009, 13, 781.

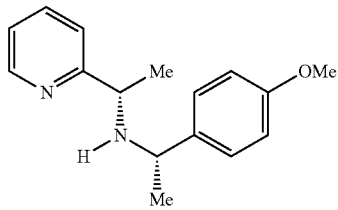 [SMILES: COc1ccc([C@H](C)N[C@@H](C)c2ccccn2)cc1]

To a 250 mL RBF was added (S)-1-(4-methoxyphenyl)ethanamine (5.65 ml, 38.1 mmol 1.0 equiv.), 1-(pyridin-2-yl)ethanone (4.49 ml, 40 mmol, 1.05 equiv.), DCE (Volume: 38.1 ml, 1.0M) and STAB-H (16.15 g, 76 mmol, 2.0 equiv.) at rt and the reaction was stirred for 24 h. The reaction was quenched by the addition of 1N NaOH until a pH of 8 was achieved. The phases were separated and the organic layer was treated with 1N NaOH until pH 11 was observed. The DCM layer was dried with $MgSO_4$, filtered and concentrated to an oily residue. The residue was purified via combiflash to separate the diastereomers (~4:1 by crude NMR, 80 g column 10-30% EtOAc in hexanes over 40 min). The fractions were concentrated to a clear oil which solidified upon standing. (S)-1-(4-methoxyphenyl)-N—((S)-1-(pyridin-2-yl)ethyl)ethanamine (3.86 g, 15.06 mmol, 40% yield). $^1$H NMR (400 MHz, $CDCl_3$): δ=8.60 (d, J 5.2 Hz, 1H), 7.61 (dt, J 7.6, 1.8 Hz, 1H), 7.21-7.12 (m, 1H), 7.13 (d, J 9.2 Hz, 2H), 7.06 (d, J 7.2 Hz 1H), 3.80 (s, 3H), 3.57 (q, J 7.4 Hz, 1H), 3.39 (q, J 6.9 Hz, 1H), 1.29 (d, J 6.8 Hz, 3H), 1.26 (d, J 7.3 Hz, 3H); LC/MS 75% MeOH in $H_2O$ over 3 minutes, $r_t$=0.480 at 254 nM, MS (+) 257.2

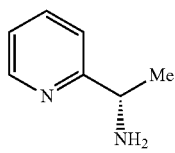

Commercially Available from Astatech:

To a 50 mL RBF was added (S)-1-(4-methoxyphenyl)-N—((S)-1-(pyridin-2-yl)ethyl)ethanamine (2 g, 7.80 mmol) and TFA (12.02 ml, 156 mmol) with stirring. The solid was slowly dissolved and the solution turned brick red and the reaction was allowed to stir overnight. The reaction was diluted with water and extracted with ether. The ether layer was washed with water and then set aside. The aqueous layers were made basic, pH 14, with 2M NaOH then extracted with DCM. The DCM layer was dried with MgSO$_4$, filtered and concentrated to a yellow oil (S)-1-(pyridin-2-yl)ethanamine (0.938 g, 7.68 mmol, 98% yield) which was used without further purification. $^1$H NMR (400 MHz, CDCl$_3$): δ=8.55 (d, J 4.5 Hz, 1H), 7.64 (dt, J 7.7, 1.8 Hz, 1H), 7.29 (d, J 8.2 Hz, 1H), 7.14 (ddd, J 7.6, 4.9, 1.2 Hz 1H), 4.16 (q, J 6.7 Hz, 1H), 1.43 (d, J 6.7 Hz, 3H); LC/MS 75% MeOH in H$_2$O over 3 minutes, r$_t$=0.484 at 254 nM, MS (+) 123.2

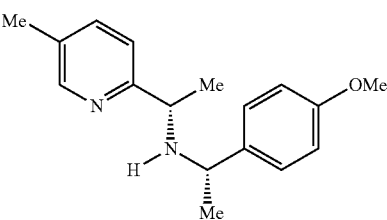 [SMILES: COc1ccc([C@H](C)N[C@@H](C)c2ccc(C)cn2)cc1]

To a 250 mL RBF was added (S)-1-(4-methoxyphenyl) ethanamine (6.24 ml, 42.3 mmol), 1-(5-methylpyridin-2-yl) ethanone (6.0 g, 44.4 mmol), DCM (Volume: 106 ml) and STAB-H (17.92 g, 85 mmol) at rt and the reaction was stirred for 24 h. The reaction was quenched by the addition of 1N NaOH until a pH of 8 was achieved. The phases were separated and the organic layer was treated with 1N NaOH until pH 11 was observed. The DCM layer was dried with MgSO$_4$, filtered and concentrated to an oily residue. The residue was purified via combiflash to separate the diastereomers (~4:1 by crude NMR, 80 g column 10-30% EtOAc in hexanes, over 40 min). The fractions were concentrated to a clear oil which was crystallized using hexanes (S)-1-(4-methoxyphenyl)-N—((S)-1-(5-methylpyridin-2-yl)ethyl) ethanamine (5.1 g, 18.86 mmol, 45% yield). $^1$H NMR (400 MHz, CDCl$_3$): δ=8.40 (d, J 2.1 Hz, 1H), 7.39 (ddd, J=7.8, 2.4, 0.8 Hz, 1H), 7.15 (d, J=8.5 Hz, 2H), 6.93 (d, J 8.1 Hz, 1H), 6.83 (d, J 8.5 Hz, 2H), 3.78 (s, 3H), 3.53 (q, J 6.8 Hz, 1H), 3.37 (q, J 6.6 Hz, 1H), 1.26 (d, J 6.4 Hz, 3H), 1.24 (d, J 6.5 Hz, 3H); LC/MS 75% MeOH in H$_2$O over 3 minutes, r$_t$=0.480 at 254 nM, MS (+) 271.2.

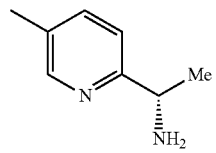

To a 50 mL RBF was added (S)-1-(4-methoxyphenyl)-N—((S)-1-(5-methylpyridin-2-yl)ethyl)ethanamine (2 g, 7.40 mmol) and TFA (11.40 ml, 148 mmol) with stirring. The solid was slowly dissolved and the solution turned brick red and the reaction was allowed to stir overnight. The reaction was diluted with water and extracted with ether. The ether layer was washed with water and then set aside. The aqueous layers were made basic, pH 14, with 2M NaOH then extracted with DCM. The DCM layer was dried with MgSO4, filtered and concentrated to a yellow oil (S)-1-(5-methylpyridin-2-yl)ethanamine (0.76 g, 5.58 mmol, 75% yield) which was used without further purification. $^1$H NMR (400 MHz, CDCl$_3$): δ=8.35 (d, J 2.2 Hz, 1H), 7.43 (ddd, J=8.0, 2.2, 0.8 Hz, 1H), 7.17 (d, J=7.8 Hz, 1H), 4.10 (q, J 6.6 Hz, 1H), 1.39 (d, J 6.6 Hz, 3H);

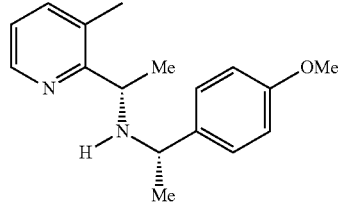 [SMILES: COc1ccc([C@H](C)N[C@@H](C)c2ncccc2C)cc1]

To a 250 mL RBF was added (S)-1-(4-methoxyphenyl) ethanamine (6.39 g, 42.3 mmol), 1-(3-methylpyridin-2-yl) ethanone (6 g, 44.4 mmol), DCM (Volume: 106 ml) and STAB-H (17.92 g, 85 mmol) at rt and the reaction was stirred for 24 h. The reaction was quenched by the addition of 1N NaOH until a pH of 8 was achieved. The phases were separated and the organic layer was treated with 1N NaOH until pH 11 was observed. The DCM layer was dried with MgSO$_4$ filtered and concentrated to an oily residue. The residue was purified via combiflash to separate the diastereomers (4:1 by crude NMR, 80 g column 10-30% gradient over 40 min). $^1$H NMR (400 MHz, CDCl$_3$): δ=8.45 (d, J 4.8 Hz, 1H), 7.34 (d, J=7.6 Hz, 1H), 7.13 (d, J=8.5 Hz, 2H), 7.04 (dd, J 7.8, 4.6 Hz, 1H), 6.82 (d, J 9.2 Hz, 2H), 3.79 (s, 3H), 3.74 (q, J 6.0 Hz, 1H), 3.27 (q, J 5.9 Hz, 1H), 1.24 (d, J 6.3 Hz, 3H), 1.20 (d, J 6.3 Hz, 3H); LC/MS 75% MeOH in H$_2$O over 3 minutes, r$_t$=0.480 at 254 nM, MS (+) 271.2

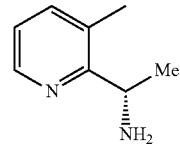

To a 50 mL RBF was added (S)-1-(4-methoxyphenyl)-N—((S)-1-(3-methylpyridin-2-yl)ethyl)ethanamine (2.26 g, 8.36 mmol) and TFA (12.88 ml, 167 mmol) with stirring. The solid was slowly dissolved and the solution turned brick red and the reaction was allowed to stir o/n. The reaction was diluted with water and extracted with ether. The ether layer was washed with water and then set aside. The aqueous layers were made basic, pH 14, with 2M NaOH then extracted with DCM. The DCM layer was dried with MgSO4, filtered and concentrated to a yellow oil (S)-1-(3-methylpyridin-2-yl)ethanamine (0.56 g, 4.11 mmol, 49% yield) which was used without further purification. $^1$H NMR (400 MHz, CDCl$_3$): δ=8.39 (d, J 4.0 Hz, 1H), 7.38 (d, J=7.8 Hz, 1H), 7.03 (dd, J=7.6, 4.7 Hz, 1H), 4.27 (q, J 6.2 Hz, 1H), 1.33 (d, J 6.6 Hz, 3H);

Procedure for EMU065, EMU066, EMU067 and EMU108

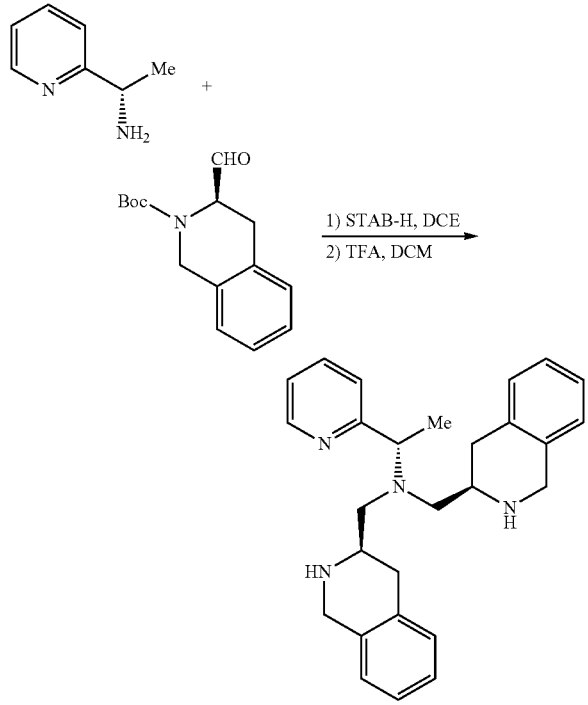

EMU065

(S)-1-(pyridin-2-yl)ethanamine (0.45 g, 3.68 mmol), DCE (18 ml), THIQ (1.011 g, 3.87 mmol) and STAB-H (1.405 g, 6.63 mmol). The reaction was stirred for 24 h then quenched with 2M NaOH, extracted with DCM, dried with MgSO$_4$, filtered and concentrated to a semisolid. The crude material was dissolved in DCM and TFA then stirred overnight. The reaction was diluted with DCM and made basic with 1M NaOH. The layers were separated and the aqueous was extracted with DCM (2×10 mL). the organics were dried with Na$_2$SO$_4$, filtered and concentrated to a brown oil which was purified via combiflash (DCM 2 minutes, 10% B (B=80:20:3 DCM:MeOH:NH$_4$OH) 7 minutes, 50% B 8 minutes) to afford (S)-1-(pyridin-2-yl)-N,N-bis(((R)-1,2,3,4-tetrahydroisoquinolin-3-yl)methyl)ethanamine (0.095 g, 0.230 mmol, 53% yield). $^1$H NMR (400 MHz, CDCl$_3$): δ=8.57 (d, J 4.5 Hz, 1H), 7.65 (t, J 7.5 Hz, 1H), 7.29 (d, J 7.8 Hz, 1H), 7.17 (dd, J 7.4, 4.8 Hz, 1H), 7.15-6.99 (m, 8H), 4.16 (q, J 6.9 Hz, 1H), 4.08 (d, J 15.3 Hz, 1H), 4.02 (d, J 15.3 Hz, 1H), 3.00-2.93 (m, 2H), 2.73-2.62 (m, 8H), 2.45 (dd, J 16.3, 10.6 Hz, 2H), 1.54 (d, J 6.9 Hz, 3H); $^{13}$C NMR (125 MHz, CDCl$_3$): δ=161.5, 148.9, 136.0, 135.4, 134.3, 129.1, 126.3, 126.0, 125.6, 122.6, 122.1, 61.4, 57.3, 48.4, 33.6, 16.5; HRMS (ESI) [M+H]$^+$, calcd for C$_{27}$H$_{33}$N$_4$ 413.26997, found 413.26952; LC/MS 75-95% MeOH in H$_2$O over 3 minutes, r$_f$=0.951 at 254 nM, MS (+) 413.2, MS(+)/2 207.2

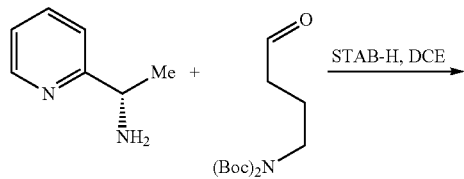

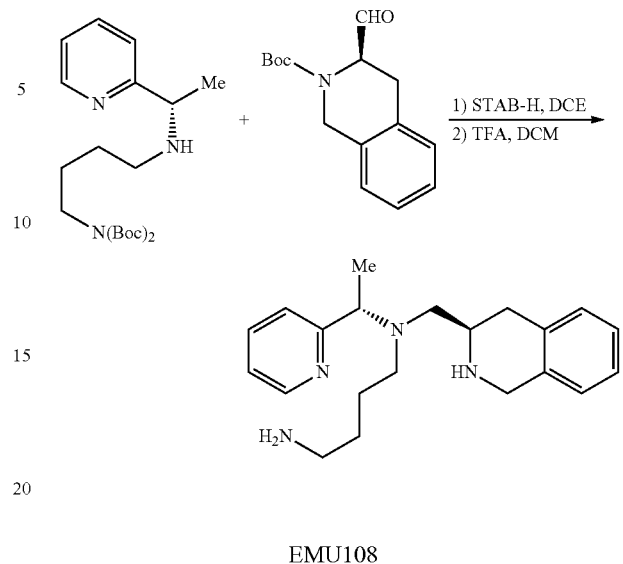

EMU108

To a 20 mL vial was added (S)-1-(pyridin-2-yl)ethanamine (0.3 g, 2.456 mmol), DCE (Volume: 5.85 ml), butyl-aldehyde (0.672 g, 2.339 mmol) and STAB-H (0.744 g, 3.51 mmol) and the reaction was allowed to stir overnight. The reaction was stirred for 16 h then quenched with 2M NaOH, extracted with DCM, dried with MgSO$_4$, filtered and concentrated to a semisolid. The crude material was purified via combiflash (DCM 2 minutes, 10% B (B=80:20:3 DCM:MeOH:NH$_4$OH) 7 minutes, 50% B 8 minutes) to afford secondary amine (0.733 g, 1.863 mmol, 80% yield). To a 20 mL vial was added THIQ (0.203 g, 0.777 mmol), DCE (Volume: 1.943 ml), secondary amine (0.312 g, 0.793 mmol) and STAB-H (0.247 g, 1.166 mmol). The reaction was stirred overnight for 14 h. The reaction was diluted with DCM, washed with 2M NaOH, dried with MgSO$_4$, filtered and concentrated to a yellow oil. The oil was dissolved in 10 mL DCM and allowed to stir with TFA (1 mL) for 12 h. The reaction was diluted with DCM and made basic with 1M NaOH. The layers were separated and the aqueous was extracted with DCM (2×10 mL). the organics were dried with Na$_2$SO$_4$, filtered and concentrated to a brown oil which was purified via combiflash (DCM 2 minutes, 10% B (B=80:20:3 DCM:MeOH:NH$_4$OH) 7 minutes, 50% B 8 minutes) to afford N1-((S)-1-(pyridin-2-yl)ethyl)-N1-(((R)-1,2,3,4-tetrahydroisoquinolin-3-yl)methyl)butane-1,4-diamine (0.097 g, 0.287 mmol, 37% yield over three steps) as a yellow oil. $^1$H NMR (500 MHz, CDCl$_3$): δ=8.51 (dd, J=4.8, 0.8 Hz, 1H), 7.61 (dt, J=7.6, 1.8 Hz, 1H), 7.31 (d, J=7.8 Hz, 1H), 7.11 (ddd, J=7.4, 5.0, 0.8 Hz, 1H), 7.08-6.96 (m, 4H), 4.03 (d, J=14.6 Hz, 1H), 4.03 (q, J=6.9 Hz, 1H), 3.96 (d, J=14.9 Hz, 1H), 2.85-2.80 (m, 1H), 2.62 (t, J=6.9 Hz, 2H), 2.59-2.53 (m, 2H), 2.52 (dd, J=13.1, 4.2 Hz, 1H), 2.45 (dd, J 13.8, 7.1 Hz, 1H), 2.39 (dd, J=15.4, 10.5 Hz, 1H), 1.80 (bs, 2NH), 1.49-1.41 (m, 2H), 1.43 (d, J=6.9 Hz, 3H), 1.41-1.32 (m, 2H); $^{13}$C NMR (125 MHz, CDCl$_3$): δ=162.5, 148.7, 136.0, 135.6, 134.6, 129.1, 126.4, 125.9, 125.5, 122.6, 121.9, 60.1, 56.6, 52.2, 51.3, 48.7, 42.1, 33.9, 31.5, 25.7, 16.2; HRMS (ESI) [M+H]$^+$, calcd for C$_{21}$H$_{31}$N$_4$ 339.25432, found 339.25409; LC/MS 75% MeOH in H$_2$O over 3 minutes, r$_f$=0.763 at 254 nM, MS (+) 339.2, MS(+)/2 170.2

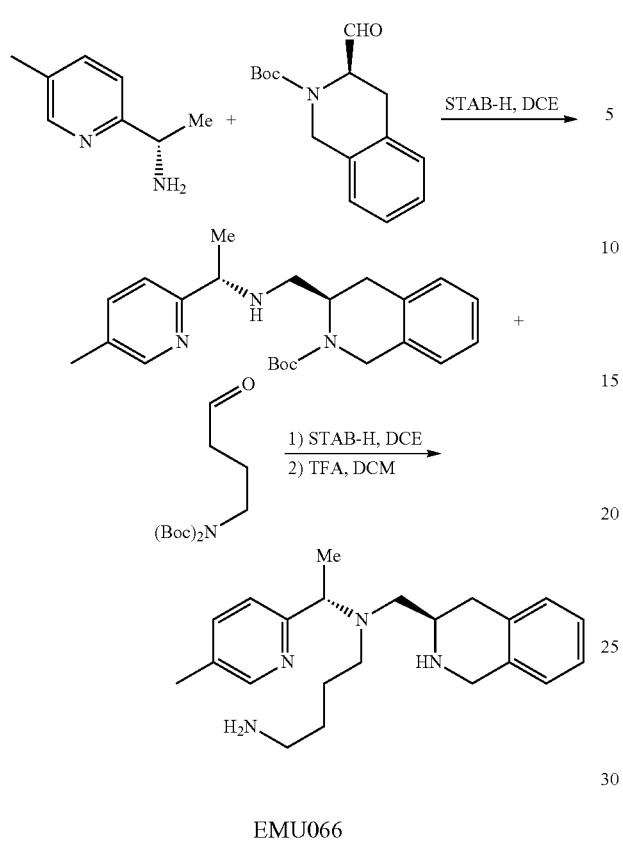

EMU066

To a 50 mL RBF was added (S)-1-(5-methylpyridin-2-yl)ethanamine (0.45 g, 3.30 mmol), DCE (Volume: 16.52 ml), THIQ (0.907 g, 3.47 mmol) and STAB-H (1.260 g, 5.95 mmol). The reaction was stirred for 16 h, then quenched with 2M NaOH, extracted with DCM, dried with MgSO$_4$, filtered and concentrated to a semisolid. The crude material was purified via combiflash (DCM 5 min, 10% B (80:20:3, DCM:MeOH:NH$_4$OH) 7 min, 50% B 10 min) to afford (R)-tert-butyl 3-((((S)-1-(5-methylpyridin-2-yl)ethyl)amino)methyl)-3,4-dihydroisoquinoline-2(1H)-carboxylate (1.01 g, 2.65 mmol, 80% yield) which was taken directly to the next step. To a 20 mL vial was added (R)-tert-butyl 3-((((S)-1-(5-methylpyridin-2-yl)ethyl)amino)methyl)-3,4-dihydroisoquinoline-2(1H)-carboxylate (0.5 g, 1.311 mmol), DCE (Volume: 4.37 ml) and butyl amine aldehyde followed by STAB-H (0.500 g, 2.359 mmol) and the reaction was stirred overnight. The reaction was quenched by the addition of 2M NaOH and extracted with DCM. The organic phase was dried with MgSO$_4$, filtered and concentrated to a yellow oil. The crude oil was dissolved in 3 mL DCM and TFA (1 mL) was added and the mixture was allowed to stir overnight. The reaction was quenched with 2M NaOH extracted with DCM, dried with MgSO$_4$, filtered and concentrated to a yellow oil. The oil was purified via combiflash (DCM 5 min, 10% B (80:20:3, DCM:MeOH:NH$_4$OH) 7 min, 50% B 10 min) to afford N1-((S)-1-(5-methylpyridin-2-yl)ethyl)-N1-(((R)-1,2,3,4-tetrahydroisoquinolin-3-yl)methyl)butane-1,4-diamine (0.167 g, 0.474 mmol, 36% yield over three steps). $^1$H NMR (400 MHz, CDCl$_3$): δ=8.36 (s, 1H), 7.44 (d, J=8.6 Hz, 1H), 7.22 (d, J=8.4 Hz, 1H), 7.10-7.08 (m, 2H), 7.05-7.00 (m, 2H), 4.06 (d, J=15.4 Hz, 1H), 4.01 (q, J=7.0 Hz, 1H), 4.00 (d, J=14.8 Hz, 1H), 2.89-2.83 (m, 1H), 2.67-2.38 (m, 9H), 2.30 (s, 3H), 1.52-1.35 (m, 6H), 1.43 (d, J=6.8 Hz, 3H); $^{13}$C NMR (100 MHz, CDCl$_3$): δ=159.5, 149.4, 136.5, 135.6, 134.6, 131.1, 129.0, 126.3, 125.8, 125.4, 122.0, 60.7, 56.5, 52.1, 51.2, 48.7, 42.1, 33.89, 31.51, 25.6, 18.0, 16.5; HRMS (ESI) [M+H]$^+$, calcd for C$_{22}$H$_{33}$N$_4$ 353.26997, found 353.26950; LC/MS 75-95% MeOH in H$_2$O over 3 minutes, r$_t$=0.781 at 254 nM, MS (+) 353.2, MS(+)/2 177.2

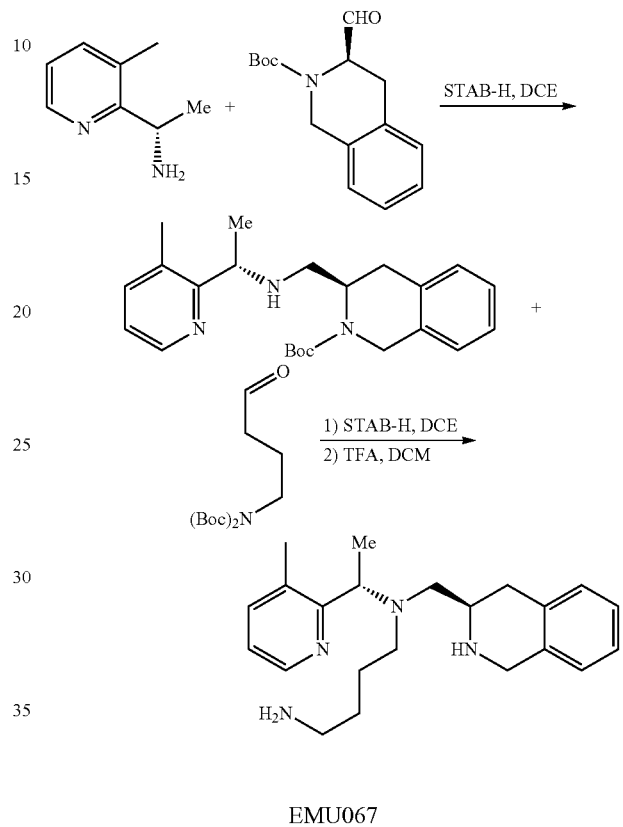

EMU067

To a 50 mL RBF was added (S)-1-(3-methylpyridin-2-yl)ethanamine (0.45 g, 3.30 mmol), DCE (Volume: 16.52 ml), THIQ (0.907 g, 3.47 mmol) and STAB-H (1.260 g, 5.95 mmol). The reaction was stirred for 16 h, then quenched with 2M NaOH, extracted with DCM, dried with MgSO$_4$, filtered and concentrated to a semisolid. The crude material was purified via combiflash (DCM 5 min, 10% B (80:20:3, DCM:MeOH:NH$_4$OH) 7 min, 50% B 10 min) to afford (R)-tert-butyl 3-((((S)-1-(3-methylpyridin-2-yl)ethyl)amino)methyl)-3,4-dihydroisoquinoline-2(1H)-carboxylate (0.85 g, 2.228 mmol, 67% yield) To a 20 mL vial was added (R)-tert-butyl 3-((((S)-1-(3-methylpyridin-2-yl)ethyl)amino)methyl)-3,4-dihydroisoquinoline-2(1H)-carboxylate (0.5 g, 1.311 mmol), DCE (Volume: 4.37 ml) and aldehyde (0.753 g) followed by STAB-H (0.500 g, 2.359 mmol) and the reaction was stirred overnight. The reaction was quenched by the addition of 2M NaOH and extracted with DCM. The organic phase was dried with MgSO$_4$, filtered and concentrated to a yellow oil. The crude oil was dissolved in 3 mL DCM and TFA (1 mL) was added then the mixture was allowed to stir overnight. The reaction was quenched with 2M NaOH extracted with DCM, dried with MgSO$_4$, filtered and concentrated to a yellow oil. The oil was purified via combiflash (DCM 5 min, 10% B (80:20:3, DCM:MeOH: NH$_4$OH) 7 min, 50% B 10 min) to afford N1-((S)-1-(3-methylpyridin-2-yl)ethyl)-N1-(((R)-1,2,3,4-tetrahydroisoquinolin-3-yl)methyl)butane-1,4-diamine (0.281 g, 0.797 mmol, 61% yield). ¹H NMR (400 MHz, CDCl₃): δ=8.37 (d, J=4.7 Hz, 1H), 7.42 (d, J=7.6 Hz, 1H), 7.08-7.04 (m, 3H), 6.99-6.96 (m, 2H), 4.27 (q, J=6.6 Hz, 1H), 3.99 (d, J=15.2 Hz, 1H), 3.87 (d, J=15.2 Hz, 1H), 2.81 (dd, J=11.4, 2.8 Hz, 1H), 2.71-2.65 (m, 1H), 2.60-2.49 (m, 8H), 2.46 (s, 3H), 2.22 (dd, J=16.6, 10.4 Hz, 1H), 1.43 (d, J=6.6 Hz, 3H), 1.32-1.24 (m, 4H); ¹³C NMR (100 MHz, CDCl₃): δ=160.3, 145.8, 137.7, 135.5, 134.6, 132.3, 129.1, 126.2, 125.8, 125.4, 121.9, 58.4, 57.8, 52.7, 52.0, 48.6, 42.0, 33.8, 31.6, 26.8, 18.7, 11.8; HRMS (ESI) [M+H]⁺, calcd for $C_{22}H_{33}N_4$ 353.26997, found 353.26955; LC/MS 85% MeOH in H₂O over 3 minutes, $r_f$=0.689 at 254 nM, MS (+) 353.2, MS(+)/2 177.2

Procedure for EMU107, EMU127 and EMU130 was allowed to stir for an additional 20 minutes then judged complete by TLC. The reaction mixture was poured into 50 mL of water and extracted with EtOAc (50 mL). The organic layer was washed with an additional 75 mL of water, then dried with MgSO₄, filtered and concentrated to a yellow oil. The oil was purified via combiflash (gradient 10-25% EA in hexanes) to afford tert-butyl ((3,5-dimethylpyridin-2-yl)methyl)(methyl)carbamate (0.256 g, 1.023 mmol, 60% yield). To a 20 mL vial was added tert-butyl ((3,5-dimethylpyridin-2-yl)methyl)(methyl)carbamate (0.250 g, 0.999 mmol), DCM (Volume: 4.54 ml, Ratio: 10) and TFA (Volume: 0.454 ml, Ratio: 1). The reaction was stirred overnight then diluted with DCM, quenched with 2M NaOH, dried with MgSO₄, filtered and concentrated to a clear oil. The

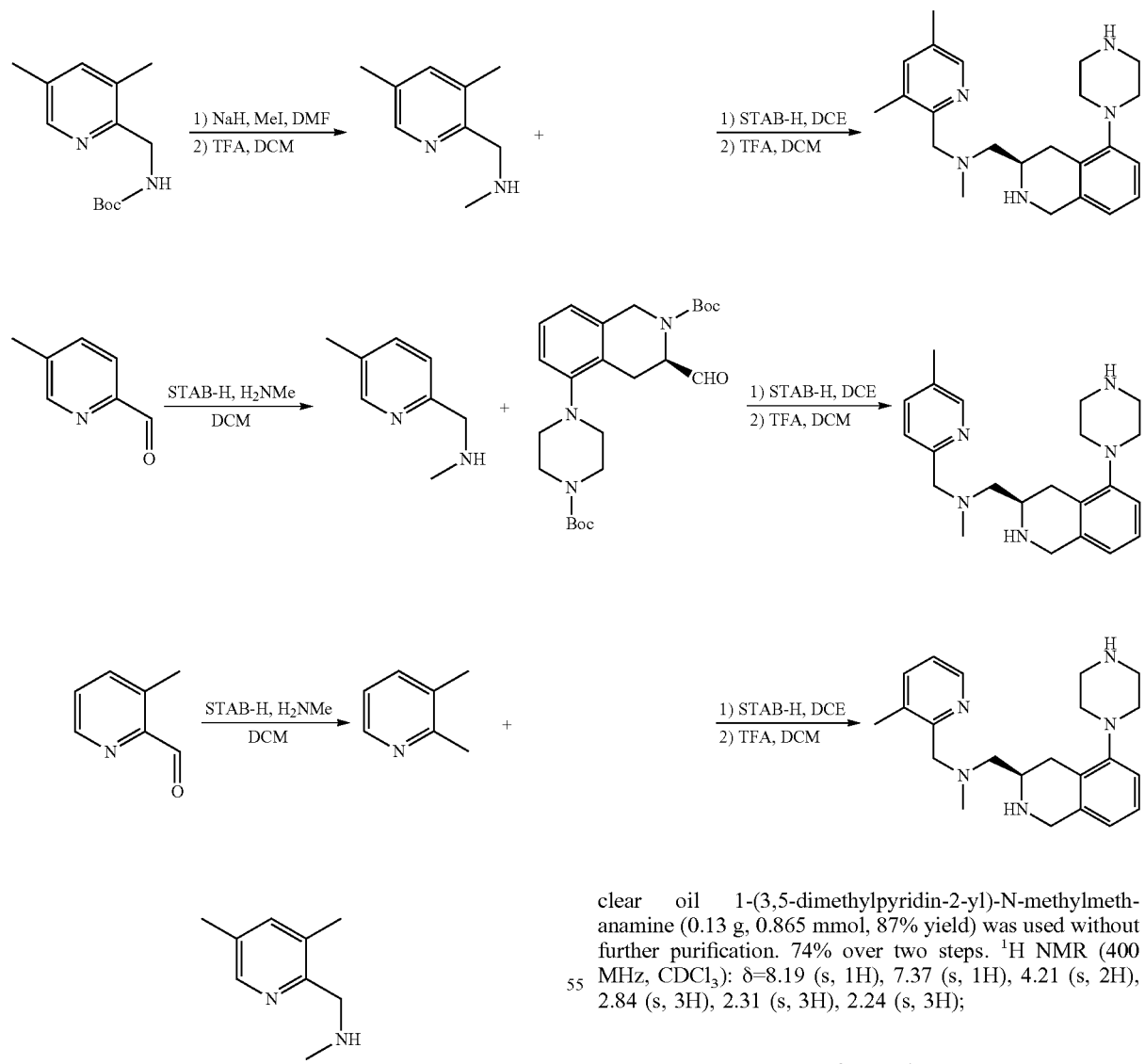

clear oil 1-(3,5-dimethylpyridin-2-yl)-N-methylmethanamine (0.13 g, 0.865 mmol, 87% yield) was used without further purification. 74% over two steps. ¹H NMR (400 MHz, CDCl₃): δ=8.19 (s, 1H), 7.37 (s, 1H), 4.21 (s, 2H), 2.84 (s, 3H), 2.31 (s, 3H), 2.24 (s, 3H);

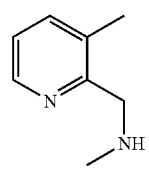

To a 25 mL rbf was added tert-butyl ((3,5-dimethylpyridin-2-yl)methyl)carbamate (0.4 g, 1.693 mmol) and DMF (Volume: 8.46 ml). To the clear solution was added sodium hydride (0.102 g, 2.54 mmol) in one portion and the solution turned red with a small amount of gas evolution. The red solution was allowed to stir for 15 minutes followed by the dropwise addition of iodomethane (0.158 ml, 2.54 mmol). The solution turned yellow during the addition. The mixture To a 100 mL RBF was added 3-methylpicolinaldehyde (1 g, 8.26 mmol) and DCE (Volume: 40.0 ml, Ratio: 8). To the stirred solution was added methanamine hydrochloride (1.672 g, 24.77 mmol) in one portion. MeOH (Volume: 5 ml, Ratio: 1.000) was added followed by STAB-H (3.15 g, 14.86 mmol) in one portion and the reaction was allowed to stir overnight. The reaction was diluted with DCM and washed with 1 M NaOH, dried with $Na_2SO_4$, filtered and concentrated to afford N-methyl-1-(3-methylpyridin-2-yl)methanamine (0.890 g, 6.53 mmol, 79% yield) which was sufficiently pure by $^1$H NMR. $^1$H NMR (400 MHz, $CDCl_3$): δ=8.37 (d, J=4.4 Hz, 1H), 7.40 (d, J=7.6 Hz, 1H), 7.05 (dd, J=7.6, 4.8 Hz, 1H), 3.82 (s, 2H), 2.50 (s, 3H), 2.29 (s, 3H); LC/MS 75-95% MeOH in $H_2O$ over 3 minutes, $r_t$=0.491 at 254 nM, MS (+) 137.2

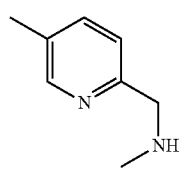

To a 100 mL RBF was added 5-methylpicolinaldehyde (1 g, 8.26 mmol) and DCE (Volume: 40.0 ml, Ratio: 8). To the stirred solution was added methanamine hydrochloride (1.672 g, 24.77 mmol) in one portion. MeOH (Volume: 5 ml, Ratio: 1.000) was added followed by STAB-H (3.15 g, 14.86 mmol) in one portion and the reaction was allowed to stir overnight. The reaction was diluted with DCM and washed with 1 M NaOH, dried with $Na_2SO_4$, filtered and concentrated to afford N-methyl-1-(5-methylpyridin-2-yl)methanamine (0.92 g, 6.76 mmol, 82% yield) which was sufficiently pure by $^1$H NMR. $^1$H NMR (400 MHz, $CDCl_3$): δ=8.37 (s, 1H), 7.44 (d, J=8.4 Hz, 1H), 7.17 (d, J=7.9 Hz, 1H), 3.82 (s, 2H), 2.46 (s, 3H), 2.30 (s, 3H); LC/MS 75-95% MeOH in $H_2O$ over 3 minutes, $r_t$=0.488 at 254 nM, MS (+) 137.2

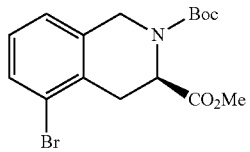 [SMILES: COC(=O)[C@H]1Cc2c(Br)cccc2CN1C(=O)OC(C)(C)C]

2-(tert-butyl) 3-methyl (R)-5-bromo-3,4-dihydroisoquinoline-2,3(1H)-dicarboxylate: prepared according to PCT Int. Appl. (2014), WO 2014193781 A1 20141204

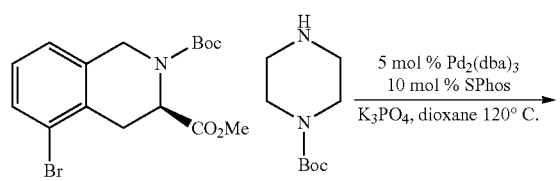

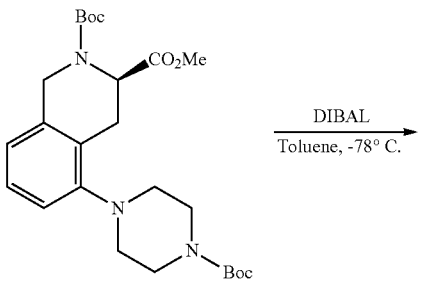

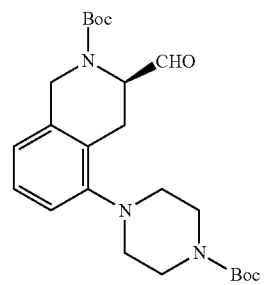

Step 1) To a 50 mL Schlenk tube was added all solids and the vessel was placed under vacuum. The Dioxane (Volume: 6.10 ml) was degassed for 1 h then added to (R)-2-tert-butyl 3-methyl 5-bromo-3,4-dihydroisoquinoline-2,3(1H)-dicarboxylate (0.904 g, 2.440 mmol) in a 20 mL vial and dissolved. The solution was added to a stirring mixture of solids then the solution was degassed with three cycles of evacuation and argon purge. The solution was then heated in an oil bath (pre-heated to 120° C.) with a cold finger attached to the schlenk tube. The reaction turned from red to light green and was monitored by TLC (10% EA/hex). The reaction was allowed to stir overnight (22 h). The reaction was red-brown and was cooled to RT, diluted with DCM, filtered through celite and concentrated to an orange oil which was purified via silica gel chromatography (0-30% EA/hex) (R)-2-tert-butyl 3-methyl 5-(4-(tert-butoxycarbonyl)piperazin-1-yl)-3,4-dihydroisoquinoline-2,3(1H)-dicarboxylate (ester 1 0.705 g, 1.482 mmol, 61% yield). Step 2) To a 50 mL schlenk tube was added ester 1 (0.5 g, 1.051 mmol) and Toluene (Volume: 5.26 ml). The solution was cooled to −78° C. then diisobutylaluminum hydride (2.63 ml, 3.15 mmol) was added dropwise. The reaction was allowed to stir at −78° C. until the SM was consumed. The reaction was diluted with methanol and poured into a sat. solution of rochelle salt and stirred for 30 minutes. The aqueous phase was extracted with EtOAc (3×25 mL) dried with $Na_2SO_4$, filtered and concentrated to a white solid (R)-tert-butyl 5-(4-(tert-butoxycarbonyl)piperazin-1-yl)-3-formyl-3,4-dihydroisoquinoline-2(1H)-carboxylate (CHO 1, 0.44 g, 0.988 mmol, 94% yield) which was used without further manipulation.

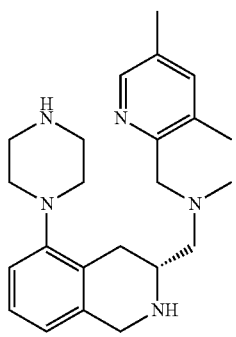 [SMILES: Cc1cnc(CN(C)C[C@H]2Cc3c(cccc3N3CCNCC3)CN2)c(C)c1]

EMU107

To a 20 mL vial was added CHO 1 (0.270 g, 0.605 mmol), 1-(3,5-dimethylpyridin-2-yl)-N-methylmethanamine (0.1 g, 0.666 mmol), DCE (Volume: 3.03 ml) and STAB-H (0.192 g, 0.908 mmol) then the mixture was allowed to stir overnight. The reaction was diluted with DCM, washed with 1M NaOH, dried with $Na_2SO_4$, filtered and concentrated to afford a yellow oil. The crude material was purified via combiflash (DCM 2 minutes, 10% B (80:20:3, DCM:MeOH:$NH_4OH$) 5 minutes and 50% B 9 minutes). The fractions were concentrated to afford a yellow oil which was dissolved in 5 mL DCM and 0.5 mL TFA. The solution turned blue then green. The reaction was allowed to stir overnight. The reaction was diluted with DCM, washed with 1M NaOH, dried with $Na_2SO_4$, filtered and concentrated to afford a yellow oil. The crude material was purified via combiflash (DCM 2 minutes, 10% B (80:20:3, DCM:MeOH:$NH_4OH$) 5 minutes and 50% B 9 minutes). The fractions were concentrated to afford (R)-1-(3,5-dimethylpyridin-2-yl)-N-methyl-N-((5-(piperazin-1-yl)-1,2,3,4-tetrahydroisoquinolin-3-yl)methyl)methanamine (0.110 g, 0.290 mmol, 48% yield over two steps) as an orange semi solid. $^1$H NMR (500 MHz, $CDCl_3$): δ=8.19 (s, 1H), 7.09 (t, J 7.7 Hz, 1H), 6.87 (d, J 7.8 Hz, 1H), 6.75 (d, J 7.5 Hz, 1H), 4.04 (s, 2H), 3.73 (d, J 12.4 Hz, 1H), 3.60 (d, J 12.4 Hz, 1H), 3.03-2.88 (m, 9H), 2.69-2.65 (m, 2H), 2.58 (dd, J 12.3, 9.6 Hz, 1H), 2.51 (dd, J 12.3, 3.4 Hz, 1H), 2.41 (s, 3H), 2.27 (3, 3H), 2.26 (s, 3H), 2.16 (dd, J 16.8, 11.0 Hz, 1H); $^{13}$C NMR (100 MHz, $CDCl_3$): δ=153.7, 151.7, 146.4, 138.9, 136.3, 132.2, 131.8, 129.8, 126.0, 121.6, 116.8, 63.4, 63.1, 53.1, 51.2, 48.6, 46.5, 42.9, 30.1, 18.3, 17.9; HRMS (ESI) [M+H]$^+$, calcd for $C_{23}H_{34}N_5$ 380.28087, found 380.28068; LC/MS 10-95% MeOH in $H_2O$ over 10 minutes, $r_t$=5.701 at 254 nM, MS (+) 380.3, MS(+)/2 190.7

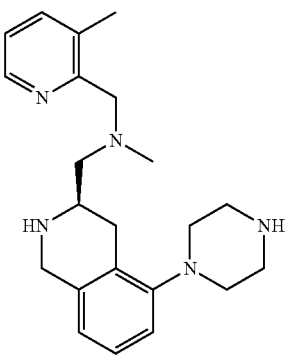 [SMILES: Cc1cccnc1CN(C)C[C@H]1Cc2c(cccc2N2CCNCC2)CN1]

EMU127

To a 20 mL vial was added N-methyl-1-(3-methylpyridin-2-yl)methanamine (0.110 g, 0.808 mmol), DCE (Volume: 1.68 ml), STAB-H (0.257 g, 1.212 mmol) and CHO 1 (0.3 g, 0.673 mmol) then the mixture was allowed to stir overnight. The reaction was diluted with DCM, washed with 1M NaOH, dried with $Na_2SO_4$, filtered and concentrated to afford a yellow oil. The crude material was purified via combiflash (DCM 2 minutes, 10% B (80:20:3, DCM:MeOH:$NH_4OH$) 5 minutes and 50% B 9 minutes). The fractions were concentrated to afford a yellow oil which was dissolved in 5 mL DCM and 0.5 mL TFA. The solution turned blue then green. The reaction was allowed to stir overnight. The reaction was diluted with DCM, washed with 1M NaOH, dried with $Na_2SO_4$, filtered and concentrated to afford a yellow oil. The crude material was purified via combiflash (DCM 2 minutes, 10% B (80:20:3, DCM:MeOH:$NH_4OH$) 5 minutes and 50% B 9 minutes). The fractions were concentrated to afford (R)—N-methyl-1-(3-methylpyridin-2-yl)-N-((5-(piperazin-1-yl)-1,2,3,4-tetrahydroisoquinolin-3-yl)methyl)methanamine (0.145 g, 0.397 mmol, 59% yield over two steps) as an orange semi solid. $^1$H NMR (500 MHz, $CDCl_3$): δ=8.35 (d, J=4.7 Hz, 1H), 7.43 (d, J=7.5 Hz, 1H), 7.09-7.06 (m, 2H), 6.84 (d, J=7.5 Hz, 1H), 6.73 (d, J=7.5 Hz, 1H), 4.03 (d, J=15.0 Hz, 1H), 4.00 (d, J=15.0 Hz, 1H), 3.73 (d, J=12.5 Hz, 1H), 3.62 (d, J=12.5 Hz, 1H), 3.02-2.88 (m, 8H), 2.66 (t, J=7.2 Hz, 3H), 2.61 (dd, J=12.0, 9.5 Hz, 1H), 2.52 (dd, J=12.2, 3.5 Hz, 1H), 2.44 (s, 3H), 2.28 (s, 3H), 2.18 (dd, J=17.0, 11.0 Hz, 1H); $^{13}$C NMR (125 MHz, $CDCl_3$): δ=156.8, 151.8, 146.2, 138.1, 136.4, 133.0, 129.8, 126.1, 122.5, 121.6, 116.8, 63.7, 63.6, 53.2, 51.3, 48.7, 46.6, 43.0, 30.3, 18.5; HRMS (ESI) [M+H]$^+$, calcd for $C_{22}H_{32}N_5$ 366.26522, found 366.26504; LC/MS 10-95% MeOH in $H_2O$ over 10 minutes, $r_t$=6.687 at 254 nM, MS (+) 364.4, MS(+)/2 182.8; LC/MS 75% MeOH in $H_2O$ over 3 minutes, $r_t$=0.800 at 254 nM, MS (+) 366.6, MS(+)/2 183.8

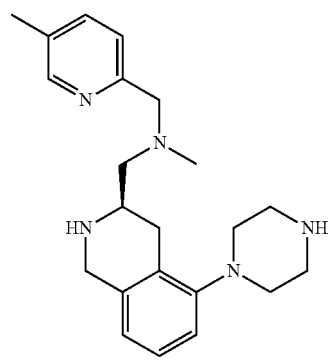 [SMILES: Cc1ccc(CN(C)C[C@H]2Cc3c(cccc3N3CCNCC3)CN2)nc1]

EMU130

To a 20 mL vial was added N-methyl-1-(5-methylpyridin-2-yl)methanamine (0.110 g, 0.808 mmol), DCE (Volume: 1.683 ml), STAB-H (0.257 g, 1.212 mmol) and CHO 1 (0.3 g, 0.673 mmol) then the mixture was allowed to stir overnight. The reaction was diluted with DCM, washed with 1M NaOH, dried with $Na_2SO_4$, filtered and concentrated to afford a yellow oil. The crude material was purified via combiflash (DCM 2 minutes, 10% B (80:20:3, DCM:MeOH:$NH_4OH$) 5 minutes and 50% B 9 minutes). The fractions were concentrated to afford a yellow oil which was dissolved in 5 mL DCM and 0.5 mL TFA. The solution turned blue then green. The reaction was allowed to stir overnight. The reaction was diluted with DCM, washed with 1M NaOH, dried with Na$_2$SO$_4$, filtered and concentrated to afford a yellow oil. The crude material was purified via combiflash (DCM 2 minutes, 10% B (80:20:3, DCM:MeOH:NH$_4$OH) 5 minutes and 50% B 9 minutes). The fractions were concentrated to afford (R)—N-methyl-1-(5-methylpyridin-2-yl)-N-((5-(piperazin-1-yl)-1,2,3,4-tetrahydroisoquinolin-3-yl)methyl)methanamine (0.166 g, 0.454 mmol, 67% yield) as an orange semi solid. $^1$H NMR (500 MHz, CDCl$_3$): δ=8.32 (d, J=0.5 Hz, 1H), 7.42 (dd, J=7.9, 1.6 Hz, 1H), 7.29 (d, J=7.9 Hz, 1H), 7.05 (t, J=7.6 Hz, 1H), 6.82 (d, J=7.6 Hz, 1H), 6.72 (d, J=7.6 Hz, 1H), 4.04 (d, J=15.3 Hz, 1H), 4.01 (d, J=15.3 Hz, 1H), 3.71 (d, J=13.9 Hz, 1H), 3.57 (d, J=13.9 Hz, 1H), 2.99-2.85 (m, 8H), 2.65 (brs, 2H), 2.56 (dd, J=12.6, 10.0 Hz, 1H), 2.47 (dd, J=12.6, 3.4 Hz, 1H), 2.34 (brs, 3H), 2.28 (s, 3H), 2.25 (s, 3H), 2.14 (dd, J=16.8, 11.3 Hz, 1H); $^{13}$C NMR (125 MHz, CDCl$_3$): δ=156.3, 151.7, 149.4, 137.1, 136.5, 131.4, 129.8, 126.0, 122.6, 121.6, 116.8, 64.4, 63.2, 53.2, 51.3, 48.7, 46.5, 43.2, 30.2, 18.1; HRMS (ESI) [M+H]$^+$, calcd for C$_{22}$H$_{32}$N$_5$ 366.26522, found 366.26501; LC/MS 75% MeOH in H$_2$O over 3 minutes, r$_f$=0.810 at 254 nM, MS (+) 366.6, MS(+)/2 183.9

Procedure for N-Propyl-Piperazine Side Chain

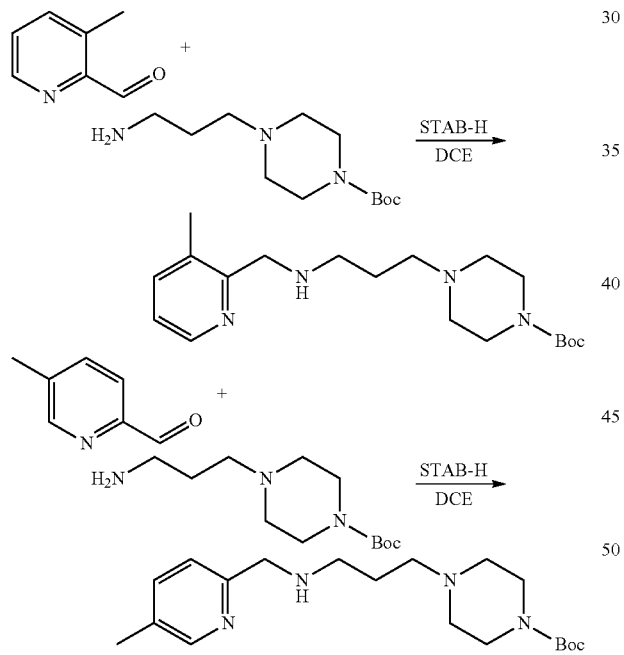

To a 50 mL RBF was added tert-butyl 4-(3-aminopropyl)piperazine-1-carboxylate (1.105 g, 4.54 mmol), DCE (Volume: 10.32 ml), 5-methylpicolinaldehyde (0.5 g, 4.13 mmol) and STAB-H (1.575 g, 7.43 mmol). The reaction was stirred overnight then diluted with DCM and quenched with 2M NaOH. The organic layer was dried with Na$_2$SO$_4$, filtered and concentrated to a yellow oil which was purified via silica gel chromatography (DCM 2 minutes, 10% B (80:20:3, DCM:MeOH:NH$_4$OH) 5 minutes and 50% B 9 minutes) to afford tert-butyl 4-(3-(((5-methylpyridin-2-yl)methyl)amino)propyl)piperazine-1-carboxylate (0.75 g, 2.152 mmol, 52% yield). $^1$H NMR (400 MHz, CDCl$_3$): δ=8.36 (d, J=2.0 Hz, 1H), 7.44 (dd, J=7.9, 2.2 Hz, 1H), 7.18 (d, J=7.9 Hz, 1H), 3.87 (s, 2H), 3.42 (t, J=5.1 Hz, 4H), 2.73 (t, J=6.8 Hz, 2H), 2.42 (t, J=7.1 Hz, 2H), 2.38 (t, J=5.0 Hz, 4H), 2.31 (s, 3H), 1.75 (pent, J=6.9 Hz, 2H), 1.45 (s, 9H);

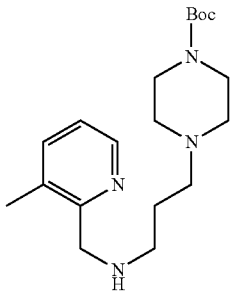 [SMILES: Cc1cccnc1CNCCCN1CCN(C(=O)OC(C)(C)C)CC1]

To a 50 mL RBF was added tert-butyl 4-(3-aminopropyl)piperazine-1-carboxylate (1.105 g, 4.54 mmol), DCE (Volume: 10.32 ml), 3-methylpicolinaldehyde (0.5 g, 4.13 mmol) and STAB-H (1.575 g, 7.43 mmol). The reaction was stirred overnight then diluted with DCM and quenched with 2M NaOH. The organic layer was dried with Na$_2$SO$_4$, filtered and concentrated to a yellow oil which was purified via silica gel chromatography (DCM 2 minutes, 10% B (80:20:3, DCM:MeOH:NH$_4$OH) 5 minutes and 50% B 9 minutes) to afford tert-butyl 4-(3-(((3-methylpyridin-2-yl)methyl)amino)propyl)piperazine-1-carboxylate (0.88 g, 2.53 mmol, 61% yield). $^1$H NMR (400 MHz, CDCl$_3$): δ=8.37 (d, J=5.0 Hz, 1H), 7.42 (d, J=7.3 Hz, 1H), 7.07 (dd, J=7.6, 4.8 Hz, 1H), 3.88 (s, 2H), 3.43 (t, J=5.2 Hz, 4H), 2.79 (t, J=6.8 Hz, 2H), 2.45 (t, J=7.2 Hz, 2H), 2.39 (t, J=5.2 Hz, 4H), 2.30 (s, 3H), 1.78 (pent, J=7.0 Hz, 2H), 1.45 (s, 9H);

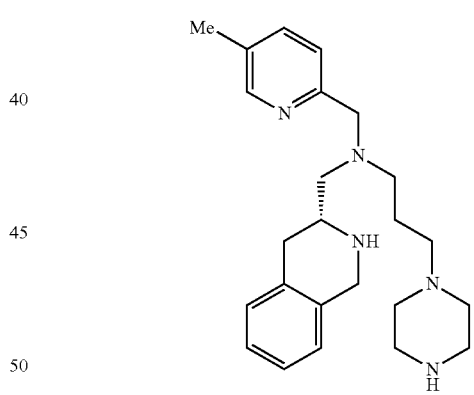

EMU148

To a 20 mL vial was added tert-butyl 4-(3-(((5-methylpyridin-2-yl)methyl)amino)propyl)piperazine-1-carboxylate (0.2 g, 0.574 mmol), STAB-H (0.219 g, 1.033 mmol) and THIQ (0.165 g, 0.631 mmol)(R)-then the mixture was allowed to stir overnight. The reaction was diluted with DCM, washed with 1M NaOH, dried with Na$_2$SO$_4$, filtered and concentrated to afford a yellow oil. The crude material was purified via combiflash (DCM 2 minutes, 10% B (80:20:3, DCM:MeOH:NH$_4$OH) 5 minutes and 50% B 9 minutes). The fractions were concentrated to afford a yellow oil which was dissolved in 2.5 mL DCM and 0.5 mL TFA. The reaction was allowed to stir overnight. The reaction was diluted with DCM, washed with 1M NaOH, dried with Na₂SO₄, filtered and concentrated to afford a yellow oil. The crude material was purified via combiflash (DCM 2 minutes, 10% B (80:20:3, DCM:MeOH:NH₄OH) 5 minutes and 50% B 9 minutes). The fractions were concentrated to afford (R)—N-((5-methylpyridin-2-yl)methyl)-3-(piperazin-1-yl)-N-((1,2,3,4-tetrahydroisoquinolin-3-yl)methyl)propan-1-amine (0.101 g, 0.257 mmol, 45% yield). ¹H NMR (500 MHz, CDCl₃): δ=8.30 (s, 1H), 7.42 (d, J=8.4 Hz, 1H), 7.28 (d, J=8.4 Hz, 1H), 7.06-7.00 (m, 3H), 6.97-6.95 (m, 1H), 3.98 (d, J=15.3 Hz, 1H), 3.92 (d, J=15.1 Hz, 1H), 3.78 (d, J 14.3 Hz, 1H), 3.64 (d, J=14.3 Hz, 1H), 2.90-2.86 (m, 1H), 2.82 (t, J=4.8 Hz, 3H), 2.65-2.29 (m, 16H), 2.27 (s, 3H), 1.76-1.63 (m, 2H); ¹³C NMR (125 MHz, CDCl₃): δ=156.9, 149.3, 137.1, 135.5, 134.4, 131.3, 129.1, 126.3, 125.9, 125.5, 122.4, 61.1, 60.4, 57.0, 54.6, 53.4, 51.7, 48.5, 46.0, 33.8, 24.2, 18.1; HRMS (ESI) [M+H]⁺, calcd for C₂₄H₃₆N₅ 394.29652, found 394.29578; LC/MS 10-95% MeOH in H₂O over 10 minutes, $r_t$=6.430 at 254 nM, MS (+) 394.3, MS(+)/2 197.8

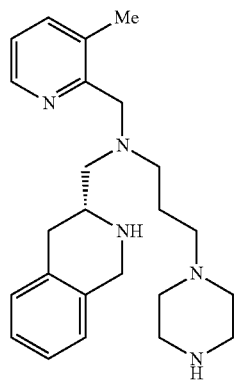 [SMILES: Cc1cccnc1CN(CCCN1CCNCC1)C[C@H]1Cc2ccccc2CN1]

EMU149

To a 20 mL vial was added tert-butyl 4-(3-(((3-methylpyridin-2-yl)methyl)amino)propyl)piperazine-1-carboxylate (0.2 g, 0.574 mmol), DCE (1.5 mL), STAB-H (0.219 g, 1.033 mmol) and THIQ (0.165 g, 0.631 mmol) then the mixture was allowed to stir overnight. The reaction was diluted with DCM, washed with 1M NaOH, dried with Na₂SO₄, filtered and concentrated to afford a yellow oil. The crude material was purified via combiflash (DCM 2 minutes, 10% B (80:20:3, DCM:MeOH:NH₄OH) 5 minutes and 50% B 9 minutes). The fractions were concentrated to afford a yellow oil which was dissolved in 2.5 mL DCM and 0.5 mL TFA The reaction was allowed to stir overnight. The reaction was diluted with DCM, washed with 1M NaOH, dried with Na₂SO₄, filtered and concentrated to afford a yellow oil. The crude material was purified via combiflash (DCM 2 minutes, 10% B (80:20:3, DCM:MeOH:NH₄OH) 5 minutes and 50% B 9 minutes). The fractions were concentrated to afford (R)—N-((3-methylpyridin-2-yl)methyl)-3-(piperazin-1-yl)-N-((1,2,3,4-tetrahydroisoquinolin-3-yl)methyl)propan-1-amine (0.134 g, 0.340 mmol, 59% yield). ¹H NMR (500 MHz, CDCl₃): δ=8.31 (d, J=3.6 Hz, 1H), 7.40 (d, J=7.3 Hz, 1H), 7.10-6.94 (m, 5H), 3.94 (d, J=15.6 Hz, 1H), 3.86 (d, J=15.6 Hz, 1H), 3.85 (d, J=12.8 Hz, 1H), 3.65 (d, J=12.8 Hz, 1H), 2.84-2.79 (m, 1H), 2.80 (t, J=4.6 Hz, 3H), 2.63-2.46 (m, 8H), 2.40 (s, 3H), 2.34-2.19 (m, 3H), 1.68-1.62 (m, 2H); ¹³C NMR (125 MHz, CDCl₃): δ=157.0, 146.2, 138.1, 135.3, 134.4, 132.8, 129.1, 126.3, 126.0, 125.5, 122.5, 60.6, 60.5, 57.0, 54.5, 53.5, 51.7, 48.4, 45.9, 33.7, 23.9, 18.4; HRMS (ESI) [M+H]⁺, calcd for C₂₄H₃₆N₅ 394.29652, found 394.29593; LC/MS 10-95% MeOH in H₂O over 10 minutes, $r_t$=6.080 at 254 nM, MS (+) 394.3, MS(+)/2 197.8

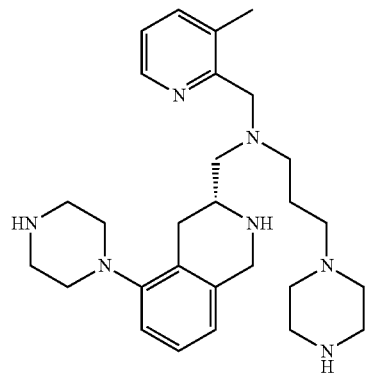 [SMILES: Cc1cccnc1CN(CCCN1CCNCC1)C[C@H]1Cc2c(cccc2N2CCNCC2)CN1]

EMU164

To a 20 mL vial was added tert-butyl 4-(3-(((3-methylpyridin-2-yl)methyl)amino)propyl)piperazine-1-carboxylate (0.2 g, 0.574 mmol), DCE (Volume: 1.435 ml), STAB-H (0.219 g, 1.033 mmol) and CHO 1 (0.281 g, 0.631 mmol) then the mixture was allowed to stir overnight. The reaction was diluted with DCM, washed with 1M NaOH, dried with Na₂SO₄, filtered and concentrated to afford a yellow oil. The crude material was purified via combiflash (DCM 2 minutes, 10% B (80:20:3, DCM:MeOH:NH₄OH) 5 minutes and 50% B 9 minutes). The fractions were concentrated to afford a yellow oil which was dissolved in 2.5 mL DCM and 0.5 mL TFA The reaction was allowed to stir overnight. The reaction was diluted with DCM, washed with 1M NaOH, dried with Na₂SO₄, filtered and concentrated to afford a yellow oil. The crude material was purified via combiflash (DCM 2 minutes, 10% B (80:20:3, DCM:MeOH:NH₄OH) 5 minutes, 50% B 9 minutes, 100% B 10 minutes). The fractions were concentrated to afford (R)—N-((3-methylpyridin-2-yl)methyl)-3-(piperazin-1-yl)-N-((5-(piperazin-1-yl)-1,2,3,4-tetrahydroisoquinolin-3-yl)methyl)propan-1-amine (0.134 g, 0.281 mmol, 49% yield). ¹H NMR (500 MHz, CDCl₃): δ=8.32 (dd, J 4.8, 1.1 Hz, 1H), 7.40 (d, J 7.0 Hz, 1H), 7.05 (t, J 7.7 Hz, 1H), 7.04 (dd, J 7.0, 4.8 Hz, 1H), 6.82 (d, J 7.7 Hz, 1H), 6.71 (d, J 7.7 Hz, 1H), 4.02 (d, J 15.3 Hz, 1H), 3.93 (d, J 15.3 Hz, 1H), 3.86 (d, J 12.8 Hz, 1H), 3.65 (d, J 12.8 Hz, 1H), 2.99-2.83 (m, 6H), 2.79 (t, J 4.8 Hz, 4H), 2.67-2.56 (m, 3H), 2.51-2.44 (m, 2H), 2.39 (s, 3H), 2.24-2.17 (m, 4H), 2.13 (dd, J 15.8, 10.4 Hz, 1H), 1.70-1.59 (m, 2H); ¹³C NMR (125 MHz, CDCl₃): δ=157.1, 151.8, 146.2, 138.1, 136.1, 132.7, 129.7, 126.1, 122.5, 121.6, 116.9, 60.6, 60.6, 57.1, 54.5, 53.4, 53.2, 51.7, 48.4, 46.6, 46.0, 30.0, 23.9, 18.5; HRMS (ESI) [M+H]⁺, calcd for C₂₈H₄₄N₇ 478.36527, found 478.36487; LC/MS 75% MeOH in H₂O over 3 minutes, $r_t$=0.481 at 254 nM, MS (+) 478.4, MS(+)/2 239.8

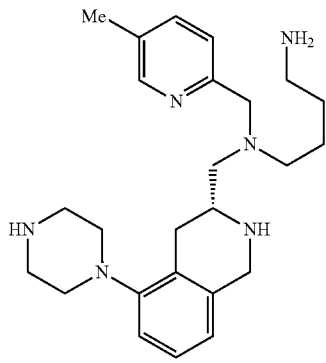 [SMILES: Cc1ccc(CN(CCCCN)C[C@H]2Cc3c(cccc3N3CCNCC3)CN2)nc1]

EMU165

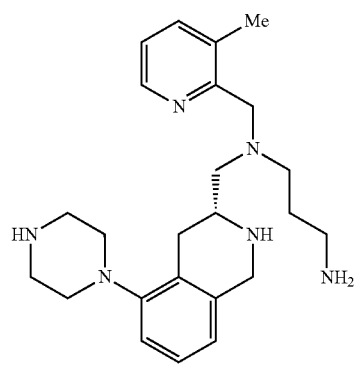 [SMILES: Cc1cccnc1CN(CCCN)C[C@H]1Cc2c(cccc2N2CCNCC2)CN1]

EMU166

To a 20 mL vial was added tert-butyl (4-(((5-methylpyridin-2-yl)methyl)amino)butyl)carbamate (0.15 g, 0.511 mmol), DCE (Volume: 1.162 ml), CHO 1 (0.207 g, 0.465 mmol) and STAB-H (0.177 g, 0.837 mmol) then the mixture was allowed to stir overnight. The reaction was diluted with DCM, washed with 1M NaOH, dried with $Na_2SO_4$, filtered and concentrated to afford a yellow oil. The crude material was purified via combiflash (DCM 2 minutes, 10% B (80:20:3, DCM:MeOH:$NH_4OH$) 5 minutes and 50% B 9 minutes). The fractions were concentrated to afford a yellow oil (R)-tert-butyl 3-(((4-((tert-butoxycarbonyl)amino)butyl)((5-methylpyridin-2-yl)methyl)amino)methyl)-5-(4-(tert-butoxycarbonyl)piperazin-1-yl)-3,4-dihydroisoquinoline-2(1H)-carboxylate (0.238 g, 0.329 mmol, 71% yield). To a 20 mL vial was added (R)-tert-butyl 3-(((4-((tert-butoxycarbonyl)amino)butyl)((5-methylpyridin-2-yl)methyl)amino)methyl)-5-(4-(tert-butoxycarbonyl)piperazin-1-yl)-3,4-dihydroisoquinoline-2(1H)-carboxylate (0.238 g, 0.329 mmol), DCM (Volume: 1.372 ml, Ratio: 5) and TFA (Volume: 0.274 ml, Ratio: 1.000) then the mixture was allowed to stir overnight. The reaction was diluted with DCM, washed with 1M NaOH, dried with $Na_2SO_4$, filtered and concentrated to afford a yellow oil. The crude material was purified via combiflash (DCM 2 minutes, 10% B (80:20:3, DCM:MeOH:$NH_4OH$) 5 minutes and 50% B 9 minutes). The fractions were concentrated to afford (R)—N1-((5-methylpyridin-2-yl)methyl)-N1-((5-(piperazin-1-yl)-1,2,3,4-tetrahydroisoquinolin-3-yl)methyl)butane-1,4-diamine (0.072 g, 0.170 mmol, 52% yield) as a yellow semi solid. $^1H$ NMR (500 MHz, $CD_3OD$): δ=8.58 (s, 1H), 8.15 (d, J=7.8 Hz, 1H), 7.74 (d, J=7.8 Hz, 1H), 7.12 (t, J=7.8 Hz, 1H), 6.96 (d, J=7.8 Hz, 1H), 6.86 (d, J=7.8 Hz, 1H), 4.34 (d, J=16.6 Hz, 1H), 4.27 (d, J=16.6 Hz, 1H), 4.18 (d, J=16.6 Hz, 1H), 3.84 (d, J=15.8 Hz, 1H), 3.62-3.58 (m, 1H), 3.21-3.10 (m, 5H), 3.02-2.99 (m, 2H), 2.93-2.83 (m, 4H), 2.71 (t, J=7.0 Hz, 1H), 2.56 (dd, J=17.5, 11.4 Hz, 1H), 2.45 (t, J=7.0 Hz, 1H), 2.35 (s, 3H), 1.51-1.37 (m, 4H); $^{13}C$ NMR (125 MHz, $CD_3OD$): δ=152.4, 151.3, 147.9, 143.0, 138.5, 130.7, 129.1, 128.2, 127.5, 124.1, 120.6, 57.4, 56.5, 55.2, 53.0, 50.1, 45.9, 45.2, 40.3, 26.6, 26.1, 23.6, 18.0; HRMS (ESI) [M+H]$^+$, calcd for $C_{25}H_{39}N_6$ 423.32307, found 423.32311; LC/MS 75% MeOH in $H_2O$ over 3 minutes, $r_t$=0.449 at 254 nM, MS (+) 423.2, MS(+)/2 212.2; LC/MS 10-95% MeOH in $H_2O$ over 10 minutes, $r_t$=0.702 at 254 nM, MS (+) 423.2, MS(+)/2 212.2

To a 20 mL vial was added tert-butyl (4-(((3-methylpyridin-2-yl)methyl)amino)butyl)carbamate (0.15 g, 0.511 mmol), DCE (Volume: 1.162 ml), (R)-tert-butyl 5-(4-(tert-butoxycarbonyl)piperazin-1-yl)-3-formyl-3,4-dihydroisoquinoline.) then the mixture was allowed to stir overnight. The reaction was diluted with DCM, washed with 1M NaOH, dried with $Na_2SO_4$, filtered and concentrated to afford a yellow oil. The crude material was purified via combiflash (DCM 2 minutes, 10% B (80:20:3, DCM:MeOH:$NH_4OH$) 5 minutes and 50% B 9 minutes). The fractions were concentrated to afford a yellow oil (R)-tert-butyl 3-(((4-((tert-butoxycarbonyl)amino)butyl)((3-methylpyridin-2-yl)methyl)amino)methyl)-5-(4-(tert-butoxycarbonyl)piperazin-1-yl)-3,4-dihydroisoquinoline-2(1H)-carboxylate (0.208 g, 0.288 mmol, 62% yield) which was dissolved in DCM (Volume: 1.199 ml, Ratio: 5) and TFA (Volume: 0.240 ml, Ratio: 1.000) then the mixture was allowed to stir overnight. The reaction was diluted with DCM, washed with 1M NaOH, dried with $Na_2SO_4$, filtered and concentrated to afford a yellow oil. The crude material was purified via combiflash (DCM 2 minutes, 10% B (80:20:3, DCM:MeOH:$NH_4OH$) 5 minutes and 50% B 9 minutes). The fractions were concentrated to afford (R)—N1-((3-methylpyridin-2-yl)methyl)-N1-((5-(piperazin-1-yl)-1,2,3,4-tetrahydroisoquinolin-3-yl)methyl)butane-1,4-diamine (0.077 g, 0.182 mmol, 63% yield) as a yellow oil. $^1H$ NMR (500 MHz, $CDCl_3$): δ=8.36 (d, J 4.3 Hz, 1H), 7.43 (d, J 8.0 Hz, 1H), 7.10-7.06 (m, 1H), 7.07 (t, J 8.0 Hz, 1H), 6.85 (d, J 8.0 Hz, 1H), 6.73 (d, J 8.0 Hz, 1H), 4.04 (d, J 15.5 Hz, 1H), 3.90 (d, J 15.5 Hz, 1H), 3.87 (d, J 13.0 Hz, 1H), 3.64 (d, J 13.6 Hz, 1H), 3.01-2.92 (m, 11H), 2.66-2.62 (m, 5H), 2.60-2.54 (m, 1H), 2.50-2.43 (m, 1H), 2.39 (s, 3H), 2.18 (dd, J 16.1, 10.5 Hz, 1H), 1.55-1.47 (m, 2H), 1.45-1.37 (m, 2H); $^{13}C$ NMR (125 MHz, $CDCl_3$): δ=157.0, 151.8, 146.3, 138.3, 136.0, 132.6, 129.6, 126.3, 122.6, 121.7, 117.0, 60.8, 60.2, 55.4, 53.2, 51.7, 48.2, 46.6, 41.4, 30.6, 29.9, 24.4, 18.5; HRMS (ESI) [M+H]$^+$, calcd for $C_{25}H_{39}N_6$ 423.32307, found 423.32311; LC/MS 75% MeOH in $H_2O$ over 3 minutes, $r_t$=0.450 at 254 nM, MS (+) 423.2, MS(+)/2 212.2

Scheme 1: Synthesis of EMU023 and EMU024

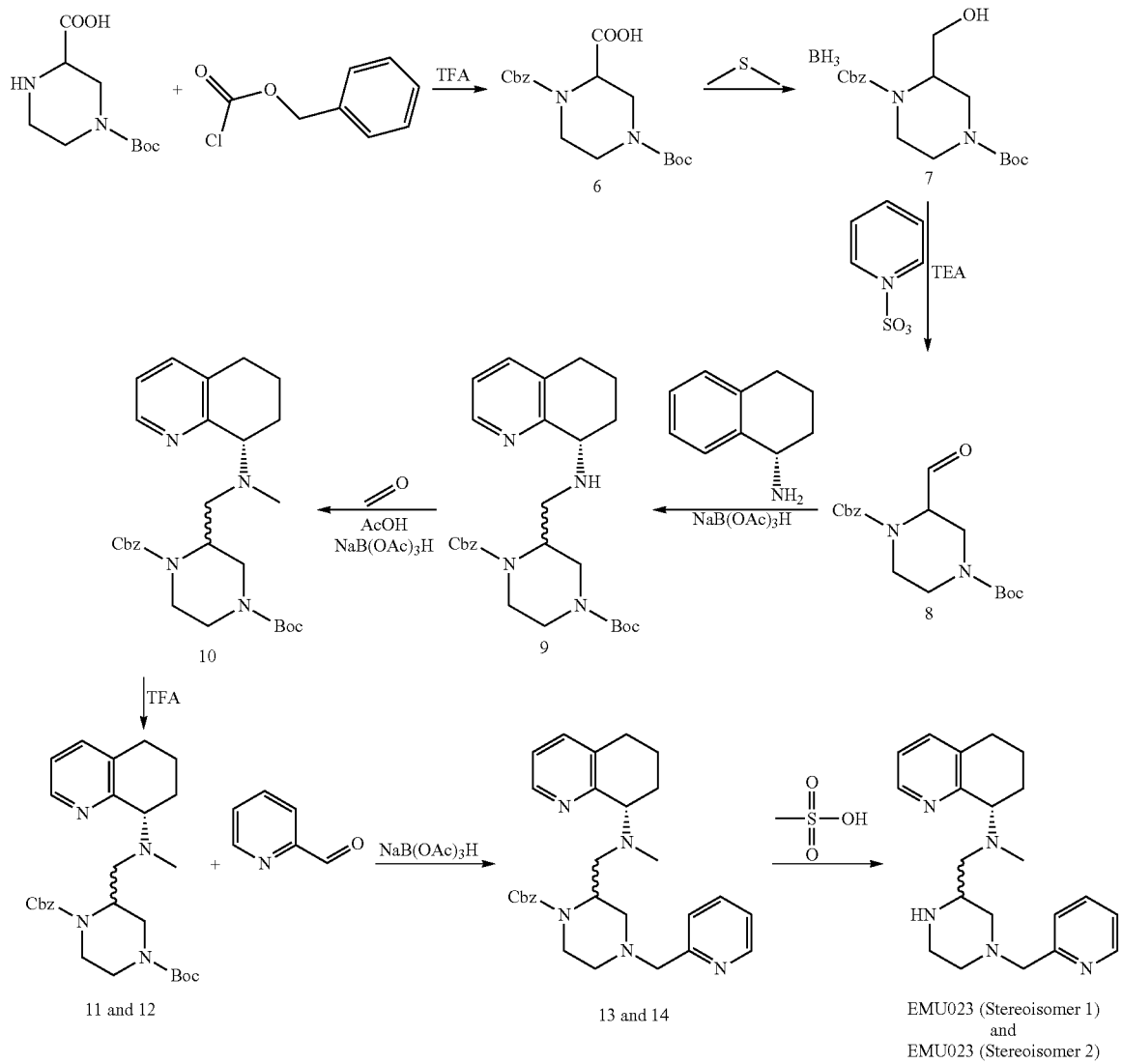

1-((Benzyloxy)carbonyl)-4-(tert-butoxycarbonyl) piperazine-2-carboxylic Acid (Compound 6)

The solution of 4-(tert-butoxycarbonyl)piperazine-2-carboxylic acid (7.12 g, 30.9 mmol) in 1,4-dioxane (100 ml), water (50 ml), and trimethylamine (TEA) (10.78 ml, 77 mmol) was cooled to 0° C. and benzyl chloroformate (5.5 ml, 37.1 mmol) was added slowly. The reaction was stirred at 0° C. for 30 minutes then let it warm to room temperature and stirred for another 2 hours. The reaction was diluted with 1N HCl and then extracted with DCM 3 times. Combined organic layers was dried over $Na_2SO_4$; filtered off and evaporated. The crude product was used as it is for the next step.

1-Benzyl-4-(tert-butyl)-2-(hydroxymethyl)piperazine-1,4-dicarboxylate (Compound 7)

The solution of compound 6 (11.27 g, 30.9 mmol) in 155 ml of anhydrous THF was cooled to 0° C. and borane-methyl sulfide complex (27.8 ml, 55.7 mmol) was added dropwise to the reaction mixture. After addition was completed the reaction mixture was let to warm up and stirred overnight at room temperature. After cooling with ice-bath, it was quenched with brine; stirred for 10 minutes then extracted with DCM 3 times. Combined organic layers was dried over $MgSO_4$, filtered off and evaporated. The crude product was used as it for the next step.

1-Benzyl-4-(tert-butyl)-2-formylpiperazine-1,4-dicarboxylate (Compound 8)

The solution of compound 7 (8.87 g, 25.3 mmol) in 80 ml anhydrous DCM and TEA (14.11 ml, 101 mmol) was cooled to 0° C. Sulfurtrioxide-pyridine complex (12.33 g, 76 mmol) in 80 ml DMSO was added to the solution and continued to stir for 2 hours. The reaction was quenched with saturated $NaHCO_3$ and diluted with ether. Aqueous phase was washed with ether 3 times. Combined organic layer was washed with $NaHPO_4$ solution, 1N HCl and brine then dried over

1-Benzyl-4-(tert-butyl) 2-((((S)-5,6,7,8-tetrahydroquinolin-8-yl)amino)methyl)pipera-zine-1,4-dicarboxylate (Compound 9)

((S)-5,6,7,8-tetrahydroquinolin-8-amine (4.39 g, 29.6 mmol)) and (1-benzyl 4-tert-butyl 2-formylpiperazine-1,4-dicarboxylate (8.26 g, 23.71 mmol)) were dissolved in 30 ml 1,2-dichloroethane at room temperature and stirred for 10-15 minutes. Then sodium triacetoxyborohydride (7.54 g, 35.6 mmol) was added and continued to stir for an hour. The reaction was quenched with saturated NaHCO₃ solution. Organic phase was washed with water and brine; dried over Na₂SO₄; filtered off and concentrated. Purified with column chromatography using DCM:MeOH:NH₄OH (9:1:0.1) to give 100% yield. $^1$H NMR (400 Hz, CDCl₃): δ 1.400 (s, 4.5H), 1.468 (s, 4.5H) 1.625-2.021 (m, 4H), 2.519 (broad s, 1H), 2.684-3.017 (m, 7H), 3.719-4.321 (m, 5H), 5.152 (m, 2H), 7.042 (m, 1H), 7.336 (m, 6H), 8.336 (s, 1H); MS: m/z 481.0 (M+H)

1-Benzyl-4-(tert-butyl) 2-((methyl((S)-5,6,7,8-tetrahydroquinolin-8-yl)amino)methyl)piperazine-1,4-dicarboxylate (Compound 10)

To the solution of compound 9 (11.39 g, 23.70 mmol) in 100 ml 1,2-DCE paraformaldehyde (3.75 g, 118 mmol) and acetic acid (1.05 ml, 18.25 mmol) was added and stirred at room temperature for 1 hour. After treating with sodium triacetoxyborohydride (12.56 g, 59.2 mmol) the reaction mixture was stirred for another 2 hours, followed by addition of 3.75 g paraformaldehyde, 1.05 ml acetic acid and 6.0 g sodium triacetoxyborohydride. This was allowed to stir at room temperature overnight and quenched with saturated NaHCO₃ solution. Aqueous phase was extracted with DCM. Combined organic phase was washed with water and brine, dried over Na₂SO₄ and filtered off and evaporated. It was purified with column chromatography using DCM:MeOH:NH₄OH (9:1:0.1) to give yellow oil (59% yield). $^1$H NMR (400 Hz, CDCl₃): δ 1.39 (s, 4.5H), 1.46 (s, 4.5H) 1.60-2.10 (m, 4H), 2.29 (s, 3H), 2.67-3.02 (m, 7H), 3.70-4.32 (m, 5H), 5.12-5.15 (m, 2H), 7.02-7.05 (m, 1H), 7.31-7.36 (m, 6H), 8.34 (s, 1H)

Benzyl (R)-2-((methyl((S)-5,6,7,8-tetrahydroquinolin-8-yl)amino)methyl)piperazine-1-carboxylate and Benzyl (S)-2-((methyl((S)-5,6,7,8-tetrahydroquinolin-8-yl)amino)methyl)piperazine-1-carboxylate (Compounds 11 and 12)

Compound 10 (6.46 g, 13.06 mmol) was treated TFA (20.12 ml, 261 mmol) and the reaction was stirred at room temperature for overnight. It was basified with 1N NaOH solution to pH>10-12. The aqueous phase was extracted with DCM 2 times. Combined organic layers was dried over anhydrous Na₂SO₄; filtered off and evaporated. The diasteromers were separated with column chromatography starting with DCM, then increased the polarity with DCM:MeOH:NH₄OH (9:1:0.1). (Compound 11: 31% yield). $^1$H NMR (400 Hz, CDCl₃): δ 1.65-1.79 (m, 2H), 1.80-2.10 (m, 2H), 2.29 (s, 3H), 2.30-2.51 (m, 1H), 2.60-2.83 (m, 7H), 3.83-3.85 (m, 1H), 3.73-4.07 (m, 3H), 5.12 (q, J=12.4 Hz, 2H), 7.04-7.08 (m, 1H), 7.26-7.38 (m, 6H), 8.47 (d, J=4.4 Hz, 1H); Compound 12 (22% yield): $^1$H NMR (400 Hz, CDCl₃): δ 1.65-1.80 (m, 2H), 1.82-2.10 (m, 2H), 2.29 (s, 3H), 2.30-2.51 (m, 1H), 2.60-3.22 (m, 8H), 3.73-4.01 (m, 3H), 5.11 (d, J=3.6 Hz, 2H), 7.04-7.08 (m, 1H), 7.28-7.36 (m, 6H), 8.43 (d, J=3.6 Hz, 1H)

Benzyl (R)-2-((methyl((S)-5,6,7,8-tetrahydroquinolin-8-yl)amino)methyl)-4-(pyridine-2-ylmethyl)piperazine-1-carboxylate (Compound 13)

The solution of compound 11 in 10 ml DCM was treated with 2-pyridinecarboxaldehyde (0.097 ml, 1.022 mmol) and sodium triacetoxyborohydride (0.335 g, 1.532 mmol). After stirring at room temperature for 6 hours it was quenched with saturated NaHCO₃ solution. The aqueous phase was extracted with DCM; combined organic layers was extracted with water and dried over anhydrous MgSO₄ and filtered off and evaporated. Product was purified with column chromatography using DCM:MeOH:NH₄OH (9:1:0.1) with 88% yield. $^1$H NMR (400 MHz, Chloroform-d) δ 8.49 (d, J=4.0 Hz, 1H), 8.39 (d, J=4.9 Hz, 1H), 7.56 (td, J=7.7, 1.8 Hz, 1H), 7.37-7.26 (m, 6H), 7.17-7.10 (m, 1H), 7.08 (d, J=7.8 Hz, 1H), 6.87 (dd, J=7.6, 4.7 Hz, 1H), 5.19-5.07 (m, 2H), 4.20-4.04 (m, 1H), 3.88-3.73 (m, 2H), 3.57 (d, J=14.3 Hz, 1H), 3.46 (d, J=14.3 Hz, 1H), 3.10 (t, J=11.0 Hz, 2H), 2.80 (ddd, J=15.2, 9.3, 5.0 Hz, 2H), 2.65 (dt, J=17.0, 4.9 Hz, 1H), 2.53 (s, 2H), 2.20 (dd, J=11.2, 4.0 Hz, 1H), 2.03-1.83 (m, 5H), 1.75 (s, 2H), 1.60 (s, 1H).

Benzyl (S)-2-((methyl((S)-5,6,7,8-tetrahydroquinolin-8-yl)amino)methyl)-4-(pyridine-2-ylmethyl)piperazine-1-carboxylate (Compound 14)

To the solution of compound 12 in 10 ml DCM, 2-pyridinecarboxaldehyde (0.098 ml, 1.022 mmol) and sodium triacetoxyhydroborate (0.325 g, 1.532 mmol) were added and stirred at room temperature for overnight. The reaction was quenched with saturated NaHCO₃ solution. Aqueous phase was extracted with DCM; combined organic layers was extracted with water and dried over anhydrous MgSO₄ and filtered off and evaporated. Product was purified with column chromatography with DCM:MeOH:NH₄OH (9:1:0.1) with 58% yield. $^1$H NMR (400 MHz, Chloroform-d) δ 8.48 (d, J=4.0 Hz, 1H), 8.39 (d, J=4.0 Hz, 1H), 7.57 (td, J=7.7, 1.9 Hz, 1H), 7.40-7.27 (m, 7H), 7.07 (dd, J=7.4, 5.0 Hz, 1H), 7.00 (dd, J=7.5, 4.8 Hz, 1H), 5.09 (s, 2H), 4.26-4.04 (m, 1H), 3.98-3.69 (m, 2H), 3.58 (q, J=13.8 Hz, 2H), 3.13-2.94 (m, 3H), 2.70 (d, J=31.6 Hz, 4H), 2.34-2.22 (m, 3H), 2.21-2.03 (m, 1H), 1.87 (d, J=18.5 Hz, 2H), 1.74 (s, 3H).

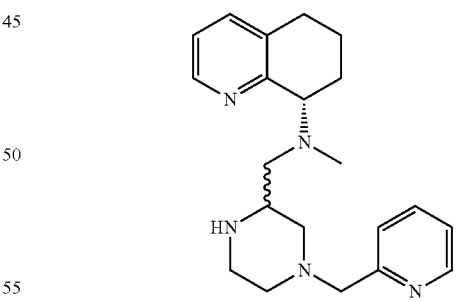

EMU023: (Stereoisomer 1)

To the solution of compound 13 (0.338 g, 0.696 mmol) in 15 ml DCM methanesulfonic acid (0.904 ml, 13.92 mmol) was added and stirred for overnight at room temperature. The reaction was cooled to 0° C. and the reaction was basified with saturated NaHCO₃ solution until the pH>8-9. The organic phase was washed with water; dried over MgSO₄; filtered off and evaporated. It was purified with column chromatography using DCM:MeOH:NH₄OH (9:1:

0.1) to give yellow oil (37% yield). ¹H NMR (400 MHz, Chloroform-d) δ 1.78-1.58 (m, 2H), 2.04-1.90 (m, 3H), 2.41-2.30 (m, 4H), 2.21-2.12 (m, 1H), 1.89-1.58 (m, 4H), 2.96-2.60 (m, 9H), 2.42 (s, 3H), 2.17 (td, J=11.0, 3.3 Hz, 1H), 2.04-1.91 (m, 2H), 1.90-1.79 (m, 1H), 2.44-2.41 (m, 4H), 8.53 (ddd, J=4.9, 1.9, 0.9 Hz, 1H), 8.41 (dd, J=4.7, 1.7 Hz, 1H), 7.62 (td, J=7.6, 1.8 Hz, 1H), 7.36 (dt, J=7.9, 1.1 Hz, 1H), 7.32 (ddt, J=7.7, 1.8, 0.8 Hz, 1H), 7.13 (ddd, J=7.5, 4.9, 1.2 Hz, 1H), 7.04-6.99 (m, 1H), 3.91 (dd, J=9.2, 5.7 Hz, 1H), 3.70-3.54 (m, 2H), 2.97-2.58 (m, 9H); MS: m/z 352.2 (M+H); HRMS Calc. for $C_{21}H_{30}N_5$ (M+H): 352.24230, Found: 352.24919; EMU023 (Stereoisomer 2): To the solution of 14 (0.282 g, 0.581 mmol) in 15 ml DCM methanesulfonic acid (0.754 ml, 11.61 mmol) was added at room temperature and stirred for overnight. The reaction was cooled to 0° C. and basified with saturated $NaHCO_3$ solution until the pH is around 8. The organic phase was washed with water; dried over $MgSO_4$; filtered off and evaporated. It was purified with column chromatography using DCM:MeOH:$NH_4OH$ (9:1:0.1) to give yellow oil (39% yield). ¹H NMR (400 MHz, Chloroform-d) δ 8.57-8.54 (m, 1H), 8.47-8.42 (m, 1H), 7.63 (td, J=7.7, 1.9 Hz, 1H), 7.36 (d, J=7.8 Hz, 1H), 7.35-7.30 (m, 1H), 7.15 (ddd, J=7.5, 4.9, 1.2 Hz, 1H), 7.03 (dd, J=7.7, 4.7 Hz, 1H), 3.87 (dd, J=9.4, 6.0 Hz, 1H), 3.64 (s, 2H), 2.94-2.85 (m, 4H), 2.83-2.58 (m, 5H), 2.57-2.42 (m, 2H), 2.32 (s, 3H), 2.22 (dt, J=10.8, 6.8 Hz, 1H), 2.11-2.02 (m, 1H), 1.98 (dd, J=13.0, 7.5 Hz, 1H), 1.91-1.74 (m, 2H); MS: m/z 352.2 (M+H); HRMS Calc. for $C_{21}H_{30}N_5$ (M+H): 351.24230, Found: 352.24910

Scheme 2: Racemic route to S,R and S,S-diastereomers

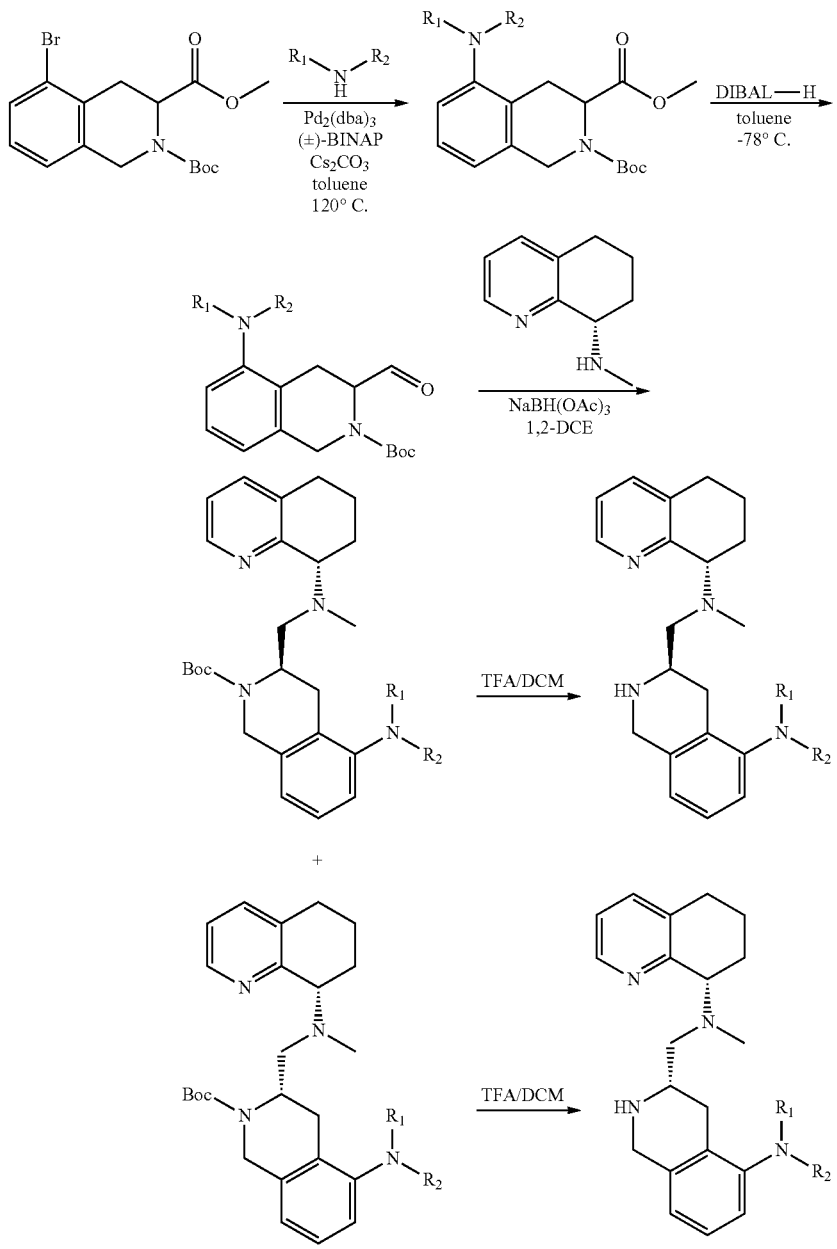

Synthesis of EMU034 and EMU035 by Scheme 2

2-tert-butyl 3-methyl 5-(4-(tert-butoxycarbonyl)piperazin-1-yl)-3,4-dihydroisoquinoline-2,3(1H)-dicarboxylate

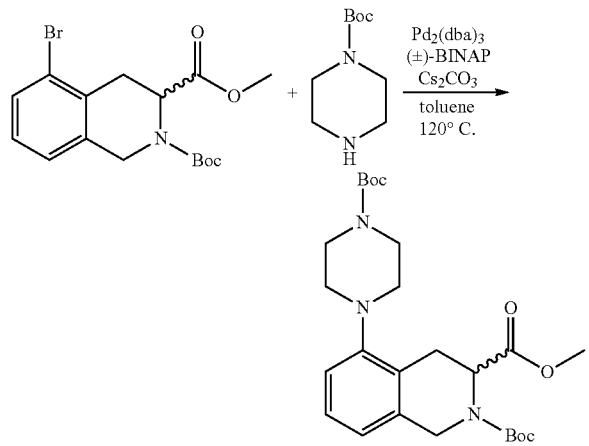

To an oven-dried Biotage 10-20 mL microwave vial equipped with a Teflon-coated magnetic stir bar was charged with racemic 2-tert-butyl 3-methyl 5-bromo-3,4-dihydroisoquinoline-2,3(1H)-dicarboxylate (1.03 g, 2.78 mmol), tert-butyl piperazine-1-carboxylate (0.622 g, 3.34 mmol), Pd$_2$(dba)$_3$ (0.127 g, 0.139 mmol), rac-BINAP (0.260 g, 0.417 mmol), and cesium carbonate (1.269 g, 3.89 mmol). The vial was sealed with a Teflon-lined septum and purged with argon for 5 minutes. Degassed toluene (13.91 mL) was added, and the vessel was degassed with argon for another 5 minutes. The resulting mixture was heated at 120° C. for 48 hours in an oil bath. Upon the completion of the reaction as judged by TLC analysis, the mixture was allowed to cool to room temperature, filtered through a Celite pad, and concentrated to a crude material which was purified by CombiFlash system (40 gram silica column, 5 minutes hexane then 30 minutes 0-30% ethyl acetate) to afford the product as a light yellow gel (1.4011 g, 2.95 mmol, quantitative yield). $^1$H NMR (400 MHz, Chloroform-d) δ 7.13 (td, J=7.8, 4.2 Hz, 1H), 6.98-6.65 (m, 2H), 5.03 (dd, J=6.1, 3.5 Hz, 0.5H), 4.80-4.55 (m, 1.5H), 4.42 (dd, J=34.5, 16.1 Hz, 1H), 3.75-3.39 (m, 7H), 3.15 (ddd, J=52.9, 15.5, 5.9 Hz, 1H), 2.98-2.60 (m, 5H), 1.62-1.27 (m, 18H). HRMS calculated for [C25H37N3O6+H]$^+$: 476.27606, found: 476.27542.

Tert-butyl 5-(4-(tert-butoxycarbonyl)piperazin-1-yl)-3-formyl-3,4-dihydroisoquinoline-2(1H)-carboxylate

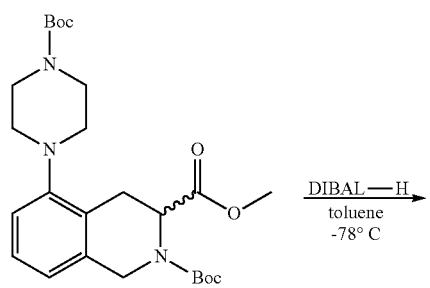

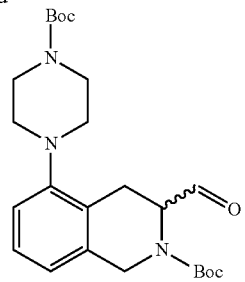

To a 100 mL round-bottom flask containing a Teflon-coated stir bar was charged with racemic 2-tert-butyl 3-methyl 5-(4-(tert-butoxycarbonyl)piperazin-1-yl)-3,4-dihydroisoquinoline-2,3(1H)-dicarboxylate (0.50 g, 1.051 mmol) and anhydrous toluene (13.14 mL). Diisobutylaluminum hydride 1 M solution in toluene (5.26 ml, 5.26 mmol) was added dropwise at −78° C. After 2 h at −78 C, reaction was quenched carefully with methanol under argon atmosphere then allowed to warm to 0° C. A saturated solution of Rochelle salt was added and stirred for 1-2 hour at room temperature. The biphasic mixture was transferred to a separatory funnel. The aqueous layer was separated and extracted with ethyl acetate (2 times). The combined organic extract was dried over anhydrous sodium sulfate and concentrated under reduced pressure to afford the crude aldehyde, which was used for the next step without purification. $^1$H NMR (400 MHz, Chloroform-d) δ 9.54-9.21 (m, 1H), 7.12 (td, J=7.6, 5.1 Hz, 1H), 6.95-6.69 (m, 2H), 4.91-4.17 (m, 3H), 3.90-3.09 (m, 5H), 3.09-2.50 (m, 5H), 1.64-1.26 (m, 18H).

(R)-tert-butyl 5-(4-(tert-butoxycarbonyl)piperazin-1-yl)-3-((methyl((S)-5,6,7,8-tetrahydroquinolin-8-yl)amino)methyl)-3,4-dihydroisoquinoline-2(1H)-carboxylate and (S)-tert-butyl 5-(4-(tert-butoxycarbonyl)piperazin-1-yl)-3-((methyl((S)-5,6,7,8-tetrahydroquinolin-8-yl)amino)methyl)-3,4-dihydroisoquinoline-2(1H)-carboxylate

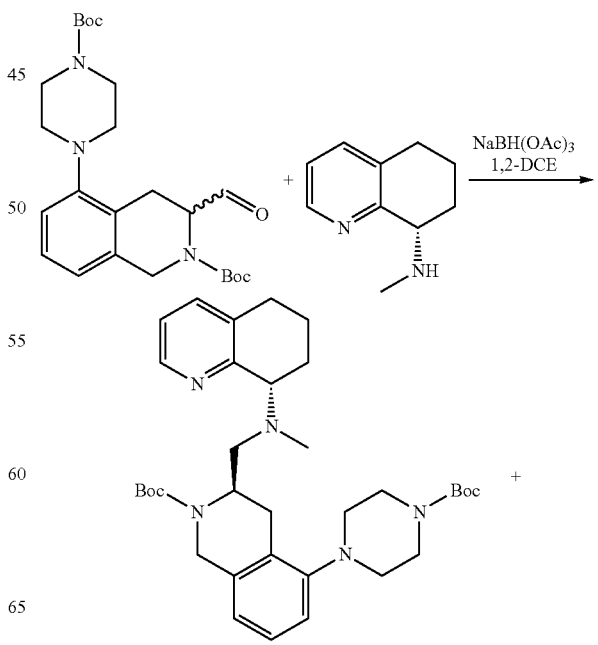

-continued

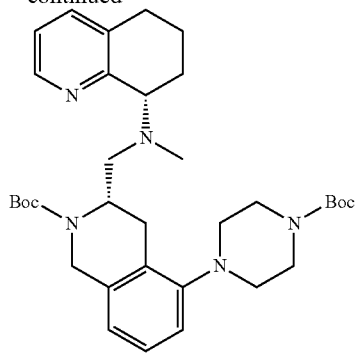

To a 20 mL scintillation vial equipped with a Teflon-coated magnetic stir bar was charged with (S)—N-methyl-5,6,7,8-tetrahydroquinolin-8-amine (0.114 g, 0.705 mmol), sodium triacetoxyhydroborate (0.179 g, 0.846 mmol), and 1,2-dichloroethane (1.349 mL). After stirring for 5 minutes, a solution of racemic tert-butyl 5-(4-(tert-butoxycarbonyl)piperazin-1-yl)-3-formyl-3,4-dihydroisoquinoline-2(1H)-carboxylate (0.2093 g, 0.470 mmol) in 1,2-dichloroethane (1 mL) was added dropwise. The resulting mixture was stirred at room temperature for 48 hours. Upon the completion of the reaction as judged by TLC and LCMS analysis, the mixture was quenched by addition of 1M NaOH. The biphasic mixture was transferred to a separatory funnel. The aqueous layer was separated and extracted with DCM (3 times). The combined organic extract was dried over anhydrous sodium sulfate and concentrated under reduced pressure to a crude diastereomeric mixture which was separated and purified by CombiFlash system (24 g gold silica column, 5 minutes DCM then 30 minutes 0-10% MeOH/DCM) to afford the two diastereomers. Stereoisomer 1: yellow foam (0.147 g, 0.249 mmol, 53% yield). $^1$H NMR (400 MHz, Chloroform-d) δ 8.23 (d, J=4.7 Hz, 1H), 7.29 (d, J=7.8 Hz, 1H), 7.05 (t, J=7.7 Hz, 1H), 6.96 (dd, J=7.7, 4.6 Hz, 1H), 6.79 (d, J=7.9 Hz, 1H), 6.66 (dd, J=14.9, 7.5 Hz, 1H), 4.66-4.37 (m, 2H), 3.85 (d, J=17.0 Hz, 1H), 3.68-3.35 (m, 5H), 3.21 (d, J=16.0 Hz, 1H), 2.92 (dt, J=10.4, 4.5 Hz, 2H), 2.83-2.53 (m, 7H), 2.24 (s, 3H), 1.99-1.90 (m, 1H), 1.84 (q, J=6.2 Hz, 2H), 1.47 (d, J=2.7 Hz, 19H). ESI-MS calculated for [C34H49N5O4+H]$^+$: 592.38628, found: 592.38611. Stereoisomer 2: yellow foam (0.086 g, 0.146 mmol, 31% yield). $^1$H NMR (400 MHz, Chloroform-d) δ 8.44-8.29 (m, 1H), 7.26-7.17 (m, 1H), 7.09 (q, J=6.3, 4.8 Hz, 1H), 7.01-6.90 (m, 1H), 6.77 (dd, J=20.4, 7.7 Hz, 2H), 4.51 (dd, J=67.8, 12.3 Hz, 2H), 4.24 (d, J=16.8 Hz, 1H), 3.71-3.19 (m, 6H), 2.93 (t, J=9.0 Hz, 2H), 2.68-2.53 (m, 5H), 2.46 (dd, J=12.8, 5.4 Hz, 1H), 2.33 (s, 3H), 1.86 (d, J=8.5 Hz, 2H), 1.56 (d, J=52.6 Hz, 21H). ESI-MS calculated for [C34H49N5O4+H]$^+$: 592.38628, found: 592.38507.

General Procedure for Global Deprotection:

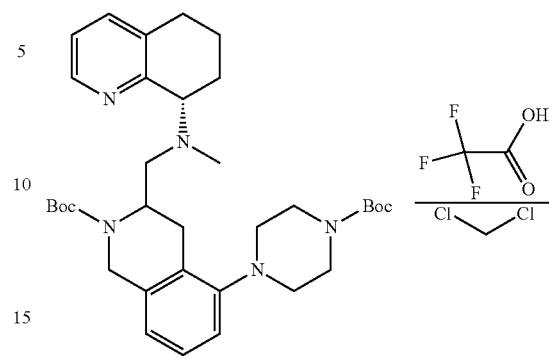

To a 20 mL scintillation vial equipped with a Teflon-coated magnetic stir bar was charged with Boc-protected substrate (1 equiv) and DCM (0.13 M). Trifluoroacetic acid (36 equiv) was added dropwise, and the resulting mixture was stirred at room temperature overnight. Upon the completion of the reaction as judged by LCMS analysis, the mixture was diluted with DCM, cooled in an ice-bath, and quenched by addition of 3M NaOH until pH>12. The biphasic mixture was transferred to a separatory funnel. The aqueous layer was separated and extracted with DCM (3 times). The combined organic extract was dried over anhydrous sodium sulfate and concentrated under reduced pressure to a crude material which was purified by CombiFlash system using a gradient of solvent A (DCM) to solvent B (8:2:0.6 DCM/MeOH/NH$_3$ solution, 7N in MeOH) as eluent on a silica gel column to afford the final product.

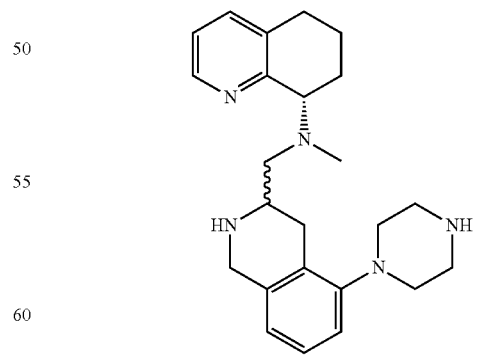

EMU034 (Stereoisomer 1)

Prepared according to the general procedure for global deprotection. The crude material was purified by Combi- Flash (12 g column, 5 minutes A then 30 minutes 0-100% B) to afford product (67.5 mg, quantitative yield) as a light yellow foam. $^1$H NMR (400 MHz, Chloroform-d) δ 8.43 (d, J=4.7 Hz, 1H), 7.36 (d, J=7.6 Hz, 1H), 7.17-7.01 (m, 2H), 6.88 (d, J=7.8 Hz, 1H), 6.77 (d, J=7.5 Hz, 1H), 4.66 (s, 2H), 4.22-4.11 (m, 1H), 4.08-3.95 (m, 2H), 3.05-2.87 (m, 8H), 2.86-2.56 (m, 6H), 2.44 (s, 4H), 2.11-1.87 (m, 3H), 1.80-1.64 (m, 1H). HRMS calculated for [C24H33N5+H]$^+$: 392.28142, found: 392.28082. EMU034 (Stereoisomer 2): Prepared according to the general procedure for global deprotection. The crude material was purified by Combi-Flash (12 g column, 5 minutes A then 30 minutes 0-100% B) to afford product (32.7 mg, 83% yield) as a light yellow foam. $^1$H NMR (400 MHz, Chloroform-d) δ 8.44 (dd, J=4.7, 2.0 Hz, 1H), 7.35 (dd, J=7.7, 1.7 Hz, 1H), 7.15-7.02 (m, 2H), 6.94-6.85 (m, 1H), 6.85-6.75 (m, 1H), 6.58 (s, 1H), 4.23 (t, J=6.4 Hz, 2H), 3.86 (dd, J=9.9, 5.5 Hz, 1H), 3.37-3.17 (m, 1H), 3.07-2.86 (m, 5H), 2.69 (ddd, J=41.9, 20.3, 10.7 Hz, 7H), 2.49 (s, 3H), 2.24-2.09 (m, 1H), 2.09-1.92 (m, 1H), 1.87-1.59 (m, 2H), 1.23 (s, 2H).

HRMS calculated for [C24H33N5+H]$^+$: 392.28142, found: 392.28090.

These following compounds were obtained according to Scheme 2:

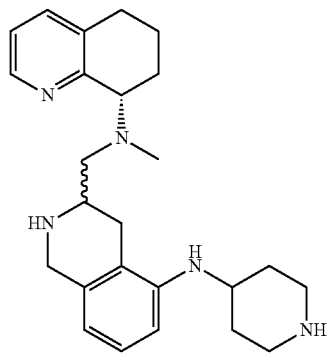 [SMILES: CN(CC1Cc2c(cccc2NC2CCNCC2)CN1)[C@H]1CCCc2cccnc21]

EMU044 (Stereoisomer 1)

Light yellow foam. $^1$H NMR (400 MHz, Methanol-d4) δ 8.45 (dd, J=4.9, 1.6 Hz, 1H), 7.61 (dd, J=7.8, 1.6 Hz, 1H), 7.28 (dd, J=7.7, 4.8 Hz, 1H), 7.13 (t, J=7.9 Hz, 1H), 6.72 (d, J=8.2 Hz, 1H), 6.59 (d, J=7.7 Hz, 1H), 4.98 (s, 3H), 4.37 (d, J=3.2 Hz, 1H), 4.12-4.08 (m, 1H), 3.73 (dtd, J=10.9, 5.6, 2.3 Hz, 2H), 3.44 (dt, J=13.1, 4.0 Hz, 2H), 3.18-3.03 (m, 4H), 2.98-2.54 (m, 5H), 2.25-2.17 (m, 2H), 2.12 (s, 5H), 1.96-1.70 (m, 4H). HRMS calculated for [C25H35N5+H]$^+$: 406.29707, found: 406.29646. EMU044 (Stereoisomer 2): Off-white foam. $^1$H NMR (400 MHz, Chloroform-d) δ 8.41 (d, J=4.7 Hz, 1H), 7.23 (d, J=7.7 Hz, 1H), 7.01-6.81 (m, 2H), 6.33 (dd, J=7.9, 4.5 Hz, 2H), 3.97 (d, J=15.0 Hz, 1H), 3.93-3.83 (m, 2H), 3.43-3.20 (m, 4H), 2.94 (dtd, J=23.6, 10.5, 9.3, 5.4 Hz, 3H), 2.74-2.55 (m, 5H), 2.39 (s, 3H), 2.19-1.73 (m, 8H), 1.61 (dp, J=11.4, 4.2, 3.1 Hz, 1H), 1.30-1.16 (m, 2H). HRMS calculated for [C25H35N5+H]$^+$: 406.29707, found: 406.29599.

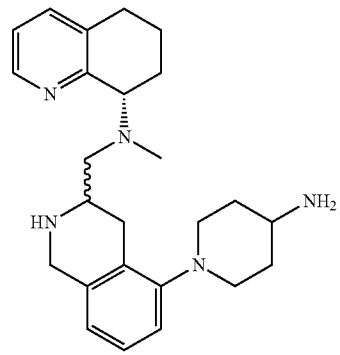 [SMILES: CN(CC1Cc2c(cccc2N2CCC(N)CC2)CN1)[C@H]1CCCc2cccnc21]

EMU058 (Stereoisomer 1)

$^1$H NMR (400 MHz, Chloroform-d) δ 8.44 (dd, J=4.9, 1.7 Hz, 1H), 7.38-7.31 (m, 1H), 7.12-7.03 (m, 2H), 6.86 (dd, J=7.9, 1.2 Hz, 1H), 6.75 (dd, J=7.8, 1.2 Hz, 1H), 4.13 (d, J=15.5 Hz, 1H), 4.04-3.92 (m, 2H), 3.47-3.22 (m, 4H), 3.13-2.93 (m, 2H), 2.90-2.81 (m, 4H), 2.68 (dt, J=17.0, 5.2 Hz, 2H), 2.43 (s, 3H), 2.30 (dd, J=17.6, 10.9 Hz, 1H), 2.03-1.81 (m, 4H), 1.71 (dddd, J=18.6, 13.3, 6.7, 3.4 Hz, 1H), 1.61-1.44 (m, 2H); HRMS Calc. for $C_{25}H_{36}N_5$ (M+H): 406.28925, Found: 406.29826

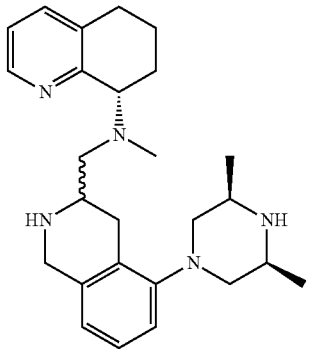 [SMILES: C[C@@H]1CN(c2cccc3c2CC(CN(C)[C@H]2CCCc4cccnc42)NC3)C[C@H](C)N1]

EMU096 (Stereoisomer 1)

White foam. H NMR (400 MHz, Chloroform-d) δ 8.38 (dd, J=4.7, 1.7 Hz, 1H), 7.29-7.19 (m, 1H), 7.02-6.90 (m, 2H), 6.75 (d, J=7.9 Hz, 1H), 6.66 (d, J=7.6 Hz, 1H), 3.97 (d, J=15.2 Hz, 1H), 3.88-3.76 (m, 2H), 2.98-2.55 (m, 11H), 2.41 (d, J=26.6 Hz, 5H), 2.19-2.02 (m, 2H), 1.91 (td, J=15.0, 12.9, 7.9 Hz, 3H), 1.66-1.57 (m, 1H), 0.97 (dd, J=22.7, 6.3 Hz, 6H). HRMS calculated for [C26H37N5+H]$^+$: 420.31272, found: 420.31131. EMU096 (Stereoisomer 2): White foam. $^1$H NMR (400 MHz, Chloroform-d) δ 8.41 (dd, J=4.7, 1.7 Hz, 1H), 7.27-7.18 (m, 1H), 7.00-6.92 (m, 2H), 6.73 (d, J=7.9 Hz, 1H), 6.66 (d, J=7.6 Hz, 1H), 4.03 (q, J=15.3 Hz, 2H), 3.86 (dd, J=9.7, 6.0 Hz, 1H), 2.98-2.65 (m, 8H), 2.59 (d, J=13.0 Hz, 2H), 2.37 (d, J=21.4 Hz, 5H), 2.07 (dt, J=13.9, 7.7 Hz, 2H), 1.95-1.85 (m, 2H), 1.74 (td, J=9.8, 5.0 Hz, 1H), 1.60 (tdd, J=12.1, 7.4, 4.2 Hz, 1H), 0.96 (dd, J=28.0, 6.3 Hz, 6H). HRMS calculated for [C26H37N5+H]$^+$: 420.31272, found: 420.31202.

Scheme 3: Chiral route: side chain modification

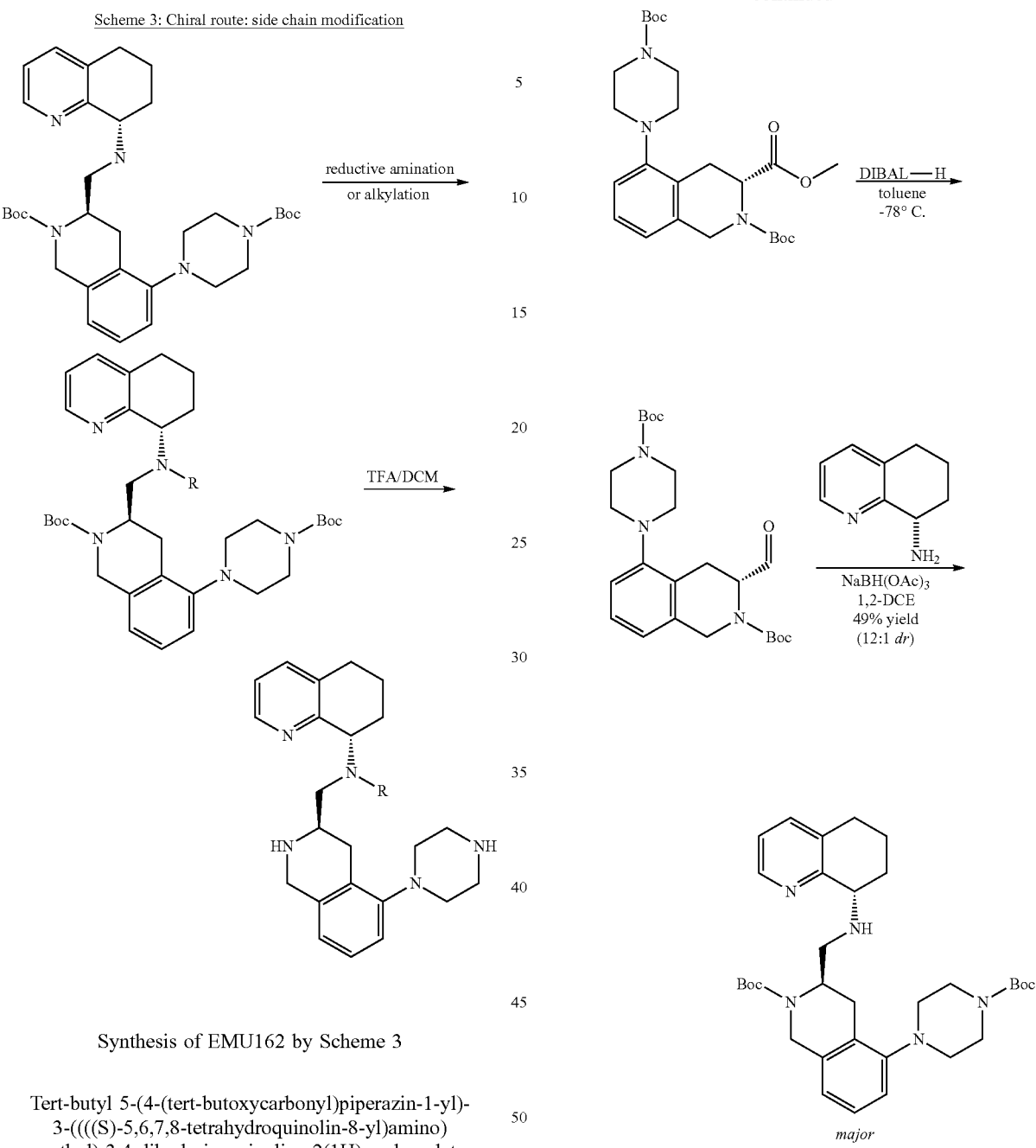

Synthesis of EMU162 by Scheme 3

Tert-butyl 5-(4-(tert-butoxycarbonyl)piperazin-1-yl)-3-((((S)-5,6,7,8-tetrahydroquinolin-8-yl)amino)methyl)-3,4-dihydroisoquinoline-2(1H)-carboxylate

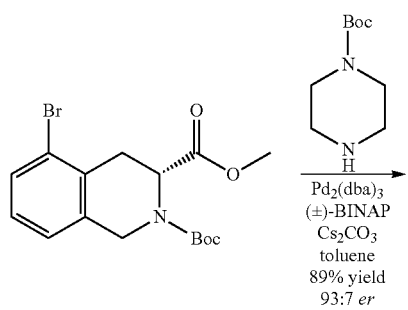

Following a similar route described in the synthesis of EMU034 starting from (R)-2-tert-butyl 3-methyl 5-bromo-3,4-dihydroisoquinoline-2,3(1H)-dicarboxylate, which was prepared in gram scale using literature method by Beadle et al. (PCT Int. Appl., 2014193781, 4 Dec. 2014). Yellow gel. $^1$H NMR (400 MHz, Chloroform-d) δ 8.36-8.29 (m, 1H), 7.35 (d, J=7.5 Hz, 1H), 7.16 (t, J=7.8 Hz, 1H), 7.09-7.01 (m, 1H), 6.93-6.79 (m, 2H), 4.67 (d, J=16.8 Hz, 2H), 4.32 (d, J=16.5 Hz, 1H), 3.86-3.22 (m, 6H), 2.95 (s, 2H), 2.85-2.61 (m, 6H), 2.59-2.24 (m, 2H), 1.95 (s, 2H), 1.65 (d, J=8.7 Hz, 2H), 1.49 (d, J=8.8 Hz, 18H). HRMS calculated for [C33H47N5O4+H]$^+$: 578.37063, found: 578.36923.

(R)-tert-butyl 5-(4-(tert-butoxycarbonyl)piperazin-1-yl)-3-((ethyl((S)-5,6,7,8-tetrahydroquinolin-8-yl)amino)methyl)-3,4-dihydroisoquinoline-2(1H)-carboxylate

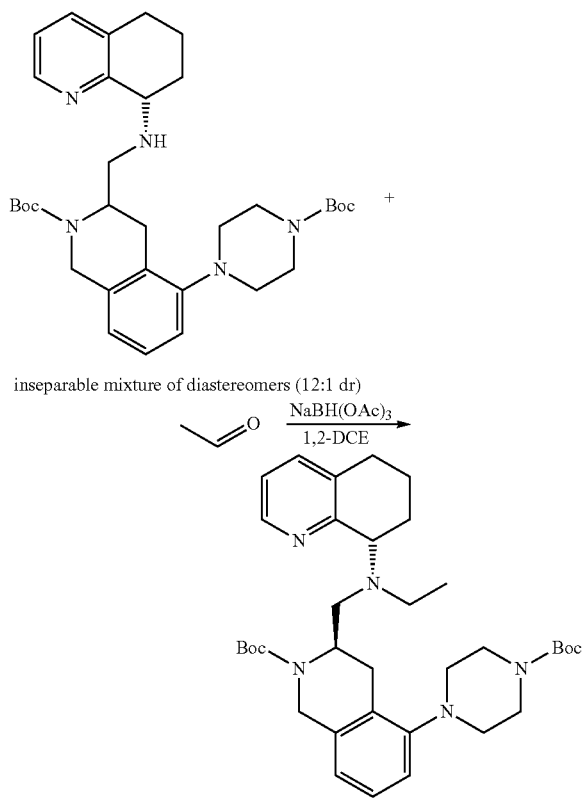

inseparable mixture of diastereomers (12:1 dr)

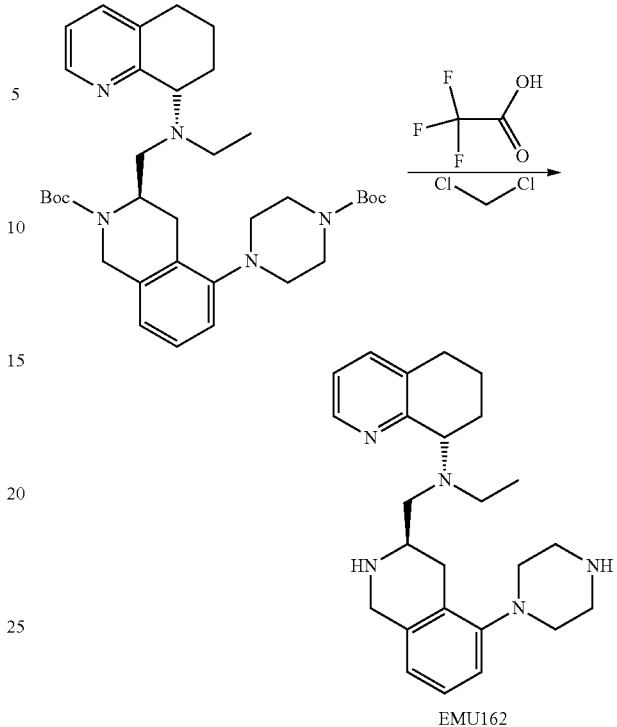

To a 20 mL scintillation vial equipped with a Teflon-coated magnetic stir bar was charged with tert-butyl 5-(4-(tert-butoxycarbonyl)piperazin-1-yl)-3-((((S)-5,6,7,8-tetrahydroquinolin-8-yl)amino)methyl)-3,4-dihydroisoquinoline-2(1H)-carboxylate (0.15 g, 0.260 mmol), sodium triacetoxyhydroborate (0.099 g, 0.467 mmol), and 1,2-dichloroethane (2.60 mL). After stirring for 5 minutes, acetaldehyde (0.073 mL, 1.298 mmol) was added. The resulting mixture was stirred at room temperature for 48 hours. Upon the completion of the reaction as judged by TLC and LCMS analysis, the mixture was quenched by addition of 1M NaOH. The biphasic mixture was transferred to a separatory funnel. The aqueous layer was separated and extracted with DCM (3 times). The combined organic extract was dried over anhydrous sodium sulfate and concentrated under reduced pressure to a crude material which was purified by CombiFlash system (24 g gold silica column, 5 minutes DCM then 30 minutes 0-10% MeOH/DCM) to afford the product (0.0874 g, 0.144 mmol, 55.6% yield) as yellow foam. $^1$H NMR (400 MHz, Chloroform-d) δ 8.29 (d, J=5.5 Hz, 1H), 7.28 (d, J=7.6 Hz, 1H), 7.09 (t, J=7.8 Hz, 1H), 6.97 (dd, J=7.7, 4.6 Hz, 1H), 6.82 (d, J=7.9 Hz, 1H), 6.79-6.67 (m, 1H), 4.61 (d, J=17.5 Hz, 2H), 4.06 (d, J=16.9 Hz, 1H), 3.79-3.30 (m, 6H), 2.98 (s, 2H), 2.76-2.57 (m, 7H), 2.38 (dd, J=13.8, 7.0 Hz, 1H), 2.05 (s, 1H), 1.94 (s, 1H), 1.75 (dd, J=17.2, 6.8 Hz, 1H), 1.48 (s, 20H), 0.92 (t, J=7.0 Hz, 3H). HRMS calculated for [C35H51N5O4+H]$^+$: 606.40193, found: 606.40175.

Prepared according to the general procedure for global deprotection. The crude material was purified by CombiFlash (12 g column, 5 minutes A then 30 minutes 0-60% B) to afford product (47.9 mg, 82% yield) as a light yellow foam. $^1$H NMR (400 MHz, Chloroform-d) δ 8.43 (dd, J=4.7, 1.7 Hz, 1H), 7.30 (dd, J=7.7, 1.7 Hz, 1H), 7.12-6.97 (m, 2H), 6.84 (d, J=7.8 Hz, 1H), 6.74 (d, J=7.6 Hz, 1H), 4.14-4.03 (m, 2H), 3.88 (d, J=15.2 Hz, 1H), 3.09-2.61 (m, 17H), 2.46 (dd, J=13.2, 10.4 Hz, 1H), 2.17 (dd, J=16.5, 10.8 Hz, 1H), 2.06-1.85 (m, 3H), 1.76-1.64 (m, 1H), 1.09 (t, J=7.1 Hz, 3H). HRMS calculated for [C25H35N5+H]$^+$: 406.29707, found: 406.29618.

These following compounds were obtained according to Scheme 3:

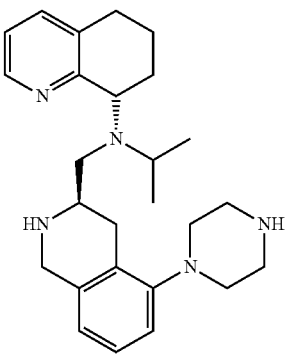

EMU163

White foam. $^1$H NMR (400 MHz, Chloroform-d) δ 8.41 (dd, J=4.7, 1.7 Hz, 1H), 7.25 (dd, J=9.5, 1.9 Hz, 1H), 7.08-6.95 (m, 2H), 6.82 (d, J=7.7 Hz, 1H), 6.68 (d, J=7.6 Hz, 1H), 4.12-3.97 (m, 2H), 3.43 (d, J=15.3 Hz, 1H), 3.24-3.07 (m, 2H), 3.07-2.49 (m, 13H), 2.26 (d, J=10.9 Hz, 2H), 2.05-1.94 (m, 3H), 1.74 (dt, J=11.2, 5.6 Hz, 1H), 1.11 (dd, J=27.8, 6.6 Hz, 6H). HRMS calculated for [C26H37N5+H]⁺: 420.31272, found: 420.31198.

Scheme 4: Late-state Buchwald-Hartwig coupling

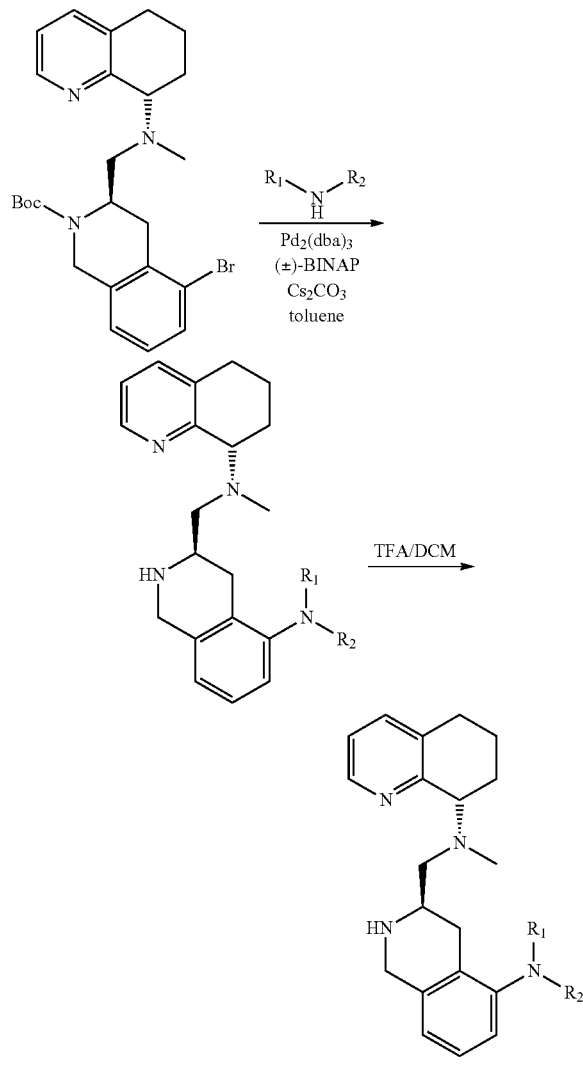

Synthesis of EMU183 by Scheme 4

(R)-tert-butyl 5-bromo-3-((methyl((S)-5,6,7,8-tetra-hydroquinolin-8-yl)amino)methyl)-3,4-dihydroiso-quinoline-2(1H)-carboxylate

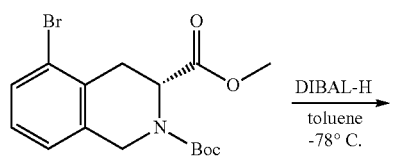

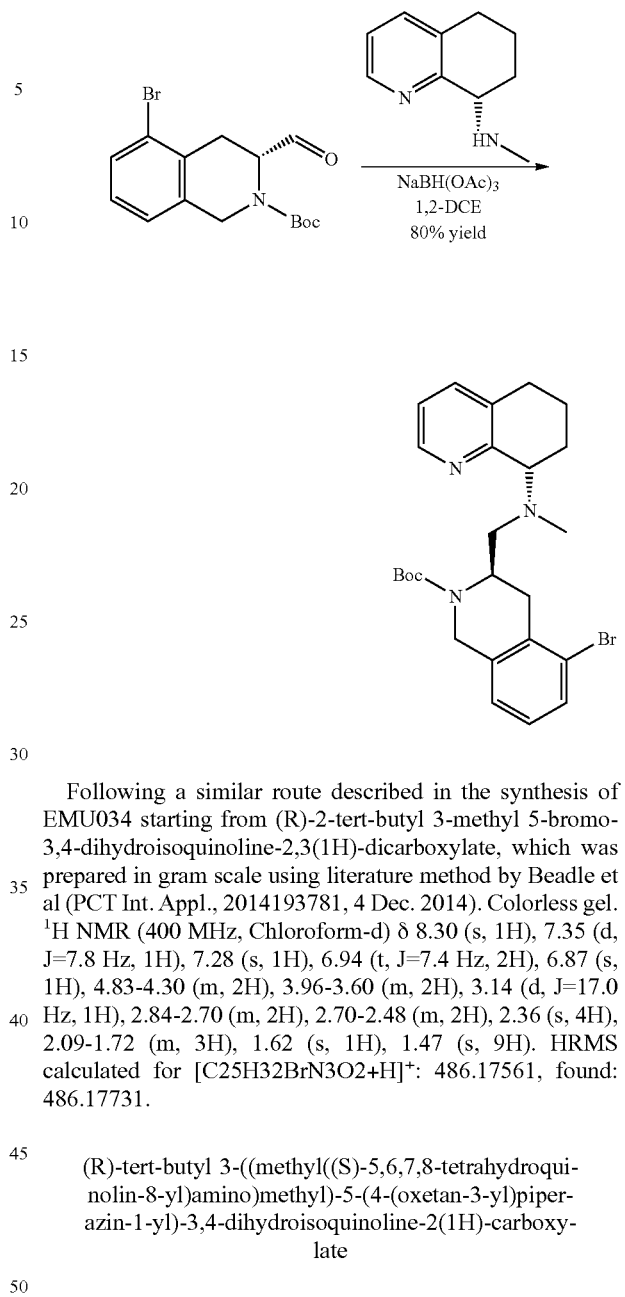

Following a similar route described in the synthesis of EMU034 starting from (R)-2-tert-butyl 3-methyl 5-bromo-3,4-dihydroisoquinoline-2,3(1H)-dicarboxylate, which was prepared in gram scale using literature method by Beadle et al (PCT Int. Appl., 2014193781, 4 Dec. 2014). Colorless gel. ¹H NMR (400 MHz, Chloroform-d) δ 8.30 (s, 1H), 7.35 (d, J=7.8 Hz, 1H), 7.28 (s, 1H), 6.94 (t, J=7.4 Hz, 2H), 6.87 (s, 1H), 4.83-4.30 (m, 2H), 3.96-3.60 (m, 2H), 3.14 (d, J=17.0 Hz, 1H), 2.84-2.70 (m, 2H), 2.70-2.48 (m, 2H), 2.36 (s, 4H), 2.09-1.72 (m, 3H), 1.62 (s, 1H), 1.47 (s, 9H). HRMS calculated for [C25H32BrN3O2+H]⁺: 486.17561, found: 486.17731.

(R)-tert-butyl 3-((methyl((S)-5,6,7,8-tetrahydroqui-nolin-8-yl)amino)methyl)-5-(4-(oxetan-3-yl)piper-azin-1-yl)-3,4-dihydroisoquinoline-2(1H)-carboxy-late

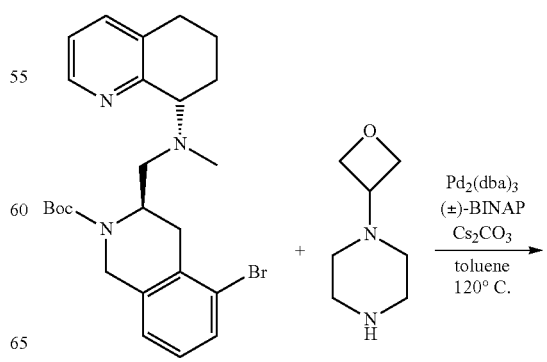

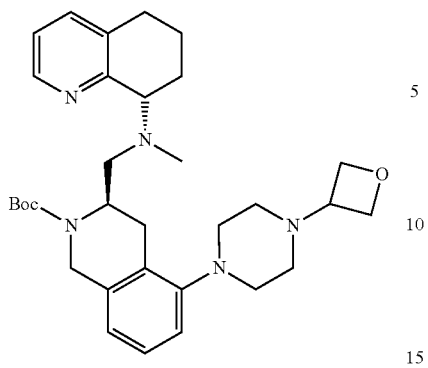

To an oven-dried Biotage 5-10 mL microwave vial equipped with a Teflon-coated magnetic stir bar was charged with (R)-tert-butyl 5-bromo-3-((methyl((S)-5,6,7,8-tetrahydroquinolin-8-yl)amino)methyl)-3,4-dihydroisoquinoline-2(1H)-carboxylate (0.254 g, 0.522 mmol), Pd$_2$(dba)$_3$ (0.024 g, 0.026 mmol), rac-BINAP (0.049 g, 0.078 mmol), and cesium carbonate (0.238 g, 0.731 mmol). The vial was sealed with a Teflon-lined septum and purged with argon for 5 minutes. Degassed toluene (2.61 ml, 0.522 mmol) was added, and the vessel was degassed with argon for another 5 minutes. 1-(oxetan-3-yl)piperazine (0.089 g, 0.627 mmol) was added in one portion via a syringe. The resulting mixture was heated at 120° C. for 24 hours in an oil bath. Upon the completion of the reaction as judged by TLC and LCMS analysis, the mixture was allowed to cool to room temperature, filtered through a Celite pad, and concentrated to a crude material which was purified by CombiFlash system (24 gram silica Gold column, 5 minutes DCM then 30 minutes 0-10% MeOH) to afford the product as a yellow foam (0.1975 g, 0.361 mmol, 69.1% yield). $^1$H NMR (400 MHz, Chloroform-d) δ 8.14 (d, J=5.1 Hz, 1H), 7.20 (d, J=7.7 Hz, 1H), 6.97 (t, J=7.8 Hz, 1H), 6.87 (t, J=6.2 Hz, 1H), 6.76 (d, J=7.9 Hz, 1H), 6.56 (dd, J=15.7, 7.6 Hz, 1H), 4.60-4.44 (m, 5H), 3.77 (d, J=16.8 Hz, 1H), 3.47 (p, J=6.2 Hz, 2H), 3.11-2.95 (m, 3H), 2.73-2.13 (m, 16H), 1.82 (dq, J=39.9, 6.1 Hz, 3H), 1.39 (s, 9H). HRMS calculated for [C32H45N5O3+H]$^+$: 548.36007, found: 548.35931.

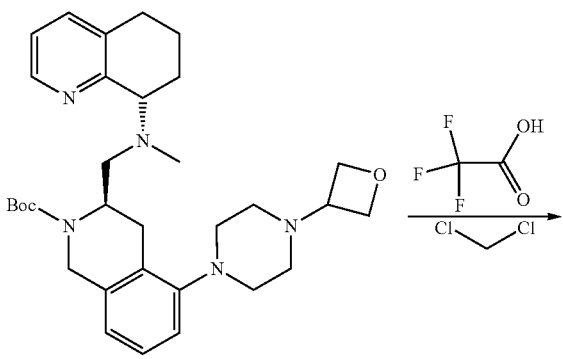

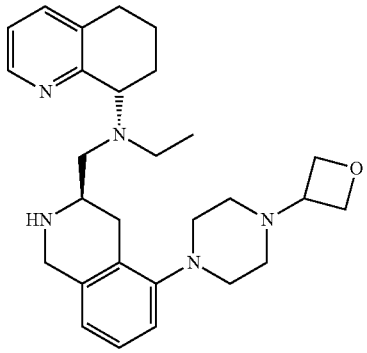

EMU183

Prepared according to the general procedure for global deprotection. The crude material was purified by CombiFlash (12 g column, 5 minutes A then 30 minutes 0-50% B) to afford product (146.2 mg, 91% yield) as a white foam. $^1$H NMR (400 MHz, Chloroform-d) δ 8.46 (dd, J=4.7, 1.7 Hz, 1H), 7.40-7.32 (m, 1H), 7.15-7.04 (m, 2H), 6.90 (dd, J=7.8, 1.2 Hz, 1H), 6.78 (dd, J=7.6, 1.1 Hz, 1H), 4.70-4.64 (m, 4H), 4.11 (d, J=15.5 Hz, 1H), 3.97 (q, J=8.1 Hz, 2H), 3.58 (q, J=6.5 Hz, 1H), 3.05 (dt, J=10.5, 4.3 Hz, 2H), 2.86-2.40 (m, 16H), 2.24 (s, 1H), 2.08-1.91 (m, 3H), 1.78-1.67 (m, 1H). HRMS calculated for [C27H37N5O+H]$^+$: 448.30764, found: 448.30681.

These following compounds were obtained according to Scheme 4:

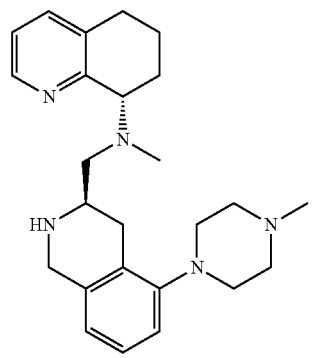 [SMILES: CN1CCN(c2cccc3c2C[C@H](CN(C)[C@H]2CCCc4cccnc42)NC3)CC1]

EMU116

White foam. $^1$H NMR (400 MHz, Chloroform-d) δ 8.42 (dd, J=4.8, 1.7 Hz, 1H), 7.36-7.28 (m, 1H), 7.10-6.99 (m, 2H), 6.86 (dd, J=7.9, 1.2 Hz, 1H), 6.73 (dd, J=7.6, 1.1 Hz, 1H), 4.07 (d, J=15.4 Hz, 1H), 3.98-3.87 (m, 2H), 3.00 (dt, J=10.2, 4.6 Hz, 2H), 2.85-2.45 (m, 15H), 2.37-2.14 (m, 5H), 2.06-1.87 (m, 3H), 1.68 (dddd, J=15.5, 10.3, 7.2, 4.8 Hz, 1H). HRMS calculated for [C25H35N5+H]$^+$: 406.29707, found: 406.29649.

191

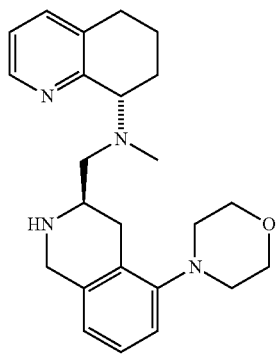 [SMILES: CN(C[C@H]1Cc2c(cccc2N2CCOCC2)CN1)[C@H]1CCCc2cccnc21]

EMU172

(S)—N-methyl-N—(((R)-5-morpholino-1,2,3,4-tetrahydroisoquinolin-3-yl)methyl)-5,6,7,8-tetrahydroquinolin-8-amine. $^1$H NMR (400 MHz, CDCl$_3$): ☐ 1.71 (m, 1H), 1.98 (m, 3H), 2.22 (m, 1H), 2.47 (s, 3H), 2.59 (m, 1H), 2.69 (m, 3H), 2.83 (m, 3H), 2.98 (m, 2H), 3.79 (m, 4H), 3.97 (m, 2H), 4.09 (d, 1H, J=16 Hz), 6.77 (d, 1H, J=8 Hz), 6.86 (d, 1H, J=8 Hz), 7.05 (dd, 1H, J=5 Hz, J=8 Hz), 7.1 (t, 1H, J=8 Hz), 7.34 (d, 1H, J=7 Hz), 8.44 (dd, 1H, J=1 Hz, J=4 Hz); MS (m/z): 393.2 (M+H)

192

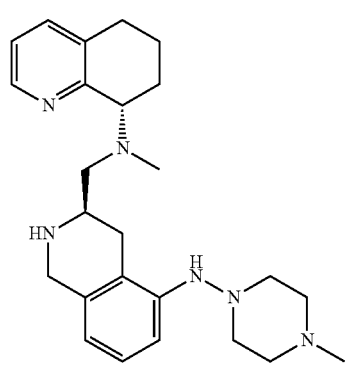 [SMILES: CN1CCN(Nc2cccc3c2C[C@H](CN(C)[C@H]2CCCc4cccnc42)NC3)CC1]

EMU229

Light orange foam. $^1$H NMR (400 MHz, Chloroform-d) δ 8.45 (dd, J=4.7, 1.7 Hz, 1H), 7.37-7.29 (m, 1H), 7.10-6.93 (m, 3H), 6.47 (dd, J=6.3, 2.6 Hz, 1H), 4.24 (s, 1H), 4.06-3.86 (m, 3H), 3.06-2.33 (m, 17H), 2.30 (s, 3H), 2.10-1.84 (m, 4H), 1.68 (dddt, J=16.1, 11.2, 8.0, 3.0 Hz, 1H). HRMS calculated for [C25H36N6+H]$^+$: 421.30797, found: 421.30811.

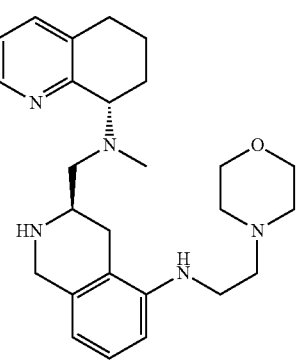

EMU173

(S)—N-methyl-N—(((R)-5-((2-morpholinoethyl)amino)-1,2,3,4-tetrahydroisoquinolin-3-yl)methyl)-5,6,7,8-tetrahydroquinolin-8-amine. $^1$H NMR (400 MHz, CDCl$_3$): ☐ 1.74 (m, 1H), 1.91 (m, 2H), 2.07 (m, 1H), 2.37 (s, 3H), 2.45 (m, 4H), 2.65 (m, 4H), 2.82 (m, 2H), 3.15 (m, 4H), 3.69 (t, 4H, J=5 Hz), 4.07 (m, 2H), 4.15 (m, 2H), 6.44 (dd, 2H, J=2 Hz, J=8 Hz), 7.05 (t, 1H, J=8 Hz), 7.08 (t, 1H, J=3 Hz), 7.36 (d, 1H, J=8 Hz), 8.4 (d, 1H, J=4 Hz); MS (m/z): 436.2 (M+H)$^+$.

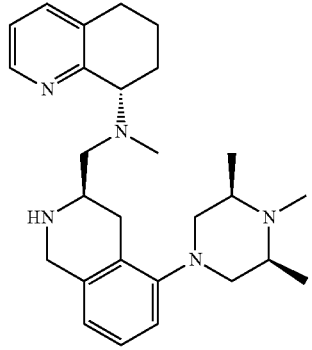 [SMILES: C[C@@H]1CN(c2cccc3c2C[C@H](CN(C)[C@H]2CCCc4cccnc42)NC3)C[C@H](C)N1C]

EMU198

Light yellow foam. $^1$H NMR (400 MHz, Chloroform-d) δ 8.38 (dd, J=4.7, 1.7 Hz, 1H), 7.33-7.20 (m, 1H), 7.06-6.91 (m, 2H), 6.76 (d, J=7.9 Hz, 1H), 6.66 (d, J=7.6 Hz, 1H), 3.99 (d, J=15.4 Hz, 1H), 3.91-3.79 (m, 2H), 2.88-2.54 (m, 8H), 2.44 (s, 4H), 2.33-2.09 (m, 7H), 2.01-1.83 (m, 3H), 1.65 (t, J=6.4 Hz, 1H), 1.02 (dd, J=25.3, 6.2 Hz, 6H). HRMS calculated for [C27H39N5+H]$^+$: 434.32837, found: 434.32964.

193

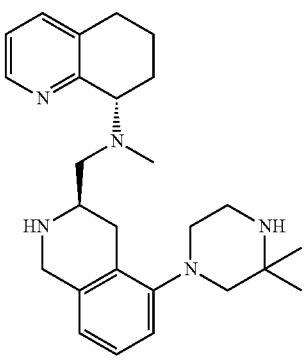 [SMILES: CN(C[C@H]1Cc2c(cccc2N2CCNC(C)(C)C2)CN1)[C@H]1CCCc2cccnc21]

EMU136

Yellow foam. $^1$H NMR (400 MHz, Chloroform-d) δ 8.38 (dd, J=4.8, 1.7 Hz, 1H), 7.25-7.20 (m, 1H), 7.03-6.90 (m, 2H), 6.75 (d, J=7.8 Hz, 1H), 6.67 (d, J=7.6 Hz, 1H), 3.96 (d, J=15.3 Hz, 1H), 3.89-3.76 (m, 2H), 3.00-2.30 (m, 17H), 2.12 (dd, J=16.5, 10.4 Hz, 1H), 1.99-1.83 (m, 3H), 1.65-1.56 (m, 1H), 1.12 (d, J=25.6 Hz, 6H). HRMS calculated for [C26H37N5+H]$^+$: 420.31272, found: 420.31334.

194

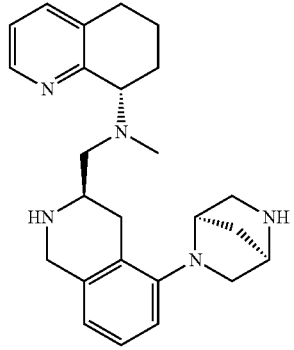

EMU200

Light yellow foam. $^1$H NMR (400 MHz, Chloroform-d) δ 8.37 (s, 1H), 7.38 (d, J=7.7 Hz, 1H), 7.16-7.02 (m, 2H), 6.99 (d, J=8.0 Hz, 1H), 6.73 (d, J=7.6 Hz, 1H), 6.22 (s, 2H), 4.34 (dd, J=16.0, 4.7 Hz, 1H), 4.21-3.96 (m, 4H), 3.79-3.70 (m, 1H), 3.50-3.38 (m, 1H), 3.27-2.54 (m, 9H), 2.27 (d, J=2.9 Hz, 3H), 2.11-1.80 (m, 5H), 1.73 (d, J=8.9 Hz, 1H). HRMS calculated for [C25H33N5+H]$^+$: 404.28142, found: 404.28088.

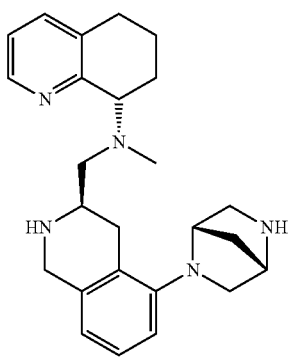

EMU135

Yellow foam. $^1$H NMR (400 MHz, Chloroform-d) δ 8.31 (dd, J=4.7, 1.8 Hz, 1H), 7.20 (dd, J=7.7, 1.7 Hz, 1H), 6.95-6.83 (m, 2H), 6.41 (dd, J=14.1, 7.8 Hz, 2H), 3.96-3.79 (m, 4H), 3.69 (dd, J=9.0, 2.5 Hz, 1H), 3.57 (s, 1H), 3.35-3.30 (m, 1H), 2.92 (dd, J=10.2, 2.1 Hz, 1H), 2.71-2.51 (m, 7H), 2.43-2.30 (m, 5H), 2.11 (dd, J=15.8, 10.2 Hz, 1H), 1.96-1.78 (m, 4H), 1.58 (ddd, J=9.7, 5.2, 2.8 Hz, 2H). HRMS calculated for [C25H33N5+H]$^+$: 404.28142, found: 404.28069.

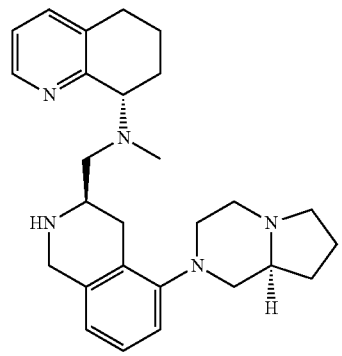 [SMILES: CN(C[C@H]1Cc2c(cccc2N2CCN3CCC[C@H]3C2)CN1)[C@H]1CCCc2cccnc21]

EMU160

White foam. $^1$H NMR (400 MHz, Chloroform-d) δ 8.35 (dd, J=4.8, 1.7 Hz, 1H), 7.21 (dd, J=7.7, 1.7 Hz, 1H), 7.00-6.88 (m, 2H), 6.78 (d, J=7.9 Hz, 1H), 6.63 (d, J=7.6 Hz, 1H), 3.96 (d, J=15.5 Hz, 1H), 3.87-3.78 (m, 2H), 2.95 (dddd, J=26.7, 13.1, 6.7, 2.2 Hz, 4H), 2.77-2.59 (m, 5H), 2.58-2.49 (m, 2H), 2.46-2.33 (m, 4H), 2.29 (td, J=10.9, 3.1 Hz, 1H), 2.07 (ddp, J=15.1, 10.4, 5.6, 5.1 Hz, 3H), 1.96-1.54 (m, 8H), 1.36 (dq, J=15.6, 5.0 Hz, 1H). HRMS calculated for [C27H37N5+H]$^+$: 432.31272, found: 432.31401.

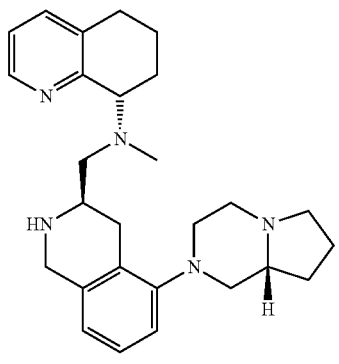

EMU161

White foam. ¹H NMR (400 MHz, Chloroform-d) δ 8.38 (dd, J=4.8, 1.7 Hz, 1H), 7.24 (dd, J=7.7, 1.7 Hz, 1H), 7.04-6.91 (m, 2H), 6.83 (d, J=7.8 Hz, 1H), 6.67 (d, J=7.6 Hz, 1H), 3.97 (d, J=15.4 Hz, 1H), 3.91-3.76 (m, 2H), 3.09-2.96 (m, 4H), 2.75 (tdd, J=26.2, 11.2, 4.4 Hz, 5H), 2.57 (dd, J=16.6, 4.8 Hz, 1H), 2.52-2.37 (m, 4H), 2.31-2.09 (m, 5H), 2.01-1.55 (m, 8H), 1.31 (tt, J=10.9, 4.6 Hz, 1H). HRMS calculated for [C27H37N5+H]⁺: 432.31272, found: 432.31206.

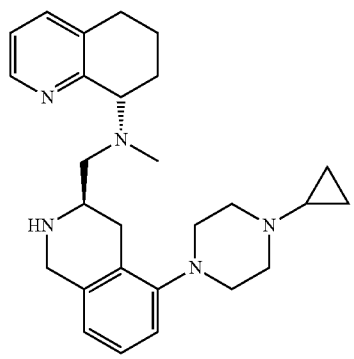

EMU196

White foam. ¹H NMR (400 MHz, Chloroform-d) δ 8.46 (dd, J=4.8, 1.7 Hz, 1H), 7.36 (ddd, J=7.6, 1.8, 0.9 Hz, 1H), 7.12-7.04 (m, 2H), 6.87 (dd, J=7.9, 1.1 Hz, 1H), 6.76 (dd, J=7.6, 1.1 Hz, 1H), 4.13 (d, J=15.4 Hz, 1H), 3.99 (q, J=8.6 Hz, 2H), 3.01-2.62 (m, 15H), 2.48 (s, 3H), 2.35-2.26 (m, 1H), 2.09-1.91 (m, 3H), 1.75-1.63 (m, 2H), 0.49-0.42 (m, 4H). HRMS calculated for [C27H37N5+H]⁺: 432.31272, found: 432.31173.

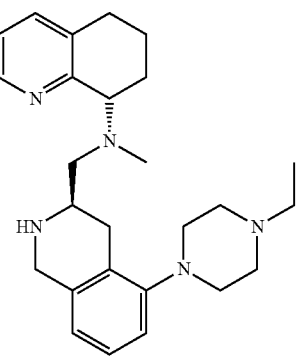

EMU199

White foam. ¹H NMR (400 MHz, Chloroform-d) δ 8.45 (dd, J=4.8, 1.7 Hz, 1H), 7.39-7.32 (m, 1H), 7.12-7.05 (m, 2H), 6.90 (dd, J=7.9, 1.2 Hz, 1H), 6.77 (dd, J=7.6, 1.1 Hz, 1H), 4.13 (d, J=15.5 Hz, 1H), 4.02-3.95 (m, 2H), 3.05 (dd, J=11.7, 5.0 Hz, 2H), 2.89-2.45 (m, 18H), 2.40-2.23 (m, 1H), 2.08-1.92 (m, 3H), 1.78-1.67 (m, 1H), 1.12 (t, J=7.2 Hz, 3H). HRMS calculated for [C26H37N5+H]⁺: 420.31272, found: 420.31300.

EMU197

Light yellow foam. ¹H NMR (400 MHz, Chloroform-d) δ 8.39 (dd, J=4.7, 1.7 Hz, 1H), 7.29-7.23 (m, 1H), 7.04-6.95 (m, 2H), 6.81 (d, J=7.9 Hz, 1H), 6.68 (d, J=7.6 Hz, 1H), 4.00 (d, J=15.4 Hz, 1H), 3.92-3.82 (m, 2H), 3.01-2.44 (m, 19H), 2.12 (dd, J=16.3, 10.5 Hz, 1H), 1.99-1.83 (m, 3H), 1.65 (s, 1H), 1.02 (d, J=6.7 Hz, 6H). HRMS calculated for [C27H39N5+H]⁺: 434.32837, found: 434.32803.

197

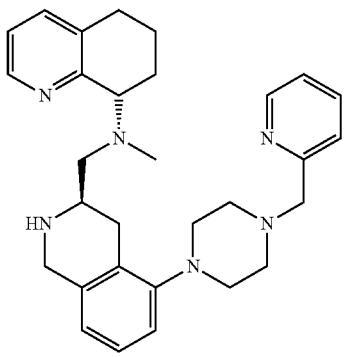

EMU202

White foam. ¹H NMR (400 MHz, Chloroform-d) δ 8.50 (d, J=4.9 Hz, 1H), 8.40 (d, J=4.6 Hz, 1H), 7.58 (td, J=7.6, 1.8 Hz, 1H), 7.37 (d, J=7.8 Hz, 1H), 7.25 (s, 1H), 7.08 (dd, J=7.4, 5.1 Hz, 1H), 7.03-6.96 (m, 2H), 6.80 (d, J=7.9 Hz, 1H), 6.68 (d, J=7.6 Hz, 1H), 4.00 (d, J=15.4 Hz, 1H), 3.91-3.82 (m, 2H), 3.69-3.64 (m, 2H), 2.99 (dt, J=10.0, 4.1 Hz, 2H), 2.80-2.41 (m, 16H), 2.10 (dd, J=16.5, 10.2 Hz, 1H), 2.01-1.84 (m, 3H), 1.67-1.58 (m, 1H). HRMS calculated for [C30H38N6+H]⁺: 483.32362, found: 483.32315.

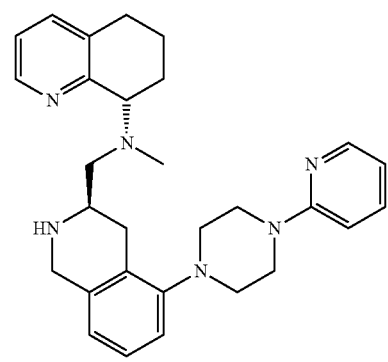

EMU201

White foam. ¹H NMR (400 MHz, Chloroform-d) δ 8.43 (dd, J=4.7, 1.8 Hz, 1H), 8.17 (dd, J=5.0, 1.9 Hz, 1H), 7.44 (ddd, J=8.9, 7.1, 2.0 Hz, 1H), 7.29 (dd, J=7.8, 1.7 Hz, 1H), 7.11-6.96 (m, 2H), 6.84 (d, J=7.9 Hz, 1H), 6.75 (d, J=7.6 Hz, 1H), 6.64 (d, J=8.6 Hz, 1H), 6.59 (t, J=7.1, 5.0 Hz, 1H), 4.04 (d, J=15.4 Hz, 1H), 3.99-3.84 (m, 2H), 3.60 (d, J=33.1 Hz, 4H), 3.07 (dt, J=10.4, 4.5 Hz, 2H), 2.90-2.44 (m, 11H), 2.19 (dd, J=16.4, 10.4 Hz, 1H), 2.07-1.86 (m, 3H), 1.72-1.60 (m, 1H). HRMS calculated for [C29H36N6+H]⁺: 469.30797, found: 469.30711.

198

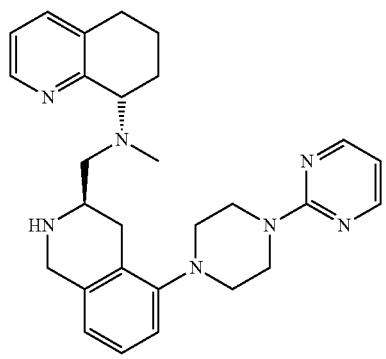

EMU203

Light yellow foam. ¹H NMR (400 MHz, Chloroform-d) δ 8.43 (d, J=4.6 Hz, 1H), 8.28 (t, J=4.6 Hz, 2H), 7.29 (d, J=7.7 Hz, 1H), 7.07-6.97 (m, 2H), 6.81 (d, J=7.9 Hz, 1H), 6.74 (d, J=7.6 Hz, 1H), 6.44 (t, J=4.8 Hz, 1H), 4.20-3.69 (m, 7H), 2.99 (dq, J=12.2, 7.2, 5.9 Hz, 2H), 2.89 (dd, J=16.3, 3.0 Hz, 1H), 2.81-2.59 (m, 6H), 2.57-2.40 (m, 4H), 2.19 (dd, J=16.2, 10.2 Hz, 1H), 2.06-1.88 (m, 3H), 1.67 (h, J=9.4 Hz, 1H). HRMS calculated for [C28H35N7+H]⁺: 470.30322, found: 470.30297.

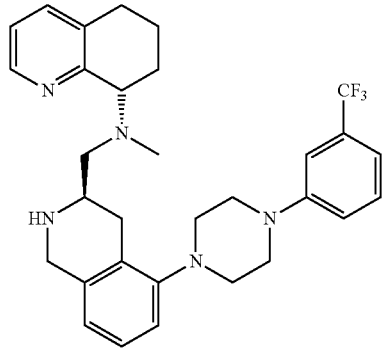

EMU226

Light yellow foam. ¹H NMR (399 MHz, Chloroform-d) δ 8.46 (dd, J=4.8, 1.7 Hz, 1H), 7.39-7.29 (m, 2H), 7.16-7.01 (m, 5H), 6.90 (d, J=7.8 Hz, 1H), 6.80 (d, J=7.6 Hz, 1H), 4.08 (d, J=15.4 Hz, 1H), 4.01-3.90 (m, 2H), 3.33 (dt, J=31.4, 10.7 Hz, 5H), 3.15 (ddd, J=10.3, 6.2, 3.7 Hz, 2H), 2.91-2.74 (m, 6H), 2.66 (dt, J=16.6, 4.6 Hz, 1H), 2.52 (s, 4H), 2.21 (dd, J=16.3, 10.4 Hz, 1H), 1.99 (dddd, J=29.6, 22.0, 11.3, 3.3 Hz, 3H), 1.75-1.62 (m, 1H). HRMS calculated for [C31H36F3N5+H]⁺: 536.30011, found: 536.29919.

199

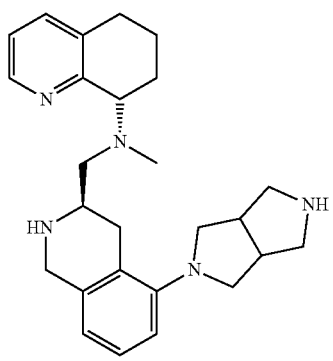

EMU062

Off-white solid. $^1$H NMR (399 MHz, Methanol-d4) δ 8.41 (d, J=5.0 Hz, 1H), 7.57 (d, J=7.9 Hz, 1H), 7.29-7.14 (m, 2H), 7.02 (d, J=8.0 Hz, 1H), 6.97-6.85 (m, 1H), 4.31 (t, J=8.4 Hz, 2H), 4.02 (dd, J=10.2, 5.5 Hz, 1H), 3.50-3.41 (m, 2H), 3.29-2.57 (m, 17H), 2.15-2.00 (m, 5H), 1.91 (q, J=11.7, 11.1 Hz, 1H), 1.71 (d, J=13.7 Hz, 1H). HRMS calculated for [C26H35N5+H]$^+$: 418.29707, found: 418.29653.

200

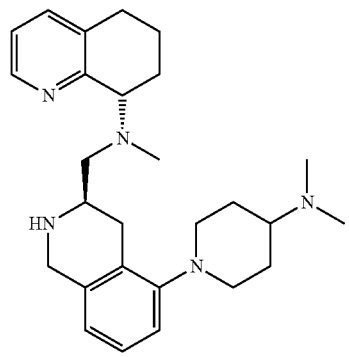

EMU228

White foam. $^1$H NMR (400 MHz, Chloroform-d) δ 8.44 (dd, J=4.8, 1.7 Hz, 1H), 7.39-7.33 (m, 1H), 7.12-7.06 (m, 2H), 6.86 (dd, J=8.0, 1.1 Hz, 1H), 6.75 (dd, J=7.6, 1.1 Hz, 1H), 4.17 (d, J=15.5 Hz, 1H), 4.00 (d, J=15.8 Hz, 2H), 3.16-3.05 (m, 2H), 2.90-2.65 (m, 7H), 2.44 (s, 3H), 2.33 (s, 6H), 2.29-2.14 (m, 2H), 2.09-1.83 (m, 6H), 1.79-1.54 (m, 4H). HRMS calculated for [C27H39N5+H]$^+$: 434.32837, found: 434.32751.

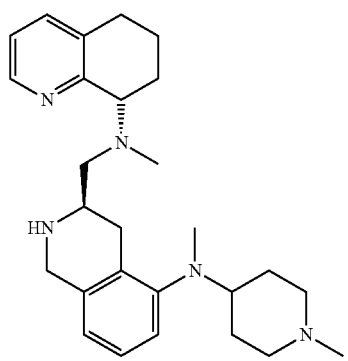

EMU240

Yellow foam. $^1$H NMR (400 MHz, Chloroform-d) δ 8.44 (dd, J=4.8, 1.7 Hz, 1H), 7.38-7.32 (m, 1H), 7.10-7.03 (m, 2H), 6.93 (dd, J=7.9, 1.2 Hz, 1H), 6.76 (dd, J=7.6, 1.1 Hz, 1H), 4.13 (d, J=15.4 Hz, 1H), 4.03-3.93 (m, 2H), 2.88-2.65 (m, 9H), 2.59 (s, 3H), 2.45 (s, 3H), 2.24 (s, 3H), 2.08-1.53 (m, 12H). HRMS calculated for [C27H39N5+H]$^+$: 434.32837, found: 434.32803.

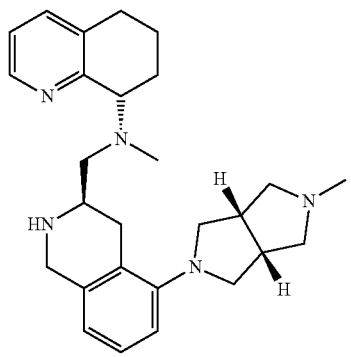

EMU227

White foam. $^1$H NMR (400 MHz, Chloroform-d) δ 8.44 (dd, J=4.8, 1.7 Hz, 1H), 7.36 (dd, J=7.7, 1.7 Hz, 1H), 7.10-7.04 (m, 2H), 6.83 (dd, J=8.1, 1.1 Hz, 1H), 6.71 (dd, J=7.6, 1.1 Hz, 1H), 4.16 (d, J=15.5 Hz, 1H), 4.04-3.98 (m, 2H), 3.28 (dd, J=9.2, 6.5 Hz, 1H), 3.11 (dd, J=9.2, 2.5 Hz, 1H), 2.89-2.63 (m, 13H), 2.44 (s, 3H), 2.34 (d, J=8.1 Hz, 5H), 2.26 (dd, J=8.8, 4.9 Hz, 1H), 2.08-1.91 (m, 3H), 1.79-1.65 (m, 1H). HRMS calculated for [C27H37N5+H]$^+$: 432.31272, found: 432.31279.

201

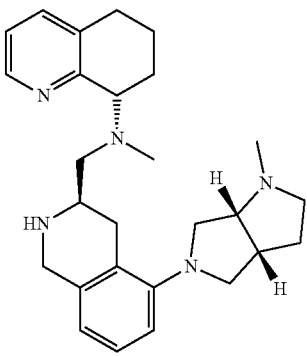

EMU235

White foam. ¹H NMR (400 MHz, Chloroform-d) δ 8.42 (ddd, J=9.6, 4.8, 1.7 Hz, 1H), 7.37 (ddd, J=7.7, 1.8, 0.9 Hz, 1H), 7.10-7.03 (m, 2H), 6.79 (t, J=7.6 Hz, 1H), 6.69 (ddd, J=7.6, 4.2, 1.1 Hz, 1H), 4.22 (dd, J=29.2, 15.7 Hz, 1H), 4.13-3.97 (m, 2H), 3.31 (dq, J=7.4, 2.5 Hz, 1H), 3.07-2.63 (m, 13H), 2.39 (dd, J=9.4, 3.8 Hz, 6H), 2.13-1.86 (m, 5H), 1.85-1.61 (m, 3H). HRMS calculated for [C27H37N5+H]⁺: 432.31272, found: 432.31329.

202

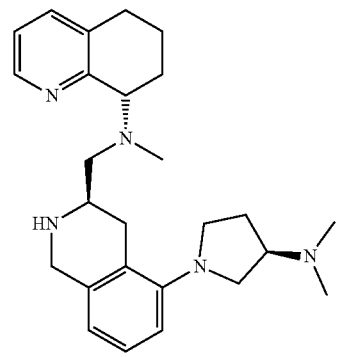

EMU237

Light yellow foam. ¹H NMR (400 MHz, Chloroform-d) δ 8.43 (dd, J=4.7, 1.7 Hz, 1H), 7.37-7.33 (m, 1H), 7.08-7.03 (m, 2H), 6.74 (d, J=8.0 Hz, 1H), 6.67-6.62 (m, 1H), 4.21 (d, J=15.5 Hz, 1H), 4.07-3.98 (m, 2H), 3.50-3.44 (m, 1H), 3.30 (d, J=8.5 Hz, 1H), 3.08-3.04 (m, 1H), 2.99-2.94 (m, 1H), 2.85-2.60 (m, 8H), 2.43 (s, 3H), 2.27 (s, 6H), 2.14-1.69 (m, 7H). HRMS calculated for [C26H37N5+H]⁺: 420.31272, found: 420.31315.

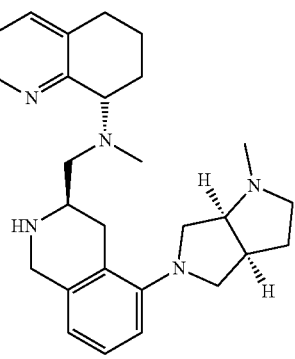

EMU236

White foam. ¹H NMR (400 MHz, Chloroform-d) δ 8.40 (dd, J=4.8, 1.6 Hz, 1H), 7.38 (dd, J=7.7, 1.7 Hz, 1H), 7.10-7.05 (m, 2H), 6.81-6.77 (m, 1H), 6.72-6.66 (m, 1H), 4.29 (d, J=15.6 Hz, 1H), 4.13-4.00 (m, 2H), 3.34-3.30 (m, 1H), 3.08-3.02 (m, 3H), 2.96-2.67 (m, 10H), 2.40 (d, J=3.5 Hz, 3H), 2.36 (s, 3H), 2.11-1.92 (m, 5H), 1.86-1.65 (m, 3H). HRMS calculated for [C27H37N5+H]⁺: 432.31272, found: 432.31243

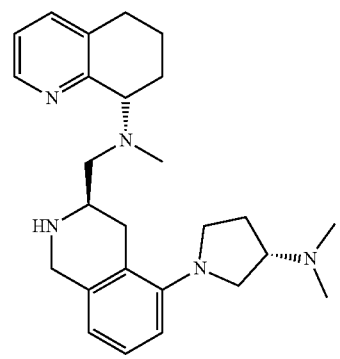

EMU238

Light yellow foam. ¹H NMR (400 MHz, Chloroform-d) δ 8.45 (dd, J=4.7, 1.7 Hz, 1H), 7.38-7.33 (m, 1H), 7.10-7.02 (m, 2H), 6.81 (dd, J=8.0, 1.1 Hz, 1H), 6.67 (dd, J=7.6, 1.1 Hz, 1H), 4.12 (d, J=15.5 Hz, 1H), 4.04-3.94 (m, 2H), 3.38-3.27 (m, 2H), 3.01-2.75 (m, 7H), 2.71-2.62 (m, 2H), 2.44 (s, 3H), 2.25 (s, 7H), 2.12-1.79 (m, 6H), 1.76-1.65 (m, 1H). HRMS calculated for [C26H37N5+H]⁺: 420.31272, found: 420.31278.

Scheme 5. Synthesis of EMU234

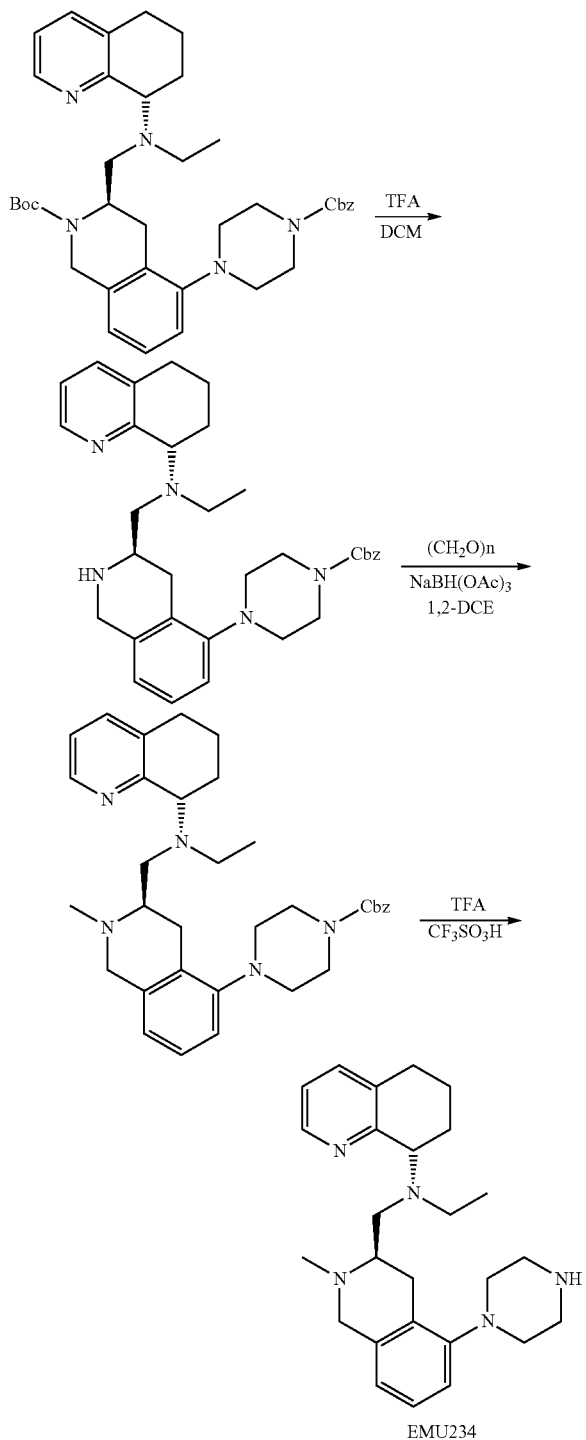

Benzyl 4-((R)-3-((methyl((S)-5,6,7,8-tetrahydroquinolin-8-yl)amino)methyl)-1,2,3,4-tetrahydroisoquinolin-5-yl)piperazine-1-carboxylate: prepared by the Boc-deprotection of (R)-tert-butyl 5-(4-((benzyloxy)carbonyl)piperazin-1-yl)-3-((methyl((S)-5,6,7,8-tetrahydroquinolin-8-yl)amino)methyl)-3,4-dihydroisoquinoline-2(1H)-carboxylate, which was synthesized according to Scheme 4. The crude material was used for next step without purification.

Benzyl 4-((R)-2-methyl-3-((methyl((S)-5,6,7,8-tetrahydroquinolin-8-yl)amino)methyl)-1,2,3,4-tetrahydroisoquinolin-5-yl)piperazine-1-carboxylate: To a 20-mL scintillation vial equipped with a Teflon-coated magnetic stir bar was charged with benzyl 4-((R)-3-((methyl((S)-5,6,7,8-tetrahydroquinolin-8-yl)amino)methyl)-1,2,3,4-tetrahydroisoquinolin-5-yl)piperazine-1-carboxylate (0.336 g, 0.639 mmol), sodium triacetoxyborohydride (0.406 g, 1.918 mmol), dichloromethane (6.39 ml). After stirring for 5 minutes, paraformaldehyde (0.058 g, 1.918 mmol) was added in one portion. The resulting mixture was stirred at room temperature for 48 hours. Upon the completion of the reaction as judged by TLC and LCMS analysis, the mixture was quenched by addition of saturated $NaHCO_3$. The biphasic mixture was transferred to a separatory funnel. The aqueous layer was separated and extracted with DCM (3 times). The combined organic extract was dried over anhydrous sodium sulfate and concentrated under reduced pressure to a crude material which was purified by CombiFlash system (24 g silica column, 5 minutes DCM then 30 minutes 0-30% 8:2:0.6 DCM/MeOH/$NH_3$ solution, 7N in MeOH) to afford the product as a yellow gel (0.4101 g, 0.760 mmol, quantitative yield). $^1$H NMR (400 MHz, Chloroform-d) δ 8.46-8.37 (m, 1H), 7.41-7.30 (m, 6H), 7.10 (t, J=7.7 Hz, 1H), 7.02 (dd, J=7.7, 4.7 Hz, 1H), 6.84 (d, J=7.9 Hz, 1H), 6.77 (d, J=7.6 Hz, 1H), 5.17 (s, 2H), 3.84-3.61 (m, 7H), 2.88 (t, J=25.2 Hz, 8H), 2.67 (dd, J=16.7, 5.3 Hz, 2H), 2.48 (d, J=23.7 Hz, 4H), 2.30 (s, 3H), 1.95 (s, 3H), 1.65 (dt, J=9.2, 4.8 Hz, 1H). HRMS calculated for $[C33H41N5O2+H]^+$: 540.33385, found: 540.33370.

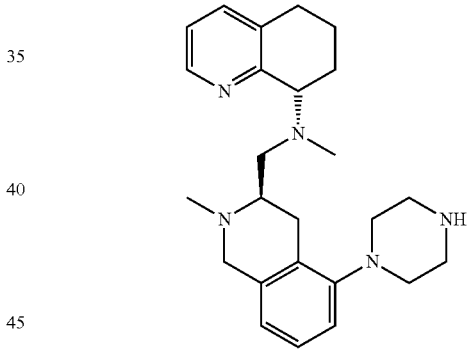

EMU234

To a 20 mL scintillation vial equipped with a Teflon-coated magnetic stir bar was charged with benzyl 4-((R)-2-methyl-3-((methyl((S)-5,6,7,8-tetrahydroquinolin-8-yl)amino)methyl)-1,2,3,4-tetrahydroisoquinolin-5-yl)piperazine-1-carboxylate (0.4101 g, 0.760 mmol) and trifluoroacetic acid (3.80 ml). Trifluoromethanesulfonic acid (0.202 ml, 2.280 mmol) was added dropwise at 0° C., and the resulting mixture was stirred at room temperature for 1 hour. Upon the completion of the reaction as judged by LCMS analysis, the mixture was diluted with DCM, cooled in an ice-bath, and carefully quenched by addition of 3M NaOH until pH>12. The biphasic mixture was transferred to a separatory funnel. The aqueous layer was separated and extracted with DCM (3 times). The combined organic extract was dried over anhydrous sodium sulfate and concentrated under reduced pressure to a crude material which was purified by CombiFlash system (12 g silica column, 5 minutes DCM then 30 minutes 0-80% 8:2:0.6 DCM/MeOH/NH₃ solution, 7N in MeOH) to afford the final product as a light yellow foam (193.1 mg, 63% yield). ¹H NMR (400 MHz, Chloroform-d) δ 8.44 (td, J=4.5, 1.6 Hz, 1H), 7.38-7.30 (m, 1H), 7.12 (t, J=7.7 Hz, 1H), 7.05 (ddd, J=7.4, 4.8, 2.6 Hz, 1H), 6.95-6.86 (m, 1H), 6.81-6.72 (m, 1H), 4.23 (s, 1H), 3.90-3.77 (m, 3H), 3.13 (t, J=4.8 Hz, 3H), 3.02-2.78 (m, 8H), 2.74-2.44 (m, 7H), 2.29 (s, 3H), 2.07-1.86 (m, 3H), 1.73-1.61 (m, 1H). HRMS calculated for [C25H35N5+H]⁺: 406.29707, found: 406.29641.

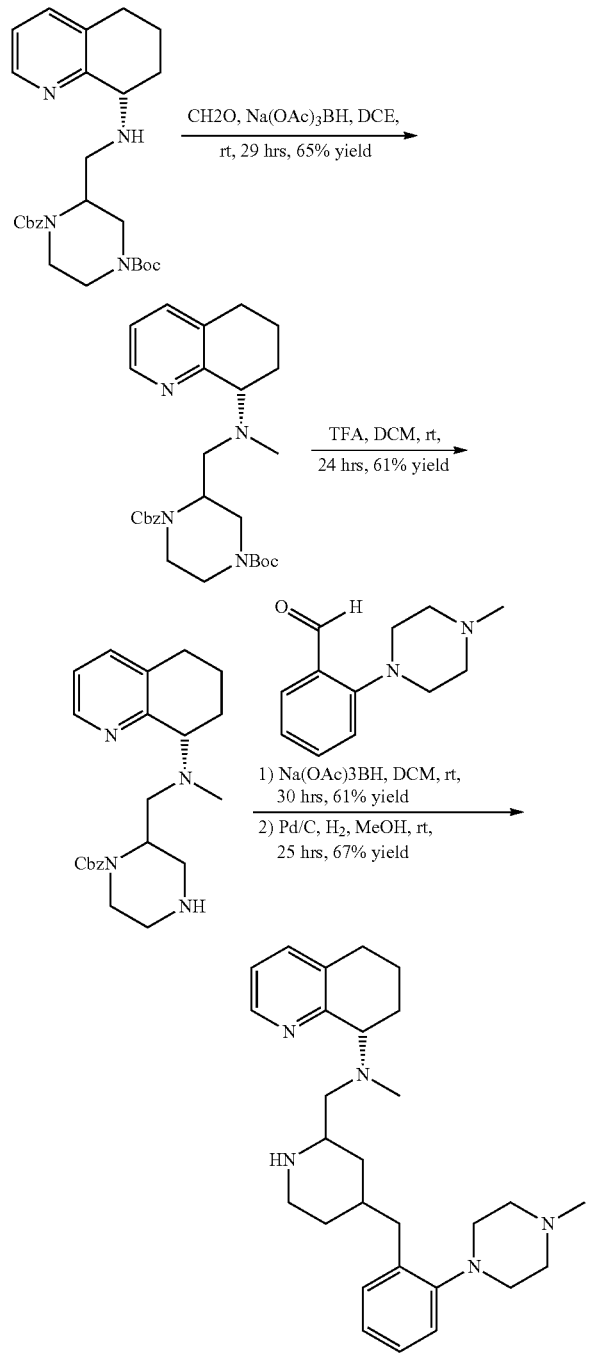

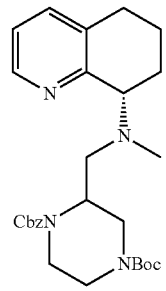 [SMILES: CN(CC1CN(C(=O)OC(C)(C)C)CCN1C(=O)OCc1ccccc1)[C@H]1CCCc2cccnc21]

1-benzyl 4-(tert-butyl) 2-((methyl((S)-5,6,7,8-tetrahydroquinolin-8-yl)amino)methyl)piperazine-1,4-dicarboxylate 1-Benzyl 4-(tert-butyl) 2-((((S)-5,6,7,8-tetrahydroquinolin-8-yl)amino)methyl)piperazine-1,4-dicarboxylate (mixture of diastereomers) was prepared according to Zhao, H., et al.; *Bioorg. Med. Chem. Lett.;* 2015; 25; 4950-4955. To a solution of a mixture of diastereomers of 1-benzyl 4-(tert-butyl) 2-((((S)-5,6,7,8-tetrahydroquinolin-8-yl)amino)methyl)piperazine-1,4-dicarboxylate (5.50 g, 11.4 mmol, 1.00 eq) in DCE (114 mL) was added paraformaldehyde (2.06 g, 68.6 mmol, 6.00 eq), and the resulting mixture was stirred at room temperature for 30 min. Sodium triacetoxyborohydride (7.27 g, 34.3 mmol, 3.00 eq) was then added, and the resulting reaction mixture was stirred at room temperature for 29 hrs. After this time, the reaction was quenched with saturated aqueous sodium bicarbonate, and the resulting aqueous layer was extracted with DCM. Combined organic layers were washed once with water, washed once with brine, dried over anhydrous sodium sulfate, filtered, and evaporated under reduced pressure. The crude material was purified via column chromatography to yield the desired mixture of diastereomers (3.65 g, 7.38 mmol, 65% yield).

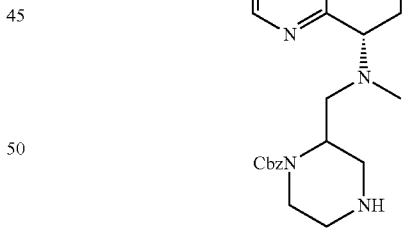

benzyl 2-((methyl((S)-5,6,7,8-tetrahydroquinolin-8-yl)amino)methyl)piperazine-1-carboxylate A solution of a mixture of diastereomers of 1-benzyl 4-(tert-butyl) 2-((methyl((S)-5,6,7,8-tetrahydroquinolin-8-yl)amino)methyl)piperazine-1,4-dicarboxylate (0.650 g, 1.31 mmol, 1.00 eq) in DCM (20.0 mL) was added to a flask with a stir bar, and the resulting solution was stirred at room temperature under Ar. TFA (2.00 mL, 26.0 mmol, 19.8 eq) was added, and the resulting reaction mixture was stirred at room temperature under Ar for 24 hrs. After this time, the reaction was quenched and basified with 1 M aqueous sodium hydroxide, and the resulting aqueous layer was extracted twice with DCM. Combined organic layers were washed once with water, washed once with brine, dried over anhydrous sodium sulfate, filtered, and evaporated under reduced pressure. The crude mixture of diastereomers was purified via column chromatography eluting with DCM, followed by 25% 90:10:1 DCM/MeOH/NH₄OH in DCM, followed by 50% 90:10:1 DCM/MeOH/NH₄OH in DCM, followed by 90:10:1 DCM/MeOH/NH₄OH to yield a single diastereomer (0.140 g, 0.355 mmol, 27% yield).

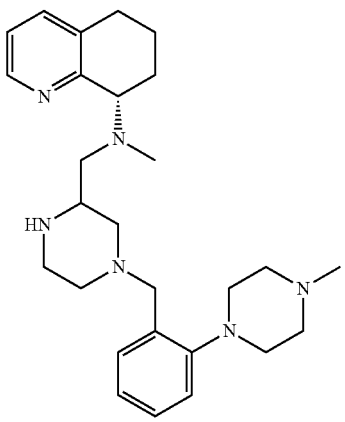 [SMILES: CN1CCN(c2ccccc2CN2CCNC(CN(C)[C@H]3CCCc4cccnc43)C2)CC1]

EMU070: (8S)—N-methyl-N-((4-(2-(4-methylpiperazin-1-yl)benzyl)piperazin-2-yl)methyl)-5,6,7,8-tetrahydroquinolin-8-amine A solution of benzyl 2-((methyl((S)-5,6,7,8-tetrahydroquinolin-8-yl)amino)methyl)piperazine-1-carboxylate (0.285 g, 0.722 mmol, 1.00 eq) and 2-(4-methylpiperazin-1-yl)benzaldehyde (0.221 g, 1.08 mmol, 1.50 eq) in DCM (4.82 mL) was stirred for 6 hrs at room temperature. After this time, sodium triacetoxyborohydride (0.258 g, 1.16 mmol, 1.60 eq) was added, and the resulting reaction mixture was stirred at room temperature for 24 hrs. After this time, the reaction was quenched with 1 N aqueous potassium carbonate. The resulting aqueous layer was extracted with DCM (3×40 mL), and combined organic layers were washed with 1 N aqueous potassium carbonate (2×100 mL), washed once with brine, dried over anhydrous sodium sulfate, filtered, and evaporated under reduced pressure. The crude material was purified via column chromatography eluting with DCM, followed by 99:1 DCM/MeOH, followed by 50:1 DCM/MeOH, followed by 25:1 DCM/MeOH, followed by 9:1 DCM/MeOH, followed by 44:5:1 DCM/MeOH/NH₄OH to yield the desired product (0.255 g, 0.438 mmol, 61% yield). ¹H NMR (600 MHz, CDCl₃) δ 8.30 (d, J=3.6 Hz, 1H), 7.23-7.29 (m, 6H), 7.12-7.15 (m, 1H), 7.09 (d, J=6.0 Hz, 1H), 7.00 (d, J=6.0 Hz, 1H), 6.93 (t, J=7.2 Hz, 1H), 6.86 (dd, J=4.5 Hz, J=7.5 Hz, 1H), 5.08 (q, J=12.6 Hz, 2H), 4.12 (m, 1H), 3.75 (m, 2H), 3.43 (d, J=13.2 Hz, 1H), 3.27 (d, J=12.6 Hz, 1H), 2.91-2.97 (m, 7H), 2.69-2.72 (m, 2H), 2.43-2.59 (m, 7H), 2.35-2.37 (m, 1H), 2.32 (s, 3H), 2.09-2.19 (m, 3H), 1.85-1.88 (m, 1H), 1.69 (m, 2H), 1.51 (m, 1H). HRMS (ESI) m/z=583.37575 (M+H); Theo. for C₃₅H₄₆O₂N₆+H=583.37550. To a solution of benzyl 2-((methyl((S)-5,6,7,8-tetrahydroquinolin-8-yl)amino)methyl)piperazine-1-carboxylate (0.255 g, 0.438 mmol, 1.00 eq) in MeOH (11.0 mL) was added palladium on carbon (0.250 g, 0.235 mmol, 0.54 eq), and the resulting mixture was stirred vigorously under Ar. After two cycles of weak vacuum followed by Ar flush, the flask was evacuated using weak vacuum once again, followed by a final flush with hydrogen. The resulting reaction mixture was stirred vigorously at room temperature under hydrogen for 25 hrs. After this time, the reaction mixture was filtered through a plug of celite, which was subsequently washed with MeOH, and the resulting mother liquor was evaporated under reduced pressure. The crude material was purified via column chromatography eluting with 9:1 DCM/MeOH, followed by 38:10:1 DCM/MeOH/NH₄OH to yield the desired product as a yellow foam (0.132 g, 0.294 mmol, 67% yield). ¹H NMR (600 MHz, CDCl₃) δ 8.32 (d, J=4.2 Hz, 1H), 7.43 (d, J=7.8 Hz, 1H), 7.36 (d, J=7.8 Hz, 1H), 7.21 (m, 1H), 7.03-7.12 (m, 3H), 4.70 (s, 2H), 4.19 (m, 1H), 3.67 (d, J=12.6 Hz, 1H), 3.57 (d, J=12.6 Hz, 1H), 3.49 (dd, J=11.7 Hz, J=14.1 Hz, 1H), 3.36 (m, 1H), 3.27 (m, 1H), 2.92-3.06 (m, 6H), 2.86-2.92 (m, 2H), 2.58-2.82 (m, 7H), 2.47 (s, 3H), 2.13-2.17 (m, 3H), 2.04-2.06 (m, 1H), 1.96-1.98 (m, 1H), 1.80-1.87 (m, 1H), 1.73-1.77 (m, 1H). HRMS (APCI) m/z=449.33818 (M+H); Theo. for C₂₇H₄₀N₆+H=449.33872.

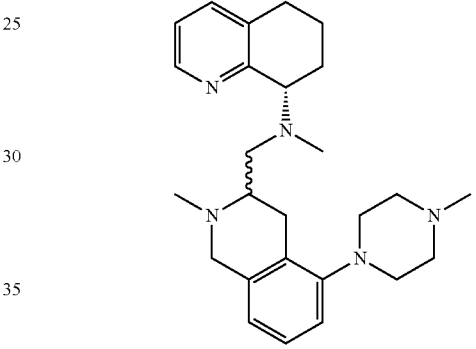

EMU090 prepared by the methylation of EMU034 with paraformaldehyde (5 equiv) using condition described in Scheme 4. Yellow gel. ¹H NMR (400 MHz, Chloroform-d) δ 8.40 (dd, J=4.8, 1.7 Hz, 1H), 7.30-7.23 (m, 1H), 7.07-6.95 (m, 2H), 6.84 (dd, J=8.0, 1.2 Hz, 1H), 6.71-6.65 (m, 1H), 3.78-3.63 (m, 3H), 2.88-2.75 (m, 7H), 2.65-2.45 (m, 7H), 2.39 (s, 3H), 2.33 (s, 3H), 2.27 (s, 3H), 2.04-1.80 (m, 4H), 1.61 (tdd, J=10.9, 5.6, 3.2 Hz, 1H). HRMS calculated for [C26H37N5+H]⁺: 420.31272, found: 420.31212.

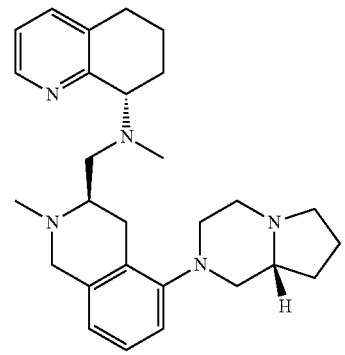 [SMILES: CN1Cc2cccc(N3CCN4CCC[C@@H]4C3)c2C[C@@H]1CN(C)[C@H]1CCCc2cccnc21]

EMU239 prepared by the methylation of EMU161 with paraformaldehyde (3 equiv) using condition described in Scheme 5. Orange gel. $^1$H NMR (400 MHz, Chloroform-d) δ 8.42 (dd, J=4.8, 1.7 Hz, 1H), 7.31 (ddd, J=7.8, 1.9, 1.0 Hz, 1H), 7.07 (t, J=7.7 Hz, 1H), 7.00 (dd, J=7.7, 4.7 Hz, 1H), 6.90 (dd, J=7.9, 1.2 Hz, 1H), 6.72 (dd, J=7.6, 1.1 Hz, 1H), 3.82-3.70 (m, 3H), 3.15-2.98 (m, 4H), 2.96-2.75 (m, 5H), 2.75-2.37 (m, 8H), 2.34-2.13 (m, 5H), 2.05-1.58 (m, 7H), 1.52-1.39 (m, 1H). HRMS calculated for [C28H39N5+H]$^+$: 446.32837, found: 446.32747.

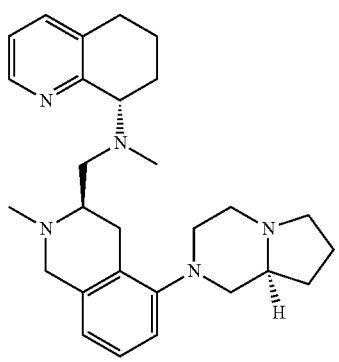 [SMILES: CN1Cc2cccc(N3CCN4CCC[C@H]4C3)c2C[C@@H]1CN(C)[C@H]1CCCc2cccnc21]

EMU241 prepared by the methylation of EMU160 with paraformaldehyde (3 equiv) using condition described in Scheme 5. Orange gel. $^1$H NMR (400 MHz, Chloroform-d) δ 8.42 (dd, J=4.7, 1.7 Hz, 1H), 7.32 (dd, J=7.7, 1.7 Hz, 1H), 7.07 (t, J=7.7 Hz, 1H), 7.01 (dd, J=7.6, 4.7 Hz, 1H), 6.90 (dd, J=7.9, 1.2 Hz, 1H), 6.72 (dd, J=7.6, 1.2 Hz, 1H), 3.84-3.69 (m, 3H), 3.17-2.73 (m, 9H), 2.73-2.33 (m, 8H), 2.33-2.15 (m, 5H), 2.04-1.60 (m, 7H), 1.45 (tt, J=11.2, 5.3 Hz, 1H). HRMS calculated for [C28H39N5+H]$^+$: 446.32837, found: 446.32761.

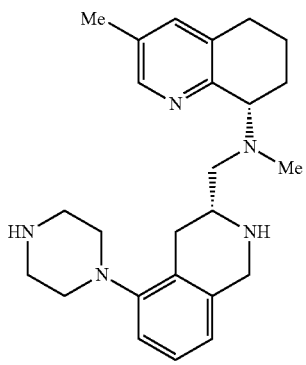 [SMILES: Cc1cnc2c(c1)CCC[C@@H]2N(C)C[C@H]1Cc2c(cccc2N2CCNCC2)CN1]

EMU230

To a 20 mL vial was added (S)-3-methyl-5,6,7,8-tetrahydroquinolin-8-amine (0.2 g, 1.233 mmol), DCE (Volume: 2.80 ml), (R)-tert-butyl 5-(4-(tert-butoxycarbonyl)piperazin-1-yl)-3-formyl-3,4-dihydroisoquinoline-2(1H)-carboxylate (0.499 g, 1.121 mmol) and STAB-H (0.428 g, 2.017 mmol) then the reaction was allowed to stir overnight. The reaction was diluted with DCM, washed with 1M NaOH, dried with Na$_2$SO$_4$, filtered and concentrated to afford a yellow oil. The crude material was purified via combiflash (DCM 2 minutes, 10% B (80:20:3, DCM:MeOH:NH$_4$OH) 5 minutes and 50% B 9 minutes) to afford (R)-tert-butyl 5-(4-(tert-butoxycarbonyl)piperazin-1-yl)-3-((((S)-3-methyl-5,6,7,8-tetrahydroquinolin-8-yl)amino)methyl)-3,4-dihydroisoquinoline-2(1H)-carboxylate (0.268 g, 0.453 mmol, 40% yield). To a 20 mL vial was added secondary amine (0.268 g, 0.453 mmol), DCE (Volume: 3.0 ml), paraformaldehyde (0.041 g, 1.359 mmol) and STAB-H (0.173 g, 0.815 mmol) then the reaction was stirred overnight. The reaction was diluted with DCM, washed with 1M NaOH, dried with Na$_2$SO$_4$, filtered and concentrated to afford a yellow oil. The crude material was purified via combiflash (DCM 2 minutes, 10% B (80:20:3, DCM:MeOH:NH$_4$OH) 5 minutes and 50% B 9 minutes) to afford an off white solid (0.257 g, 0.424 mmol, 94% yield). To a 20 mL vial was added (R)-tert-butyl 5-(4-(tert-butoxycarbonyl)piperazin-1-yl)-3-((methyl((S)-3-methyl-5,6,7,8-tetrahydroquinolin-8-yl)amino)methyl)-3,4-dihydroisoquinoline-2(1H)-carboxylate (0.18 g, 0.297 mmol), DCM (Volume: 3 ml, Ratio: 5) and TFA (Volume: 0.600 ml, Ratio: 1.000) then the mixture was allowed to stir overnight. The reaction was diluted with DCM, washed with 1M NaOH, dried with Na$_2$SO$_4$, filtered and concentrated to afford a yellow oil. The crude material was purified via combiflash (DCM 2 minutes, 10% B (80:20:3, DCM:MeOH:NH$_4$OH) 5 minutes and 50% B 9 minutes). The fractions were concentrated to afford (S)—N,3-dimethyl-N—(((R)-5-(piperazin-1-yl)-1,2,3,4-tetrahydroisoquinolin-3-yl)methyl)-5,6,7,8-tetrahydroquinolin-8-amine (0.091 g, 0.224 mmol, 76% yield) as a yellow oil. $^1$H NMR (500 MHz, CDCl$_3$): δ=8.28 (d, J=1.4 Hz, 1H), 7.14 (d, J=1.0 Hz, 1H), 7.07 (t, J=7.8 Hz, 1H), 6.85 (d, J=7.6 Hz, 1H), 6.74 (d, J=7.6 Hz, 1H), 4.04 (d, J=15.2 Hz, 1H), 3.91 (d, J=15.2 Hz, 1H), 3.91-3.88 (m, 1H), 3.01-2.91 (m, 6H), 2.85-2.60 (m, 6H), 2.55-2.47 (m, 1H), 2.51 (s, 3H), 2.26 (s, 3H), 2.14 (dd, J=16.1, 10.6 Hz, 1H), 2.05-1.91 (m, 2H), 1.72-1.63 (m, 1H); $^{13}$C NMR (125 MHz, CDCl$_3$): δ=155.1, 151.9, 147.4, 137.2, 136.8, 133.2, 130.8, 130.1, 126.0, 121.8, 116.8, 64.3, 59.9, 53.3, 51.7, 48.8, 46.7, 41.6, 30.3, 29.2, 26.3, 21.3, 18.1; HRMS (ESI) [M+H]$^+$, calcd for C$_{25}$H$_{36}$N$_5$ 406.29652, found 406.29611; LC/MS 75% MeOH in H$_2$O over 3 minutes, r$_t$=0.460 at 254 nM, MS (+) 406.2, MS(+)/2 203.6

Reductive Amination with Secondary Amine and Bulky Carbonyls

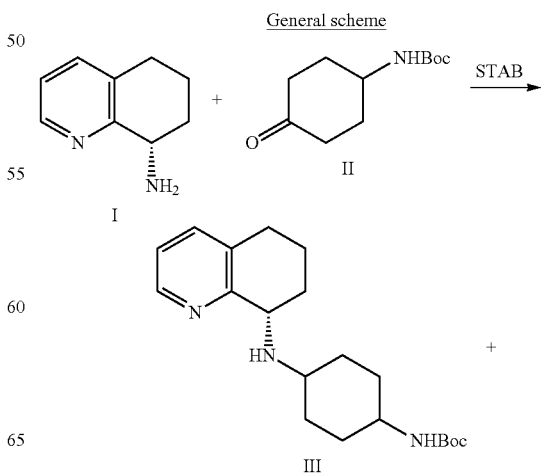

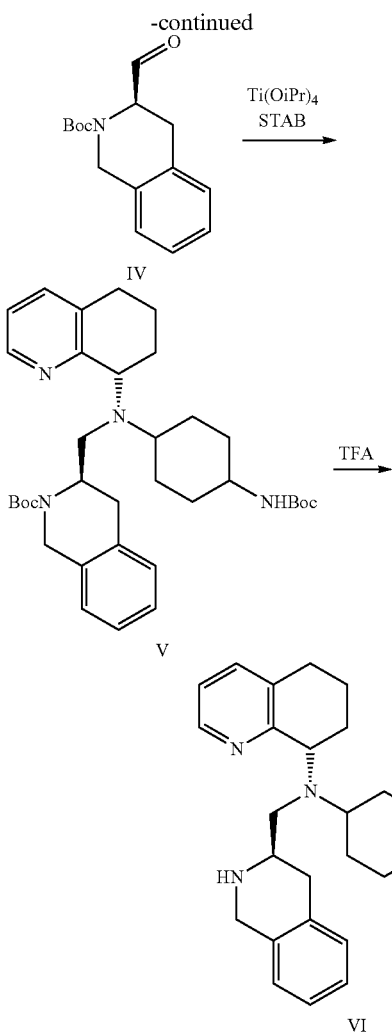

Synthesis of EMU073 (Stereoisomer 1) and EMU073 (Stereoisomer 2)

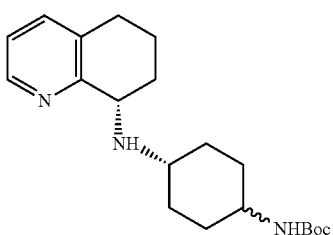
25 and 26

A 100 mL rb flask equipped with a rubber septum and stir bar was charged with 1.00 g of tert-butyl (4-oxocyclohexyl)carbamate (4.69 mmol, 1 equiv), 0.834 g of (S)-5,6,7,8-tetrahydroquinolin-8-amine (5.63 mmol, 1.2 equiv), 403 μL of acetic acid (7.03 mmol, 1.5 equiv) and 23.4 mL of DCE. Then 1.49 g of STAB (7.03 mmol, 1.5 equiv) was added and the suspension was stirred at rt for 20 h. The reaction mixture was quenched by addition of sat. Na$_2$CO$_3$ solution, extracted with CH$_2$Cl$_2$ (3×) and dried over Na$_2$SO$_4$. The crude product was purified on silica gel column using 0-10% MeOH in EA as eluent affording 626 mg (39%) of the stereoisomer 26 and 785 mg of stereoisomer 25 as a mixture with minor by-product. The isomer 25 was recrystallized from EA affording 538 mg (33%) of pure isomer 25. For the isomer 26: $^1$H NMR (400 MHz, CDCl$_3$, ppm) δ: 8.40-8.37 (m, 1H), 7.37-7.34 (m, 1H), 7.05 (ddd, J=7.7, 4.7, 0.7 Hz, 1H), 4.68 (br s, 1H), 3.88 (t, J=6.4 Hz, 1H), 3.69 (br s, 1H), 2.87-2.70 (m, 2H), 2.13 (dt, J=13.2, 6.2 Hz, 1H), 2.02-1.94 (m, 1H), 1.90-1.48 (m, 11H), 1.44 (s, 9H).

LC-MS (ESI-API, 254 nm) 95% MeOH in H$_2$O (0.1% HCO$_2$H), 3 min, 1.00 mL/min, C18 (Agilent Zorbax XDB-18, 50 mm×4.6 mm, 3.5 μm), m/z=346.2 (M+H), t=0.462 min; For the isomer 25: $^1$H NMR (400 MHz, CDCl$_3$, ppm) δ: 8.38 (dd, J=4.7, 1.7 Hz, 1H), 7.35 (dd, J=7.7, 1.7 Hz, 1H), 7.04 (dd, J=7.7, 4.7 Hz, 1H), 4.39 (br s, 1H), 3.91 (t, J=6.5 Hz, 1H), 3.45 (br s, 1H), 2.86-2.75 (m, 1H), 2.73 (dt, J=17.1, 5.1 Hz, 1H), 2.63 (tt, J=10.9, 3.7 Hz, 1H), 2.25-1.92 (m, 4H), 1.79-1.65 (m, 2H), 1.44 (s, 9H), 1.35-1.08 (m, 6H). LC-MS (ESI-API, 254 nm) 75-95% MeOH in H$_2$O (0.1% HCO$_2$H), 3 min, 1.00 mL/min, C18 (Agilent Zorbax XDB-18, 50 mm×4.6 mm, 3.5 μm), m/z=346.2 (M+H), t=0.479 min;

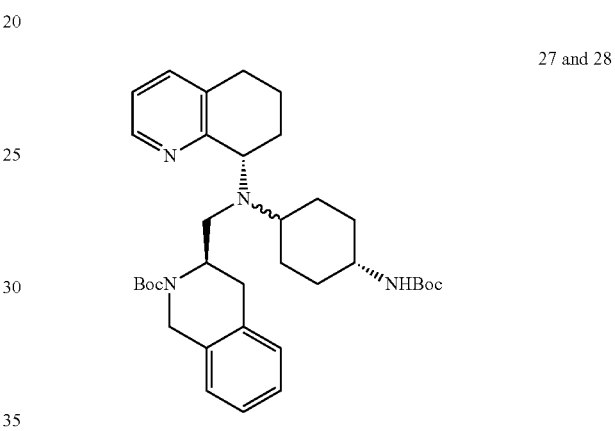
27 and 28

A 50 mL Schlenk tube equipped with a stir bar and rubber septum was charged with 0.314 g of the amine 26 (0.912 mmol, 1 equiv), 0.262 g of tert-butyl (R)-3-formyl-3,4-dihydroisoquinoline-2(1H)-carboxylate (1.00 mmol, 1.1 equiv) and 9.1 mL of CH$_2$Cl$_2$. Then 401 μL of titanium isopropoxide (1.37 mmol, 1.5 equiv) was added. After stirring at rt for 1 h, 0.386 g of STAB (1.82 mmol, 2 equiv) was added and the reaction mixture was stirred at rt for 5 h. The reaction mixture was quenched by addition of sat. NaHCO$_3$ solution, extracted with CH$_2$Cl$_2$ (3×), washed with brine and dried over Na$_2$SO$_4$. The crude product was purified on silica gel column using 0 to 50% EA in hexanes as eluent affording 0.492 g (92%) of the product 27 as a slightly yellow oil. $^1$H NMR (400 MHz, CDCl$_3$, ppm) δ: 8.40 (s, 1H), 7.24 (d, J=7.2 Hz, 1H), 7.15-6.94 (m, 5H), 4.94 (br s, 0.5H), 4.73-4.61 (m, 1H), 4.56 (br s, 1H), 4.35 (br s, 0.5H), 4.23 (B of AB, J$_{AB}$=17.0 Hz, 1H), 3.96 (dd, J=6.4, 8.7 Hz, 1H), 3.70 (br s, 1H), 3.17-2.37 (m, 7H), 2.06 (br s, 1H), 1.95-1.86 (m, 1H), 1.84-1.23 (m, 10H), 1.48 (s, 9H), 1.43 (s, 9H). LC-MS (ESI-API, 254 nm) 75-95% MeOH in H$_2$O (0.1% HCO$_2$H), 3 min, 1.00 mL/min, C18 (Agilent Zorbax XDB-18, 50 mm×4.6 mm, 3.5 μm), m/z=591.3 (M+H), t=1.549 min; Compound 28 was synthesized from amine 25 and tert-butyl (R)-3-formyl-3,4-dihydroisoquinoline-2(1H)-carboxylate following the procedure for the synthesis of compound 27. The crude product was purified on silica gel column using 0 to 100% EA in CH$_2$Cl$_2$ affording 0.523 g (94%) of the product 28 as a slightly yellow powder. $^1$H NMR (400 MHz, CDCl$_3$, ppm) δ: 8.39 (s, 1H), 7.25 (d, J=7.7 Hz, 1H), 7.14-6.95 (m, 5H), 4.69 (d, J=16.7 Hz, 1H), 4.53 (br s, 0.5H), 4.36 (s, 0.5H), 4.23 (br s, 1H), 4.19 (d, J=17.2 Hz, 1H), 4.06-3.91 (m, 1H), 3.26-2.30 (m, 7H), 2.10-1.23 (m, 8H), 1.48 (s, 9H), 1.41 (s, 9H), 1.05-0.82 (m, 2H). LC-MS (ESI-API, 254 nm) 75-95% MeOH in H$_2$O (0.1% HCO$_2$H), 3 min, 1.00 mL/min, C18 (Agilent Zorbax XDB-18, 50 mm×4.6 mm, 3.5 μm), m/z=591.2 (M+H), t=0.663 min, 93% purity;

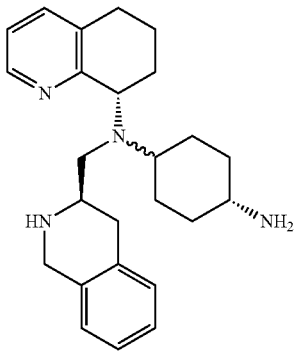

EMU073 (Stereoisomer 1)

A 20 mL vial equipped with a stir bar was charged with 187 mg of the amine 28 (0.317 mmol, 1 equiv) dissolved in 3.2 mL of CH$_2$Cl$_2$. Then 733 μL of TFA (9.51 mmol, 30 equiv) was added. After stirring at rt for 12 h, the reaction mixture was quenched by addition of sat. Na$_2$CO$_3$ and 2 N NaOH solutions, extracted with CH$_2$Cl$_2$ (3×), washed with brine and dried over Na$_2$SO$_4$. The crude material was purified on silica gel column using 0 to 60% of solvent 2 in CH$_2$Cl$_2$ (solvent 2=70% CH$_2$Cl$_2$, 30% MeOH, 3% NH$_4$OH) as eluent affording 61 mg (49%) of the product EMU073 (Stereoisomer 1) as a slightly yellow powder. $^1$H NMR (600 MHz, CDCl$_3$, ppm) δ: 8.44 (d, J=4.6 Hz, 1H), 7.26 (d, J=7.0 Hz, 1H), 7.07-6.99 (m, 4H), 6.95-6.92 (m, 1H), 4.08 (t, J=7.6 Hz, 1H), 3.89 (A of AB, J$_{AB}$=15.2 Hz, 1H), 3.37 (B of AB, J$_{AB}$=15.1 Hz, 1H), 3.13 (dd, J=13.5, 3.1 Hz, 1H), 2.77 (ddd, J=15.6, 10.6, 4.7 Hz, 1H), 2.72-2.63 (m, 2H), 2.59 (tt, J=11.0, 3.9 Hz, 1H), 2.54 (dd, J=15.9, 3.5 Hz, 1H), 2.46-2.34 (m, 2H), 2.24 (br s, 1H), 2.09-1.70 (m, 8H), 1.50 (qd, J=12.8, 3.5 Hz, 1H), 1.42 (qd, J=12.8, 3.4 Hz, 1H), 1.15 (qd, J=12.7, 3.4 Hz, 1H), 1.06 (qd, J=12.9, 3.5 Hz, 1H). $^{13}$C NMR (400 MHz, CDCl$_3$, ppm) δ: 159.18, 146.82, 136.34, 135.77, 134.56, 133.27, 128.87, 126.34, 125.62, 125.25, 121.22, 62.59, 60.56, 53.08, 52.27, 50.35, 48.43, 36.51, 36.41, 33.77, 31.04, 29.99, 29.44, 29.13, 21.87. HRMS (ESI+) calcd for C$_{25}$H$_{35}$N$_4$ ([M+H]$^+$): 391.2856. Found: 391.2857, error 0.1 ppm. LC-MS (ESI-API, 254 nm) 75-95% MeOH in H$_2$O (0.1% HCO$_2$H), 3 min, 1.00 mL/min, C18 (Agilent Zorbax XDB-18, 50 mm×4.6 mm, 3.5 μm), m/z=391.2 (M+H), 196.2 (M/2+H), t=0.887 min;

EMU073 (Stereoisomer 2): A 20 mL vial equipped with a stir bar was charged with 170 mg of the amine 27 (0.288 mmol, 1 equiv) dissolved in 2.9 mL of CH$_2$Cl$_2$. Then 666 μL of TFA (8.65 mmol, 30 equiv) was added. After stirring at rt for 12 h, the reaction mixture was quenched by addition of sat. Na$_2$CO$_3$ and 2 N NaOH solutions, extracted with CH$_2$Cl$_2$ (3×) and dried over Na$_2$SO$_4$. The crude material was purified on silica gel column using 0 to 60% of solvent 2 in CH$_2$Cl$_2$ (solvent 2=70% CH$_2$Cl$_2$, 30% MeOH, 3% NH$_4$OH) as eluent affording 93 mg (83%) of the product EMU073 (Stereoisomer 2) as a slightly yellow powder. $^1$H NMR (600 MHz, CDCl$_3$, ppm) δ: 8.45 (d, J=4.7 Hz, 1H), 7.26 (d, J=7.0 Hz, 1H), 7.09-6.99 (m, 4H), 6.94 (d, J=6.5 Hz, 1H), 4.15 (t, J=7.8 Hz, 1H), 3.89 (d, J=15.0 Hz, 1H), 3.38 (d, J=15.0 Hz, 1H), 3.14 (dd, J=13.5, 3.0 Hz, 1H), 3.08 (t, J=3.5 Hz, 1H), 2.82-2.71 (m, 2H), 2.66 (dt, J=16.4, 4.2 Hz, 1H), 2.54 (dd, J=15.6, 3.1 Hz, 2H), 2.43 (dt, J=45.3, 13.3 Hz, 1H), 2.26 (br s, 1H), 2.09-1.96 (m, 2H), 1.85-1.47 (m, 9H). $^{13}$C NMR (400 MHz, CDCl$_3$, ppm) δ: 159.31, 146.80, 136.28, 135.75, 134.56, 133.29, 128.85, 126.32, 125.60, 125.22, 121.14, 62.70, 60.13, 53.39, 52.39, 48.45, 45.26, 33.79, 32.96, 32.87, 29.46, 29.03, 26.43, 25.54, 21.99. HRMS (ESI+) calcd for C$_{25}$H$_{35}$N$_4$ ([M+H]$^+$): 391.2856. Found: 391.2935, error 7.9 ppm. LC-MS (ESI-API, 254 nm) 75-95% MeOH in H$_2$O (0.1% HCO$_2$H), 3 min, 1.00 mL/min, C18 (Agilent Zorbax XDB-18, 50 mm×4.6 mm, 3.5 μm), m/z=391.2 (M+H), 196.2 (M/2+H), t=0.739 min;

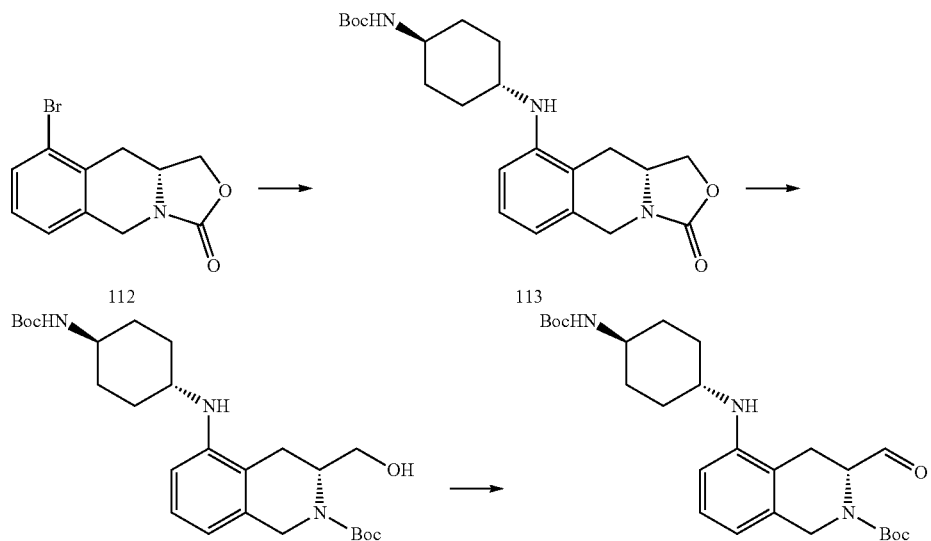

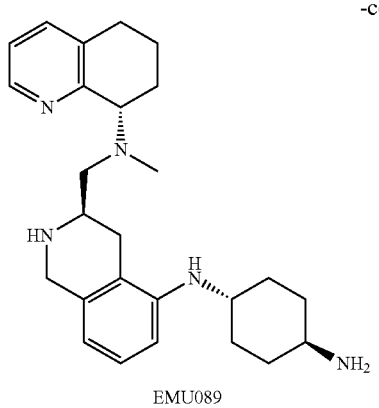

EMU089

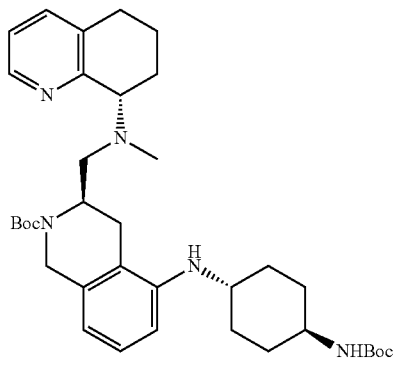

116

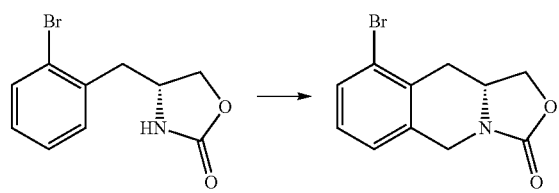 [SMILES: O=C1N[C@H](Cc2ccccc2Br)CO1 ; O=C1OC[C@H]2Cc3c(Br)cccc3CN12]

Similar as in ref (Organic Syntheses, Coll. Vol. 8, p. 528 (1993); Vol. 68, p. 77 (1990), 111 was synthesized from (R)-2-amino-3-(2-bromophenyl)propanoic acid in 78% yield. A 50 mL rb flask equipped with a stir bar was charged with 3.76 g of the oxazolidinone 111 (14.7 mmol, 1 equiv), 0.485 g of paraformaldehyde (16.2 mmol, 1.1 equiv), 14.3 mL of acetic acid and 4.8 mL of sulfuric acid (acids must be premixed). After stirring at rt for 12 h, the reaction mixture was poured portion wise into sat. $Na_2CO_3$ solution, extracted with $CH_2Cl_2$ (3×) and dried over $Na_2SO_4$. The crude product was purified on silica gel column using 0 to 10% EA in $CH_2Cl_2$ as eluent. The product was allowed to crystallize out of $CH_2Cl_2$ solution affording 3.04 g (77%) of the product 112 as white needles. $^1$H NMR (400 MHz, $CDCl_3$, ppm) δ: 7.51-7.47 (m, 1H), 7.14-7.11 (m, 2H), 4.84 (A of AB, $J_{AB}$=17.1 Hz, 1H), 4.62 (dd, J=8.7, 7.9 Hz, 1H), 4.36 (B of AB, $J_{AB}$=17.1 Hz, 1H), 4.22 (dd, J=8.7, 4.8 Hz, 1H), 3.96 (ddt, J=10.8, 7.8, 4.6 Hz, 1H), 3.25 (A of ABX, $J_{AB}$=16.4 Hz, $J_{AX}$=4.2 Hz, 1H), 2.67 (B of ABX, $J_{AB}$=16.4 Hz, $J_{BX}$=11.1 Hz, 1H).

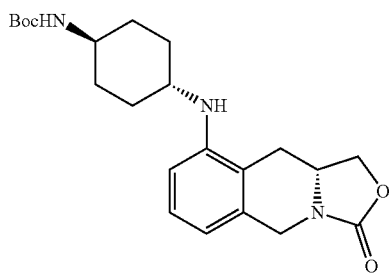 [SMILES: CC(C)(C)OC(=O)N[C@H]1CC[C@H](Nc2cccc3c2C[C@@H]2COC(=O)N2C3)CC1]

A 10-20 mL μW tube equipped with a stir bar was charged with 500 mg of the bromide 112 (1.87 mmol, 1 equiv), 480 mg of tert-butyl ((1r,4r)-4-aminocyclohexyl)carbamate (2.24 mmol, 1.2 equiv), 186 mg of BINAP (0.298 mmol, 0.16 equiv), 1.22 g of $Cs_2CO_3$ (3.73 mmol, 2 equiv) and 85.0 mg of $Pd_2(dba)_3$ (0.093 mmol, 0.05 equiv) and the system was set under Ar atmosphere by flashing through Ar for 1 h. Then 12.4 mL of dioxane (degassed by bubbling through Ar for 1 h) was added. After stirring at 140° C. for 3 h in the μW reactor (normal power), EA was added and the suspension was filtered through celite plug. The crude product was purified on silica gel column using 0-100% EA in hexanes as eluent affording 227 mg (30%) of the product 113 as a white solid and 193 mg (26%) of the de-Boc product as a white solid. $^1$H NMR (400 MHz, $CDCl_3$, ppm) δ: 7.12 (t, J=7.9 Hz, 1H), 6.54 (d, J=3.8 Hz, 1H), 6.52 (d, J=4.3 Hz, 1H), 4.77 (A of AB, $J_{AB}$=16.7 Hz, 1H), 4.61 (t, J=8.1 Hz, 1H), 4.42 (d, J=7.7 Hz, 1H), 4.33 (B of AB, $J_{AB}$=16.9 Hz, 1H), 4.19 (dd, J=8.7, 5.0 Hz, 1H), 3.97 (ddd, J=12.6, 9.8, 4.8 Hz, 1H), 3.49 (br s, 1H), 3.25 (br s, 2H), 2.68 (A of ABX, $J_{AB}$=14.9 Hz, $J_{AX}$=4.6 Hz, 1H), 2.41 (B of ABX, $J_{AB}$=15.0 Hz, $J_{BX}$=10.6 Hz, 1H), 2.21-2.03 (m, 4H), 1.45 (s, 9H), 1.31-1.20 (m, 4H).

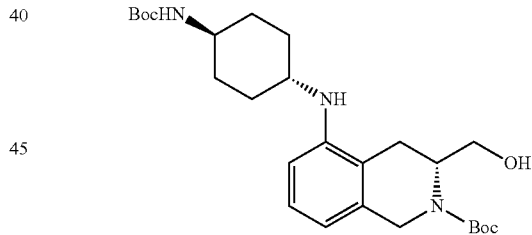

A 10-20 mL μW tube equipped with a stir bar was charged with 0.330 g of the oxazilidinone 113 (0.822 mmol, 1 equiv), 3.0 mL of 3 M NaOH solution (9.00 mmol, 11 equiv) and 7.0 mL of EtOH. After stirring at 110° C. for 1.5 h in a μW reactor (normal power), the reaction mixture was transferred to 50 mL rb flask, cooled to 0° C. and charged with 0.538 g of $Boc_2O$ (2.47 mmol, 3 equiv) dissolved in 6.6 mL of dioxanes and 3.3 mL of water. After stirring at rt for 48 h, the reaction mixture was neutralized by addition of sat. $NH_4Cl$ solution and diluted HCl, extracted with $CH_2Cl_2$ (3×) and dried over $Na_2SO_4$. The crude product was purified on silica gel column (40 g) using 0-100% EA in hexanes as eluent to afford 0.208 g (53%) of the product 114 as a white solid. $^1$H NMR (400 MHz, $CDCl_3$, ppm) δ: 7.07 (t, J=7.8 Hz, 1H), 6.49 (d, J=8.4 Hz, 2H), 4.71 (br s, 1H), 4.63-4.55 (m, 1H), 4.46-4.36 (m, 1H), 4.31-4.18 (m, 1H), 3.66-3.17 (m, 3H), 2.63 (A of ABX, $J_{AB}$=15.9 Hz, $J_{AX}$=6.5 Hz, 1H), 2.45

(B of ABX, $J_{AB}$=15.9 Hz, $J_{BX}$=2.6 Hz, 1H), 2.20-2.12 (m, 2H), 2.11-2.03 (m, 2H), 1.60 (br s, 3H), 1.48 (s, 9H), 1.45 (s, 9H), 1.31-1.17 (m, 2H).

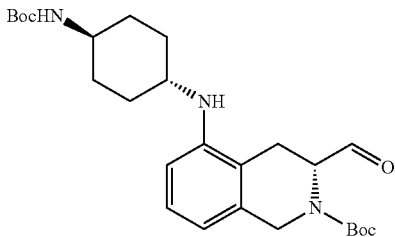 [SMILES: CC(C)(C)OC(=O)N[C@H]1CC[C@H](Nc2cccc3c2C[C@H](C=O)N(C(=O)OC(C)(C)C)C3)CC1]

A 50 mL Schlenk tube equipped with a magnetic stir bar and septum was charged with 0.208 g of the alcohol 114 (0.437 mmol, 1 equiv), 0.323 mL of TEA (2.32 mmol, 5.3 equiv) and 1.33 mL of CH$_2$Cl$_2$. After the reaction mixture was cooled to 0° C., 0.278 g of SO$_3$*Py (1.75 mmol, 4 equiv) dissolved in 1.33 mL of DMSO was added dropwise and the reaction mixture was allowed to warm up to rt in 5 h. The reaction mixture was quenched by addition of sat. NaHCO$_3$ solution, extracted with CH$_2$Cl$_2$ (3×) and dried over Na$_2$SO$_4$. The crude product was purified on silica gel column using 0 to 10% EA in CH$_2$Cl$_2$ as eluent affording 150 mg (72%) of the product 115 as a slightly yellow oil.

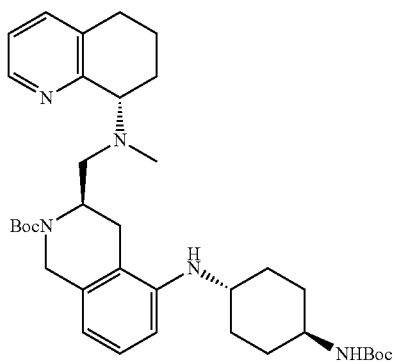 [SMILES: CN(C[C@H]1Cc2c(cccc2N[C@H]2CC[C@H](NC(=O)OC(C)(C)C)CC2)CN1C(=O)OC(C)(C)C)[C@H]1CCCc2cccnc21]

A 20 mL vial equipped with a stir bar was charged with 0.150 g of the aldehyde 115 (0.317 mmol, 1 equiv), 0.067 g of the amine V (0.412 mmol, 1.3 equiv) and 3.2 mL of DCE. Then 0.101 g of STAB (0.475 mmol, 1.5 equiv) was added and the suspension was stirred at rt for 3 h. The reaction mixture was quenched by addition of sat. NaHCO$_3$ solution, extracted with CH$_2$Cl$_2$ (3×) and dried over Na$_2$SO$_4$. The crude product was purified on silica gel column using 0 to 100% EA in hexanes as eluent affording 131 mg (67%) of the product 116 as a slightly yellow oil. $^1$H NMR (400 MHz, CDCl$_3$, ppm) δ: 8.33 (br s, 1H), 7.24 (d, J=7.7 Hz, 1H), 6.98-6.89 (m, 2H), 6.38 (d, J=8.1 Hz, 1H), 6.31 (br s, 1H), 4.78-4.43 (m, 2H), 3.86 (d, J=17.0 Hz, 1H), 3.79 (dd, J=8.8, 4.9 Hz, 1H), 3.49 (br s, 2H), 3.27-3.15 (m, 1H), 2.75 (A of AB, $J_{AB}$=15.8 Hz, 1H), 2.76-2.68 (m, 1H), 2.60 (dt, J=16.8, 5.0 Hz, 1H), 2.55-2.45 (m, 2H), 2.39 (s, 3H), 2.23-2.16 (m, 1H), 2.14-2.03 (m, 3H), 1.99-1.88 (m, 2H), 1.80-1.69 (m, 1H), 1.67-1.55 (m, 1H), 1.46 (s, 9H), 1.44 (s, 9H), 1.33-1.17 (m, 4H). LC-MS (ESI-API, 254 nm) 75-95% MeOH in H$_2$O (0.1% HCO$_2$H), 6 min, 1.00 mL/min, C18 (Agilent Zorbax XDB-18, 50 mm×4.6 mm, 3.5 μm), m/z=620.3 (M+H), t=0.730 min;

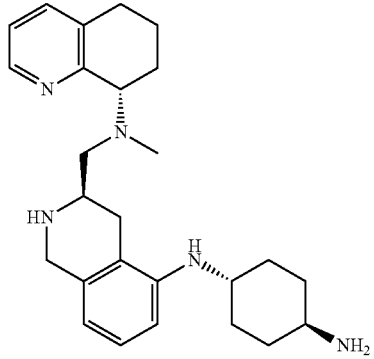 [SMILES: CN(C[C@H]1Cc2c(cccc2N[C@H]2CC[C@H](N)CC2)CN1)[C@H]1CCCc2cccnc21]

EMU089

A 20 mL vial equipped with a stir bar was charged with 131 mg of the amine 116 (0.211 mmol, 1 equiv) dissolved in 2.1 mL of CH$_2$Cl$_2$. Then 488 μL of TFA (6.34 mmol, 30 equiv) was added. After stirring at rt for 20 h, the reaction mixture was quenched by addition of 1 N KOH solution, extracted with CH$_2$Cl$_2$ (3×) and dried over Na$_2$SO$_4$. The crude material was purified on silica gel column using 0 to 60% Solvent 2 in CH$_2$Cl$_2$ (solvent 2=70% CH$_2$Cl$_2$, 30% MeOH, 3% NH$_4$OH) as eluent affording 77 mg (87%) of the product EMU089 as a slightly yellow powder. $^1$H NMR (600 MHz, CDCl$_3$, ppm) δ: 8.47 (d, J=4.7 Hz, 1H), 7.34 (d, J=7.7 Hz, 1H), 7.06 (dd, J=7.7, 4.7 Hz, 1H), 7.00 (t, J=7.8 Hz, 1H), 6.45 (d, J=8.1 Hz, 1H), 6.39 (d, J=7.6 Hz, 1H), 4.00 (dd, J=8.9, 6.4 Hz, 1H), 3.94 (A of AB, $J_{AB}$=15.3 Hz, 1H), 3.89 (B of AB, $J_{AB}$=15.3 Hz, 1H), 3.33-3.22 (m, 2H), 2.91 (br s, 1H), 2.82-2.64 (m, 4H), 2.54 (s, 3H), 2.35 (dd, J=15.5, 4.2 Hz, 1H), 2.17-1.64 (m, 9H), 1.30-1.14 (m, 4H). $^{13}$C NMR (400 MHz, CDCl$_3$, ppm) δ: 157.70, 146.80, 144.74, 136.52, 136.25, 133.88, 126.03, 121.43, 118.60, 114.61, 107.61, 64.13, 59.67, 51.57, 51.18, 50.21, 48.95, 41.37, 35.35, 35.31, 32.18, 32.11, 29.19, 28.82, 24.84, 21.24. HRMS (ESI+) calcd for C$_{26}$H$_{38}$N$_5$ ([M+H]$^+$): 420.3122. Found: 420.3123, error 0.2 ppm. LC-MS (ESI-API, 254 nm) 75-95% MeOH in H$_2$O (0.1% HCO$_2$H), 3 min, 1.00 mL/min, C18 (Agilent Zorbax XDB-18, 50 mm×4.6 mm, 3.5 μm), m/z=420.2 (M+H), 210.6 (M/2+H), t=0.495 min; The Pyridine TIQ-15

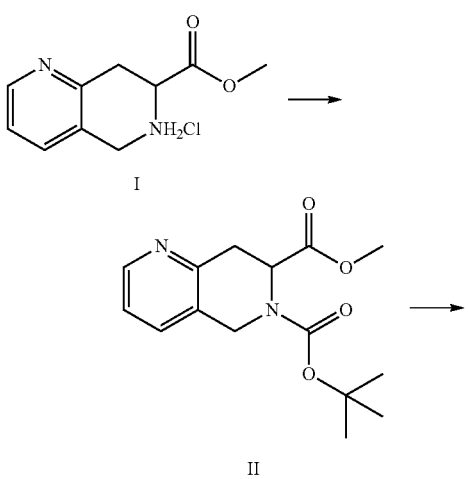

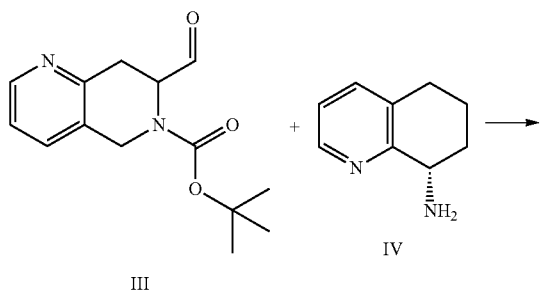

III

IV

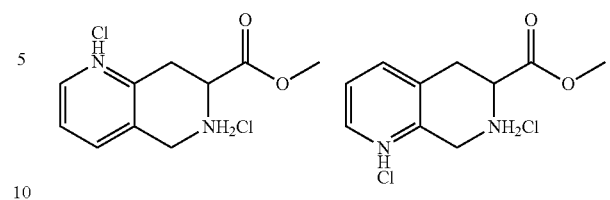

74

As in ref., (Organic Process Research & Development 2002, 6, 938-942, Bioorganic & Medicinal Chemistry 2003, 11, 433-450) 74 was synthesized from pyridine-2,3-dicarboxylic acid in 55% yield.

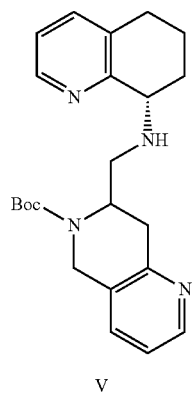

V

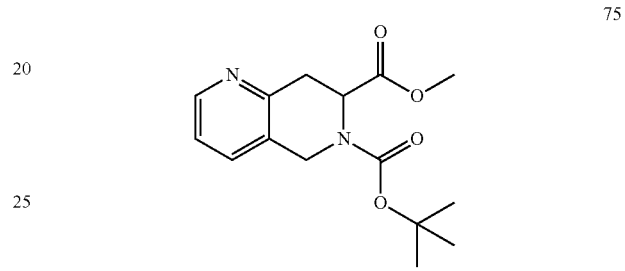

75

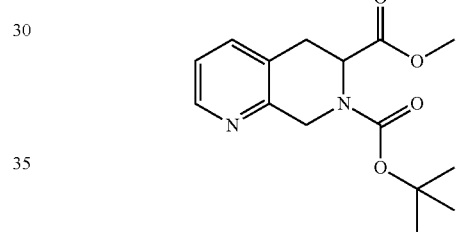

76

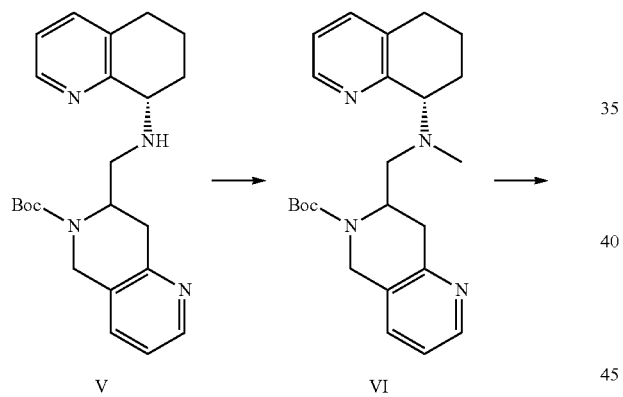

V                     VI

A 1 L rb flask equipped with a magnetic stir bar and rubber septum was charged with 26.9 g of the ester 74 (101 mol, 1 equiv), 42.2 mL of TEA (303 mmol, 3 equiv), 1.23 g of DMAP (10.1 mmol, 0.1 equiv) and 253 mL of THF. Then 27.6 g of Boc$_2$O (126 mmol, 1.25 equiv) was added and the suspension was stirred for 3 h. The suspension was not going into solution and another portion of 21 mL of TEA (151 mmol, 1.5 equiv) was added followed by 300 mL of acetonitrile and 100 mL of MeOH. After the clear solution was stirred at rt for 12 h, the reaction mixture was concentrated and EA was added. The ammonium salts were separated by filtration and the organics were concentrated under vacuum. The crude material was purified on silica gel column using 0-65% EA in hexanes as eluent affording 2.24 g (8%) of 76 as a yellow oil and 8.12 g (28%) of 75 as a yellow oil which crystallizes in freezer to white solid. For 76 (4:1 mixture of conformers): $^1$H NMR (400 MHz, CDCl$_3$, ppm) δ: 8.47-8.41 (m, 1.25H), 7.46 (d, J=7.7 Hz, 1.25H), 7.11 (dd, J=7.7, 4.8 Hz, 1.25H), 5.27 (dd, J=5.9, 2.1 Hz, 1H), 5.02 (br s, 0.25H), 4.89 (A of AB, J$_{AB}$=18.1 Hz, 0.25H), 4.87 (A of AB, J$_{AB}$=17.9 Hz, 1H), 4.56 (B of AB, J$_{AB}$=18.2 Hz, 1H), 4.51 (B of AB, J$_{AB}$=18.2 Hz, 0.25H), 3.63 (s, 3.75H), 3.29 (A of ABX, J$_{AB}$=16.5 Hz, J$_{AX}$=2.2 Hz, 1H), 3.24 (A of ABX, J$_{AB}$=16.5 Hz, J$_{AX}$=2.2 Hz, 0.25H), 3.17 (B of ABX, J$_{AB}$=16.2 Hz, J$_{BX}$=6.3 Hz, 1H), 1.52 (s, 9H), 1.48 (s, 2.25H). LC-MS (ESI-API, 254 nm) 95% MeOH in H$_2$O (0.1% HCO$_2$H), 3 min, 1.00 mL/min, C18 (Agilent Zorbax XDB-18, 50 mm×4.6 mm, 3.5 μm), m/z=315.0 (M+Na), 293.0

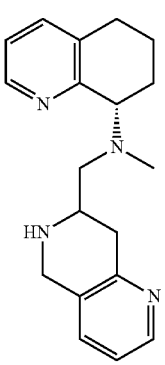

VII (M+H), t=0.562 min; For 75 (1:1 mixture of conformers): ¹H NMR (400 MHz, CDCl₃, ppm) δ: 8.42 (d, J=4.9 Hz, 1H), 7.44 (d, J=7.9 Hz, 0.5H), 7.41 (d, J=7.7 Hz, 0.5H), 7.14 (dd, J=7.8, 4.9 Hz, 1H), 5.32 (d, J=6.9 Hz, 0.5H), 5.01 (dd, J=6.5, 3.7 Hz, 0.5H), 4.80 (A of AB, $J_{AB}$=17.4 Hz, 0.5H), 4.76 (B of AB, $J_{AB}$=17.4 Hz, 0.5H), 4.57 (B of AB, $J_{AB}$=17.0 Hz, 0.5H), 4.50 (d, J=16.7 Hz, 1H), 3.65 (s, 1.5H), 3.63 (s, 1.5H), 3.47 (A of AB, $J_{AB}$=16.8 Hz, 0.5H), 3.40 (A of ABX, $J_{AB}$=17.1 Hz, $J_{AX}$=3.9 Hz, 0.5H), 3.32 (B of ABX, $J_{AB}$=17.5 Hz, $J_{BX}$=6.6 Hz, 1H), 1.53 (s, 4.5H), 1.47 (s, 4.5H). LC-MS (ESI-API, 254 nm) 95% MeOH in H₂O (0.1% HCO₂H), 3 min, 1.00 mL/min, C18 (Agilent Zorbax XDB-18, 50 mm×4.6 mm, 3.5 µm), m/z=315.0 (M+Na), 293.1 (M+H), t=0.560 min;

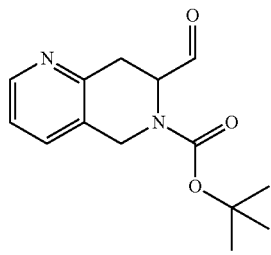

77

A 100 mL rb flask equipped with a stir bar and rubber septum was charged with 1.00 g of the ester 75 (3.42 mmol, 1 equiv) and 17.1 mL of toluene. After the reaction mixture was cooled to 78° C., 5.70 mL of 1.2 M solution of DIBAL-H (6.84 mL, 2 equiv) was added dropwise and the solution was stirred at 78° C. for 2 h. Then the reaction mixture was quenched by addition of 2.5 mL of MeOH followed by sat. solution of Rochelle's salt. After stirring at rt for 30 min, the product was extracted with EA (3×) and dried over Na₂SO₄. The crude product 77 (994 mg) was used in the next step without purification.

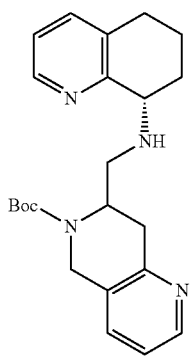

78

To a 20 mL vial equipped with a stir bar was added 608 mg of (S)-5,6,7,8-tetrahydroquinolin-8-amine (4.10 mmol, 1.2 equiv), 897 mg of the aldehyde 77 (3.42 mmol, 1 equiv), 942 mg of STAB (4.45 mmol, 1.3 equiv) and 11.4 mL of DCE. After stirring at rt for 1.5 h, the reaction mixture was quenched by addition of sat. Na₂CO₃ solution and the product was extracted with CH₂Cl₂ (3×), washed with sat. Na₂CO₃ solution, brine and dried over Na₂SO₄. The crude product was purified on silica gel column using EA, followed by 20% MeOH in CH₂Cl₂ as eluent affording 0.905 (67%) g of the product 78. ¹H NMR (400 MHz, CDCl₃, ppm) δ: 8.44-8.40 (m, 1H), 8.35 (d, J=4.5 Hz, 1H), 7.39 (d, J=7.4 Hz, 1H), 7.34 (d, J=7.7 Hz, 1H), 7.14 7.09 (m, 1H), 7.05 (t, J=4.2 Hz, 0.5H), 7.03 (t, J=4.2 Hz, 0.5H), 5.02-4.58 (m, 2H), 4.24 (B of AB, $J_{AB}$=18.3 Hz, 1H), 3.76 (br s, 0.5H), 3.69 (br s, 0.5H), 3.23 (A of ABX, $J_{AB}$=16.6 Hz, $J_{AX}$=6.2 Hz, 0.5H), 3.19 (A of ABX, $J_{AB}$=16.6 Hz, $J_{AX}$=6.2 Hz, 0.5H), 3.07 (B of AB, $J_{AB}$=16.9 Hz, 0.5H), 2.94 (B of AB, $J_{AB}$=16.8 Hz, 0.5H), 2.85-2.63 (m, 4H), 2.04-1.91 (m, 1H), 1.72-1.63 (m, 1H), 1.52-1.28 (m, 2H), 1.49 (s, 4.5H), 1.42 (s, 4.5H). LC-MS (ESI-API, 254 nm) 75-95% MeOH in H₂O (0.1% HCO₂H), 3 min, 1.00 mL/min, C18 (Agilent Zorbax XDB-18, 50 mm×4.6 mm, 3.5 µm), m/z=417.2 (M+Na), 395.2 (M+H), t=0.511 min, 86% purity;

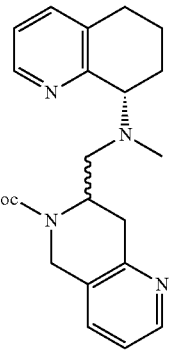

97

A 20 mL vial equipped with a stir bar was charged with 0.086 g of paraformaldehyde (2.85 mmol, 2 equiv), 0.563 g of the amine 78 (1.43 mmol, 1 equiv), 82 µL of acetic acid (1.43 mmol, 1 equiv) and 14.3 mL of DCE. Then 0.605 g of STAB (2.85 mmol, 2 equiv) was added. After stirring for 2 days, the reaction mixture was quenched by addition of sat. NaHCO₃ solution, extracted with CH₂Cl₂ (3×) and dried over Na₂SO₄. The crude product is purified on silica gel column using 0 to 10% MeOH in EA as eluent affording 208 mg (36%) of URf-97 (Stereoisomer 1), 66 mg (11%) of mixture of the isomers and 189 mg (32%) of LRf-97 (Stereoisomer 2). The stereoisomer 2 elutes faster than stereoisomer 1 on TLC using 10% MeOH in EA. For the stereoisomer 1: ¹H NMR (400 MHz, CDCl₃, ppm) δ: 8.30 (d, J=4.1 Hz, 1H), 8.24 (s, 1H), 7.31-7.15 (m, 2H), 7.00 (dd, J=7.8, 4.8 Hz, 1H), 6.89 (s, 1H), 4.85-4.66 (m, 1.5H), 4.55 (br s, 0.5H), 4.29-4.12 (m, 1H), 3.70 (dd, J=8.8, 5.1 Hz, 1H), 3.06 (A of ABX, $J_{AB}$=16.7, $J_{AX}$=6.3 Hz, 1H), 2.97-2.87 (m, 1H), 2.72-2.44 (m, 4H), 2.40-2.25 (m, 1H), 2.29 (s, 3H), 1.96-1.82 (m, 2H), 1.80-1.67 (m, 1H), 1.63-1.52 (m, 1H), 1.44 (s, 9H). LC-MS (ESI-API, 254 nm) 75-95% MeOH in H₂O (0.1% HCO₂H), 6 min, 1.00 mL/min, C18 (Agilent Zorbax XDB-18, 50 mm×4.6 mm, 3.5 µm), m/z=431.2 (M+Na), 409.2 (M+H), 205.2 (M/2+H), t=0.499 min; For the stereoisomer 2: ¹H NMR (400 MHz, CDCl₃, ppm) δ: 8.31 (s, 1H), 8.22 (s, 1H), 7.24 (d, J=7.6 Hz, 1H), 7.14 (d, J=7.7 Hz, 1H), 6.97 (dd, J=7.7, 4.8 Hz, 1H), 6.92 (br s, 1H), 4.79-4.48 (m, 2H), 3.81-3.43 (m, 2H), 3.03 (s, 2H), 2.78-2.66 (m, 1H), 2.62-2.53 (m, 2H), 2.33 (s, 3H), 1.96-1.86 (m, 1H), 1.86-1.76 (m, 2H), 1.63-1.51 (m, 1H), 1.44 (s, 9H). LC-MS (ESI-API, 254 nm) 75-95% MeOH in H₂O (0.1% HCO₂H), 6 min, 1.00 mL/min, C18 (Agilent Zorbax XDB-18, 50 mm×4.6 mm, 3.5 µm), m/z=431.2 (M+Na), 409.2 (M+H), 205.2 (M/2+H), t=0.481 min;

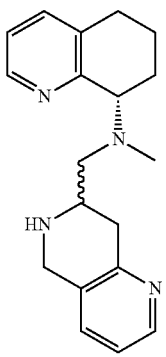 [SMILES: CN(CC1Cc2ncccc2CN1)[C@H]1CCCc2cccnc21]

EMU174 (Stereoisomer 1)

A 20 mL vial equipped with a stir bar was charged with 192 mg of the amine URf-97 (0.470 mmol, 1 equiv) dissolved in 4.7 mL of $CH_2Cl_2$. Then 1.09 mL of TFA (14.1 mmol, 30 equiv) was added. After stirring at rt for 12 h, the reaction mixture was quenched by addition of 2 N NaOH solution, extracted with $CH_2Cl_2$ (3×) and dried over $Na_2SO_4$. The crude material was purified on silica gel column using 0 to 45% of solvent2 (solvent2=30% MeOH, 70% $CH_2Cl_2$ and 3% $NH_4OH$) in $CH_2Cl_2$ as eluent affording 131 mg (90%) of the product EMU174 (stereoisomer 1). $^1$H NMR (600 MHz, $CDCl_3$, ppm) δ: 8.52 (d, J=4.4 Hz, 1H), 8.34 (d, J=4.7 Hz, 1H), 7.34 (d, J=1.0 Hz, 1H), 7.31 (d, J=7.7 Hz, 1H), 7.06 (dd, J=7.7, 4.7 Hz, 1H), 7.01 (dd, J=7.7, 4.7 Hz, 1H), 4.10 (A of AB, $J_{AB}$=15.2 Hz, 1H), 4.00 (B of AB, $J_{AB}$=14.9 Hz, 1H), 3.98 (dd, J=9.7, 6.0 Hz, 1H), 3.06 (t, J=10.8 Hz, 1H), 2.81 (ddd, J=16.3, 10.9, 5.2 Hz, 1H), 2.75 (dd, J=16.7, 3.7 Hz, 1H), 2.70 (dt, J=16.6, 4.6 Hz, 1H), 2.59 (dd, J=12.9, 2.0 Hz, 1H), 2.53 (s, 3H), 2.53 (dd, J=16.3, 11.9 Hz, 1H), 2.40 (dd, J=12.7, 10.1 Hz, 1H), 2.23-2.17 (m, 1H), 2.06-2.00 (m, 1H), 1.84 (tdd, J=12.5, 9.4, 3.0 Hz, 1H), 1.70-1.67 (m, 1H). $^{13}$C NMR (400 MHz, $CDCl_3$, ppm) δ: 156.72, 155.14, 147.22, 146.92, 136.53, 133.99, 133.86, 131.16, 121.73, 120.51, 64.52, 58.51, 51.85, 47.73, 40.24, 36.97, 29.12, 22.61, 21.18. HRMS (ESI+) calcd for $19H_{25}N_4$ $([M+H]^+)$: 309.2074. Found: 309.2071, error −1.0 ppm. LC-MS (ESI-API, 254 nm) 75-95% MeOH in $H_2O$ (0.1% $HCO_2H$), 3 min, 1.00 mL/min, C18 (Agilent Zorbax XDB-18, 50 mm×4.6 mm, 3.5 µm), m/z=309.2 (M+H), 155.2 (M/2+H), t=0.465 min; EMU174 (Stereoisomer 2): A 20 mL vial equipped with a stir bar was charged with 127 mg of the amine LRf-97 (0.311 mmol, 1 equiv) dissolved in 3.1 mL of $CH_2Cl_2$. Then 0.718 mL of TFA (9.33 mmol, 30 equiv) was added. After stirring at rt for 12 h, the reaction mixture was quenched by addition of 2 N NaOH solution, extracted with $CH_2Cl_2$ (3×) and dried over $Na_2SO_4$. The crude material was purified on silica gel column using 0 to 45% of solvent2 (solvent2=30% MeOH, 70% $CH_2Cl_2$ and 3% $NH_4OH$) in $CH_2Cl_2$ as eluent affording 80 mg (83%) of the product EMU174 (Stereoisomer 2). $^1$H NMR (600 MHz, $CDCl_3$, ppm) δ: 8.47 (d, J=4.1 Hz, 1H), 8.35 (d, J=4.8 Hz, 1H), 7.35 (dd, J=7.6, 0.9 Hz, 1H), 7.31 (d, J=7.2 Hz, 1H), 7.06 (dd, J=7.7, 4.7 Hz, 1H), 7.02 (dd, J=7.7, 4.8 Hz, 1H), 4.00 (A of AB, $J_{AB}$=15.2 Hz, 1H), 3.96 (dd, J=9.3, 6.0 Hz, 1H), 3.89 (B of AB, $J_{AB}$=15.2 Hz, 1H), 2.92 (tt, J=10.5, 3.5 Hz, 1H), 2.83-2.76 (m, 3H), 2.68 (dt, J=16.2, 4.5 Hz, 1H), 2.57 (d, J=16.9, 10.9 Hz, 1H), 2.51 (dd, J=12.9, 10.1 Hz, 1H), 2.52 (s, 3H), 2.10-2.04 (m, 1H), 2.05-1.98 (m, 1H), 1.97-1.90 (m, 1H), 1.74-1.67 (m, 1H). $^{13}$C NMR (400 MHz, $CDCl_3$, ppm) δ: 157.76, 155.06, 147.13, 146.75, 136.46, 133.86, 133.64, 130.94, 121.38, 120.63, 64.36, 59.44, 51.72, 47.48, 41.14, 37.00, 29.10, 25.80, 21.22. HRMS (ESI+) calcd for $C_{19}H_{25}N_4$ $([M+H]^+)$: 309.2074. Found: 309.2074, error 0.0 ppm. LC-MS (ESI-API, 254 nm) 75-95% MeOH in $H_2O$ (0.1% $HCO_2H$), 3 min, 1.00 mL/min, C18 (Agilent Zorbax XDB-18, 50 mm×4.6 mm, 3.5 µm), m/z=309.2 (M+H), 155.2 (M/2+H), t=0.475 min;

The stereochemical assignment of select compounds were determined as described below and the protected precursors used to generate the various stereoisomers (for example, EMU142, EMU174, EMU192, EMU193, EMU194, EMU209, EMU212, vide infra and vide supra).

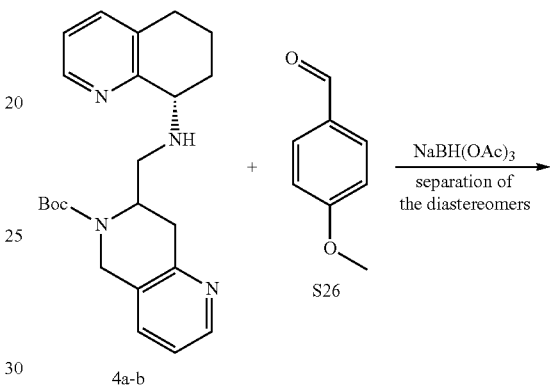

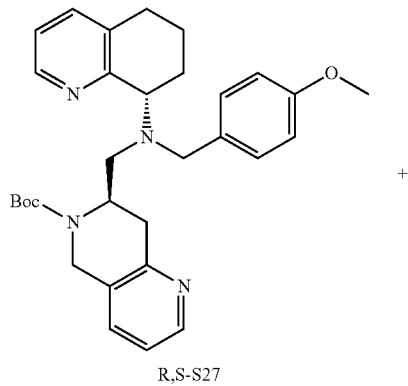

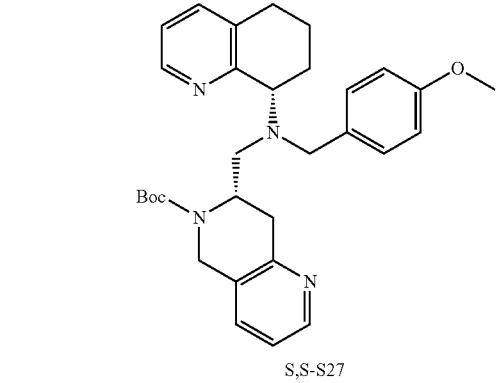

-continued

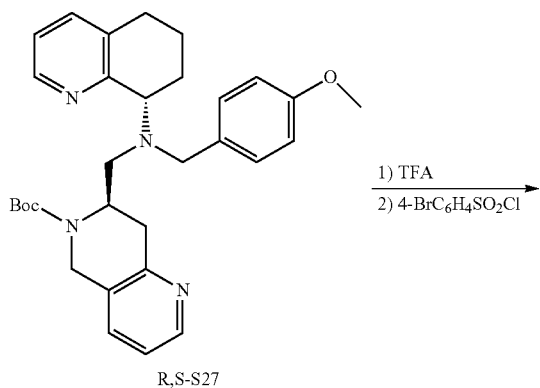

R,S-S27

1) TFA
2) 4-BrC$_6$H$_4$SO$_2$Cl

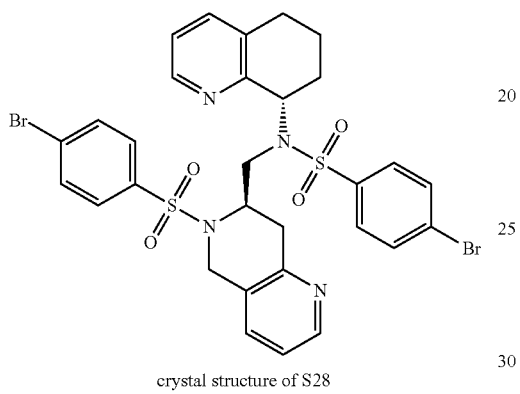

crystal structure of S28

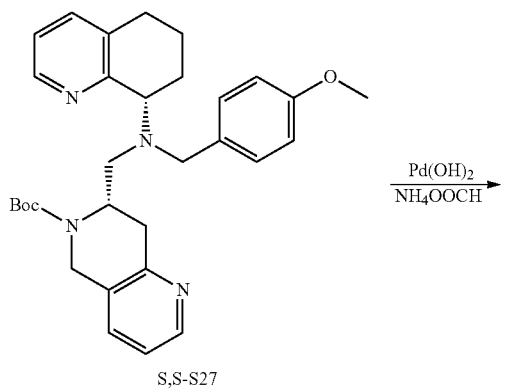

S,S-S27

Pd(OH)$_2$
NH$_4$OOCH

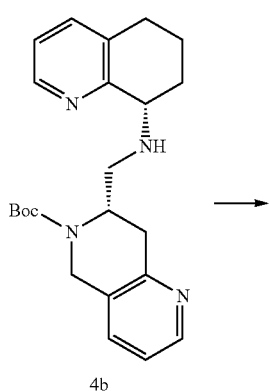

4b

-continued

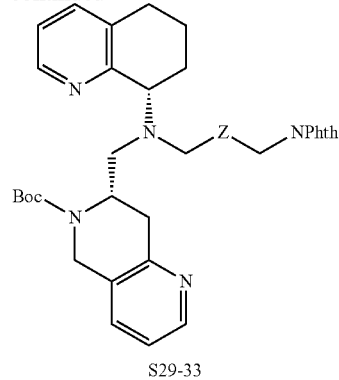

S29-33

Synthesis of the analogs with different side-chains. The synthesis was started from the amine S,S-S27 with known stereochemistry, and $^1$H NMR of the products S29-33 were compared with the $^1$H NMR of previously synthesized different side-chain analogs.

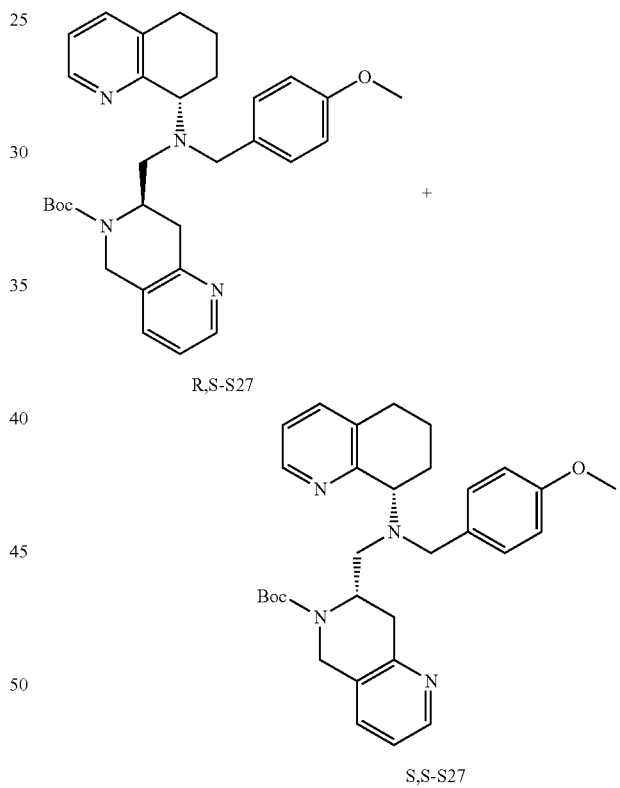

A 20 mL vial equipped with a stir bar was charged with 824 μL of p-anisaldehyde (6.78 mmol, 1.1 equiv), 2.43 g of the amine 4a-b (6.16 mmol, 1 equiv), 70.5 μL of acetic acid (1.23 mmol, 0.2 equiv) and 41.1 mL of DCE. Then 1.70 g of NaBH(OAc)$_3$ (8.01 mmol, 1.3 equiv) was added. After stirring at rt for 4 h, the reaction had not gone to completion and 353 μL of acetic acid (6.15 mmol, 1 equiv) and 0.392 g of NaBH(OAc)$_3$ (2.33 mmol, 0.3 equiv) were added. After stirring at rt for 12 h, the reaction mixture was quenched by addition of sat. NaHCO$_3$ solution, extracted with CH$_2$Cl$_2$ (3×) and dried over Na$_2$SO$_4$. The crude product is purified on silica gel column using 0 to 100% EA in hexanes as eluent affording 1.00 g (32%) of S,S-S27, 350 mg (11%) of the mixture of the isomers and 600 mg (19%) of R,S-S27. The R,S-isomer elutes faster than S,S-isomer on TLC using 10% MeOH in EA. For S,S-isomer: $^1$H NMR (400 MHz, CDCl$_3$, ppm) δ: 8.41-8.35 (m, 2H), 7.38-7.24 (m, 3H), 7.21 (d, J=7.6 Hz, 1H), 7.05 (dd, J=5.0, 6.4 Hz, 1H), 6.96 (dd, J=7.7, 4.8 Hz, 1H), 6.80 (d, J=7.5 Hz, 2H), 4.72 (A of AB, $J_{AB}$=17.7 Hz, 1H), 4.71 (br s, 0.5H), 4.53 (br s, 0.5H), 4.26 (br s, 1H), 4.12 (A of AB, $J_{AB}$=17.5 Hz, 1H), 3.97-3.89 (m, 1H), 3.83-3.74 (m, 1H), 3.79 (s, 3H), 3.30 (br s, 1H), 3.04 (B of ABX, $J_{AB}$=16.6 Hz, $J_{BX}$=6.1 Hz, 1H), 2.77 (d, J=13.1 Hz, 1H), 2.56-2.39 (m, 2H), 2.31-2.13 (m, 1H), 2.02-1.93 (m, 1H), 1.83-1.67 (m, 2H), 1.56-1.37 (m, 1H), 1.45 (s, 9H). LC-MS (ESI-API, 254 nm) 75-95% MeOH in H$_2$O (0.1% HCO2H), 3 min, 1.00 mL/min, C18 (Agilent Zorbax XDB-18, 50 mm×4.6 mm, 3.5 μm), m/z=515.0 (M+H), 258.0 (M/2+H), t=0.744 min; For R,S-isomer: $^1$H NMR (400 MHz, CDCl$_3$, ppm) δ: 8.39 (s, 1H), 8.35 (dd, J=4.8, 1.6 Hz, 1H), 7.25 (d, J=7.7 Hz, 1H), 7.23-7.13 (m, 2H), 7.10-6.95 (m, 2H), 6.97 (dd, J=7.7, 4.7 Hz, 1H), 6.75 (d, J=8.5 Hz, 2H), 4.93 (br s, 0.5H), 4.77 (d, J=17.6 Hz, 0.5H), 4.65 (br s, 0.5H), 4.47 (d, J=17.7 Hz, 0.5H), 4.14 (br s, 0.5H), 3.96 (br s, 0.5H), 3.78 (s, 3H), 3.86-3.26 (m, 3H), 3.21-2.93 (m, 2H), 2.72-2.42 (m, 3H), 2.27 (br s, 0.5H), 2.15 (br s, 0.5H), 1.99-1.88 (m, 1H), 1.81-1.38 (m, 3H), 1.53 (s, 4.5H), 1.44 (s, 4.5H). LC-MS (ESI-API, 254 nm) 75-95% MeOH in H$_2$O (0.1% HCO2H), 3 min, 1.00 mL/min, C18 (Agilent Zorbax XDB-18, 50 mm×4.6 mm, 3.5 μm), m/z=515.0 (M+H), 258.0 (M/2+H), t=0.738 min;

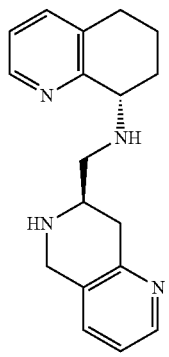

4a

A 5 mL microwave vial equipped with a stir bar was charged with 378 mg of the R,S-S27 (0.735 mmol, 1 equiv) and 3.40 mL of CF$_3$COOH (44.1 mmol, 60 equiv) and the vial was sealed. After stirring at 40° C. for 4 h, the reaction mixture was quenched by addition of 2 M NaOH solution, extracted with CH$_2$Cl$_2$ (3×) and dried over Na$_2$SO$_4$. The organics were concentrated in vacuuo (rotatory evaporator) and the crude product was purified on silica gel column using 0 to 60% solvent2 (solvent2=30% MeOH in CH$_2$Cl$_2$+ 3% NH$_4$OH) in CH$_2$Cl$_2$ as eluent affording 216 mg (100%) of the product 4a as a yellowish oil. $^1$H NMR (400 MHz, CDCl$_3$, ppm) δ: 8.24 (dd, J=4.7, 1.7 Hz, 1H), 8.21 (dd, J=4.8, 1.7 Hz, 1H), 7.20 (dd, J=7.7, 1.7 Hz, 1H), 7.14 (dd, J=7.7, 1.7 Hz, 1H), 6.89 (dd, J=7.9, 4.7 Hz, 1H), 6.87 (dd, J=7.5, 4.9 Hz, 1H), 3.87 (s, 2H), 3.66 (dd, J=7.6, 5.2 Hz, 1H), 2.96 (ddt, J=10.8, 8.2, 3.9 Hz, 1H), 2.84 (dd, J=4.0, 1.7 Hz, 1H), 2.80 (dd, J=6.8, 3.9 Hz, 1H), 2.64 (A of AB, $J_{AB}$=8.8 Hz, 1H), 2.61 (B of AB, $J_{AB}$=8.9 Hz, 1H), 2.69-2.47 (m, 2H), 2.39 (br s, 2H), 2.03-1.95 (m, 1H), 1.91-1.78 (m, 1H), 1.70-1.52 (m, 2H). $^{13}$C NMR (400 MHz, CDCl$_3$, ppm) δ: 157.09, 154.74, 146.97, 146.46, 136.41, 133.25, 131.95, 131.02, 121.38, 120.56, 57.89, 54.03, 52.38, 46.92, 36.43, 28.74, 28.43, 19.21. LC-MS (ESI-API, 254 nm) 75-95% MeOH in H$_2$O (0.1% HCO2H), 3 min, 1.00 mL/min, C18 (Agilent Zorbax XDB-18, 50 mm×4.6 mm, 3.5 μm), m/z=295.0 (M+H), t=0.508 min;

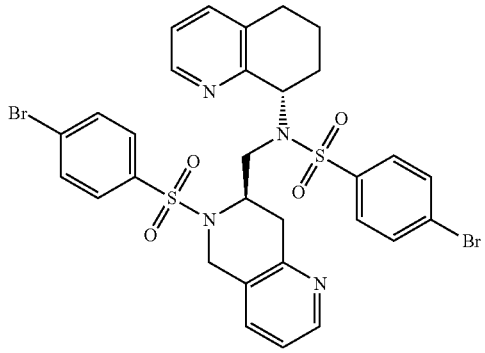

S28

A 20 mL vial equipped with stir bar was charged with 200 mg of the amine 4a (0.679 mmol, 1 equiv), 237 μL of Et$_3$N (1.70 mmol, 2.5 equiv), 8.30 mg of DMAP (0.0679 mmol. 0.1 equiv) and 6.7 mL of CH$_2$Cl$_2$. Then 399 mg of 4-bromobenzenesulfonyl chloride (1.56 mmol, 2.3 equiv) was added and the reaction mixture was stirred at rt for 12 h. The reaction mixture was quenched by addition of sat. NaHCO$_3$ solution, extracted with CH$_2$Cl$_2$ (2×), and dried over Na$_2$SO$_4$. The organics were concentrated and the crude product was purified on silica gel column using 0-100% EA in hexanes as eluent affording 380 mg (76%) of the product S28 as a white solid. The product was recrystallized from the mixture of ethyl acetate and CH$_2$Cl$_2$ (5:1) affording colorless needles which were submitted for X-ray crystallography. $^1$H NMR (400 MHz, CDCl$_3$, ppm) δ: 8.39 (dd, J=4.9, 1.6 Hz, 1H), 7.93 (dd, J=4.7, 1.6 Hz, 1H), 7.58-7.44 (m, 8H), 7.31 (dd, J=7.7, 1.6 Hz, 1H), 7.26 (dd, J=7.7, 1.6 Hz, 1H), 7.05 (dd, J=7.7, 4.8 Hz, 1H), 6.96 (dd, J=7.7, 4.6 Hz, 1H), 4.83 (dd, J=11.2, 6.4 Hz, 1H), 4.70-4.60 (m, 1H), 4.60 (A of AB, $J_{AB}$=17.0 Hz, 1H), 4.28 (B of AB, $J_{AB}$=16.9 Hz, 1H), 3.39-3.27 (m, 2H), 3.16 (A of ABX, $J_{AB}$=17.2 Hz, $J_{AX}$=2.7 Hz, 1H), 2.91 (B of ABX, $J_{AB}$=17.3 Hz, $J_{BX}$=6.7 Hz, 1H), 2.89-2.77 (m, 1H), 2.67 (B of AB, $J_{AB}$=16.7 Hz, 1H), 2.52-2.43 (m, 1H), 2.29 (q, J=12.2 Hz, 1H), 2.10-2.01 (m, 1H), 1.78-1.65 (m, 1H). $^{13}$C NMR (400 MHz, CDCl3, ppm) δ: 153.22, 152.41, 148.71, 146.80, 139.15, 138.35, 136.70, 134.24, 133.38, 132.34, 131.50, 129.37, 128.49, 127.78, 126.95, 126.34, 122.10, 121.49, 61.43, 51.74, 50.14, 42.88, 32.45, 30.89, 28.79, 22.58. LC-MS (ESI-API, 254 nm) 75-95% MeOH in H$_2$O (0.1% HCO2H), 3 min, 1.00 mL/min, C18 (Agilent Zorbax XDB-18, 50 mm×4.6 mm, 3.5 μm), m/z=732.4 (M+H), 365.8 (M/2+H), t=2.265 min;

To prove the stereochemistry of all 2,6-naphthyridines, all common intermediates with different side-chains were synthesized, and the $^1$H NMR spectra were obtained and compared with previously recorded data.

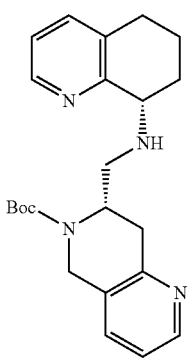

4b

A 20 mL microwave vial equipped with a stir bar was charged with 109 mg of 20 w % of Pd(OH)$_2$ on carbon (0.155 mmol, 0.1 equiv) and 392 mg of ammonium formate (6.22 mmol, 4 equiv) and the vial was sealed and set under Ar. Then 800 mg of the carbamate S,S-S27 (1.55 mmol, 1 equiv) dissolved in 16 mL of dry ethanol (degassed by bubbling Ar for 30 min) was added. After stirring at 45° C. for 12 h, the reaction was not completed and 109 mg of 20 w % of Pd(OH)$_2$ on carbon (0.155 mmol, 0.1 equiv) and 250 mg of ammonium formate (3.96 mmol, 2.6 equiv) were added and the stirring was continued for 18 more hours. Then the reaction mixture was filtered through a celite plug and the celite plug was washed with ethanol. The organics were concentrated in vacuo (rotatory evaporator) and the crude product was purified on silica gel column using 0 to 30% solvent2 (solvent2=30% MeOH in CH$_2$Cl$_2$+3% NH$_4$OH) in CH$_2$Cl$_2$ as eluent affording 314 mg (51%) of the product 4b as a white foam. $^1$H NMR (600 MHz, CDCl$_3$, ppm) δ: 8.39 (dd, J=4.9, 1.6 Hz, 1H), 8.33 (d, J=4.7 Hz, 1H), 7.37 (d, J=7.8 Hz, 1H), 7.31 (d, J=7.7 Hz, 1H), 7.09 (dd, J=7.7, 4.8 Hz, 1H), 7.01 (dd, J=7.7, 4.7 Hz, 1H), 4.97-4.62 (m, 2H), 4.23 (br s, 2H), 3.75 (s, 1H), 3.21 (A of ABX, J$_{AB}$=16.9 Hz, J$_{AX}$=6.4 Hz, 1H), 2.92 (B of ABX, J$_{AB}$=16.9, J$_{BX}$=1.6 Hz, 1H), 2.80-2.63 (m, 4H), 2.04-1.90 (m, 2H), 1.66 (br s, 2H), 1.40 (s, 9H). LC-MS (ESI-API, 254 nm) 75-95% MeOH in H$_2$O (0.1% HCO2H), 3 min, 1.00 mL/min, C18 (Agilent Zorbax XDB-18, 50 mm×4.6 mm, 3.5 μm), m/z=395.0 (M+H), t=0.527 min.

HCO$_2$H), 3 min, 1.00 mL/min, C18 (Agilent Zorbax XDB-18, 50 mm×4.6 mm, 3.5 μm), m/z=596.0 (M+H), 298.6 (M/2+H), t=0.644 min;

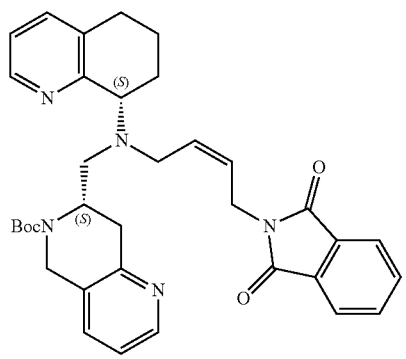

S30

The compound S30 was synthesized from 30 mg of amine 4b and purified according to the procedure for the synthesis of S9 affording 25 mg (55%) of the product. The $^1$H NMR for compound S30 and S,S-isomer-S9 were identical. LC-MS (ESI-API, 254 nm) 75-95% MeOH in H$_2$O (0.1% HCO$_2$H), 3 min, 1.00 mL/min, C18 (Agilent Zorbax XDB-18, 50 mm×4.6 mm, 3.5 μm), m/z=594.0 (M+H), 297.5 (M/2+H), t=0.740 min;

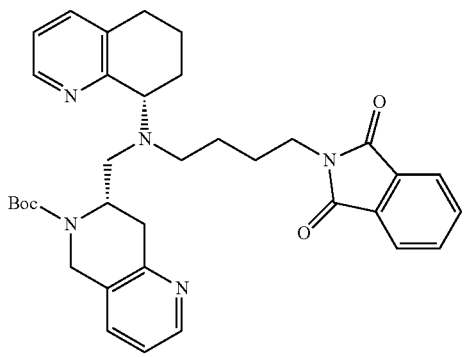 [SMILES: CC(C)(C)OC(=O)N1Cc2cccnc2C[C@H]1CN(CCCCN1C(=O)c2ccccc2C1=O)[C@H]1CCCc2cccnc21]

S31

The compound S29 was synthesized from 30 mg of amine 4b and purified according to the procedure for the synthesis of S8 affording 20 mg (44%) of the product. The $^1$H NMR for compound S29 and S,S-isomer-S8 were identical. LC-MS (ESI-API, 254 nm) 75-95% MeOH in H$_2$O (0.1%

The compound S31 was synthesized from 30 mg of amine 4b and purified according to the procedure for the synthesis of S10 affording 35 mg (78%) of the product. The $^1$H NMR for compound S30 and S,S-isomer-S10 were identical. LC-MS (ESI-API, 254 nm) 75-95% MeOH in H$_2$O (0.1% HCO2H), 3 min, 1.00 mL/min, C18 (Agilent Zorbax XDB-18, 50 mm×4.6 mm, 3.5 μm), m/z=593.8 (M+H), 297.5 (M/2+H), t=0.654 min;

S32

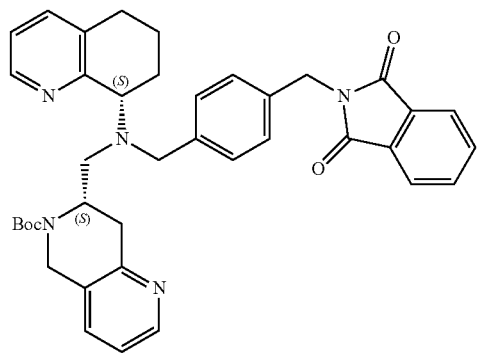

The compound S32 was synthesized from 30 mg of amine 4b and purified according to the procedure for the synthesis of S11 affording 39 mg (81%) of the product. The $^1$H NMR for compound S32 and S,S-isomer-S11 were identical. LC-MS (ESI-API, 254 nm) 75-95% MeOH in H$_2$O (0.1% HCO$_2$H), 3 min, 1.00 mL/min, C18 (Agilent Zorbax XDB-18, 50 mm×4.6 mm, 3.5 μm), m/z=643.8 (M+H), 322.5 (M/2+H), t=0.720 min;

S33

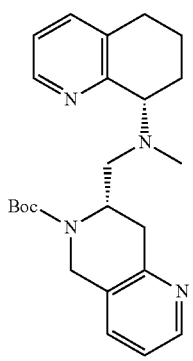

The compound S33 was synthesized from 30 mg of amine 4b and purified according to the procedure for the synthesis of S7 affording 25 mg (81%) of the product. The $^1$H NMR for compound S33 and S,S-isomer-S7 were identical. LC-MS (ESI-API, 254 nm) 75-95% MeOH in H$_2$O (0.1% HCO2H), 3 min, 1.00 mL/min, C18 (Agilent Zorbax XDB-18, 50 mm×4.6 mm, 3.5 μm), m/z=409.0 (M+H), t=0.578 min;

Synthesis of Thiomorpholine Analogs

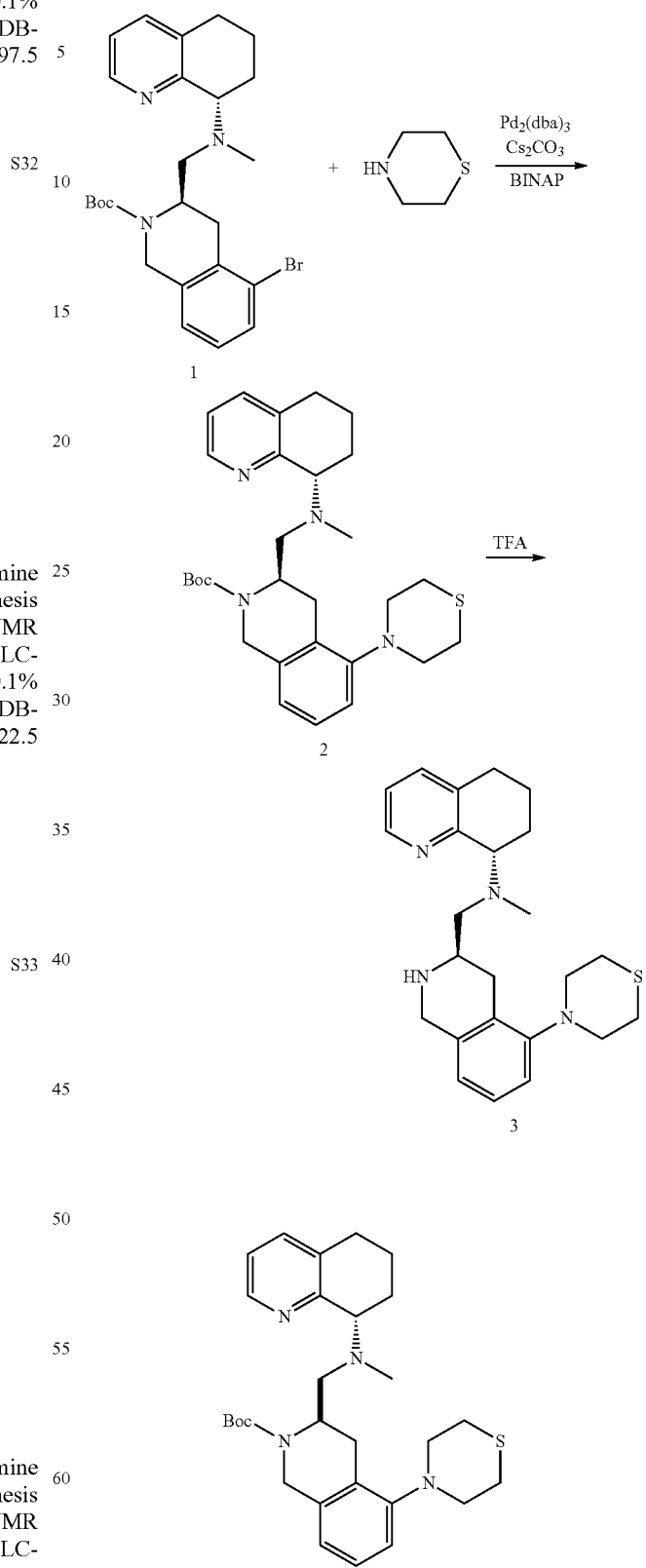

To an oven dried Biotage 5-10 ml Microwave vial was charged with compound 1 (0.268 g, 0.551 mmol), Pd$_2$ (dba)₃ (0.025 g, 0.028 mmol), BINAP (0.051 g, 0.083 mmol), and cesium carbonate (0.251 g, 0.771 mmol). The vial was sealed with the teflon septum and purged with argon for a few minutes. Then added 2.75 ml degassed toluene and thiomorpholine (0.066 ml, 0.661 mmol) via syringe and degassed for another 5 minutes. After heating to 120° C. for 24 hours, the reaction mixture was filtered off over celite and celite was washed with EtOAc. Combined filtrate was evaporated and purified with column chromatography using 0-100% DCM:MeOH:NH₃ (9:1:0.2). ¹H NMR (400 MHz, Chloroform-d) δ 8.26 (s, 1H), 7.36-7.30 (m, 1H), 7.08 (t, J=7.7 Hz, 1H), 7.03-6.95 (m, 1H), 6.84 (dd, J=7.9, 1.2 Hz, 1H), 6.69 (d, J=11.1 Hz, 1H), 4.57 (d, J=16.7 Hz, 1H), 4.43 (s, 1H), 3.83 (d, J=17.1 Hz, 1H), 3.57 (s, 1H), 3.26-3.11 (m, 4H), 3.03 (s, 2H), 2.92-2.71 (m, 4H), 2.65 (m, 4H), 2.26 (s, 3H), 2.04-1.92 (m, 1H), 1.88 (m, 2H), 1.60 (m, 1H), 1.49 (s, 9H).

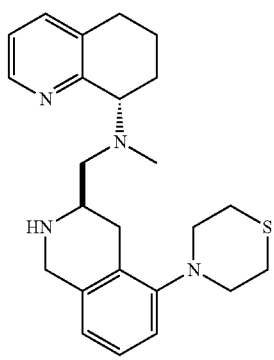

Compound 3 (0.170 g, 0.334 mmol) was dissolved in DCM and added TFA (0.515 ml, 6.68 mmol) and stirred at room temperature overnight. The reaction mixture was cooled with ice bath and basified to pH>12 with 1 M NaOH solution and extracted with DCM 3 times. Combined organic layer was dried over anhydrous sodium sulfate and concentrated. The product was purified with column chromatography using 0-100% DCM:MeOH:NH3 (9:1:0.2). ¹H NMR (500 MHz, Chloroform-d) δ 8.37 (dd, J=4.7, 1.8 Hz, 1H), 7.43 (dd, J=7.5, 1.9 Hz, 1H), 7.18-7.10 (m, 2H), 6.92 (dd, J=7.8, 1.2 Hz, 1H), 6.77 (d, J=7.7 Hz, 1H), 4.69 (s, 2H), 4.44 (d, J=16.1 Hz, 1H), 4.27 (d, J=16.1 Hz, 1H), 4.17 (dd, J=10.6, 6.0 Hz, 1H), 3.44-3.34 (m, 2H), 3.05-2.97 (m, 3H), 2.79-2.69 (m, 8H), 2.15 (s, 3H), 2.10-2.02 (m, 1H), 2.02-1.94 (m, 1H), 1.91-1.79 (m, 1H), 1.76-1.65 (m, 1H), 1.22 (s, 1H); ¹³C NMR (126 MHz, CDCl₃) δ 156.54, 152.35, 146.00, 138.28, 134.74, 129.54, 127.45, 122.35, 121.92, 121.71, 119.09, 74.69, 64.55, 57.98, 54.41, 52.47, 43.53, 35.34, 28.98, 28.43, 25.20, 21.22.

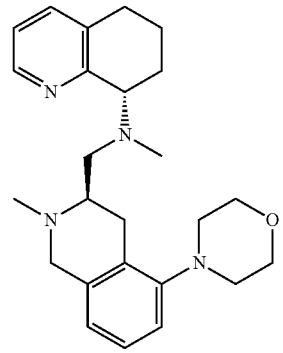

1

A 20 mL vial equipped with a stir bar was charged with 0.030 g of paraformaldehyde (1.00 mmol, 3 equiv), 0.131 g of (S)—N-methyl-N—(((R)-5-morpholino-1,2,3,4-tetrahydroisoquinolin-3-yl)methyl)-5,6,7,8-tetrahydroquinolin-8-amine (0.334 mmol, 1 equiv) and 3.3 mL of DCE. Then 0.212 g of NaBH(OAc)₃ (1.00 mmol, 3 equiv) was added. After stirring for 2 days, the reaction mixture was quenched by addition of sat. NaHCO₃ solution, extracted with CH₂Cl₂ (3×) and dried over Na₂SO₄. The crude product was purified on silica gel column (12 g) using 0 to 50% of solvent 2 (30% MeOH in CH₂Cl₂ and 3% of NH₄OH) in CH₂Cl₂ affording 123 mg (91%) of the product 1 as a yellowish thick oil. ¹H NMR (400 MHz, CDCl₃) δ 8.41 (d, J=4.9 Hz, 1H), 7.30 (d, J=7.8 Hz, 1H), 7.08 (t, J=7.7 Hz, 1H), 7.00 (dd, J=7.7, 4.7 Hz, 1H), 6.85 (d, J=7.9 Hz, 1H), 6.73 (d, J=7.5 Hz, 1H), 3.84 (t, J=4.5 Hz, 4H), 3.80-3.74 (m, 1H), 3.75 (A of AB, JAB=17.5 Hz, 1H), 3.68 (B of AB, JAB=15.8 Hz, 1H), 2.98-2.75 (m, 8H), 2.70-2.58 (m, 2H), 2.48 (dd, J=12.2, 7.5 Hz, 1H), 2.41 (s, 3H), 2.28 (s, 3H), 2.08-1.95 (m, 1H), 1.95-1.87 (m, 2H), 1.68-1.57 (m, 1H). (7% of the other conformer was noticed 8.46 (d, J=4.9 Hz, 0.07H); ¹³C NMR (100 MHz, CDCl₃) δ 157.64, 151.02, 146.49, 136.37, 135.43, 133.68, 129.10, 125.89, 121.57, 121.39, 116.49, 67.30, 64.86, 57.02, 56.35, 55.94, 52.12, 40.72, 39.49, 28.60, 27.33, 25.76, 20.09; HRMS (ESI+) calcd for C25H35N4O ([M+H]⁺): 407.2805. Found: 407.2806, error 0.1 ppm; LC-MS (ESI-API, 254 nm) 75-95% MeOH in H2O (0.1% HCO2H), 3 min, 1.00 mL/min, C18 (Agilent Zorbax XDB-18, 50 mm×4.6 mm, 3.5 μm), m/z=407.2 (M+H), 204.2 (M/2+H), t=0.502 min.

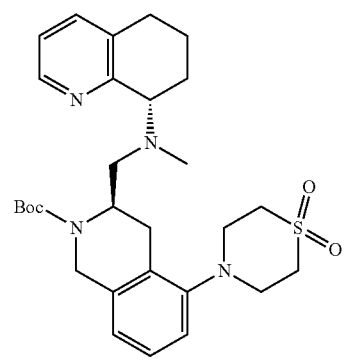

15

A 5 mL μW tube equipped with a stir bar was charged with 250 mg of tert-butyl (R)-5-bromo-3-((methyl((S)-5,6,7,8-tetrahydroquinolin-8-yl)amino)methyl)-3,4-dihydroisoquinoline-2(1H)-carboxylate (0.514 mmol, 1 equiv), 90.0 mg of thiomorpholine 1,1-dioxide (0.668 mmol, 1.3 equiv), 48.0 mg of BINAP (0.077 mmol, 0.15 equiv), 0.251 g of $Cs_2CO_3$ (0.771 mmol, 1.5 equiv), and 24.0 mg of $Pd_2(dba)_3$ (0.026 mmol, 0.05 equiv) and the system was set under Ar atmosphere by flashing through Ar for 1 h. Then 2.57 mL of dioxane (degassed by bubbling through Ar for 1 h) was added. After stirring at 140° C. for 3 h in the μW reactor (normal power), EA was added and the suspension was filtered through celite plug. The crude product was purified on silica gel column using 0-100% EA in hexanes as eluent affording 252 mg (91%) of the product 15. $^1$H NMR (400 MHz, $CDCl_3$) δ 8.28 (s, 1H), 7.35 (d, J=7.6 Hz, 1H), 7.11 (t, J=7.8 Hz, 1H), 7.07-6.99 (m, 1H), 6.91 (d, J=7.6 Hz, 1H), 6.80-6.72 (m, 1H), 4.70 (br s, 0.5H), 4.58 (d, J=17.1 Hz, 1H), 4.50 (br s, 0.5H), 3.89-3.77 (m, 1H), 3.65 (s, 1H), 3.50-3.34 (m, 4H), 3.31-3.15 (m, 5H), 2.87-2.61 (m, 4H), 2.47-2.20 (m, 1H), 2.23 (s, 3H), 2.02-1.80 (m, 3H), 1.66-1.56 (m, 1H), 1.50 (s, 9H); LC-MS (ESI-API, 254 nm) 75-95% MeOH in $H_2O$ (0.1% $HCO_2H$), 3 min, 1.00 mL/min, C18 (Agilent Zorbax XDB-18, 50 mm×4.6 mm, 3.5 μm), m/z=541.2 (M+H), t=0.514 min.

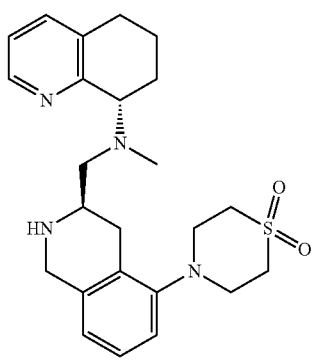

3

A 20 mL vial equipped with a stir bar was charged with 192 mg of the amine 15 (0.355 mmol, 1 equiv) dissolved in 3.6 mL of $CH_2Cl_2$. Then 821 μL of TFA (10.7 mmol, 30 equiv) was added. After stirring at rt for 20 h, the reaction mixture was quenched by addition of 1 N KOH solution, extracted with $CH_2Cl_2$ (3×) and dried over $Na_2SO_4$. The crude material was purified on silica gel column using 0 to 25% Solvent 2 in $CH_2Cl_2$ (solvent 2=70% $CH_2Cl_2$, 30% MeOH, 3% $NH_4OH$) as eluent affording 132 mg (84%) of the product 3 as a yellowish thick oil. $^1$H NMR (400 MHz, $CDCl_3$) δ 8.42 (dd, J=4.7, 1.7 Hz, 1H), 7.32 (d, J=7.6 Hz, 1H), 7.05 (t, J=8.8 Hz, 1H), 7.03 (dd, J=8.7, 3.7 Hz, 1H), 6.86 (dd, J=7.9, 1.1 Hz, 1H), 6.80 (dd, J=7.6, 1.1 Hz, 1H), 4.01 (A of AB, JAB=15.5 Hz, 1H), 3.96-3.89 (m, 1H), 3.89 (B of AB, JAB=15.7 Hz, 1H), 3.41-3.04 (m, 10H), 2.82-2.70 (m, 3H), 2.68-2.60 (m, 1H), 2.50 (dd, J=13.0, 9.8 Hz, 1H), 2.44 (s, 3H), 2.13 (dd, J=17.0, 11.1 Hz, 1H), 2.06-1.85 (m, 3H), 1.72-1.60 (m, 1H); $^{13}$C NMR (100 MHz, $CDCl_3$) δ 157.54, 149.77, 146.64, 137.04, 136.57, 133.72, 129.65, 126.07, 123.07, 121.43, 117.84, 64.18, 59.66, 52.39, 51.27, 50.32, 48.31, 40.56, 29.72, 29.05, 25.26, 21.15; HRMS (ESI+) calcd for $C_{24}H_{33}N_4O_2S$ ([M+H]$^+$): 441.2319. Found: 441.2317, error 0.15 ppm; LC-MS (ESI-API, 254 nm) 75-95% MeOH in H2O (0.1% HCO2H), 3 min, 1.00 mL/min, C18 (Agilent Zorbax XDB-18, 50 mm×4.6 mm, 3.5 μm), m/z=441.2 (M+H), 221.2 (M/2+H), t=0.495 min.

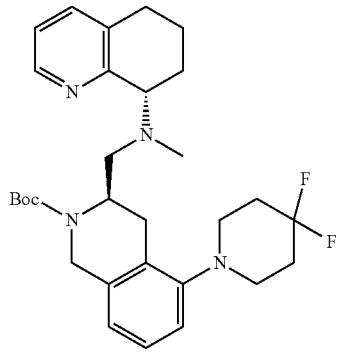

16

A 5 mL μW tube equipped with a stir bar was charged with 250 mg of tert-butyl (R)-5-bromo-3-((methyl((S)-5,6,7,8-tetrahydroquinolin-8-yl)amino)methyl)-3,4-dihydroisoquinoline-2(1H)-carboxylate (0.514 mmol, 1 equiv), 90.0 mg of 4,4-difluoropioeridine (0.668 mmol, 1.3 equiv), 48.0 mg of BINAP (0.077 mmol, 0.15 equiv), 0.251 g of $Cs_2CO_3$ (0.771 mmol, 1.5 equiv), and 24.0 mg of $Pd_2(dba)_3$ (0.026 mmol, 0.05 equiv) and the system was set under Ar atmosphere by flashing through Ar for 1 h. Then 2.57 mL of dioxane (degassed by bubbling through Ar for 1 h) was added. After stirring at 140° C. for 3 h in the μW reactor (normal power), EA was added and the suspension was filtered through celite plug. The crude product was purified on silica gel column using 0-100% EA in hexanes as eluent affording 252 mg (91%) of the product 16. $^1$H NMR (400 MHz, $CDCl_3$) δ 8.25 (s, 1H), 7.33 (d, J=7.7 Hz, 1H), 7.08 (t, J=7.8 Hz, 1H), 7.00 (t, J=6.3 Hz, 1H), 6.86 (dd, J=8.0, 1.1 Hz, 1H), 6.74-6.63 (m, 1H), 4.66 (br s, 0.5H), 4.58 (A of AB, JAB=17.1 Hz, 1H), 4.44 (br s, 0.5H), 3.85 (B of AB, JAB=17.0 Hz, 1H), 3.63-3.54 (m, 1H), 3.24-3.13 (m, 1H), 3.08 (ddd, J=11.8, 7.4, 4.1 Hz, 2H), 2.93-2.77 (m, 3H), 2.72-2.59 (m, 3H), 2.43 (br s, 0.5H), 2.32 (dd, J=13.1, 8.2 Hz, 0.5H), 2.27 (s, 3H), 2.24-1.93 (m, 5H), 1.90-1.83 (m, 2H), 1.64-1.53 (m, 1H), 1.50 (s, 9H); LC-MS (ESI-API, 254 nm) 75-95% MeOH in H2O (0.1% HCO2H), 3 min, 1.00 mL/min, C18 (Agilent Zorbax XDB-18, 50 mm×4.6 mm, 3.5 μm), m/z=527.2 (M+H), t=0.616 min.

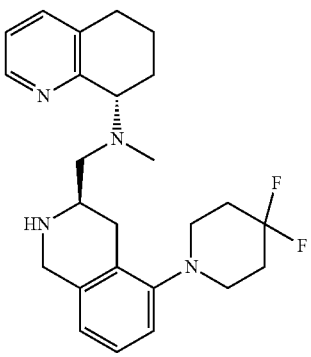

2

A 20 mL vial equipped with a stir bar was charged with 148 mg of the amine 16 (0.281 mmol, 1 equiv) dissolved in 2.8 mL of $CH_2Cl_2$. Then 650 μL of TFA (8.43 mmol, 30 equiv) was added. After stirring at rt for 20 h, the reaction mixture was quenched by addition of 1 N KOH solution, extracted with $CH_2Cl_2$ (3×) and dried over $Na_2SO_4$. The crude material was purified on silica gel column using 0 to 25% Solvent 2 in CH$_2$Cl$_2$ (solvent 2=70% CH$_2$Cl$_2$, 30% MeOH, 3% NH$_4$OH) as eluent affording 92.0 mg (77%) of the product 2 as an orange thick oil. $^1$H NMR (400 MHz, CDCl$_3$) δ 8.46 (dd, J=4.7, 1.7 Hz, 1H), 7.34 (d, J=7.6 Hz, 1H), 7.10-7.03 (m, 2H), 6.86 (dd, J=7.9, 1.1 Hz, 1H), 6.78 (dd, J=7.7, 1.1 Hz, 1H), 4.05 (A of AB, JAB=15.5 Hz, 1H), 3.98-3.92 (m, 1H), 3.92 (B of AB, JAB=15.6 Hz, 1H), 3.12-2.99 (m, 4H), 2.87-2.74 (m, 5H), 2.71-2.63 (m, 1H), 2.51 (dd, J=12.3, 9.7 Hz, 1H), 2.49 (s, 3H), 2.19-1.89 (m, 8H), 1.77-1.63 (m, 1H). $^{13}$C NMR (100 MHz, CDCl$_3$) δ 157.86, 150.68, 146.76, 136.85, 136.62, 133.78, 129.89, 125.95, 122.15, 121.87 (t, J=241.6 Hz), 121.48, 117.05, 64.42, 59.93, 51.43, 48.89 (t, J=5.5 Hz), 48.60, 41.00, 34.76 (t, J=22.6 Hz), 29.92, 29.18, 25.72, 21.25. $^{19}$F NMR (376 MHz, CDCl$_3$) δ −98.69 (br s). HRMS (ESI+) calcd for C25H33N4F4 ([M+H]$^+$): 427.2668. Found: 427.2667, error 0.13 ppm. LC-MS (ESI-API, 254 nm) 75-95% MeOH in H2O (0.1% HCO2H), 3 min, 1.00 mL/min, C18 (Agilent Zorbax XDB-18, 50 mm×4.6 mm, 3.5 μm), m/z=427.2 (M+H), 214.2 (M/2+H), t=0.548 min.

17

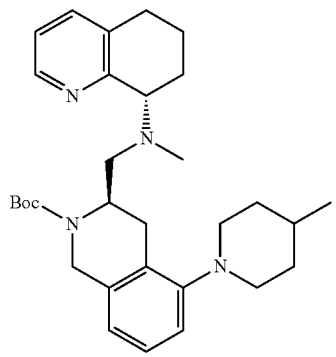

A 5 mL μW tube equipped with a stir bar was charged with 250 mg of tert-butyl (R)-5-bromo-3-((methyl((S)-5,6,7,8-tetrahydroquinolin-8-yl)amino)methyl)-3,4-dihydroisoquinoline-2(1H)-carboxylate (0.514 mmol, 1 equiv), 66.0 mg of 4-methylpiperidine (0.668 mmol, 1.3 equiv), 48.0 mg of BINAP (0.077 mmol, 0.15 equiv), 0.251 g of Cs$_2$CO$_3$ (0.771 mmol, 1.5 equiv), and 24.0 mg of Pd$_2$(dba)$_3$ (0.026 mmol, 0.05 equiv) and the system was set under Ar atmosphere by flashing through Ar for 1 h. Then 2.57 mL of dioxane (degassed by bubbling through Ar for 1 h) was added. After stirring at 140° C. for 3 h in the μW reactor (normal power), EA was added and the suspension was filtered through celite plug. The crude product was purified on silica gel column using 0-30% EA in hexanes as eluent affording 143 mg (55%) of the product 17. $^1$H NMR (400 MHz, CDCl$_3$) δ 8.27 (s, 1H), 7.32 (d, J=8.4 Hz, 1H), 7.06 (t, J=7.8 Hz, 1H), 6.99 (dd, J=7.7, 4.6 Hz, 1H), 6.83 (d, J=8.2 Hz, 1H), 6.66 (d, J=7.6 Hz, 0.6H), 6.61 (d, J=7.6 Hz, 0.4H), 4.64-4.59 (m, 0.4H), 4.55 (A of AB, JAB=16.9 Hz, 1H), 4.43-4.34 (m, 0.6H), 3.90 (B of AB, JAB=16.3 Hz, 1H), 3.60-3.53 (m, 1H), 3.24-3.16 (m, 1H), 3.08 (d, J=10.8 Hz, 1H), 3.01 (d, J=11.4 Hz, 1H), 2.86-2.75 (m, 2H), 2.69-2.57 (m, 3H), 2.50-2.29 (m, 2H), 2.27 (s, 3H), 2.02-1.81 (m, 3H), 1.76 (d, J=12.6 Hz, 1H), 1.69-1.29 (m, 5H), 1.49 (s, 9H), 0.99 (d, J=6.0 Hz, 3H). LC-MS (ESI-API, 254 nm) 75-95% MeOH in H2O (0.1% HCO$_2$H), 3 min, 1.00 mL/min, C18 (Agilent Zorbax XDB-18, 50 mm×4.6 mm, 3.5 μm), m/z=505.2 (M+H), 253.2 (M/2+H), t=0.726 min.

6

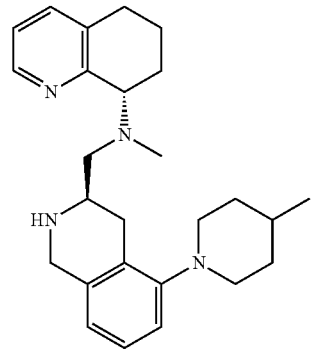

A 20 mL vial equipped with a stir bar was charged with 143 mg of the amine 17 (0.283 mmol, 1 equiv) dissolved in 2.8 mL of CH$_2$Cl$_2$. Then 655 μL of TFA (8.50 mmol, 30 equiv) was added. After stirring at rt for 20 h, the reaction mixture was quenched by addition of 1 N KOH solution, extracted with CH$_2$Cl$_2$ (3×) and dried over Na$_2$SO$_4$. The crude material was purified on silica gel column using 0 to 20% Solvent 2 in CH$_2$Cl$_2$ (solvent 2=70% CH$_2$Cl$_2$, 30% MeOH, 3% NH$_4$OH) as eluent affording 102.0 mg (89%) of the product 6 as a yellowish thick oil. $^1$H NMR (400 MHz, CDCl$_3$) δ 8.46 (dd, J=4.8, 1.7 Hz, 1H), 7.32 (dd, J=7.7, 1.0 Hz, 1H), 7.08-7.02 (m, 2H), 6.83 (dd, J=7.9, 1.1 Hz, 1H), 6.71 (dd, J=7.6, 1.1 Hz, 1H), 4.05 (A of AB, JAB=15.4 Hz, 1H), 3.98-3.91 (m, 1H), 3.90 (B of AB, JAB=15.4 Hz, 1H), 3.29 (br s, 1H), 3.09-3.01 (m, 1H), 3.00-2.91 (m, 1H), 2.85-2.61 (m, 6H), 2.52 (s, 3H), 2.50 (dd, J=12.7, 9.9 Hz, 1H), 2.31 (td, J=11.8, 2.4 Hz, 1H), 2.15 (dd, J=16.3, 10.4 Hz, 1H), 2.09-1.90 (m, 3H), 1.75-1.57 (m, 3H), 1.52-1.24 (m, 3H), 0.96 (d, J=6.3 Hz, 3H). $^{13}$C NMR (100 MHz, CDCl$_3$) δ 158.01, 152.35, 146.71, 136.52, 136.33, 129.82, 125.73, 121.39, 121.05, 116.51, 64.39, 59.83, 53.07, 51.93, 51.52, 48.60, 41.40, 35.02, 34.83, 30.74, 30.01, 29.15, 25.97, 21.97, 21.23. HRMS (ESI+) calcd for C26H37N4 ([M+H]$^+$): 405.3013. Found: 405.3013, error 0.00 ppm. LC-MS (ESI-API, 254 nm) 75-95% MeOH in H2O (0.1% HCO2H), 3 min, 1.00 mL/min, C18 (Agilent Zorbax XDB-18, 50 mm×4.6 mm, 3.5 μm), m/z=405.2 (M+H), 203.2 (M/2+H), t=0.654 min.

18

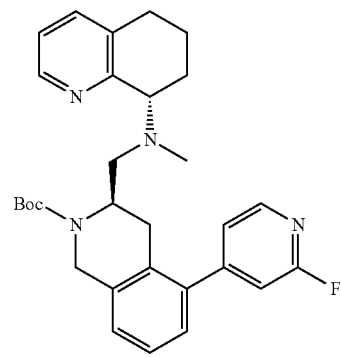

A 50 mL Schlenk tube equipped with a stir bar and cold-finger reflux condenser was charged with 250 mg of tert-butyl (R)-5-bromo-3-((methyl((S)-5,6,7,8-tetrahydroquinolin-8-yl)amino)methyl)-3,4-dihydroisoquinoline-2(1H)-carboxylate (0.514 mmol, 1 equiv), 94.0 mg of (2-fluoropyridin-4-yl)boronic acid (0.668 mmol, 1.3 equiv), 54.0 mg of PPh₃ (0.206 mmol, 0.4 equiv), 1.0 mL of 2 M K₂CO₃ aq. solution (2.06 mmol, 4 equiv) (degassed by bubbling through Ar for 30 min), 24.0 mg of Pd₂(dba)₃ (0.026 mmol, 0.05 equiv) and 5.1 mL of dioxane (degassed by bubbling through Ar for 1 h). After stirring at 100° C. for 12 h, the reaction mixture was quenched by addition of water, extracted with CH₂Cl₂ (3×) and dried over Na₂SO₄. The organics were concentrated and the crude product was purified on silica gel column using 0-100% EA in hexanes as eluent affording 121 mg (47%) of the product 18. ¹H NMR (400 MHz, CDCl₃) δ 8.26 (d, J=5.1 Hz, 1H), 8.18 (dd, J=4.8, 1.7 Hz, 1H), 7.30 (d, J=7.6 Hz, 1H), 7.23 (t, J=7.6 Hz, 1H), 7.19 (dt, J=5.2, 1.7 Hz, 1H), 7.12-7.04 (m, 1H), 7.11 (d, J=7.7 Hz, 1H), 6.98 (dd, J=7.6, 4.6 Hz, 1H), 6.92 (s, 1H), 4.64 (A of AB, JAB=17.0 Hz, 1H), 4.52 (br s, 0.5H), 4.33 (br s, 0.5H), 4.05 (B of AB, JAB=16.9 Hz, 1H), 3.47 (br s, 1H), 2.92 (d, J=4.0 Hz, 2H), 2.76 (dd, J=12.8, 5.5 Hz, 1H), 2.70 (dd, J=9.1, 6.6 Hz, 1H), 2.60 (dt, J=16.8, 5.3 Hz, 1H), 2.42-2.27 (m, 1H), 2.17 (s, 3H), 1.94-1.83 (m, 1H), 1.75-1.46 (m, 3H), 1.50 (s, 9H). LC-MS (ESI-API, 254 nm) 75-95% MeOH in H₂O (0.1% HCO₂H), 3 min, 1.00 mL/min, C18 (Agilent Zorbax XDB-18, 50 mm×4.6 mm, 3.5 μm), m/z=503.2 (M+H), t=0.530 min;

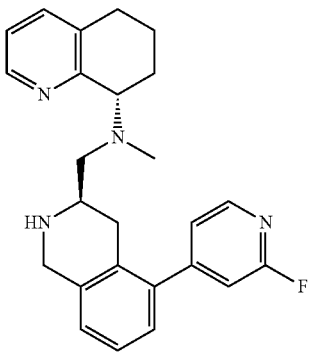

4

A 20 mL vial equipped with a stir bar was charged with 101 mg of the amine 18 (0.201 mmol, 1 equiv) dissolved in 2.0 mL of CH₂Cl₂. Then 464 μL of TFA (6.03 mmol, 30 equiv) was added. After stirring at rt for 20 h, the reaction mixture was quenched by addition of 1 N KOH solution, extracted with CH₂Cl₂ (3×) and dried over Na₂SO₄. The crude material was purified on silica gel column using 0 to 25% Solvent 2 in CH₂Cl₂ (solvent 2=70% CH₂Cl₂, 30% MeOH, 3% NH₄OH) as eluent affording 81.0 mg (100%) of the product 4 as a yellowish thick oil. ¹H NMR (400 MHz, CDCl₃) δ 8.39 (dd, J=4.8, 1.7 Hz, 1H), 8.20 (d, J=5.1 Hz, 1H), 7.31 (d, J=7.7 Hz, 1H), 7.18 (t, J=7.6 Hz, 1H), 7.10-7.06 (m, 2H), 7.03 (dd, J=7.7, 4.7 Hz, 1H), 6.98 (d, J=7.3 Hz, 1H), 6.81 (s, 1H), 4.11 (A of AB, JAB=15.4 Hz, 1H), 3.98 (B of AB, JAB=15.4 Hz, 1H), 3.91 (dd, J=9.2, 5.8 Hz, 1H), 2.99 (br s, 1H), 2.80-2.70 (m, 2H), 2.68-2.58 (m, 2H), 2.45 (s, 3H), 2.39 (dd, J=12.9, 9.6 Hz, 1H), 2.35-2.26 (m, 2H), 2.06-1.81 (m, 3H), 1.73-1.58 (m, 1H). ¹³C NMR (100 MHz, CDCl₃) δ 163.64 (d, J=238.9 Hz), 157.66, 155.11 (d, J=7.8 Hz), 147.18 (d, J=15.3 Hz), 146.79, 138.21 (d, J=3.1 Hz), 136.60, 136.48, 133.77, 131.66, 127.14, 126.67, 125.71, 122.09 (d, J=4.0 Hz), 121.49, 109.75 (d, J=37.1 Hz), 64.40, 59.53, 51.59, 48.83, 41.07, 32.78, 29.16, 25.52, 21.25. ¹⁹F NMR (376 MHz, CDCl₃) δ -69.21. HRMS (ESI+) calcd for C25H28N4F ([M+H]⁺): 403.2293. Found: 403.2294, error 0.14 ppm. LC-MS (ESI-API, 254 nm) 75-95% MeOH in H2O (0.1% HCO2H), 3 min, 1.00 mL/min, C18 (Agilent Zorbax XDB-18, 50 mm×4.6 mm, 3.5 μm), m/z=403.2 (M+H), 203.2 (M/2+H), t=0.517 min.

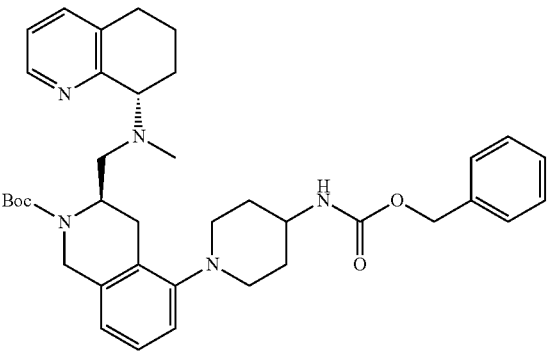

19

A 5 mL μW tube equipped with a stir bar was charged with 350 mg of tert-butyl (R)-5-bromo-3-((methyl((S)-5,6,7,8-tetrahydroquinolin-8-yl)amino)methyl)-3,4-dihydroisoquinoline-2(1H)-carboxylate (0.720 mmol, 1 equiv), 219 mg of benzyl piperidin-4-ylcarbamate (0.935 mmol, 1.3 equiv), 67.0 mg of BINAP (0.108 mmol, 0.15 equiv), 0.352 g of Cs₂CO₃ (1.08 mmol, 1.5 equiv), and 33.0 mg of Pd₂(dba)₃ (0.036 mmol, 0.05 equiv) and the system was set under Ar atmosphere by flashing through Ar for 1 h. Then 3.60 mL of dioxane (degassed by bubbling through Ar for 1 h) was added. After stirring at 140° C. for 3 h in the μW reactor (normal power), EA was added and the suspension was filtered through celite plug. The crude product was purified on silica gel column using 0-100% EA in hexanes as eluent affording 180 mg (39%) of the product 19. LC-MS (ESI-API, 254 nm) 75-95% MeOH in H₂O (0.1% HCO₂H), 3 min, 1.00 mL/min, C18 (Agilent Zorbax XDB-18, 50 mm×4.6 mm, 3.5 μm), m/z=640.2 (M+H), 320.6 (M/2+H), t=0.717 min; (90% purity, there is 10% of the dehalogenated starting material: m/z=408.2 (M+H), t=0.545 min).

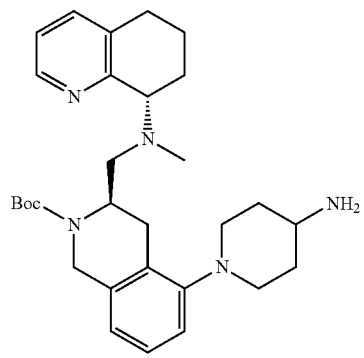

13

A 20 mL vial equipped with a stir bar and septum was set under argon atmosphere and charged with 180 mg of the amine 19 (0.281 mmol, 1 equiv), 30 mg of Pd/C (10 w %) (0.028 mmol, 0.1 equiv) and 1.4 mL of degassed MeOH (Ar was bubbled for 30 min). Then 32 mg of NaBH₄ (0.844 mmol, 3 equiv) was added in several portion. A rapid bubbling of hydrogen was noticed. The system was closed and empty balloon was attached. After stirring at rt for 3 h, the reaction mixture was quenched by addition of sat. NH₄Cl aq. solution, followed by sat. Na₂CO₃ solution, extracted with CH₂Cl₂ (3×) and dried over Na₂SO₄. The crude material was purified on silica gel column using EA, followed by 30% MeOH in CH₂Cl₂ with 3% of NH₄OH as eluents affording 80.0 mg (56%) of the product 13. $^1$H NMR (400 MHz, CDCl₃) δ 8.26 (dd, J=5.0, 1.6 Hz, 1H), 7.32 (d, J=7.6 Hz, 1H), 7.06 (t, J=7.8 Hz, 1H), 6.99 (dd, J=7.6, 4.7 Hz, 1H), 6.83 (dd, J=8.0, 1.1 Hz, 1H), 6.70-6.59 (m, 1H), 4.63 (br s, 0.5H), 4.57 (A of AB, JAB=16.9 Hz, 1H), 4.46-4.36 (m, 0.5H), 3.87 (B of AB, JAB=17.0 Hz, 1H), 3.60-3.52 (m, 1H), 3.24-3.00 (m, 3H), 2.92-2.76 (m, 3H), 2.71-2.57 (m, 3H), 2.49-2.28 (m, 2H), 2.26 (s, 3H), 2.04-1.52 (m, 10H), 1.49 (s, 9H). LC-MS (ESI-API, 254 nm) 75-95% MeOH in H₂O (0.1% HCO₂H), 3 min, 1.00 mL/min, C18 (Agilent Zorbax XDB-18, 50 mm×4.6 mm, 3.5 μm), m/z=528.2 (M+Na), 506.2 (M+H), 253.6 (M/2+H), t=0.489 min,

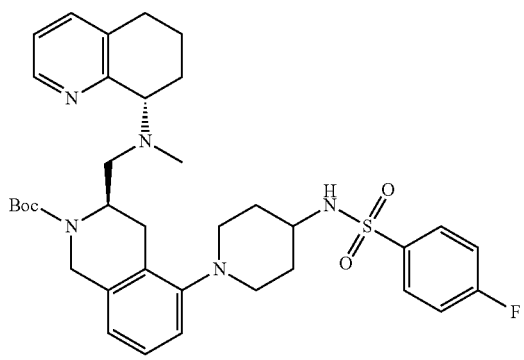

A 20 mL vial equipped with a stir bar was charged with 80.0 mg of the amine 13 (0.158 mmol, 1 equiv), 33.0 μL of TEA (0.237 mmol, 1.5 equiv) and 1.6 mL of CH₂Cl₂. Then 37.0 mg of 4-fluorobenzenesulfonyl chloride (0.190 mmol, 1.2 equiv) dissolved in 0.8 mL of CH₂Cl₂ was added dropwise at 0° C. After stirring at rt for 12 h, the reaction mixture was quenched by addition of sat. NaHCO₃ solution, extracted with CH₂Cl₂ (2×), and dried over Na₂SO₄. The organics were concentrated and the crude product was purified on silica gel column using 0-100% EA in hexanes as eluent affording 84.0 mg (80%) of the product 20. $^1$H NMR (400 MHz, CDCl₃) δ 8.23 (d, J=4.8 Hz, 1H), 7.95-7.90 (m, 2H), 7.32 (d, J=8.2 Hz, 1H), 7.24-7.19 (m, 2H), 7.05 (t, J=7.8 Hz, 1H), 7.02-6.96 (m, 1H), 6.77 (d, J=7.9 Hz, 1H), 6.70-6.59 (m, 1H), 4.63 (br s, 0.5H), 4.55 (A of AB, JAB=17.0 Hz, 1H), 4.46-4.35 (m, 1.5H), 3.88-3.77 (m, 1H), 3.56 (br s, 1H), 3.31 (br s, 1H), 3.14-2.91 (m, 3H), 2.87-2.76 (m, 2H), 2.69-2.57 (m, 4H), 2.46-2.25 (m, 1H), 2.27 (s, 3H), 2.01-1.51 (m, 8H), 1.48 (s, 9H). LC-MS (ESI-API, 254 nm) 75-95% MeOH in H₂O (0.1% HCO₂H), 3 min, 1.00 mL/min, C18 (Agilent Zorbax XDB-18, 50 mm×4.6 mm, 3.5 μm), m/z=664.2 (M+H), 332.6 (M/2+H), t=0.707 min.

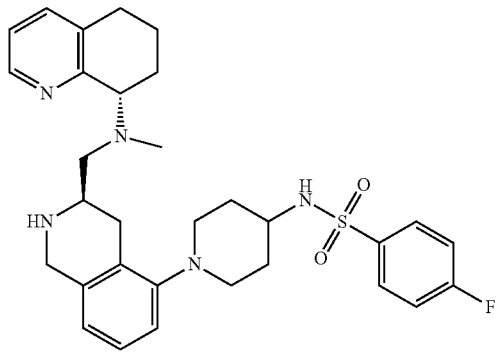

A 20 mL vial equipped with a stir bar was charged with 80.0 mg of the amine 20 (0.121 mmol, 1 equiv) dissolved in 1.2 mL of CH₂Cl₂. Then 279 μL of TFA (3.62 mmol, 30 equiv) was added. After stirring at rt for 20 h, the reaction mixture was quenched by addition of 1 N KOH solution, extracted with CH₂Cl₂ (3×) and dried over Na₂SO₄. The crude material was purified on silica gel column using 0 to 30% Solvent 2 in CH₂Cl₂ (solvent 2=70% CH₂Cl₂, 30% MeOH, 3% NH₄OH) as eluent affording 58.0 mg (85%) of the product 5 as a white solid. $^1$H NMR (400 MHz, CDCl₃) δ 8.46 (d, J=4.2 Hz, 1H), 7.95-7.89 (m, 2H), 7.35 (dd, J=7.8, 1.7 Hz, 1H), 7.23-7.17 (m, 2H), 7.06 (dd, J=7.4, 4.3 Hz, 1H), 7.05 (t, J=7.7 Hz, 1H), 6.78 (d, J=7.8 Hz, 1H), 6.75 (d, J=7.5 Hz, 1H), 4.45 (br s, 1H), 4.03 (A of AB, JAB=15.3 Hz, 1H), 3.97-3.89 (m, 1H), 3.89 (B of AB, JAB=16.7 Hz, 1H), 3.29 (br s, 1H), 2.98 (d, J=12.7 Hz, 1H), 2.93-2.64 (m, 7H), 2.55 (s, 3H), 2.50-2.34 (m, 2H), 2.12-1.46 (m, 10H). $^{13}$C NMR (100 MHz, CDCl₃) δ 164.75 (d, J=254.3 Hz), 157.94, 151.30, 146.75, 137.54 (d, J=3.4 Hz), 136.60 (2 signals), 133.76, 129.93, 129.46 (d, J=9.2 Hz), 125.88, 121.88, 121.46, 116.77, 116.17 (d, J=22.5 Hz), 64.41, 59.75, 51.62, 51.10, 50.88, 50.62, 48.61, 41.19, 33.74, 33.40, 29.83, 29.14, 25.99, 21.20. $^{19}$F NMR (376 MHz, CDCl₃) δ −106.33. HRMS (ESI+) calcd for C31H39N5O2FS ([M+H]$^+$): 564.2803. Found: 564.2804, error 0.07 ppm. LC-MS (ESI-API, 254 nm) 75-95% MeOH in H₂O (0.1% HCO₂H), 3 min, 1.00 mL/min, C18 (Agilent Zorbax XDB-18, 50 mm×4.6 mm, 3.5 μm), m/z=564.2 (M+H), 282.6 (M/2+H), t=0.544 min;

General Reduction Protocol:

Carboxylic acid (1.00 eq) was added to a flame-dried flask with a stir bar. Diluted with THF (0.10 M), and the resulting solution was stirred vigorously under Ar at room temperature. Added borane-dimethyl sulfide complex (3.50 eq) dropwise via syringe pump at a rate of 6.0 mL/hr, and the resulting reaction mixture was allowed to stir overnight at room temperature under Ar. In the morning, the reaction was quenched dropwise with MeOH at room temperature, ensuring that the ensuing gas expulsion did not become too vigorous. 1 M Aqueous sodium hydroxide was added, and the resulting aqueous layer was extracted 3 times with EtOAc. Combined organic layers were washed once with 1 M aqueous sodium hydroxide, washed once with brine, dried over anhydrous sodium sulfate, filtered, and evaporated under reduced pressure.

General Reductive Amination Protocol A:

Dess-Martin periodinane (1.25 eq) was added to a flask with a stir bar. Diluted with DCM (0.25 M), and the resulting slurry was stirred vigorously at room temperature. Added a solution of alcohol (1.00 eq) in DCM (0.20 M) in dropwise fashion, and the resulting reaction mixture was stirred vigorously under Ar at room temperature. After 2.5 hrs, TLC indicated complete conversion of starting material. The reaction mixture was poured over a 1:1 mixture of saturated aqueous NaHCO$_3$ and saturated aqueous Na$_2$S$_2$O$_3$ (55 mL per mmol alcohol). The resulting organic layer was dried over anhydrous sodium sulfate, filtered, and evaporated under reduced pressure. A solution of amine (1.00 eq) in DCM (0.12 M) was added to a flask with a stir bar. Added a solution of aldehyde (1.05 eq) in DCM (0.53 M), and the resulting mixture was stirred under Ar at room temperature for 5 min. After this time, acetic acid (1.00 eq) was added, and the resulting mixture was stirred under Ar at room temperature for 15 min. After this time, sodium triacetoxyborohydride (3.00 eq) was added, and the resulting reaction mixture was allowed to stir overnight at room temperature under Ar. In the morning, the reaction mixture was diluted with DCM and washed once with 1 M aqueous sodium hydroxide. The resulting aqueous layer was extracted 3 times with DCM. Combined organic layers were dried over anhydrous sodium sulfate, filtered, and evaporated under reduced pressure. The crude material was taken up in DCM (40 mL per mmol amine), filtered, and evaporated under reduced pressure.

General Reductive Amination Protocol B:

A solution of amine (1.00 eq) in DCM (0.30 M) was added to a flask with a stir bar. Added a solution of aldehyde (1.00 eq) in DCM (0.30 M), and the resulting mixture was stirred under Ar at room temperature for 10 min. Added titanium isopropoxide (1.50 eq) in dropwise fashion, and the resulting mixture was stirred under Ar at room temperature for 2 hrs. After this time, sodium borohydride (3.00 eq) and MeOH (0.90 M) were added, and the resulting reaction mixture was stirred under Ar at room temperature. After 2 hrs, TLC indicated almost complete conversion of starting material. The reaction was quenched with 1 M aqueous sodium hydroxide. The organic layer was separated, and MeOH from the aqueous layer was evaporated under reduced pressure. The resulting aqueous layer was extracted twice with DCM, and combined organic layers were dried over anhydrous sodium sulfate, filtered, and evaporated under reduced pressure.

General Reductive Amination Protocol C:

A solution of amine (1.00 eq) in DCM (0.12 M) was added to a flask with a stir bar. Added a solution (0.54 M) of ketone (1.00 eq) in DCM, and the resulting reaction mixture was stirred at room temperature under Ar for 5 min. Added acetic acid (0.031 mL, 0.538 mmol, 1.00 eq), and the resulting mixture was stirred at room temperature under Ar for 2.5 hrs. Added sodium triacetoxyborohydride (0.342 g, 1.61 mmol, 3.00 eq), and the resulting reaction mixture was stirred under Ar at room temperature overnight. Once LC-MS indicated disappearance of starting material, the reaction mixture was diluted with DCM and washed once with 1 M aqueous sodium hydroxide. The resulting aqueous layer was extracted three times with DCM. Combined organic layers were dried over anhydrous sodium sulfate, filtered, and evaporated under reduced pressure.

General Deprotection Protocol:

Boc-protected amine (1.00 eq) was added to a flask with a stir bar. Diluted with DCM (0.10 M), and the resulting solution was stirred under Ar and room temperature for 5 min. Added 2,2,2-trifluoroacetic acid (32.0 eq), and the resulting reaction mixture was allowed to stir at room temperature under Ar overnight. Once TLC indicated complete conversion of starting material, the reaction mixture was quenched with 1 M aqueous sodium hydroxide until the pH reached 13-14. The resulting aqueous layer was extracted 3 times with DCM, and combined organic layers were dried over anhydrous sodium sulfate, filtered, and evaporated under reduced pressure.

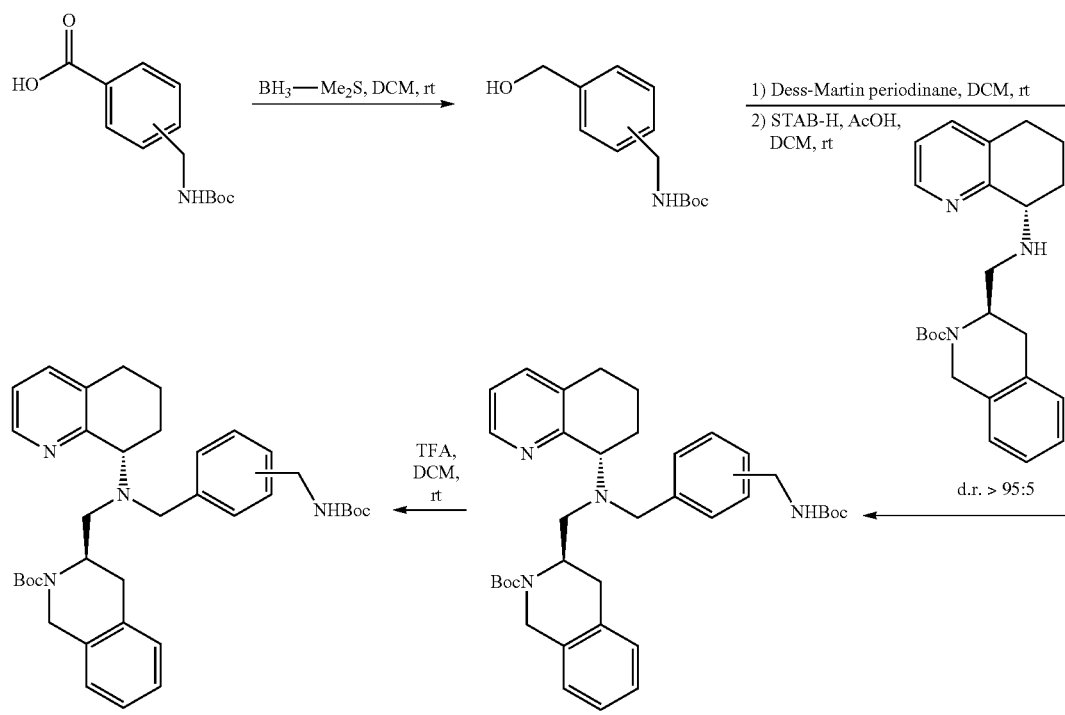

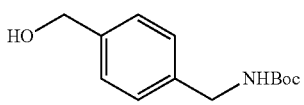

Tert-butyl (4-(hydroxymethyl)benzyl)carbamate

Synthesis was carried out according to the General Reduction Protocol. Purified via column chromatography (CombiFlash, 24 g column, 30 mL/min) eluting with the following gradient to yield a white solid (462 mg, 1.95 mmol, 49% yield): 0-5 min, 5% MeOH in DCM; 5-10 min, 5-10% MeOH in DCM; 10-20 min, 10% MeOH in DCM; 20-25 min, 10-50% MeOH in DCM. $^1$H NMR (500 MHz, CDCl$_3$) δ 7.33 (d, J=8.0 Hz, 2H), 7.26-7.28 (m, 2H), 4.87 (br s, 1H), 4.68 (s, 2H), 4.31 (d, J=5.5 Hz, 2H), 1.87 (br s, 1H), 1.46 (s, 9H). HRMS (NSI) m/z=238.14408 (M+H); Theo. for C$_{13}$H$_{19}$O$_3$N+H=238.14377. LC-MS (ESI-API, 254 nm) 75-95% MeOH in H$_2$O (0.1% HCO$_2$H), 5 min, 1.00 mL/min, C18 (Agilent Zorbax XDB-18, 50 mm×4.6 mm, 3.5 μm), m/z=260.2 (M+Na), 164.2 (M-tBuO), t=1.862 min.

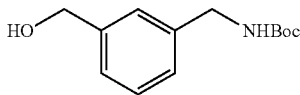

tert-butyl (3-(hydroxymethyl)benzyl)carbamate

Synthesis was carried out according to the General Reduction Protocol. Purified via column chromatography (CombiFlash, 24 g column, 30 mL/min) eluting with the following gradient to yield a slightly yellow oil (700 mg, 2.95 mmol, 74% yield): 0-5 min, 0% MeOH in DCM; 5-10 min, 0-5% MeOH in DCM; 10-15 min, 5% MeOH in DCM; 15-20 min, 5-10% MeOH in DCM; 20-30 min, 10% MeOH in DCM; 30-35 min, 10-50% MeOH in DCM. $^1$H NMR (500 MHz, CDCl$_3$) δ 7.32 (app t, J=7.5 Hz, 1H), 7.28 (m, 1H), 7.25-7.27 (m, 1H), 7.21 (d, J=7.5 Hz, 1H), 4.92 (br s, 1H), 4.67 (s, 2H), 4.31 (d, J=6.0 Hz, 2H), 2.11 (br s, 1H), 1.46 (s, 9H). HRMS (NSI) m/z=238.14399 (M+H); Theo. for C$_{13}$H$_{19}$O$_3$N+H=238.14377. LC-MS (ESI-API, 254 nm) 75-95% MeOH in H$_2$O (0.1% HCO$_2$H), 5 min, 1.00 mL/min, C18 (Agilent Zorbax XDB-18, 50 mm×4.6 mm, 3.5 μm), m/z=260.2 (M+Na), 196.2 (M-tBuO+MeOH), 164.2 (M-tBuO), 138.2 (M+H-Boc), t=1.362 min.

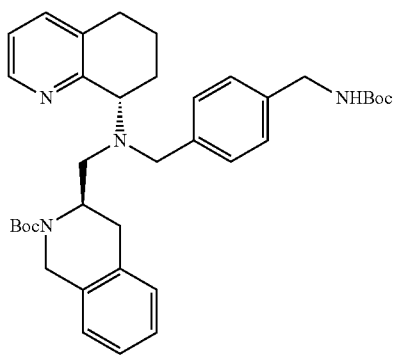 [SMILES: CC(C)(C)OC(=O)NCc1ccc(CN(C[C@H]2Cc3ccccc3CN2C(=O)OC(C)(C)C)[C@H]2CCCc3cccnc32)cc1]

tert-butyl (R)-3-(((4-(((tert-butoxycarbonyl)amino)methyl)benzyl)((S)-5,6,7,8-tetrahydroquinolin-8-yl)amino)methyl)-3,4-dihydroisoquinoline-2(1H)-carboxylate Synthesis was carried out according to General Reductive Amination Protocol A. Purified via column chromatography (CombiFlash, 24 g column, 30 mL/min) eluting with 40:1 DCM/MeOH to yield a white foam (275 mg, 0.449 mmol, 51% yield). $^1$H NMR (500 MHz, CDCl$_3$) δ 8.44 (d, J=12.5 Hz, 1H), 7.24-7.32 (m, 3H), 7.16 (br s, 2H), 7.06 (m, 2H), 6.83-7.00 (m, 3H), 4.65-4.80 (m, 2H), 4.44-4.51 (m, 1H), 4.29 (s, 2H), 3.86-4.09 (m, 2H), 3.55-3.71 (m, 2H), 2.85-3.05 (m, 2H), 2.51-2.69 (m, 4H), 2.10-2.22 (m, 1H), 1.95 (br s, 1H), 1.66-1.82 (m, 2H), 1.45-1.53 (m, 18H). HRMS (NSI) m/z=613.37490 (M+H); Theo. for C$_{37}$H$_{48}$O$_4$N$_4$+H=613.37483. LC-MS (ESI-API, 254 nm) 75-95% MeOH in H$_2$O (0.1% HCO$_2$H), 5 min, 1.00 mL/min, C18 (Agilent Zorbax XDB-18, 50 mm×4.6 mm, 3.5 μm), m/z=613.3 (M+H), t=4.666 min; 50-95% MeOH in H$_2$O (0.1% HCO$_2$H), 8 min, 1.00 mL/min, C18 (Agilent Zorbax XDB-18, 50 mm×4.6 mm, 3.5 μm), m/z=613.2 (M+H), t=6.799 min.

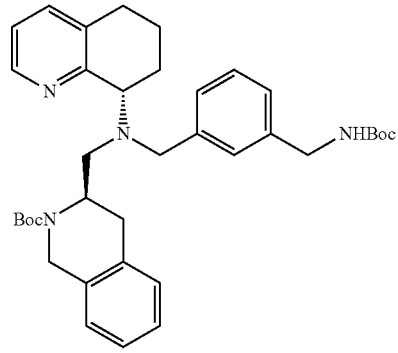 [SMILES: CC(C)(C)OC(=O)NCc1cccc(CN(C[C@H]2Cc3ccccc3CN2C(=O)OC(C)(C)C)[C@H]2CCCc3cccnc32)c1]

tert-butyl (R)-3-(((3-(((tert-butoxycarbonyl)amino)methyl)benzyl)((S)-5,6,7,8-tetrahydroquinolin-8-yl)amino)methyl)-3,4-dihydroisoquinoline-2(1H)-carboxylate Synthesis was carried out according to General Reductive Amination Protocol A. Purified via column chromatography (CombiFlash, 24 g column, 30 mL/min) eluting with the following gradient to yield a white foam (298 mg, 0.486 mmol, 55% yield): 0-3 min, 0% MeOH in DCM; 3-15 min, 0-5% MeOH in DCM; 15-20 min, 5% MeOH in DCM; 20-25 min, 5-25% MeOH in DCM. $^1$H NMR (600 MHz, CDCl$_3$) δ 8.45 (d, J=9.0 Hz, 1H), 7.25-7.29 (m, 2H), 7.17-7.24 (m, 2H), 7.14 (d, J=6.0 Hz, 1H), 7.04-7.09 (m, 2H), 6.84-7.01 (m, 3H), 5.34 (br s, 0.5H), 4.96 (br s, 0.5H), 4.62 (d, J=16.8 Hz, 1H), 4.49 (d, J=16.8 Hz, 1H), 4.24-4.35

(m, 2H), 3.99-4.03 (m, 1H), 3.55-3.78 (m, 3H), 2.88-3.00 (m, 3H), 2.60-2.71 (m, 3H), 2.21 (br s, 1H), 1.97 (br s, 1H), 1.79-1.83 (m, 2H), 1.64-1.71 (m, 1H), 1.47-1.52 (m, 18H). HRMS (NSI) m/z=613.37482 (M+H); Theo. for $C_{37}H_{48}O_4N_4$+H=613.37483. LC-MS (ESI-API, 254 nm) 75-95% MeOH in $H_2O$ (0.1% $HCO_2H$), 8 min, 1.00 mL/min, C18 (Agilent Zorbax XDB-18, 50 mm×4.6 mm, 3.5 μm), m/z=613.3 (M+H), t=5.047 min; 50-95% MeOH in $H_2O$ (0.1% $HCO_2H$), 8 min, 1.00 mL/min, C18 (Agilent Zorbax XDB-18, 50 mm×4.6 mm, 3.5 μm), m/z=613.2 (M+H), t=4.848 min.

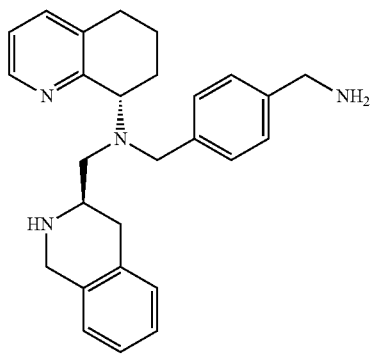 [SMILES: NCc1ccc(CN(C[C@H]2Cc3ccccc3CN2)[C@H]2CCCc3cccnc32)cc1]

EMU093: (S)—N-(4-(aminomethyl)benzyl)-N—(((R)-1,2,3,4-tetrahydroisoquinolin-3-yl)methyl)-5,6,7,8-tetrahydroquinolin-8-amine Synthesis was carried out according to the General Deprotection Protocol. Purified via column chromatography (CombiFlash, 12 g column, 25 mL/min) eluting with the following gradient to yield a clear oil (82 mg, 0.199 mmol, 49% yield): 0-3 min, 0% 100:10:1 DCM/MeOH/$NH_4OH$ in DCM; 3-15 min, 0-100% 100:10:1 DCM/MeOH/$NH_4OH$ in DCM; 15-25 min, 100% 100:10:1 DCM/MeOH/$NH_4OH$. $^1$H NMR (500 MHz, $CDCl_3$) δ 8.51 (dd, J=1.5 Hz, J=4.5 Hz, 1H), 7.43 (d, J=8.0 Hz, 2H), 7.34 (dt, J=0.9 Hz, J=7.8 Hz, 1H), 7.26 (d, J=8.0 Hz, 2H), 7.03-7.07 (m, 3H), 6.96-7.02 (m, 2H), 4.37 (d, J=14.0 Hz, 1H), 4.11 (dd, J=6.5 Hz, J=10.0 Hz, 1H), 3.97 (d, J=15.0 Hz, 1H), 3.90 (d, J=14.5 Hz, 1H), 3.84 (s, 2H), 3.68 (d, J=15.0 Hz, 1H), 2.91 (dd, J=2.8 Hz, J=13.3 Hz, 1H), 2.74-2.80 (m, 1H), 2.64-2.70 (m, 2H), 2.55 (dd, J=3.5 Hz, J=16.0 Hz, 1H), 2.36-2.46 (m, 3H), 2.11-2.16 (m, 1H), 1.91-2.00 (m, 3H), 1.62-1.88 (m, 2H). $^{13}$C NMR (125 MHz, $CDCl_3$) δ 158.9, 146.9, 141.8, 140.5, 136.5, 135.7, 134.7, 134.2, 129.1, 128.6 (2C), 127.1 (2C), 126.5, 125.9, 125.5, 121.5, 62.1, 59.2, 58.0, 52.1, 48.6, 46.4, 33.8, 29.6, 29.5, 22.2. HRMS (NSI) m/z=413.26930 (M+H); Theo. for $C_{27}H_{32}N_4$+H=413.26997. LC-MS (ESI-API, 254 nm) 50-95% MeOH in $H_2O$ (0.1% $HCO_2H$), 8 min, 1.00 mL/min, C18 (Agilent Zorbax XDB-18, 50 mm×4.6 mm, 3.5 μm), m/z=413.3 (M+H), 207.2 (M/2+H), t=0.844 min; 10-95% MeOH in $H_2O$ (0.1% $HCO_2H$), 10 min, 1.00 mL/min, C18 (Agilent Zorbax XDB-18, 50 mm×4.6 mm, 3.5 μm), m/z=413.3 (M+H), 207.2 (M/2+H), t=6.354 min.

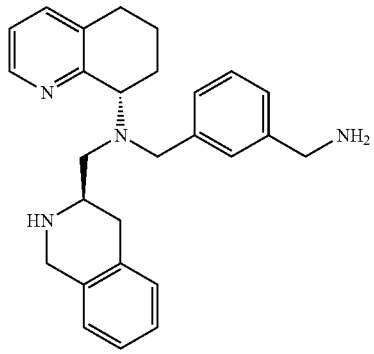 [SMILES: NCc1cccc(CN(C[C@H]2Cc3ccccc3CN2)[C@H]2CCCc3cccnc32)c1]

EMU094: (S)—N-(3-(aminomethyl)benzyl)-N—(((R)-1,2,3,4-tetrahydroisoquinolin-3-yl)methyl)-5,6,7,8-tetrahydroquinolin-8-amine Synthesis was carried out according to the General Deprotection Protocol. Purified via column chromatography (CombiFlash, 12 g column, 25 mL/min) eluting with the following gradient to yield a white foam (121 mg, 0.293 mmol, 65% yield): 0-3 min, 0% 100:10:1 DCM/MeOH/$NH_4OH$ in DCM; 3-15 min, 0-100% 100:10:1 DCM/MeOH/$NH_4OH$ in DCM; 15-25 min, 100% 100:10:1 DCM/MeOH/$NH_4OH$. $^1$H NMR (500 MHz, $CDCl_3$) δ 8.47-8.49 (m, 1H), 7.23-7.39 (m, 4H), 7.14 (d, J=7.5 Hz, 1H), 7.01-7.05 (m, 3H), 6.93-6.98 (m, 2H), 4.34-4.43 (m, 1H), 4.08 (dd, J=6.5 Hz, J=10.5 Hz, 1H), 3.94 (d, J=15.0 Hz, 1H), 3.86 (d, J=14.5 Hz, 1H), 3.84 (s, 2H), 3.62-3.68 (m, 1H), 2.89 (m, 1H), 2.71-2.77 (m, 1H), 2.60-2.65 (m, 2H), 2.53 (dd, J=3.5 Hz, J=16.0 Hz, 1H), 2.32-2.44 (m, 2H), 2.09-2.15 (m, 2H), 1.89-1.97 (m, 3H), 1.59-1.68 (m, 2H). $^{13}$C NMR (125 MHz, $CDCl_3$) δ 158.9, 146.9, 143.3, 142.4, 136.5, 135.8, 134.7, 134.2, 129.1, 128.5, 127.2, 126.9, 126.5, 125.9, 125.5, 125.5, 121.5, 62.3, 59.5, 58.2, 52.1, 48.7, 46.7, 33.9, 29.5, 29.5, 22.2. HRMS (NSI) m/z=413.26977 (M+H); Theo. for $C_{27}H_{32}N_4$+H=413.26997. LC-MS (ESI-API, 254 nm) 50-95% MeOH in $H_2O$ (0.1% $HCO_2H$), 8 min, 1.00 mL/min, C18 (Agilent Zorbax XDB-18, 50 mm×4.6 mm, 3.5 μm), m/z=413.2 (M+H), 207.2 (M/2+H), t=0.885 min; 10-95% MeOH in $H_2O$ (0.1% $HCO_2H$), 10 min, 1.00 mL/min, C18 (Agilent Zorbax XDB-18, 50 mm×4.6 mm, 3.5 μm), m/z=413.2 (M+H), 207.2 (M/2+H), t=6.694 min.

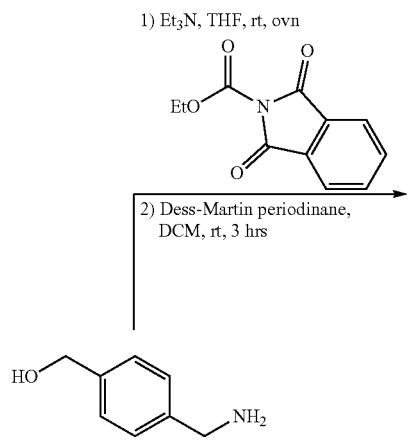
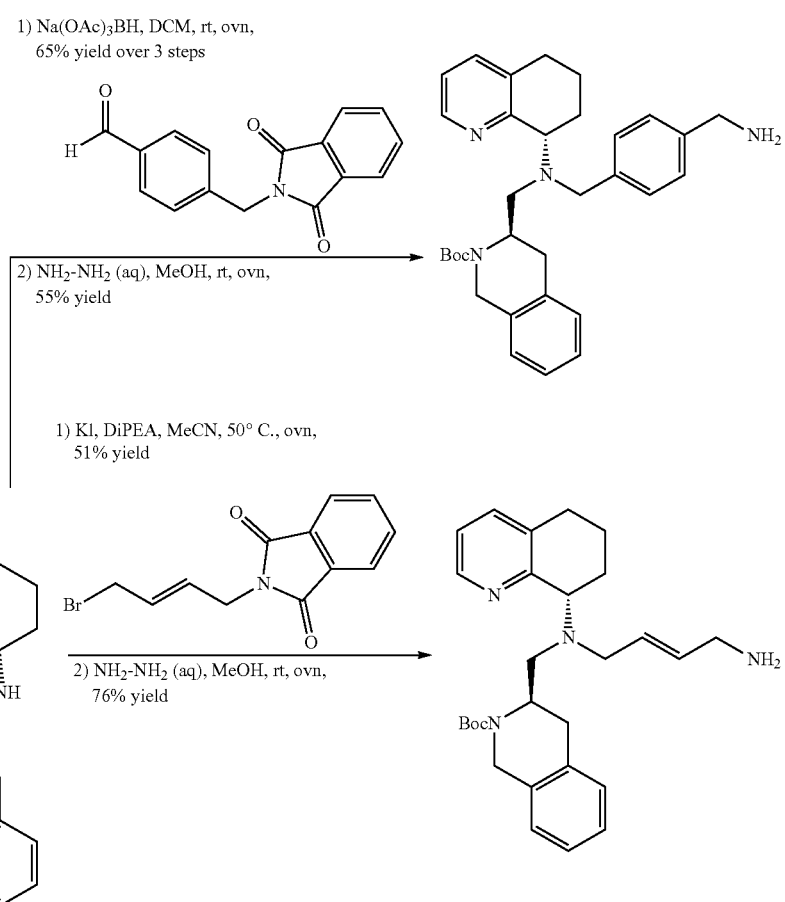
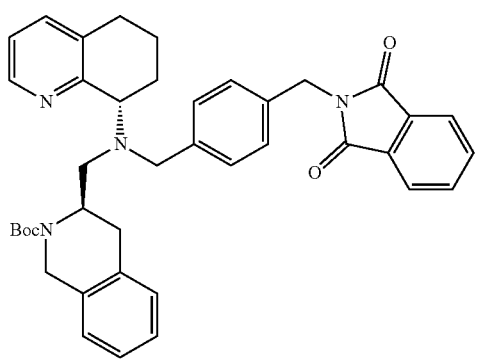 [SMILES: CC(C)(C)OC(=O)N1Cc2ccccc2C[C@@H]1CN(Cc1ccc(CN2C(=O)c3ccccc3C2=O)cc1)[C@H]1CCCc2cccnc21]

Tert-butyl (R)-3-(((4-((1,3-dioxoisoindolin-2-yl)methyl)benzyl)((S)-5,6,7,8-tetrahydroquinolin-8-yl)amino)methyl)-3,4-dihydroisoquinoline-2(1H)-carboxylate (4-(Aminomethyl)phenyl)methanol (5.00 g, 36.4 mmol, 1.00 eq) was added to a 500 mL flask with a stir bar. Diluted with THF (121 mL), added triethylamine (5.08 mL, 36.4 mmol, 1.00 eq) and ethyl 1,3-dioxoisoindoline-2-carboxylate (7.99 g, 36.4 mmol, 1.00 eq), and the resulting reaction mixture was stirred vigorously at room temperature under Ar overnight. After 17 hrs, TLC indicated complete conversion of starting material to one major spot. Solvent was evaporated under reduced pressure to yield a yellow paste, which was carried forward without further purification. Dess-Martin periodinane (17.0 g, 40.1 mmol, 1.10 eq) was added to a 500 mL flask with a stir bar. The white solid was diluted with DCM (121 mL), and the resulting slurry was stirred vigorously at room temperature. Added a solution of 2-(4-(hydroxymethyl)benzyl)isoindoline-1,3-dione (9.74 g, 36.4 mmol, 1.00 eq) in DCM (121 mL) in dropwise fashion via addition funnel, and the resulting reaction mixture was stirred vigorously at room temperature under Ar. After 3 hrs, TLC indicated complete consumption of starting material. The reaction mixture was poured over 750 mL of a 1:1 mixture of saturated aqueous sodium bicarbonate and saturated aqueous sodium thiosulfate. The resulting organic layer was washed once with 150 mL of a 1:1 mixture of saturated aqueous sodium bicarbonate and saturated aqueous sodium thiosulfate, washed once with brine, dried over anhydrous sodium sulfate, filtered, and evaporated under reduced pressure to yield an orange oil. Half of the crude material was immediately carried forward without further purification. $^1$H NMR (400 MHz, CDCl$_3$) δ 9.99 (s, 1H), 7.84-7.89 (m, 4H), 7.71-7.76 (m, 2H), 7.58 (d, J=8.0 Hz, 2H), 4.93 (s, 2H). Sodium triacetoxyborohydride (11.1 g, 52.1 mmol, 3.00 eq) was added to a 500 mL flask with a stir bar. Diluted with DCM (87.0 mL), and the resulting slurry was stirred vigorously at room temperature under Ar. Added a solution of (R)-tert-butyl 3-((((S)-5,6,7,8-tetrahydroquinolin-8-yl)amino)methyl)-3,4-dihydroisoquinoline-2(1H)-carboxylate (6.84 g, 17.4 mmol, 1.00 eq) in DCM (43.4 mL), followed by a solution of 4-((1,3-dioxoisoindolin-2-yl)methyl)benzaldehyde (4.84 g, 18.3 mmol, 1.05 eq) in DCM (43.4 mL), and the resulting reaction mixture was stirred vigorously at room temperature under Ar overnight. After 15 hrs, TLC indicated complete consumption of starting material. The reaction mixture was diluted with DCM and washed three times with 1 M aqueous sodium hydroxide. The resulting aqueous layer was extracted twice with DCM. Combined organic layers were washed once with brine, dried over anhydrous sodium sulfate, filtered, and evaporated under reduced pressure to yield a yellow foam (11.0 g). The crude material was purified via column chromatography (CombiFlash, 120 g column, 75 mL/min) eluting with the following gradient to yield a white foam (7.30 g, 11.4 mmol, 65% yield): 0-3 min: 0% MeOH in DCM; 3-8 min: 0-1% MeOH in DCM; 8-13 min: 1% MeOH in DCM; 13-23 min: 1-2% MeOH in DCM; 23-30 min: 2% MeOH in DCM; 30-40 min: 2-20% MeOH in DCM. $^1$H NMR (600 MHz, CDCl$_3$) δ 8.40 (d, J=14.4 Hz, 1H), 7.85-7.87 (m, 2H), 7.72 (dd, J=3.0 Hz, J=5.4 Hz, 2H), 7.29-7.30 (m, 3H), 7.19-7.26 (m, 2H), 7.03 (app t, J=6.6 Hz, 1.5H), 6.93-6.97 (m, 3H), 6.74 (d, J=6.6 Hz, 0.5H), 4.83-4.88 (m, 2H), 4.61-4.76 (m, 1H), 4.36-4.39 (m, 1H), 4.01-4.10 (m, 1H), 3.85-3.88 (m, 1H), 3.60 (app t, J=16.2 Hz, 1H), 3.50 (d, J=14.4 Hz, 0.5H), 3.36 (d, J=17.4 Hz, 0.5H), 2.89-3.09 (m, 2H), 2.80 (d, J=16.2 Hz, 0.5H), 2.62-2.66 (m, 3H), 2.48 (dd, J=9.6 Hz, J=12.0 Hz, 0.5H), 2.25-2.27 (m, 0.5H), 2.08 (m, 0.5H), 1.93-1.95 (m, 1H), 1.75 (dd, J=11.7 Hz, J=23.1 Hz, 1H), 1.59-1.69 (m, 1H), 1.48 (s, 4.5H), 1.42 (s, 4.5H). HRMS (NSI) m/z=643.32782 (M+H); Theo. for C$_{40}$H$_{42}$N$_4$O$_4$+H=643.32788. LC-MS (ESI-API, 254 nm) 75-95% MeOH in H$_2$O (0.1% HCO$_2$H), 5 min, 1.00 mL/min, C18 (Agilent Zorbax XDB-18, 50 mm×4.6 mm, 3.5 μm), m/z=643.2 (M+H), t=1.137 min; 50-95% MeOH in H$_2$O (0.1% HCO$_2$H), 8 min, 1.00 mL/min, C18 (Agilent Zorbax XDB-18, 50 mm×4.6 mm, 3.5 μm), m/z=643.2 (M+H), t=3.216 min.

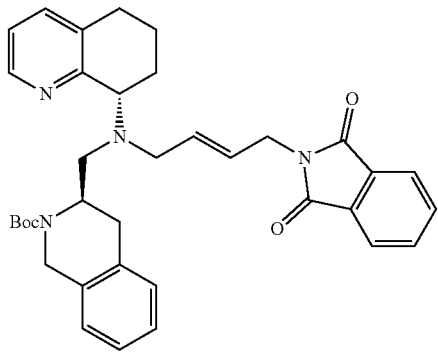 [SMILES: CC(C)(C)OC(=O)N1Cc2ccccc2C[C@@H]1CN(C/C=C/CN1C(=O)c2ccccc2C1=O)[C@H]1CCCc2cccnc21]

Tert-butyl (R)-3-((((E)-4-(1,3-dioxoisoindolin-2-yl)but-2-en-1-yl)((S)-5,6,7,8-tetrahydroquinolin-8-yl)amino)methyl)-3,4-dihydroisoquinoline-2(1H)-carboxylate (R)-tert-Butyl 3-((((S)-5,6,7,8-tetrahydroquinolin-8-yl)amino)methyl)-3,4-dihydroisoquinoline-2(1H)-carboxylate (4.96 g, 12.6 mmol, 1.00 eq) was added to a 250 mL flask equipped with a stir bar and a reflux condenser. Diluted with acetonitrile (126 mL), and the resulting solution was stirred vigorously at room temperature under Ar. Added (E)-2-(4-bromobut-2-en-1-yl)isoindoline-1,3-dione (4.24 g, 15.1 mmol, 1.20 eq), potassium iodide (0.209 g, 1.26 mmol, 0.100 eq), and diisopropylethylamine (4.39 mL, 25.2 mmol, 2.00 eq), warmed to 50° C., and the resulting reaction mixture was stirred under Ar overnight. After 19 hrs, TLC indicated complete conversion of starting material to one major spot. The reaction mixture was washed once with brine, and the resulting aqueous layer was extracted 3 times with DCM. Combined organic layers were washed once with brine, dried over anhydrous sodium sulfate, filtered, and evaporated under reduced pressure to yield a brown oil. Purified via column chromatography (CombiFlash, 120 g column, 75 mL/min) eluting with the following gradient to yield a yellow foam (3.78 g, 6.38 mmol, 51% yield): 0-3 min: 0% 100:10:1 DCM/MeOH/NH$_4$OH in DCM; 3-18 min: 0-100% 100:10:1 DCM/MeOH/NH$_4$OH in DCM; 18-30 min: 100% 100:10:1 DCM/MeOH/NH$_4$OH in DCM. $^1$H NMR (600 MHz, CDCl$_3$) δ 8.34 (br s, 1H), 7.83-7.88 (m, 2H), 7.71-7.78 (m, 2H), 7.19 (d, J=7.2 Hz, 1H), 7.07-7.08 (m, 2H), 6.98-7.03 (m, 2H), 6.92 (dd, J=4.8 Hz, J=7.8 Hz, 1H), 5.75-5.76 (m, 1H), 5.57 (dt, J=6.0 Hz, J=15.6 Hz, 1H), 4.61-4.67 (m, 1.5H), 4.40 (br s, 0.5H), 4.18 (d, J=6.0 Hz, 2H), 4.06-4.10 (m, 1H), 3.91 (m, 1H), 3.33-3.40 (m, 1H), 3.14-3.15 (m, 1H), 2.89-3.00 (m, 2H), 2.60-2.67 (m, 2H), 2.44-2.57 (m, 2H), 1.91-1.98 (m, 2H), 1.57-1.71 (m, 2H), 1.47 (s, 9H). LC-MS (ESI-API, 254 nm) 75-95% MeOH in H$_2$O (0.1% HCO$_2$H), 5 min, 1.00 mL/min, C18 (Agilent Zorbax XDB-18, 50 mm×4.6 mm, 3.5 μm), m/z=593.2 (M+H), t=0.709 min; 50-95% MeOH in H$_2$O (0.1% HCO$_2$H), 8 min, 1.00 mL/min, C18 (Agilent Zorbax XDB-18, 50 mm×4.6 mm, 3.5 μm), m/z=593.2 (M+H), t=2.762 min.

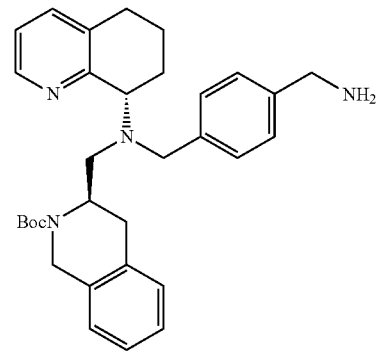 [SMILES: CC(C)(C)OC(=O)N1Cc2ccccc2C[C@@H]1CN(Cc1ccc(CN)cc1)[C@H]1CCCc2cccnc21]

Tert-butyl (R)-3-(((4-(aminomethyl)benzyl)((S)-5,6,7,8-tetrahydroquinolin-8-yl)amino)methyl)-3,4-dihydroisoquinoline-2(1H)-carboxylate (R)-tert-Butyl 3-(((4-((1,3-dioxoisoindolin-2-yl)methyl)benzyl)((S)-5,6,7,8-tetrahydroquinolin-8-yl)amino)methyl)-3,4-dihydroisoquinoline-2(1H)-carboxylate (0.769 g, 1.20 mmol, 1.00 eq) was added to a 50 mL flask with a stir bar. Diluted with MeOH (12.0 mL), added a small volume of DCM to coerce all of the starting material into solution, and the resulting solution was stirred vigorously at room temperature under Ar. Added a solution of hydrazine (1.29 mL, 9.57 mmol, 8.00 eq) in water (24% by wt.) in dropwise fashion via syringe pump at a rate of 4 mL/hr, and the resulting reaction mixture was stirred vigorously at room temperature under Ar overnight. After 17 hrs, TLC indicated almost complete conversion of starting material to one major product spot. The reaction mixture was partitioned between DCM and 1 M aqueous sodium hydroxide. The resulting aqueous layer was extracted 3 times with DCM, and combined organic layers were dried over anhydrous sodium sulfate, filtered, and evaporated under reduced pressure to yield a yellow foam (617 mg). The crude material was purified via column chromatography (CombiFlash, 24 g column, 30 mL/min) eluting with the following gradient to yield a white foam (474 mg, 0.925 mmol, 77% yield): 0-3 min: 0% 100:10:1 DCM/MeOH/NH$_4$OH in DCM; 3-18 min: 0-100% 100:10:1 DCM/MeOH/NH$_4$OH in DCM; 18-30 min: 100% 100:10:1 DCM/MeOH/NH$_4$OH. $^1$H NMR (500 MHz, CDCl$_3$) δ 8.43 (d, J=10.0 Hz, 1H), 7.29-7.34 (m, 2H), 7.25 (d, J=7.5 Hz, 1H), 7.19-7.20 (m, 2H), 7.04-7.09 (m, 2H), 6.82-7.00 (m, 3H), 4.65-4.78 (m, 1H), 4.45-4.52 (m, 1H), 3.89-4.10 (m, 2H), 3.85 (s, 2H), 3.57-3.81 (m, 2H), 2.86-3.05 (m, 2H), 2.52-2.75 (m, 3H), 2.10-2.24 (m, 1H), 1.94-1.95 (m, 1H), 1.79 (app p, J=11.0 Hz, 1H), 1.42-1.66 (m, 12H). HRMS (NSI) m/z=513.32201 (M+H); Theo. for C$_{32}$H$_{40}$N$_4$O$_2$+H=513.32240. LC-MS (ESI-API, 254 nm) 50-95% MeOH in H$_2$O (0.1% HCO$_2$H), 6 min, 1.00 mL/min, C18 (Agilent Zorbax XDB-18, 50 mm×4.6 mm, 3.5 μm), m/z=513.2 (M+H), 457.2 (M-tBu+H), 413.2 (M-Boc+H), 257.1 (M/2+H), t=0.854 min; 25-95% MeOH in H$_2$O (0.1% HCO$_2$H), 8 min, 1.00 mL/min, C18 (Agilent Zorbax XDB-18, 50 mm×4.6 mm, 3.5 μm), m/z=513.2 (M+H), 457.2 (M-tBu+H), 413.2 (M-Boc+H), 257.1 (M/2+H), t=4.136 min.

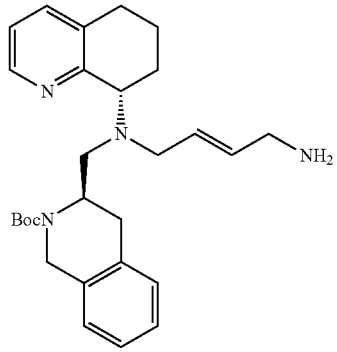 [SMILES: CC(C)(C)OC(=O)N1Cc2ccccc2C[C@@H]1CN(C/C=C/CN)[C@H]1CCCc2cccnc21]

Tert-butyl (R)-3-((((E)-4-aminobut-2-en-1-yl)((S)-5,6,7,8-tetrahydroquinolin-8-yl)amino)methyl)-3,4-dihydroisoquinoline-2(1H)-carboxylate (R)-tert-Butyl 3-((((E)-4-(1,3-dioxoisoindolin-2-yl)but-2-en-1-yl)((S)-5,6,7,8-tetrahydroquinolin-8-yl)amino)methyl)-3,4-dihydroisoquinoline-2(1H)-carboxylate (3.76 g, 6.34 mmol, 1.00 eq) was added to a 500 mL flask with a stir bar. The starting material was diluted with MeOH (63.4 mL), and the resulting solution was stirred vigorously at room temperature under Ar. Added a solution of hydrazine (6.78 mL, 50.7 mmol, 8.00 eq) in water (24% by wt.) in dropwise fashion via syringe pump at a rate of 6 mL/hr, and the resulting reaction mixture was stirred vigorously at room temperature under Ar overnight. After 23 hrs, the reaction mixture was partitioned between DCM and 1 M aqueous sodium hydroxide. The resulting aqueous layer was extracted 3 times with DCM, and combined organic layers were dried over anhydrous sodium sulfate, filtered, and evaporated under reduced pressure to yield a white foam (2.64 g). The crude material was purified via column chromatography (CombiFlash, 80 g column, 50 mL/min) eluting with the following gradient to yield a white foam (2.23 g, 4.81 mmol, 76% yield): 0-3 min: 0% 100:10:1 DCM/MeOH/NH$_4$OH in DCM; 3-18 min: 0-100% 100:10:1 DCM/MeOH/NH$_4$OH in DCM; 18-40 min: 100% 100:10:1 DCM/MeOH/NH$_4$OH in DCM. $^1$H NMR (500 MHz, CDCl$_3$) δ 8.39 (d, J=17.5 Hz, 1H), 7.25 (d, J=6.5 Hz, 1H), 7.06-7.11 (m, 2H), 6.98-7.03 (m, 3H), 5.55-5.64 (m, 2H), 4.68 (dd, J=17.8 Hz, J=26.8 Hz, 1.5H), 4.47 (br s, 0.5H), 4.10 (app t, J=15.3 Hz, 1H), 3.98 (dd, J=6.0 Hz, J=8.5 Hz, 1H), 3.27-3.35 (m, 1H), 3.18 (d, J=4.5 Hz, 2H), 3.09 (dd, J=4.5 Hz, J=14.0 Hz, 1H), 2.92-3.03 (m, 2H), 2.63-2.72 (m, 2H), 2.51-2.59 (m, 2H), 1.92-2.02 (m, 2H), 1.74 (dd, J=10.5 Hz, J=21.0 Hz, 1H), 1.58-1.66 (m, 1H), 1.50 (s, 9H), 1.26-1.42 (m, 2H). HRMS (NSI) m/z=463.30612 (M+H); Theo. for C$_{28}$H$_{38}$N$_4$O$_2$+H=463.30675. LC-MS (ESI-API, 254 nm) 75-95% MeOH in H$_2$O (0.1% HCO$_2$H), 5 min, 1.00 mL/min, C18 (Agilent Zorbax XDB-18, 50 mm×4.6 mm, 3.5 μm), m/z=463.2 (M+H), t=0.558 min; 50-95% MeOH in H$_2$O (0.1% HCO$_2$H), 8 min, 1.00 mL/min, C18 (Agilent Zorbax XDB-18, 50 mm×4.6 mm, 3.5 μm), m/z=463.2 (M+H), 363.2 (M-Boc+H), 232.2 (M/2+H), t=0.719 min.

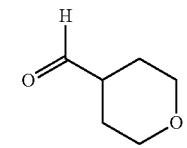
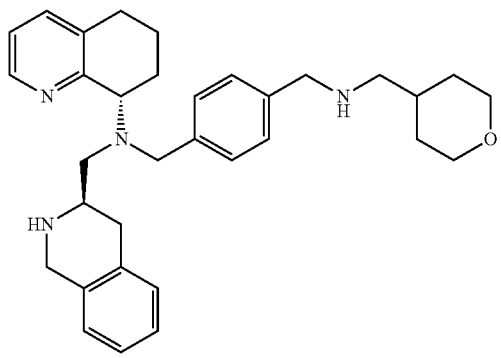

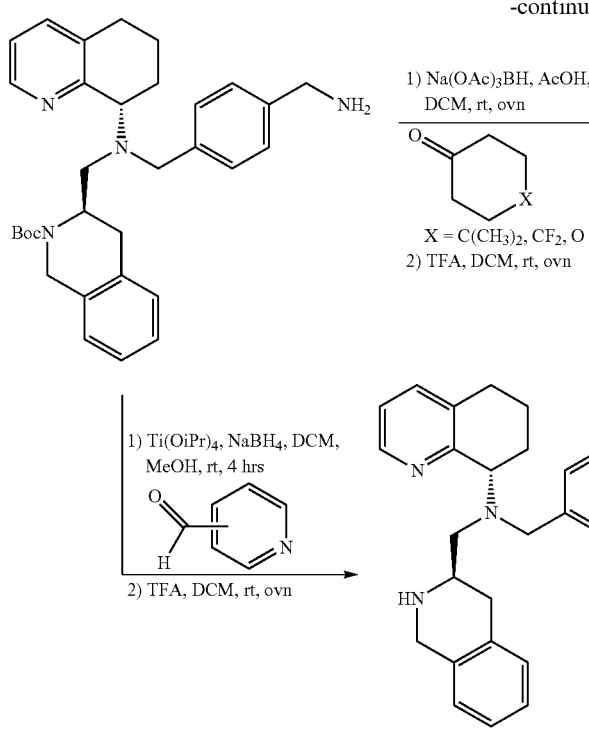

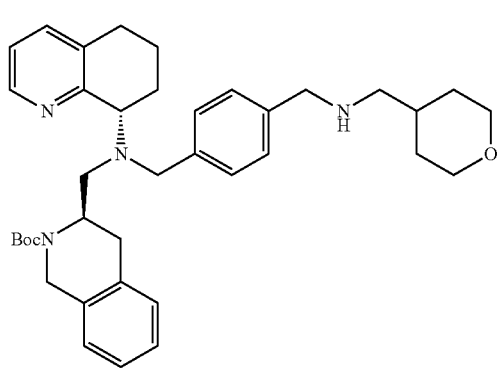 [SMILES: CC(C)(C)OC(=O)N1Cc2ccccc2C[C@@H]1CN(Cc1ccc(CNCC2CCOCC2)cc1)[C@H]1CCCc2cccnc21]

Tert-butyl (R)-3-(((4-(((((tetrahydro-2H-pyran-4-yl)methyl)amino)methyl)benzyl)((S)-5,6,7,8-tetrahydroquinolin-8-yl)amino)methyl)-3,4-dihydroisoquinoline-2(1H)-carboxylate Synthesis was carried out according to General Reductive Amination Protocol B. Purified via column chromatography (CombiFlash, 24 g column, 30 mL/min) eluting with the following gradient to yield a clear oil (110 mg, 0.180 mmol, 37% yield): 0-3 min: 0% 100:10:1 DCM/MeOH/NH$_4$OH in DCM; 3-18 min: 0-100% 100:10:1 DCM/MeOH/NH$_4$OH in DCM; 18-30 min: 100% 100:10:1 DCM/MeOH/NH$_4$OH. $^1$H NMR (500 MHz, CDCl$_3$) δ 8.43 (d, J=10.0 Hz, 1H), 7.29-7.32 (m, 2H), 7.24 (d, J=7.0 Hz, 1H), 7.19 (br s, 2H), 7.04-7.07 (m, 2H), 6.81-7.00 (m, 3H), 4.65-4.78 (m, 1H), 4.45-4.50 (m, 1H), 3.89-4.09 (m, 4H), 3.57-3.81 (m, 4H), 3.40 (dt, J=1.8 Hz, J=11.8 Hz, 2H), 2.85-3.03 (m, 3H), 2.57-2.75 (m, 3H), 2.54 (d, J=7.0 Hz, 2H), 2.10-2.24 (m, 1H), 1.93-1.95 (m, 1H), 1.71-1.78 (m, 2H), 1.66-1.67 (m, 3H), 1.46-1.58 (m, 10H), 1.26-1.36 (m, 2H). HRMS (NSI) m/z=611.39646 (M+H); Theo. for C$_{38}$H$_{50}$N$_4$O$_3$+H=611.39557. LC-MS (ESI-API, 254 nm) 50-95% MeOH in H$_2$O (0.1% HCO$_2$H), 6 min, 1.00 mL/min, C18 (Agilent Zorbax XDB-18, 50 mm×4.6 mm, 3.5 μm), m/z=611.2 (M+H), 306.2 (M/2+H), t=1.126 min; 25-95% MeOH in H$_2$O (0.1% HCO$_2$H), 8 min, 1.00 mL/min, C18 (Agilent Zorbax XDB-18, 50 mm×4.6 mm, 3.5 μm), m/z=611.2 (M+H), 306.2 (M/2+H), t=4.534 min.

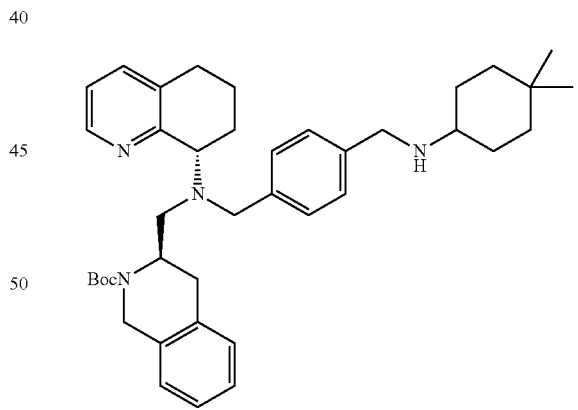

Tert-butyl (R)-3-(((4-(((4,4-dimethylcyclohexyl)amino)methyl)benzyl)((S)-5,6,7,8-tetrahydroquinolin-8-yl)amino)methyl)-3,4-dihydroisoquinoline-2(1H)-carboxylate Synthesis was carried out according to General Reductive Amination Protocol C. Purified via column chromatography (CombiFlash, 24 g column, 30 mL/min) eluting with the following gradient to yield a white foam (166 mg, 0.267 mmol, 59% yield): 0-3 min: 0% 100:10:1 DCM/MeOH/

NH₄OH in DCM; 3-18 min: 0-100% 100:10:1 DCM/MeOH/NH₄OH in DCM; 18-30 min: 100% 100:10:1 DCM/MeOH/NH₄OH. ¹H NMR (500 MHz, CDCl₃) δ 8.43 (d, J=9.0 Hz, 1H), 7.23-7.31 (m, 3H), 7.19 (br s, 2H), 7.05-7.07 (m, 2H), 6.82-7.00 (m, 3H), 4.65-4.79 (m, 1H), 4.44-4.51 (m, 1H), 4.00-4.11 (m, 1H), 3.89-3.92 (m, 1H), 3.79 (s, 2H), 3.56-3.75 (m, 2H), 3.02-3.05 (m, 1H), 2.71-2.99 (m, 2H), 2.52-2.74 (m, 3H), 2.46 (m, 1H), 2.10-2.24 (m, 1H), 1.94-1.95 (m, 1H), 1.63-1.77 (m, 5H), 1.46-1.58 (m, 9H), 1.32-1.43 (m, 4H), 1.18-1.24 (m, 2H), 0.92 (s, 3H), 0.91 (s, 3H). HRMS (NSI) m/z=623.43140 (M+H); Theo. for C₄₀H₅₄N₄O₂+H=623.43195. LC-MS (ESI-API, 254 nm) 50-95% MeOH in H₂O (0.1% HCO₂H), 8 min, 1.00 mL/min, C18 (Agilent Zorbax XDB-18, 50 mm×4.6 mm, 3.5 μm), m/z=623.3 (M+H), 312.2 (M/2+H), t=2.592 min; 25-95% MeOH in H₂O (0.1% HCO₂H), 8 min, 1.00 mL/min, C18 (Agilent Zorbax XDB-18, 50 mm×4.6 mm, 3.5 μm), m/z=623.2 (M+H), 312.2 (M/2+H), t=5.806 min.

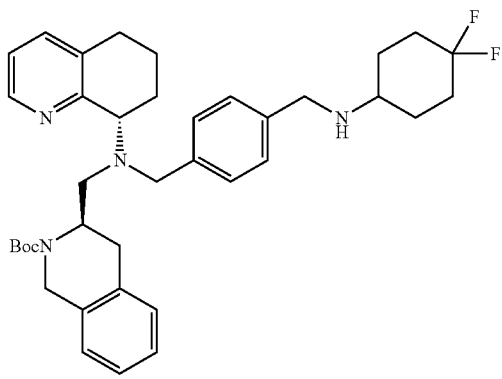 [SMILES: CC(C)(C)OC(=O)N1Cc2ccccc2C[C@@H]1CN(Cc1ccc(CNC2CCC(F)(F)CC2)cc1)[C@H]1CCCc2cccnc21]

Tert-butyl (R)-3-(((4-(((4,4-difluorocyclohexyl)amino)methyl)benzyl)((S)-5,6,7,8-tetrahydroquinolin-8-yl)amino)methyl)-3,4-dihydroisoquinoline-2(1H)-carboxylate Synthesis was carried out according to General Reductive Amination Protocol C. Purified via column chromatography (CombiFlash, 24 g column, 30 mL/min) eluting with the following gradient to yield a clear oil (238 mg, 0.377 mmol, 84% yield): 0-3 min: 0% 100:10:1 DCM/MeOH/NH₄OH in DCM; 3-18 min: 0-100% 100:10:1 DCM/MeOH/NH₄OH in DCM; 18-30 min: 100% 100:10:1 DCM/MeOH/NH₄OH. ¹H NMR (500 MHz, CDCl₃) δ 8.43 (d, J=9.5 Hz, 1H), 7.30-7.32 (m, 2H), 7.24 (d, J=7.5 Hz, 1H), 7.19 (m, 2H), 7.04-7.07 (m, 2H), 6.82-7.00 (m, 3H), 4.65-4.77 (m, 1H), 4.45-4.52 (m, 1H), 3.90-4.08 (m, 2H), 3.59-3.82 (m, 4H), 2.87-3.03 (m, 2H), 2.53-2.75 (m, 4H), 2.10-2.24 (m, 3H), 1.90-1.94 (m, 3H), 1.71-1.87 (m, 4H), 1.64-1.66 (m, 1H), 1.46-1.60 (m, 12H). HRMS (NSI) m/z=631.38184 (M+H); Theo. for C₃₈H₄₈F₂N₄O₂+H=631.38181. LC-MS (ESI-API, 254 nm) 50-95% MeOH in H₂O (0.1% HCO₂H), 8 min, 1.00 mL/min, C18 (Agilent Zorbax XDB-18, 50 mm×4.6 mm, 3.5 μm), m/z=631.2 (M+H), 316.2 (M/2+H), t=1.620 min; 25-95% MeOH in H₂O (0.1% HCO₂H), 8 min, 1.00 mL/min, C18 (Agilent Zorbax XDB-18, 50 mm×4.6 mm, 3.5 μm), m/z=631.2 (M+H), 316.2 (M/2+H), t=4.864 min.

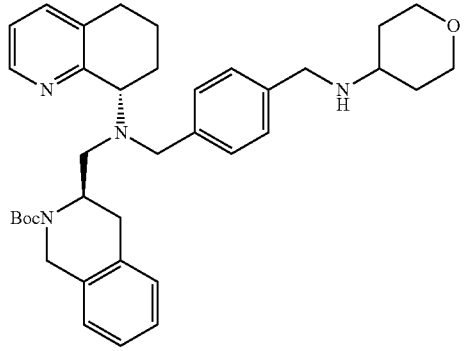 [SMILES: CC(C)(C)OC(=O)N1Cc2ccccc2C[C@@H]1CN(Cc1ccc(CNC2CCOCC2)cc1)[C@H]1CCCc2cccnc21]

Tert-butyl (R)-3-(((4-((((tetrahydro-2H-pyran-4-yl)amino)methyl)benzyl)((S)-5,6,7,8-tetrahydroquinolin-8-yl)amino)methyl)-3,4-dihydroisoquinoline-2(1H)-carboxylate Synthesis was carried out according to General Reductive Amination Protocol C. Purified via column chromatography (CombiFlash, 24 g column, 30 mL/min) eluting with the following gradient to yield a white foam (220 mg, 0.369 mmol, 76% yield): 0-3 min: 0% 100:10:1 DCM/MeOH/NH₄OH in DCM; 3-18 min: 0-100% 100:10:1 DCM/MeOH/NH₄OH in DCM; 18-30 min: 100% 100:10:1 DCM/MeOH/NH₄OH. ¹H NMR (500 MHz, CDCl₃) δ 8.43 (d, J=9.0 Hz, 1H), 7.29-7.32 (m, 2H), 7.24 (d, J=7.5 Hz, 1H), 7.20 (br s, 2H), 7.04-7.07 (m, 2H), 6.83-7.00 (m, 3H), 4.66-4.77 (m, 1H), 4.45-4.52 (m, 1H), 3.90-4.08 (m, 4H), 3.59-3.85 (m, 4H), 3.41 (dt, J=2.0 Hz, J=11.8 Hz, 2H), 2.86-3.03 (m, 3H), 2.53-2.78 (m, 4H), 2.11-2.22 (m, 1H), 1.93 (m, 1H), 1.87 (dd, J=1.5 Hz, J=12.5 Hz, 2H), 1.78 (app p, J=10.3 Hz, 1H), 1.64-1.65 (m, 1H), 1.43-1.58 (m, 12H). HRMS (NSI) m/z=597.38109 (M+H); Theo. for C₃₇H₄₈N₄O₃+H=597.37992. LC-MS (ESI-API, 254 nm) 50-95% MeOH in H₂O (0.1% HCO₂H), 6 min, 1.00 mL/min, C18 (Agilent Zorbax XDB-18, 50 mm×4.6 mm, 3.5 μm), m/z=597.2 (M+H), 299.2 (M/2+H), t=0.906 min; 25-95% MeOH in H₂O (0.1% HCO₂H), 8 min, 1.00 mL/min, C18 (Agilent Zorbax XDB-18, 50 mm×4.6 mm, 3.5 μm), m/z=597.2 (M+H), 299.2 (M/2+H), t=4.219 min.

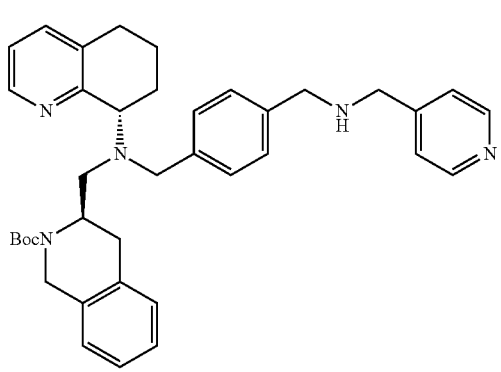 [SMILES: CC(C)(C)OC(=O)N1Cc2ccccc2C[C@@H]1CN(Cc1ccc(CNCc2ccncc2)cc1)[C@H]1CCCc2cccnc21]

Tert-butyl (R)-3-(((4-(((pyridin-4-ylmethyl)amino)methyl)benzyl)((S)-5,6,7,8-tetrahydroquinolin-8-yl)amino)methyl)-3,4-dihydroisoquinoline-2(1H)-carboxylate Synthesis was carried out according to General Reductive Amination Protocol B. Purified via column chromatography (CombiFlash, 24 g column, 30 mL/min) eluting with the following gradient to yield a white foam (192 mg, 0.318 mmol, 65% yield): 0-3 min: 0% 100:10:1 DCM/MeOH/NH$_4$OH in DCM; 3-18 min: 0-100% 100:10:1 DCM/MeOH/NH$_4$OH in DCM; 18-30 min: 100% 100:10:1 DCM/MeOH/NH$_4$OH. $^1$H NMR (500 MHz, CDCl$_3$) δ 8.56-8.57 (m, 2H), 8.44 (d, J=10.0 Hz, 1H), 7.31-7.32 (m, 4H), 7.22-7.26 (m, 3H), 7.04-7.05 (m, 2H), 6.78-7.00 (m, 3H), 4.65-4.78 (m, 1H), 4.46-4.52 (m, 1H), 3.87-4.09 (m, 2H), 3.83 (s, 2H), 3.56-3.79 (4H), 2.72-3.03 (m, 3H), 2.53-2.70 (m, 3H), 2.12-2.25 (m, 1H), 1.94 (m, 1H), 1.65-1.81 (m, 3H), 1.53 (s, 4.5H), 1.46 (s, 4.5H). HRMS (NSI) m/z=604.36456 (M+H); Theo. for C$_{38}$H$_{45}$N$_5$O$_2$+H=604.36460. LC-MS (ESI-API, 254 nm) 75-95% MeOH in H$_2$O (0.1% HCO$_2$H), 5 min, 1.00 mL/min, C18 (Agilent Zorbax XDB-18, 50 mm×4.6 mm, 3.5 μm), m/z=604.2 (M+H), 302.8 (M/2+H), t=0.553 min; 25-95% MeOH in H$_2$O (0.1% HCO$_2$H), 8 min, 1.00 mL/min, C18 (Agilent Zorbax XDB-18, 50 mm×4.6 mm, 3.5 μm), m/z=604.2 (M+H), 302.6 (M/2+H), t=4.253 min.

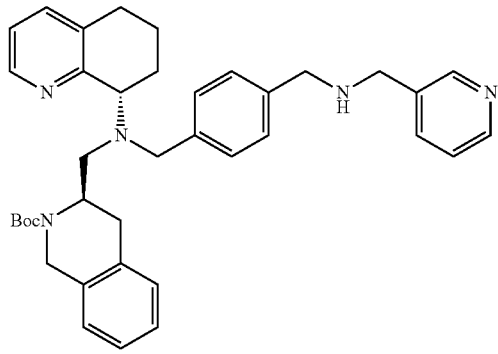 [SMILES: CC(C)(C)OC(=O)N1Cc2ccccc2C[C@@H]1CN(Cc1ccc(CNCc2cccnc2)cc1)[C@H]1CCCc2cccnc21]

Tert-butyl (R)-3-(((4-(((pyridin-3-ylmethyl)amino)methyl)benzyl)((S)-5,6,7,8-tetrahydroquinolin-8-yl)amino)methyl)-3,4-dihydroisoquinoline-2(1H)-carboxylate Synthesis was carried out according to General Reductive Amination Protocol B. Purified via column chromatography (CombiFlash, 24 g column, 30 mL/min) eluting with the following gradient to yield a white foam (179 mg, 0.296 mmol, 61% yield): 0-3 min: 0% 100:10:1 DCM/MeOH/NH$_4$OH in DCM; 3-18 min: 0-100% 100:10:1 DCM/MeOH/NH$_4$OH in DCM; 18-30 min: 100% 100:10:1 DCM/MeOH/NH$_4$OH. $^1$H NMR (500 MHz, CDCl$_3$) δ 8.59 (br s, 1H), 8.52 (dd, J=1.5 Hz, J=4.5 Hz, 1H), 8.43 (d, J=9.5 Hz, 1H), 7.72 (dt, J=1.8 Hz, J=7.8 Hz, 1H), 7.30-7.32 (m, 2H), 7.27 (dd, J=5.0 Hz, J=7.5 Hz, 1H), 7.22-7.25 (m, 3H), 7.04-7.05 (m, 2H), 6.78-7.00 (m, 3H), 4.65-4.78 (m, 1H), 4.45-4.52 (m, 1H), 3.86-4.09 (m, 2H), 3.82 (s, 2H), 3.58-3.80 (m, 4H), 2.71-3.04 (m, 3H), 2.53-2.70 (m, 3H), 2.11-2.24 (m, 1H), 1.95 (m, 1H), 1.65-1.80 (m, 3H), 1.53 (s, 4.5H), 1.46 (s, 4.5H). HRMS (NSI) m/z=604.36444 (M+H); Theo. for C$_{38}$H$_{45}$N$_5$O$_2$+H=604.36460. LC-MS (ESI-API, 254 nm) 75-95% MeOH in H$_2$O (0.1% HCO$_2$H), 5 min, 1.00 mL/min, C18 (Agilent Zorbax XDB-18, 50 mm×4.6 mm, 3.5 μm), m/z=604.2 (M+H), 302.6 (M/2+H), t=0.592 min; 25-95% MeOH in H$_2$O (0.1% HCO$_2$H), 8 min, 1.00 mL/min, C18 (Agilent Zorbax XDB-18, 50 mm×4.6 mm, 3.5 μm), m/z=604.2 (M+H), 302.6 (M/2+H), t=4.309 min.

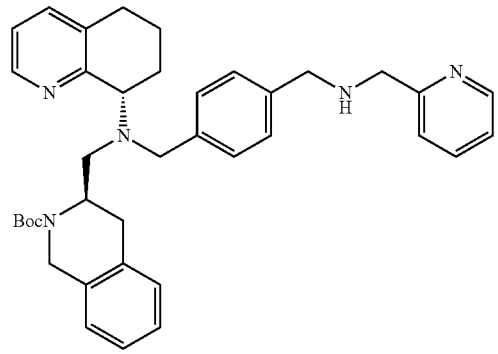 [SMILES: CC(C)(C)OC(=O)N1Cc2ccccc2C[C@@H]1CN(Cc1ccc(CNCc2ccccn2)cc1)[C@H]1CCCc2cccnc21]

Tert-butyl (R)-3-(((4-(((pyridin-2-ylmethyl)amino)methyl)benzyl)((S)-5,6,7,8-tetrahydroquinolin-8-yl)amino)methyl)-3,4-dihydroisoquinoline-2(1H)-carboxylate Synthesis was carried out according to General Reductive Amination Protocol B. Purified via column chromatography (CombiFlash, 24 g column, 30 mL/min) eluting with the following gradient to yield a yellow foam (181 mg, 0.300 mmol, 62% yield): 0-3 min: 0% 100:10:1 DCM/MeOH/NH$_4$OH in DCM; 3-18 min: 0-100% 100:10:1 DCM/MeOH/NH$_4$OH in DCM; 18-30 min: 100% 100:10:1 DCM/MeOH/NH$_4$OH. $^1$H NMR (500 MHz, CDCl$_3$) δ 8.58 (d, J=5.0 Hz, 1H), 8.43 (d, J=10.0 Hz, 1H), 7.65 (dt, J=1.8 Hz, J=7.9 Hz, 1H), 7.34 (d, J=8.0 Hz, 1H), 7.29-7.31 (m, 2H), 7.25 (m, 3H), 7.17 (dd, J=4.5 Hz, J=7.5 Hz, 1H), 7.04-7.06 (m, 2H), 6.79-7.00 (m, 3H), 4.65-4.79 (m, 1H), 4.44-4.50 (m, 1H), 3.99-4.11 (m, 1H), 3.95 (s, 2H), 3.89-3.92 (m, 1H), 3.84 (app d, J=4.0 Hz, 2H), 3.56-3.71 (m, 2H), 3.02-3.09 (m, 1H), 2.91-2.99 (m, 1H), 2.72-2.87 (m, 1H), 2.52-2.69 (m, 3H), 2.11-2.26 (m, 2H), 1.94-1.95 (m, 1H), 1.77-1.80 (m, 1H), 1.58-1.69 (m, 1H), 1.53 (s, 4.5H), 1.46 (s, 4.5H). HRMS (NSI) m/z=604.36452 (M+H); Theo. for C$_{38}$H$_{45}$N$_5$O$_2$+H=604.36460. LC-MS (ESI-API, 254 nm) 75-95% MeOH in H$_2$O (0.1% HCO$_2$H), 5 min, 1.00 mL/min, C18 (Agilent Zorbax XDB-18, 50 mm×4.6 mm, 3.5 μm), m/z=604.2 (M+H), 302.6 (M/2+H), t=0.535 min; 25-95% MeOH in H$_2$O (0.1% HCO$_2$H), 8 min, 1.00 mL/min, C18 (Agilent Zorbax XDB-18, 50 mm×4.6 mm, 3.5 μm), m/z=604.2 (M+H), 302.7 (M/2+H), t=4.604 min.

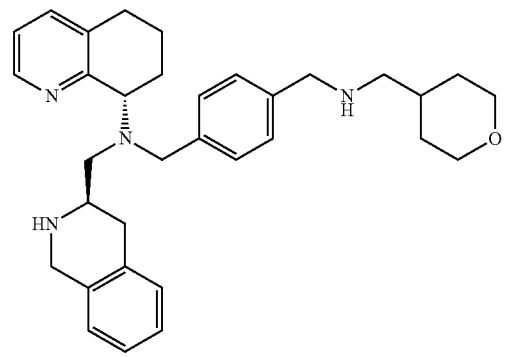 [SMILES: c1ccc2c(c1)CN[C@@H](CN(Cc1ccc(CNCC3CCOCC3)cc1)[C@H]1CCCc3cccnc31)C2]

EMU216: (S)—N-(4-((((tetrahydro-2H-pyran-4-yl)methyl)amino)methyl)benzyl)-N—(((R)-1,2,3,4-tetrahydroisoquinolin-3-yl)methyl)-5,6,7,8-tetrahydroquinolin-8-amine Synthesis was carried out according to the General Deprotection Protocol. Purified via column chromatography (CombiFlash, 12 g column, 25 mL/min) eluting with the following gradient to yield a clear oil (81.0 mg, 0.159 mmol, 88% yield): 0-3 min: 0% 100:10:1 DCM/MeOH/NH$_4$OH in DCM; 3-18 min: 0-100% 100:10:1 DCM/MeOH/NH$_4$OH in DCM; 18-30 min: 100% 100:10:1 DCM/MeOH/NH$_4$OH. $^1$H NMR (500 MHz, CDCl$_3$) δ 8.51 (d, J=4.0 Hz, 1H), 7.42 (d, J=7.5 Hz, 2H), 7.33 (d, J=7.5 Hz, 1H), 7.25 (d, J=8.0 Hz, 2H), 7.04-7.08 (m, 3H), 6.95-7.01 (m, 2H), 4.38 (d, J=14.0 Hz, 1H), 4.11 (dd, J=6.5 Hz, J=9.5 Hz, 1H), 3.90-3.98 (m, 4H), 3.76 (s, 2H), 3.67 (d, J=15.0 Hz, 1H), 3.38 (dt, J=1.3 Hz, J=11.8 Hz, 2H), 2.90 (dd, J=2.8 Hz, J=13.3 Hz, 1H), 2.73-2.80 (m, 1H), 2.63-2.68 (m, 2H), 2.55 (dd, J=3.5 Hz, J=16.0 Hz, 1H), 2.51 (d, J=7.0 Hz, 2H), 2.35-2.48 (m, 2H), 2.12-2.16 (m, 1H), 1.91-1.99 (m, 3H), 1.66-1.76 (m, 2H), 1.62-1.65 (m, 2H), 1.25-1.33 (m, 3H). $^{13}$C NMR (125 MHz, CDCl$_3$) δ 159.0, 146.9, 140.8, 139.0, 136.6, 135.7, 134.7, 134.2, 129.2, 128.5 (2C), 128.1 (2C), 126.5, 126.0, 125.5, 121.5, 68.0 (2C), 62.4, 59.4, 58.1, 55.7, 54.0, 52.1, 48.7, 35.6, 33.9, 31.5 (2C), 29.7, 29.6, 22.2. HRMS (NSI) m/z=511.34459 (M+H); Theo. for C$_{33}$H$_{42}$N$_4$O+ H=511.34314. LC-MS (ESI-API, 254 nm) 25-95% MeOH in H$_2$O (0.1% HCO$_2$H), 8 min, 1.00 mL/min, C18 (Agilent Zorbax XDB-18, 50 mm×4.6 mm, 3.5 μm), m/z=511.2 (M+H), 256.2 (M/2+H), t=0.722 min; 10-95% MeOH in H$_2$O (0.1% HCO$_2$H), 10 min, 1.00 mL/min, C18 (Agilent Zorbax XDB-18, 50 mm×4.6 mm, 3.5 μm), m/z=511.2 (M+H), 256.2 (M/2+H), t=3.070 min.

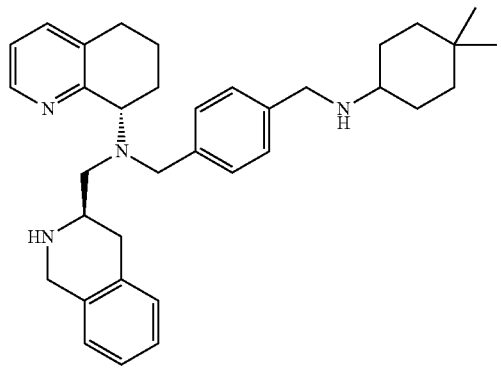 [SMILES: CC1(C)CCC(NCc2ccc(CN(C[C@H]3Cc4ccccc4CN3)[C@H]3CCCc4cccnc43)cc2)CC1]

EMU181: (S)—N-(4-(((4,4-dimethylcyclohexyl)amino)methyl)benzyl)-N—(((R)-1,2,3,4-tetrahydroisoquinolin-3-yl)methyl)-5,6,7,8-tetrahydroquinolin-8-amine Synthesis was carried out according to the General Deprotection Protocol. Purified via column chromatography (CombiFlash, 12 g column, 25 mL/min) eluting with the following gradient to yield a white foam (99.0 mg, 0.189 mmol, 71% yield): 0-3 min: 0% 100:10:1 DCM/MeOH/NH$_4$OH in DCM; 3-18 min: 0-100% 100:10:1 DCM/MeOH/NH$_4$OH in DCM; 18-30 min: 100% 100:10:1 DCM/MeOH/NH$_4$OH. $^1$H NMR (500 MHz, CDCl$_3$) δ 8.51 (dd, J=1.5 Hz, J=5.0 Hz, 1H), 7.41 (d, J=8.0 Hz, 2H), 7.33 (dt, J=0.8 Hz, J=7.8 Hz, 1H), 7.26 (d, J=8.0 Hz, 2H), 7.04-7.08 (m, 3H), 6.95-7.02 (m, 2H), 4.40 (d, J=14.0 Hz, 1H), 4.10 (dd, J=6.5 Hz, J=10.0 Hz, 1H), 3.94 (dd, J=14.3 Hz, J=26.3 Hz, 2H), 3.79 (s, 2H), 3.69 (d, J=15.0 Hz, 1H), 2.89 (dd, J=2.8 Hz, J=13.3 Hz, 1H), 2.63-2.79 (m, 4H), 2.55 (dd, J=3.5 Hz, J=16.0 Hz, 1H), 2.35-2.47 (m, 3H), 2.10-2.15 (m, 1H), 1.90-1.99 (m, 2H), 1.70-1.75 (m, 2H), 1.61-1.69 (m, 1H), 1.37-1.40 (m, 2H), 1.27-1.34 (m, 3H), 1.19 (dt, J=3.5 Hz, J=12.8 Hz, 2H), 0.91 (s, 3H), 0.90 (s, 3H). $^{13}$C NMR (125 MHz, CDCl$_3$) δ 159.0, 146.9, 140.6, 139.4, 136.5, 135.8, 134.8, 134.2 129.2, 128.5 (2C), 128.1 (2C), 126.5, 125.9, 125.5, 121.5, 62.2, 59.4, 58.0, 56.5, 52.1, 51.1, 48.7, 37.9, 33.9, 32.3, 30.3, 29.8, 29.5, 29.4, 25.0, 22.2. HRMS (NSI) m/z=523.37923 (M+H); Theo. for C$_{35}$H$_{46}$N$_4$+ H=523.37952. LC-MS (ESI-API, 254 nm) 25-95% MeOH in H$_2$O (0.1% HCO$_2$H), 8 min, 1.00 mL/min, C18 (Agilent Zorbax XDB-18, 50 mm×4.6 mm, 3.5 μm), m/z=523.2 (M+H), 262.2 (M/2+H), t=3.052 min; 10-95% MeOH in H$_2$O (0.1% HCO$_2$H), 10 min, 1.00 mL/min, C18 (Agilent Zorbax XDB-18, 50 mm×4.6 mm, 3.5 μm), m/z=523.2 (M+H), 262.2 (M/2+H), t=4.873 min.

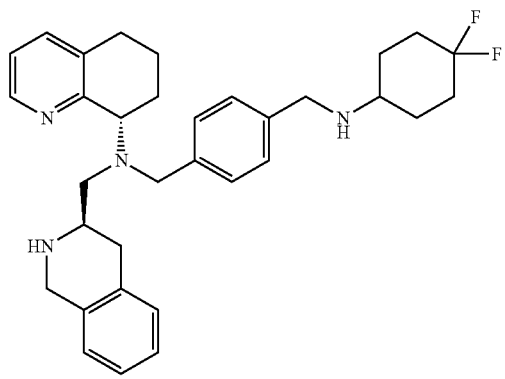 [SMILES: FC1(F)CCC(NCc2ccc(CN(C[C@H]3Cc4ccccc4CN3)[C@H]3CCCc4cccnc43)cc2)CC1]

EMU182: (S)—N-(4-(((4,4-difluorocyclohexyl)amino)methyl)benzyl)-N—(((R)-1,2,3,4-tetrahydroisoquinolin-3-yl)methyl)-5,6,7,8-tetrahydroquinolin-8-amine Synthesis was carried out according to the General Deprotection Protocol. Purified via column chromatography (CombiFlash, 12 g column, 25 mL/min) eluting with the following gradient to yield a white foam (147 mg, 0.277 mmol, 73% yield): 0-3 min: 0% 100:10:1 DCM/MeOH/NH$_4$OH in DCM; 3-18 min: 0-100% 100:10:1 DCM/MeOH/NH$_4$OH in DCM; 18-30 min: 100% 100:10:1 DCM/MeOH/NH$_4$OH. $^1$H NMR (500 MHz, CDCl$_3$) δ 8.51 (dd, J=1.5 Hz, J=5.0 Hz, 1H), 7.43 (d, J=8.0 Hz, 2H), 7.33 (dt, J=0.8 Hz, J=7.5 Hz, 1H), 7.26 (d, J=8.0 Hz, 2H), 7.04-7.08 (m, 3H), 6.95-7.02 (m, 2H), 4.39 (d, J=14.5 Hz, 1H), 4.10 (dd, J=6.8 Hz, J=10.3 Hz, 1H), 3.94 (dd, J=14.8 Hz, J=24.8 Hz, 2H), 3.78 (s, 2H), 3.68 (d, J=15.0 Hz, 1H), 2.90 (dd, J=3.0 Hz, J=13.0 Hz, 1H), 2.74-2.80 (m, 2H), 2.63-2.70 (m, 3H), 2.55 (dd, J=3.5 Hz, J=16.0 Hz, 1H), 2.35-2.45 (m, 2H), 2.07-2.16 (m, 3H), 1.88-1.99 (m, 4H), 1.65-1.80 (m, 4H), 1.50-1.58 (m, 2H). $^{13}$C NMR (125 MHz, CDCl$_3$) δ 158.9, 146.9, 140.9, 138.9, 136.5, 135.7, 134.7, 134.2, 129.1, 128.6 (2C), 128.0 (2C), 126.5, 125.9, 125.5, 123.5 (t, J=239.4 Hz), 121.5, 62.3, 59.4, 58.0, 53.2, 52.1, 51.2, 48.7, 33.9, 31.5 (t, J=23.8 Hz, 2C), 29.6, 29.5, 28.8 (t, J=4.4 Hz, 2C), 22.2. $^{19}$F NMR (376 MHz, CDCl$_3$, TFA standard) 6-95.7 (app d, J=236.9 Hz), −98.6 (app d, J=229.4 Hz). HRMS (NSI)

m/z=531.32872 (M+H); Theo. for C₃₃H₄₀F₂N₄+H=531.32938. LC-MS (ESI-API, 254 nm) 25-95% MeOH in H₂O (0.1% HCO₂H), 8 min, 1.00 mL/min, C18 (Agilent Zorbax XDB-18, 50 mm×4.6 mm, 3.5 μm), m/z=531.2 (M+H), 266.2 (M/2+H), t=1.124 min; 10-95% MeOH in H₂O (0.1% HCO₂H), 10 min, 1.00 mL/min, C18 (Agilent Zorbax XDB-18, 50 mm×4.6 mm, 3.5 μm), m/z=531.2 (M+H), 266.2 (M/2+H), t=3.512 min.

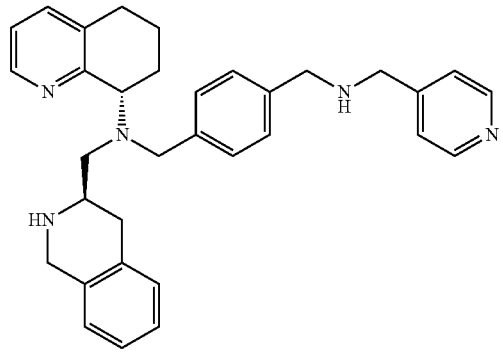

EMU218: (S)—N-(4-(((pyridin-4-ylmethyl)amino) methyl)benzyl)-N—(((R)-1,2,3,4-tetrahydroisoquinolin-3-yl)methyl)-5,6,7,8-tetrahydroquinolin-8-amine Synthesis was carried out according to the General Deprotection Protocol. Purified via column chromatography (CombiFlash, 12 g column, 25 mL/min) eluting with 100:10:1 DCM/MeOH/NH₄OH to yield a white foam (132 mg, 0.262 mmol, 82% yield). ¹H NMR (500 MHz, CDCl₃) δ 8.54-8.55 (m, 2H), 8.52 (d, J=4.5 Hz, 1H), 8.45 (d, J=8.0 Hz, 2H), 7.34 (d, J=7.5 Hz, 1H), 7.27-7.29 (m, 4H), 6.99-7.08 (m, 3H), 6.93-7.00 (m, 2H), 4.38 (d, J=14.0 Hz, 1H), 4.11 (dd, J=6.8 Hz, J=9.8 Hz, 1H), 3.94 (app t, J=15.8 Hz, 2H), 3.80 (s, 2H), 3.79 (s, 2H), 3.66 (d, J=15.0 Hz, 1H), 2.90 (dd, J=2.3 Hz, J=13.3 Hz, 1H), 2.74-2.80 (m, 1H), 2.62-2.68 (m, 2H), 2.55 (dd, J=3.0 Hz, J=16.0 Hz, 1H), 2.43 (dd, J=11.0 Hz, J=12.5 Hz, 1H), 2.37 (dd, J=11.3 Hz, J=15.8 Hz, 1H), 2.13-2.17 (m, 1H), 1.92-1.99 (m, 3H), 1.64-1.71 (m, 2H). ¹³C NMR (125 MHz, CDCl₃) δ 158.9, 149.9 (2C), 149.5, 146.9, 141.1, 138.3, 136.5, 135.7, 134.7, 134.2, 129.1, 128.6 (2C), 128.1 (2C), 126.5, 125.9, 125.5, 123.1 (2C), 121.5, 62.4, 59.4, 58.1, 53.1, 52.1, 51.8, 48.7, 33.9, 29.5, 29.5, 22.2. HRMS (NSI) m/z=504.31252 (M+H); Theo. for C₃₃H₃₇N₅+H=504.31217. LC-MS (ESI-API, 254 nm) 25-95% MeOH in H₂O (0.1% HCO₂H), 8 min, 1.00 mL/min, C18 (Agilent Zorbax XDB-18, 50 mm×4.6 mm, 3.5 μm), m/z=504.2 (M+H), 252.6 (M/2+H), t=0.636 min; 10-95% MeOH in H₂O (0.1% HCO₂H), 10 min, 1.00 mL/min, C18 (Agilent Zorbax XDB-18, 50 mm×4.6 mm, 3.5 μm), m/z=504.2 (M+H), 252.7 (M/2+H), t=2.506 min.

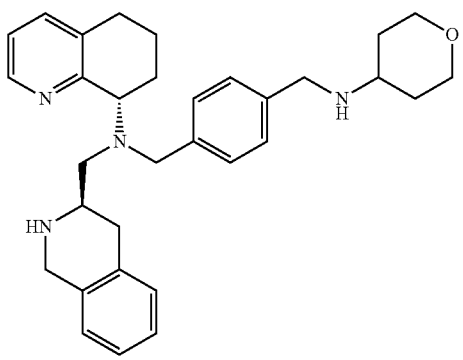 [SMILES: c1ccc2c(c1)CN[C@@H](CN(Cc1ccc(CNC3CCOCC3)cc1)[C@H]1CCCc3cccnc31)C2]

EMU217: (S)—N-(4-(((tetrahydro-2H-pyran-4-yl) amino)methyl)benzyl)-N—(((R)-1,2,3,4-tetrahydroisoquinolin-3-yl)methyl)-5,6,7,8-tetrahydroquinolin-8-amine Synthesis was carried out according to the General Deprotection Protocol. Purified via column chromatography (CombiFlash, 12 g column, 25 mL/min) eluting with the following gradient to yield a white foam (159 mg, 0.320 mmol, 87% yield). 0-3 min: 0% 100:10:1 DCM/MeOH/NH₄OH in DCM; 3-18 min: 0-100% 100:10:1 DCM/MeOH/NH₄OH in DCM; 18-30 min: 100% 100:10:1 DCM/MeOH/NH₄OH. ¹H NMR (500 MHz, CDCl₃) δ 8.51 (d, J=3.5 Hz, 1H), 7.43 (d, J=8.0 Hz, 2H), 7.33 (dd, J=0.5 Hz, J=7.5 Hz, 1H), 7.26 (d, J=7.0 Hz, 2H), 7.04-7.07 (m, 3H), 6.95-7.01 (m, 2H), 4.39 (d, J=14.0 Hz, 1H), 4.10 (dd, J=6.5 Hz, J=10.0 Hz, 1H), 3.90-3.98 (m, 4H), 3.81 (s, 2H), 3.68 (d, J=15.0 Hz, 1H), 3.70 (dt, J=2.0 Hz, J=11.8 Hz, 2H), 2.90 (dd, J=2.5 Hz, J=8.3 Hz, 1H), 2.64-2.80 (m, 5H), 2.55 (dd, J=3.5 Hz, J=16.0 Hz, 1H), 2.35-2.45 (m, 2H), 2.11-2.15 (m, 1H), 1.91-1.99 (m, 2H), 1.83-1.86 (m, 2H), 1.62-1.70 (m, 1H), 1.26-1.49 (m, 3H). ¹³C NMR (125 MHz, CDCl₃) δ 158.9, 146.9, 140.7, 138.9, 136.5, 135.7, 134.7, 134.1, 129.1, 128.5 (2C), 128.0 (2C), 126.4, 125.9, 125.5, 121.4, 66.8 (2C), 62.2, 59.3, 58.0, 53.2, 52.1, 50.3, 48.7, 33.9, 33.8, 33.8, 29.6, 29.5, 22.2. HRMS (NSI) m/z=497.32792 (M+H); Theo. for C₃₂H₄₀N₄O+H=497.32749 LC-MS (ESI-API, 254 nm) 25-95% MeOH in H₂O (0.1% HCO₂H), 8 min, 1.00 mL/min, C18 (Agilent Zorbax XDB-18, 50 mm×4.6 mm, 3.5 μm), m/z=497.2 (M+H), 249.2 (M/2+H), t=0.631 min; 10-95% MeOH in H₂O (0.1% HCO₂H), 10 min, 1.00 mL/min, C18 (Agilent Zorbax XDB-18, 50 mm×4.6 mm, 3.5 μm), m/z=497.2 (M+H), 249.2 (M/2+H), t=2.688 min.

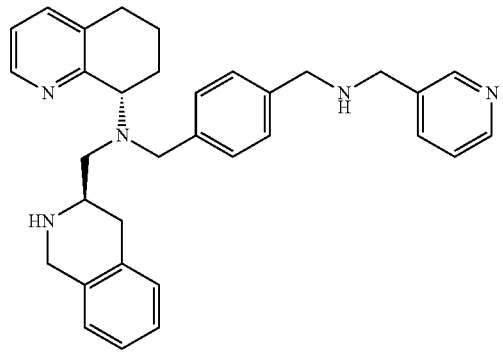 [SMILES: c1cncc(CNCc2ccc(CN(C[C@H]3Cc4ccccc4CN3)[C@H]3CCCc4cccnc43)cc2)c1]

265

EMU219: (S)—N-(4-(((pyridin-3-ylmethyl)amino)methyl)benzyl)-N—(((R)-1,2,3,4-tetrahydroisoquinolin-3-yl)methyl)-5,6,7,8-tetrahydroquinolin-8-amine

Synthesis was carried out according to the General Deprotection Protocol. Purified via column chromatography (CombiFlash, 12 g column, 25 mL/min) eluting with 100:10:1 DCM/MeOH/NH$_4$OH to yield a white foam (137 mg, 0.272 mmol, 92% yield). $^1$H NMR (500 MHz, CDCl$_3$) δ 8.57 (m, 1H), 8.50-8.52 (m, 2H), 7.67-7.70 (m, 1H), 7.44 (d, J=7.5 Hz, 2H), 7.33 (d, J=7.5 Hz, 1H), 7.24-7.29 (m, 3H), 7.02-7.08 (m, 3H), 6.92-7.01 (m, 2H), 4.39 (d, J=14.0 Hz, 1H), 4.10 (dd, J=6.8 Hz, J=10.3 Hz, 1H), 3.94 (dd, J=14.8 Hz, J=18.8 Hz, 2H), 3.80 (s, 2H), 3.79 (s, 2H), 3.67 (d, J=15.0 Hz, 1H), 2.90 (dd, J=2.5 Hz, J=13.0 Hz, 1H), 2.74-2.80 (m, 2H), 2.63-2.67 (m, 2H), 2.55 (dd, J=3.0 Hz, J=16.0 Hz, 1H), 2.43 (dd, J=10.5 Hz, J=13.0 Hz, 1H), 2.37 (dd, J=11.0 Hz, J=16.0 Hz, 1H), 2.12-2.16 (m, 1H), 1.91-1.99 (m, 3H), 1.62-1.71 (m, 1H). $^{13}$C NMR (125 MHz, CDCl$_3$) δ 158.9, 149.8, 148.5, 146.9, 141.0, 138.4, 136.5, 135.9, 135.8, 134.7, 134.2, 129.1, 128.6 (2C), 128.1 (2C), 126.5, 125.9, 125.5, 123.5, 121.5, 62.3, 59.4, 58.1, 53.1, 52.1, 50.4, 48.7, 33.9, 29.6, 29.5, 22.2. HRMS (NSI) m/z=504.31292 (M+H); Theo. for C$_{33}$H$_{37}$N$_5$+H=504.31217. LC-MS (ESI-API, 254 nm) 25-95% MeOH in H$_2$O (0.1% HCO$_2$H), 8 min, 1.00 mL/min, C18 (Agilent Zorbax XDB-18, 50 mm×4.6 mm, 3.5 μm), m/z=504.2 (M+H), 252.6 (M/2+H), t=0.663 min; 10-95% MeOH in H$_2$O (0.1% HCO$_2$H), 10 min, 1.00 mL/min, C18 (Agilent Zorbax XDB-18, 50 mm×4.6 mm, 3.5 μm), m/z=504.2 (M+H), 252.6 (M/2+H), t=2.495 min.

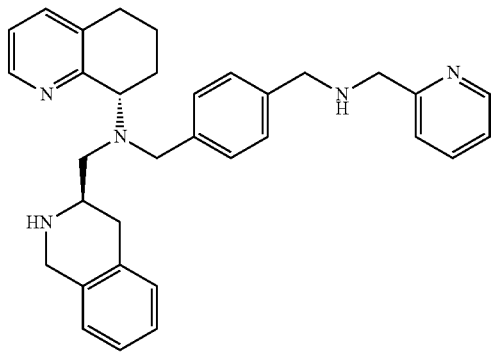 [SMILES: c1ccc(CNCc2ccc(CN(C[C@H]3Cc4ccccc4CN3)[C@H]3CCCc4cccnc43)cc2)nc1]

266

EMU220: (S)—N-(4-(((pyridin-2-ylmethyl)amino)methyl)benzyl)-N—(((R)-1,2,3,4-tetrahydroisoquinolin-3-yl)methyl)-5,6,7,8-tetrahydroquinolin-8-amine

Synthesis was carried out according to the General Deprotection Protocol. Purified via column chromatography (CombiFlash, 12 g column, 25 mL/min) eluting with 100:10:1 DCM/MeOH/NH$_4$OH to yield a white foam (106 mg, 0.210 mmol, 70% yield). $^1$H NMR (500 MHz, CDCl$_3$) δ 8.56-8.57 (m, 1H), 8.51 (d, J=4.5 Hz, 1H), 7.63 (dt, J=1.8 Hz, J=7.8 Hz, 1H), 7.43 (d, J=8.0 Hz, 2H), 7.29-7.34 (m, 4H), 7.15-7.17 (m, 1H), 7.02-7.07 (m, 3H), 6.94-7.01 (m, 2H), 4.42 (d, J=14.0 Hz, 1H), 4.10 (dd, J=6.5 Hz, J=10.0 Hz, 1H), 3.94 (dd, J=15.0 Hz, J=17.5 Hz, 2H), 3.92 (s, 2H), 3.84 (s, 2H), 3.68 (d, J=14.5 Hz, 1H), 2.73-2.91 (m, 3H), 2.63-2.71 (m, 2H), 2.55 (dd, J=3.5 Hz, J=16.0 Hz, 1H), 2.35-2.44 (m, 2H), 2.11-2.15 (m, 2H), 1.91-1.98 (m, 2H), 1.62-1.71 (m, 1H). $^{13}$C NMR (125 MHz, CDCl$_3$) δ 159.9, 159.0, 149.4, 146.9, 140.8, 138.6, 136.5, 135.8, 134.8, 134.2, 129.1, 128.5 (2C), 128.3 (2C), 126.5, 125.9, 125.5, 122.4, 122.0, 121.4, 62.2, 59.4, 58.0, 54.6, 53.4, 52.1, 48.7, 33.9, 29.7, 29.5, 22.2. HRMS (NSI) m/z=504.31269 (M+H); Theo. for C$_{33}$H$_{37}$N$_5$+H=504.31217. LC-MS (ESI-API, 254 nm) 25-95% MeOH in H$_2$O (0.1% HCO$_2$H), 8 min, 1.00 mL/min, C18 (Agilent Zorbax XDB-18, 50 mm×4.6 mm, 3.5 μm), m/z=504.2 (M+H), 252.6 (M/2+H), t=0.852 min; 10-95% MeOH in H$_2$O (0.1% HCO$_2$H), 10 min, 1.00 mL/min, C18 (Agilent Zorbax XDB-18, 50 mm×4.6 mm, 3.5 μm), m/z=504.2 (M+H), 252.6 (M/2+H), t=3.286 min.

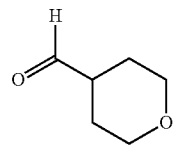

1) Ti(OiPr)$_4$, NaBH$_4$, DCM, MeOH, rt, 4 hrs, 40% yield
2) TFA, DCM, rt, ovn, 75% yield

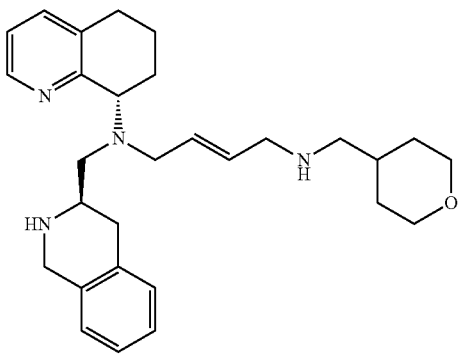

-continued

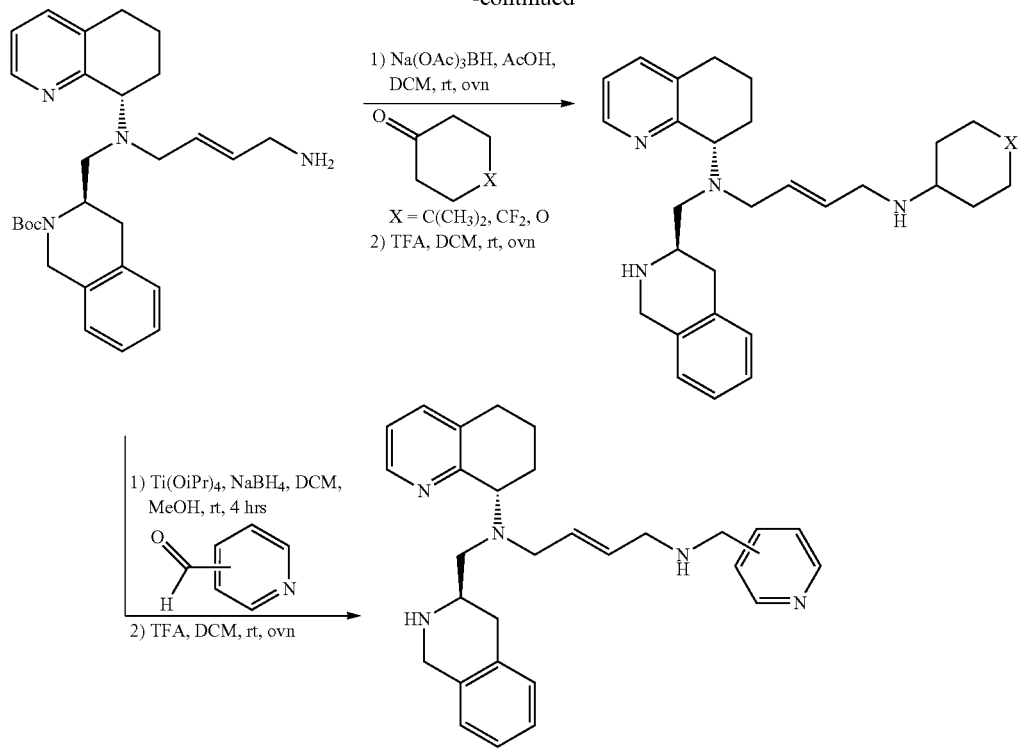

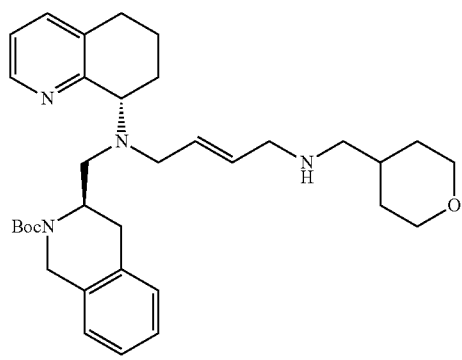 [SMILES: CC(C)(C)OC(=O)N1Cc2ccccc2C[C@@H]1CN(C/C=C/CNCC1CCOCC1)[C@H]1CCCc2cccnc21]

tert-butyl (R)-3-((((E)-4-(((tetrahydro-2H-pyran-4-yl)methyl)amino)but-2-en-1-yl)((S)-5,6,7,8-tetrahydroquinolin-8-yl)amino)methyl)-3,4-dihydroisoquinoline-2(1H)-carboxylate Synthesis was carried out according to General Reductive Amination Protocol B. Purified via column chromatography (CombiFlash, 24 g column, 30 mL/min) eluting with the following gradient to yield a clear oil (120 mg, 0.214 mmol, 40% yield): 0-3 min: 0% 100:10:1 DCM/MeOH/NH$_4$OH in DCM; 3-18 min: 0-100% 100:10:1 DCM/MeOH/NH$_4$OH in DCM; 18-30 min: 100% 100:10:1 DCM/MeOH/NH$_4$OH. $^1$H NMR (500 MHz, CDCl$_3$) δ 8.39 (d, J=14.0 Hz, 1H), 7.24 (d, J=7.0 Hz, 1H), 7.05-7.10 (m, 2H), 6.97 (m, 3H), 5.58-5.70 (m, 2H), 4.45-4.69 (m, 2H), 4.04-4.09 (m, 1H), 3.95-3.97 (m, 3H), 3.35-3.41 (m, 3H), 3.09-3.19 (m, 3H), 2.91-3.00 (m, 2H), 2.65-2.71 (m, 1H), 2.49-2.61 (m, 3H) 2.46 (d, J=6.5 Hz, 2H), 1.91-1.98 (m, 2H), 1.53-1.77 (m, 6H), 1.49 (s, 9H), 1.28 (ddd, J=4.5 Hz, J=12.3 Hz, J=24.0 Hz, 2H).

HRMS (NSI) m/z=561.37977 (M+H); Theo. for C$_{34}$H$_{48}$N$_4$O$_3$+H=561.37992. LC-MS (ESI-API, 254 nm) 50-95% MeOH in H$_2$O (0.1% HCO$_2$H), 8 min, 1.00 mL/min, C18 (Agilent Zorbax XDB-18, 50 mm×4.6 mm, 3.5 μm), m/z=561.2 (M+H), 281.2 (M/2+H), t=0.793 min; 25-95% MeOH in H$_2$O (0.1% HCO$_2$H), 8 min, 1.00 mL/min, C18 (Agilent Zorbax XDB-18, 50 mm×4.6 mm, 3.5 μm), m/z=561.2 (M+H), 281.2 (M/2+H), t=3.987 min.

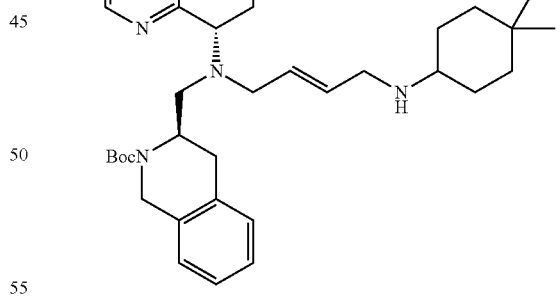

tert-butyl (R)-3-((((E)-4-((4,4-dimethylcyclohexyl)amino)but-2-en-1-yl)((S)-5,6,7,8-tetrahydroquinolin-8-yl)amino)methyl)-3,4-dihydroisoquinoline-2(1H)-carboxylate Synthesis was carried out according to General Reductive Amination Protocol C. Purified via column chromatography (CombiFlash, 24 g column, 30 mL/min) eluting with the following gradient to yield a clear oil (173 mg, 0.302 mmol, 63% yield): 0-3 min: 0% 100:10:1 DCM/MeOH/NH$_4$OH in DCM; 3-18 min: 0-100% 100:10:1 DCM/MeOH/NH$_4$OH in DCM; 18-30 min: 100% 100:10:1 DCM/MeOH/NH$_4$OH. $^1$H NMR (500 MHz, CDCl$_3$) δ 4.39 (d, J=14.5 Hz, 1H), 7.24 (d, J=7.5 Hz, 1H), 7.05-7.10 (m, 2H), 6.97 (m, 3H), 5.58-5.67 (m, 2H), 4.44-4.69 (m, 2H), 4.07 (app t, J=16.5 Hz, 1H), 3.97 (app t, J=7.0 Hz, 1H), 3.34-3.41 (m, 1H), 3.18 (d, J=5.0 Hz, 2H), 3.11 (dd, J=5.5 Hz, J=14.0 Hz, 1H), 2.91-3.00 (m, 2H), 2.65-2.72 (m, 1H), 2.48-2.62 (m, 3H), 2.35-2.39 (m, 1H), 1.92-1.98 (m, 2H), 1.58-1.77 (m, 5H), 1.50 (s, 9H), 1.36-1.39 (m, 2H), 1.15-1.29 (m, 4H), 0.89 (s, 3H), 0.89 (s, 3H). HRMS (NSI) m/z=573.41600 (M+H); Theo. for C$_{36}$H$_{52}$N$_4$O$_2$+H=573.41630. LC-MS (ESI-API, 254 nm) 25-95% MeOH in H$_2$O (0.1% HCO$_2$H), 8 min, 1.00 mL/min, C18 (Agilent Zorbax XDB-18, 50 mm×4.6 mm, 3.5 µm), m/z=573.2 (M+H), 287.2 (M/2+H), t=2.102 min; 25-95% MeOH in H$_2$O (0.1% HCO$_2$H), 8 min, 1.00 mL/min, C18 (Agilent Zorbax XDB-18, 50 mm×4.6 mm, 3.5 µm), m/z=574.2 (M+H), 287.2 (M/2+H), t=5.200 min.

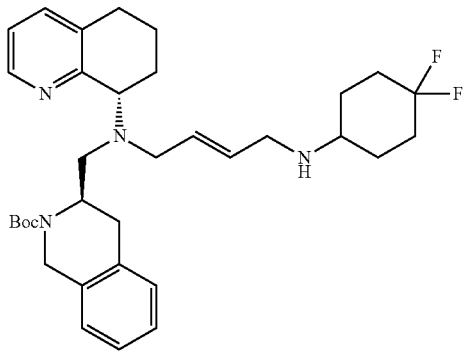 [SMILES: CC(C)(C)OC(=O)N1Cc2ccccc2C[C@@H]1CN(C/C=C/CNC1CCC(F)(F)CC1)[C@H]1CCCc2cccnc21]

Tert-butyl (R)-3-((((E)-4-((4,4-difluorocyclohexyl)amino)but-2-en-1-yl)((S)-5,6,7,8-tetrahydroquinolin-8-yl)amino)methyl)-3,4-dihydroisoquinoline-2(1H)-carboxylate Synthesis was carried out according to General Reductive Amination Protocol C. Purified via column chromatography (CombiFlash, 24 g column, 30 mL/min) eluting with the following gradient to yield a clear oil (143 mg, 0.246 mmol, 51% yield): 0-3 min: 0% 100:10:1 DCM/MeOH/NH$_4$OH in DCM; 3-18 min: 0-100% 100:10:1 DCM/MeOH/NH$_4$OH in DCM; 18-30 min: 100% 100:10:1 DCM/MeOH/NH$_4$OH. $^1$H NMR (500 MHz, CDCl$_3$) δ 8.39 (d, J=13.5 Hz, 1H), 7.25 (d, J=7.0 Hz, 1H), 7.06-7.10 (m, 2H), 6.98 (m, 3H), 5.58-5.70 (m, 2H), 4.46-4.70 (m, 2H), 4.07 (app t, J=15.5 Hz, 1H), 3.96 (br s, 1H), 3.36-3.37 (m, 1H), 3.17 (d, J=5.5 Hz, 2H), 3.12 (dd, J=5.8 Hz, J=14.3 Hz, 1H), 2.91-3.00 (m, 2H), 2.51-2.71 (m, 5H), 2.06-2.13 (m, 2H), 1.86-1.99 (m, 4H), 1.67-1.80 (m, 4H), 1.57-1.64 (m, 1H), 1.42-1.53 (m, 11H). HRMS (NSI) m/z=581.36530 (M+H); Theo. for C$_{34}$H$_{46}$F$_2$N$_4$O$_2$+H=581.36616. LC-MS (ESI-API, 254 nm) 50-95% MeOH in H$_2$O (0.1% HCO$_2$H), 8 min, 1.00 mL/min, C18 (Agilent Zorbax XDB-18, 50 mm×4.6 mm, 3.5 µm), m/z=581.2 (M+H), 291.2 (M/2+H), t=1.106 min; 25-95% MeOH in H$_2$O (0.1% HCO$_2$H), 8 min, 1.00 mL/min, C18 (Agilent Zorbax XDB-18, 50 mm×4.6 mm, 3.5 µm), m/z=581.2 (M+H), 291.1 (M/2+H), t=4.471 min.

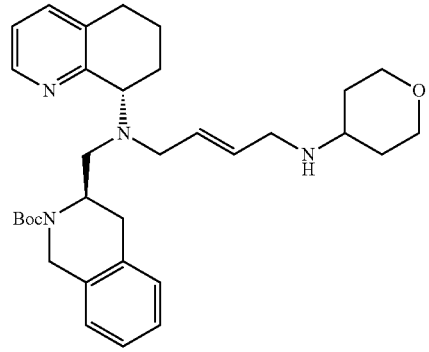 [SMILES: CC(C)(C)OC(=O)N1Cc2ccccc2C[C@@H]1CN(C/C=C/CNC1CCOCC1)[C@H]1CCCc2cccnc21]

Tert-butyl (R)-3-((((E)-4-((tetrahydro-2H-pyran-4-yl)amino)but-2-en-1-yl)((S)-5,6,7,8-tetrahydroquinolin-8-yl)amino)methyl)-3,4-dihydroisoquinoline-2 (1H)-carboxylate Synthesis was carried out according to General Reductive Amination Protocol C. Purified via column chromatography (CombiFlash, 24 g column, 30 mL/min) eluting with the following gradient to yield a clear oil (160 mg, 0.160 mmol, 61% yield): 0-3 min: 0% 100:10:1 DCM/MeOH/NH$_4$OH in DCM; 3-18 min: 0-100% 100:10:1 DCM/MeOH/NH$_4$OH in DCM; 18-30 min: 100% 100:10:1 DCM/MeOH/NH$_4$OH. $^1$H NMR (500 MHz, CDCl$_3$) δ 8.38 (d, J=13.5 Hz, 1H), 7.24 (d, J=5.5 Hz, 1H), 7.05-7.09 (m, 2H), 6.97 (m, 3H), 5.59-5.70 (m, 2H), 4.45-4.69 (m, 2H), 4.07 (app t, J=14.5 Hz, 1H), 3.95-3.97 (m, 3H), 3.34-3.39 (m, 3H), 3.20 (d, J=4.5 Hz, 2H), 3.11 (dd, J=5.3 Hz, J=14.3 Hz, 1H), 2.91-3.00 (m, 2H), 2.50-2.68 (m, 5H), 1.91-1.98 (m, 2H), 1.70-1.82 (m, 4H), 1.57-1.64 (m, 1H), 1.45-1.54 (m, 9H), 1.36-1.41 (m, 2H). HRMS (NSI) m/z=547.36397 (M+H); Theo. for C$_{33}$H$_{46}$N$_4$O$_3$+H=547.36427. LC-MS (ESI-API, 254 nm) 50-95% MeOH in H$_2$O (0.1% HCO$_2$H), 8 min, 1.00 mL/min, C18 (Agilent Zorbax XDB-18, 50 mm×4.6 mm, 3.5 µm), m/z=547.2 (M+H), 274.2 (M/2+H), t=0.859 min; 25-95% MeOH in H$_2$O (0.1% HCO$_2$H), 8 min, 1.00 mL/min, C18 (Agilent Zorbax XDB-18, 50 mm×4.6 mm, 3.5 µm), m/z=547.2 (M+H), 274.2 (M/2+H), t=4.085 min.

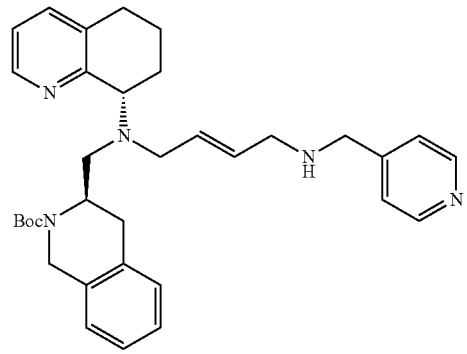 [SMILES: CC(C)(C)OC(=O)N1Cc2ccccc2C[C@@H]1CN(C/C=C/CNCc1cccnc1)[C@H]1CCCc2cccnc21]

Tert-butyl (R)-3-((((E)-4-((pyridin-4-ylmethyl)amino)but-2-en-1-yl)((S)-5,6,7,8-tetrahydroquinolin-8-yl)amino)methyl)-3,4-dihydroisoquinoline-2(1H)-carboxylate Synthesis was carried out according to General Reductive Amination Protocol B. Purified via column chromatography (CombiFlash, 24 g column, 30 mL/min) eluting with the following gradient to yield a yellow foam (175 mg, 0.316 mmol, 59% yield): 0-3 min: 0% 100:10:1 DCM/MeOH/NH$_4$OH in DCM; 3-18 min: 0-100% 100:10:1 DCM/MeOH/NH$_4$OH in DCM; 18-30 min: 100% 100:10:1 DCM/MeOH/NH$_4$OH. $^1$H NMR (500 MHz, CDCl$_3$) δ 8.54 (dd, J=1.5 Hz, J=4.5 Hz, 2H), 8.38 (d, J=14.5 Hz, 1H), 7.25 (m, 3H), 7.04-7.06 (m, 2H), 6.97 (m, 3H), 5.61-5.71 (m, 2H), 4.47-4.70 (m, 2H), 4.09 (app t, J=15.8 Hz, 1H), 3.96-3.97 (m, 1H), 3.76 (s, 2H), 3.31-3.37 (m, 1H), 3.10-3.17 (m, 3H), 2.91-3.01 (m, 2H), 2.53-2.68 (m, 4H), 1.91-2.00 (m, 2H), 1.71-1.77 (m, 2H), 1.53-1.65 (m, 1H), 1.48 (s, 9H). HRMS (NSI) m/z=554.34869 (M+H); Theo. for C$_{34}$H$_{43}$N$_5$O$_2$+H=554.34895. LC-MS (ESI-API, 254 nm) 50-95% MeOH in H$_2$O (0.1% HCO$_2$H), 8 min, 1.00 mL/min, C18 (Agilent Zorbax XDB-18, 50 mm×4.6 mm, 3.5 μm), m/z=554.2 (M+H), 277.6 (M/2+H), t=0.861 min; 25-95% MeOH in H$_2$O (0.1% HCO$_2$H), 8 min, 1.00 mL/min, C18 (Agilent Zorbax XDB-18, 50 mm×4.6 mm, 3.5 μm), m/z=554.2 (M+H), 277.6 (M/2+H), t=3.979 min.

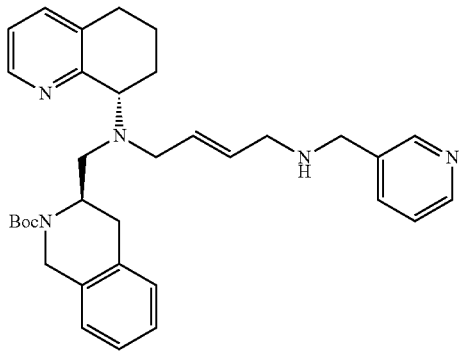

Tert-butyl (R)-3-((((E)-4-((pyridin-3-ylmethyl)amino)but-2-en-1-yl)((S)-5,6,7,8-tetrahydroquinolin-8-yl)amino)methyl)-3,4-dihydroisoquinoline-2(1H)-carboxylate Synthesis was carried out according to General Reductive Amination Protocol B. Purified via column chromatography (CombiFlash, 24 g column, 30 mL/min) eluting with the following gradient to yield a yellow foam (188 mg, 0.340 mmol, 63% yield): 0-3 min: 0% 100:10:1 DCM/MeOH/NH$_{40}$OH in DCM; 3-18 min: 0-100% 100:10:1 DCM/MeOH/NH$_{40}$OH in DCM; 18-30 min: 100% 100:10:1 DCM/MeOH/NH$_{40}$OH. $^1$H NMR (500 MHz, CDCl$_3$) δ 8.54 (d, J=1.5 Hz, 1H), 8.51 (dd, J=1.8 Hz, J=4.8 Hz, 1H), 8.39 (d, J=15.5 Hz, 1H), 7.67 (m, 1H), 7.24-7.26 (m, 2H), 7.03-7.06 (m, 2H), 6.97 (m, 3H), 5.60-5.70 (m, 2H), 4.46-4.70 (m, 2H), 4.09 (app t, J=16.0 Hz, 1H), 3.97 (dd, J=6.0 Hz, J=8.0 Hz, 1H), 3.75 (s, 2H), 3.31-3.38 (m, 1H), 3.18 (d, J=5.5 Hz, 2H), 3.11 (dd, J=5.8 Hz, J=14.3 Hz, 1H), 2.92-3.01 (m, 2H), 2.52-2.72 (m, 4H), 1.92-2.00 (m, 2H), 1.74 (dd, J=10.0 Hz, J=21.0 Hz, 1H), 1.58-1.66 (m, 2H), 1.48 (s, 9H). HRMS (NSI) m/z=554.34895 (M+H); Theo. for C$_{34}$H$_{43}$N$_5$O$_2$+H=554.34895. LC-MS (ESI-API, 254 nm) 50-95% MeOH in H$_2$O (0.1% HCO$_2$H), 8 min, 1.00 mL/min, C18 (Agilent Zorbax XDB-18, 50 mm×4.6 mm, 3.5 μm), m/z=554.2 (M+H), 277.6 (M/2+H), t=0.932 min; 25-95% MeOH in H$_2$O (0.1% HCO$_2$H), 8 min, 1.00 mL/min, C18 (Agilent Zorbax XDB-18, 50 mm×4.6 mm, 3.5 μm), m/z=554.2 (M+H), 277.6 (M/2+H), t=4.144 min.

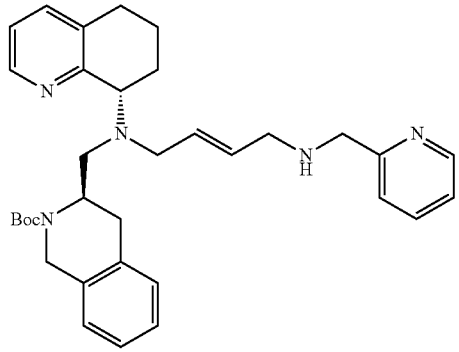 [SMILES: CC(C)(C)OC(=O)N1Cc2ccccc2C[C@@H]1CN(C/C=C/CNCc1ccccn1)[C@H]1CCCc2cccnc21]

Tert-butyl (R)-3-((((E)-4-((pyridin-2-ylmethyl)amino)but-2-en-1-yl)((S)-5,6,7,8-tetrahydroquinolin-8-yl)amino)methyl)-3,4-dihydroisoquinoline-2(1H)-carboxylate Synthesis was carried out according to General Reductive Amination Protocol B. Purified via column chromatography (CombiFlash, 24 g column, 30 mL/min) eluting with the following gradient to yield a yellow foam (161 mg, 0.291 mmol, 54% yield): 0-3 min: 0% 100:10:1 DCM/MeOH/NH$_4$OH in DCM; 3-18 min: 0-100% 100:10:1 DCM/MeOH/NH$_4$OH in DCM; 18-30 min: 100% 100:10:1 DCM/MeOH/NH$_4$OH. $^1$H NMR (500 MHz, CDCl$_3$) δ 8.56 (dd, J=0.8 Hz, J=4.8 Hz, 1H), 8.38 (d, J=12.5 Hz, 1H), 7.64 (dt, J=1.8 Hz, J=7.6 Hz, 1H), 7.24-7.29 (m, 2H), 7.16 (dd, J=5.3 Hz, J=6.8 Hz, 1H), 7.04-7.07 (m, 2H), 6.97 (m, 3H), 5.61-5.71 (m, 2H), 4.45-4.69 (m, 2H), 4.07 (app t, J=16.5 Hz, 1H), 3.98 (m, 1H), 3.86 (s, 2H), 3.32-3.40 (m, 1H), 3.18-3.25 (m, 2H), 3.11 (dd, J=5.5 Hz, J=14.5 Hz, 1H), 2.91-3.02 (m, 2H), 2.51-2.72 (m, 4H), 1.92-2.00 (m, 3H), 1.74 (dd, J=10.0 Hz, J=21.0 Hz, 1H), 1.57-1.65 (m 1H), 1.49 (s, 9H). HRMS (NSI) m/z=554.34870 (M+H); Theo. for C$_{34}$H$_{43}$N$_5$O$_2$+H=554.34895. LC-MS (ESI-API, 254 nm) 50-95% MeOH in H$_2$O (0.1% HCO$_2$H), 8 min, 1.00 mL/min, C18 (Agilent Zorbax XDB-18, 50 mm×4.6 mm, 3.5 μm), m/z=554.2 (M+H), 277.6 (M/2+H), t=1.029 min; 25-95% MeOH in H$_2$O (0.1% HCO$_2$H), 8 min, 1.00 mL/min, C18 (Agilent Zorbax XDB-18, 50 mm×4.6 mm, 3.5 μm), m/z=554.2 (M+H), 277.6 (M/2+H), t=4.339 min.

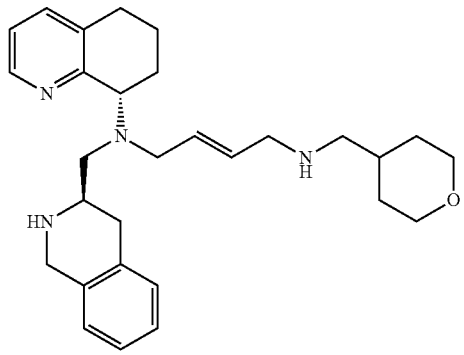 [SMILES: C(=C\CN(C[C@H]1Cc2ccccc2CN1)[C@H]1CCCc2cccnc21)/CNCC1CCOCC1]

EMU180: (E)-N1-((tetrahydro-2H-pyran-4-yl)methyl)-N4-(((R)-1,2,3,4-tetrahydroisoquinolin-3-yl)methyl)-N4-((S)-5,6,7,8-tetrahydroquinolin-8-yl)but-2-ene-1,4-diamine Synthesis was carried out according to the General Deprotection Protocol. Purified via column chromatography (CombiFlash, 12 g column, 25 mL/min) eluting with the following gradient to yield a clear oil (74.0 mg, 0.161 mmol, 75% yield): 0-3 min: 0% 100:10:1 DCM/MeOH/NH$_4$OH in DCM; 3-18 min: 0-100% 100:10:1 DCM/MeOH/NH$_4$OH in DCM; 18-30 min: 100% 100:10:1 DCM/MeOH/NH$_4$OH. $^1$H NMR (500 MHz, CDCl$_3$) δ 8.46 (dd, J=1.3 Hz, J=4.8 Hz, 1H), 7.32 (m, 1H), 7.07-7.09 (m, 2H), 7.02-7.06 (m, 2H), 6.97-7.01 (m, 1H), 5.69-5.78 (m, 2H), 4.10 (dd, J=6.3 Hz, J=9.8 Hz, 1H), 4.01 (d, J=10.5 Hz, 1H), 3.94 (dt, J=2.0 Hz, J=11.5 Hz, 2H), 3.82 (d, J=15.0 Hz, 1H), 3.63 (dd, J=5.3 Hz, J=14.3 Hz, 1H), 3.32-3.38 (m, 3H), 3.22 (d, J=4.5 Hz, 2H), 2.87 (dd, J=3.5 Hz, J=13.0 Hz, 1H), 2.71-2.80 (m, 2H), 2.65-2.68 (m, 1H), 2.60 (dd, J=3.5 Hz, J=16.0 Hz, 1H), 2.47 (d, J=7.0 Hz, 2H), 2.37-2.44 (m, 3H), 2.05-2.09 (m, 1H), 1.94-2.01 (m, 1H), 1.87-1.93 (m, 1H), 1.63-1.74 (m, 2H), 1.58-1.61 (m, 2H), 1.22-1.30 (m, 3H). $^{13}$C NMR (125 MHz, CDCl$_3$) δ 158.7, 146.9, 136.6, 135.7, 134.8, 134.0, 131.9, 130.3, 129.2, 126.5, 126.0, 125.6, 121.5, 68.0 (2C), 61.3, 57.2, 56.6, 55.7, 52.1, 51.7, 48.7, 35.5, 33.9, 31.4 (2C), 29.5, 28.1, 22.0. HRMS (NSI) m/z=461.32697 (M+H); Theo. for C$_{29}$H$_{40}$N$_4$O+H=461.32749. LC-MS (ESI-API, 254 nm) 25-95% MeOH in H$_2$O (0.1% HCO$_2$H), 8 min, 1.00 mL/min, C18 (Agilent Zorbax XDB-18, 50 mm×4.6 mm, 3.5 μm), m/z=461.2 (M+H), 231.2 (M/2+H), t=0.535 min; 10-95% MeOH in H$_2$O (0.1% HCO$_2$H), 10 min, 1.00 mL/min, C18 (Agilent Zorbax XDB-18, 50 mm×4.6 mm, 3.5 μm), m/z=461.2 (M+H), 231.2 (M/2+H), t=1.198 min.

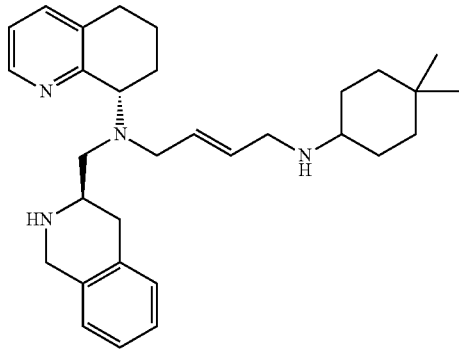 [SMILES: CC1(C)CCC(NC/C=C/CN(C[C@H]2Cc3ccccc3CN2)[C@H]2CCCc3cccnc32)CC1]

EMU153: (E)-N1-(4,4-dimethylcyclohexyl)-N4-(((R)-1,2,3,4-tetrahydroisoquinolin-3-yl)methyl)-N4-((S)-5,6,7,8-tetrahydroquinolin-8-yl)but-2-ene-1,4-diamine Synthesis was carried out according to the General Deprotection Protocol. Purified via column chromatography (CombiFlash, 12 g column, 25 mL/min) eluting with the following gradient to yield a clear oil (27.0 mg, 0.057 mmol, 19% yield): 0-3 min: 0% 100:10:1 DCM/MeOH/NH$_4$OH in DCM; 3-18 min: 0-100% 100:10:1 DCM/MeOH/NH$_4$OH in DCM; 18-30 min: 100% 100:10:1 DCM/MeOH/NH$_4$OH. $^1$H NMR (500 MHz, CDCl$_3$) δ 8.45 (dd, J=1.0 Hz, J=4.5 Hz, 1H), 7.31 (d, J=7.0 Hz, 1H), 7.06-7.09 (m, 2H), 6.98-7.05 (m, 3H), 5.69-5.77 (m, 2H), 4.10 (dd, J=6.3 Hz, J=9.8 Hz, 1H), 4.00 (d, J=15.0 Hz, 1H), 3.81 (d, J=15.0 Hz, 1H), 3.59-3.63 (m, 1H), 3.28-3.32 (m, 1H), 3.21-3.25 (m, 2H), 2.88 (dd, J=3.0 Hz, J=13.0 Hz, 1H), 2.70-2.79 (m, 2H), 2.64-2.67 (m, 1H), 2.59 (dd, J=3.5 Hz, J=16.0 Hz, 1H), 2.36-2.44 (m, 5H), 2.04-2.09 (m, 1H), 1.94-2.01 (m, 1H), 1.87-1.92 (m, 1H), 1.66-1.74 (m, 3H), 1.33-1.38 (m, 2H), 1.21-1.29 (m, 3H), 1.12-1.19 (m, 1H), 0.88 (s, 3H), 0.87 (s, 3H). $^{13}$C NMR (125 MHz, CDCl$_3$) δ 158.8, 147.0, 136.7, 135.8, 134.8, 134.1, 131.6, 130.8, 129.2, 126.6, 126.0, 125.6, 121.6, 61.2, 57.2, 56.6, 53.6, 52.2, 48.8, 48.7, 38.0, 38.0, 33.9, 32.4, 30.3, 29.6, 29.4 (2C), 28.1, 24.8, 22.1. HRMS (NSI) m/z=473.36329 (M+H); Theo. for C$_{31}$H$_{44}$N$_4$+H=473.36387. LC-MS (ESI-API, 254 nm) 25-95% MeOH in H$_2$O (0.1% HCO$_2$H), 8 min, 1.00 mL/min, C18 (Agilent Zorbax XDB-18, 50 mm×4.6 mm, 3.5 μm), m/z=473.2 (M+H), 237.2 (M/2+H), t=2.547 min; 10-95% MeOH in H$_2$O (0.1% HCO$_2$H), 10 min, 1.00 mL/min, C18 (Agilent Zorbax XDB-18, 50 mm×4.6 mm, 3.5 μm), m/z=473.2 (M+H), 237.2 (M/2+H), t=4.437 min.

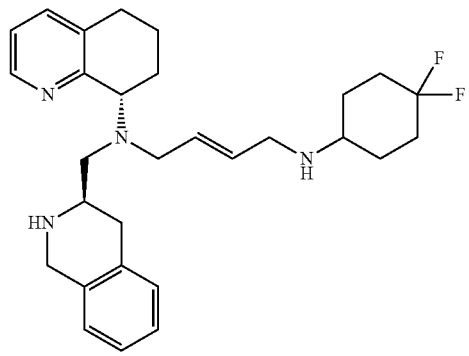 [SMILES: FC1(F)CCC(NC/C=C/CN(C[C@H]2Cc3ccccc3CN2)[C@H]2CCCc3cccnc32)CC1]

EMU154: (E)-N1-(4,4-difluorocyclohexyl)-N4-(((R)-1,2,3,4-tetrahydroisoquinolin-3-yl)methyl)-N4-((S)-5,6,7,8-tetrahydroquinolin-8-yl)but-2-ene-1,4-diamine Synthesis was carried out according to the General Deprotection Protocol. Purified via column chromatography (CombiFlash, 12 g column, 25 mL/min) eluting with the following gradient to yield a clear oil (116 mg, 0.241 mmol, 98% yield): 0-3 min: 0% 100:10:1 DCM/MeOH/NH$_4$OH in DCM; 3-18 min: 0-100% 100:10:1 DCM/MeOH/NH$_4$OH in DCM; 18-30 min: 100% 100:10:1 DCM/MeOH/NH$_{40}$OH. $^1$H NMR (500 MHz, CDCl$_3$) δ 8.46 (dd, J=1.0 Hz, J=4.5 Hz, 1H), 7.32 (dd, J=0.5 Hz, J=7.5 Hz, 1H), 7.06-7.10 (m, 2H), 2.99 (m, 3H), 5.68-5.78 (m, 2H), 4.10 (dd, J=6.3 Hz, J=9.8 Hz, 1H), 4.01 (d, J=15.0 Hz, 1H), 3.82 (d, J=15.0 Hz, 1H), 3.62 (dd, J=6.0 Hz, J=14.0 Hz, 1H), 3.33 (dd, J=5.3 Hz, J=14.3 Hz, 1H), 3.24 (d, J=5.5 Hz, 2H), 2.87 (dd, J=3.5 Hz, J=13.0 Hz, 1H), 2.71-2.80 (m, 2H), 2.70 (m, 1H), 2.58-2.65 (m, 2H), 2.38-2.44 (m, 2H), 1.92-2.13 (m, 5H), 1.86-1.91 (m, 3H), 1.65-1.79 (m, 3H), 1.42-1.49 (m, 2H). $^{13}$C NMR (125 MHz, CDCl$_3$) δ 158.6, 146.9, 136.6, 135.6, 134.7, 134.0, 131.9, 130.3, 129.2, 126.5, 126.0, 125.6, 123.4 (t, J=239.4 Hz), 121.5, 61.2, 57.2, 56.5, 53.5, 52.1, 48.9, 48.6, 33.9, 31.8 (t, J=24.4 Hz, 2C), 29.5, 28.9 (t, J=2.5 Hz), 28.9 (t, J=3.8 Hz), 27.9, 22.0. $^{19}$F NMR (400 MHz, CDCl$_3$, TFA standard) 6-96.8 (app d, J=248.0 Hz), −101.1 (app d, J=220.0 Hz). HRMS (NSI) m/z=481.31303 (M+H); Theo. for C$_{29}$H$_{38}$F$_2$N$_4$+H=481.31373. LC-MS (ESI-API, 254 nm) 25-95% MeOH in H$_2$O (0.1% HCO$_2$H), 8 min, 1.00 mL/min, C18 (Agilent Zorbax XDB-18, 50 mm×4.6 mm, 3.5 µm), m/z=481.2 (M+H), 241.2 (M/2+H), t=0.591 min; 10-95% MeOH in H₂O (0.1% HCO₂H), 10 min, 1.00 mL/min, C18 (Agilent Zorbax XDB-18, 50 mm×4.6 mm, 3.5 µm), m/z=481.2 (M+H), 241.2 (M/2+H), t=2.382 min.

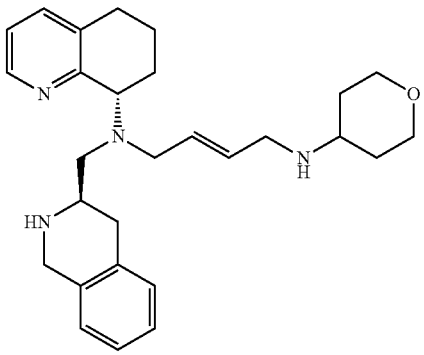 [SMILES: C(=C\CN(C[C@H]1Cc2ccccc2CN1)[C@H]1CCCc2cccnc21)/CNC1CCOCC1]

EMU155: (E)-N1-(tetrahydro-2H-pyran-4-yl)-N4-(((R)-1,2,3,4-tetrahydroisoquinolin-3-yl)methyl)-N4-((S)-5,6,7,8-tetrahydroquinolin-8-yl)but-2-ene-1,4-diamine Synthesis was carried out according to the General Deprotection Protocol. Purified via column chromatography (CombiFlash, 12 g column, 25 mL/min) eluting with the following gradient to yield a clear oil (126 mg, 0.282 mmol, 96% yield): 0-3 min: 0% 100:10:1 DCM/MeOH/NH₄OH in DCM; 3-18 min: 0-100% 100:10:1 DCM/MeOH/NH₄OH in DCM; 18-30 min: 100% 100:10:1 DCM/MeOH/NH₄OH. ¹H NMR (500 MHz, CDCl₃) δ 8.46 (dd, J=1.3 Hz, J=4.8 Hz, 1H), 7.32 (dd, J=0.8 Hz, J=7.8 Hz, 1H), 7.06-7.10 (m, 2H), 6.98-7.05 (m, 3H), 5.69-5.79 (m, 2H), 4.10 (dd, J=6.3 Hz, J=9.8 Hz, 1H), 4.01 (d, J=15.0 Hz, 1H), 3.92-3.97 (m, 2H), 3.81 (d, J=15.0 Hz, 1H), 3.63 (dd, J=5.3 Hz, J=14.3 Hz, 1H), 3.31-3.38 (m, 3H), 3.27 (d, J=5.0 Hz, 2H), 2.88 (dd, J=3.5 Hz, J=13.0 Hz, 1H), 2.58-2.80 (m, 6H), 2.38-2.44 (m, 2H), 2.04-2.09 (m, 1H), 1.94-2.01 (m, 1H), 1.87-1.93 (m, 1H), 1.79-1.82 (m, 2H), 1.65-1.74 (m, 1H), 1.34-1.42 (m, 2H). ¹³C NMR (125 MHz, CDCl₃) δ 158.6, 146.8, 136.5, 135.6, 134.6, 133.9, 131.7, 130.3, 129.1, 126.4, 125.9, 125.5, 121.4, 66.9, 66.8, 61.0, 57.1, 56.4, 53.3, 52.0, 48.6, 48.0, 33.8, 33.7 (2C), 29.4, 27.9, 21.9. HRMS (NSI) m/z=447.31120 (M+H); Theo. for C₂₈H₃₈N₄O+H=447.31184. LC-MS (ESI-API, 254 nm) 25-95% MeOH in H₂O (0.1% HCO₂H), 8 min, 1.00 mL/min, C18 (Agilent Zorbax XDB-18, 50 mm×4.6 mm, 3.5 µm), m/z=447.2 (M+H), 224.2 (M/2+H), t=0.523 min; 10-95% MeOH in H₂O (0.1% HCO₂H), 10 min, 1.00 mL/min, C18 (Agilent Zorbax XDB-18, 50 mm×4.6 mm, 3.5 µm), m/z=447.2 (M+H), 224.2 (M/2+H), t=1.126 min.

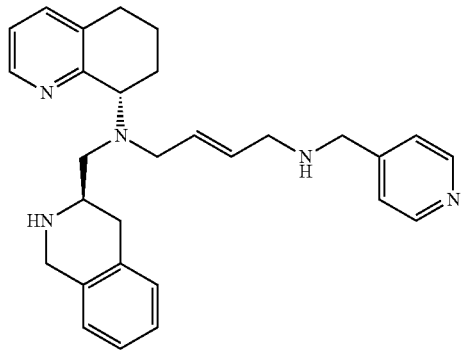 [SMILES: C(=C\CN(C[C@H]1Cc2ccccc2CN1)[C@H]1CCCc2cccnc21)/CNCc1ccncc1]

EMU221: (E)-N1-(pyridin-4-ylmethyl)-N4-(((R)-1,2,3,4-tetrahydroisoquinolin-3-yl)methyl)-N4-((S)-5,6,7,8-tetrahydroquinolin-8-yl)but-2-ene-1,4-diamine Synthesis was carried out according to the General Deprotection Protocol. Purified via column chromatography (CombiFlash, 12 g column, 25 mL/min) eluting with 100:10:1 DCM/MeOH/NH₄OH to yield a yellow oil (137 mg, 0.302 mmol, 96% yield). ¹H NMR (500 MHz, CDCl₃) δ 8.50-8.51 (m, 2H), 8.45 (dd, J=1.5 Hz, J=4.5 Hz, 1H), 7.31 (d, J=7.5 Hz, 1H), 7.22-7.23 (m, 2H), 7.07-7.10 (m, 2H), 7.01-7.06 (m, 2H), 6.98-6.99 (m, 1H), 5.70-5.80 (m, 2H), 4.10 (dd, J=6.5 Hz, J=9.5 Hz, 1H), 4.00 (d, J=15.5 Hz, 1H), 3.82 (d, J=15.0 Hz, 1H), 3.78 (s, 2H), 3.64 (dd, J=5.8 Hz, J=14.3 Hz, 1H), 3.34 (dd, J=5.0 Hz, J=14.0 Hz, 1H), 3.25 (d, J=5.5 Hz, 2H), 2.87 (dd, J=3.5 Hz, J=13.0 Hz, 1H), 2.58-2.80 (m, 5H), 2.37-2.43 (m, 2H), 2.04-2.09 (m, 1H), 1.87-2.00 (m, 2H), 1.65-1.73 (m, 1H), 1.40 (br s, 1H). ¹³C NMR (125 MHz, CDCl₃) δ 158.6, 149.8 (2C), 149.4, 146.9, 136.6, 135.7, 134.7, 134.0, 132.4, 129.7, 129.1, 126.4, 125.9, 125.5, 123.0 (2C), 121.5, 61.2, 57.2, 56.5, 52.1, 51.9, 50.9, 48.7, 33.9, 29.5, 28.1, 21.9. HRMS (NSI) m/z=454.29778 (M+H); Theo. for C₂₉H₃₅N₅+H=454.29652. LC-MS (ESI-API, 254 nm) 25-95% MeOH in H₂O (0.1% HCO₂H), 8 min, 1.00 mL/min, C18 (Agilent Zorbax XDB-18, 50 mm×4.6 mm, 3.5 µm), m/z=454.2 (M+H), 227.6 (M/2+H), t=0.528 min; 10-95% MeOH in H₂O (0.1% HCO₂H), 10 min, 1.00 mL/min, C18 (Agilent Zorbax XDB-18, 50 mm×4.6 mm, 3.5 µm), m/z=454.2 (M+H), 227.8 (M/2+H), t=0.834 min.

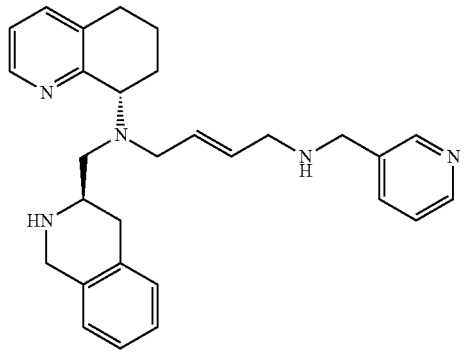 [SMILES: C(=C\CN(C[C@H]1Cc2ccccc2CN1)[C@H]1CCCc2cccnc21)/CNCc1cccnc1]

EMU222: (E)-N1-(pyridin-3-ylmethyl)-N4-(((R)-1,2,3,4-tetrahydroisoquinolin-3-yl)methyl)-N4-((S)-5,6,7,8-tetrahydroquinolin-8-yl)but-2-ene-1,4-diamine Synthesis was carried out according to the General Deprotection Protocol. Purified via column chromatography (CombiFlash, 12 g column, 25 mL/min) eluting with 100:10:1 DCM/MeOH/NH$_4$OH to yield a yellow oil (138 mg, 0.304 mmol, 90% yield). $^1$H NMR (500 MHz, CDCl$_3$) δ 8.53 (d, J=2.0 Hz, 1H), 8.49 (dd, J=1.8 Hz, J=4.8 Hz, 1H), 8.46 (d, J=5.0 Hz, 1H), 7.64-7.66 (m, 1H), 7.31 (d, J=8.0 Hz, 1H), 7.22 (dd, J=4.8 Hz, J=7.8 Hz, 1H), 7.06-7.09 (m, 2H), 7.01-7.05 (m, 2H), 6.98-6.99 (m, 1H), 5.70-5.80 (m, 2H), 4.10 (dd, J=6.3 Hz, J=9.8 Hz, 1H), 4.00 (d, J=15.0 Hz, 1H), 3.82 (d, J=15.0 Hz, 1H), 3.78 (s, 2H), 3.63-3.68 (m, 1H), 3.34 (dd, J=4.8 Hz, J=13.8 Hz, 1H), 3.25 (d, J=5.0 Hz, 2H), 2.87 (dd, J=3.5 Hz, J=13.5 Hz, 1H), 2.58-2.79 (m, 5H), 2.37-2.43 (m, 2H), 2.05-2.09 (m, 1H), 1.87-2.00 (m, 2H), 1.65-1.73 (m, 1H) 1.34 (br s, 1H). $^{13}$C NMR (125 MHz, CDCl$_3$) δ 158.6, 149.7, 148.5, 146.8, 136.5, 135.9, 135.7, 135.6, 134.7, 134.0, 132.3, 129.8, 129.1, 126.4, 125.9, 125.5, 123.4, 121.5, 61.1, 57.2, 56.4, 52.0, 50.8, 50.6, 48.6, 33.8, 29.4, 28.1, 21.9. HRMS (NSI) m/z=454.29690 (M+H); Theo. for C$_{29}$H$_{35}$N$_5$+H=454.29652. LC-MS (ESI-API, 254 nm) 25-95% MeOH in H$_2$O (0.1% HCO$_2$H), 8 min, 1.00 mL/min, C18 (Agilent Zorbax XDB-18, 50 mm×4.6 mm, 3.5 μm), m/z=454.2 (M+H), 227.6 (M/2+H), t=0.534 min; 10-95% MeOH in H$_2$O (0.1% HCO$_2$H), 10 min, 1.00 mL/min, C18 (Agilent Zorbax XDB-18, 50 mm×4.6 mm, 3.5 μm), m/z=454.2 (M+H), 227.6 (M/2+H), t=1.015 min.

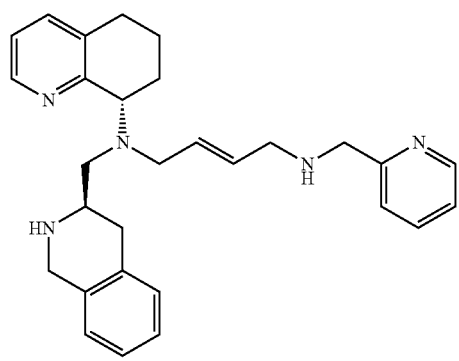 [SMILES: C(=C\CN(C[C@H]1Cc2ccccc2CN1)[C@H]1CCCc2cccnc21)/CNCc1ccccn1]

EMU223: (E)-N1-(pyridin-2-ylmethyl)-N4-(((R)-1,2,3,4-tetrahydroisoquinolin-3-yl)methyl)-N4-((S)-5,6,7,8-tetrahydroquinolin-8-yl)but-2-ene-1,4-diamine Synthesis was carried out according to the General Deprotection Protocol. Purified via column chromatography (CombiFlash, 12 g column, 25 mL/min) eluting with 100:10:1 DCM/MeOH/NH$_4$OH to yield a yellow oil (130 mg, 0.287 mmol, 99% yield). $^1$H NMR (500 MHz, CDCl$_3$) δ 8.53-8.54 (m, 1H), 8.45-8.46 (m, 1H), 7.58-7.62 (m, 1H), 7.31 (d, J=8.0 Hz, 1H), 7.25-7.27 (m, 1H), 7.13-7.15 (m, 1H), 7.05-7.09 (m, 2H), 7.01-7.05 (m, 2H), 6.98-6.99 (m, 1H), 5.73-5.81 (m, 2H), 4.10 (dd, J=6.5 Hz, J=9.5 Hz, 1H), 4.00 (d, J=15.5 Hz, 1H), 3.88 (s, 2H), 3.83 (d, J=15.0 Hz, 1H), 3.68 (dd, J=2.8 Hz, J=15.8 Hz, 1H), 3.33-3.36 (m, 1H), 3.28-3.29 (m, 2H), 2.86 (dd, J=3.0 Hz, J=13.0 Hz, 1H), 2.58-2.79 (m, 5H), 2.37-2.43 (m, 2H), 2.05-2.09 (m, 1H), 1.87-1.99 (m, 2H), 1.65-1.73 (m, 1H). $^{13}$C NMR (125 MHz, CDCl$_3$) δ 159.7, 158.6, 149.3, 146.8, 136.5, 136.4, 135.7, 134.7, 133.9, 132.0, 130.1, 129.1, 126.4, 125.9, 125.4, 122.4, 121.9, 121.4, 61.1, 57.2, 56.4, 54.6, 54.6, 52.0, 51.0, 48.6, 33.8, 29.4, 28.1, 21.9. HRMS (NSI) m/z=454.29750 (M+H); Theo. for C$_{29}$H$_{35}$N$_5$+H=454.29652. LC-MS (ESI-API, 254 nm) 25-95% MeOH in H$_2$O (0.1% HCO$_2$H), 8 min, 1.00 mL/min, C18 (Agilent Zorbax XDB-18, 50 mm×4.6 mm, 3.5 μm), m/z=454.2 (M+H), 227.6 (M/2+H), t=0.551 min; 10-95% MeOH in H$_2$O (0.1% HCO$_2$H), 10 min, 1.00 mL/min, C18 (Agilent Zorbax XDB-18, 50 mm×4.6 mm, 3.5 μm), m/z=454.2 (M+H), 227.8 (M/2+H), t=2.148 min.

Racemic Route: Syntheses of EMU100 (Stereoisomer 1) and EMU100 (Stereoisomer 2)

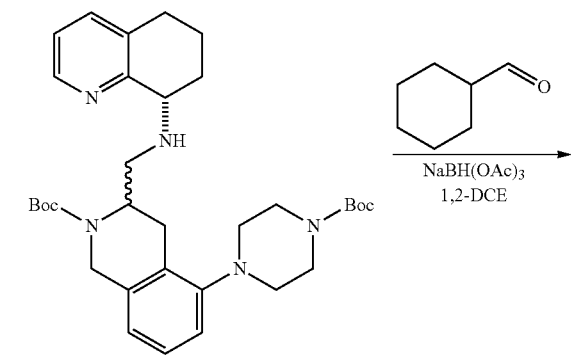

279
-continued

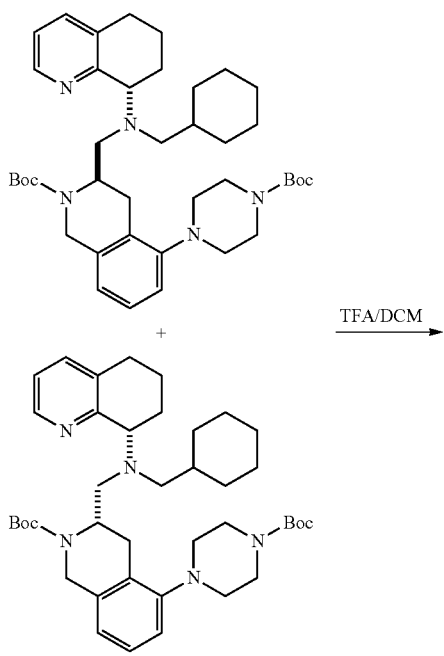

TFA/DCM →

EMU100 (Stereoisomers 1 and 2)

280

2-tert-butyl 3-methyl 5-(4-(tert-butoxycarbonyl)piperazin-1-yl)-3,4-dihydroisoquinoline-2,3(1H)-dicarboxylate

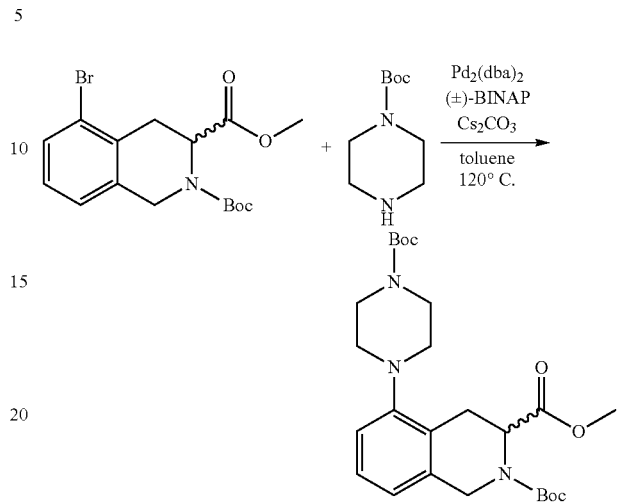

To an oven-dried Biotage 10-20 mL microwave vial equipped with a Teflon-coated magnetic stir bar was charged with racemic 2-tert-butyl 3-methyl 5-bromo-3,4-dihydroisoquinoline-2,3(1H)-dicarboxylate (1.03 g, 2.78 mmol), tert-butyl piperazine-1-carboxylate (0.622 g, 3.34 mmol), Pd$_2$(dba)$_3$ (0.127 g, 0.139 mmol), rac-BINAP (0.260 g, 0.417 mmol), and cesium carbonate (1.269 g, 3.89 mmol). The vial was sealed with a Teflon-lined septum and purged with argon for 5 minutes. Degassed toluene (13.91 mL) was added, and the vessel was degassed with argon for another 5 minutes. The resulting mixture was heated at 120° C. for 48 hours in an oil bath. Upon the completion of the reaction as judged by TLC analysis, the mixture was allowed to cool to room temperature, filtered through a Celite pad, and concentrated to a crude material which was purified by CombiFlash system (40 gram silica column, 5 minutes hexane then 30 minutes 0-30% ethyl acetate) to afford the product as a light yellow gel (1.4011 g, 2.95 mmol, quantitative yield). $^1$H NMR (400 MHz, Chloroform-d) δ 7.13 (td, J=7.8, 4.2 Hz, 1H), 6.98-6.65 (m, 2H), 5.03 (dd, J=6.1, 3.5 Hz, 0.5H), 4.80-4.55 (m, 1.5H), 4.42 (dd, J=34.5, 16.1 Hz, 1H), 3.75-3.39 (m, 7H), 3.15 (ddd, J=52.9, 15.5, 5.9 Hz, 1H), 2.98-2.60 (m, 5H), 1.62-1.27 (m, 18H). HRMS calculated for [C25H37N3O6+H]$^+$: 476.27606, found: 476.27542.

Tert-butyl 5-(4-(tert-butoxycarbonyl)piperazin-1-yl)-3-formyl-3,4-dihydroisoquinoline-2(1H)-carboxylate

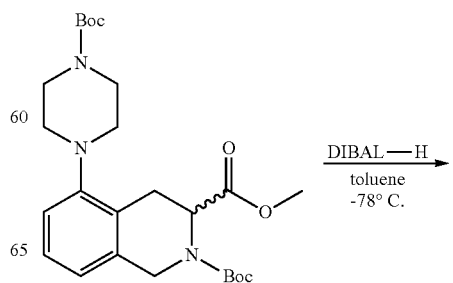

-continued

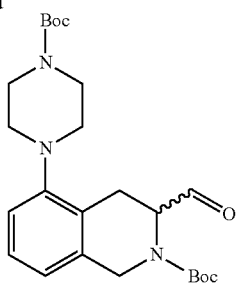

To a 100 mL round-bottom flask containing a Teflon-coated stir bar was charged with racemic 2-tert-butyl 3-methyl 5-(4-(tert-butoxycarbonyl)piperazin-1-yl)-3,4-dihydroisoquinoline-2,3(1H)-dicarboxylate (0.50 g, 1.051 mmol) and anhydrous toluene (13.14 mL). Diisobutylaluminum hydride 1 M solution in toluene (5.26 ml, 5.26 mmol) was added dropwise at −78° C. After 2 h at −78 C, reaction was quenched carefully with methanol under argon atmosphere then allowed to warm to 0° C. A saturated solution of Rochelle salt was added and stirred for 1-2 hour at room temperature. The biphasic mixture was transferred to a separatory funnel. The aqueous layer was separated and extracted with ethyl acetate (2 times). The combined organic extract was dried over anhydrous sodium sulfate and concentrated under reduced pressure to afford the crude aldehyde, which was used for the next step without purification. 1H NMR (400 MHz, Chloroform-d) δ 9.54-9.21 (m, 1H), 7.12 (td, J=7.6, 5.1 Hz, 1H), 6.95-6.69 (m, 2H), 4.91-4.17 (m, 3H), 3.90-3.09 (m, 5H), 3.09-2.50 (m, 5H), 1.64-1.26 (m, 18H).

Tert-butyl 5-(4-(tert-butoxycarbonyl)piperazin-1-yl)-3-((((S)-5,6,7,8-tetrahydroquinolin-8-yl)amino)methyl)-3,4-dihydroisoquinoline-2(1H)-carboxylate tetrahydroquinolin-8-amine (0.105 g, 0.705 mmol), sodium triacetoxyborohydride (0.179 g, 0.846 mmol), and 1,2-dichloroethane (1.349 mL). After stirring for 5 minutes, a solution of racemic tert-butyl 5-(4-(tert-butoxycarbonyl)piperazin-1-yl)-3-formyl-3,4-dihydroisoquinoline-2(1H)-carboxylate (0.2093 g, 0.470 mmol) in 1,2-dichloroethane (1 mL) was added dropwise. The resulting mixture was stirred at room temperature for 48 hours. Upon the completion of the reaction as judged by TLC and LCMS analysis, the mixture was quenched by addition of saturated NaHCO₃. The biphasic mixture was transferred to a separatory funnel. The aqueous layer was separated and extracted with DCM (3 times). The combined organic extract was dried over anhydrous sodium sulfate and concentrated under reduced pressure to a crude material which was purified by CombiFlash system (24 g gold silica column, 5 minutes DCM then 30 minutes 0-10% MeOH/DCM) to afford the inseparable mixture of two diastereomers as a light yellow gel (0.1847 g, 0.320 mmol, 68% yield). ¹H NMR (400 MHz, Chloroform-d) δ 8.29 (d, J=4.5 Hz, 1H), 7.29 (t, J=6.6 Hz, 1H), 7.11 (t, J=7.8 Hz, 1H), 6.99 (dd, J=7.9, 4.6 Hz, 1H), 6.84 (dt, J=10.7, 5.3 Hz, 2H), 4.72-4.19 (m, 3H), 3.75-3.09 (m, 5H), 3.04-2.25 (m, 10H), 2.10-1.77 (m, 2H), 1.60 (t, J=9.8 Hz, 2H), 1.53-1.25 (m, 18H). HRMS calculated for [C33H47N5O4+H]⁺: 578.37063, found: 578.37036.

(R)-tert-butyl 5-(4-(tert-butoxycarbonyl)piperazin-1-yl)-3-(((cyclohexylmethyl)((S)-5,6,7,8-tetrahydroquinolin-8-yl)amino)methyl)-3,4-dihydroisoquinoline-2(1H)-carboxylate and (S)-tert-butyl 5-(1-(tert-butoxycarbonyl)piperidin-4-yl)-3-(((cyclohexylmethyl)((S)-5,6,7,8-tetrahydroquinolin-8-yl)amino)methyl)-3,4-dihydroisoquinoline-2(1H)-carboxylate

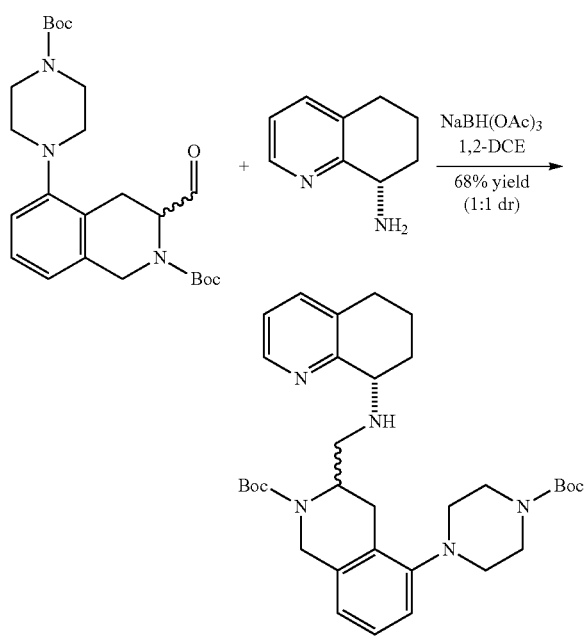

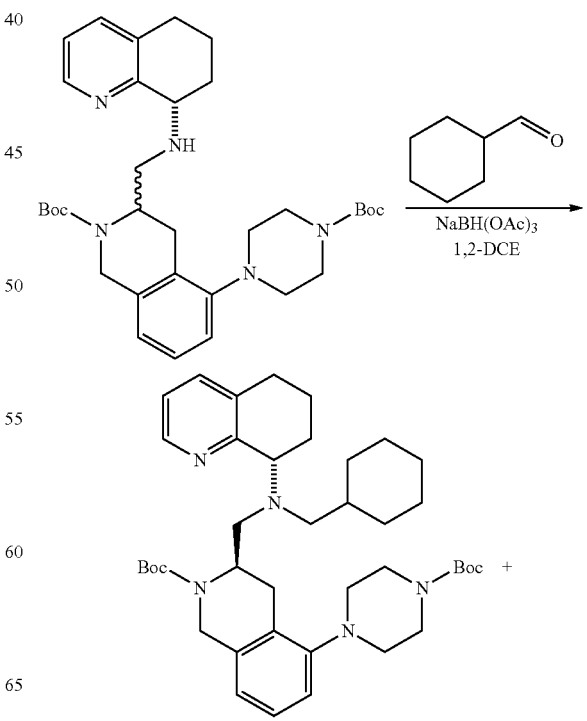

To a 20-mL scintillation vial equipped with a Teflon-coated magnetic stir bar was charged with (S)-5,6,7,8-

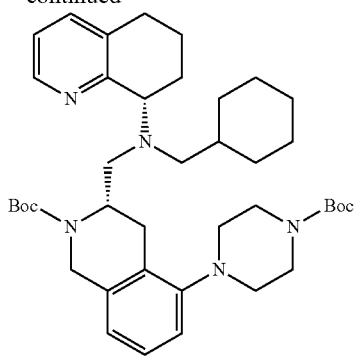

To a 20-mL scintillation vial equipped with a Teflon-coated magnetic stir bar was charged with tert-butyl 5-(4-(tert-butoxycarbonyl)piperazin-1-yl)-3-((((S)-5,6,7,8-tetrahydroquinolin-8-yl)amino)methyl)-3,4-dihydroisoquinoline-2(1H)-carboxylate (1:1 mixture of diastereomers) (0.4899 g, 0.848 mmol), sodium triacetoxyhydroborate (0.323 g, 1.526 mmol), and 1,2-dichloroethane (4.24 mL). After stirring for 5 minutes, cyclohexanecarbaldehyde (0.308 ml, 2.54 mmol) was added dropwise. The resulting mixture was stirred at room temperature for 48-72 hours. Upon the completion of the reaction as judged by TLC and LCMS analysis, the mixture was quenched by addition of 1M NaOH. The biphasic mixture was transferred to a separatory funnel. The aqueous layer was separated and extracted with DCM (3 times). The combined organic extract was dried over anhydrous sodium sulfate and concentrated under reduced pressure to a crude diastereomeric mixture which was separated and purified by CombiFlash system (24 g gold silica column, 5 minutes DCM then 30 minutes 0-10% MeOH/DCM) to afford Stereoisomer 1 (0.2345 g, 0.348 mmol, 41% yield) and Stereoisomer 2 (0.0956 g, 0.142 mmol, 17% yield) as light yellow gel, which was pushed to the deprotection step.

General Procedure for Global Deprotection:

To a 20-mL scintillation vial equipped with a Teflon-coated magnetic stir bar was charged with Boc-protected substrate (1 equiv) and DCM (0.13 M). Trifluoroacetic acid (36 equiv) was added dropwise, and the resulting mixture was stirred at room temperature overnight. Upon the completion of the reaction as judged by LCMS analysis, the mixture was diluted with DCM, cooled in an ice-bath, and quenched by addition of 3M NaOH until pH>12. The biphasic mixture was transferred to a separatory funnel. The aqueous layer was separated and extracted with DCM (3 times). The combined organic extract was dried over anhydrous sodium sulfate and concentrated under reduced pressure to a crude material which was purified by CombiFlash system using a gradient of solvent A (DCM) to solvent B (8:2:0.6 DCM/MeOH/NH$_3$ solution, 7N in MeOH) as eluent on a silica gel column to afford the final product.

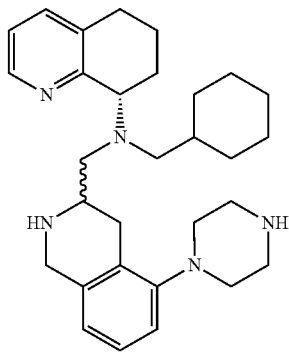 [SMILES: c1cnc2c(c1)CCC[C@@H]2N(CC1CCCCC1)CC1Cc2c(cccc2N2CCNCC2)CN1]

EMU100 (Stereoisomer 1)

White foam. $^1$H NMR (400 MHz, Chloroform-d) δ 8.42 (dd, J=4.7, 1.7 Hz, 1H), 7.30 (dd, J=7.7, 1.7 Hz, 1H), 7.13-6.96 (m, 2H), 6.84 (dt, J=8.0, 1.9 Hz, 1H), 6.80-6.68 (m, 1H), 4.12 (d, J=15.1 Hz, 1H), 4.08-3.96 (m, 2H), 3.11 (dd, J=12.8, 5.3 Hz, 1H), 3.00-2.59 (m, 14H), 2.39-2.28 (m, 2H), 2.10 (dd, J=16.0, 11.1 Hz, 2H), 1.99-1.58 (m, 9H), 1.45-1.37 (m, 1H), 1.25-1.09 (m, 3H), 0.86-0.74 (m, 2H). HRMS calculated for [C30H43N5+H]$^+$: 474.35967, found: 474.35953.

EMU100 (Stereoisomer 2)

White foam. $^1$H NMR (400 MHz, Chloroform-d) δ 8.46 (dd, J=4.8, 1.7 Hz, 1H), 7.30 (dd, J=7.7, 1.7 Hz, 1H), 7.10-7.00 (m, 2H), 6.84 (d, J=7.8 Hz, 1H), 6.76 (d, J=7.6 Hz, 1H), 4.13 (d, J=6.9 Hz, 2H), 3.97 (dd, J=9.8, 5.9 Hz, 1H), 3.04-2.83 (m, 9H), 2.81-2.58 (m, 7H), 2.44 (dd, J=13.1, 6.4 Hz, 1H), 2.29 (ddd, J=27.1, 12.0, 5.9 Hz, 2H), 2.13 (ddt, J=13.0, 5.3, 2.2 Hz, 1H), 2.01-1.90 (m, 2H), 1.78-1.57 (m, 6H), 1.38 (dtd, J=14.4, 7.1, 3.3 Hz, 1H), 1.20-1.06 (m, 3H), 0.74 (ddd, J=25.4, 12.7, 3.1 Hz, 2H). HRMS calculated for [C30H43N5+H]$^+$: 474.35967, found: 474.35881.

These following compounds were obtained according to the above scheme but starting from the enantiomerically pure (R)-2-tert-butyl 3-methyl 5-bromo-3,4-dihydroisoquinoline-2,3(1H)-dicarboxylate, which was prepared in gram scale using literature method by Beadle et al (PCT Int. Appl., 2014193781, 4

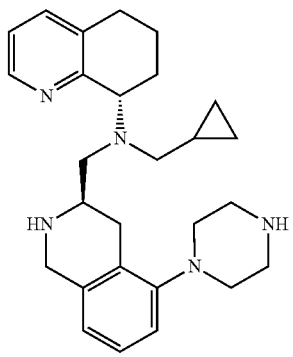 [SMILES: c1cnc2c(c1)CCC[C@@H]2N(CC1CC1)C[C@H]1Cc2c(cccc2N2CCNCC2)CN1]

EMU119

White foam. $^1$H NMR (400 MHz, Chloroform-d) δ 8.48 (dd, J=4.7, 1.7 Hz, 1H), 7.36 (dd, J=7.7, 1.7 Hz, 1H), 7.19-7.02 (m, 2H), 6.91 (dd, J=7.9, 4.1 Hz, 1H), 6.81 (dd, J=7.7, 4.1 Hz, 1H), 4.28 (dd, J=10.3, 6.2 Hz, 1H), 4.18 (d, J=15.2 Hz, 1H), 3.97 (d, J=15.2 Hz, 1H), 3.58-2.56 (m, 18H), 2.32-2.11 (m, 2H), 2.07-1.91 (m, 2H), 1.84-1.71 (m, 1H), 1.04-0.93 (m, 1H), 0.53 (dqt, J=26.1, 8.8, 4.3 Hz, 2H), 0.28-0.01 (m, 2H). HRMS calculated for $[C27H37N5+H]^+$: 432.31272, found: 432.31179.

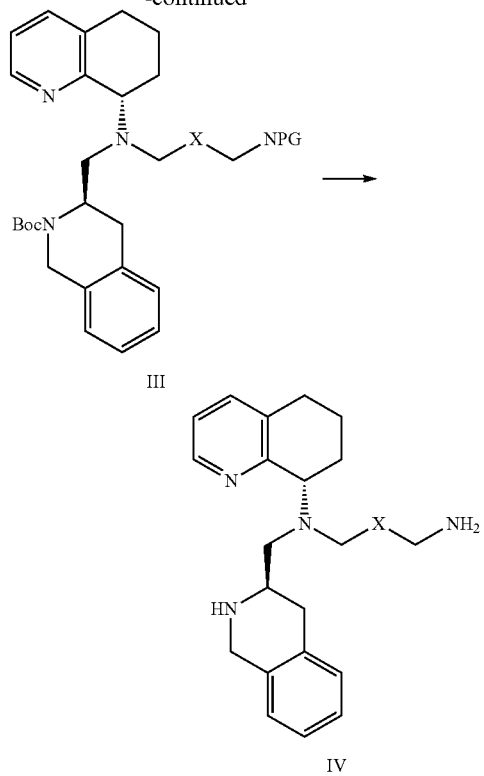

III

IV

Synthesis of EMU030 and EMU031

EMU120

White foam. $^1$H NMR (400 MHz, Chloroform-d) δ 8.43 (dd, J=4.8, 1.7 Hz, 1H), 7.38-7.31 (m, 1H), 7.14-7.04 (m, 2H), 6.88 (dd, J=7.9, 1.1 Hz, 1H), 6.79 (dd, J=7.6, 1.1 Hz, 1H), 4.23-3.96 (m, 3H), 3.12-2.85 (m, 9H), 2.84-2.60 (m, 6H), 2.37 (dd, J=13.5, 8.5 Hz, 1H), 2.16-1.79 (m, 9H), 1.52 (s, 5H), 1.16 (t, J=12.1 Hz, 2H). HRMS calculated for $[C30H41F2N5+H]^+$: 510.34083, found: 510.34065.

TIQ-15 Analogs: Reductive Amination with Secondary Amine

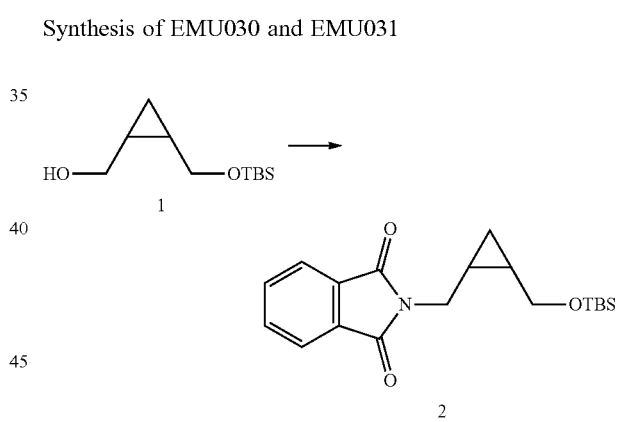

General scheme

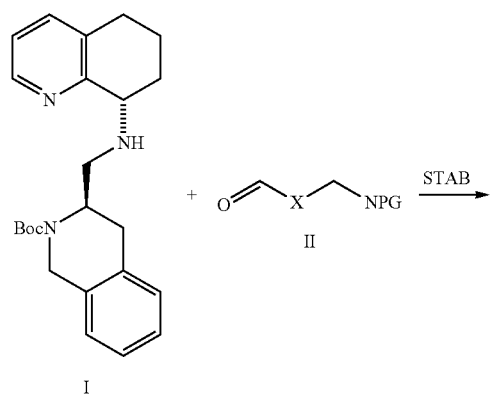

The compound 1 was synthesized from (Z)-but-2-ene-1,4-diol in 32% yield according to the ref. *J. Am. Chem. Soc.* 2009, 131, 4513-4520. A 100 mL rb flask equipped with a stir bar and septum was charged with 939 mg of the alcohol 1 (4.34 mmol, 1 equiv), 766 mg of phtalimide (5.21 mmol. 1.2 equiv), 1.31 g of triphenylphosphine (4.99 mmol, 1.15 equiv) and 22 mL of THF. Then 1.02 mL of DIAD (5.25 mmol, 1.21 equiv) was added at r$_t$. The yellow color disappeared immediately and a clear solution was obtained. After stirring at rt for 2.5 h, the reaction mixture was quenched by addition of water, extracted with $CH_2Cl_2$ (2×), washed with water and brine and dried over $Na_2SO_4$. The crude product was purified on silica gel column using 10% EA in hexanes as eluent affording 1.28 g (85%) of the product 2 as a white solid. $^1$H NMR (400 MHz, CDCl$_3$, ppm) δ: 7.84 (dd, J=5.5, 3.1 Hz, 2H), 7.70 (dd, J=5.5, 3.0 Hz, 2H), 3.97-3.85 (m, 2H), 3.64-3.54 (m, 2H), 1.50-1.35 (m, 1H), 1.26-1.09 (m, 1H), 0.87 (s, 9H), 0.70 (td, J=8.4, 5.0 Hz, 1H), 0.36 (q, J=5.5 Hz, 1H), 0.04 (s, 2H), 0.03 (s, 2H); $^{13}$C NMR (300 MHz, CDCl$_3$, ppm) δ: 167.89, 133.39, 132.04, 122.75, 62.72, 37.58, 25.66, 18.34, 18.05, 18.00, 14.75, 8.51, −5.47, −5.59; LC-MS (ESI-API, 254 nm) 95% MeOH in H$_2$O (0.1% HCO$_2$H), 3 min, 1.00 mL/min, C18 (Agilent Zorbax XDB-18, 50 mm×4.6 mm, 3.5 μm), m/z=368.0 (M+Na), 346.0 (M+H), t=1.081 min.

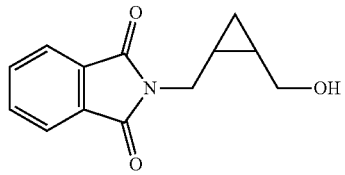

3

A 25 mL rb flask equipped with a stir bar and septum was charged with 1.23 g of the TBS ether 2 (3.66 mmol, 1 equiv), 3.7 mL 2 M HCl (7.40 mmol, 2 equiv) and 3.7 mL of THF. After stirring at rt for 1.5 h, the reaction mixture was quenched by addition of sat. NaHCO$_3$ solution, extracted with CH$_2$Cl$_2$ (2×) and dried over Na$_2$SO$_4$. The crude product was purified on silica gel column using 30-100% EA in hexanes affording 0.826 g (97%) of the product 3 as a white solid. $^1$H NMR (400 MHz, CDCl$_3$, ppm) δ: 7.86 (dd, J=5.4, 3.1 Hz, 2H), 7.73 (dd, J=5.4, 3.1 Hz, 2H), 4.03-3.94 (m, 2H), 3.59-3.50 (m, 2H), 2.89 (dd, J=8.3, 4.4 Hz, 1H), 1.34-1.19 (m, 2H), 0.80 (td, J=8.7, 5.1 Hz, 1H), 0.18 (q, J=5.6 Hz, 1H); LC-MS (ESI-API, 254 nm) 95% MeOH in H$_2$O (0.1% HCO$_2$H), 3 min, 1.00 mL/min, C18 (Agilent Zorbax XDB-18, 50 mm×4.6 mm, 3.5 μm), m/z=254.0 (M+Na), t=0.546 min.

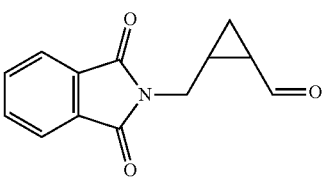

4

A 50 mL Schlenk flask equipped with a magnetic stir bar and septum was charged with 415 mg of the alcohol 3 (1.80 mmol, 1 equiv), 1.33 mL of TEA (9.51 mmol, 5.3 equiv) and 5.4 mL of CH$_2$Cl$_2$. After the reaction mixture was cooled to 0° C., 1.14 g of SO$_3$*Py (7.18 mmol, 4 equiv) dissolved in 5.4 mL of DMSO was added dropwise and the reaction mixture was stirred at rt for 2 h. Then the reaction mixture was quenched by addition of water, extracted with diethyl ether (3×), washed with water, brine and dried over Na$_2$SO$_4$. The crude product was purified on silica gel column using 30% EA in hexanes as eluent affording 0.323 g (79%) of the product 4 as a white solid. $^1$H NMR (400 MHz, CDCl$_3$, ppm) δ: 9.57 (d, J=4.8 Hz, 1H), 7.82-7.75 (m, 2H), 7.71-7.65 (m, 2H), 3.96 (dd, J=14.4, 6.8 Hz, 1H), 3.72 (dd, J=14.4, 7.7 Hz, 1H), 2.03-1.94 (m, 2H), 1.82 (sext, J=7.6 Hz, 1H), 1.40 (dt, J=7.0, 5.3 Hz, 1H), 1.23 (td, J=8.1, 5.0 Hz, 1H); $^{13}$C NMR (400 MHz, CDCl$_3$, ppm) δ: 199.98, 167.83, 133.91, 131.83, 123.16, 36.24, 27.03, 22.26, 12.82.

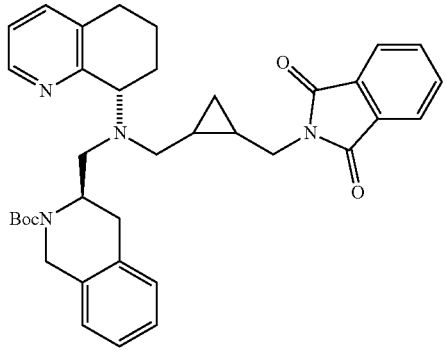

5

To a 50 mL Schlenk tube equipped with a septum and stir bar was added 554 mg of the amine I (1.41 mmol, 1 equiv), 323 mg of the aldehyde 4 (1.41 mmol, 1 equiv), 105 μL of acetic acid (1.83 mmol, 1.3 equiv), 373 mg of STAB (1.76 mmol, 1.25 equiv) and 14.1 mL of DCE. After stirring at rt for 12 h, the reaction mixture was quenched by addition of 1N K$_2$CO$_3$ solution, extracted with ether (3×), washed with 1N K$_2$CO$_3$ solution, brine and dried over Na$_2$SO$_4$. The crude product was purified on silica gel column using 0-70% EA in hexanes as eluent affording 291 mg (34%) of URf-5 isomer, 174 mg (20%) of mixture of both isomers and 340 mg (40%) of LRf-5 isomer as clear oils. For URf-5 isomer: $^1$H NMR (400 MHz, CDCl$_3$, ppm) δ: 8.38 (br s, 1H), 7.80 (dd, J=5.5, 3.0 Hz, 2H), 7.67 (dd, J=5.4, 3.1 Hz, 2H), 7.28-7.22 (m, 1H), 7.13-7.05 (m, 3H), 7.05-6.99 (m, 1H), 6.97 (br s, 1H), 4.79 (br s, 0.5H), 4.72 (s, 0.5H), 4.68 (s, 0.5H), 4.56 (s, 0.5H), 4.30 (d, J=17.2 Hz, 0.5H), 4.19 (d, J=16.5 Hz, 0.5H), 4.10-3.76 (m, 2H), 3.41 (dd, J=13.8, 10.0 Hz, 1H), 3.22-2.40 (m, 7H), 2.15-2.02 (m, 1H), 1.99-1.88 (m, 1H), 1.86-1.73 (m, 1H), 1.71-1.56 (m, 1H), 1.48 (s, 9H), 1.51-1.31 (m, 1H), 1.25-1.12 (m, 1H), 1.05 (h, J=7.4 Hz, 1H), 0.61 (td, J=8.3, 4.7 Hz, 1H), 0.18 (q, J=5.4 Hz, 1H); LC-MS (ESI-API, 254 nm) 75-95% MeOH in H$_2$O (0.1% HCO$_2$H), 6 min, 1.00 mL/min, C18 (Agilent Zorbax XDB-18, 50 mm×4.6 mm, 3.5 μm), m/z=607.2 (M+H), t=0.624 min, 97% purity. For LRf-5 isomer: $^1$H NMR (400 MHz, CDCl$_3$, ppm) δ: 8.41-8.28 (m, 1H), 7.84-7.73 (m, 2H), 7.72-7.62 (m, 2H), 7.23 (d, J=6.7 Hz, 1H), 7.11-6.86 (m, 5H), 4.75-4.43 (m, 2H), 4.25-4.09 (m, 2H), 3.86-3.68 (m, 1H), 3.37-3.26 (m, 1H), 3.19-3.03 (m, 1H), 3.02-2.48 (m, 6H), 2.14-1.30 (m, 5H), 1.48 (s, 9H), 1.28-1.18 (m, 1H), 0.96 (dt, J=14.2, 7.0 Hz, 1H), 0.54 (td, J=8.3, 4.7 Hz, 1H), 0.13 (q, J=5.4 Hz, 1H); LC-MS (ESI-API, 254 nm) 75-95% MeOH in H$_2$O (0.1% HCO$_2$H), 6 min, 1.00 mL/min, C18 (Agilent Zorbax XDB-18, 50 mm×4.6 mm, 3.5 μm), m/z=607.2 (M+H), t=0.640 min;

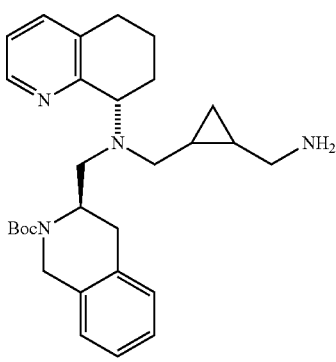

A 20 mL vial equipped with a stir bar was charged with 202 mg of the amine URf-5 (0.333 mmol, 1 equiv) dissolved in 1.7 mL of MeOH. Then 352 μL of 24% hydrazine solution in water (2.66 mmol, 8 equiv) was added. After stirring at rt for 12 h, the reaction mixture was quenched by addition of sat. Na$_2$CO$_3$ solution, extracted with CH$_2$Cl$_2$ (4×) and dried over Na$_2$SO$_4$. The crude product URf-6 was used in the next step without purification. The same procedure was used to synthesize LRf-6 isomer.

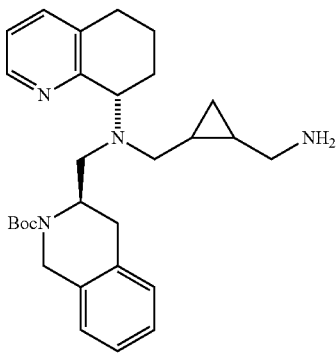

A 20 mL vial equipped with a stir bar was charged with 159 mg of the amine URf-6 (0.334 mmol, 1 equiv) dissolved in 3.34 mL of CH$_2$Cl$_2$. Then 771 μL of TFA (10.0 mmol, 30 equiv) was added. After stirring at rt for 5 h, the reaction mixture was quenched by addition of sat. Na$_2$CO$_3$ solution and 2 N KOH solution, extracted with CH$_2$Cl$_2$ (3×), washed with brine and dried over Na$_2$SO$_4$. The crude material (94 mg) was purified on silica gel column using 0-20% MeOH in CH$_2$Cl$_2$ with 1% NH$_4$OH as eluent affording 87 mg (69%) of the product EMU030 as a slightly yellow solid. The same procedure was used to synthesize 98 mg (70%) of EMU031 as a slightly yellow solid, beginning with LRf-6.

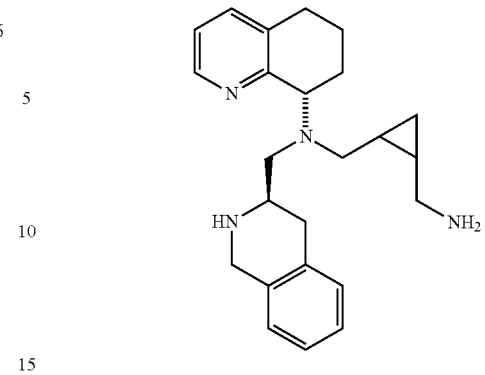

For EMU030 (Stereoisomer 1): $^1$H NMR (600 MHz, CDCl$_3$, ppm) δ: 8.58 (s, 1H), 7.35 (d, J=7.7 Hz, 1H), 7.14-6.99 (m, 5H), 4.17-4.05 (m, 1H), 4.10 (A of AB, J$_{AB}$=16.2 Hz, 1H), 3.81 (B of AB, J$_{AB}$=16.2 Hz, 1H), 3.35 (br s, 1H), 3.28 (dd, J=13.2, 4.6 Hz, 1H), 2.88 (d, J=12.8 Hz, 1H), 2.81-2.61 (m, 3H), 2.56 (dd, J=11.4, 13.0 Hz, 2H), 2.51-2.40 (m, 2H), 2.33 (br s, 1H), 2.15-2.09 (m, 1H), 2.07-1.95 (m, 2H), 1.79-1.69 (m, 1H), 0.98 (br s, 1H), 0.77 (q, J=9.0, 7.8 Hz, 1H), 0.07 (d, J=5.1 Hz, 1H); $^{13}$C NMR (400 MHz, CDCl$_3$, ppm) δ: 157.90, 146.57, 136.69, 135.39, 134.06, 133.16. 128.90, 126.04, 125.74, 125.49, 121.50, 62.12, 57.28, 53.11, 51.45, 47.58, 40.68, 33.43, 29.25, 25.68, 21.97, 16.87, 15.14, 10.67; HRMS (ESI+) calcd for C$_{25}$H$_{33}$N$_4$ ([M+H]$^+$): 377.2700. Found: 377.2695, error −0.5 ppm; LC-MS (ESI-API, 254 nm) 55% MeOH in H$_2$O (0.1% HCO$_2$H), 6 min, 1.00 mL/min, C18 (Agilent Zorbax XDB-18, 50 mm×4.6 mm, 3.5 μm), m/z=377.2 (M+H), 189.2 (M/2+H), t=0.754 min. For EMU030 (Stereoisomer) 2: $^1$H NMR (600 MHz, CDCl$_3$, ppm) δ: 8.44 (d, J=4.6 Hz, 1H), 7.31 (d, J=7.7 Hz, 1H), 7.09-6.97 (m, 5H), 4.27 (dd, J=10.0, 6.4 Hz, 1H), 4.00 (A of AB, J$_{AB}$=15.2 Hz, 1H), 3.81 (B of AB, J$_{AB}$=15.2 Hz, 1H), 2.92 (A of ABX, J$_{AB}$=13.2 Hz, J$_{AX}$=6.3 Hz, 1H), 2.89-2.70 (m, 5H), 2.67 (B of AB, J$_{AB}$=16.5 Hz, 1H), 2.61 (dd, J=16.1, 3.8 Hz, 1H), 2.57 (dd, J=13.1, 8.4 Hz, 1H), 2.41-2.35 (m, 2H), 2.13-2.07 (m, 1H), 2.02-1.89 (m, 2H), 1.76-1.66 (m, 1H), 1.16-1.02 (m, 2H), 0.73 (td, J=8.4, 4.6 Hz, 1H), 0.03 (q, J=5.2 Hz, 1H); $^{13}$C NMR (400 MHz, CDCl$_3$, ppm) δ: 158.30, 146.71, 136.32, 135.61, 134.51, 133.74. 128.96, 126.20, 125.68, 125.28, 121.25, 60.76, 57.49, 53.89, 52.33, 48.47, 41.99, 33.78, 29.35, 26.35, 21.92, 19.70, 15.54, 9.36. HRMS (ESI+) calcd for C$_{25}$H$_{33}$N$_4$ ([M+H]$^+$): 377.2700. Found: 377.2699, error −0.1 ppm; LC-MS (ESI-API, 254 nm) 55% MeOH in H$_2$O (0.1% HCO$_2$H), 3 min, 1.00 mL/min, C18 (Agilent Zorbax XDB-18, 50 mm×4.6 mm, 3.5 μm), m/z=377.2 (M+H), 189.2 (M/2+H), t=0.783 min.

Synthesis of EMU074

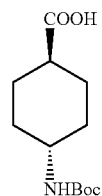

A 100 mL rb flask equipped with magnetic stir bar was charged with 2.5 g of 4-aminocyclohexanecarboxylic acid (17.5 mmol, 1 equiv), 17.5 mL of dioxane and 36.7 mL of 1 M NaOH solution (36.7 mmol, 2.1 equiv). The solution was cooled to 0° C. and 4.38 g of Boc$_2$O (20.1 mmol, 1.15 equiv) dissolved in 17.5 mL of dioxane was added dropwise. After stirring at rt for 5 h the pH of the emulsion reached 7. The reaction mixture was acidified to pH 5 by addition of diluted HCl, extracted with CH$_2$Cl$_2$ (3×) and dried over Na$_2$SO$_4$. The organics were concentrated and 4.03 g (95%) of the crude product 17 was obtained as a white solid which was used in the next step without purification. $^1$H NMR (400 MHz, CDCl$_3$, ppm) δ: 4.41 (br s, 1H), 3.42 (br s, 1H), 2.25 (tt, J=11.8, 3.3 Hz, 1H), 2.11-2.00 (m, 4H), 1.60-1.41 (m, 2H), 1.44 (s, 9H), 1.12 (q, J=12.7 Hz, 2H).

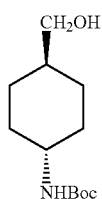

18

A 100 mL rb flask equipped with a stir bar, adapter, septum and addition funnel was charged with 4.25 g of the acid 17 (17.5 mmol, 1 equiv) and 58 mL of THF. Then the reaction mixture was cooled to 0° C. and 5.14 mL of borane (54.1 mmol, 3.1 equiv) was added dropwise. After stirring at rt for 18 h, the reaction mixture was quenched by addition of 5 mL of MeOH at 0° C., followed by addition of 1 N NaOH solution. The product was extracted with EA (3×), washed with brine and dried over Na$_2$SO$_4$. The crude product was purified by crystallization from CH$_2$Cl$_2$ affording 1.64 g of the product 18 as a white solid. The filtrate was concentrated and triturated with diethyl ether affording 1.01 g of more product 18 (total 2.65 g, 66%). $^1$H NMR (400 MHz, CDCl$_3$, ppm) δ: 4.39 (br s, 1H), 3.45 (t, J=6.0 Hz, 2H), 3.39 (br s, 1H), 2.04 (d, J=10.0 Hz, 2H), 1.82 (d, J=10.8 Hz, 2H), 1.44 (s, 9H), 1.33 (t, J=5.6 Hz, 1H), 1.15-0.98 (m, 4H).

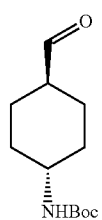

19

Compound 19 was synthesized from alcohol 18 following the procedure for the synthesis of compound 4. The crude product was purified on silica gel column using 0-30% EA in hexanes as eluent affording 734 mg (74%) of the product 19 as a pale yellow oil which crystallize to white solid. $^1$H NMR (400 MHz, CDCl$_3$, ppm) δ: 9.61 (d, J=1.5 Hz, 1H), 4.42 (br s, 1H), 3.40 (br s, 1H), 2.21-1.97 (m, 4H), 1.43 (s, 10H), 1.39 (A of ABX, J$_{AB}$=13.1 Hz, J$_{AX}$=3.7 Hz, 1H), 1.34 (B of ABX, J$_{AB}$=13.1 Hz, J$_{BX}$=3.4 Hz, 1H), 1.18 (A of ABX, J$_{AB}$=12.8 Hz, J$_{AX}$=3.6 Hz, 1H), 1.11 (B of ABX, J$_{AB}$=12.7 Hz, J$_{BX}$=3.6 Hz, 1H).

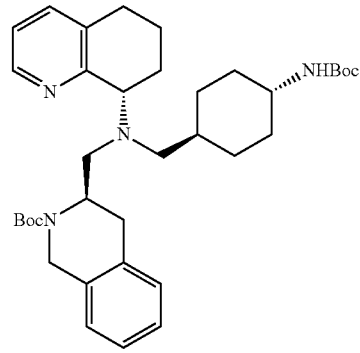

20

Compound 20 was synthesized from amine I and aldehyde 19 following the procedure for the synthesis of compound 5. The crude product was purified on silica gel column using 0 to 30% EA in hexanes as eluent affording 263 mg (84%) of the product 20 as a slightly yellow oil. $^1$H NMR (400 MHz, CDCl$_3$, ppm) δ: 8.41-8.29 (m, 1H), 7.23 (dd, J=7.7, 1.7 Hz, 1H), 7.17-6.90 (m, 5H), 4.76-4.64 (m, 1.5H), 4.45-4.32 (m, 1.5H), 4.29-4.17 (m, 1H), 3.97 (br s, 0.5H), 3.79 (br s, 0.5H), 3.29 (br s, 1H), 3.18 (d, J=15.8 Hz, 1H), 3.13-2.88 (m, 2H), 2.74-2.50 (m, 4H), 2.33-2.21 (m, 1H), 2.17-1.78 (m, 5H), 1.73-1.42 (m, 3H), 1.49 (s, 9H), 1.42 (s, 9H), 1.10-0.94 (m, 1H), 0.96 (qd, J=12.5, 3.6 Hz, 1H), 0.76 (q, J=13.0 Hz, 1H), 0.71-0.59 (m, 1H); LC-MS (ESI-API, 254 nm) 75-95% MeOH in H$_2$O (0.1% HCO$_2$H), 6 min, 1.00 mL/min, C18 (Agilent Zorbax XDB-18, 50 mm×4.6 mm, 3.5 μm), m/z=605.2 (M+H), t=0.761 min.

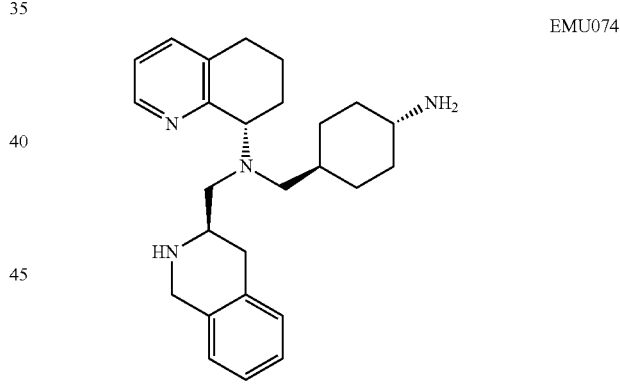

EMU074

Compound EMU074 was synthesized from amine 20 following the procedure for the synthesis of compound EMU030. The crude material was purified on silica gel column using 0-60% of solvent 2 in CH$_2$Cl$_2$ (solvent 2=70% CH$_2$Cl$_2$, 30% MeOH, 3% NH$_4$OH) as eluent affording 107 mg (94%) of the product EMU074 as a slightly yellow oil. $^1$H NMR (600 MHz, CDCl$_3$, ppm) δ: 8.42 (dd, J=4.8, 1.6 Hz, 1H), 7.32 (d, J=8.5 Hz, 1H), 7.10-7.06 (m, 2H), 7.06-6.99 (m, 3H), 4.07 (A of AB, J$_{AB}$=14.8 Hz, 1H), 4.03 (dd, J=10.5, 6.4 Hz, 1H), 3.97 (B of AB, J$_{AB}$=14.9 Hz, 1H), 3.16 (dd, J=13.8, 5.6 Hz, 1H), 2.90 (d, J=13.1 Hz, 1H), 2.82-2.71 (m, 2H), 2.65 (B of AB, J$_{AB}$=16.6 Hz, 1H), 2.62-2.53 (m, 2H), 2.44-2.38 (m, 1H), 2.37 (dd, J=13.6, 8.1 Hz, 1H), 2.24 (dd, J=13.4, 10.2 Hz, 1H), 2.14-2.07 (m, 1H), 2.01-1.94 (m, 2H), 1.90-1.83 (m, 4H), 1.74-1.65 (m, 1H), 1.42-1.34 (m, 1H), 1.12-1.03 (m, 2H), 0.92-0.84 (m, 2H); $^{13}$C NMR (400 MHz, CDCl$_3$, ppm) δ:158.91, 146.51, 136.22, 135.61, 134.69, 133.79, 128.99, 126.37, 125.74, 125.33, 121.17, 61.97, 61.73, 58.13, 52.34, 51.07, 48.78, 37.26, 36.72, 36.61, 33.71, 30.46, 30.31, 29.37, 22.12; HRMS (ESI+) calcd for C$_{26}$H$_{37}$N$_4$ ([M+H]$^+$): 405.3013. Found: 405.3062, error 5.0 ppm; LC-MS (ESI-API, 254 nm) 75-95% MeOH in H$_2$O (0.1% HCO$_2$H), 3 min, 1.00 mL/min, C18 (Agilent Zorbax XDB-18, 50 mm×4.6 mm, 3.5 µm), m/z=405.2 (M+H), 203.2 (M/2+H), t=0.767 min.

Synthesis of EMU121

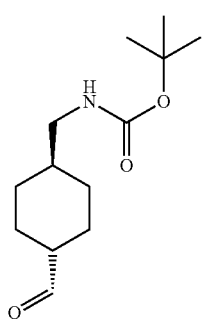

Compound 21 was synthesized from tert-butyl (((1r,4r)-4-(hydroxymethyl)cyclohexyl)methyl)carbamate following the procedure for the synthesis of compound 4. The crude product was purified on silica gel column using 0-50% EA in hexanes as eluent affording 390 mg (79%) of the product 21 as a white solid. $^1$H NMR (400 MHz, CDCl$_3$, ppm) δ: 9.62 (d, J=1.5 Hz, 1H), 4.59 (br s, 1H), 3.00 (t, J=6.5 Hz, 2H), 2.18 (ttd, J=12.2, 3.6, 1.6 Hz, 1H), 2.05-1.98 (m, 2H), 1.91-1.84 (m, 2H), 1.44 (s, 9H), 1.29 (A of ABX, J$_{AB}$=12.7 Hz, J$_{AX}$=3.1 Hz, 1H), 1.23 (B of ABX, J$_{AB}$=13.2 Hz, J$_{BX}$=3.5 Hz, 1H), 1.02 (A of ABX, J$_{AB}$=13.1 Hz, J$_{AX}$=3.5 Hz, 1H), 0.96 (B of ABX, J$_{AB}$=13.0 Hz, J$_{BX}$=3.6 Hz, 1H).

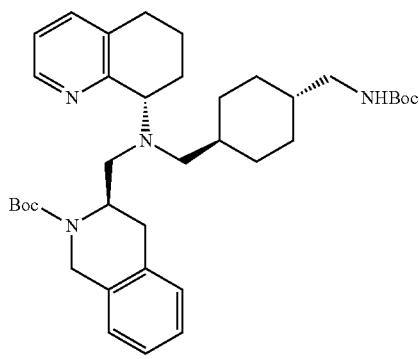 [SMILES: CC(C)(C)OC(=O)NC[C@H]1CC[C@H](CN(C[C@H]2Cc3ccccc3CN2C(=O)OC(C)(C)C)[C@H]2CCCc3cccnc32)CC1]

Compound 20 was synthesized from tert-butyl (R)-3-((((S)-5,6,7,8-tetrahydroquinolin-8-yl)amino)methyl)-3,4-dihydroisoquinoline-2(1H)-carboxylate and aldehyde 21 following the procedure for the synthesis of compound 5. The crude product is purified on silica gel column using 0 to 50% EA in hexanes as eluent affording 342 mg (76%) of the product 22 as a slightly clear glass. $^1$H NMR (400 MHz, CDCl$_3$, ppm) δ: 8.38 (br s, 0.5H), 8.34 (br s, 0.5H), 7.25 (d, J=8.0 Hz, 1H), 7.16-7.04 (m, 4H), 7.02-6.93 (m, 1H), 4.72 (br s, 0.5H), 4.73 (A of AB, J$_{AB}$=14.8 Hz, 0.5H), 4.68 (A of AB, J$_{AB}$=14.8 Hz, 0.5H), 4.55 (br s, 1H), 4.35 (br s, 0.5H), 4.25 (B of AB, J$_{AB}$=15.3 Hz, 0.5H), 4.21 (B of AB, J$_{AB}$=15.3 Hz, 0.5H), 3.98 (br s, 0.5H), 3.77 (br s, 0.5H), 3.19 (A of AB, J$_{AB}$=15.9 Hz, 0.5H), 3.13-2.88 (m, 4.5H), 2.75-2.50 (m, 3H), 2.28 (dd, J=13.2, 6.1 Hz, 1H), 2.16-1.79 (m, 4H), 1.78-1.40 (m, 5H), 1.50 (s, 9H), 1.44 (s, 9H), 1.36-1.23 (m, 1H), 1.05 (br s, 1H), 0.90-0.52 (m, 4H). LC-MS (ESI-API, 254 nm) 75-95% MeOH in H$_2$O (0.1% HCO$_2$H), 6 min, 1.00 mL/min, C18 (Agilent Zorbax XDB-18, 50 mm×4.6 mm, 3.5 µm), m/z=619.3 (M+H), t=0.744 min.

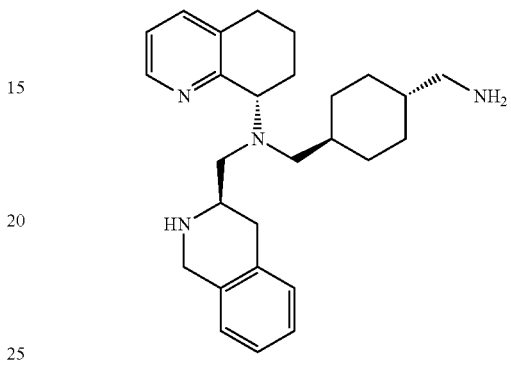

EMU121

Compound EMU121 was synthesized from amine 22 following the procedure for the synthesis of compound EMU030. The crude material was purified on silica gel column using 0-60% of solvent 2 in CH$_2$Cl$_2$ (solvent 2=70% CH$_2$Cl$_2$, 30% MeOH, 3% NH$_4$OH) as eluent affording 110 mg (quant.) of the product EMU121 as a slightly yellow oil. $^1$H NMR (600 MHz, CDCl$_3$, ppm) δ: 8.42 (d, J=4.1 Hz, 1H), 7.32 (d, J=7.6 Hz, 1H), 7.10-7.01 (m, 5H), 4.15-3.95 (m, 3H), 3.12 (br s, 1H), 2.93 (d, J=13.2 Hz, 1H), 2.82 (br s, 1H), 2.75 (ddd, J=16.5, 11.5, 5.0 Hz, 1H), 2.65 (B of AB, J$_{AB}$=16.5 Hz, 1H), 2.58 (d, J=15.4 Hz, 1H), 2.52 (dd, J=6.4 Hz, 4H), 2.47-2.22 (m, 1H), 2.14-1.65 (m, 8H), 1.39 (s, 1H), 1.28-1.18 (m, 1H), 0.97-0.78 (m, 4H). $^{13}$C NMR (400 MHz, CDCl$_3$, ppm) δ: 158.93, 146.45, 136.26, 135.41, 134.63, 133.80, 128.98, 126.36, 125.77, 125.34, 121.17, 62.03, 61.74, 58.09, 52.38, 48.70, 48.64, 41.54, 38.04, 33.56, 31.19, 31.10, 30.46, 30.38, 29.34, 22.08. HRMS (ESI+) calcd for C$_{27}$H$_{39}$N$_4$ ([M+H]$^+$): 419.3169. Found: 419.3168, error −0.1 ppm. LC-MS (ESI-API, 254 nm) 75-95% MeOH in H$_2$O (0.1% HCO$_2$H), 3 min, 1.00 mL/min, C18 (Agilent Zorbax XDB-18, 50 mm×4.6 mm, 3.5 µm), m/z=419.2 (M+H), 210.2 (M/2+H), t=0.499 min.

Reductive Amination with Secondary Amine and Bulky Carbonyls

General scheme

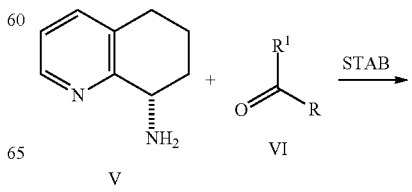

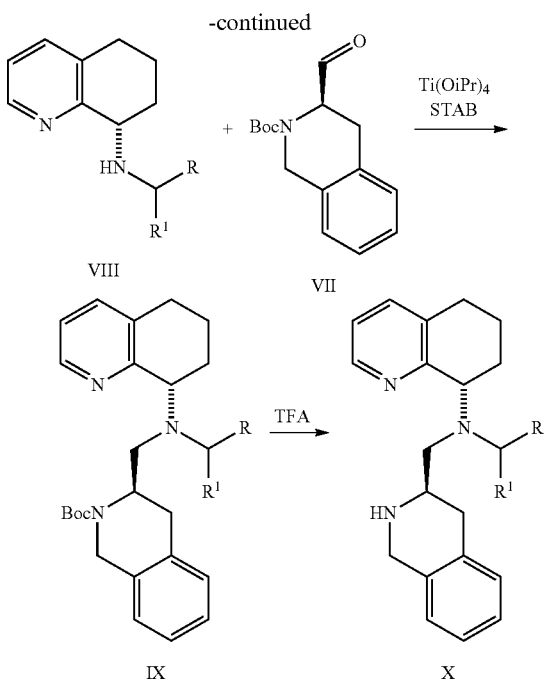

Synthesis of EMU075

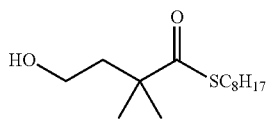

A 250 mL rb flask equipped with a rubber septum and a magnetic stir bar was set under Ar atmosphere and charged with 19.7 mL of 2 M trimethyl aluminum solution (39.4 mmol, 3 equiv) and the solution was cooled to 0° C. Then 6.84 mL of 1-octane thiol (39.4 mmol, 3 equiv) was added dropwise. After stirring at rt for 20 min, 1.50 g of 3,3-dimethyldihydrofuran-2(3H)-one (13.1 mmol, 1 equiv) dissolved in 30.6 mL of $CH_2Cl_2$ was added dropwise and the reaction mixture was stirred at rt for 12 h. Then the reaction mixture was quenched by addition of 77 mL of diethyl ether and 116 mL of 1 N HCl solution. The product was extracted with diethyl ether (3×), washed with 1 N HCl and sat. $NaHCO_3$ solution and dried over $Na_2SO_4$. The crude product was purified on silica gel column using 5-25% EA in hexanes as eluent affording 2.26 g (66%) of the product 13 as a clear liquid.

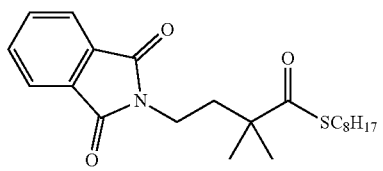

Compound 29 was synthesized from alcohol 13 following the procedure for the synthesis of compound 2. The crude product was purified on silica gel column using 10 to 20% EA in hexanes as eluent affording 594 mg (93%) of the product 29 as a clear oil. $^1$H NMR (400 MHz, $CDCl_3$, ppm) δ: 7.79 (dd, J=5.4, 3.1 Hz, 2H), 7.67 (dd, J=5.5, 3.0 Hz, 2H), 3.68-3.63 (m, 2H), 2.70 (t, J=7.4 Hz, 2H), 1.97-1.92 (m, 2H), 1.45 (p, J=7.5 Hz, 1H), 1.28 (s, 6H), 1.34-1.18 (m, 10H), 0.83 (t, J=6.8 Hz, 3H). $^{13}$C NMR (400 MHz, $CDCl_3$, ppm) δ: 205.38, 167.88, 133.73, 132.09, 123.03, 48.45, 38.57, 34.07, 31.69, 29.32, 29.05, 28.97, 28.84, 28.59, 25.20, 22.54, 14.00. LC-MS (ESI-API, 254 nm) 95% MeOH in $H_2O$ (0.1% $HCO_2H$), 3 min, 1.00 mL/min, C18 (Agilent Zorbax XDB-18, 50 mm×4.6 mm, 3.5 μm), m/z=412.0 (M+Na), t=1.407 min;

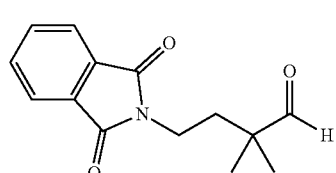

A 20 mL vial equipped with a stir bar was charged with 594 mg of the thioester 29 (1.53 mmol, 1 equiv), 27.0 mg of $PdCl_2$ (0.152 mmol, 0.1 equiv), 43 μL of TEA (0.305 mmol, 0.2 equiv) and 3.1 mL $CH_2Cl_2$. Then 731 μL of triethylsilane (4.57 mmol, 3 equiv) was added dropwise and the solution turned to black suspension. After stirring at rt for 20 min, the reaction mixture was quenched by addition of 10% citric acid solution, filtered through celite plug, extracted with $CH_2Cl_2$ (2×) and dried over $Na_2SO_4$. The crude product was purified on silica gel column using 10-30% EA in hexanes as eluent affording 321 mg (86%) of the product 30 as a clear oil. $^1$H NMR (400 MHz, $CDCl_3$, ppm) δ: 9.47 (s, 1H), 7.84 (dd, J=5.4, 3.1 Hz, 2H), 7.71 (dd, J=5.5, 3.0 Hz, 2H), 3.70-3.61 (m, 2H), 1.93-1.84 (m, 2H), 1.16 (s, 6H). LC-MS (ESI-API, 254 nm) 95% MeOH in $H_2O$ (0.1% $HCO_2H$), 3 min, 1.00 mL/min, C18 (Agilent Zorbax XDB-18, 50 mm×4.6 mm, 3.5 μm), m/z=246.0 (M+H), t=0.580 min;

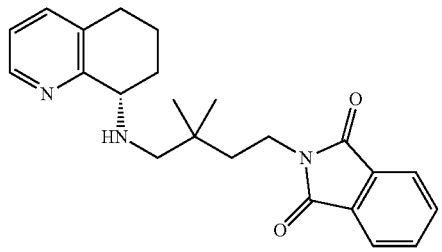

Compound 31 was synthesized from aldehyde 30 and (S)-5,6,7,8-tetrahydroquinolin-8-amine following the procedure for the synthesis of compound 25. The crude product was purified on silica gel column using EA as eluent affording 492 mg (100%) of the product 31 which crystallizes in freezer to white solid. $^1$H NMR (400 MHz, $CDCl_3$, ppm) δ: 8.38 (d, J=4.7 Hz, 1H), 7.82 (dd, J=5.5, 3.0 Hz, 2H), 7.68 (dd, J=5.5, 3.0 Hz, 2H), 7.35 (d, J=7.7 Hz, 1H), 7.05 (dd, J=7.6, 4.7 Hz, 2H), 3.75-3.69 (m, 3H), 2.81 (dt, J=13.6, 6.6 Hz, 1H), 2.72 (dt, J=16.8, 5.6 Hz, 1H), 2.61 (A of AB, $J_{AB}$=11.3 Hz, 1H), 2.55 (B of AB, $J_{AB}$=11.4 Hz, 1H), 2.14-1.98 (m, 2H), 1.84-1.62 (m, 4H), 1.04 (s, 3H), 1.03 (s, 3H). LC-MS (ESI-API, 254 nm) 95% MeOH in $H_2O$ (0.1% $HCO_2H$), 3 min, 1.00 mL/min, C18 (Agilent Zorbax XDB-18, 50 mm×4.6 mm, 3.5 μm), m/z=378.2 (M/2+H), t=0.469 min.

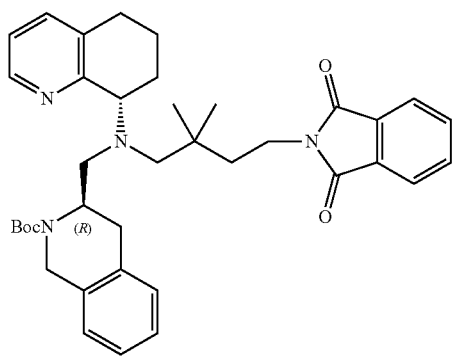

32

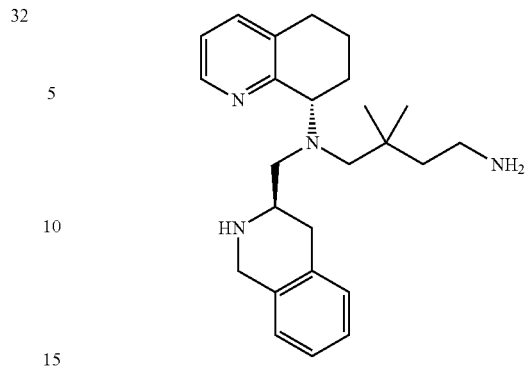

EMU075

Compound 32 was synthesized from tert-butyl (R)-3-formyl-3,4-dihydroisoquinoline-2(1H)-carboxylate and amine 31 following the procedure for the synthesis of compound 27. The crude product was purified on silica gel column using 0 to 40% EA in hexanes as eluent affording 0.207 g (56%) of the product 32 as a slightly yellow powder. $^1$H NMR (400 MHz, CDCl$_3$, ppm) δ: 8.38 (br s, 0.7H), 8.33 (br s, 0.3H), 7.82 (dd, J=5.5, 3.0 Hz, 2H), 7.70 (dd, J=5.5, 3.1 Hz, 2H), 7.21-7.10 (m, 1H), 7.08-6.92 (m, 4H), 6.88 (dd, J=7.7, 4.6 Hz, 1H), 4.71 (br s, 0.3H), 4.71 (A of AB, J$_{AB}$=16.8 Hz, 0.7H), 4.67 (A of AB, J$_{AB}$=16.8 Hz, 0.3H), 4.44 (br s, 0.7H), 4.27 (B of AB, J$_{AB}$=17.4 Hz, 0.3H), 4.15 (B of AB, J$_{AB}$=17.2 Hz, 0.7H), 4.05 (br s, 0.3H), 3.94 (br s, 0.7H), 3.69-3.54 (m, 2H), 3.30 (A of AB, J$_{AB}$=16.1 Hz, 0.7H), 3.15 (A of AB, J$_{AB}$=16.2 Hz, 0.3H), 3.02-2.82 (m, 2H), 2.68-2.08 (m, 7H), 1.95-1.87 (m, 1H), 1.80-1.31 (m, 3H), 1.49 (s, 6.3H), 1.46 (s, 2.7H), 0.98 (s, 2.1H), 0.91 (s, 2.1H), 0.87 (s, 0.9H), 0.84 (s, 0.9H). LC-MS (ESI-API, 254 nm) 75-95% MeOH in H$_2$O (0.1% HCO$_2$H), 6 min, 1.00 mL/min, C18 (Agilent Zorbax XDB-18, 50 mm×4.6 mm, 3.5 μm), m/z=623.2 (M+H), t=0.946 min, 97% purity.

Compound EMU075 was synthesized from amine 33 following the procedure for the synthesis of compound EMU030. The crude material was purified on silica gel column using 0 to 60% of solvent 2 in CH$_2$Cl$_2$ (solvent 2=70% CH$_2$Cl$_2$, 30% MeOH, 3% NH$_4$OH) as eluent affording 69 mg (85%) of the product EMU075 as a slightly yellow powder. $^1$H NMR (600 MHz, CDCl$_3$, ppm) δ: 8.44 (d, J=4.7 Hz, 1H), 7.30 (d, J=7.7 Hz, 1H), 7.08-7.02 (m, 3H), 7.01-6.98 (m, 2H), 4.02 (dd, J=11.0, 6.2 Hz, 1H), 4.00 (A of AB, J$_{AB}$=14.5 Hz, 1H), 3.79 (B of AB, J$_{AB}$=14.9 Hz, 1H), 3.54 (d, J=14.5 Hz, 1H), 2.84 (d, J=13.5 Hz, 1H), 2.78-2.71 (m, 2H), 2.66-2.58 (m, 1H), 2.48 (dd, J=15.8, 3.4 Hz, 1H), 2.44 (d, J=14.5 Hz, 1H), 2.34 (dd, J=16.0, 11.2 Hz, 1H), 2.2-2.19 (m, 1H), 2.12 (t, J=12.0 Hz, 1H), 2.00-1.88 (m, 2H), 1.73-1.64 (m, 1H), 1.53 (dt, J=13.1, 8.2 Hz, 1H), 1.44 (dt, J=13.1, 8.2 Hz, 1H), 0.97 (s, 3H), 0.95 (s, 3H). $^{13}$C NMR (400 MHz, CDCl$_3$, ppm) δ: 158.94, 146.43, 136.33, 135.52, 134.56, 133.57, 128.93, 126.44, 125.74, 125.34, 121.28, 68.89, 64.31, 59.58, 52.14, 48.40, 44.73, 37.81, 35.39, 33.63, 29.94, 29.50, 25.79, 25.30, 22.48. HRMS (ESI+) calcd for C$_{25}$H$_{37}$N$_4$ ([M+H]$^+$): 393.3013. Found: 393.3092, error 7.9 ppm. LC-MS (ESI-API, 254 nm) 75-95% MeOH in H$_2$O (0.1% HCO$_2$H), 3 min, 1.00 mL/min, C18 (Agilent Zorbax XDB-18, 50 mm×4.6 mm, 3.5 μm), m/z=393.2 (M+H), 197.2 (M/2+H), t=0.855 min;

Synthesis of the Analogs with Alkene Side-Chain

General scheme

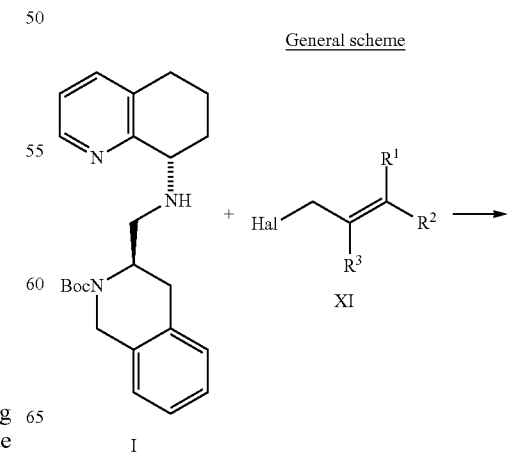

33

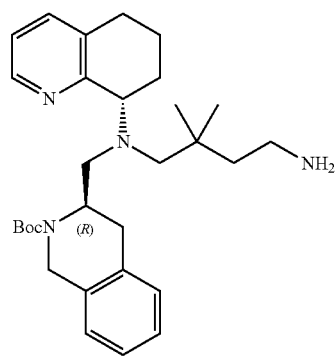

Compound 33 was synthesized from amine 32 following the procedure for the synthesis of compound 6. The crude material was used in the next step.

-continued

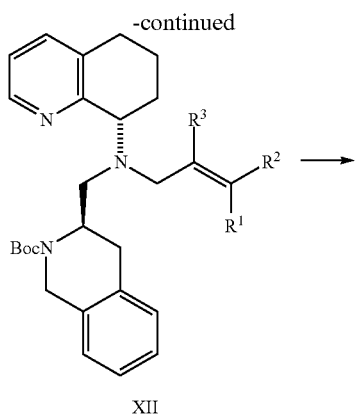

XII

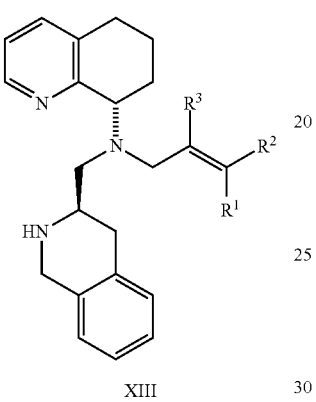

XIII

Synthesis of EMU124

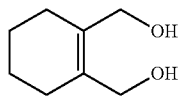
34

A 250 mL rb flask equipped with a stir bar and rubber septum was charged with 5.24 g of LAH (138 mmol, 4.2 equiv) and 33 mL of diethyl ether. After the suspension was cooled to 0° C., 5.00 g of 4,5,6,7-tetrahydroisobenzofuran-1,3-dione (32.9 mol, 1 equiv) dissolved in 33 mL of diethyl ether was added drop wise and the suspension was stirred at rt for 3 h. The reaction mixture was quenched by careful addition of 5 mL of water and 10 mL of 2 N NaOH, followed by 25 mL of water. Then diethyl ether and celite was added and the suspension was filtered through celite plug and dried over Na$_2$SO$_4$. The organics were concentrated and 2.89 g (62%) of the product 34 was obtained. $^1$H NMR (400 MHz, CDCl$_3$, ppm) δ: δ 4.12 (s, 4H), 2.32-2.22 (m, 2H), 2.17-2.11 (m, 4H), 1.65-1.58 (m, 4H).

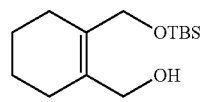
35

A 250 mL rb flask equipped with a stir bar and rubber septum was charged with 2.89 g of the diol 34 (20.3 mmol, 1 equiv), 1.52 g of imidazole (22.4 mmol, 1.1 equiv), 3.22 g of TBSCl (21.3 mmol, 1.05 equiv) and 20.3 mL of CH$_2$Cl$_2$. After stirring at rt for 12 h, the reaction mixture was quenched by addition of NH$_4$Cl solution, extracted with CH$_2$Cl$_2$ (3×) and dried over Na$_2$SO$_4$. The crude product was purified on silica gel column using 0 to 20% EA in hexanes as eluent affording 1.71 g (33%) of the product 35. $^1$H NMR (400 MHz, CDCl$_3$, ppm) δ: δ 4.15 (s, 2H), 4.05 (s, 2H), 2.16-2.03 (m, 5H), 1.62-1.57 (m, 4H), 0.90 (s, 9H), 0.08 (s, 6H).

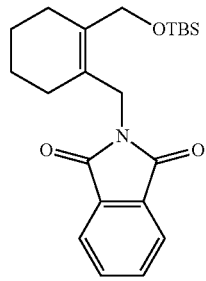
36

Compound 36 was synthesized from alcohol 35 following the procedure for the synthesis of compound 2. The crude product was purified on silica gel column using 0 to 10% of EA in hexanes as eluent affording 2.17 g (88%) of the product 36. $^1$H NMR (400 MHz, CDCl$_3$, ppm) δ: 7.85-783 (m, 2H), 7.72-7.68 (m, 2H), 4.42 (s, 2H), 4.36 (s, 2H), 2.11 (br s, 2H), 1.96 (br s, 2H), 1.60-1.50 (m, 4H), 0.92 (s, 9H), 0.11 (s, 6H).

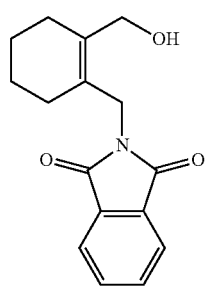
37

Compound 37 was synthesized from TBS ether 36 following the procedure for the synthesis of compound 3. The crude product was purified by dissolving the product in minimal amount of CH$_2$Cl$_2$ and precipitating the product by addition of diethyl ether. Ether was decanted off and the product was triturated with diethyl ether. The product was dried under high vacuum affording 1.28 g (84%) of the product 37 as a white solid. $^1$H NMR (400 MHz, CDCl$_3$, ppm) δ: 7.84 (dd, J=5.5, 3.0 Hz, 2H), 7.73 (dd, J=5.4, 3.1 Hz, 2H), 4.42 (s, 2H), 4.24 (d, J=6.4 Hz, 2H), 3.28 (t, J=6.5 Hz, 1H), 2.20 (br s, 2H), 1.93 (br s, 2H), 1.62-1.52 (m, 4H). LC-MS (ESI-API, 254 nm) 95% MeOH in H$_2$O (0.1% HCO$_2$H), 3 min, 1.00 mL/min, C18 (Agilent Zorbax XDB-18, 50 mm×4.6 mm, 3.5 μm), m/z=294.0 (M+Na), t=0.615 min, 86% purity;

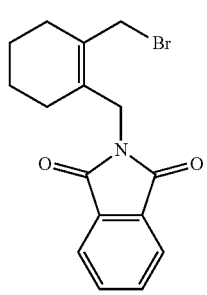

38

A 100 mL rb flask equipped with a stir bar and rubber septum was charged with 0.350 g of the alcohol 37 (1.29 mmol, 1 equiv), 0.389 g of triphenylphosphine (1.48 mmol, 1.15 equiv) and 6.5 mL of $CH_2Cl_2$. Then 0.492 g of $CBr_4$ (1.48 mmol, 1.15 equiv) was added portion wise and the mixture was stirred at rt for 2 h. The reaction mixture was quenched by addition of water, extracted with $CH_2Cl_2$ (2×) and dried over $Na_2SO_4$. The crude product was purified on silica gel column using $CH_2Cl_2$ as eluent affording 414 mg (96%) of the product 38 as a white solid. $^1$H NMR (400 MHz, $CDCl_3$, ppm) δ: 7.87-7.81 (m, 2H), 7.74-7.70 (m, 2H), 4.36 (s, 2H), 4.30 (s, 2H), 2.22-2.17 (m, 2H), 2.07-2.01 (m, 2H), 1.64-1.52 (m, 4H).

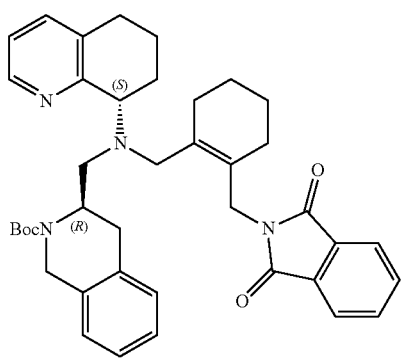

39

A 50 mL Schlenk tube equipped with a cold finger condenser and stir bar was charged with 0.386 g of the bromide 38 (1.16 mmol, 1.2 equiv) and 0.016 g of KI (0.096 mmol, 0.1 equiv). Then 0.379 g of the tert-butyl (R)-3-((((S)-5,6,7,8-tetrahydroquinolin-8-yl)amino)methyl)-3,4-dihydroisoquinoline-2(1H)-carboxylate (0.962 mmol, 1 equiv) and 0.252 mL of DIPEA (1.44 mmol, 1.5 equiv) dissolved in 3.2 mL of acetonitrile was added. After stirring at 60° C. for 24 h, the reaction mixture was quenched by addition of water, extracted with diethyl ether (3×) and dried over $Na_2SO_4$. The crude product was purified on silica gel column using 0 to 30% EA in hexanes as eluent affording 408 mg (66%) of the product 39. $^1$H NMR (400 MHz, $CDCl_3$, ppm) δ: 8.38 (s, 1H), 7.79-7.73 (m, 2H), 7.70-7.63 (m, 2H), 7.28-7.23 (m, 1H), 7.19-7.02 (m, 4H), 6.96 (dd, J=7.6, 4.7 Hz, 1H), 4.82 (br s, 0.5H), 4.86-4.69 (m, 1H), 4.59 (br s, 0.5H), 4.36 (d, J=14.8 Hz, 1H), 4.28-4.03 (m, 3H), 3.63-3.51 (m, 1H), 3.20-2.83 (m, 4H), 2.77-2.47 (m, 3H), 2.30-1.64 (m, 8H), 1.50 (s, 9H), 1.54-1.38 (4H). LC-MS (ESI-API, 254 nm) 75-95% MeOH in $H_2O$ (0.1% $HCO_2H$), 6 min, 1.00 mL/min, C18 (Agilent Zorbax XDB-18, 50 mm×4.6 mm, 3.5 μm), m/z=647.2 (M+H), t=1.119 min;

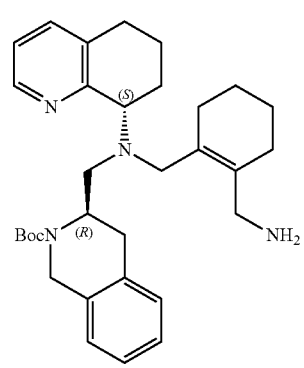

40

Compound 40 was synthesized from amine 39 following the procedure for the synthesis of compound 6. The organics were concentrated and the crude product was used in the next step.

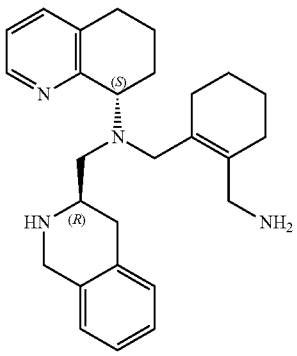

EMU124

Compound EMU124 was synthesized from amine 40 following the procedure for the synthesis of EMU030. The crude material was purified on silica gel column using 0 to 60% of solvent2 (solvent2=30% MeOH, 70% $CH_2Cl_2$ and 3% $NH_4OH$) in $CH_2Cl_2$ as eluent affording 59 mg (43%) of the product EMU124. $^1$H NMR (600 MHz, $CDCl_3$, ppm) δ: 8.53 (d, J=4.8 Hz, 1H), 7.35 (d, J=7.5 Hz, 1H), 7.11-6.98 (m, 5H), 4.05 (A of AB, $J_{AB}$=15.8 Hz, 1H), 4.02 (dd, J=10.1, 6.5 Hz, 1H), 3.81 (B of AB, $J_{AB}$=15.9 Hz, 1H), 3.64 (d, J=12.8 Hz, 1H), 3.33 (d, J=12.8 Hz, 1H), 3.10 (d, J=13.0 Hz, 1H), 2.87-2.73 (m, 2H), 2.70-2.63 (m, 1H), 2.59 (d, J=16.2 Hz, 1H), 2.41-2.26 (m, 3H), 2.18-2.04 (d, J=11.2 Hz, 3H), 2.02-1.89 (m, 3H), 1.69 (q, J=11.5, 10.9 Hz, 1H), 1.62-1.47 (m, 6H). $^{13}$C NMR (400 MHz, $CDCl_3$, ppm) δ: 157.82, 146.58, 136.83, 135.45, 134.23, 134.16, 134.13, 133.00, 129.10, 126.14, 125.88, 125.54, 121.63, 59.14, 56.96, 56.06, 51.53, 47.90, 42.23, 33.63, 30.68, 29.37, 29.23, 25.72, 22.77, 22.75, 22.00. HRMS (ESI+) calcd for $C_{27}H_{37}N_4$ ([M+H]$^+$): 417.3013. Found: 417.3010, error 0.3 ppm. LC-MS (ESI-API, 254 nm) 75-95% MeOH in $H_2O$ (0.1% $HCO_2H$), 3 min, 1.00 mL/min, C18 (Agilent Zorbax XDB-18, 50 mm×4.6 mm, 3.5 μm), m/z=417.2 (M+H), 209.2 (M/2+H), t=0.856 min;

Synthesis of EMU125, EMU126, EMU140 and EMU141

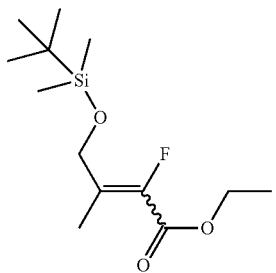

41

As in ref (*Nucleosides, Nucleotides, and Nucleic Acids* 2008, 27, 213-223), a 1 L 3 neck flask equipped with a stir bar, addition funnel and rubber septa was charged with 20.9 mL of ethyl 2-(diethoxyphosphoryl)-2-fluoroacetate (103 mmol, 1 equiv) and 313 mL of THF. After cooling the reaction mixture to −78° C., 41.3 mL of 2.5 M nBuLi solution in hexanes (103 mmol, 1 equiv) was added dropwise and the reaction mixture was allowed to warm to 0° C. during 30 min. The solution was cooled to −78° C., and 19.9 mL of 1-((tert-butyldimethylsilyl)oxy)propan-2-one (103 mmol, 1 equiv) dissolved in 38 mL of THF was added drop wise through addition funnel. After stirring at −78° C. for 1 h and 0° C. for 1 h, the reaction mixture was allowed to warm up to rt and the stirring was continued for 12 more h. Then the reaction mixture was quenched by addition of sat. NH$_4$Cl solution, extracted with hexanes (1x) and diethyl ether (2×), washed with brine and dried over Na$_2$SO$_4$. The crude product was purified on silica gel column using 0 to 5% EA in hexanes as eluent to afford 25.9 g (91%) of the product 41 as a mixture of Z/E (2:1) isomers. $^1$H NMR (400 MHz, CDCl$_3$, ppm) δ: 4.67 (d, J=2.7 Hz, 0.8H), 4.36 (d, J=3.7 Hz, 2H), 4.28 (q, J=7.1 Hz, 2H), 4.27 (q, J=7.1 Hz, 0.8H), 2.12 (d, J=3.2 Hz, 2H), 1.92 (d, J=4.4 Hz, 0.8H), 1.34 (t, J=7.1 Hz, 3H), 1.34 (t, J=7.1 Hz, 1.2H), 0.90 (s, 12.6H), 0.08 (s, 6H), 0.07 (s, 2.4H).

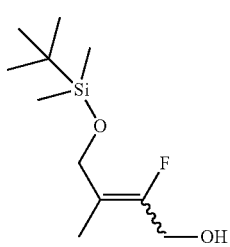

42

A 1 L rb flask equipped with a stir bar and rubber septum was charged with 13.6 g of the ester 41 (49.2 mmol, 1 equiv) and 246 ml of CH$_2$Cl$_2$. After cooling to −78° C., 90 mL of 1.2 M DIBAL-H solution in toluene (108 mmol, 2.2 equiv) was added and the reaction mixture was stirred at 0° C. for 2 h. Then the reaction mixture was quenched by addition of 40 mL of MeOH and the stirring was continued at rt for 12 h. The suspension was filtered through a celite plug and concentrated. The crude product was purified on silica gel column using 0 to 30% EA in hexanes as eluent affording 10.1 g (88%) of the product 42 as a yellow oil. $^1$H NMR (400 MHz, CDCl$_3$, ppm) δ: 4.27 (d, J=22.4 Hz, 1H), 4.26 (d, J=3.2 Hz, 2H), 4.25 (d, J=22.1 Hz, 2H), 4.15 (d, J=2.4 Hz, 1H), 1.72 (d, J=2.9 Hz, 4.5H), 1.69 (br s, 1.5H), 0.90 (s, 4.9H), 0.90 (s, 9H), 0.08 (s, 3H), 0.07 (s, 6H).

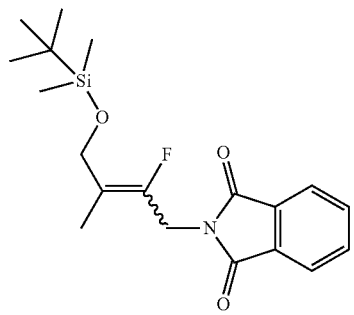

43

Compound 43 was synthesized from alcohol 42 following the procedure for the synthesis of compound 2. The crude product was purified on silica gel column using 0 to 10% of EA in hexanes as eluent affording 7.45 g (89%) of the product 43. $^1$H NMR (400 MHz, CDCl$_3$, ppm) δ: 7.86-7.82 (m, 3H), 7.73-7.69 (m, 3H), 4.52 (d, J=20.9 Hz, 1H), 4.46 (d, J=20.3 Hz, 2H), 4.35 (d, J=2.0 Hz, 1H), 4.22 (d, J=3.2 Hz, 2H), 1.88 (d, J=2.9 Hz, 3H), 1.70 (d, J=3.5 Hz, 1.5H), 0.91 (s, 4.5H), 0.87 (s, 9H), 0.11 (s, 3H), 0.02 (s, 6H).

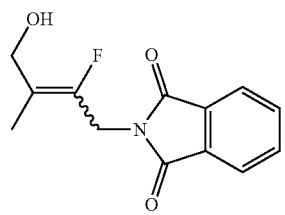

44

Compound 44 was synthesized from TBS ether 43 following the procedure for the synthesis of compound 3. The crude product was purified by crystallization affording 2.46 g (48%, 7:1 Z/E), 1.04 g (20%, 1:3 Z/E). 0.916 g (18%, 1.8:1 Z/E) of the product 44 as white solids.

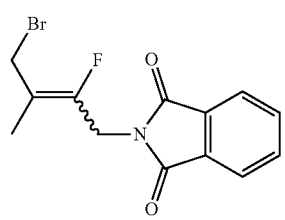

45

Compound 45 was synthesized from alcohol 44 following the procedure for the synthesis of compound 38. The organics were filtered through a silica gel plug and concentrated to afford 801 mg (85%) of the product 45 as a white solid.

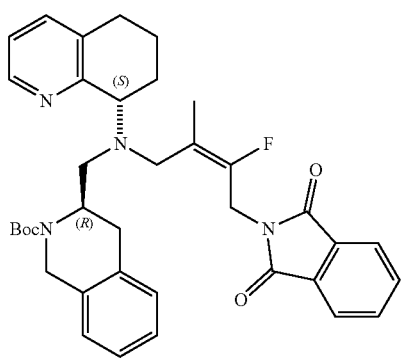

46

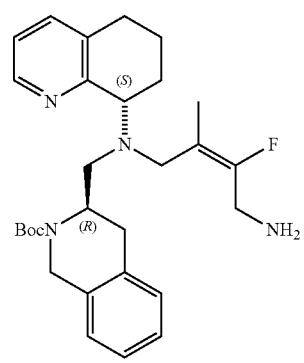

48

Compound 48 was synthesized from amine 46 following the procedure for the synthesis of compound 6. The crude material was used in the next step without purification.

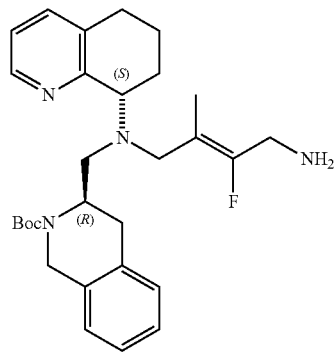

49

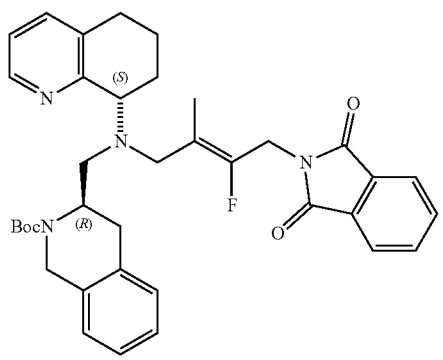

47

Compound 49 was synthesized from amine 47 following the procedure for the synthesis of compound 6. The crude material was used in the next step without purification.

Compounds 46 and 47 were synthesized from tert-butyl (R)-3-((((S)-5,6,7,8-tetrahydroquinolin-8-yl)amino)methyl)-3,4-dihydroisoquinoline-2(1H)-carboxylate and bromide 45 following the procedure for the synthesis of compound 39. The crude product was purified on silica gel column using 0 to 20% EA in $CH_2Cl_2$ affording 330 mg (31%) of 46, 158 mg (15%) of the mixture of the isomers and 339 mg (32%) of 47. For the 46 isomer: $^1$H NMR (400 MHz, $CDCl_3$, ppm) δ: 8.40 (br s, 1H), 7.79 (br s, 2H), 7.70 (br s, 2H), 7.27 (br s, 1H), 7.17-6.94 (m, 5H), 4.81-4.65 (m, 2H), 4.58-4.36 (m, 1H), 4.29-4.14 (m, 2H), 4.15-3.99 (m, 1H), 3.62 (d, J=13.4 Hz, 1H), 3.24-2.78 (m, 3H), 2.77-2.46 (m, 4H), 2.25-2.09 (m, 1H), 1.95 (br s, 1H), 1.87-1.63 (m, 2H), 1.74 (s, 3H), 1.50 (s, 9H). LC-MS (ESI-API, 254 nm) 75-95% MeOH in $H_2O$ (0.1% $HCO_2H$), 6 min, 1.00 mL/min, C18 (Agilent Zorbax XDB-18, 50 mm×4.6 mm, 3.5 μm), m/z=625.2 (M+H), t=1.272 min; For 47 isomer: $^1$H NMR (400 MHz, $CDCl_3$, ppm) δ: 8.41 (br s, 1H), 7.84-7.79 (dd, J=5.4, 3.0 Hz, 2H), 7.70 (dd, J=5.5, 3.0 Hz, 2H), 7.22 (br s, 1H), 7.12-6.90 (m, 5H), 4.74-4.62 (m, 1H), 4.53-4.07 (m, 3H), 3.98 (br s, 1H), 3.28-2.89 (m, 4H), 2.84-2.46 (m, 4H), 2.21-2.05 (m, 1H), 1.90 (s, 3H), 1.94-1.56 (m, 4H), 1.48 (s, 9H). LC-MS (ESI-API, 254 nm) 75-95% MeOH in $H_2O$ (0.1% $HCO_2H$), 6 min, 1.00 mL/min, C18 (Agilent Zorbax XDB-18, 50 mm×4.6 mm, 3.5 μm), m/z=625.2 (M+H), t=0.849 min, 95% purity;

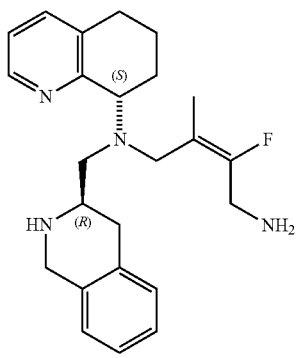

EMU125

Compound EMU125 was synthesized from amine 48 following the procedure for the synthesis of compound EMU030. The crude material was purified on silica gel column using 0 to 60% of solvent2 (solvent2=30% MeOH, 70% $CH_2Cl_2$ and 3% $NH_4OH$) in $CH_2C_2$ as eluent affording 118 mg (100%) of the product EMU125. $^1$H NMR (400 MHz, $CDCl_3$, ppm) δ: 8.42 (d, J=4.1 Hz, 1H), 7.32 (d, J=7.9

Hz, 1H), 7.12-7.06 (m, 2H), 7.05-7.01 (m, 3H), 4.16 (br s, 1H), 4.11 (A of AB, $J_{AB}$=14.9 Hz, 1H), 4.06-4.01 (m, 1H), 4.00 (B of AB, $J_{AB}$=15.1 Hz, 1H), 3.60 (A of ABX, $J_{AX}$=24.5 Hz, $J_{AB}$=14.9 Hz, 1H), 3.52 (B of ABX, $J_{BX}$=21.8 Hz, $J_{AB}$=14.9 Hz, 1H), 3.16 (dd, J=13.0, 4.0 Hz, 1H), 2.93-2.88 (m, 1H), 2.79-2.70 (m, 1H), 2.70-2.61 (m, 2H), 2.57 (dd, J=16.0, 3.6 Hz, 1H), 2.51-2.32 (m, 2H), 2.09-2.03 (m, 1H), 1.99-1.85 (m, 2H), 1.76 (d, J=3.2 Hz, 3H), 1.73-1.63 (m, 1H). $^{13}$C NMR (400 MHz, CDCl$_3$, ppm) δ: 158.92, 158.04 (d, J=247.6 Hz), 146.52, 136.24, 135.12, 134.27, 134.03, 128.91, 126.30, 125.82, 125.40, 121.16, 111.24 (d, J=14.6 Hz), 57.90, 56.04, 54.39 (d, J=8.9 Hz), 51.47, 48.52, 39.34 (d, J=30.1 Hz), 33.51, 29.86, 29.26, 22.21, 12.76 (d, J=8.3 Hz). $^{19}$F NMR (400 MHz, CDCl$_3$, ppm) δ: −114.36 (t, J=23.4 Hz). HRMS (ESI+) calcd for $C_{24}H_{32}FN_4$ ([M+H]$^+$): 395.2606. Found: 395.2603, error −0.3 ppm. LC-MS (ESI-API, 254 nm) 75-95% MeOH in H$_2$O (0.1% HCO$_2$H), 3 min, 1.00 mL/min, C18 (Agilent Zorbax XDB-18, 50 mm×4.6 mm, 3.5 μm), m/z=395.2 (M+H), 198.2 (M/2+H), t=0.773 min;

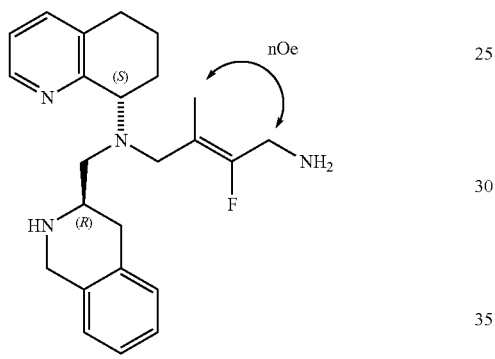

EMU126

Compound EMU126 was synthesized from amine 49 following the procedure for the synthesis of compound EMU030. The crude material was purified on silica gel column using 0 to 60% of solvent2 (solvent2=30% MeOH, 70% CH$_2$Cl$_2$ and 3% NH$_4$OH) in CH$_2$Cl$_2$ as eluent affording 129 mg (100%) of the product EMU126. $^1$H NMR (400 MHz, CDCl$_3$, ppm) δ: 8.45 (d, J=4.7 Hz, 1H), 7.31 (d, J=7.7 Hz, 1H), 7.13-6.98 (m, 5H), 4.10-4.00 (m, 2H), 3.86 (d, J=15.1 Hz, 1H), 3.81-4.75 (m, 1H), 3.40 (d, J=21.7 Hz, 2H), 3.19 (d, J=13.3 Hz, 1H), 2.99 (d, J=13.3 Hz, 1H), 2.76 (ddd, J=16.3, 10.9, 4.9 Hz, 2H), 2.66 (B of AB, $J_{AB}$=16.4 Hz, 1H), 2.61 (d, J=15.1 Hz, 1H), 2.45 (br s, 2H), 2.12-2.06 (m, 1H), 2.00-1.89 (m, 2H), 1.76 (s, 3H), 1.78-1.67 (m, 1H). $^{13}$C NMR (400 MHz, CDCl$_3$, ppm) δ: 158.43, 156.06 (d, J=245.6 Hz), 146.62, 136.20, 135.08, 134.38, 133.64, 128.92, 126.24, 125.78, 125.32, 121.18, 111.53 (d, J=12.7 Hz), 60.90, 57.16, 52.08, 52.00 (d, J=14.2 Hz), 48.28, 39.56 (d, J=30.8 Hz), 33.41, 29.29, 28.07, 21.92, 14.03 (d, J=4.8 Hz). $^{19}$F NMR (400 MHz, CDCl$_3$, ppm) δ: −120.90 (t, J=21.7 Hz). HRMS (ESI+) calcd for $C_{24}H_{32}FN_4$ ([M+H]$^+$): 395.2606. Found: 395.2649, error 4.3 ppm. LC-MS (ESI-API, 254 nm) 75-95% MeOH in H$_2$O (0.1% HCO$_2$H), 3 min, 1.00 mL/min, C18 (Agilent Zorbax XDB-18, 50 mm×4.6 mm, 3.5 μm), m/z=395.2 (M+H), 198.2 (M/2+H), t=0.797 min;

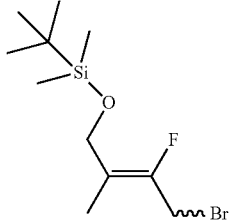

50

Compound 50 was synthesized from alcohol 42 following the procedure for the synthesis of compound 38. The product was used in the next step without purification.

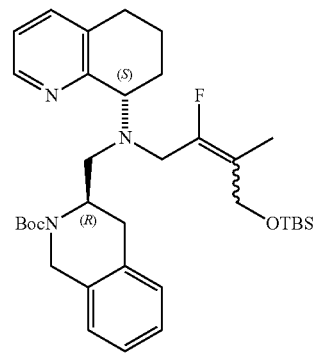

51

Compound 51 was synthesized from tert-butyl (R)-3-((((S)-5,6,7,8-tetrahydroquinolin-8-yl)amino)methyl)-3,4-dihydroisoquinoline-2(1H)-carboxylate and bromide 50 following the procedure for the synthesis of compound 39. The crude product was purified on silica gel column using 0 to 30% EA in hexanes as eluent affording 408 mg of the product 51.

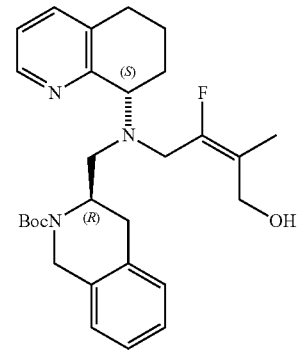

52

53

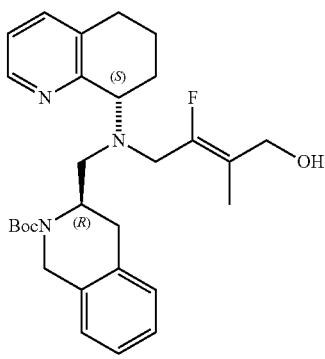

Compounds 52 and 53 were synthesized from amine I and bromide 51 following the procedure for the synthesis of compound 39. The crude product was purified on silica gel column using 0 to 60% EA in CH$_2$Cl$_2$ affording 0.440 g (16%) of 52 and 1.04 g (37%) of 53. For 52: $^1$H NMR (400 MHz, CDCl$_3$, ppm) δ: 8.44 (br s, 1H), 7.19 (d, J=8.0 Hz, 1H), 7.06-6.84 (m, 5H), 4.64-4.43 (m, 2.5H), 4.36 (br s, 0.5H), 4.17 (d, J=16.6 Hz, 1H), 4.13-3.98 (m, 1H), 3.75 (br s, 1H), 3.20-2.90 (m, 2H), 2.86 (dd, J=15.8, 5.6 Hz, 1H), 2.55-2.47 (m, 2H), 2.37-1.97 (m, 4H), 1.83 (s, 3H), 1.89-1.31 (m, 2H), 1.50 (s, 9H). LC-MS (ESI-API, 254 nm) 95% MeOH in H$_2$O (0.1% HCO$_2$H), 3 min, 1.00 mL/min, C18 (Agilent Zorbax XDB-18, 50 mm×4.6 mm, 3.5 μm), m/z=496.2 (M+H), t=1.031 min; For 53: $^1$H NMR (400 MHz, CDCl$_3$, ppm) δ: 8.34 (d, J=4.5 Hz, 1H), 7.29 (d, J=7.7 Hz, 1H), 7.16-6.95 (m, 5H), 4.61 (A of AB, J$_{AB}$=17.0 Hz, 1H), 4.55 (d, J=11.7 Hz, 1H), 4.52-4.45 (m, 1H), 4.26 (B of AB, J$_{AB}$=17.1 Hz, 1H), 3.87-3.78 (m, 1H), 3.69 (dd, J=10.6, 6.1 Hz, 1H), 3.44-3.28 (m, 2H), 3.18 (A of AB, J$_{AB}$=15.9 Hz, 1H), 3.03-2.58 (m, 5H), 2.26-2.18 (m, 1H), 2.02-1.95 (m, 1H), 1.82 (q, J=11.3 Hz, 1H), 1.73-1.58 (m, 1H), 1.70 (s, 3H), 1.48 (s, 9H). LC-MS (ESI-API, 254 nm) 95% MeOH in H$_2$O (0.1% HCO$_2$H), 3 min, 1.00 mL/min, C18 (Agilent Zorbax XDB-18, 50 mm×4.6 mm, 3.5 μm), m/z=496.2 (M+H), t=0.725 min;

54

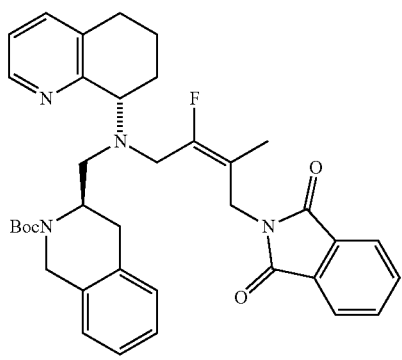

Compound 54 was synthesized from alcohol 52 following the procedure for the synthesis of compound 2. The crude product was purified on silica gel column using 0 to 40% of EA in hexanes as eluent affording 0.640 g (128%) of the product 54. $^1$H NMR (400 MHz, CDCl$_3$, ppm) δ: 8.36 (br s, 1H), 7.79 (dd, J=5.4, 3.1 Hz, 2H), 7.69 (dd, J=5.5, 3.1 Hz, 2H), 7.30 (d, J=7.3 Hz, 1H), 7.11 (s, 3H), 7.05-6.98 (m, 1H), 6.98 (dd, J=7.8, 4.8 Hz, 1H), 4.81-4.66 (m, 1.5H), 4.54 (br s, 0.5H), 4.30-4.02 (m, 4H), 3.51-3.28 (m, 1H), 3.16-2.91 (m, 3H), 2.83-2.62 (m, 4H), 2.25-1.66 (m, 4H), 1.54 (d, J=3.3 Hz, 3H), 1.50 (s, 9H). LC-MS (ESI-API, 254 nm) 75-95% MeOH in H$_2$O (0.1% HCO$_2$H), 6 min, 1.00 mL/min, C18 (Agilent Zorbax XDB-18, 50 mm×4.6 mm, 3.5 μm), m/z=625.2 (M+H), t=0.989 min;

55

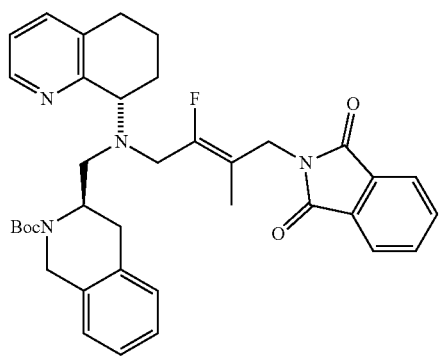

Compound 55 was synthesized from alcohol 53 following the procedure for the synthesis of compound 2. The crude product was purified on silica gel column using 0 to 40% of EA in hexanes as eluent affording 0.958 g (78%) of the product 55. $^1$H NMR (400 MHz, CDCl$_3$, ppm) δ: 8.31 (br s, 1H), 7.83 (dd, J=5.4, 3.0 Hz, 2H), 7.74-7.67 (m, 2H), 7.27 (d, J=7.2 Hz, 1H), 7.16-7.06 (m, 3H), 7.03 (br s, 1H), 6.98-6.93 (m, 1H), 4.74-4.62 (m, 1.5H), 4.43 (br s, 0.5H), 4.39 (A of AB, J$_{AB}$=17.6 Hz, 1H), 4.33 (B of AB, J$_{AB}$=15.6 Hz, 1H), 4.14 (B of AB, J$_{AB}$=17.1 Hz, 1H), 3.95 (br s, 1H), 3.28-2.88 (m, 3H), 2.77-2.56 (m, 5H), 2.15-1.63 (m, 4H), 1.46 (s, 9H), 1.39 (d, J=2.8 Hz, 3H). LC-MS (ESI-API, 254 nm) 75-95% MeOH in H$_2$O (0.1% HCO$_2$H), 6 min, 1.00 mL/min, C18 (Agilent Zorbax XDB-18, 50 mm×4.6 mm, 3.5 μm), m/z=625.2 (M+H), t=0.987 min, 96% purity;

56

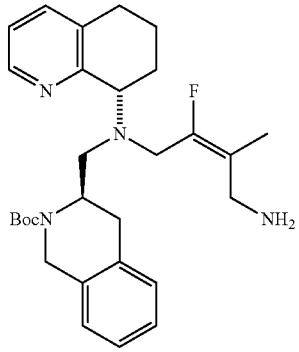

Compound 56 was synthesized from amine 54 following the procedure for the synthesis of compound 6. The crude material was used in the next step without purification.

57

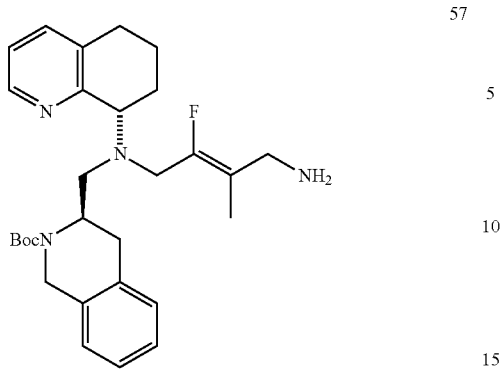

Compound 57 was synthesized from amine 55 following the procedure for the synthesis of compound 6. The crude material was used in the next step without purification.

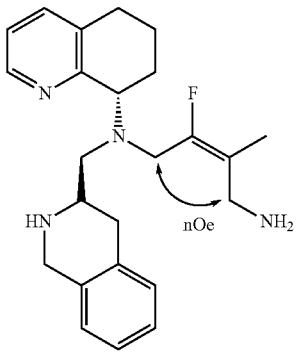

EMU140

Compound EMU140 was synthesized from amine 56 following the procedure for the synthesis of compound EMU030. The crude material was purified on silica gel column using 0 to 60% of solvent2 (solvent2=30% MeOH, 70% CH$_2$Cl$_2$ and 3% NH$_4$OH) in CH$_2$Cl$_2$ as eluent affording 109 mg (56%) of the product EMU140. $^1$H NMR (600 MHz, CDCl$_3$, ppm) δ: 8.43 (d, J=4.7 Hz, 1H), 7.33 (d, J=7.7 Hz, 1H), 7.10-7.00 (m, 5H), 4.27 (dd, J=30.3, 14.6 Hz, 1H), 4.09 (dd, J=10.7, 6.5 Hz, 1H), 4.05 (A of AB, J$_{AB}$=15.0 Hz, 1H), 3.94 (B of AB, J$_{AB}$=15.1 Hz, 1H), 3.46 (t, J=14.9 Hz, 1H), 3.34 (A of AB, J$_{AB}$=13.5 Hz, 1H), 3.30 (B of AB, J$_{AB}$=13.5 Hz, 1H), 2.87 (t, J=10.9 Hz, 1H), 2.82 (dd, J=13.3, 2.9 Hz, 1H), 2.78-2.71 (m, 1H), 2.65 (B of AB, J$_{AB}$=16.6 Hz, 1H), 2.57 (dd, J=15.8, 3.6 Hz, 1H), 2.41 (dd, J=16.0, 10.9 Hz, 1H), 2.35 (dd, J=12.5, 11.0 Hz, 1H), 2.15-2.08 (m, 1H), 2.00-1.94 (m, 1H), 1.93-1.86 (m, 1H), 1.76 (d, J=3.1 Hz, 3H), 1.74-1.65 (m, 1H). $^{13}$C NMR (400 MHz, CDCl$_3$, ppm) δ: 158.60, 154.19 (d, J=248.9 Hz), 146.57, 136.40, 135.56, 134.37, 133.96, 128.92, 126.36, 125.73, 125.37, 121.33, 116.73 (d, J=12.9 Hz), 60.01, 56.49, 51.54, 51.46 (d, J=26.6 Hz), 48.57, 42.81 (d, J=7.6 Hz), 33.62, 29.22, 22.08, 12.37 (d, J=8.3 Hz). $^{19}$F NMR (400 MHz, CDCl$_3$, ppm) δ: −112.40 (br s). HRMS (ESI+) calcd for C$_{24}$H$_{32}$FN$_4$ ([M+H]$^+$): 395.2606. Found: 395.2618, error 1.2 ppm. LC-MS (ESI-API, 254 nm) 75-95% MeOH in H$_2$O (0.1% HCO$_2$H), 3 min, 1.00 mL/min, C18 (Agilent Zorbax XDB-18, 50 mm×4.6 mm, 3.5 μm), m/z=395.2 (M+H), 198.2 (M/2+H), t=0.815 min;

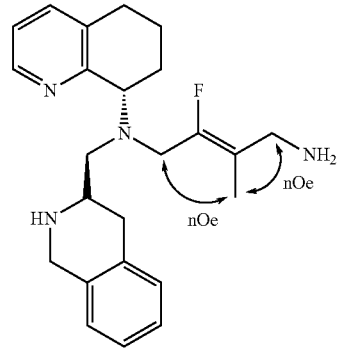

EMU141

Compound EMU141 was synthesized from amine 57 following the procedure for the synthesis of compound EMU030. The crude material was purified on silica gel column using 0 to 60% of solvent2 (solvent2=30% MeOH, 70% CH$_2$Cl$_2$ and 3% NH$_4$OH) in CH$_2$Cl$_2$ as eluent affording 186 mg (90%) of the product EMU141. $^1$H NMR (600 MHz, CDCl$_3$, ppm) δ: 8.43 (d, J=4.7 Hz, 1H), 7.33 (d, J=7.7 Hz, 1H), 7.11-6.99 (m, 5H), 4.24 (dd, J=29.9, 14.8 Hz, 1H), 4.09 (dd, J=10.8, 6.5 Hz, 1H), 4.07 (A of AB, J$_{AB}$=15.1 Hz, 1H), 3.98 (B of AB, J$_{AB}$=15.0 Hz, 1H), 3.43 (t, J=15.5 Hz, 1H), 3.36 (A of ABX, J$_{AB}$=13.3 Hz, J$_{AX}$=2.5 Hz, 1H), 3.32 (B of ABX, J$_{AB}$=13.3 Hz, J$_{BX}$=2.6 Hz, 1H), 2.94-2.87 (m, 2H), 2.75 (ddd, J=16.7, 11.6, 5.0 Hz, 1H), 2.65 (B of AB, J$_{AB}$=16.6 Hz, 1H), 2.57 (dd, J=16.0, 3.4 Hz, 1H), 2.48-2.31 (m, 2H), 2.13-2.07 (m, 1H), 2.00-1.86 (m, 2H), 1.73 (d, J=2.6 Hz, 3H), 1.79-1.65 (m, 1H). $^{13}$C NMR (400 MHz, CDCl$_3$, ppm) δ: 158.60, 153.23 (d, J=245.9 Hz), 146.43, 136.26, 135.47, 134.37, 133.78, 128.83, 126.29, 125.63, 125.24, 121.20, 116.11 (d, J=15.2 Hz), 60.56, 56.62, 51.71, 51.43 (d, J=26.5 Hz), 48.58, 40.65 (d, J=9.9 Hz), 33.48, 30.08, 29.08, 21.93, 13.88 (d, J=5.3 Hz). $^{19}$F NMR (400 MHz, CDCl$_3$, ppm) δ: −116.37 (dd, J=30.3, 16.2 Hz). HRMS (ESI+) calcd for C$_{24}$H$_{32}$FN$_4$ ([M+H]$^+$): 395.2606. Found: 395.2602, error −0.3 ppm. LC-MS (ESI-API, 254 nm) 75-95% MeOH in H$_2$O (0.1% HCO$_2$H), 3 min, 1.00 mL/min, C18 (Agilent Zorbax XDB-18, 50 mm×4.6 mm, 3.5 μm), m/z=395.2 (M+H), 198.2 (M/2+H), t=0.818 min; Synthesis of EMU177 and EMU208

58

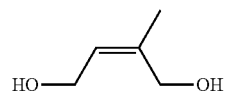

A 250 mL rb flask equipped with a stir bar and rubber septum was charged with 5.00 mL of 3-methylfuran-2(5H)-one (57.6 mmol, 1 equiv) and 48.0 ml of toluene. After cooling to 0° C., 106 mL of 1.2 M DIBAL-H solution in toluene (127 mmol, 2.2 equiv) and the reaction mixture was stirred at 0° C. for 2 h. Then reaction was quenched by addition of 32 mL of MeOH, followed by 51 mL of toluene and 11 mL of water. The reaction mixture was stirred for 30 min and celite was added. After stirring for 30 min, the suspension was filtered through celite plug and the celite plug was washed with EA. The organics were concentrated and 5.71 g (97%) of the product 58 was obtained. $^1$H NMR (400 MHz, CDCl$_3$, ppm) δ: 5.60 (t, J=7.1 Hz, 1H), 4.16 (d, J=7.9 Hz, 2H), 4.15 (s, 2H), 2.46 (br s, 1H), 2.26 (br s, 1H), 1.83 (s, 3H).

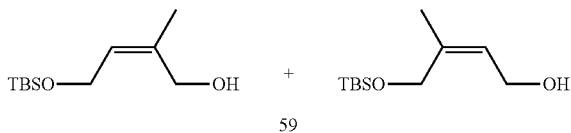

59

Compound 59 was synthesized from diol 58 following the procedure for the synthesis of compound 35. The crude product was purified on silica gel column using 0-30% EA in hexanes as eluent affording 3.42 g (27%) of the product 59 as a mixture of regioisomers. $^1$H NMR (400 MHz, CDCl$_3$, ppm) δ: 5.54 (t, J=7.0 Hz, 0.3H), 5.51 (t, J=7.0 Hz, 0.7H), 4.21 (d, J=6.4 Hz, 0.7H), 4.18 (s, 0.3H), 4.15 (t, J=6.7 Hz, 0.3H), 4.11 (d, J=6.1 Hz, 0.7H), 2.14 (t, J=6.1 Hz, 1H), 1.81 (s, 2.1H), 1.77 (s, 0.9H), 0.90 (s, 9H), 0.08 (s, 6H).

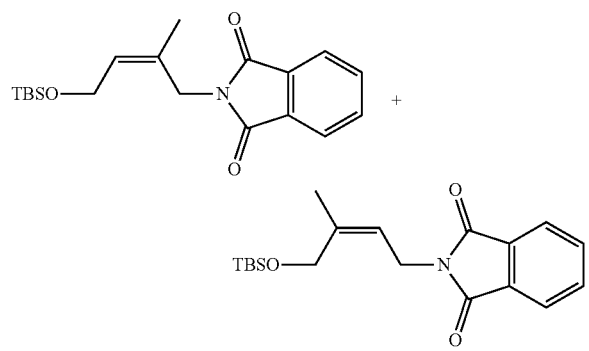

60

Compound 60 was synthesized from alcohol 59 following the procedure for the synthesis of compound 2. The crude product was purified on silica gel column using 0 to 10% of EA in hexanes as eluent. The organics were concentrated and the product was used in the next step.

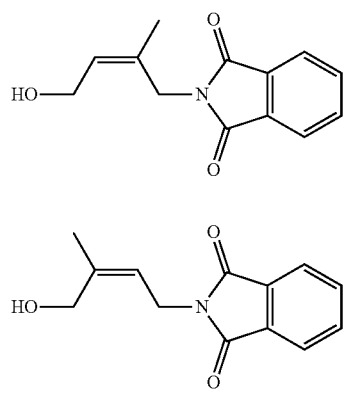

61

62

Compounds 61 and 62 were synthesized from TBS ether 60 following the procedure for the synthesis of compound 3. The crude product was purified on silica gel column using 0 to 60% EA in hexanes as eluent affording 0.297 g (8%) of 62, 1.36 g (37%) of the mixture of the isomers and 1.91 g (52%) of 61. For the first isomer 62: $^1$H NMR (300 MHz, CDCl$_3$, ppm) δ: 7.85-7.81 (m, 2H), 7.74-7.69 (m, 2H), 5.32 (t, J=8.0 Hz, 1H), 4.38 (dd, J=8.0, 0.9 Hz, 2H), 4.28 (s, 2H), 2.83 (br s, 1H), 1.83-1.81 (m, 3H). LC-MS (ESI-API, 254 nm) 95% MeOH in H$_2$O (0.1% HCO$_2$H), 3 min, 1.00 mL/min, C18 (Agilent Zorbax XDB-18, 50 mm×4.6 mm, 3.5 μm), m/z=254.0 (M+Na), 232.0 (M+H), t=0.548 min; For the second isomer 61: $^1$H NMR (400 MHz, CDCl$_3$, ppm) δ: 7.85 (dd, J=5.5, 3.0 Hz, 2H), 7.74 (dd, J=5.4, 3.1 Hz, 2H), 5.76 (t, J=7.6 Hz, 1H), 4.40 (d, J=0.8 Hz, 2H), 4.31 (d, J=7.5 Hz, 2H), 2.82 (br s, 1H), 1.72-1.70 (m, 3H). LC-MS (ESI-API, 254 nm) 95% MeOH in H$_2$O (0.1% HCO$_2$H), 3 min, 1.00 mL/min, C18 (Agilent Zorbax XDB-18, 50 mm×4.6 mm, 3.5 μm), m/z=254.0 (M+Na), t=0.548 min.

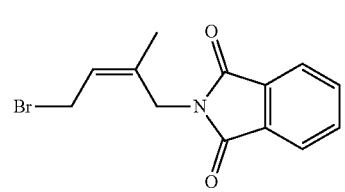

63

Compound 63 was synthesized from alcohol 61 following the procedure for the synthesis of compound 38. The crude product was purified on silica gel column using CH$_2$Cl$_2$ as eluent affording 883 mg (68%) of the product 63 as a white solid. $^1$H NMR (600 MHz, CDCl$_3$, ppm) δ: 7.86 (dd, J=5.5, 3.0 Hz, 2H), 7.73 (dd, J=5.5, 3.0 Hz, 2H), 5.73 (t, J=8.6 Hz, 1H), 4.36 (s, 2H), 4.27 (dt, J=8.6, 0.8 Hz, 2H), 1.78 (d, J=0.8 Hz, 3H).

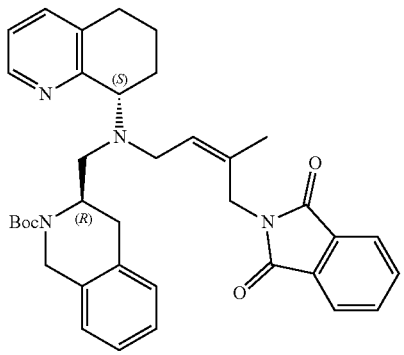

64

Compound 64 was synthesized from tert-butyl (R)-3-((((S)-5,6,7,8-tetrahydroquinolin-8-yl)amino)methyl)-3,4-dihydroisoquinoline-2(1H)-carboxylate and bromide 63 following the procedure for the synthesis of compound 39. The crude product was purified on silica gel column using 0 to 40% EA in hexanes as eluent affording 374 mg (60%) of the product 64. $^1$H NMR (400 MHz, CDCl$_3$, ppm) δ: 8.40 (br s, 1H), 7.83-7.77 (m, 2H), 7.72-7.67 (m, 2H), 7.26 (d, J=6.6 Hz, 1H), 7.07-6.92 (m, 5H), 5.47 (t, J=6.6 Hz, 1H), 4.74-4.59 (m, 1.5H), 4.51 (br s, 0.5H), 4.26 (A of AB, J$_{AB}$=14.7 Hz, 1H), 4.20 (B of AB, J$_{AB}$=14.8 Hz, 1H), 4.14-4.00 (m, 2H), 3.62-3.53 (m, 1H), 3.47-3.30 (m, 1H), 3.06-2.91 (m, 2H), 2.79-2.44 (m, 4H), 2.14-1.91 (m, 1H), 1.82 (q, J=11.1 Hz, 1H), 1.74-1.61 (m, 2H), 1.58 (s, 3H), 1.50 (s, 9H). LC-MS (ESI-API, 254 nm) 95% MeOH in H$_2$O (0.1%

HCO₂H), 3 min, 1.00 mL/min, C18 (Agilent Zorbax XDB-18, 50 mm×4.6 mm, 3.5 μm), m/z=607.2 (M+H), t=0.480 min;

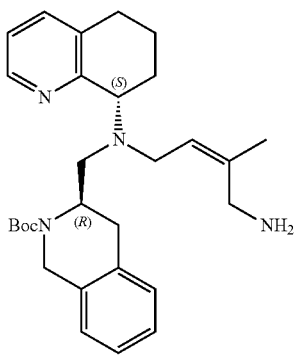

65

Compound 65 was synthesized from amine 64 following the procedure for the synthesis of compound 6. The organics were concentrated and the crude product was used in the next step.

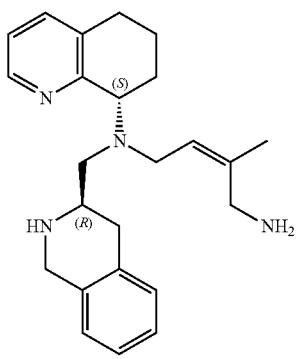

EMU177

Compound EMU177 was synthesized from amine 65 following the procedure for the synthesis of compound EMU030. The crude material was purified on silica gel column using 0 to 45% of solvent2 (solvent2=30% MeOH, 70% CH₂Cl₂ and 3% NH₄OH) in CH₂Cl₂ as eluent affording 74 mg (74%) of the product EMU177. ¹H NMR (600 MHz, CDCl₃, ppm) δ: 8.45 (d, J=4.7 Hz, 1H), 7.31 (d, J=7.6 Hz, 1H), 7.09-6.98 (m, 5H), 5.43 (t, J=7.0 Hz, 1H), 4.10 (dd, J=10.2, 6.5 Hz, 1H), 4.02 (A of AB, $J_{AB}$=15.1 Hz, 1H), 3.84 (B of AB, $J_{AB}$=15.0 Hz, 1H), 3.81 (dd, J=13.8, 8.0 Hz, 1H), 3.39 (A of AB, $J_{AB}$=13.1 Hz, 1H), 3.29 (dd, J=13.9, 5.9 Hz, 1H), 3.24 (B of AB, $J_{AB}$=13.2 Hz, 1H), 2.82-2.72 (m, 3H), 2.65 (B of AB, $J_{AB}$=16.5 Hz, 1H), 2.58 (A of ABX, $J_{AB}$=16.1 Hz, $J_{AB}$=3.7 Hz, 1H), 2.44-2.34 (m, 2H), 2.08-2.03 (m, 1H), 2.00-1.94 (m, 1H), 1.94-1.85 (m, 1H), 1.81 (s, 3H), 1.74-1.63 (m, 1H). ¹³C NMR (400 MHz, CDCl₃, ppm) δ: 158.75, 146.66, 139.09, 136.33, 135.57, 134.52, 133.92, 128.97, 126.29, 125.76, 125.53, 125.36, 121.22, 59.92, 57.02, 51.66, 51.20, 48.50, 42.44, 33.81, 29.37, 28.27, 22.08, 21.99. HRMS (ESI+) calcd for C₂₄H₃₃N₄ ([M+H]⁺): 377.2700. Found: 377.2696, error −0.4 ppm. LC-MS (ESI-API, 254 nm) 75-95% MeOH in H₂O (0.1% HCO₂H), 3 min, 1.00 mL/min, C18 (Agilent Zorbax XDB-18, 50 mm×4.6 mm, 3.5 μm), m/z=377.2 (M+H), 189.2 (M/2+H), t=0.465 min;

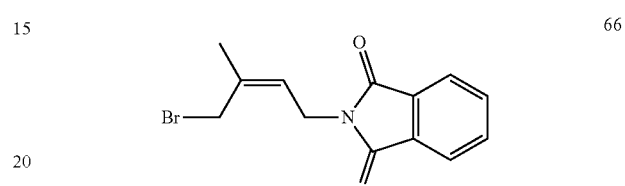

66

Compound 66 was synthesized from alcohol 62 following the procedure for the synthesis of compound 38. The crude product was purified on silica gel column using CH₂Cl₂ as eluent affording 785 mg (139%) of the product 66 as a white solid. ¹H NMR (400 MHz, CDCl₃, ppm) δ: 7.84 (dd, J=5.5, 3.0 Hz, 2H), 7.71 (dd, J=5.4, 3.1 Hz, 2H), 5.51 (tq, J=7.5, 1.5 Hz, 1H), 4.31 (dd, J=7.6, 1.0 Hz, 2H), 4.19 (s, 2H), 1.87-1.86 (m, 3H).

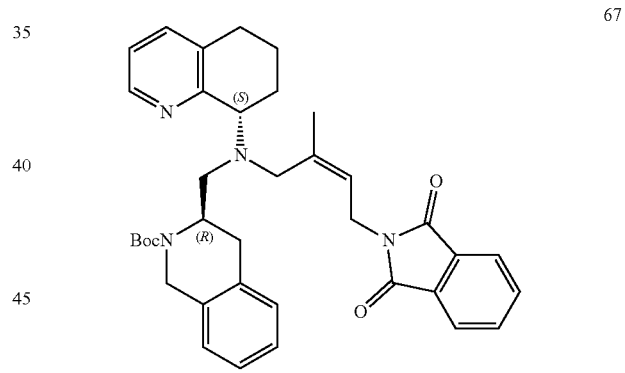

67

Compound 67 was synthesized from tert-butyl (R)-3-((((S)-5,6,7,8-tetrahydroquinolin-8-yl)amino)methyl)-3,4-dihydroisoquinoline-2(1H)-carboxylate and bromide 66 following the procedure for the synthesis of compound 39. The crude product was purified on silica gel column using 0 to 30% EA in hexanes as eluent affording 312 mg (76%) of the product 67. ¹H NMR (400 MHz, CDCl₃, ppm) δ: 8.44 (br s, 1H), 7.78 (br s, 2H), 7.68 (br s, 2H), 7.25 (d, J=6.5 Hz, 1H), 7.08-6.92 (m, 5H), 5.28 (br s, 1H), 4.80-4.63 (m, 1.5H), 4.49 (br s, 0.5H), 4.32-3.98 (m, 4H), 3.57 (A of AB, $J_{AB}$=13.4 Hz, 0.5H), 3.44 (A of AB, $J_{AB}$=13.6 Hz, 0.5H), 3.22 (B of AB, $J_{AB}$=13.3 Hz, 0.5H), 3.11-2.84 (m, 2.5H), 2.74-2.47 (m, 4H), 2.18 (br s, 1H), 2.00-1.61 (m, 3H), 1.81 (s, 3H), 1.49 (s, 9H). LC-MS (ESI-API, 254 nm) 75-95% MeOH in H₂O (0.1% HCO₂H), 6 min, 1.00 mL/min, C18 (Agilent Zorbax XDB-18, 50 mm×4.6 mm, 3.5 μm), m/z=607.2 (M+H), t=0.972 min, 96% purity;

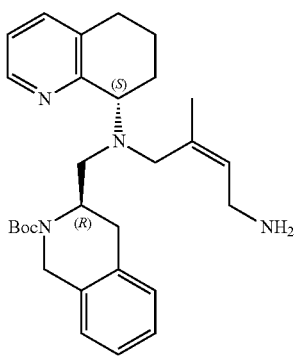

68

Compound 68 was synthesized from amine 67 following the procedure for the synthesis of compound 6. The organics were concentrated and the crude product was used in the next step.

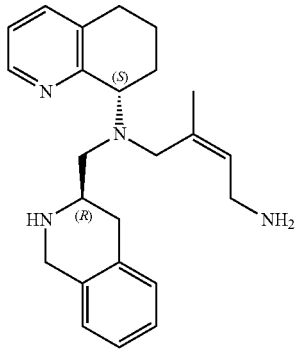

EMU208

Compound EMU208 was synthesized from amine 68 following the procedure for the synthesis of compound EMU030. The crude material was purified on silica gel column using 0 to 45% of solvent2 (solvent2=30% MeOH, 70% $CH_2Cl_2$ and 3% $NH_4OH$) in $CH_2Cl_2$ as eluent affording 84 mg (66%) of the product EMU208. $^1$H NMR (600 MHz, $CDCl_3$, ppm) δ: 8.45 (d, J=4.8 Hz, 1H), 7.32 (d, J=7.8 Hz, 1H), 7.10-7.06 (m, 2H), 7.05-6.99 (m, 3H), 5.55 (t, J=7.3 Hz, 1H), 4.11 (d, J=12.9 Hz, 1H), 4.06 (A of AB, $J_{AB}$=15.1 Hz, 1H), 4.00 (dd, J=10.5, 6.6 Hz, 1H), 3.91 (B of AB, $J_{AB}$=15.1 Hz, 1H), 3.51 (A of ABX, $J_{AB}$=13.7 Hz, $J_{AX}$=7.6 Hz, 1H), 3.38 (B of ABX, $J_{AB}$=13.7 Hz, $J_{BX}$=6.9 Hz, 1H), 3.10 (d, J=12.9 Hz, 1H), 2.85 (tt, J=10.8, 3.5 Hz, 1H), 2.79-2.72 (m, 1H), 2.72 (B of ABX, $J_{AB}$=13.1 Hz, $J_{BX}$=3.2 Hz, 1H), 2.65 (B of AB, $J_{AB}$=16.7 Hz, 1H), 2.57 (A of ABX, $J_{AB}$=16.2 Hz, $J_{AX}$=3.6 Hz, 1H), 2.40 (B of ABX, $J_{AB}$=16.4 Hz, $J_{BX}$=11.3 Hz, 1H), 2.33 (dd, J=13.3, 10.3 Hz, 1H), 2.11-2.05 (m, 1H), 1.99-1.86 (m, 5H), 1.85 (s, 3H), 1.73-1.64 (m, 1H). $^{13}$C NMR (400 MHz, $CDCl_3$, ppm) δ: 158.66, 146.51, 136.72, 136.35, 135.45, 134.39, 133.97, 128.97, 128.82, 128.79, 126.26, 125.76, 125.37, 121.24, 58.57, 56.59, 54.34, 51.50, 48.49, 38.54, 33.68, 29.32, 28.53, 23.05, 22.10. HRMS (ESI+) calcd for $C_{24}H_{33}N_4$ ([M+H]$^+$): 377.2700. Found: 377.2695, error 0.5 ppm. LC-MS (ESI-API, 254 nm) 75-95% MeOH in $H_2O$ (0.1% $HCO_2H$), 3 min, 1.00 mL/min, C18 (Agilent Zorbax XDB-18, 50 mm×4.6 mm, 3.5 µm), m/z=377.2 (M+H), 189.2 (M/2+H), t=0.454 min;

Synthesis of EMU143 and EMU211

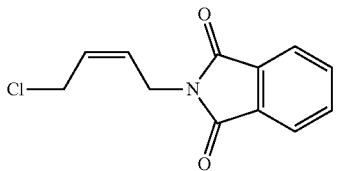

69

A 250 mL rb flask equipped with a magnetic stir bar and rubber septum was charged with 3.00 g of the HCl salt of (Z)-4-chlorobut-2-en-1-amine (21.1 mol, 1 equiv), 7.36 mL of TEA (52.8 mmol, 2.5 equiv), 0.129 g of DMAP (1.06 mmol, 0.05 equiv) and 70 mL of THF. Then 4.86 g of ethyl 1,3-dioxoisoindoline-2-carboxylate (22.2 mmol, 1.05 equiv) was added. After stirring at rt for 48 h, the reaction mixture was quenched by addition of water, extracted with diethyl ether (2×), dried over $Na_2SO_4$. The crude material was purified on silica gel column using $CH_2Cl_2$ as eluent affording 3.11 g (63%) of the product 69 as a white solid. $^1$H NMR (400 MHz, $CDCl_3$, ppm) δ: 7.84 (dd, J=5.5, 3.0 Hz, 2H), 7.72 (dd, J=5.4, 3.1 Hz, 2H), 5.84 (dtt, J=10.3, 7.7, 1.2 Hz, 1H), 5.70 (dtt, J=10.6, 7.4, 1.0 Hz, 1H), 4.35 (dd, J=7.4, 1.3 Hz, 2H), 4.32 (dd, J=7.8, 1.0 Hz, 2H).

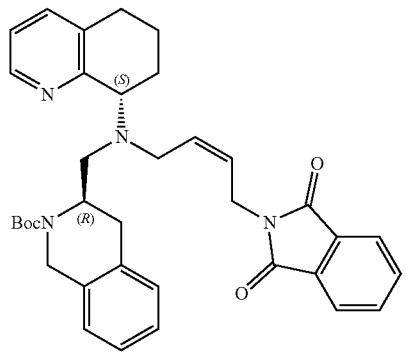

70

Compound 70 was synthesized from tert-butyl (R)-3-((((S)-5,6,7,8-tetrahydroquinolin-8-yl)amino)methyl)-3,4-dihydroisoquinoline-2(1H)-carboxylate and chloride 69 following the procedure for the synthesis of compound 39. The crude product was purified on silica gel column using 0 to 30% EA in $CH_2Cl_2$ as eluent affording 881 mg (82%) of the product 70. $^1$H NMR (400 MHz, $CDCl_3$, ppm) δ: 8.37 (s, 1H), 7.77-7.71 (m, 2H), 7.69-7.55 (m, 2H), 7.22 (d, J=7.7 Hz, 1H), 7.02-6.84 (m, 5H), 5.68 (dt, J=12.7, 6.8 Hz, 1H), 5.41 (dt, J=11.2, 6.9 Hz, 1H), 4.75-4.41 (m, 2H), 4.25 (A of ABX, $J_{AB}$=15.1, $J_{AX}$=6.8 Hz, 1H), 4.17 (B of ABX, $J_{AB}$=15.1, $J_{BX}$=6.8 Hz, 1H), 4.10-3.94 (m, 2H), 3.63-3.53 (m, 1H), 3.44-3.33 (m, 1H), 3.06-2.84 (m, 2H), 2.74-2.41 (m, 4H), 2.03 (br s, 1H), 1.92 (br s, 1H), 1.84-1.72 (m, 1H), 1.68-1.57 (m, 1H), 1.47 (s, 9H). LC-MS (ESI-API, 254 nm) 75-95% MeOH in $H_2O$ (0.1% $HCO_2H$), 6 min, 1.00 mL/min, C18 (Agilent Zorbax XDB-18, 50 mm×4.6 mm, 3.5 µm), m/z=593.2 (M+H), t=0.705 min, 96% purity;

71

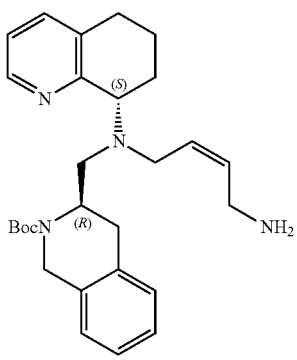

Compound 71 was synthesized from amine 70 following the procedure for the synthesis of compound 6. The crude product was purified on silica gel column using 0 to 30% of Solv 2 (Solv2=30% MeOH, 70% CH$_2$Cl$_2$, 3% NH$_4$OH) in CH$_2$Cl$_2$ affording 573 mg (87%) of the product 71. $^1$H NMR (400 MHz, CDCl$_3$, ppm) δ: 8.36 (br s, 1H), 7.23 (d, J=7.7 Hz, 1H), 7.11-6.92 (m, 5H), 5.58-5.45 (m, 2H), 4.72-4.56 (m, 1.5H), 4.45 (br s, 0.5H), 4.16-4.04 (m, 1H), 3.94 (dd, J=8.4, 5.8 Hz, 1H), 3.51-3.40 (m, 1H), 3.34-3.01 (m, 3H), 2.93 (d, J=3.1 Hz, 2H), 2.73-2.42 (m, 4H), 2.04-1.85 (m, 2H), 1.79-1.31 (m, 4H), 1.47 (s, 9H). LC-MS (ESI-API, 254 nm) 75-95% MeOH in H$_2$O (0.1% HCO$_2$H), 3 min, 1.00 mL/min, C18 (Agilent Zorbax XDB-18, 50 mm×4.6 mm, 3.5 μm), m/z=463.2 (M+H), t=0.540 min;

72

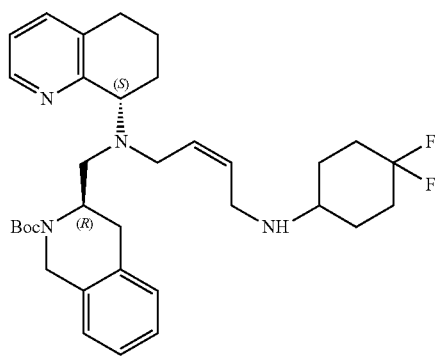

A 20 mL vial equipped with a stir bar was charged with 0.085 g of 4,4-difluorocyclohexanone (0.635 mmol, 1.3 equiv), 0.226 g of the amine 71 (0.489 mmol, 1 equiv), 34 μL of acetic acid (0.586 mmol, 1.2 equiv) and 2.0 mL of DCE. Then 0.155 g of STAB (0.733 mmol, 1.5 equiv) was added in 3 portions (30 min intervals) and the suspension was stirred at rt for 12 h. The reaction mixture was quenched by addition of sat. NaHCO$_3$ solution, extracted with CH$_2$Cl$_2$ (3×) and dried over Na$_2$SO$_4$. The crude product is purified on silica gel column using 0 to 100% EA in hexanes as eluent affording 229 mg (81%) of the product 72. $^1$H NMR (400 MHz, CDCl$_3$, ppm) δ: 8.36 (br s, 1H), 7.28-7.23 (m, 1H), 7.14-6.95 (m, 5H), 5.67-5.58 (m, 1H), 5.57-5.48 (m, 1H), 4.76-4.57 (m, 1.5H), 4.47 (br s, 0.5H), 4.17-4.07 (m, 1H), 3.99-3.92 (m, 1H), 3.62-3.48 (m, 1H), 3.32-3.05 (m, 3H), 3.01-2.87 (m, 2H), 2.74-2.45 (m, 5H), 2.13-1.56 (m, 8H), 1.49 (s, 9H), 1.54-1.32 (m, 5H). LC-MS (ESI-API, 254 nm) 75-95% MeOH in H$_2$O (0.1% HCO$_2$H), 3 min, 1.00 mL/min, C18 (Agilent Zorbax XDB-18, 50 mm×4.6 mm, 3.5 μm), m/z=581.2 (M+H), 291.2 (M/2+H), t=0.560 min;

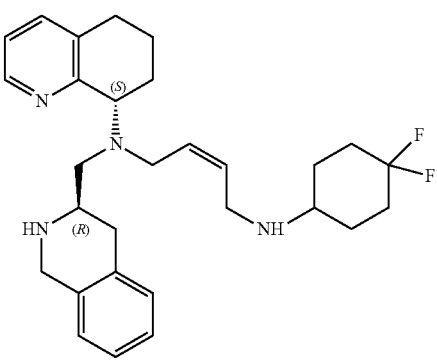

EMU143

Compound EMU143 was synthesized from amine 72 following the procedure for the synthesis of compound EMU030. The crude material was purified on silica gel column using 0 to 60% of solvent2 (solvent2=30% MeOH, 70% CH$_2$Cl$_2$ and 3% NH$_4$OH) in CH$_2$Cl$_2$ as eluent affording 89 mg (108%) of the product EMU143. $^1$H NMR (600 MHz, CDCl$_3$, ppm) δ: 8.43 (d, J=4.5 Hz, 1H), 7.32 (d, J=7.6 Hz, 1H), 7.10-6.99 (m, 5H), 5.74-5.69 (m, 1H), 5.62 (dt, J=11.7, 6.8 Hz, 1H), 4.09 (dd, J=10.2, 6.4 Hz, 1H), 4.03 (A of AB, J$_{AB}$=15.0 Hz, 1H), 3.95 (dd, J=14.3, 8.2 Hz, 1H), 3.89 (B of AB, J$_{AB}$=15.0 Hz, 1H), 3.40 (A of ABX, J$_{AB}$=13.4 Hz, J$_{AX}$=7.3 Hz, 1H), 3.32-3.25 (m, 2H), 2.84-2.72 (m, 3H), 2.65 (B of AB, J$_{AB}$=16.5 Hz, 1H), 2.65-2.59 (m, 1H), 2.58 (dd, J=16.1, 3.4 Hz, 1H), 2.43-2.33 (m, 2H), 2.10-1.80 (m, 7H), 1.75-1.61 (m, 3H), 1.48-1.37 (m, 2H). $^{13}$C NMR (400 MHz, CDCl$_3$, ppm) δ: 158.75, 146.56, 136.36, 135.54, 134.47, 133.93, 131.42, 130.37, 128.93, 126.31, 125.75, 125.36, 123.25 (t, J=240.0 Hz), 60.04, 56.89, 53.33, 51.55, 51.05, 48.61, 43.76, 33.78, 31.51 (t, J=24.3 Hz), 31.46 (t, J=24.3 Hz), 29.28, 29.08, 28.81-28.54 (m), 21.96. $^{19}$F NMR (400 MHz, CDCl$_3$, ppm) δ: −96.23 (d, J=234.4 Hz), −100.29 (d, J=233.7 Hz). HRMS (ESI+) calcd for C$_{29}$H$_{39}$F$_2$N$_4$ ([M+H]$^+$): 481.3137. Found: 481.3146, error 0.9 ppm. LC-MS (ESI-API, 254 nm) 75-95% MeOH in H$_2$O (0.1% HCO$_2$H), 3 min, 1.00 mL/min, C18 (Agilent Zorbax XDB-18, 50 mm×4.6 mm, 3.5 μm), m/z=481.2 (M+H), 241.2 (M/2+H), t=0.818 min;

73

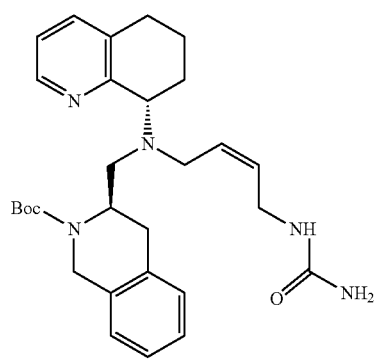

A 50 mL Schlenk tube equipped with a stir bar and rubber septum was charged with 0.181 g of the amine 71 (0.390 mmol, 1 equiv), 136 μL of DIPEA (0.781 mmol, 2 equiv) and 3.9 mL of THF. Then 81 μL of 85 w % TMSNCO (0.508 mmol, 1.3 equiv) was added dropwise. After stirring at rt for 12 h, the reaction mixture was quenched by addition of sat. Na$_2$CO$_3$ solution, extracted with CH$_2$Cl$_2$ (3×) and dried over Na$_2$SO$_4$. The crude product was purified on silica gel column using 0 to 20% MeOH in EA as eluent affording 170 mg (86%) of the product 73. $^1$H NMR (400 MHz, CDCl$_3$, ppm) δ: 8.30 (d, J=4.6 Hz, 1H), 7.22 (d, J=8.1 Hz, 1H), 7.14-6.90 (m, 5H), 5.75 (s, 2H), 4.75-4.49 (m, 3H), 4.17 (B of AB, J$_{AB}$=16.2 Hz, 1H), 4.10-3.88 (m, 2H), 3.76 (br s, 2H), 3.49 (br s, 1H), 3.24 (A of AB, J$_{AB}$=15.7 Hz, 1H), 3.05-2.82 (m, 3H), 2.76-2.41 (m, 3H), 2.22 (br s, 1H), 2.04 (br s, 1H), 1.89 (br s, 1H), 1.79-1.63 (m, 1H), 1.49 (s, 9H). LC-MS (ESI-API, 254 nm) 75-95% MeOH in H$_2$O (0.1% HCO$_2$H), 6 min, 1.00 mL/min, C18 (Agilent Zorbax XDB-18, 50 mm×4.6 mm, 3.5 μm), m/z=506.2 (M+H), t=0.533 min;

EMU211

Compound EMU211 was synthesized from amine 73 following the procedure for the synthesis of compound EMU030. The crude material was purified on silica gel column using 0 to 45% of solvent2 (solvent2=30% MeOH, 70% CH$_2$Cl$_2$ and 3% NH$_4$OH) in CH$_2$Cl$_2$ as eluent affording 128 mg (102%) of the product EMU211. $^1$H NMR (600 MHz, CDCl$_3$, ppm) δ:8.43 (d, J=4.5 Hz, 2H), 7.36 (d, J=7.3 Hz, 1H), 7.11-7.05 (m, 3H), 7.03-7.01 (m, 1H), 6.98-6.96 (m, 1H), 5.91-5.85 (m, 1H), 5.77 (dt, J=10.6, 7.1 Hz, 1H), 4.70 (s, 2H), 4.19 (dd, J=9.4, 7.0 Hz, 1H), 4.02-3.92 (m, 1H), 3.95 (A of AB, J$_{AB}$=15.4 Hz, 1H), 3.87-3.80 (m, 1H), 3.74 (B of AB, J$_{AB}$=15.4 Hz, 1H), 3.68 (dd, J=12.9, 7.9 Hz, 1H), 3.23 (dd, J=13.0, 6.2 Hz, 1H), 2.78 (ddd, J=16.3, 11.2, 4.9 Hz, 1H), 2.74-2.61 (m, 4H), 2.45 (dd, J=13.1, 8.8 Hz, 1H), 2.32 (dd, J=16.4, 10.8 Hz, 1H), 2.13-1.87 (m, 5H), 1.69 (q, J=12.3 Hz, 1H). $^{13}$C NMR (400 MHz, CDCl$_3$, ppm) δ: 159.34, 158.04, 146.48, 136.77, 135.29, 134.36, 134.24, 130.71, 130.18, 128.95, 126.10, 125.78, 125.38, 121.62, 59.97, 57.05, 51.60, 50.31, 48.22, 37.25, 33.70, 29.36, 25.71, 21.72. HRMS (ESI+) calcd for C$_{24}$H$_{32}$N$_5$O ([M+H]$^+$): 406.2601. Found: 406.2597, error −0.4 ppm. LC-MS (ESI-API, 254 nm) 75-95% MeOH in H$_2$O (0.1% HCO$_2$H), 3 min, 1.00 mL/min, C18 (Agilent Zorbax XDB-18, 50 mm×4.6 mm, 3.5 μm), m/z=406.2 (M+H), 203.6 (M/2+H), t=0.490 min;

The Pyridine TIQ-15

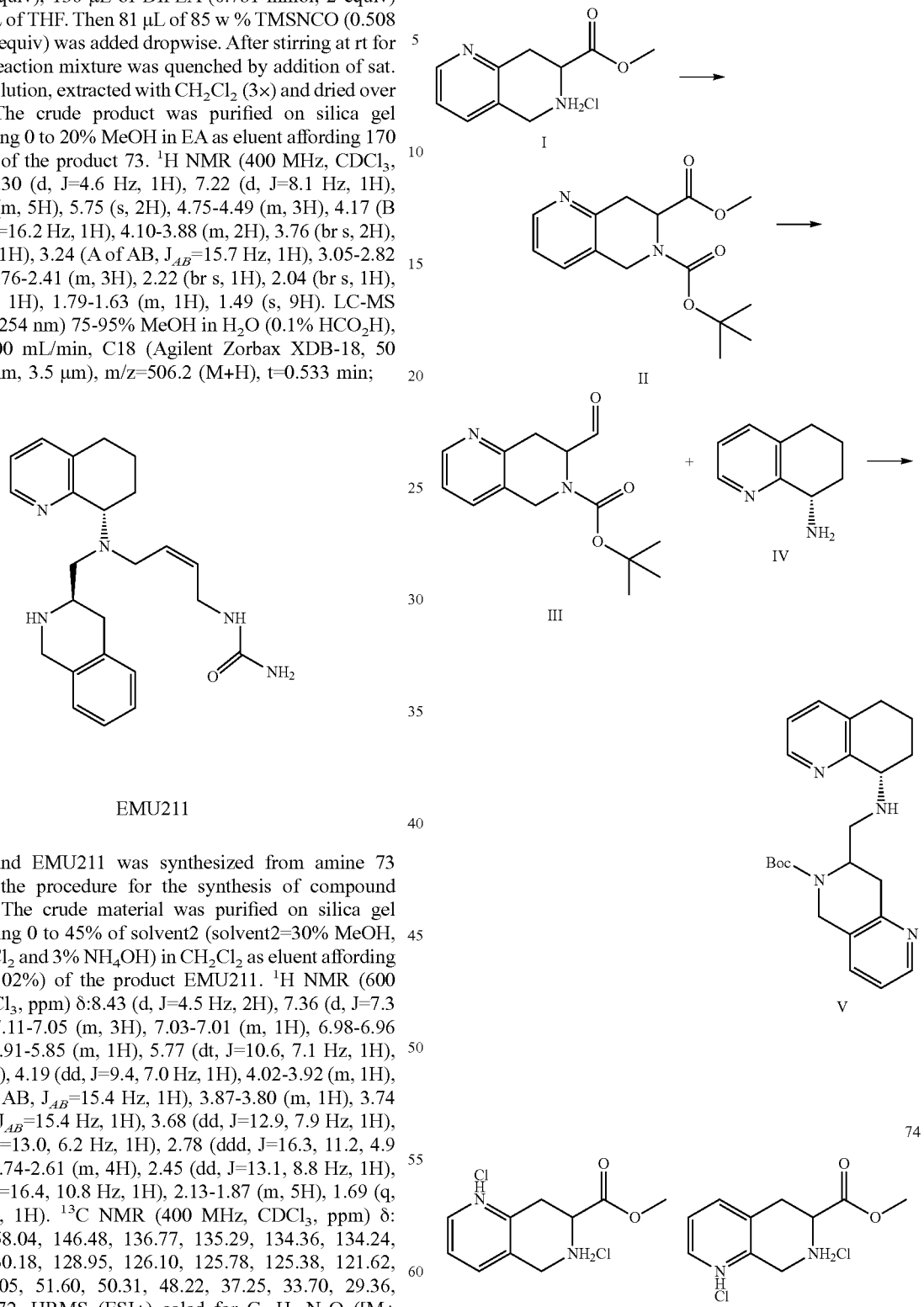

As in ref., (Organic Process Research & Development 2002, 6, 938-942, Bioorganic & Medicinal Chemistry 2003, 11, 433-450) 74 was synthesized from pyridine-2,3-dicarboxylic acid in 55% yield.

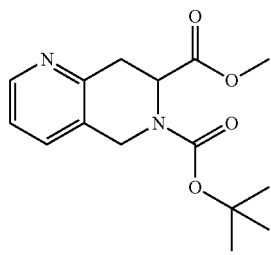

75

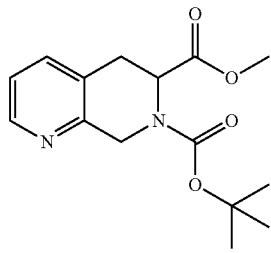

76

A 1 L rb flask equipped with a magnetic stir bar and rubber septum was charged with 26.9 g of the ester 74 (101 mol, 1 equiv), 42.2 mL of TEA (303 mmol, 3 equiv), 1.23 g of DMAP (10.1 mmol, 0.1 equiv) and 253 mL of THF. Then 27.6 g of $Boc_2O$ (126 mmol, 1.25 equiv) was added and the suspension was stirred for 3 h. The suspension was not going into solution and another portion of 21 mL of TEA (151 mmol, 1.5 equiv) was added followed by 300 mL of acetonitrile and 100 mL of MeOH. After the clear solution was stirred at rt for 12 h, the reaction mixture was concentrated and EA was added. The ammonium salts were separated by filtration and the organics were concentrated under vacuum. The crude material was purified on silica gel column using 0-65% EA in hexanes as eluent affording 2.24 g (8%) of 76 as a yellow oil and 8.12 g (28%) of 75 as a yellow oil which crystallizes in freezer to white solid. For 76 (4:1 mixture of conformers): $^1$H NMR (400 MHz, $CDCl_3$, ppm) δ: 8.47-8.41 (m, 1.25H), 7.46 (d, J=7.7 Hz, 1.25H), 7.11 (dd, J=7.7, 4.8 Hz, 1.25H), 5.27 (dd, J=5.9, 2.1 Hz, 1H), 5.02 (br s, 0.25H), 4.89 (A of AB, $J_{AB}$=18.1 Hz, 0.25H), 4.87 (A of AB, $J_{AB}$=17.9 Hz, 1H), 4.56 (B of AB, $J_{AB}$=18.2 Hz, 1H), 4.51 (B of AB, $J_{AB}$=18.2 Hz, 0.25H), 3.63 (s, 3.75H), 3.29 (A of ABX, $J_{AB}$=16.5 Hz, $J_{AX}$=2.2 Hz, 1H), 3.24 (A of ABX, $J_{AB}$=16.5 Hz, $J_{AX}$=2.2 Hz, 0.25H), 3.17 (B of ABX, $J_{AB}$=16.2 Hz, $J_{BX}$=6.3 Hz, 1H), 1.52 (s, 9H), 1.48 (s, 2.25H). LC-MS (ESI-API, 254 nm) 95% MeOH in $H_2O$ (0.1% $HCO_2H$), 3 min, 1.00 mL/min, C18 (Agilent Zorbax XDB-18, 50 mm×4.6 mm, 3.5 µm), m/z=315.0 (M+Na), 293.0 (M+H), t=0.562 min; For 75 (1:1 mixture of conformers): $^1$H NMR (400 MHz, $CDCl_3$, ppm) δ: 8.42 (d, J=4.9 Hz, 1H), 7.44 (d, J=7.9 Hz, 0.5H), 7.41 (d, J=7.7 Hz, 0.5H), 7.14 (dd, J=7.8, 4.9 Hz, 1H), 5.32 (d, J=6.9 Hz, 0.5H), 5.01 (dd, J=6.5, 3.7 Hz, 0.5H), 4.80 (A of AB, $J_{AB}$=17.4 Hz, 0.5H), 4.76 (B of AB, $J_{AB}$=17.4 Hz, 0.5H), 4.57 (B of AB, $J_{AB}$=17.0 Hz, 0.5H), 4.50 (d, J=16.7 Hz, 1H), 3.65 (s, 1.5H), 3.63 (s, 1.5H), 3.47 (A of AB, $J_{AB}$=16.8 Hz, 0.5H), 3.40 (A of ABX, $J_{AB}$=17.1 Hz, $J_{AX}$=3.9 Hz, 0.5H), 3.32 (B of ABX, $J_{AB}$=17.5 Hz, $J_{BX}$=6.6 Hz, 1H), 1.53 (s, 4.5H), 1.47 (s, 4.5H). LC-MS (ESI-API, 254 nm) 95% MeOH in $H_2O$ (0.1% $HCO_2H$), 3 min, 1.00 mL/min, C18 (Agilent Zorbax XDB-18, 50 mm×4.6 mm, 3.5 µm), m/z=315.0 (M+Na), 293.1 (M+H), t=0.560 min;

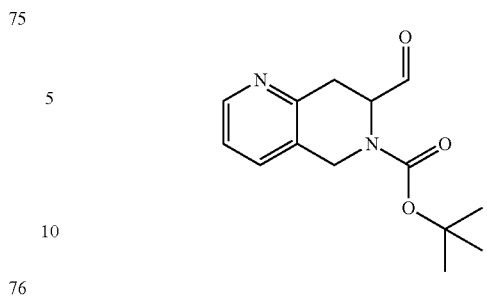

77

A 100 mL rb flask equipped with a stir bar and rubber septum was charged with 1.00 g of the ester 75 (3.42 mmol, 1 equiv) and 17.1 mL of toluene. After the reaction mixture was cooled to 78° C., 5.70 mL of 1.2 M solution of DIBAL-H (6.84 mL, 2 equiv) was added dropwise and the solution was stirred at 78° C. for 2 h. Then the reaction mixture was quenched by addition of 2.5 mL of MeOH followed by sat. solution of Rochelle's salt. After stirring at rt for 30 min, the product was extracted with EA (3×) and dried over $Na_2SO_4$. The crude product 77 (994 mg) was used in the next step without purification.

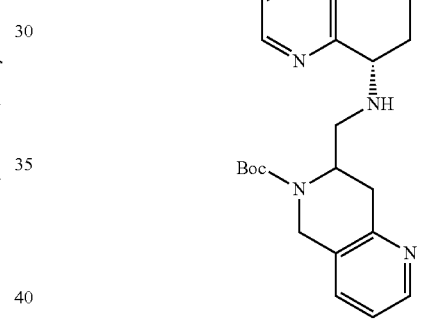

78

To a 20 mL vial equipped with a stir bar was added 608 mg of (S)-5,6,7,8-tetrahydroquinolin-8-amine (4.10 mmol, 1.2 equiv), 897 mg of the aldehyde 77 (3.42 mmol, 1 equiv), 942 mg of STAB (4.45 mmol, 1.3 equiv) and 11.4 mL of DCE. After stirring at rt for 1.5 h, the reaction mixture was quenched by addition of sat. $Na_2CO_3$ solution and the product was extracted with $CH_2Cl_2$ (3×), washed with sat. $Na_2CO_3$ solution, brine and dried over $Na_2SO_4$. The crude product was purified on silica gel column using EA, followed by 20% MeOH in $CH_2Cl_2$ as eluent affording 0.905 (67%) g of the product 78. $^1$H NMR (400 MHz, $CDCl_3$, ppm) δ: 8.44-8.40 (m, 1H), 8.35 (d, J=4.5 Hz, 1H), 7.39 (d, J=7.4 Hz, 1H), 7.34 (d, J=7.7 Hz, 1H), 7.14 7.09 (m, 1H), 7.05 (t, J=4.2 Hz, 0.5H), 7.03 (t, J=4.2 Hz, 0.5H), 5.02-4.58 (m, 2H), 4.24 (B of AB, $J_{AB}$=18.3 Hz, 1H), 3.76 (br s, 0.5H), 3.69 (br s, 0.5H), 3.23 (A of ABX, $J_{AB}$=16.6 Hz, $J_{AX}$=6.2 Hz, 0.5H), 3.19 (A of ABX, $J_{AB}$=16.6 Hz, $J_{AX}$=6.2 Hz, 0.5H), 3.07 (B of AB, $J_{AB}$=16.9 Hz, 0.5H), 2.94 (B of AB, $J_{AB}$=16.8 Hz, 0.5H), 2.85-2.63 (m, 4H), 2.04-1.91 (m, 1H), 1.72-1.63 (m, 1H), 1.52-1.28 (m, 2H), 1.49 (s, 4.5H), 1.42 (s, 4.5H). LC-MS (ESI-API, 254 nm) 75-95% MeOH in $H_2O$ (0.1% $HCO_2H$), 3 min, 1.00 mL/min, C18 (Agilent Zorbax XDB-18, 50 mm×4.6 mm, 3.5 µm), m/z=417.2 (M+Na), 395.2 (M+H), t=0.511 min, 86% purity;

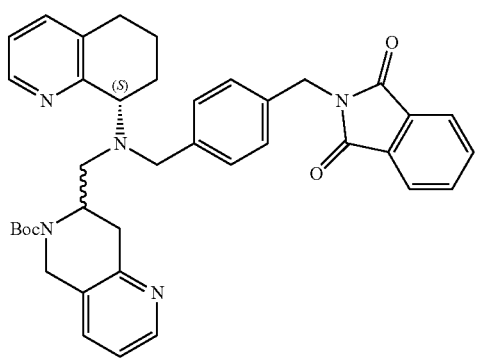

98

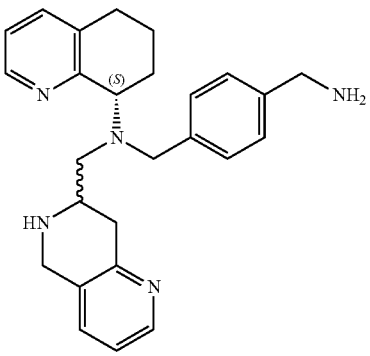

EMU193

Compound 98 was synthesized from amine 78 and 4-((1,3-dioxoisoindolin-2-yl)methyl)benzaldehyde following the procedure for the synthesis of compound 79. The crude product is purified on silica gel column using 0 to 10% MeOH in EA as eluent affording 516 mg (36%) of URf-98 (Stereoisomer 1), 337 mg (23%) of the mixture of the isomers and 304 mg (21%) of LRf-98 (Stereoisomer 2). Stereoisomer 2 elutes faster than Stereoisomer 1 on TLC using 10% MeOH in EA. For the Stereoisomer 1: LC-MS (ESI-API, 254 nm) 75-95% MeOH in H$_2$O (0.1% HCO$_2$H), 6 min, 1.00 mL/min, C18 (Agilent Zorbax XDB-18, 50 mm×4.6 mm, 3.5 μm), m/z=644.2 (M+H), 322.6 (M/2+H), t=0.556 min;

Compound EMU193 (Stereoisomer 1) was synthesized from amine 99 (Stereoisomer 1) following the procedure for the synthesis of compound EMU030. The crude material was purified on silica gel column using 0 to 45% of solvent2 (solvent2=30% MeOH, 70% CH$_2$Cl$_2$ and 3% NH$_4$OH) in CH$_2$Cl$_2$ as eluent affording 71 mg (42%) of the product EMU193. $^1$H NMR (600 MHz, CDCl$_3$, ppm) δ: 8.53 (dd, J=4.6, 1.6 Hz, 1H), 8.32 (dd, J=4.9, 1.6 Hz, 1H), 7.45 (d, J=7.7 Hz, 2H), 7.32 (d, J=7.5 Hz, 1H), 7.26 (d, J=7.3 Hz, 1H), 7.23 (d, J=7.8 Hz, 2H), 7.05 (dd, J=7.6, 4.7 Hz, 1H), 6.99 (dd, J=7.7, 4.7 Hz, 1H), 4.05 (dd, J=10.2, 6.0 Hz, 1H), 3.94 (A of AB, J$_{AB}$=15.1 Hz, 1H), 3.82 (s, 2H), 3.78 (A of AB, J$_{AB}$=14.8 Hz, 1H), 3.75 (B of AB, J$_{AB}$=14.8 Hz, 1H), 3.73 (B of AB, J$_{AB}$=15.0 Hz, 1H), 3.04 (dd, J=12.7, 2.9 Hz, 1H), 2.84-2.65 (m, 5H), 2.52 (dd, J=16.9, 11.0 Hz, 1H), 2.30-2.24 (m, 1H), 2.05-1.98 (m, 1H), 1.95-1.85 (m, 1H), 1.73-1.64 (m, 1H). $^{13}$C NMR (400 MHz, CDCl$_3$, ppm) δ: 157.95, 155.33, 147.08, 147.00, 141.68, 139.87, 136.23, 134.00, 133.88, 131.22, 128.16, 126.81, 121.47, 120.53, 62.05, 59.27, 56.03, 52.51, 47.60, 46.15, 37.10, 29.26, 26.24, 21.65. HRMS (ESI+) calcd for C$_{26}$H$_{32}$N$_5$ ([M+H]$^+$): 414.2652. Found: 414.2647, error −0.5 ppm. LC-MS (ESI-API, 254 nm) 75-95% MeOH in H$_2$O (0.1% HCO$_2$H), 3 min, 1.00 mL/min, C18 (Agilent Zorbax XDB-18, 50 mm×4.6 mm, 3.5 μm), m/z=414.2 (M+H), 207.6 (M/2+H), t=0.460 min; Compound EMU193 (Stereoisomer 2) was synthesized from amine 99 (Stereoisomer 2) following the procedure for the synthesis of compound EMU030. The crude material was purified on silica gel column using 0 to 45% of solvent2 (solvent2=30% MeOH, 70% CH$_2$Cl$_2$ and 3% NH$_4$OH) in CH$_2$Cl$_2$ as eluent affording 115 mg (77%) of the product EMU194. H NMR (600 MHz, CDCl$_3$, ppm) δ: 8.51 (d, J=4.8 Hz, 1H), 8.33 (d, J=4.4 Hz, 1H), 7.43 (d, J=8.0 Hz, 2H), 7.33 (d, J=7.5 Hz, 1H), 7.26 (d, J=7.5 Hz, 1H), 7.25 (d, J=7.8 Hz, 2H), 7.06 (dd, J=7.6, 4.7 Hz, 1H), 6.99 (dd, J=7.7, 4.7 Hz, 1H), 4.37 (d, J=14.3 Hz, 1H), 4.10 (dd, J=10.3, 6.5 Hz, 1H), 3.94 (d, J=15.0 Hz, 1H), 3.90 (d, J=14.3 Hz, 1H), 3.84 (s, 2H), 3.62 (d, J=14.9 Hz, 1H), 2.98 (dd, J=13.2, 2.7 Hz, 1H), 2.81-2.62 (m, 4H), 2.53-2.43 (m, 2H), 2.17-2.11 (m, 1H), 2.00-1.91 (m, 2H), 1.72-1.61 (m, 1H). $^{13}$C NMR (400 MHz, CDCl$_3$, ppm) δ: 158.51, 155.03, 146.99, 146.60, 141.57, 140.16, 136.15, 133.80, 133.70, 130.85, 128.27, 126.73, 121.16, 120.45, 61.89, 58.94, 57.55, 52.02, 47.45, 46.04, 36.92, 29.35, 29.15, 21.88. HRMS (ESI+) calcd for C$_{26}$H$_{32}$N$_5$ ([M+H]$^+$): 414.2652. Found: 414.2647, error −0.6 ppm. LC-MS (ESI-API, 254 nm) 75-95% MeOH in H$_2$O (0.1% HCO$_2$H), 3 min, 1.00

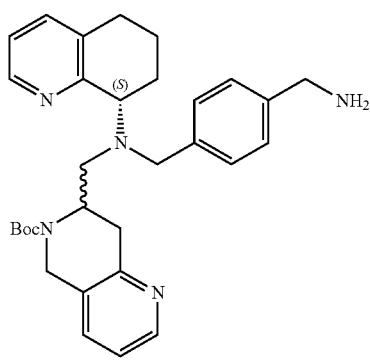

99

Compound 99 (Stereoisomer 1) was synthesized from amine URf-98 (Stereoisomer 1) following the procedure for the synthesis of compound 6. The organics were concentrated and the crude product was used in the next step. Compound 99 (Stereoisomer 2) was synthesized from amine LRf-98 (Stereoisomer 2) following the procedure for the synthesis of compound 6. The organics were concentrated and the crude product was used in the next step.

mL/min, C18 (Agilent Zorbax XDB-18, 50 mm×4.6 mm, 3.5 μm), m/z=414.2 (M+H), 207.6 (M/2+H), t=0.460 min;

General scheme

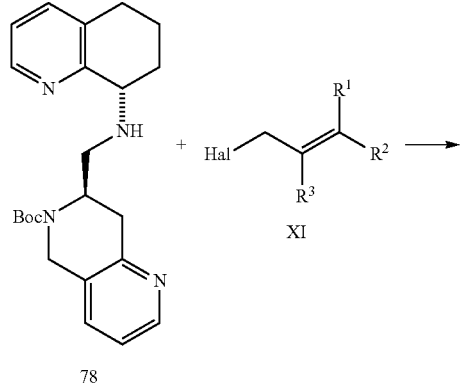

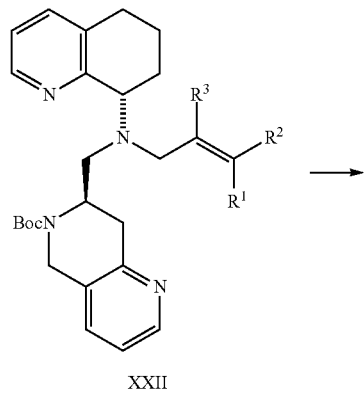

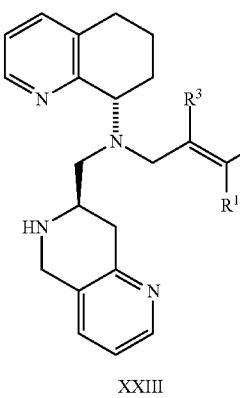

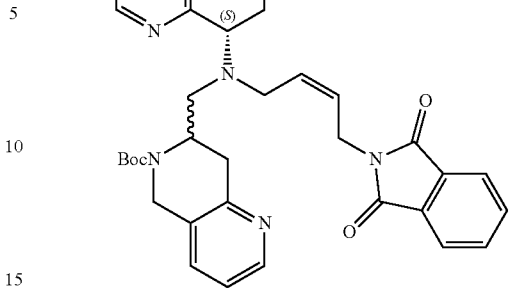

A 50 mL Schlenk tube equipped with a cold finger condenser and stir bar was charged with 0.717 g of (Z)-2-(4-chlorobut-2-en-1-yl)isoindoline-1,3-dione (3.04 mmol, 1.2 equiv) and 0.042 g of KI (0.253 mmol, 0.1 equiv). Then 1.00 g of the amine 78 (2.53 mmol, 1 equiv) and 0.662 mL of DIPEA (3.80 mmol, 1.5 equiv) dissolved in 8.5 mL of acetonitrile was added. After stirring at 50° C. for 12 h, the reaction mixture was quenched by addition of water, extracted with diethyl ether (3×) and dried over $Na_2SO_4$. The crude product is purified on silica gel column using 0 to 10% MeOH in EA as eluent affording 495 mg (33%) of the URf-103 (Stereoisomer 1) and 491 mg (33%) of LRf-103 (Stereoisomer 2). The Stereoisomer 2 elutes faster than Stereoisomer 1 on TLC using 10% MeOH in EA. For stereoisomer 1: $^1$H NMR (400 MHz, $CDCl_3$, ppm) δ: 8.37 (d, J=4.9 Hz, 1H), 8.35 (d, J=4.7 Hz, 1H), 7.81 (dd, J=5.4, 3.1 Hz, 2H), 7.70 (dd, J=5.5, 3.0 Hz, 2H), 7.25 (d, J=4.4 Hz, 1H), 7.21 (br s, 1H), 6.97 (dd, J=7.7, 4.7 Hz, 1H), 6.96 (br s, 1H), 5.67 (br s, 1H), 5.35 (br s, 1H), 4.83-4.66 (m, 1.5H), 4.56 (br s, 0.5H), 4.28-4.00 (m, 4H), 3.86-3.64 (m, 1H), 3.32-3.17 (m, 2H), 3.04 (B of ABX, $J_{AB}$=16.7, $J_{BX}$=6.1 Hz, 1H), 2.91 (A of ABX, $J_{AB}$=13.3, $J_{AX}$=5.7 Hz, 1H), 2.67-2.29 (m, 3H), 2.01-1.60 (m, 4H), 1.47 (s, 9H). LC-MS (ESI-API, 254 nm) 95% MeOH in $H_2O$ (0.1% $HCO_2H$), 3 min, 1.00 mL/min, C18 (Agilent Zorbax XDB-18, 50 mm×4.6 mm, 3.5 μm), m/z=594.2 (M+H), 297.8 (M/2+H), t=0.813 min; For stereoisomer 2: $^1$H NMR (400 MHz, $CDCl_3$, ppm) δ: 8.39-8.32 (m, 2H), 7.81 (dd, J=5.5, 3.1 Hz, 2H), 7.70 (dd, J=5.5, 3.1 Hz, 2H), 7.30 (d, J=7.7 Hz, 1H), 7.20 (br s, 1H), 7.03-6.94 (m, 2H), 5.67 (br s, 1H), 5.44-5.35 (m, 1H), 4.93-4.63 (m, 2H), 4.25 (A of ABX, $J_{AB}$=15.1, $J_{AX}$=7.3 Hz, 1H), 4.17 (B of ABX, $J_{AB}$=14.8, $J_{BX}$=6.4 Hz, 1H), 4.12-3.91 (d, J=21.9 Hz, 2H), 3.63-3.53 (m, 1H), 3.40-3.03 (s, 3H), 2.87-2.55 (m, 4H), 2.15-1.60 (m, 4H), 1.50 (s, 9H). LC-MS (ESI-API, 254 nm) 95% MeOH in $H_2O$ (0.1% $HCO_2H$), 3 min, 1.00 mL/min, C18 (Agilent Zorbax XDB-18, 50 mm×4.6 mm, 3.5 μm), m/z=594.2 (M+H), 297.7 (M/2+H), t=0.678 min;

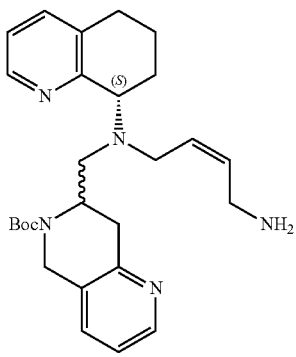

104

Compound 104 (Stereoisomer 1) was synthesized from amine LRf-103 (Stereoisomer 2) following the procedure for the synthesis of compound 6. The crude material was purified on silica gel column using 0 to 60% of solvent2 (solvent2=30% MeOH, 70% $CH_2Cl_2$ and 3% $NH_4OH$) in $CH_2Cl_2$ as eluent affording 311 mg (96%) of the product 104. $^1$H NMR (400 MHz, $CDCl_3$, ppm) δ: 8.41-8.33 (m, 2H), 7.32-7.26 (m, 2H), 7.08 (dd, J=7.8, 4.9 Hz, 1H), 6.99 (br s, 1H), 5.51 (br s, 2H), 4.87-4.61 (m, 2H), 4.17-3.93 (m, 2H), 3.45 (br s, 1H), 3.30-2.99 (m, 5H), 2.83-2.48 (m, 4H), 2.10-1.59 (m, 6H), 1.50 (s, 9H). LC-MS (ESI-API, 254 nm) 75-95% MeOH in $H_2O$ (0.1% $HCO_2H$), 3 min, 1.00 mL/min, C18 (Agilent Zorbax XDB-18, 50 mm×4.6 mm, 3.5 μm), m/z=463.2 (M+H), t=0.546 min; Compound 104 (Stereoisomer 2) was synthesized from amine URf-103 following the procedure for the synthesis of compound 6. The organics were concentrated and the crude product was used in the next step.

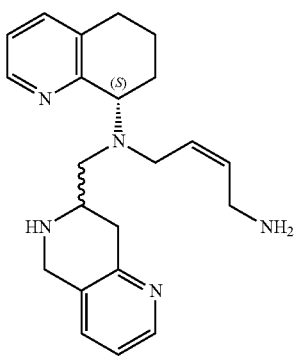

EMU142

Compound EMU142 (Stereoisomer 1)) was synthesized from amine 104 (Stereoisomer 1) following the procedure for the synthesis of compound EMU030. The crude material was purified on silica gel column using 0 to 60% of solvent2 (solvent2=30% MeOH, 70% $CH_2Cl_2$ and 3% $NH_4OH$) in $CH_2Cl_2$ as eluent affording 94 mg (77%) of the product EMU142 (Stereoisomer 1). $^1$H NMR (600 MHz, $CDCl_3$, ppm) δ: 8.44 (d, J=4.5 Hz, 1H), 8.34 (d, J=4.6 Hz, 1H), 7.32 (d, J=7.6 Hz, 1H), 7.30 (d, J=7.7 Hz, 1H), 7.04 (dd, J=7.7, 4.7 Hz, 1H), 7.01 (dd, J=7.7, 4.7 Hz, 1H), 5.63 (t, J=4.6 Hz, 2H), 4.10 (dd, J=10.2, 6.4 Hz, 1H), 4.00 (A of AB, $J_{AB}$=15.0 Hz, 1H), 3.87 (dd, J=14.5, 6.0 Hz, 1H), 3.83 (B of AB, $J_{AB}$=15.0 Hz, 1H), 3.42 (dd, J=14.2, 5.1 Hz, 1H), 3.30 (dd, J=14.4, 9.4 Hz, 1H), 3.30 (B of AB, $J_{AB}$=14.7 Hz, 1H), 2.90 (dd, J=13.2, 3.0 Hz, 1H), 2.82 (tt, J=10.6, 3.4 Hz, 1H), 2.79-2.72 (m, 2H), 2.65 (B of AB, $J_{AB}$=16.5 Hz, 1H), 2.51 (dd, J=16.9, 11.0 Hz, 1H), 2.40 (dd, J=13.2, 10.3 Hz, 1H), 2.10-2.03 (m, 1H), 2.00-1.94 (m, 1H), 1.95-1.85 (m, 1H), 1.74-1.65 (m, 1H). $^{13}$C NMR (400 MHz, $CDCl_3$, ppm) δ: 158.43, 154.95, 147.07, 146.56, 136.27, 133.90, 133.70, 132.09, 130.84, 129.65, 121.19, 120.58, 60.19, 56.70, 51.73, 50.86, 47.52, 38.78, 36.93, 29.17, 28.76, 21.83. HRMS (ESI+) calcd for $C_{22}H_{30}N_5$ ([M+H]$^+$): 364.2496. Found: 364.2491, error −0.5 ppm. LC-MS (ESI-API, 254 nm) 75-95% MeOH in $H_2O$ (0.1% $HCO_2H$), 3 min, 1.00 mL/min, C18 (Agilent Zorbax XDB-18, 50 mm×4.6 mm, 3.5 μm), m/z=364.2 (M+H), 182.7 (M/2+H), t=0.821 min; Compound EMU142 (Stereoisomer 2) was synthesized from amine 104 (Stereoisomer 2) following the procedure for the synthesis of compound EMU030. The crude material was purified on silica gel column using 0 to 60% of solvent2 (solvent2=30% MeOH, 70% $CH_2Cl_2$ and 3% $NH_4OH$) in $CH_2Cl_2$ as eluent affording 143 mg (95%) of the product EMU142 (Stereoisomer 2). $^1$H NMR (600 MHz, $CDCl_3$, ppm) δ: 8.50 (d, J=4.7 Hz, 1H), 8.34 (d, J=4.7 Hz, 1H), 7.34 (d, J=7.7 Hz, 1H), 7.31 (d, J=7.7 Hz, 1H), 7.05 (dd, J=7.7, 4.7 Hz, 1H), 7.01 (dd, J=7.7, 4.9 Hz, 1H), 5.75-5.64 (m, 2H), 4.09 (dd, J=9.8, 6.1 Hz, 1H), 4.05 (A of AB, $J_{AB}$=15.4 Hz, 1H), 4.02 (B of AB, $J_{AB}$=15.4 Hz, 1H), 3.40 (A of ABX, $J_{AB}$=14.1 Hz, $J_{AX}$=6.7 Hz, 1H), 3.40-3.32 (m, 2H), 3.32 (B of ABX, $J_{AB}$=14.5 Hz, $J_{BX}$=6.8 Hz, 1H), 3.05 (t, J=10.3 Hz, 1H), 2.83-2.65 (m, 4H), 2.51 (dd, J=16.7, 11.0 Hz, 1H), 2.46 (dd, J=13.0, 10.0 Hz, 1H), 2.15-2.10 (m, 1H), 2.04-1.98 (m, 1H), 1.89-1.79 (m, 1H), 1.74-1.64 (m, 1H). $^{13}$C NMR (400 MHz, $CDCl_3$, ppm) δ: 157.22, 154.94, 147.01, 146.90, 136.45, 134.15, 133.82, 132.66, 131.11, 129.52, 121.59, 120.55, 60.52, 56.98, 52.17, 48.24, 47.48, 38.28, 36.88, 29.09, 23.60, 21.30. HRMS (ESI+) calcd for $C_{22}H_{30}N_5$ ([M+H]$^+$): 364.2496. Found: 364.2494, error −0.2 ppm. LC-MS (ESI-API, 254 nm) 75-95% MeOH in $H_2O$ (0.1% $HCO_2H$), 3 min, 1.00 mL/min, C18 (Agilent Zorbax XDB-18, 50 mm×4.6 mm, 3.5 μm), m/z=364.2 (M+H), 182.6 (M/2+H), t=0.466 min;

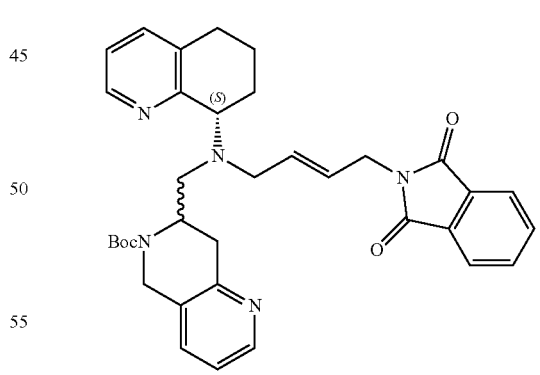

106

Compound 106 was synthesized from amine 78 and (E)-2-(4-bromobut-2-en-1-yl)isoindoline-1,3-dione following the procedure of synthesis of compound 103. The crude product is purified on silica gel column using 0 to 10% MeOH in EA as eluent affording 435 mg (34%) of URf-106 (Stereoisomer 1) and 466 mg (28%) of LRf-106 (Stereoisomer 2). The Stereoisomer 2 elutes faster than Stereoisomer 1 on TLC using 10% MeOH in EA. For Stereoisomer 1: $^1$H NMR (400 MHz, $CDCl_3$, ppm) δ: 8.39 (d, J=5.0 Hz, 1H), 8.27 (d, J=4.2 Hz, 1H), 7.82 (dd, J=5.5, 3.0 Hz, 1H), 7.70 (dd, J=5.5, 3.1 Hz, 1H), 7.31 (d, J=7.7 Hz, 1H), 7.19 (d, J=7.6 Hz, 1H), 7.06 (dd, J=7.7, 4.8 Hz, 1H), 6.90 (dd, J=7.1; 5.3 Hz 1H), 5.80-5.67 (m, 1H), 5.54 (br s, 1H), 4.80-4.62 (m, 1.5H), 4.47 (br s, 0.5H), 4.26-4.07 (m, 4H), 3.95 (t, J=7.3 Hz, 1H), 3.57-3.40 (m, 1H), 3.27-3.10 (m, 2H), 3.02 (B of ABX, $J_{AB}$=16.7, $J_{BX}$=6.0 Hz, 1H), 2.79-2.70 (m, 1H), 2.55 (s, 2H), 2.43-2.20 (m, 1H), 1.98-1.80 (m, 2H), 1.67-1.51 (m, 2H), 1.45 (s, 9H). LC-MS (ESI-API, 254 nm) 75-95% MeOH in H$_2$O (0.1% HCO$_2$H), 3 min, 1.00 mL/min, C18 (Agilent Zorbax XDB-18, 50 mm×4.6 mm, 3.5 µm), m/z=594.2 (M+H), 297.6 (M/2+H), t=0.525 min; For Stereoisomer 2: $^1$H NMR (400 MHz, CDCl$_3$, ppm) δ: 8.37 (dd, J=4.8, 1.7 Hz, 1H), 8.28 (d, J=4.7 Hz, 1H), 7.83 (dd, J=5.4, 3.1 Hz, 2H), 7.71 (dd, J=5.5, 3.1 Hz, 2H), 7.32 (dd, J=7.8, 1.6 Hz, 1H), 7.23 (d, J=7.5 Hz, 1H), 7.03 (dd, J=7.7, 4.8 Hz, 1H), 6.93 (dd, J=7.7, 4.7 Hz, 1H), 5.69 (br s, 1H), 5.59-5.46 (m, 1H), 4.90-4.59 (m, 2H), 4.20-3.86 (m, 4H), 3.31-2.91 (m, 4H), 2.77-2.46 (m, 4H), 2.00-1.76 (m, 2H), 1.64 (s, 2H), 1.47 (s, 9H). LC-MS (ESI-API, 254 nm) 75-95% MeOH in H$_2$O (0.1% HCO$_2$H), 3 min, 1.00 mL/min, C18 (Agilent Zorbax XDB-18, 50 mm×4.6 mm, 3.5 µm), m/z=594.2 (M+H), 297.6 (M/2+H), t=0.575 min;

for the synthesis of compound EMU030. The crude material was purified on silica gel column using 0 to 60% of solvent2 (solvent2=30% MeOH, 70% CH$_2$Cl$_2$ and 3% NH$_4$OH) in CH$_2$Cl$_2$ as eluent affording 82 mg (67%) of the product EMU192. $^1$H NMR (600 MHz, CDCl$_3$, ppm) δ: 8.44 (d, J=4.5 Hz, 1H), 8.35 (d, J=4.8 Hz, 1H), 7.33 (d, J=7.8 Hz, 1H), 7.30 (d, J=7.8 Hz, 1H), 7.05 (dd, J=7.7, 4.7 Hz, 1H), 7.02 (dd, J=7.7, 4.7 Hz, 1H), 5.77-5.66 (m, 2H), 4.09 (dd, J=10.1, 6.2 Hz, 1H), 4.04 (A of AB, $J_{AB}$=15.2 Hz, 1H), 3.82 (B of AB, $J_{AB}$=15.0 Hz, 1H), 3.59 (dd, J=14.3, 6.3 Hz, 1H), 3.32-3.27 (m, 1H), 3.29 (d, J=4.3 Hz, 2H), 3.01 (dd, J=13.5, 3.0 Hz, 1H), 2.86-2.73 (m, 3H), 2.70-2.64 (m, 1H), 2.57 (dd, J=16.9, 11.0 Hz, 1H), 2.50 (dd, J=13.4, 10.2 Hz, 1H), 2.11-2.05 (m, 1H), 2.01-1.95 (m, 1H), 1.95-1.85 (m, 1H), 1.75-1.66 (m, 1H). $^{13}$C NMR (400 MHz, CDCl$_3$, ppm) δ: 158.17, 154.81, 147.14, 146.51, 136.44, 133.75, 131.32, 130.66, 130.38, 121.33, 120.66, 61.33, 56.99, 55.86, 52.13, 47.24, 42.85, 36.75, 29.16, 27.70, 21.66. HRMS (ESI+) calcd for C$_{22}$H$_{30}$N$_5$ ([M+H]$^+$): 364.2496. Found: 364.2491, error −0.5 ppm. LC-MS (ESI-API, 254 nm) 75-95% MeOH in H$_2$O (0.1% HCO$_2$H), 3 min, 1.00 mL/min, C18 (Agilent Zorbax XDB-18, 50 mm×4.6 mm, 3.5 µm), m/z=364.2 (M+H), 182.6 (M/2+H), t=0.463 min;

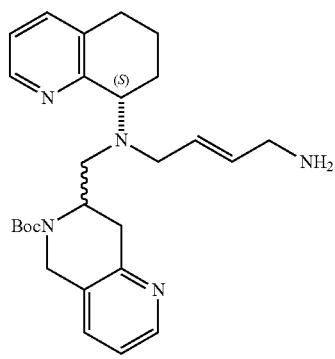

107

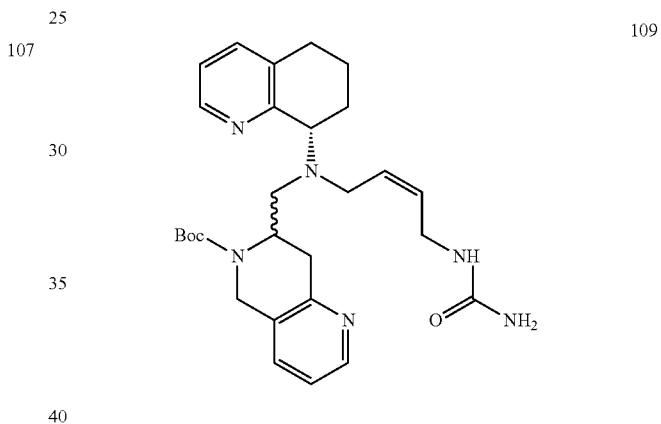

109

Compound 107 (Stereoisomer 1) was synthesized from amine LRf-106 (Stereoisomer 2) following the procedure for the synthesis of compound 6. The organics were concentrated and the crude product was used in the next step.

A 50 mL Schlenk tube equipped with a stir bar and rubber septum was charged with 0.138 g of the amine 104 (Stereoisomer 1) (0.298 mmol, 1 equiv), 104 µL of DIPEA (0.595 mmol, 2 equiv) and 3.0 mL of THF. Then 62 µL of 85 w % TMSNCO (0.387 mmol, 1.3 equiv) was added dropwise. After stirring at r$_t$ for 12 h, the reaction mixture was quenched by addition of sat. Na$_2$CO$_3$ solution, extracted with CH$_2$Cl$_2$ (3×) and dried over Na$_2$SO$_4$. The crude product was purified on silica gel column using 0 to 20% MeOH in EA as eluent affording 109 mg (72%) of the product 109.

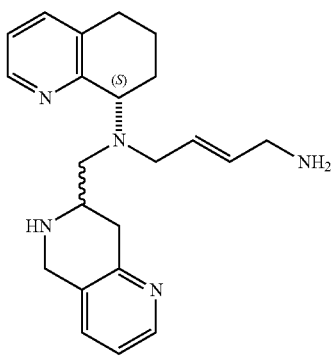

EMU192

Compound EMU192 (Stereoisomer 1) was synthesized from amine 107 (Stereoisomer 1) following the procedure

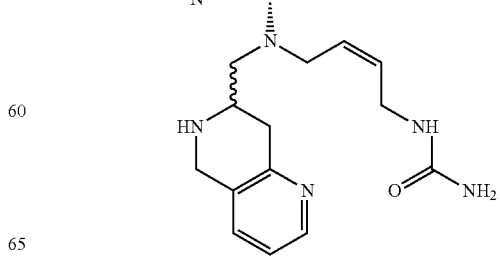

EMU209

Compound EMU209 (Stereoisomer 1) was synthesized from amine 109 (Stereoisomer 1) following the procedure for the synthesis of compound EMU030. The crude material was purified on silica gel column using 0 to 45% of solvent2 (solvent2=30% MeOH, 70% $CH_2Cl_2$ and 3% $NH_4OH$) in $CH_2Cl_2$ as eluent affording 86 mg (98%) of the product EMU209 (Stereoisomer 1). $^1H$ NMR (600 MHz, $CDCl_3$, ppm) δ: 8.44 (d, J=4.4 Hz, 1H), 8.34 (d, J=4.5 Hz, 1H), 7.37 (d, J=7.8 Hz, 1H), 7.28 (d, J=7.6 Hz, 1H), 7.10 (dd, J=7.7, 4.7 Hz, 1H), 7.02 (dd, J=7.7, 4.7 Hz, 1H), 6.73 (br s, 1H), 5.88-5.83 (m, 1H), 5.79-5.73 (m, 1H), 4.69 (s, 2H), 4.18 (dd, J=9.8, 6.7 Hz, 1H), 3.95 (A of AB, $J_{AB}$=15.3 Hz, 1H), 3.87-3.81 (m, 1H), 3.74-3.66 (m, 1H), 3.70 (B of AB, $J_{AB}$=14.7 Hz, 1H), 3.27 (dd, J=13.1, 6.0 Hz, 1H), 2.83-2.65 (m, 6H), 2.47 (A of AB, $J_{AB}$=9.8 Hz, 1H), 2.45 (B of AB, $J_{AB}$=9.7 Hz, 1H), 2.16-1.87 (m, 3H), 1.74-1.65 (m, 1H). $^{13}C$ NMR (400 MHz, $CDCl_3$, ppm) δ: 159.26, 158.05, 154.78, 147.16, 146.55, 136.86, 134.33, 133.96, 130.78, 130.68, 130.27, 121.69, 120.77, 60.15, 56.76, 51.93, 50.54, 47.37, 37.38, 36.98, 29.36, 26.09, 21.78. HRMS (ESI+) calcd for $C_{23}H_{31}N_6O$ ([M+H]+): 407.2554. Found: 407.2550, error −1.0 ppm. LC-MS (ESI-API, 254 nm) 75-95% MeOH in $H_2O$ (0.1% $HCO_2H$), 3 min, 1.00 mL/min, C18 (Agilent Zorbax XDB-18, 50 mm×4.6 mm, 3.5 μm), m/z=429.2 (M+Na), 407.2 (M+H), 204.2 (M/2+H), t=0.489 min;

EMU212

Compound EMU212 (Stereoisomer 1) was synthesized from amine 110 (Stereoisomer 1) following the procedure for the synthesis of compound EMU030. The crude material was purified on silica gel column using 0 to 45% of solvent2 (solvent2=30% MeOH, 70% $CH_2Cl_2$ and 3% $NH_4OH$) in $CH_2Cl_2$ as eluent affording 89 mg (95%) of the product EMU212 (Stereoisomer 1). $^1H$ NMR (600 MHz, $CDCl_3$, ppm) δ: 8.44 (d, J=4.2 Hz, 1H), 8.35 (d, J=4.9 Hz, 1H), 7.33 (d, J=7.6 Hz, 1H), 7.31 (d, J=7.6 Hz, 1H), 7.06 (dd, J=7.7, 4.7 Hz, 1H), 7.03 (dd, J=7.7, 4.7 Hz, 1H), 5.75 (dt, J=13.3, 6.3 Hz, 1H), 5.66 (dt, J=15.4, 5.5 Hz, 1H), 5.20 (s, 1H), 4.46 (s, 2H), 4.07 (dd, J=9.9, 6.3 Hz, 1H), 3.98 (A of AB, $J_{AB}$=15.1 Hz, 1H), 3.80-3.71 (m, 3H), 3.45 (dd, J=14.2, 7.4 Hz, 1H), 3.25 (dd, J=14.3, 5.2 Hz, 1H), 3.09 (dd, J=13.5, 3.2 Hz, 1H), 2.77 (dd, J=16.6, 4.2 Hz, 2H), 2.81-2.65 (m, 3H), 2.54 (dd, J=16.3, 10.4 Hz, 1H), 2.50 (dd, J=13.3, 9.9 Hz, 1H), 2.11-1.86 (m, 3H), 1.75-1.66 (m, 1H). $^{13}C$ NMR (400 MHz, $CDCl_3$, ppm) δ: 159.34, 158.07, 154.90, 147.04, 146.59, 136.47, 134.03, 133.79, 130.86, 130.82, 128.77, 121.38, 120.72, 61.18, 56.85, 55.86, 52.08, 47.30, 41.55, 36.79, 29.18, 27.49, 21.62. HRMS (ESI+) calcd for $C_{23}H_{31}N_6O$ ([M+H]+): 407.2554. Found: 407.2549, error −1.1 ppm. LC-MS (ESI-API, 254 nm) 75-95% MeOH in $H_2O$ (0.1% $HCO_2H$), 3 min, 1.00 mL/min, C18 (Agilent Zorbax XDB-18, 50 mm×4.6 mm, 3.5 μm), m/z=407.2 (M+H), 204.2 (M/2+H), t=0.605 min;

Compound EMU232 was Prepared According to the Following General Scheme:

110

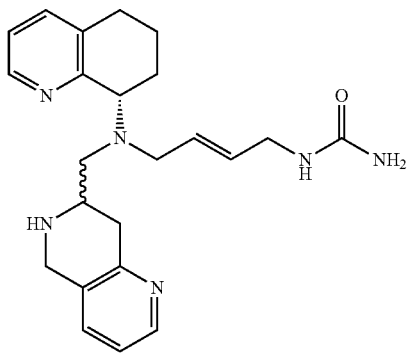 [SMILES: NC(=O)NC/C=C/CN(CC1Cc2ncccc2CN1)[C@H]1CCCc2cccnc21]

Compound 110 (Stereoisomer 1) was synthesized from amine 107 (Stereoisomer 1) following the procedure for the synthesis of compound 109 (Stereoisomer 1). The crude product was purified on silica gel column using 0 to 20% MeOH in EA as eluent affording 128 mg (83%) of the product 110.

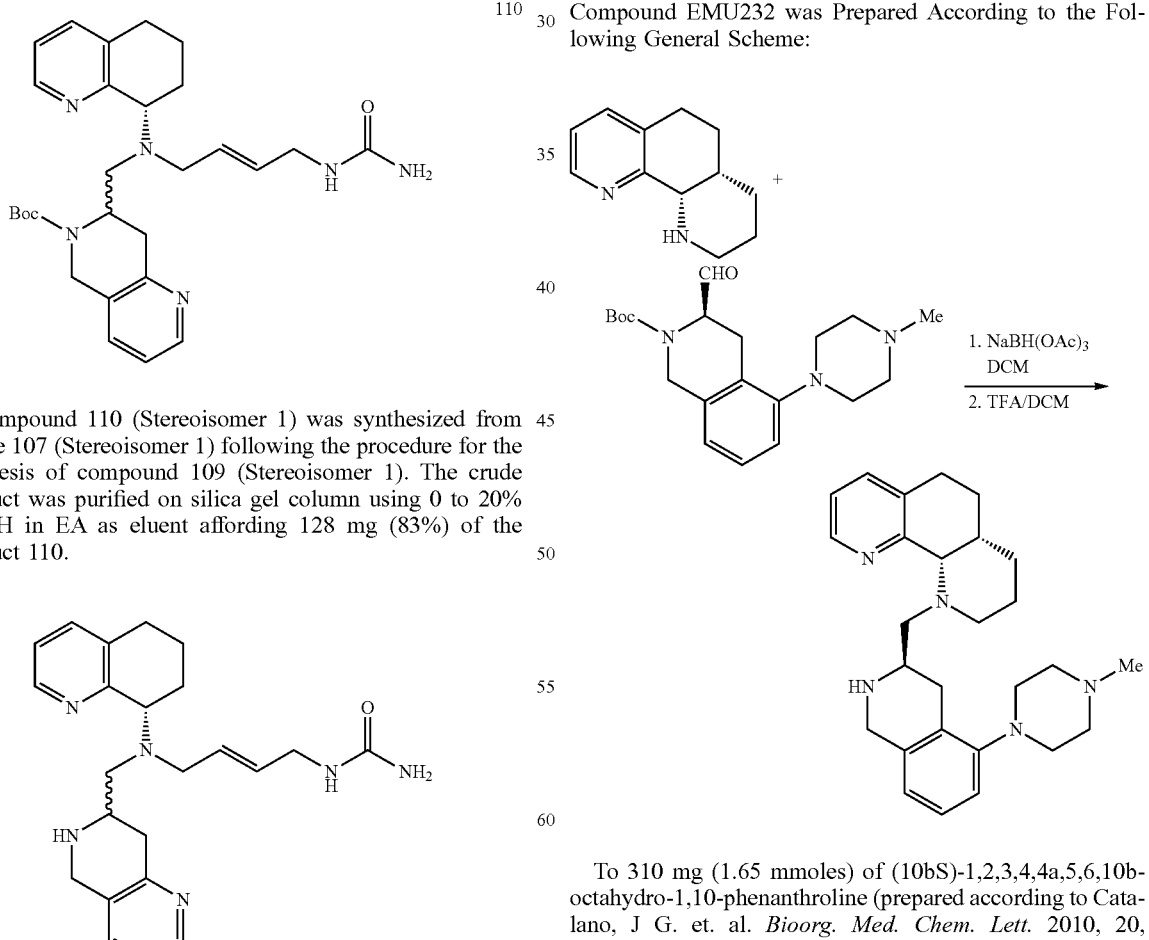

To 310 mg (1.65 mmoles) of (10bS)-1,2,3,4,4a,5,6,10b-octahydro-1,10-phenanthroline (prepared according to Catalano, J G. et. al. Bioorg. Med. Chem. Lett. 2010, 20, 2186-2190) and 365 mg (1.02 mmoles) of tert-butyl-(R)-3-formyl-5-(4-methylpiperazin-1-yl)-3,4-dihydroisoquinoline-2(1H)-carboxylate in 10 mL of dichloromethane was added 667 mg of sodium triacetoxyborohydride. The reaction was stirred for 24 hours and worked up to yield 388 mg of a white foam after column chromatography (73% yield). This material was then subjected to a global deprotection procedure using trifluoroacetic acid to yield 209 mg of the title compound as a pale yellow foam (79% yield).

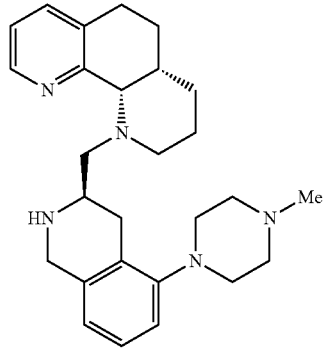 [SMILES: CN1CCN(c2cccc3c2C[C@H](CN2CCC[C@H]4CCc5cccnc5[C@H]42)NC3)CC1]

EMU232

(4aR,10bS)-1-(((R)-5-(4-methylpiperazin-1-yl)-1,2,3,4-tetrahydroisoquinolin-3-yl)methyl)-1,2,3,4,4a,5,6,10b-octahydro-1,10-phenanthroline. $^1$H NMR (400 MHz, CDCl$_3$): □ 1.69 (m, 6H), 2.11 9 m, 1H), 2.24 (m, 3H), 2.34 (s, 3H), 2.51 (m, 4H), 2.73 (m, 6H), 2.97 (m, 6H), 3.61 (m, 1H), 4.04 (m, 2H), 6.69 (d, 1H, J=8 Hz), 6.85 (d, 1H, J=7 Hz), 7.08 (m, 2H), 7.39 (d, 1H, J=8 Hz), 8.36 (d, 1H, J=5 Hz); MS (m/z): 432.2 (M+H)$^+$ Scheme 1:

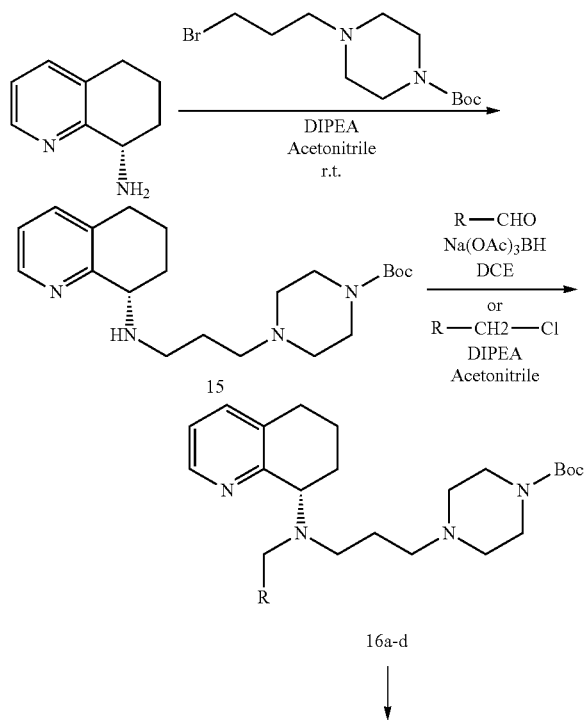

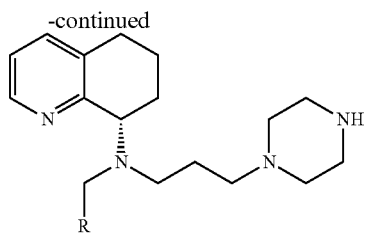

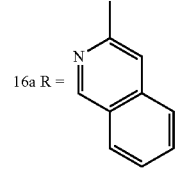 16a R =

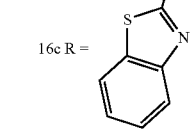 16c R =

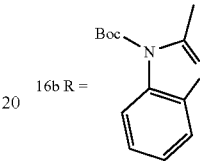 16b R =

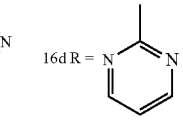 16d R =

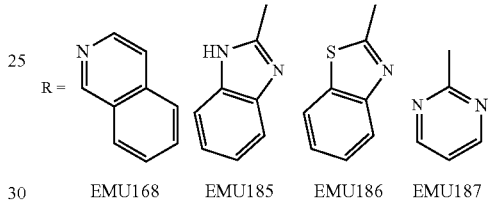

R = EMU168  EMU185  EMU186  EMU187

Tert-butyl (S)-4-(3-((5,6,7,8-tetrahydroquinolin-8-yl)amino)propyl)piperazine-1-carboxylate (Compound 15)

(S)-5,6,7,8-tetrahydroquinolin-8-amine (0.941 g, 6.35 mmol), tert-butyl 4-(3-bromopropyl)piperazine-1-carboxylate (1.5 g, 4.88 mmol) and DIPEA (2.132 ml, 12.21 mmol) were dissolved in 20 ml acetonitrile and stirred for overnight. The reaction mixture was diluted with EtOAc; extracted with saturated NaHCO$_3$ solution, water and brine; dried over anhydrous MgSO$_4$, filtered off and evaporated. It was purified with column chromatography using DCM: MeOH:NH$_4$OH (9:1:0.1). $^1$H NMR (400 MHz, Chloroform-d) δ 8.35 (dd, J=4.8, 1.5 Hz, 1H), 7.41-7.32 (m, 1H), 7.05 (dd, J=7.7, 4.7 Hz, 1H), 3.77 (d, J=8.2 Hz, 1H), 3.49-3.39 (m, 4H), 2.77 (m, 4H), 2.38 (d, J=5.0 Hz, 4H), 2.32-2.23 (m, 2H), 2.23-2.05 (m, 1H), 2.05-1.87 (m, 2H), 1.83-1.67 (m, 4H), 1.43 (s, 9H).

Tert-butyl (S)-4-(3-((isoquinolin-3-ylmethyl)-(5,6,7,8-tetrahydroquinolin-8-yl)amino)propyl)piperazine-1-carboxylate (Compound 16a)

To the solution of tert-butyl (S)-4-(3-((5,6,7,8-tetrahydroquinolin-8-yl)amino)propyl)piperazine-1-carboxylate (0.300 g, 0.801 mmol) (compound 15) in 10 ml DCE, isoquinoline-3-carbaldehyde (0.126 g, 0.801 mmol) and sodium triacetoxyhydroborate (0.340 g, 1.602 mmol) were added and stirred at room temperature for overnight. The reaction was quenched with saturated NaHCO$_3$ solution. Aqueous phase was extracted with DCM; combined organic layers was extracted with water and dried over anhydrous MgSO$_4$ and filtered off and evaporated. It was used as it is for the next step.

General Procedure for Compound 16b-d:

Tert-butyl (S)-4-(3-((5,6,7,8-tetrahydroquinolin-8-yl)amino)propyl)piperazine-1-carboxylate (0.500 g, 1.3 mmol) (compound 15), 2.0 mmol of R—Cl (corresponding chloride), DIPEA (0.93 ml, 5.34 mmol) and KI (0.022 g, 0.13 mmol) were suspended in 20 ml of acetonitrile and heated to 65° C. for overnight. The reaction mixture was diluted with EtOAc; extracted with saturated NaHCO$_3$ solution, water and brine; dried over anhydrous MgSO$_4$, filtered off and evaporated. It was used as it is for the next step.

General Procedure for Boc Deprotection for EMU168, EMU185, EMU186 and EMU187

Boc protected compound 16a-d (0.5 mmol) was dissolved in 5 ml DCM and 0.8 ml TFA was added to the reaction solution. It was stirred 1-24 hour at room temperature. The reaction mixture was basified with 1N NaOH solution to pH>10-12 and aqueous phase was extracted with DCM 3 times. Combined organic layer was dried over anhydrous MgSO4. Filtered off and evaporated. The product was purified with column chromatography using DCM/MeOH/NH$_4$OH gradient.

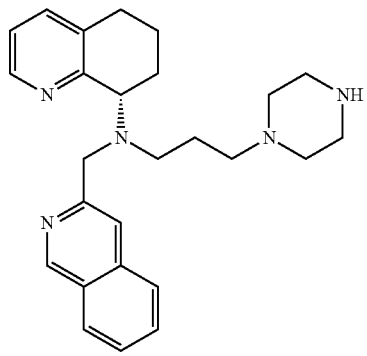 [SMILES: c1cnc2c(c1)CCC[C@@H]2N(CCCN1CCNCC1)Cc1cc2ccccc2cn1]

(S)—N-(isoquinolin-3-ylmethyl)-N-(3-piperazin-yl)propyl)-5,6,7,8-tetrahydroquinolin-8-amine (EMU168)

$^1$H NMR (500 MHz, Chloroform-d) δ 9.20-9.18 (m, 1H), 8.50 (dd, J=4.7, 1.7 Hz, 1H), 8.01 (s, 1H), 7.95 (dq, J=8.3, 1.0 Hz, 1H), 7.84 (dt, J=8.3, 1.0 Hz, 1H), 7.68 (ddd, J=8.2, 6.9, 1.2 Hz, 1H), 7.56 (ddd, J=8.1, 6.9, 1.1 Hz, 1H), 7.37 (dd, J=7.6, 1.8 Hz, 1H), 7.07 (dd, J=7.7, 4.7 Hz, 1H), 4.23-4.13 (m, 2H), 4.02 (d, J=15.1 Hz, 1H), 3.08-3.03 (m, 4H), 2.86-2.79 (m, 3H), 2.77-2.70 (m, 1H), 2.70-2.59 (m, 6H), 2.49 (t, J=7.0 Hz, 2H), 2.26-2.20 (m, 1H), 2.08-1.99 (m, 1H), 1.93 (m, 1H), 1.68 (m, 4H); MS: m/z 416.2 (M+H); HRMS Calc. for C$_{26}$H$_{34}$N$_5$ (M+H): 416.27360, Found: 416.28096

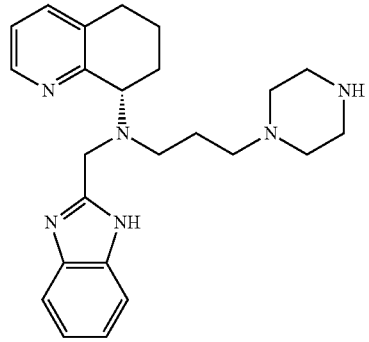 [SMILES: c1cnc2c(c1)CCC[C@@H]2N(CCCN1CCNCC1)Cc1nc2ccccc2[nH]1]

(S)—N-((1H-benzo[d]imidazole-2yl)methyl)-N-(3-(piperazine-1yl)propyl)-5,6,7,8-tetrahydroquinolin-8-amine (EMU185)

$^1$H NMR (500 MHz, Chloroform-d) δ 8.57 (dd, J=4.8, 1.7 Hz, 1H), 7.58 (dt, J=7.1, 3.6 Hz, 2H), 7.47-7.44 (m, 1H), 7.21 (dd, J=6.0, 3.2 Hz, 2H), 7.19-7.13 (m, 1H), 4.16-3.99 (m, 4H), 2.94 (q, J=5.8 Hz, 3H), 2.89-2.80 (m, 1H), 2.77-2.70 (m, 2H), 2.59 (m, 1H), 2.49-2.43 (m, 4H), 2.31-2.19 (m, 2H), 2.10-2.01 (m, 1H), 1.96-1.84 (m, 1H), 1.70 (m, 1H), 1.60-1.51 (m, 2H), 1.30-1.23 (m, 1H). MS: m/z 405.2 (M+H); HRMS Calc. for C$_{24}$H$_{33}$N$_6$ (M+H): 405.26885, Found: 405.27644

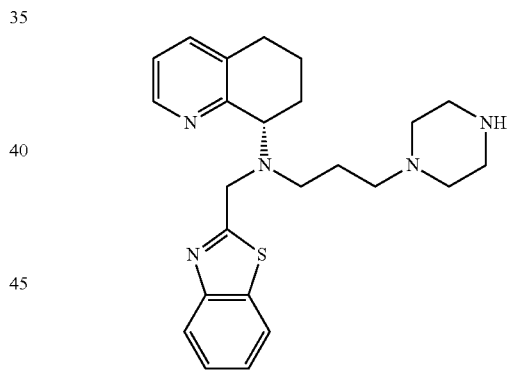

(S)—N-((1H-benzo[d]thiazol-2yl)methyl)-N-(3-(piperazine-1yl)propyl)-5,6,7,8-tetrahydroquinolin-8-amine (EMU186)

$^1$H NMR (500 MHz, Chloroform-d) δ 8.46 (dd, J=4.7, 1.8 Hz, 1H), 7.91 (dt, J=8.1, 0.9 Hz, 1H), 7.89-7.84 (m, 1H), 7.43 (dd, J=8.3, 7.2 Hz, 1H), 7.38-7.31 (m, 2H), 7.06 (dd, J=7.7, 4.6 Hz, 1H), 4.52 (d, J=16.8 Hz, 1H), 4.15 (td, J=9.3, 8.7, 6.6 Hz, 1H), 4.04 (d, J=16.7 Hz, 1H), 3.00 (m, 5H), 2.81-2.68 (m, 3H), 2.55 (m, 4H), 2.48 (t, J=7.4 Hz, 2H), 2.24 (m, 1H), 2.07-1.96 (m, 1H), 1.86 (m, 1H), 1.76-1.69 (m, 3H); MS: m/z 423.2 (M+H); HRMS Calc. for C$_{24}$H$_{32}$N$_5$S (M+H): 422.23002, Found: 422.23720

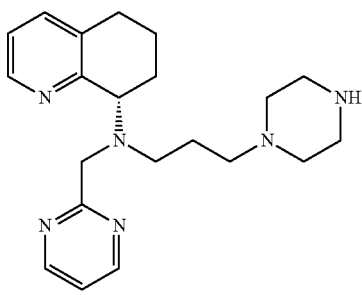 [SMILES: c1cnc(CN(CCCN2CCNCC2)[C@H]2CCCc3cccnc32)nc1]

(S)—N-(3-(piperazin-1yl)propyl)-N-(pyrimidin-2ylmethyl)-5,6,7,8-tetrahydroquinolin-8-amine (EMU187)

$^1$H NMR (500 MHz, Chloroform-d) δ 8.77-8.72 (m, 4H), 7.27-7.22 (m, 1H), 7.21 (t, J=4.9 Hz, 1H), 4.27-3.90 (m, 5H), 3.55-3.27 (m, 1H), 3.17 (m, 3H), 2.94 (m, 1H), 2.86-2.60 (m, 6H), 2.41 (m, 1H), 2.09 (m, 2H), 1.95-1.55 (m, 2H), 1.26 (m, 1H), 0.88 (m, 1H); MS: m/z 367.3 (M+H); HRMS Calc. for $C_{21}H_{31}N_6$ (M+H): 367.25319, Found: 367.23720

CXCR4-CEM Calcium Flux Assays

Exemplary compounds of the invention were tested for their ability to induce or inhibit calcium flux in CCRF-CEM cells, a human cell line that endogenously expresses CXCR4. Activation of CXCR4 stimulates G protein signaling which, in CCRF-CEM cells, causes a series of downstream events that leads to the release of intracellular calcium stores, or calcium flux. Calcium ion concentrations can be easily measured using a wide variety of colorimetric calcium indicators and, as a result, calcium flux assays are commonly employed methods for measuring G protein-coupled receptor (GPCR) activity. Because the therapeutic potential of CXCR4 antagonists as anti-cancer agents likely relies on their ability to inhibit CXCR4-mediated G protein signaling, this assay was utilized as a first-pass measure of inhibitor potency. Experimental procedures and results are provided below. The exemplified biological assays, which follow, have been carried out with compounds of the invention and/or salts thereof.

Procedure:

Human T lymphoblast cells (CCRF-CEM) expressing endogenous CXCR4 receptors were grown in suspension culture and plated in clear bottom 384-well microplates (Greiner bio-one Cat #789146) in assay buffer [Hank's Buffered Saline Solution (Gibco Cat #14025-092) supplemented with 20 mM HEPES (Gibco Cat #15630-080) and 0.1% fatty-acid free BSA (Sigma Cat #A9205)] at 40,000 cells per well. The cells were loaded with equal volume of calcium indicator dye (AAT Bioquest Inc, Cat #34601) for 30 minutes at 37° C. The cells were then equilibrated to room temperature for 30 minutes before assay. Test compounds solubilized and serially diluted in DMSO were transferred to 384 well plates (Matrix Cat #4307). The serially diluted compounds were diluted to working concentrations with the same assay buffer to 0.5% DMSO. They were added to the cells by FDSS6000 (Hamamatsu) at final concentrations ranging from 25,000 nM to 0.423 nM. Activity of the compounds to induce calcium flux was monitored by FDSS in the "agonist mode" for 90 sec. For "antagonist mode" assessment, the cells are subsequently incubated for 25 minutes at room temperature. SDF-1α (R&D System Cat #350-NS/CF) was then added at a final concentration of 4 nM to stimulate the cells. Inhibition of SDF-1α-induced calcium flux was monitored by FDSS6000 for 90 seconds.

Activation data for the test compound over a range of concentrations was plotted as percentage activation of the test compound (100%=maximum response triggered by a saturating concentration of SDF-1α, i.e., 160 nM). After correcting for background, $EC_{50}$ values were determined. The $EC_{50}$ is defined as the concentration of test compound, which produces 50% of the maximal response and was quantified using the 4-parameter logistic equation to fit the data. Inhibition data for the test compound over a range of concentrations was plotted as percentage inhibition of the test compound as compared to an internal control compound. The $IC_{50}$ is defined as the concentration of test compound, which inhibits 50% of the maximal response and was quantified using the 4-parameter logistic equation to fit the data.

None of the compounds tested demonstrated agonist activity in the calcium flux assay. All compounds demonstrated $EC_{50}$ values >30 μM, indicating that they are not agonists of GPCRs that are endogenously expressed by CCRF-CEM cells, including CXCR4. In contrast, compounds demonstrated a range of potencies in inhibiting SDF-1α-induced calcium flux, indicating that they inhibit CXCR4-mediated G protein signaling.

| Compound Number | CXCR4 $Ca^{2+}$ Flux $IC_{50}$/nM |
|---|---|
| EMU013 | 20.91 |
| EMU014 | 13,647.10 |
| EMU015 | 230.50 |
| EMU025 | 2,902.11 |
| EMU026 | 71.02 |
| EMU027 | 697.84 |
| EMU028 | 3,307.08 |
| EMU047 | 260.19 |
| EMU048 | 2,115.59 |
| EMU065 | 1,099.26 |
| EMU066 | 24.35 |
| EMU067 | 1,709.64 |
| EMU078 | 69.18 |
| EMU079 | 2,290.39 |
| EMU080 | 7,590.56 |
| EMU081 | >33,333.33 |
| EMU102 | 126.56 |
| EMU103 | 405.51 |
| EMU104 | ~16,558.92 |
| EMU107 | 21.40 |
| EMU108 | 61.99 |
| EMU109 | 322.62 |
| EMU110 | >33,333.33 |
| EMU111 | >33,333.33 |
| EMU112 | 8,721.41 |
| EMU127 | 91.17 |
| EMU128 | >33,333.33 |
| EMU129 | 631.07 |
| EMU130 | 510.14 |
| EMU131 | 1,855.00 |
| EMU148 | 3,098.80 |
| EMU149 | 92.12 |
| EMU164 | 33.69 |
| EMU165 | 114.62 |
| EMU166 | 9.88 |
| EMU189 | 162.78 |
| EMU190 | 484.16 |
| EMU023 | >33,333.33 |
| EMU024 | 1,001.31 |
| EMU034 (Stereoisomer 1) | 6.08 |
| EMU034 (Stereoisomer 2) | 313.78 |
| EMU044 (Stereoisomer 1) | 18.11 |
| EMU044 (Stereoisomer 2) | 1,698.65 |
| EMU058 | 33.40 |

-continued

| Compound Number | CXCR4 Ca$^{2+}$ Flux IC$_{50}$/nM |
|---|---|
| EMU062 | 10.33 |
| EMU070 | 6,269.55 |
| EMU073 (Stereoisomer 1) | 33.69 |
| EMU074 (Stereoisomer 2) | 1,828.78 |
| EMU089 | 755.06 |
| EMU090 | 171.06 |
| EMU096 (Stereoisomer 1) | 61.02 |
| EMU096 (Stereoisomer 2) | 3,844.86 |
| EMU116 | 29.61 |
| EMU135 | 146.11 |
| EMU136 | 33.94 |
| EMU160 | 2.92 |
| EMU161 | 3.59 |
| EMU163 | 363.51 |
| EMU172 | 23.83 |
| EMU173 | 21.50 |
| EMU174 (Stereoisomer 1) | >33,333.33 |
| EMU174 (Stereoisomer 2) | 476.10 |
| EMU183 | 380.49 |
| EMU196 | 23.51 |
| EMU197 | 16.93 |
| EMU198 | 14.08 |
| EMU199 | 13.84 |
| EMU200 | 20.73 |
| EMU201 | 17.9 |
| EMU202 | 4.47 |
| EMU203 | 30.74 |
| EMU226 | >16,667.67 |
| EMU227 | 9.56 |
| EMU228 | 35.88 |
| EMU229 | 47.43 |
| EMU230 | 16.13 |
| EMU234 | 31.97 |
| EMU235 | 18.66 |
| EMU236 | 11.42 |
| EMU237 | 10.41 |
| EMU238 | 10.90 |
| EMU239 | 44.55 |
| EMU240 | 13.44 |
| EMU241 | 58.14 |
| EMU007 | 9.26 |
| EMU012 | 50.79 |
| EMU030 (Stereoisomer 1) | 6.42 |
| EMU030 (Stereoisomer 2) | 19.13 |
| EMU037 | 65.41 |
| EMU074 | 283.76 |
| EMU075 | >33,333.33 |
| EMU091 | 129.30 |
| EMU093 | 114.84 |
| EMU094 | 292.20 |
| EMU100 (Stereoisomer 1) | 714.63 |
| EMU100 (Stereoisomer 2) | 1,286.97 |
| EMU119 | 26.65 |
| EMU120 | 497.91 |
| EMU121 | 343.16 |
| EMU124 | 227.28 |
| EMU125 | 79.90 |
| EMU126 | 1,884.48 |
| EMU140 | 28.30 |
| EMU141 | 43.71 |
| EMU142 (Stereoisomer 1) | 25.64 |
| EMU142 (Stereoisomer 2) | 502.51 |
| EMU143 | 97.96 |
| EMU153 | 64.63 |
| EMU154 | 82.08 |
| EMU155 | 15.47 |
| EMU177 | 13.22 |
| EMU180 | 24.19 |
| EMU181 | 661.44 |
| EMU182 | 143.11 |
| EMU192 (Stereoisomer 1) | 146.25 |
| EMU192 (Stereoisomer 2) | — |
| EMU193 | 17,047.06 |
| EMU194 | 110.69 |
| EMU208 | 28.17 |
| EMU209 (Stereoisomer 1) | 462.98 |

-continued

| Compound Number | CXCR4 Ca$^{2+}$ Flux IC$_{50}$/nM |
|---|---|
| EMU209 (Stereoisomer 2) | — |
| EMU211 | 207.05 |
| EMU212 (Stereoisomer 1) | 429.76 |
| EMU212 (Stereoisomer 2) | — |
| EMU216 | 182.68 |
| EMU217 | 90.26 |
| EMU218 | 134.46 |
| EMU219 | 60.48 |
| EMU220 | 285.84 |
| EMU221 | 40.73 |
| EMU222 | 92.82 |
| EMU223 | 58.34 |
| EMU232 | 25.24 |
| EMU168 | 17.26 |
| EMU185 | 45.30 |
| EMU186 | 1,198.45 |
| EMU187 | 4,315.51 |

What is claimed is:

1. A pharmaceutical composition comprising a compound selected from the group consisting of:

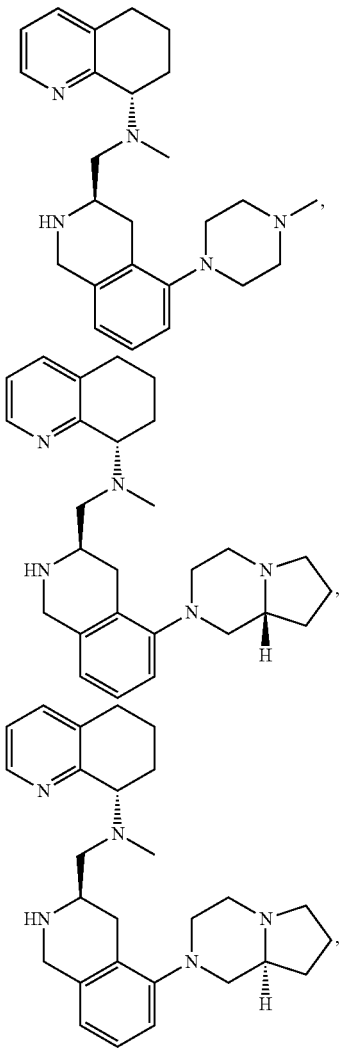

343
-continued

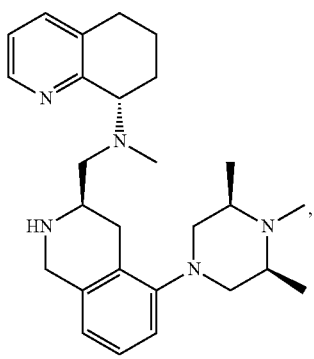

and salts thereof, and
a pharmaceutically acceptable excipient, diluent, or carrier.

2. The pharmaceutical composition as claimed in claim 1, wherein the compound is in greater than 60%, 70%, 80%, 90%, 95%, or 98% diastereomeric or enantiomeric excess.

3. The pharmaceutical composition as claimed in claim 1, further comprising a second active ingredient, optionally wherein the second active ingredient is an antiviral agent or chemotherapeutic agent.

4. The pharmaceutical composition as claimed in claim 3, wherein the second active ingredient is a CCR5 antagonist.

5. A method of treating a viral infection, comprising administering a compound selected from the group consisting of:

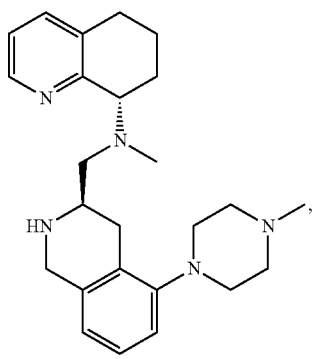

344
-continued

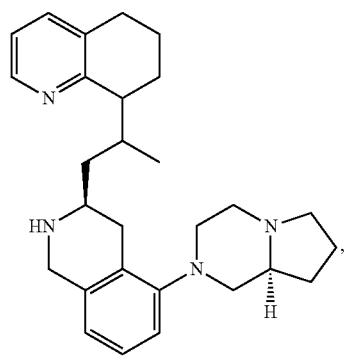

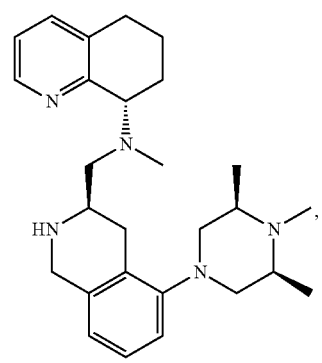

and salts thereof, optionally in combination with another active ingredient, to a subject in need thereof,
wherein the viral infection is CXCR4-related.

6. The method as claimed in claim 5, wherein the subject is exhibiting symptoms of or diagnosed with the viral infection.

7. The pharmaceutical composition as claimed in claim 1, wherein the pharmaceutical composition is in the form of an oral formulation.

8. The method as claimed in claim 5, wherein the viral infection is HIV infection.

9. The method as claimed in claim 5, wherein the compound is administered orally.

10. A compound selected from the group consisting of:

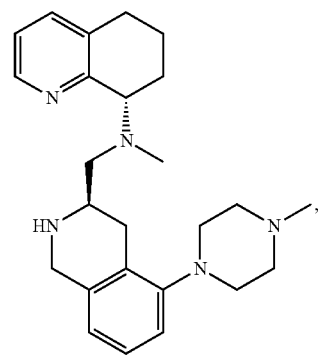

345
-continued

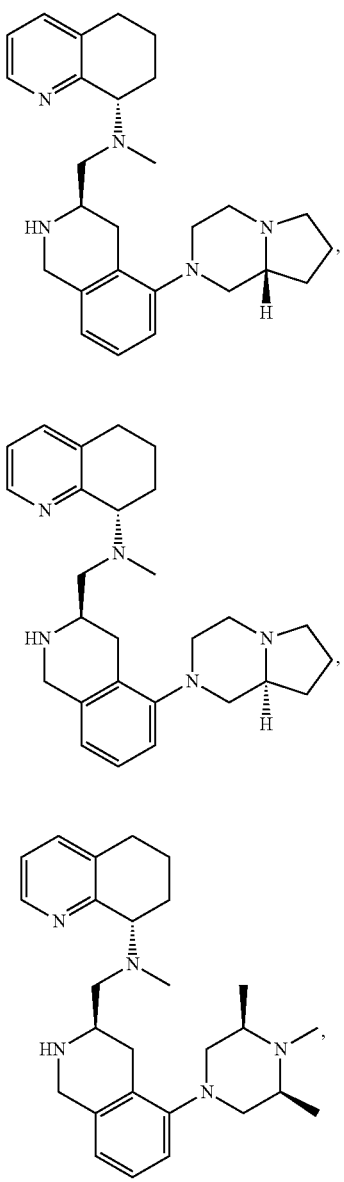

and salts thereof.

11. A method of treating a cancer, comprising administering a compound selected from the group consisting of:

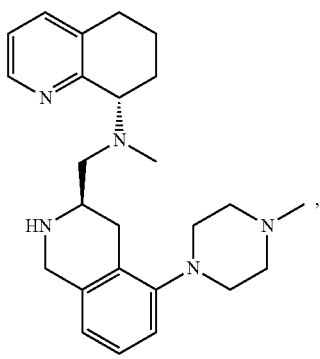

346
-continued

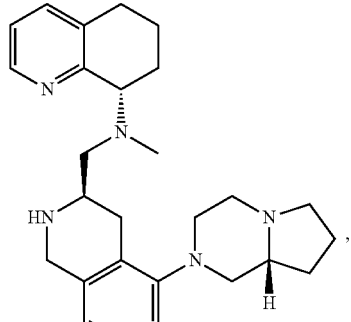

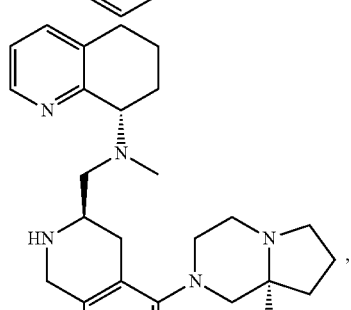

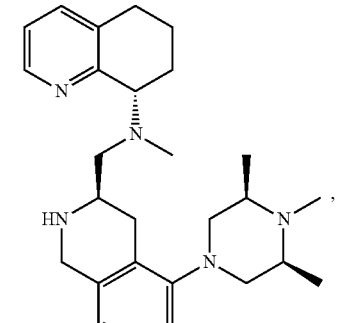

and salts thereof, optionally in combination with another active ingredient, to a subject in need thereof, wherein the cancer is CXCR4-related.

12. The method as claimed in claim 11, wherein the subject is exhibiting symptoms of or diagnosed with the cancer.

13. The method as claimed in claim 11, wherein the compound is administered orally.

14. The method as claimed in claim 11, wherein the another active ingredient comprises an antiproliferative or antineoplastic drug.

15. The method as claimed in claim 14, wherein the antiproliferative or antineoplastic drug is selected from the group consisting of 5-fluorouracil, gemcitabine, tegafur, raltitrexed, methotrexate, cytosine arabinoside, taxol, and taxotere.

16. The method as claimed in claim 11, wherein the another active ingredient comprises a tyrosine kinase inhibitor, a serine/threonine kinase inhibitor, or a combination thereof.

17. The method as claimed in claim 16, wherein the tyrosine kinase inhibitor is an inhibitor of EGFR family tyrosine kinase.

18. The method as claimed in claim 11, wherein the another active ingredient comprises an antiangiogenic agent.

19. The method as claimed in claim 18, wherein the antiangiogenic agent is an inhibitor of vascular endothelial growth factor.

20. The method as claimed in claim 11, wherein the another active ingredient comprises a cytostatic agent.

21. The method as claimed in claim 11, wherein the another active ingredient comprises an inhibitor of metalloproteinase, an inhibitor of urokinase plasminogen activator receptor, or a combination thereof.

* * * * *